United States Patent
Schönfeld et al.

(10) Patent No.: US 12,384,843 B2
(45) Date of Patent: *Aug. 12, 2025

(54) ANTI-SEMAPHORIN 3A ANTIBODIES

(71) Applicant: BAYER AKTIENGESELLSCHAFT, Leverkusen (DE)

(72) Inventors: Dorian Schönfeld, Cologne (DE); Karoline Dröbner, Velbert (DE); Ernst Weber, Langenfeld (DE); Katharina Filarsky, Düsseldorf (DE); Philipp Ellinger, Solingen (DE); Fionnuala Mary McAleese Eser, Langenfeld (DE); Ingo Flamme, Reichshof (DE); Winfried Wunderlich, Bovenden (DE); Antje Schmidt, Göttingen (DE); Yalda Sedaghat, Hamburg (DE); Kenneth Young, Hamburg (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/706,543

(22) Filed: Mar. 28, 2022

(65) Prior Publication Data
US 2022/0389096 A1 Dec. 8, 2022

(30) Foreign Application Priority Data
Mar. 30, 2021 (EP) .................. 21165960

(51) Int. Cl.
C07K 16/28 (2006.01)
A61K 39/395 (2006.01)
A61P 9/10 (2006.01)
A61P 13/12 (2006.01)
C07K 16/18 (2006.01)
A61K 39/00 (2006.01)

(52) U.S. Cl.
CPC ...... *C07K 16/2803* (2013.01); *A61K 39/3955* (2013.01); *A61P 9/10* (2018.01); *A61P 13/12* (2018.01); *C07K 16/18* (2013.01); *A61K 2039/505* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,634,665 A | 1/1987 | Axel et al. |
| 4,657,760 A | 4/1987 | Kung et al. |
| 4,816,397 A | 3/1989 | Boss et al. |
| 4,816,567 A | 3/1989 | Cabilly et al. |
| 4,968,615 A | 11/1990 | Koszinowski et al. |
| 5,168,062 A | 12/1992 | Stinski |
| 5,179,017 A | 1/1993 | Axel et al. |
| 5,206,344 A | 4/1993 | Katre et al. |
| 5,208,020 A | 5/1993 | Chari et al. |
| 5,225,212 A | 7/1993 | Martin et al. |
| 5,225,539 A | 7/1993 | Winter |
| 5,416,064 A | 5/1995 | Chari et al. |
| 5,585,089 A | 12/1996 | Queen et al. |
| 5,635,483 A | 6/1997 | Pettit et al. |
| 5,693,761 A | 12/1997 | Queen et al. |
| 5,693,762 A | 12/1997 | Queen et al. |
| 5,766,886 A | 6/1998 | Studnicka et al. |
| 5,780,588 A | 7/1998 | Pettit et al. |
| 5,821,337 A | 10/1998 | Carter et al. |
| 5,859,205 A | 1/1999 | Adair et al. |
| 6,300,064 B1 | 10/2001 | Knappik et al. |
| 6,602,684 B1 | 8/2003 | Umana et al. |
| 6,982,321 B2 | 1/2006 | Winter |
| 6,989,250 B2 | 1/2006 | Soderlind et al. |
| 7,087,409 B2 | 8/2006 | Barbas, III et al. |
| 7,498,298 B2 | 3/2009 | Doronina et al. |
| 7,527,791 B2 | 5/2009 | Adams et al. |
| 2005/0014934 A1 | 1/2005 | Hinton et al. |
| 2005/0123546 A1 | 6/2005 | Umana et al. |

FOREIGN PATENT DOCUMENTS

| | | |
|---|---|---|
| AU | 2016346595 A1 | 6/2018 |
| EP | 2955195 A1 | 12/2015 |
| WO | WO-9708320 A1 | 3/1997 |
| WO | WO-199730087 A1 | 8/1997 |
| WO | WO-199858964 A1 | 12/1998 |

(Continued)

OTHER PUBLICATIONS

Roland et al. (2001) nCoDeR concept: unique types of antibodies for diagnostic use and therapy, Expert Review of Molecular Diagnostics, 1:1, 102-108, DOI: 10.1586/14737159.1.1.102.*
Edwards et al. (J. Mol. Biol. 334: 103-118, 2003).*
Torres et al. (Trends in Immunol. 29(2): 91-97, 2008).*
Khan et al. (J. Immunol. 192: 5398-5405, 2014).*
Poosarla et al. (Biotech. Bioengineer. 124(6): 1331-1342, 2017).*
Paul, Fundamental Immunology, 3rd Edition, 1993, pp. 292-295, under the heading "Fv Structure and Diversity in Three Dimensions").*
Rudikoff et al. (PNAS 79: 1979-1983, 1982).*
MacCallum, et al. (J. Mol. Biol. 262: 732-745, 1996).*
De Pacalis et al. (J. Immunol. 169: 3076-3084, 2002).*

(Continued)

*Primary Examiner* — Christine J Saoud
(74) *Attorney, Agent, or Firm* — Harness, Dickey & Pierce, P.L.C.

(57) ABSTRACT

The present disclosure relates to an isolated antibody or antigen-binding fragment thereof that binds to human Semaphorin 3A (Sema3A). An antibody conjugate and a pharmaceutical composition each comprising the isolated antibody or antigen-binding fragment thereof that binds to human Sema3A are also provided.

11 Claims, 15 Drawing Sheets

Figure 1A:
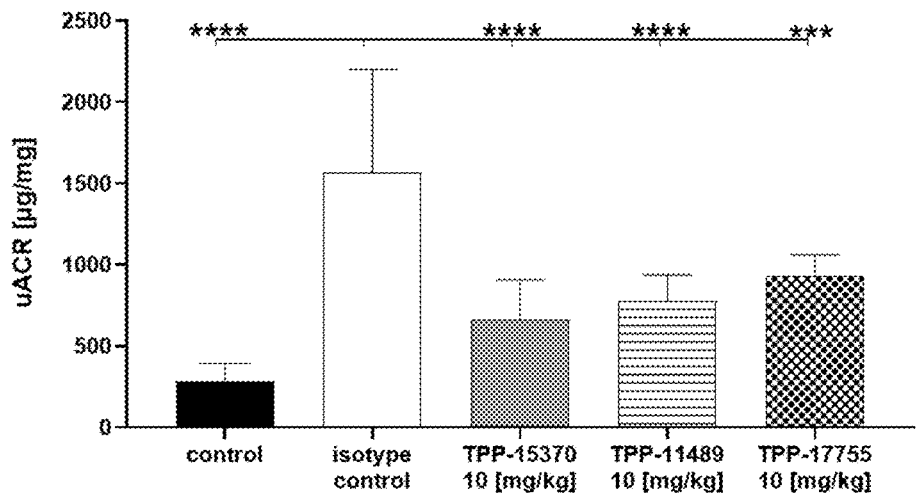

Specification includes a Sequence Listing.

(56) References Cited

FOREIGN PATENT DOCUMENTS

| | | |
|---|---|---|
| WO | WO-199922764 A1 | 5/1999 |
| WO | WO-2003011878 A2 | 2/2003 |
| WO | WO-2004056312 A2 | 7/2004 |
| WO | WO-2008077546 A1 | 7/2008 |
| WO | WO-2008112640 A2 | 9/2008 |
| WO | WO-2017074013 A1 | 5/2017 |
| WO | WO-2020225400 A1 | 11/2020 |
| WO | WO-2020261281 A1 | 12/2020 |

OTHER PUBLICATIONS

Casset et al. (Biochem. Biophys. Res. Comm. 307: 198-205, 2003).*
Chen et al. (J. Mol. Biol. 293: 865-881, 1999).*
Wu et al. (J. Mol. Biol. 294: 151-162, 1999).*
Almagro, Juan C. et al., "Humanization of antibodies" Frontiers in Bioscience 13, Jan. 2008, (15 pages).
Bebbington, C.R. et al., "High-Level Expression Of A Recombinant Antibody From Myeloma Cells Using A Glutamine Synthetase Gene As An Amplifiable Selectable Marker", Bio/Technology, vol. 10, Feb. 1992, (7 pages).
Bird, Robert E. et al., "Single-Chain Antigen-Binding Proteins", Science vol. 242, Oct. 21, 1988, (4 pages).
Bruggemann, Marianne, et al., Human Antibody Production in Transgenic Animals, Arch. Immunol. Ther. Exp., vol. 63, 2015. (8 pages).
Carlsson, Roland et al., "n-CoDeR concept: unique types of antibodies for diagnostic use and therapy" Expert Rev. Mol. Diagn., vol. 1, 2001. (7 pages).
Carter, Paul J., "Potent antibody therapeutics by design", Nature Reviews Immunology, vol. 6, May 2006. (16 pages).
Chari, Ravi V.J., et al., "Immunoconjugates Containing Novel Maytansinoids: Promising Anticancer Drugs", Cancer Research, vol. 52, Jan. 1992. (5 pages).
Chothia, Cyrus et al., "Canonical Structures for the Hypervariable Regions of Immunoglobulins", J. Mol. Biol., vol. 196, 1987. (17 pages).
Dall'Acqua, William F. et al., "Antibody humanization by framework shuffling", Methods, vol. 36, Jan. 17, 2005. (18 pages).
Durocher, Yves et al., "High-level and high-throughput recombinant protein production by transient transfection of suspension-growing human 293-EBNA1 cells" Nucleic Acids Research, vol. 30, 2002. (9 pages).
Fan, Lianchun et al., "Improving the Efficiency of CHO Cell Line Generation Using Glutamine Synthetase Gene Knockout Cells" Biotechnology and Bioengineering, vol. 109, 2012. (9 pages).
Frenzel, Andre et al., "Phage display-derived human antibodies in clinical development and therapy" MABS, vol. 8, 2016. (19 pages).
Guyer, Ruth L. et al., "Immunoglobulin Binding By Mouse Intestinal Epithelial Cell Receptors" The Journal Of Immunology, vol. 117, Aug. 1976. (7 pages).
Hoet et al., "Generation of high-affinity human antibodies by combining donor-derived and synthetic complementarity-determining-region diversity" Nature Biotechnology, vol. 23, Mar. 2005. (5 pages).
Huston, James S. et al., "Protein engineering of antibody binding sites: Recovery of specific activity in an anti-digoxin single-chain Fv analogue produced in *Escherichia coli*" Proc. Natl. Acad. Sci. USA, vol. 85, Aug. 1988. (5 pages).
Jones, Peter T. et al., "Replacing the complementarity-determining regions in a human antibody with those from a mouse" Nature, vol. 321, May 1986. (4 pages).
Kanda, Yutaka et al., "Comparison of Cell Lines for Stable Production of Fucose-Negative Antibodies With Enhanced ADCC" Biotechnology and Bioengineering, vol. 94, 2006. (10 pages).
Kashmiri et al., "SDR grafting—a new approach to antibody humanization" Methods, vol. 36, 2005. (10 pages).
Kaufman, Randal J. & Sharp, Phillip A., "Amplification and Expression of Sequences Cotransfected with a Modular Dihydrofolate Reductase Complementary DNA Gene" J. Mol. Biol., vol. 159, 1982. (21 pages).
Khorana H. G. et al., "Studies on Polynucleotides, CIII: Total Synthesis of the Structural Gene for an Alanine Transfer Ribonucleic Acid from Yeast" J. Mol. Biol., vol. 72, 1972. (9 pages).
Kim, J.K. et al., "Identifying amino acid residues that influence plasma clearance of murine IgG1 fragments by site-directed mutagenesis" Eur. J. Immunol., vol. 24, 1994. (7 pages).
Klimka, A. et al., "Human anti-CD30 recombinant antibodies by guided phage antibody selection using cell panning" British Journal of Cancer, vol. 83, 2000. (9 pages).
Knappik, Achim et al., "Fully Synethic Human Combinatorial Antibody Libraries (HuCAL) Based on Modular Consensus Frameworks and CDRs Randomized with Trinucleotides" J. Mol. Biol. vol. 296, 2000. (30 pages).
Kohler et al., "Continuous cultures of fused cells secreting antibody of predefined specificity" Nature, vol. 256, Aug. 1975. (3 pages).
Krebs, Barbara et al., "High throughput generation and engineering of recombinant human antibodies" Journal of Immunological Methods, vol. 254, 2001. (18 pages).
Liu, C. et al., "Eradication of large colon tumor xenografts by targeted delivery of maytansinoids" Proc. Natl. Acad. Sci. USA, vol. 93, Aug. 1996. (6 pages).
McCafferty, John et al., "Phage antibodies: filamentous phage displaying antibody variable domains" Naturem vol. 348, Dec. 1990. (3 pages).
Mikule, Keith et al., "Growth Cone Collapse Induced by Semaphorin 3A Requires 12/15-Lipoxygenase" The Journal of Neuroscience, vol. 22, Jun. 2002. (10 pages).
Nelson, Aaron L. et al., "Development trends for human monoclonal antibody therapeutics" Nature Reviews, vol. 9, Oct. 2010. (8 pages).
Nose, Masato et al., "Biological significance of carbohydrate chains on monoclonal antibodies" Proc. Natl. Acad. Sci. USA, vol. 80, Nov. 1983. (5 pages).
Okazaki, Akira et al., "Fucose Depletion from Human IgG1 Oligosaccharide Enhances Binding Enthalpy and Association Rate Between IgG1 and FcγRIIIa" J. Mol. Biol., vol. 336, 2004. (11 pages).
Osbourn, Jane et al., "From rodent reagents to human therapeutics using antibody guided selection" Methods, vol. 36, 2005. (8 pages).
Padlan, Eduardo A., "A Possible Procedure For Reducing The Immunogenicity Of Antibody Variable Domains While Preserving Their Ligand-Binding Properties" Molecular Immunology, vol. 28, 1991. (10 pages).
Pluckthun, A., "Antibodies from *Escherichia coli*" The Pharmacology of Monoclonal Antibodies, edition 113, 1994. (47 pages).
Presta, Leonard G., "Antibody engineering" Structural Biology, vol. 2, 1992. (4 pages).
Queen, Cary et al., "A humanized antibody that binds to the interleukin 2 receptor" Proc. Natl. Acad. Sci. USA, vol. 86, Dec. 1989. (5 pages).
Riechmann, Lutz et al., "Reshaping human antibodies for therapy" Nature, vol. 332, Mar. 1988. (5 pages).
Ripka, James et al., "Two Chinese Hamster Ovary Glycosylation Mutants Affected in the Conversion of GDP-Mannose to GDP-Fucose", Archives of Biochemistry and Biophysics, vol. 249, Apr. 1986. (13 pages).
Soderlind, Eskil et al., "Recombining germline-derived CDR sequences for creating diverse single-framework antibody libraries" Nature Biotechnology, vol. 18, Aug. 2000. (5 pages).
Urlaub, Gail et al., "Deletion of the Diploid Dihydrofolate Reductase Locus from Cultured Mammalian Cells", Cell, vol. 33, Jun. 1983. (8 pages).
Urlaub, Gail et al., "Isolation of Chinese hamster cell mutants deficient in dihydrofolate reductase activity" Proc. Natl. Acad. Sci. USA, vol. 77, Jul. 1980. (5 pages).
Virnekas, Bernhard et al., "Trinucleotide phosphoramidites: ideal reagents for the synthesis of mixed oligonucleotides for random mutagenesis" Nucleic Acids Research, vol. 22, 1994. (8 pages).

(56) References Cited

OTHER PUBLICATIONS

Winkelhake, Jeffrey L., "Effects Of Exoglycosidase Treatments On Autochthonous Antibody Survival Time In The Circulation" The Journal Of Biological Chemistry, vol. 251, Feb. 1976. (7 pages).

Wright, Ann & Morrison, Sherie L., "Effect of glycosylation on antibody function: implications for genetic engineering" TIBTECH, vol. 15, Jan. 1997. (7 pages).

Yamane-Ohnuki, Naoko et al., "Establishment of FUT8 Knockout Chinese Hamster Ovary Cells: An Ideal Hoset Cell Line for Producing Completely Defucosylated Antibodies With Enhanced Antibody-Dependent Cellular Cytotoxicity" Biotechnology and Bioengineering, vol. 87, Sep. 2004. (9 pages).

Zapata, Gerardo et al., "Engineering linear F(ab')2 fragments for efficient production in *Escherichia coli* and enhanced antiproliferative activity" Protein Engineering, vol. 8, 1995. (6 pages).

\* cited by examiner

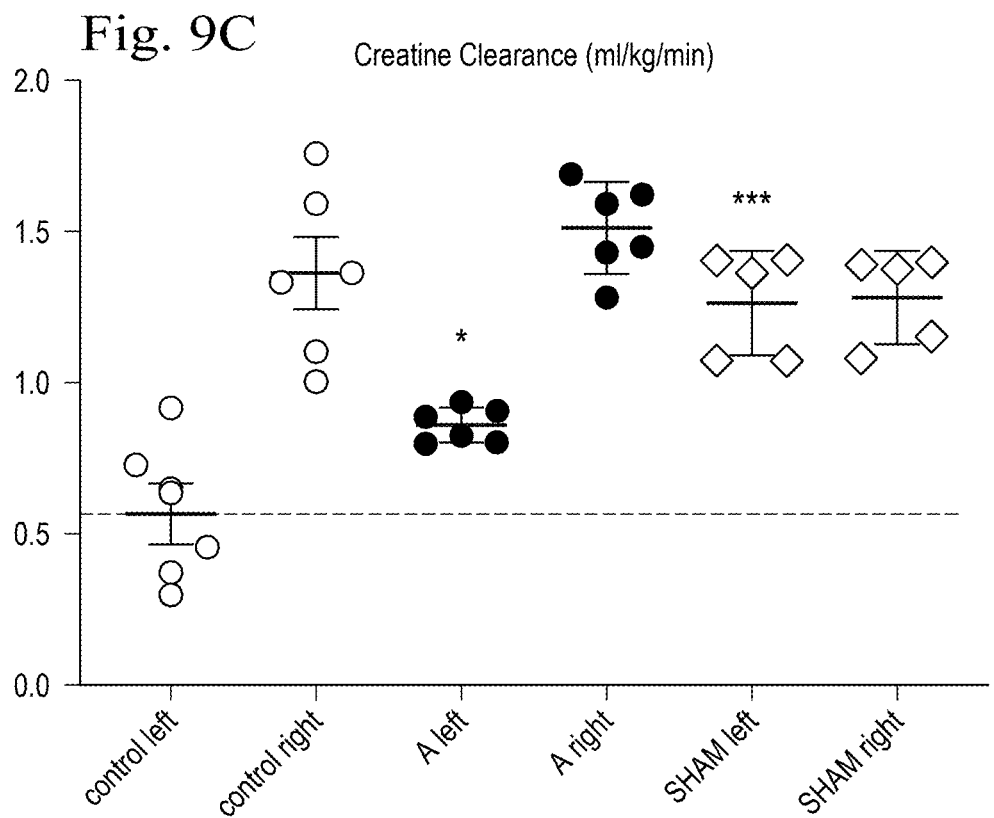
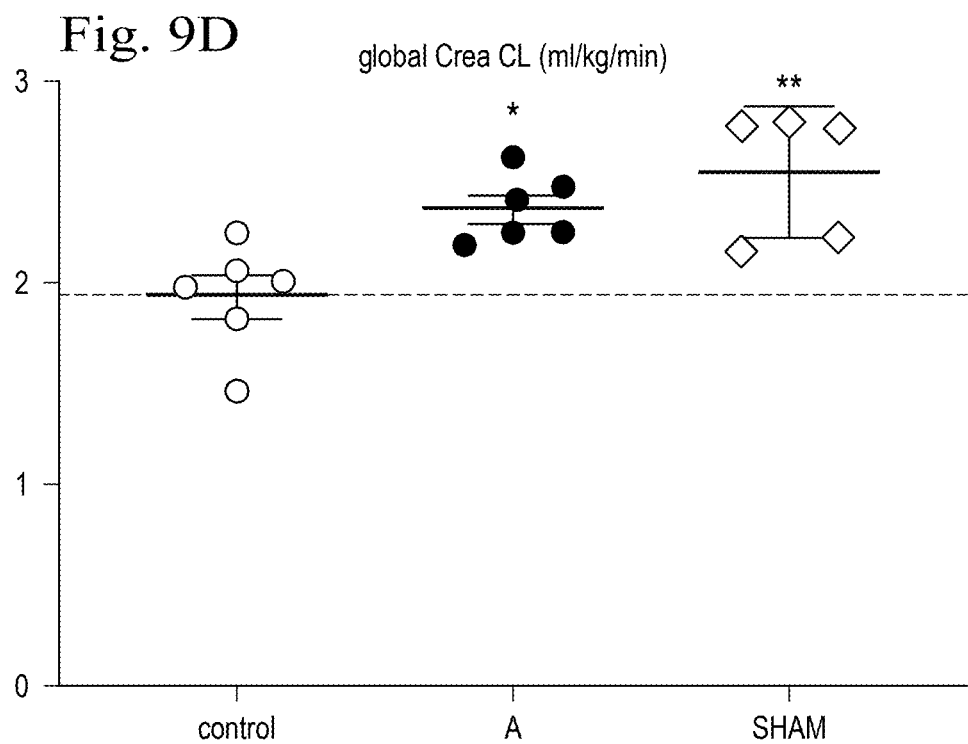

Fig. 11A  Fig. 11B  Fig. 11C
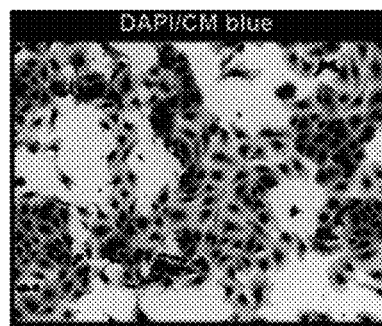
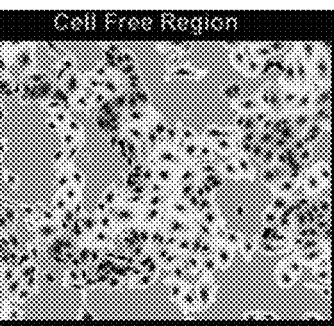
Fig. 12
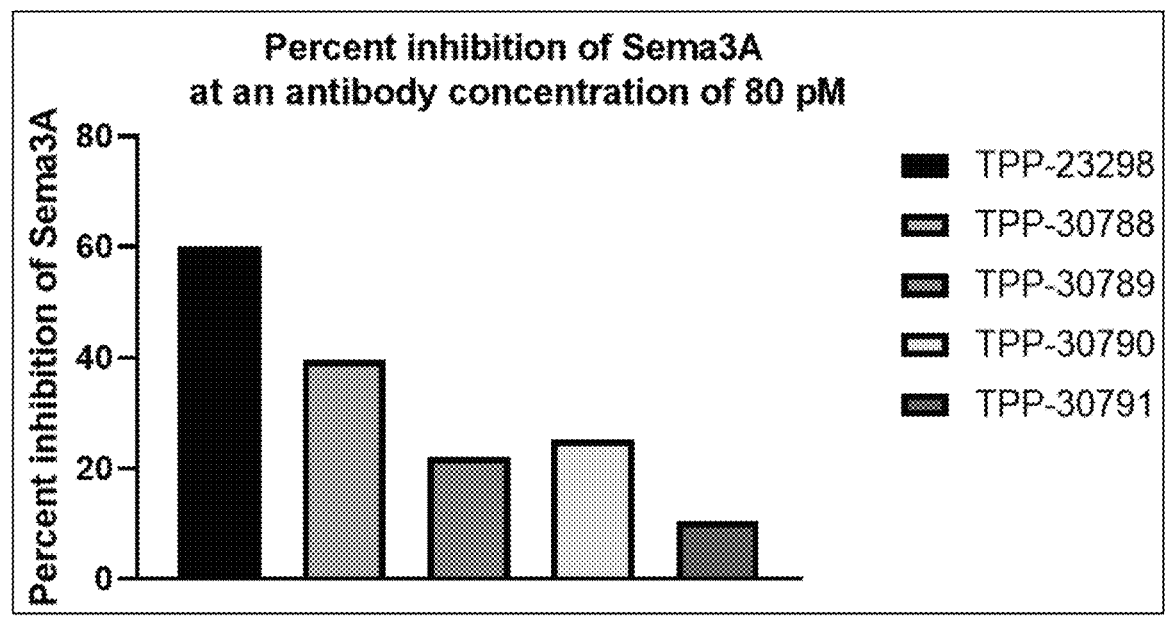

ANTI-SEMAPHORIN 3A ANTIBODIES

CROSS-REFERENCE TO RELATED APPLICATION

This application claims the benefit of, and priority to, European Patent Application Serial No. 21165960.2 filed Mar. 30, 2021, the entire disclosure of which is hereby incorporated by reference.

SEQUENCE LISTING

This application contains references to amino acid sequences and/or nucleic acid sequences which have been submitted concurrently herewith as the sequence listing text file entitled "Seqs3_BHC201071_FC_US_ST25.txt", file size 596,189 bytes, created on Jun. 14, 2022. The aforementioned sequence listing is hereby incorporated by reference in its entirety pursuant to 37 C.F.R. § 1.52 (e) (5).

FIELD

The present disclosure provides isolated antibodies or antigen-binding fragments thereof that bind to human semaphorin 3A (Sema3A). The isolated antibody or antigen-binding fragments according to the present disclosure i) bind to human Sema3A of the sequence of SEQ ID NO: 600 with a dissociation constant (KD)≤50 nM, ≤20 nM, ≤10 nM, ≤1 nM, or ≤0.1 nM; ii) cross-react with mouse, cynomolgus, rat, pig and/or dog Sema3A, particularly wherein said isolated antibodies or antigen-binding fragments thereof binds to mouse, cynomolgus, rat, pig and/or dog Sema3A with a dissociation constant (KD)≤50 nM, ≤20 nM, ≤10 nM, ≤1 nM, or ≤0.1 nM; iii) bind to human Sema3A of the sequence of SEQ ID NO: 600 with a binding activity as measured by surface plasmon resonance (SPR) of ≥60%, ≥70%, ≥80%, or ≥90%; iv) inhibit the activity of human Sema3A of the sequence of SEQ ID NO: 600 in an in vitro mesangial cell migration assay with an EC50 of ≤10 nM, ≤5 nM, ≤2.5 nM, or ≤1 nM; v) inhibit the activity of human Sema3A of the sequence of SEQ ID NO: 600 in an in vitro growth cone collapse assay with an EC50 of ≤50 nM, ≤25 nM, ≤10 nM, or ≤5 nM; and/or vi) inhibit the activity of human Sema3A of the sequence of SEQ ID NO: 600 in an in vitro HUVEC repulsion assay with an EC50 of ≤1 nM, or ≤0.3 nM, ≤0.1 nM, ≤0.07 nM, ≤0.06 nM and/or vii) exhibiting an increased potency against cellular Sema3A, of the sequence of SEQ ID NO: 600, induced HUVEC repulsion. The present disclosure further provides isolated nucleic acid sequences encoding said antibodies or antigen-binding fragments thereof and vectors comprising same, isolated cells expressing said antibodies or antigen-binding fragments thereof, methods of producing said antibodies or antigen-binding fragments thereof and pharmaceutical compositions and kits comprising said antibodies or antigen-binding fragments thereof.

Antibodies according to the present disclosure can be used in the treatment of diseases associated with increased Sema3A levels or activity such as Alport syndrome, acute kidney injury (AKI) primary focal segmental glomerular sclerosis (FSGS), or chronic kidney disease (CKD).

BACKGROUND

Semaphorin 3A (Sema3A) is a secreted dimeric protein that acts as guidance protein. It forms a ternary complex with neuropilin-1 and different plexins which leads to the activation of different signaling pathways. It is a key regulator of cell migration, adhesion, cytoskeletal stabilization and apoptosis. Sema3A is expressed in podocyte in adult kidneys where it is induced after injury.

Excess of Sema3A interferes with the glomerular filtration barrier inducing ultrastructural changes of the filtration barrier leading to podocyte foot process effacement and albuminuria. Sema3A is also highly induced after AKI and exacerbates the injury by promoting tubular inflammation, tubular epithelial cell apoptosis and ultrastructural abnormalities of the filtration barrier. Genetic deficiency or pharmacological inhibition of Sema3A in rodents results in reduced renal damage in different animal models of kidney diseases.

Furthermore, Sema3A is expressed in retinal neurons and endothelium. It has been shown to increase vascular permeability, to promote retinal inflammation and cellular senescence and to inhibit retinal vascular regeneration in rodent models. Sema3A also plays a role in CNS disorders. Sema3A inhibition results in enhanced regeneration and/or preservation of injured axons, decreased apoptotic cell numbers and enhancement of angiogenesis, resulting in considerably better functional recovery.

WO 20141/23186 discloses an avian-mouse chimeric antibody (clone No. 4-2 strain-derived) and two humanized IgG1 variants thereof and suggests their suitability in the treatment of Alzheimer's disease.

WO 2017/074013 discloses anti-Sema3A IgG antibodies A08, C10 and F11 and suggests their suitability in the treatment of cancer.

Currently, no therapeutic option to inhibit Sema3A interaction with its receptors is available to treat patients with e.g. proteinuric kidney disease like Alport syndrome and it is presumed that monoclonal therapeutic Sema3A antibodies could be optimally suited for this. Thus, there exists a great need for novel therapeutic Sema3A antibodies useful for the treatment of diseases that are associated with elevated Sema3A levels or activity such as Alport syndrome, acute kidney injury (AKI) primary focal segmental glomerular sclerosis (FSGS), or chronic kidney disease (CKD) that has not been met so far.

OBJECTS

In view of the prior art, it is an object of the present disclosure to provide novel therapeutic Sema3A antibodies that overcome the shortcomings of Sema3A antibodies of the prior art. In particular it is an object of the present disclosure to provide novel Sema3A antibodies that are high affinity binders of human Sema3A that efficiently block Sema3A activity. Desirable Sema3A antibodies are cross-reactive to Sema3A of multiple species in order to allow for preclinical experiments. They are non-immunogenic in human therapy, i.e. they are human or humanized antibodies. Desirable Sema3A antibodies are selective to Sema3A; they do not bind to off-targets and in particular do not cross-react with other semaphorin protein family members.

Such novel Sema3A antibodies would offer major advances in the treatment of diseases associated with elevated Sema3A levels or activity such as Alport syndrome, acute kidney injury (AKI) primary focal segmental glomerular sclerosis (FSGS), or chronic kidney disease (CKD).

SUMMARY

The above-mentioned object and other objects are achieved by the teaching of the present disclosure. The present disclosure is based on the discovery of novel antibodies that have a specific affinity for Sema3A and can deliver a therapeutic benefit to a subject.

Thus, in a first aspect, the present disclosure relates to an isolated antibody or antigen-binding fragment thereof that that binds to human Sema3A, wherein said isolated antibody or antigen-binding fragment thereof i) binds to human Sema3A of the sequence of SEQ ID NO: 600 with a dissociation constant (KD)≤50 nM, ≤20 nM, ≤10 nM, ≤1 nM, or ≤0.1 nM; ii) cross-reacts with mouse, cynomolgus, rat, pig and/or dog Sema3A, particularly wherein said isolated antibody or antigen-binding fragment thereof binds to mouse, cynomolgus, rat, pig and/or dog Sema3A with a dissociation constant (KD)≤50 nM, ≤20 nM, ≤10 nM, ≤1 nM, or ≤0.1 nM; iii) binds to human Sema3A of the sequence of SEQ ID NO: 600 with a binding activity as measured by surface plasmon resonance (SPR) of ≥60%, ≥70%, ≥80%, or ≥90%; iv) inhibits the activity of human Sema3A of the sequence of SEQ ID NO: 600 in an in vitro mesangial cell migration assay with an EC50 of ≤10 nM, ≤5 nM, ≤2.5 nM, or ≤1 nM; v) inhibits the activity of human Sema3A of the sequence of SEQ ID NO: 600 in an in vitro growth cone collapse assay with an EC50 of ≤50 nM, ≤25 nM, ≤10 nM, or ≤5 nM; vi) inhibits the activity of human Sema3A of the sequence of SEQ ID NO: 600 in an in vitro HUVEC repulsion assay with an EC50 of ≤1 nM, or ≤0.3 nM, ≤0.1 nM, ≤0.07 nM, ≤0.06 nM and/or vii) exhibits an increased potency against cellular Sema3A, of the sequence of SEQ ID NO: 600, induced HUVEC repulsion.

The isolated antibody or antigen-binding fragment according to the present disclosure binds with high affinity to human Sema3A and inhibits its function. Thus, the isolated antibody or antigen-binding fragment according to the present disclosure may be used in the treatment of diseases associated with increased Sema3A levels or activity such as i) renal diseases, in particular acute and chronic kidney diseases, diabetic kidney diseases, Alport syndrome, acute and chronic renal failure, polycystic kidney disease (PCKD) and syndrome of inadequate ADH secretion (SIADH); ii) sequelae of renal insufficiency, in particular pulmonary edema, heart failure, uremia, anemia, electrolyte disturbances such as hyperkaliemia and hyponatremia and disturbances in bone and carbohydrate metabolism; iii) vascular hyperpermeability, diabetic retinopathy, deterioration of the blood retinal barrier, macular edema, particularly age related macular edema, non-proliferative age-related macular edema and non-proliferative diabetic macular edema; iv) diseases of the central or peripheral nervous system in particular neuropathic pain, spinal cord injury, multiple sclerosis, traumatic brain injury, brain edema and neurodegenerative diseases, particularly Alzheimer's disease, Parkinson's disease, Huntington's disease, amyotrophic lateral sclerosis, progressive supranuclear paralysis, black substance degeneration, Shy-Drager syndrome, olivopontocerebellar atrophy and spinocerebellar degeneration; v) cancer, in particular intestinal cancer, colorectal cancer, lung cancer, breast cancer, brain cancer, melanoma, renal cell cancer, leukemia, lymphoma, T-cell lymphoma, stomach cancer, pancreatic cancer, cervical cancer, endometrial cancer, ovarian cancer, esophageal cancer, liver cancer, squamous cell carcinoma of the head and neck, skin cancer, urinary tract cancer, prostate cancer, choriocarcinoma, pharyngeal cancer and larynx cancer.

The isolated antibody or antigen-binding fragment according to the present disclosure may further be used in the diagnosis of Sema3A-related disorders.

In a further aspect, the present disclosure relates to an isolated nucleic acid sequence that encodes the antibody or antigen-binding fragment according to the present disclosure.

In a further aspect, the present disclosure relates to a vector comprising a nucleic acid sequence according to the present disclosure.

In a further aspect, the present disclosure relates to an isolated cell expressing the antibody or antigen-binding fragment according to the present disclosure and/or comprising the nucleic acid according to the present disclosure or the vector according to the present disclosure.

In a further aspect, the present disclosure relates to a method of producing the isolated antibody or antigen-binding fragment according to the present disclosure comprising culturing of the cell according to the present disclosure and optionally purification of the antibody or antigen-binding fragment thereof.

In a further aspect, the present disclosure relates to a pharmaceutical composition comprising the isolated antibody or antigen-binding fragment according to the present disclosure or the antibody conjugate according to the present disclosure.

In a further aspect, the present disclosure relates to a kit comprising the isolated antibody or antigen-binding fragment according to the present disclosure or the conjugate according to the present disclosure and instructions for use.

DETAILED DESCRIPTION

The present disclosure may be understood more readily by reference to the following detailed description of the disclosure and the examples included therein.

Definitions

Unless defined otherwise, all technical and scientific terms used herein have the meaning commonly understood by one of ordinary skill in the art to which this disclosure belongs. The following references, however, can provide one of skill in the art to which this disclosure pertains with a general definition of many of the terms used in this disclosure, and can be referenced and used so long as such definitions are consistent with the meaning commonly understood in the art. Such references include, but are not limited to, Singleton et al., Dictionary of Microbiology and Molecular Biology (2nd ed. 1994); The Cambridge Dictionary of Science and Technology (Walker ed., 1988); Hale & Marham, The Harper Collins Dictionary of Biology (1991); Lackie et al., The Dictionary of Cell & Molecular Biology (3d ed. 1999); and Cellular and Molecular Immunology, Eds. Abbas, Lichtman and Pober, 2nd Edition, W.B. Saunders Company. Any additional technical resource available to the person of ordinary skill in the art providing definitions of terms used herein having the meaning commonly understood in the art can be consulted. For the purposes of the present disclosure, the following terms are further defined. Additional terms are defined elsewhere in the description. As used herein and in the appended claims, the singular forms "a," and "the" include plural reference unless the context clearly dictates otherwise. Thus, for example, reference to "a gene" is a reference to one or more genes and includes equivalents thereof known to those skilled in the art, and so forth.

In the context of the present disclosure, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of". In one embodiment the term "comprising" as used throughout the application and in particular within the claims may be replaced by the term "consisting of".

In this context, the term "about" or "approximately" means within 80% to 120%, alternatively within 90% to 110%, including within 95% to 105% of a given value or range.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Unless otherwise indicated, a particular polypeptide sequence also implicitly encompasses conservatively modified variants thereof.

As used herein "Sema3A" designates "semaphorin 3A", also known as "HH16", "SemD", "COLL1", "SEMA1", "SEMAD", "SEMAL", "coll-1", "Hsema-I", "SEMAIII", "Hsema-III", "collapsin 1", "semaphorin D", "semaphorin III", and "semaphorin L".

The terms "anti-Sema3A antibody" and "an antibody that binds to Sema3A" refer to an antibody that is capable of binding Sema3A with sufficient affinity such that the antibody is useful as a diagnostic and/or therapeutic agent in targeting Sema3A. In one embodiment, the extent of binding of an anti-Sema3A antibody to an unrelated, non-Sema3A protein is less than about 10%, less than about 5%, or less than about 2% of the binding of the antibody to Sema3A as measured, e.g., by standard ELISA procedure. In certain embodiments, an antibody that binds to Sema3A has a binding activity (EC50) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-Sema3A antibody binds to an epitope of Sema3A that is conserved among Sema3A from different species.

The term "antibody", as used herein, is intended to refer to immunoglobulin molecules. Antibodies may comprise four polypeptide chains, two heavy (H) chains (about 50-70 kDa) and two light (L) chains (about 25 kDa) which are typically inter-connected by disulfide bonds. In particular embodiments, the antibody is composed of two identical pairs of polypeptide chains. The amino-terminal portion of each chain includes a "variable" region of about 100 to 110 or more amino acids primarily responsible for antigen recognition. The heavy chain variable region is abbreviated herein as VH, the light chain variable region is abbreviated herein as VL. The carboxyl-terminal portion of each chain defines a constant region primarily responsible for effector function. The heavy chain constant region can comprise e.g. three domains CH1, CH2 and CH3. The light chain constant region is comprised of one domain (CL). The VH and VL regions can be further subdivided into regions of hypervariability, termed complementarity determining regions (CDR), interspersed with regions that are more conserved, termed framework regions (FR). Each VH and VL is typically composed of three CDRs and up to four FRs, arranged from amino-terminus to carboxy-terminus e.g., in the following order: FR1, CDR1, FR2, CDR2, FR3, CDR3, FR4.

As used herein, the term "Complementarity Determining Regions" (CDRs; e.g., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (Kabat et al., Sequences of Proteins of Immunological Interest, 5th Ed. Public Health Service, National Institutes of Health, Bethesda, MD. (1991)) and/or those residues from a "hypervariable loop" (Chothia and Lesk; J Mol Biol 196: 901-917 (1987)). In some instances, a complementarity determining region can include amino acids from both a CDR region defined according to Kabat and a hypervariable loop.

"Framework" or FR residues are those variable domain residues other than the hypervariable region residues.

The phrase "constant region" refers to the portion of the antibody molecule that confers effector functions.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. In particular embodiments, the antibody according to the present disclosure is an IgG antibody. Several of these may be further divided into subclasses or isotypes, e.g. IgG1, IgG2, IgG3, IgG4, IgA1 and IgA2. In particular embodiments, the antibody according to the present disclosure is an IgG1, an IgG2, an IgG3 or an IgG4 antibody, more particularly an IgG1 or an IgG4 antibody. Different isotypes may have different effector functions. Human light chains are classified as kappa (K) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

A "functional fragment" or "antigen-binding antibody fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hyper variable region(s) of an antibody, e.g., the CDR1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320).

Nonlimiting examples of "functional fragments" or "antigen-binding antibody fragments" include Fab, Fab', F(ab')2, Fv fragments, domain antibodies (dAb), complementarity determining region (CDR) fragments, single-chain antibodies (scFv), single chain antibody fragments, diabodies, triabodies, tetrabodies, minibodies, linear antibodies (Zapata et al., Protein Eng., 8 (10): 1057-1062 (1995)); chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity; and multispecific antibodies such as bi- and tri-specific antibodies formed from antibody fragments (C. A. K Borrebacck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag). An antibody other than a "bispecific" or "bifunctional" antibody is understood to have each of its binding sites identical. The F(ab')$_2$ or Fab may be engineered to minimize or completely remove the intermolecular disulfide interactions that occur between the $C_{H1}$ and $C_L$ domains. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two "Fv" fragments. An "Fv" fragment is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen.

"Single-chain Fv" or "sFv" or "scFv" antibody fragments comprise the VH and VL domains of antibody, wherein these domains are present in a single polypeptide chain. Preferably, the Fv polypeptide further comprises a polypeptide linker between the VH and VL domains that enables the Fv to form the desired structure for antigen binding. For a review of Fvs see Pluckthun in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab fragments differ from Fab' fragments by the addition of a few residues at the carboxyl terminus of the heavy chain CH1 domain including one or more cysteine residues from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteine residues between them.

The term "mutein" or "variant" can be used interchangeably and refers to an antibody or antigen-binding fragment that contains at least one amino acid substitution, deletion, or insertion in the variable region or the portion equivalent to the variable region, provided that the mutein or variant retains the desired binding affinity or biological activity. Variants of the antibodies or antigen-binding antibody fragments contemplated in the disclosure are molecules in which the binding activity of the antibody or antigen-binding antibody fragment is maintained.

A "chimeric antibody" or antigen-binding fragment thereof is defined herein as one, wherein the variable domains are derived from a non-human origin and some or all constant domains are derived from a human origin.

"Humanized antibodies" contain CDR regions derived from a non-human species, such as mouse, that have, for example, been engrafted, along with any necessary framework back-mutations, into human sequence-derived V regions. Thus, for the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. See, for example, U.S. Pat. Nos. 5,225,539; 5,585,089; 5,693,761; 5,693,762; 5,859,205, each herein incorporated by reference. In some instances, framework residues of the human immunoglobulin are replaced by corresponding non-human residues (see, for example, U.S. Pat. Nos. 5,585,089; 5,693,761; 5,693,762, each herein incorporated by reference). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-25 (1986); Riechmann et al., Nature 332:323-27 (1988); and Presta, Curr. Opin. Struct. Biol. 2:593-96 (1992), each herein incorporated by reference.

"Human antibodies" or "fully human antibodies" comprise human derived CDRs, i.e. CDRs of human origin. Fully human antibodies may comprise a low number of germline deviations compared with the closest human germline reference determined based on the IMGT database (http://www.imgt.org). For example, a fully human antibody according to the current disclosure may comprise up to 1, 2, 3, 4, 5, 6, 7, 8, 9 or 10 germline deviations in the CDRs compared with the closest human germline reference. Fully human antibodies can be developed from human derived B cells by cloning techniques in combination with a cell enrichment or immortalization step. The majority of fully human antibodies, however, are isolated either from immunized mice transgenic for the human IgG locus or from sophisticated combinatorial libraries by phage display (Brüggemann M., Osborn M. J., Ma B., Hayre J., Avis S., Lundstrom B. and Buelow R., Human Antibody Production in Transgenic Animals, Arch Immunol Ther Exp (Warsz.) 63 (2015), 101-108; Carter P. J., Potent antibody therapeutics by design, Nat Rev Immunol 6 (2006), 343-357; Frenzel A., Schirrmann T. and Hust M., Phage display-derived human antibodies in clinical development and therapy, MAbs 8 (2016), 1177-1194; Nelson A. L., Dhimolea E. and Reichert J. M., Development trends for human monoclonal antibody therapeutics, Nat Rev Drug Discov 9 (2010), 767-774.)).

Several techniques are available to generate fully human antibodies (cf. WO2008/112640 A3). Cambridge Antibody Technologies (CAT) and Dyax have obtained antibody cDNA sequences from peripheral B cells isolated from immunized humans and devised phage display libraries for the identification of human variable region sequences of a particular specificity. Briefly, the antibody variable region sequences are fused either with the Gene III or Gene VIII structure of the M13 bacteriophage. These antibody variable region sequences are expressed either as Fab or single chain Fv (scFv) structures at the tip of the phage carrying the respective sequences. Through rounds of a panning process using different levels of antigen binding conditions (stringencies), phages expressing Fab or scFv structures that are specific for the antigen of interest can be selected and isolated. The antibody variable region cDNA sequences of selected phages can then be elucidated using standard sequencing procedures. These sequences may then be used for the reconstruction of a full antibody having the desired isotype using established antibody engineering techniques. Antibodies constructed in accordance with this method are considered fully human antibodies (including the CDRs). In order to improve the immunoreactivity (antigen binding affinity and specificity) of the selected antibody, an in vitro maturation process can be introduced, including a combinatorial association of different heavy and light chains, deletion/addition/mutation at the CDR3 of the heavy and light chains (to mimic V-J, and V-D-J recombination), and random mutations (to mimic somatic hypermutation). An example of a "fully human" antibody generated by this method is the anti-tumor necrosis factor α antibody, Humira (adalimumab).

"Human Engineered™" antibodies generated by altering the parent sequence according to the methods set forth in Studnicka et al., U.S. Pat. No. 5,766,886.

An antibody of the disclosure may be derived from a recombinant antibody gene library. The development of technologies for making repertoires of recombinant human antibody genes, and the display of the encoded antibody fragments on the surface of filamentous bacteriophage, has provided a recombinant means for directly making and selecting human antibodies, which also can be applied to humanized, chimeric, murine or mutein antibodies. The antibodies produced by phage technology are produced as antigen binding fragments—usually Fv or Fab fragments—in bacteria and thus lack effector functions. Effector functions can be introduced by one of two strategies: The fragments can be engineered either into complete antibodies for expression in mammalian cells, or into bispecific antibody fragments with a second binding site capable of triggering an effector function. Typically, heavy chain VH-CH1 and light chain VL-CL of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. By several rounds of antigen binding and re-amplification, a procedure termed panning, Fab specific for the antigen are enriched and finally isolated.

A variety of procedures have been described for human antibodies deriving from phage-display libraries. Such libraries may be built on a single master framework, into which diverse in vivo-formed (i. e. human-derived) CDRs are allowed to recombine as described by Carlsson and Söderlind Exp. Rev. Mol. Diagn. 1 (1), 102-108 (2001), Söderlin et al., Nat. Biotech. 18, 852-856 (2000) and U.S. Pat. No. 6,989,250. Alternatively, such an antibody library may be based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254: 67; and U.S. Pat. No. 6,300,064. For a review of phage display screening (for example see Hoet R M et al, Nat Biotechnol 2005; 23 (3): 344-8), the well-established hybridoma technology (for example see Köhler and Milstein Nature. 1975 Aug. 7; 256 (5517): 495-7), or immunization of mice inter alia immunization of hMAb mice (e.g. VelocImmune Mouse®).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the term "monoclonal" indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. The term "monoclonal" is not to be construed as to require production of the antibody by any particular method. For example, the monoclonal antibodies to be used may be made by the hybridoma method first described by Kohler et al., Nature, 256:495 [1975, or may be made by recombinant DNA methods (see, e.g., U.S. Pat. No. 4,816,567). The "monoclonal antibodies" may also be recombinant, chimeric, humanized, human, Human Engineered™, or antibody fragments, for example.

An "isolated" antibody is one that has been identified and separated from a component of the cell that expressed it. Contaminant components of the cell are materials that would interfere with diagnostic or therapeutic uses of the antibody, and may include enzymes, hormones, and other proteinaceous or non-proteinaceous solutes.

An "isolated" nucleic acid is one that has been identified and separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

As used herein, an antibody "binds specifically to", is "specific to/for" or "specifically recognizes" an antigen of interest, e.g. Sema3A, is one that binds the antigen with sufficient affinity such that the antibody is useful as a therapeutic agent in targeting a cell or tissue expressing the antigen. The term "specifically recognizes" or "binds specifically to" or is "specific to/for" a particular polypeptide or an epitope on a particular polypeptide target as used herein can be exhibited, for example, by an antibody, or antigen-binding fragment thereof, having a monovalent $K_D$ for the antigen of less than about $10^{-4}$ M, alternatively less than about $10^{-5}$ M, alternatively less than about $10^{-6}$ M, alternatively less than about $10^{-7}$ M, alternatively less than about $10^{-8}$ M, alternatively less than about $10^{-9}$ M, alternatively less than about $10^{-10}$ M, alternatively less than about $10^{-11}$ M, alternatively less than about $10^{-12}$ M, or less.

An antibody "binds selectively to," is "selective to/for" or "selectively recognizes" an antigen if such antibody is able to discriminate between such antigen and one or more reference antigen(s). In particular, an antibody that "binds selectively to" an antigen does not significantly cross-react with proteins other than orthologs and variants (e.g. mutant forms, splice variants, or proteolytically truncated forms) of the aforementioned antigen target. In its most general form, "selective binding", "binds selectively to", is "selective to/for" or "selectively recognizes" is referring to the ability of the antibody to discriminate between the antigen of interest and an unrelated antigen, as determined, for example, in accordance with one of the following methods. Such methods comprise but are not limited to surface plasmon resonance (SPR), Western blots, ELISA-, RIA-, ECL-, IRMA-tests and peptide scans. For example, a standard ELISA assay can be carried out. The scoring may be carried out by standard color development (e.g. secondary antibody with horseradish peroxidase and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative is more than 5-fold, 10-fold, 50-fold, and preferably more than 100-fold. Typically, determination of binding selectivity is performed by using not a single reference antigen, but a set of about three to five unrelated antigens, such as milk powder, BSA, transferrin or the like.

"Binding affinity" or "affinity" refers to the strength of the total sum of non-covalent interactions between a single binding site of a molecule and its binding partner. Unless indicated otherwise, as used herein, "binding affinity" refers to intrinsic binding affinity which reflects a 1:1 interaction between members of a binding pair (e.g. an antibody and an antigen). The dissociation constant "$K_D$" is commonly used to describe the affinity between a molecule (such as an antibody) and its binding partner (such as an antigen) i.e. how tightly a ligand binds to a particular protein. Ligand-protein affinities are influenced by non-covalent intermolecular interactions between the two molecules. Affinity can be measured by common methods known in the art, including those described herein. In one embodiment, the "$K_D$" or "$K_D$ value" according to this disclosure is measured by using surface plasmon resonance assays using a Biacore T200 instrument (GE Healthcare Biacore, Inc.). Other suitable devices are BIACORE T100, BIACORE (R)-2000, BIACORe 4000, a BIACORE (R)-3000 (BIAcore, Inc., Piscataway, NJ), or ProteOn XPR36 instrument (Bio-Rad Laboratories, Inc.).

As used herein, the term "epitope" includes any protein determinant capable of specific binding to an immunoglobulin or T-cell receptor. Epitopic determinants usually consist of chemically active surface groupings of molecules such as amino acids or sugar side chains, or combinations thereof and usually have specific three-dimensional structural characteristics, as well as specific charge characteristics.

An "antibody that binds to the same epitope" as a reference antibody or "an antibody which competes for binding" to a reference antibody refers to an antibody that blocks binding of the reference antibody to its antigen in a competition assay by 10%, 20%, 30%, 40%, 50% or more, and conversely, the reference antibody blocks binding of the antibody to its antigen in a competition assay by 10%, 20%, 30%, 40%, 50% or more.

The term "maturated antibodies" or "maturated antigen-binding fragments" such as maturated Fab variants or "optimized" variants includes derivatives of an antibody or antibody fragment exhibiting stronger binding—i.e. binding with increased affinity—to a given antigen such as the extracellular domain of a target protein. Maturation is the process of identifying a small number of mutations within the six CDRs of an antibody or antibody fragment leading to this affinity increase. The maturation process is the combination of molecular biology methods for introduction of mutations into the antibody and screening for identifying the improved binders.

"Percent (%) sequence identity" with respect to a reference polynucleotide or polypeptide sequence, respectively, is defined as the percentage of nucleic acid or amino acid residues, respectively, in a candidate sequence that are identical with the nucleic acid or amino acid residues, respectively, in the reference polynucleotide or polypeptide sequence, respectively, after aligning the sequences and introducing gaps, if necessary, to achieve the maximum percent sequence identity. Conservative substitutions are not considered as part of the sequence identity. Preferred are un-gapped alignments. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

"Sequence homology" indicates the percentage of amino acids that either is identical or that represent conservative amino acid substitutions.

An "antagonistic" antibody or a "blocking" antibody is one which significantly inhibits (either partially or completely) a biological activity of the antigen it binds. In particular embodiments, the antibody or antigen-binding fragment according to the present disclosure is a Sema3A blocking antibody or antigen-binding fragment thereof.

The term "antibody conjugate" refers to an antibody conjugated to one or more molecules including drugs—in which case the antibody conjugate is referred to as "antibody-drug conjugate" ("ADC")—and high molecular weight molecules such as peptides or proteins.

The term "antibody-drug conjugate" or "ADC" refers to an antibody conjugated to one or more cytotoxic or cytostatic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate). Immunoconjugates have been used for the local delivery of cytotoxic agents, i.e., drugs that kill or inhibit the growth or proliferation of cells, in the treatment of cancer (e.g. Liu et al., Proc Natl. Acad. Sci. (1996), 93, 8618-8623)). Immunoconjugates allow for the targeted delivery of a drug moiety to a tumor, and intracellular accumulation therein, where systemic administration of unconjugated drugs may result in unacceptable levels of toxicity to normal cells and/or tissues. Toxins used in antibody-toxin conjugates include bacterial toxins such as diphtheria toxin, plant toxins such as ricin, small molecule toxins such as geldanamycin. The toxins may exert their cytotoxic effects by mechanisms including tubulin binding, DNA binding, or topoisomerase inhibition.

Amino acids may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell", "host cell line", and "host cell culture" are used interchangeably and refer to cells into which at least one exogenous nucleic acid has been introduced, including the progeny of such cells. Host cells include "transformants" and "transformed cells", "transfectants" and "transfected cells" and "transduced cells" which include the primary transformed/transfected/transduced cell and progeny derived therefrom without regard to the number of passages. Progeny may not be completely identical in nucleic acid content to a parent cell but may contain mutations. Mutant progeny that have the same function or biological activity as screened or selected for in the originally transformed cell are included herein.

As used herein, the phrase "therapeutically effective amount" is meant to refer to an amount of therapeutic or prophylactic antibody that would be appropriate to elicit the desired therapeutic or prophylactic effect or response, including alleviating some or all of such symptoms of disease or reducing the predisposition to the disease, when administered in accordance with the desired treatment regimen.

The term "pharmaceutical formulation"/"pharmaceutical composition" refers to a preparation which is in such form as to permit the biological activity of an active ingredient contained therein to be effective, and which contains no additional components which are unacceptably toxic to a subject to which the formulation would be administered.

Antibodies According to the Present Disclosure

In one aspect the present disclosure relates to an isolated antibody or antigen-binding fragment thereof binding to human Sema3A, wherein said isolated antibody or antigen-binding fragment thereof binds to human Sema3A of the sequence of SEQ ID NO: 600 with a dissociation constant (KD)≤50 nM, ≤20 nM, ≤10 nM, ≤1 nM, or ≤0.1 nM. In particular embodiments, the isolated antibody or antigen-binding fragment thereof binds to the His-tagged human Sema3A domain of SEQ ID NO: 582 with a dissociation constant (KD)≤50 nM, ≤20 nM, ≤10 nM, ≤1 nM, or ≤0.1 nM.

In another aspect the present disclosure relates to an isolated antibody or antigen-binding fragment thereof binding to human Sema3A, wherein said isolated antibody or antigen-binding fragment thereof cross-reacts with mouse, cynomolgus, rat, pig and/or dog Sema3A, particularly wherein said isolated antibody or antigen-binding fragment thereof binds to mouse, cynomolgus, rat, pig and/or dog Sema3A with a dissociation constant (KD)≤50 nM, ≤20 nM, ≤10 nM, ≤1 nM, or ≤0.1 nM.

In particular such embodiments, said affinities are to mouse Sema3A of SEQ ID NO: 601, to cynomolgus Sema3A of SEQ ID NO: 602, to rat Sema3A of SEQ ID NO: 603, to pig Sema3A of SEQ ID NO: 604 and to dog Sema3A of SEQ ID NO: 605. In particular embodiments, said affinities are to His-tagged mouse Sema3A domain of SEQ ID NO: 583, to His-tagged cynomolgus Sema3A domain of SEQ ID NO: 586, to His-tagged rat Sema3A domain of SEQ ID NO: 584, to His-tagged pig Sema3A domain of SEQ ID NO: 587 and to His-tagged dog Sema3A domain of SEQ ID NO: 585.

In another aspect the present disclosure relates to an isolated antibody or antigen-binding fragment thereof binding to human Sema3A, wherein said isolated antibody or antigen-binding fragment thereof binds to human Sema3A with a binding activity as measured by surface plasmon resonance (SPR) of ≥60%, ≥70%, ≥80%, or ≥90%. In particular embodiments, the isolated antibody or antigen-binding fragment thereof bids to human Sema3A of the sequence of SEQ ID NO: 600 with a binding activity as measured by surface plasmin resonance (SPR) of ≥60%, ≥70%, ≥80%, or ≥90%. In particular embodiments, the isolated antibody or antigen-binding fragment thereof bids to His-tagged human Sema3A domain of the sequence of SEQ ID NO: 582 with a binding activity as measured by surface plasmin resonance (SPR) of ≥60%, ≥70%, ≥80%, or ≥90%.

In another aspect the present disclosure relates to an isolated antibody or antigen-binding fragment thereof binding to human Sema3A, wherein said isolated antibody or antigen-binding fragment thereof inhibits the activity of human Sema3A of the sequence of SEQ ID NO: 600 in an in vitro mesangial cell migration assay with an EC50 of ≤10 nM, ≤5 nM, ≤2.5 nM, or ≤1 nM.

In particular, the isolated antibody or antigen-binding fragment according to the present disclosure inhibits the activity of human Sema3A of the sequence of SEQ ID NO: 600 in an in vitro scratch assay using human primary mesangial cells and described in more detail in Example 9.

In another aspect the present disclosure relates to an isolated antibody or antigen-binding fragment thereof binding to human Sema3A, wherein said isolated antibody or antigen-binding fragment thereof inhibits the activity of human Sema3A of the sequence of SEQ ID NO: 600 in an in vitro growth cone collapse assay with an EC50 of ≤50 nM, ≤25 nM, ≤10 nM, or ≤5 nM.

In particular, the isolated antibody or antigen-binding fragment according to the present disclosure inhibits Sema3A-induced cytoskeletal collapse in an in vitro growth cone collapse assay using mouse dorsal root ganglion (DRG) neurons as described in more detail in Example 10. The in vitro growth cone assay described in Example 10 is a modified version of the growth cone assay described in Mikule et al. (PMID: 12077190).

In another aspect the present disclosure relates to an isolated antibody or antigen-binding fragment thereof binding to human Sema3A, wherein said isolated antibody or antigen-binding fragment thereof inhibits the activity of human Sema3A of the sequence of SEQ ID NO: 600 in an in vitro HUVEC repulsion assay with an EC50 of ≤1 nM, or ≤0.3 nM, ≤0.1 nM, ≤0.07 nM, ≤0.06 nM.

In particular, the isolated antibody or antigen-binding fragment according to the present disclosure inhibits Sema3A induced cell repulsion in an in vitro repulsion assay using Sema3A, of the sequence of SEQ ID NO: 600, expressing HEK293 cells seeded on a confluent monolayer of human umbilical vein endothelial cells (HUVEC) as described in Example 11.

In a further aspect, the present disclosure relates to an isolated antibody or antigen-binding fragment thereof binding to Sema3A, of the sequence of SEQ ID NO: 600, wherein said isolated antibody or antigen-binding fragment thereof exhibits an improved potency in HUVEC repulsion assay; i) wherein said isolated antibody or antigen-binding fragment thereof exhibits an improved potency in HUVEC repulsion assay in comparison to TPP-17755 with SEQ IDs 81, 85, 97, 98, or to TPP-11489 with SEQ IDs 1, 5, 17, 18, or to TPP-30788 with SEQ IDs 800, 804, 810, 811, or to TPP-30789 with SEQ IDs 814, 818, 824, 825, or to TPP-30790 with SEQ IDs 828, 832, 838, 839, or to TPP-30791 with SEQ IDs 842, 846, 852, 853; ii) wherein said isolated antibody or antigen-binding fragment thereof exhibits preferably a >400-fold, preferably a >50-fold, preferably >5-fold, preferably >2-fold increased potency against cellular Sema3A induced HUVEC repulsion based on the EC-50 values, in comparison to TPP-17755 with SEQ IDs 81, 85, 97, 98, or to TPP-11489 with SEQ IDs 1, 5, 17, 18, or to TPP-30788 with SEQ IDs 800, 804, 810, 811, or to TPP-30789 with SEQ IDs 814, 818, 824, 825, or to TPP-30790 with SEQ IDs 828, 832, 838, 839, or to TPP-30791 with SEQ IDs 842, 846, 852, 853; iii) wherein said isolated antibody or antigen-binding fragment thereof exhibits at least a 30% increased percent inhibition, preferably at least 50% increased percent inhibition of Sema3A in comparison to TPP-17755, to TPP-11489, to TPP-30788, to TPP-30789, TPP-30790, or to TPP-30791, with aforementioned sequences; iv) wherein said isolated antibody or antigen-binding fragment thereof has a two-digit picomolar activity against human Sema3A in vitro HUVEC repulsion assay, while prior art antibody potencies of TPP-17755, TPP-11489, TPP-30788, TPP-30789, TPP-30790, or TPP-30791, with aforementioned sequences, are in the three-digit picomolar or even nanomolar range; v) wherein said isolated antibody or antigen-binding fragment thereof inhibits the activity of human Sema3A in an in vitro HUVEC repulsion assay with an EC50 of ≤1 nM, or ≤0.3 nM, ≤0.1 nM, ≤0.07 nM, ≤0.06 nM, as described in Example 11.

The isolated antibody or antigen-binding fragment of the present disclosure show an improved potency in HUVEC repulsion assay compared to TPP-30788-TPP-30791 (BI clone I to IV), which might be due to a binding to a different epitope of human Sema3A.

In another aspect, the present disclosure relates to an isolated antibody or antigen-binding fragment thereof binding to Sema3A, wherein said isolated antibody or antigen-binding fragment thereof inhibits the activity of Sema3A in vivo, since the antibodies according to the present disclosure reduce Sema3A-induced urinary Albumin excretion. Thus in a further aspect, the present disclosure relates to an isolated antibody or antigen-binding fragment thereof binding to Sema3A, wherein said isolated antibody or antigen-binding fragment thereof exhibits an improved inhibitory activity of Sema3A in vivo, i) wherein said the antibodies exhibit an increased reduction of Sema3A-induced urinary Albumin excretion compared to TPP-30788 (BI clone I); ii) wherein said the antibodies exhibit an increased reduction of Sema3A-induced urinary Albumin excretion compared to TPP-17755 (Samsung); iii) wherein said the antibodies exhibit an increased reduction of Sema3A-induced urinary Albumin excretion compared to TPP-11489 (Chiome) as described in Example 12.

The isolated antibody or antigen-binding fragment of the present disclosure show an improved efficacy in an in vivo model for induced urinary Albumin excretion compared to TPP-30788-TPP-30791 (BI clone I to IV), which might be due to a binding to a different epitope of human Sema3A.

Thus, in a further aspect, the present disclosure relates to an isolated antibody or antigen-binding fragment thereof that binds to human Sema3A, wherein said isolated antibody or antigen-binding fragment thereof i) exhibits an increased stability (e.g. increased stress-stability when diluted in PBS to 25 mg/ml and incubated at 700 rpm and 40° C. for two weeks) compared to TPP-30788 (BI clone I); ii) wherein the increased stability exhibits an increased amount of monomeric anti-Sema3A antibody compared to TPP-30788 (BI clone I) measured by SEC; iii) wherein the increased stability exhibits a decreased percentage of the LC and HC of the anti-Sema3A antibody compared to TPP-30788 (BI clone I) measured by cGE, proving a reduced rate of degradation which is measured by the presence of remaining LC and HC, iv) wherein the increased stability exhibits that the amount of monomeric anti-Sema3A antibody is maintained, e.g. Δ % monomer=1 after the incubation at 40° C., 700 rpm for two weeks; v) wherein the increased stability exhibits that the amount of LC and HC of the anti-Sema3A antibody is maintained e.g. Δ % LC+HC<1 after the incubation at 40° C., 700 rpm for two weeks.

Thus, in a further aspect, the present disclosure relates to TPP-23298, that binds to human Sema3A, wherein said isolated antibody or antigen-binding fragment thereof i) exhibits an increased stability (e.g. increased stress-stability when diluted in PBS to 25 mg/ml and incubated at 700 rpm and 40° C. for two weeks) compared to TPP-30788 (BI clone I); ii) wherein the increased stability exhibits an increased amount of monomeric anti-Sema3A antibody compared to TPP-30788 (BI clone I) measured by SEC; iii) wherein the increased stability exhibits a decreased percentage of the LC and HC of the anti-Sema3A antibody compared to TPP-30788 (BI clone I) measured by cGE, proving a reduced rate of degradation which is measured by the presence of remaining LC and HC, iv) wherein the increased stability exhibits that the amount of monomeric anti-Sema3A antibody is maintained, e.g. Δ % monomer=1 after the incubation at 40° C., 700 rpm for two weeks; v) wherein the increased stability exhibits that the amount of LC and HC of the anti-Sema3A antibody is maintained e.g. Δ % LC+HC <1 after the incubation at 40° C., 700 rpm for two weeks.

Thus, in a further aspect, the present disclosure relates to an isolated antibody or antigen-binding fragment thereof that binds to human Sema3A, wherein said isolated antibody or antigen-binding fragment thereof i) exhibits an increased solubility; ii) wherein the increased solubility is measured in mg/ml after concentration at 90% recovery; iii) wherein the solubility is increased compared to TPP-30788 (BI clone I); iv) wherein the solubility is increased ≤1 fold, ≤1.5 fold, ≤2 fold compared to TPP-30788 (BI clone I); v) wherein the increased solubility exhibits that the percentage of monomeric anti-Sema3A antibody is not increased after concentration e.g. Δ monomer <1 measured by SEC.

Thus, in a further aspect, the present disclosure relates to TPP-23298, that binds to human Sema3A, wherein said isolated antibody or antigen-binding fragment thereof i) exhibits an increased solubility; ii) wherein the increased solubility is measured in mg/ml after concentration at 90% recovery; iii) wherein the solubility is increased compared to TPP-30788 (BI clone I); iv) wherein the solubility is increased ≤1 fold, ≤1.5 fold, ≤2 fold compared to TPP- 30788 (BI clone I); v) wherein the increased solubility exhibits that the percentage of monomeric anti-Sema3A antibody is not increased after concentration e.g. Δ % monomer<1 measured by SEC.

Thus, in a further aspect, the present disclosure relates to an isolated antibody or antigen-binding fragment thereof that binds to human Sema3A, wherein said isolated antibody or antigen-binding fragment thereof i) exhibits an increased viscosity compared to water or PBS; ii) exhibits a reduced viscosity in PBS compared to TPP-30788 (BI clone I); iii) wherein the viscosity is measured by a Viscosizer and exhibits a cP value of 5.1 (150 mg/ml).

Thus, in a further aspect, the present disclosure relates to TPP-23298, that binds to human Sema3A, wherein said isolated antibody or antigen-binding fragment thereof i) exhibits an increased viscosity compared to water or PBS; ii) exhibits a reduced viscosity in PBS compared to TPP-30788 (BI clone I); iii) wherein the viscosity is measured by a Viscosizer and exhibits a cP value of 5.1 (150 mg/ml).

In particular the isolated antibody or antigen-binding fragment according to the present disclosure shows a much higher solubility and stability, is more resistant to heat stress and is less viscous in PBS buffer than TPP-30788 as described in Example 17.

In particular TPP-23298 shows a much higher solubility and stability, is more resistant to heat stress and is less viscous in PBS buffer than TPP-30788 as described in Example 17.

In another aspect the present disclosure relates to an isolated antibody or antigen-binding fragment thereof binding to human Sema3A, which can be produced with high titers in mammalian cells; i) wherein high titer is ≤200 mg/L as described in Example 16.

In another aspect the present disclosure relates to an isolated antibody or antigen-binding fragment thereof binding to human Sema3A, wherein the antibody exhibits a higher binding selectivity to active Sema3A (TPP-13211) over cleaved Sema3A TPP-19068; i) wherein the antibody exhibits a higher binding selectivity to active Sema3A (TPP-13211) compared to the binding selectivity of TPP-30788-TPP-30791 to active Sema3A, as described in Example 8.

In another aspect the present disclosure relates to TPP-23298 binding to human Sema3A, wherein the antibody exhibits a higher binding selectivity to active Sema3A (TPP-13211) over cleaved Sema3A TPP-19068; i) wherein the antibody exhibits a higher binding selectivity to active Sema3A (TPP-13211) compared to the binding selectivity of TPP-30788-TPP-30791 to active Sema3A, as described in Example 8.

In another aspect the present disclosure relates to an isolated antibody or antigen-binding fragment thereof binding to human Sema3A, wherein the antibody binds a different epitope on Sema3A compared to TPP-30788; i) wherein the epitope binding is measured in SPR assay, as described in Example 5a. All antibodies binding the same epitope and competing with the binding of the isolated antibody or antigen-binding fragment according to the present disclosure are comprised by the present disclosure.

In another aspect the present disclosure relates to TPP-23298 binding to human Sema3A, wherein the antibody binds a different epitope on Sema3A compared to TPP-30788; i) wherein the epitope binding is measured in SPR assay, as described in Example 5a. All antibodies binding the same epitope and competing with the binding of the isolated antibody or antigen-binding fragment according to the present disclosure are comprised by the present disclosure.

In another aspect the present disclosure relates to an isolated antibody or antigen-binding fragment thereof that competes with the isolated antibody or antigen-binding fragment according to any one of the preceding claims for binding to Sema3A and wherein the isolated antibody or antigen-binding fragment does not compete with the binding of an antibody with the SEQ IDs NO 800, NO 804, NO 810 or NO 811 to Sema3A.

The isolated antibody or antigen-binding fragment according to the present disclosure may exhibit any combination of the above described characteristics.

The isolated antibody or antigen-binding fragment according to the present disclosure is a Sema3A blocking antibody or antigen-binding fragment thereof. In particular embodiments, the antibody binds specifically and more particularly selectively to the Sema3A domain of Semaphorin3A and interferes with the interaction of its receptor neuropilin-1.

In particular embodiments, the isolated antibody or antigen-binding fragment thereof according to the present disclosure cross-reacts with mouse, cynomolgus, rat, pig and/or dog Sema3A, particularly having an affinity to mouse, cynomolgus, rat, pig and/or dog Sema3A that is less than 100-fold, particularly less than 50-fold, more particularly less than 25-fold, even more particularly less than 10-fold and most particularly less than 5-fold different to that to human Sema3A.

In particular embodiments, the isolated antibody or antigen-binding fragment thereof according to the present disclosure does not significantly cross-react with human Sema3B, Sema3C, Sema3D, Sema3E, Sema3F and/or Sema3G. In particular, the isolated antibody or antigen-binding fragment thereof does not significantly cross-react with human Sema3G.

In particular embodiments, the isolated antibody or antigen-binding fragment thereof according to the present disclosure inhibits Sema3A-induced albuminuria and/or proteinuria.

In particular embodiments, the isolated antibody or antigen-binding fragment thereof according to the present disclosure inhibits Sema3A-induced fibrosis.

In particular embodiments, the isolated antibody or antigen-binding fragment according to the present disclosure comprises a heavy chain variable domain that is at least 90%, at least 95%, at least 98%, at least 99%, or 100% identical to SEQ ID NO: 141, and a light chain variable domain that is at least 90%, at least 95%, at least 98%, at least 99%, or 100% identical to SEQ ID NO: 145.

In particular other embodiments, the isolated antibody or antigen-binding fragment according to the present disclosure comprises a heavy chain variable domain that is at least 90%, at least 95%, at least 98%, at least 99%, or 100% identical to SEQ ID NO: 61, and a light chain variable domain that is at least 90%, at least 95%, at least 98%, at least 99%, or 100% identical to SEQ ID NO: 65.

In particular embodiments, the isolated antibody or antigen-binding fragment according to the present disclosure comprises a heavy chain antigen-binding region that comprises an H-CDR3 comprising the sequence RDDYTSRDAFDX (SEQ ID NO: 594), wherein X is selected from the group consisting of Y and V. Particularly, X is Y.

In particular embodiments, the isolated antibody or antigen-binding fragment according to the present disclosure comprises a light chain antigen-binding region that comprises an L-CDR3 comprising the sequence $X_1AWDDSLNX_2X_3X_4V$ (SEQ ID NO: 598), wherein $X_1$ is selected from the group consisting of A and H, wherein $X_2$ is selected from the group consisting of V, D, and G, in particular wherein $X_2$ is selected from the group consisting of V and D, wherein $X_3$ is selected from the group consisting of I and Y, and wherein $X_4$ is selected from the group consisting of P and V.

In particular embodiments, the isolated antibody or antigen-binding fragment according to the present disclosure comprises a heavy chain antigen-binding region that comprises an H-CDR3 as defined above and a light chain antigen-binding region that comprises an L-CDR3 as defined above.

In particular embodiments, the isolated antibody or antigen-binding fragment according to the present disclosure comprises a heavy chain antigen-binding region that comprises an H-CDR3 comprising the sequence SGYSSSWFDPDFDY (SEQ ID NO: 64).

In particular embodiments, the isolated antibody or antigen-binding fragment according to the present disclosure comprises a light chain antigen-binding region that comprises an L-CDR3 comprising the sequence $X_1$SY$X_2$G$X_3$NPYVV (SEQ ID NO: 599), wherein $X_1$ is selected from the group consisting of S and Q; wherein $X_2$ is selected from the group consisting of E and A; and wherein $X_3$ is selected from the group consisting of P, I, and S. In particular, $X_3$ is selected from the group consisting of P and I.

In particular embodiments, the isolated antibody or antigen-binding fragment according to the present disclosure comprises a heavy chain antigen-binding region that comprises an H-CDR3 as defined above and a light chain antigen-binding region that comprises an L-CDR3 as defined above.

In particular embodiments, the isolated antibody or antigen-binding fragment according to the present disclosure comprises a heavy chain antigen-binding region that comprises an H-CDR1 comprising the sequence SY$X_1$M$X_2$ (SEQ ID NO: 588), wherein $X_1$ is selected from G and A and wherein $X_2$ is selected from H, S and L. Particularly, the heavy chain antigen-binding region comprises an H-CDR1 comprising the sequence SYAMX (SEQ ID NO: 589), wherein X is selected from S and L.

In particular embodiments, the isolated antibody or antigen-binding fragment according to the present disclosure comprises a heavy chain antigen-binding region that comprises an H-CDR2 comprising the sequence AIG$X_1$GGDTYYADSV$X_2$G (SEQ ID NO: 590), wherein $X_1$ is selected from T and Y, and wherein $X_2$ is selected from K and M. Particularly, the heavy chain antigen-binding region comprises an H-CDR2 comprising the sequence AIGXGGDTYYADSVKG (SEQ ID NO: 591), wherein X is selected from T and Y.

In particular embodiments, the isolated antibody or antigen-binding fragment according to the present disclosure comprises a heavy chain antigen-binding region that comprises an H-CDR3 comprising the sequence RDDYTSRDAFDX (SEQ ID NO: 594), wherein X is selected from the group consisting of Y and V. Particularly, X is Y.

In particular embodiments, the isolated antibody or antigen-binding fragment according to the present disclosure comprises a heavy chain antigen-binding region that comprises an H-CDR1, an H-CDR2 and an H-CDR3 as defined above.

In particular embodiments, the isolated antibody or antigen-binding fragment according to the present disclosure comprises a light chain antigen-binding region that comprises an L-CDR1 comprising the sequence SGSSSNIGSNTVN (SEQ ID NO: 46).

In particular embodiments, the isolated antibody or antigen-binding fragment according to the present disclosure comprises a light chain antigen-binding region that comprises an L-CDR2 comprising the sequence YDDLXPS (SEQ ID NO: 596), wherein X is selected from L and R. Particularly, the light chain antigen-binding region comprises an L-CDR2 comprising the sequence YDDLRPS (SEQ ID NO: 127).

In particular embodiments, the isolated antibody or antigen-binding fragment according to the present disclosure comprises a light chain antigen-binding region that comprises an L-CDR3 comprising the sequence $X_1$AWDDSLN$X_2$$X_3$$X_4$V (SEQ ID NO: 598), wherein $X_1$ is selected from the group consisting of A and H, wherein $X_2$ is selected from the group consisting of V, D, and G, in particular wherein $X_2$ is selected from the group consisting of V and D, wherein $X_3$ is selected from the group consisting of I and Y, and wherein $X_4$ is selected from the group consisting of P and V.

In particular embodiments, the isolated antibody or antigen-binding fragment according to the present disclosure comprises a light chain antigen-binding region that comprises an L-CDR1, and L-CDR2 and an L-CDR3 as defined above.

In particular embodiments, the isolated antibody or antigen-binding fragment according to the present disclosure comprises a heavy chain antigen-binding region that comprises an H-CDR1, an H-CDR2 and an H-CDR3 as defined above and a light chain antigen-binding region that comprises an L-CDR1, and L-CDR2 and an L-CDR3 as defined above.

In particular such embodiments, the amino acid residue directly adjacent to the H-CDR1 at its 5' end (corresponding to residue 30 of reference VH domain of SEQ ID NO: 121) is S or Y.

In particular other embodiments, the isolated antibody or antigen-binding fragment according to the present disclosure comprises a heavy chain antigen-binding region that comprises an H-CDR1 comprising the sequence SYEMN (SEQ ID NO: 62).

In particular embodiments, the isolated antibody or antigen-binding fragment according to the present disclosure comprises a heavy chain antigen-binding region that comprises an H-CDR2 comprising the sequence GISWNSG$X_1$I$X_2$YADSVKG (SEQ ID NO: 592), wherein $X_1$ is selected from W and S and $X_2$ is selected from G and D. Particularly, the heavy chain antigen-binding region comprises an H-CDR2 comprising the sequence GISWNSGWIXYADSVKG (SEQ ID NO: 593), wherein X is selected from G and D.

In particular embodiments, the isolated antibody or antigen-binding fragment according to the present disclosure comprises a heavy chain antigen-binding region that comprises an H-CDR3 comprising the sequence SGYSSSWFDPDFDY (SEQ ID NO: 64).

In particular embodiments, the isolated antibody or antigen-binding fragment according to the present disclosure comprises a heavy chain antigen-binding region that comprises an H-CDR1, an H-CDR2 and an H-CDR3 as defined above.

In particular embodiments, the isolated antibody or antigen-binding fragment according to the present disclosure comprises a light chain antigen-binding region that comprises an L-CDR1 comprising the sequence TGSSSXI-GAGYDVH (SEQ ID NO: 595), wherein X is selected from N and D.

In particular embodiments, the isolated antibody or antigen-binding fragment according to the present disclosure comprises a light chain antigen-binding region that comprises an L-CDR2 comprising the sequence GXSNRPS (SEQ ID NO: 597), wherein X is selected from N and A.

In particular embodiments, the isolated antibody or antigen-binding fragment according to the present disclosure comprises a light chain antigen-binding region that comprises an L-CDR3 comprising the sequence $X_1SYX_2GX_3NPYVV$ (SEQ ID NO: 599), wherein $X_1$ is selected from the group consisting of S and Q, wherein $X_2$ is selected from the group consisting of E and A, and wherein $X_3$ is selected from the group consisting of P, I, and S. Particularly, $X_3$ is selected from the group consisting of P and I.

In particular embodiments, the isolated antibody or antigen-binding fragment according to the present disclosure comprises a light chain antigen-binding region that comprises an L-CDR1, and L-CDR2 and an L-CDR3 as defined above.

In particular embodiments, the isolated antibody or antigen-binding fragment according to the present disclosure comprises a heavy chain antigen-binding region that comprises an H-CDR1, an H-CDR2 and an H-CDR3 as defined above and a light chain antigen-binding region that comprises an L-CDR1, and L-CDR2 and an L-CDR3 as defined above.

In particular such embodiments, the three amino acid residues directly adjacent to the H-CDR1 at its 5' end (corresponding to residues 28 to 30 of reference VH domain of SEQ ID NO: 101) are $X_1FX_2$, wherein $X_1$ is selected form T and D and $X_2$ is selected from S and D.

In particular embodiments, the isolated antibody or antigen-binding fragment according to the present disclosure comprises:
  i) a heavy chain antigen-binding region that comprises an H-CDR3 comprising SEQ ID NO: 44 and a light chain antigen-binding region that comprises an L-CDR3 comprising SEQ ID NO: 48; or
  ii) a heavy chain antigen-binding region that comprises an H-CDR3 comprising SEQ ID NO: 64 and a light chain antigen-binding region that comprises an L-CDR3 comprising SEQ ID NO: 68; or.
  iii) a heavy chain antigen-binding region that comprises an H-CDR3 comprising SEQ ID NO: 104 and a light chain antigen-binding region that comprises an L-CDR3 comprising SEQ ID NO: 108; or
  iv) a heavy chain antigen-binding region that comprises an H-CDR3 comprising SEQ ID NO: 124 and a light chain antigen-binding region that comprises an L-CDR3 comprising SEQ ID NO: 128; or
  v) a heavy chain antigen-binding region that comprises an H-CDR3 comprising SEQ ID NO: 144 and a light chain antigen-binding region that comprises an L-CDR3 comprising SEQ ID NO: 148; or
  vi) a heavy chain antigen-binding region that comprises an H-CDR3 comprising SEQ ID NO: 164 and a light chain antigen-binding region that comprises an L-CDR3 comprising SEQ ID NO: 168; or
  vii) a heavy chain antigen-binding region that comprises an H-CDR3 comprising SEQ ID NO: 184 and a light chain antigen-binding region that comprises an L-CDR3 comprising SEQ ID NO: 188; or
  viii) a heavy chain antigen-binding region that comprises an H-CDR3 comprising SEQ ID NO: 204 and a light chain antigen-binding region that comprises an L-CDR3 comprising SEQ ID NO: 208; or
  ix) a heavy chain antigen-binding region that comprises an H-CDR3 comprising SEQ ID NO: 224 and a light chain antigen-binding region that comprises an L-CDR3 comprising SEQ ID NO: 228; or
  x) a heavy chain antigen-binding region that comprises an H-CDR3 comprising SEQ ID NO: 244 and a light chain antigen-binding region that comprises an L-CDR3 comprising SEQ ID NO: 248; or
  xi) a heavy chain antigen-binding region that comprises an H-CDR3 comprising SEQ ID NO: 264 and a light chain antigen-binding region that comprises an L-CDR3 comprising SEQ ID NO: 268; or
  xii) a heavy chain antigen-binding region that comprises an H-CDR3 comprising SEQ ID NO: 284 and a light chain antigen-binding region that comprises an L-CDR3 comprising SEQ ID NO: 288; or
  xiii) a heavy chain antigen-binding region that comprises an H-CDR3 comprising SEQ ID NO: 304 and a light chain antigen-binding region that comprises an L-CDR3 comprising SEQ ID NO: 308; or
  xiv) a heavy chain antigen-binding region that comprises an H-CDR3 comprising SEQ ID NO: 324 and a light chain antigen-binding region that comprises an L-CDR3 comprising SEQ ID NO: 328; or
  xv) a heavy chain antigen-binding region that comprises an H-CDR3 comprising SEQ ID NO: 344 and a light chain antigen-binding region that comprises an L-CDR3 comprising SEQ ID NO: 348; or
  xvi) a heavy chain antigen-binding region that comprises an H-CDR3 comprising SEQ ID NO: 364 and a light chain antigen-binding region that comprises an L-CDR3 comprising SEQ ID NO: 368; or
  xvii) a heavy chain antigen-binding region that comprises an H-CDR3 comprising SEQ ID NO: 384 and a light chain antigen-binding region that comprises an L-CDR3 comprising SEQ ID NO: 388; or
  xviii) a heavy chain antigen-binding region that comprises an H-CDR3 comprising SEQ ID NO: 404 and a light chain antigen-binding region that comprises an L-CDR3 comprising SEQ ID NO: 408; or
  xix) a heavy chain antigen-binding region that comprises an H-CDR3 comprising SEQ ID NO: 424 and a light chain antigen-binding region that comprises an L-CDR3 comprising SEQ ID NO: 428; or
  xx) a heavy chain antigen-binding region that comprises an H-CDR3 comprising SEQ ID NO: 444 and a light chain antigen-binding region that comprises an L-CDR3 comprising SEQ ID NO: 448; or
  xxi) a heavy chain antigen-binding region that comprises an H-CDR3 comprising SEQ ID NO: 464 and a light chain antigen-binding region that comprises an L-CDR3 comprising SEQ ID NO: 468; or
  xxii) a heavy chain antigen-binding region that comprises an H-CDR3 comprising SEQ ID NO: 484 and a light chain antigen-binding region that comprises an L-CDR3 comprising SEQ ID NO: 488; or
  xxiii) a heavy chain antigen-binding region that comprises an H-CDR3 comprising SEQ ID NO: 504 and a light chain antigen-binding region that comprises an L-CDR3 comprising SEQ ID NO: 508; or
  xxiv) a heavy chain antigen-binding region that comprises an H-CDR3 comprising SEQ ID NO: 524 and a light chain antigen-binding region that comprises an L-CDR3 comprising SEQ ID NO: 528; or xxv) a heavy chain antigen-binding region that comprises an H-CDR3 comprising SEQ ID NO: 544 and a light chain antigen-binding region that comprises an L-CDR3 comprising SEQ ID NO: 548; or xxvi) a heavy chain antigen-binding region that comprises an H-CDR3 comprising SEQ ID NO: 564 and a light chain antigen-binding region that comprises an L-CDR3 comprising SEQ ID NO: 568.

In particular embodiments, the isolated antibody or antigen-binding fragment according to the present disclosure comprises a heavy chain antigen-binding region that comprises an H-CDR1 comprising any one of SEQ ID NOs: 42, 62, 102, 122, 142, 162, 182, 202, 222, 242, 262, 282, 302, 322, 342, 362, 382, 402, 422, 442, 462, 482, 502, 522, 542, and 562.

In particular embodiments, the isolated antibody or antigen-binding fragment according to the present disclosure comprises a heavy chain antigen-binding region that comprises an H-CDR2 comprising any one of SEQ ID NOs: 43, 63, 103, 123, 143, 163, 183, 203, 223, 243, 263, 283, 303, 323, 343, 363, 383, 403, 423, 443, 463, 483, 503, 523, 543, and 563.

In particular embodiments, the isolated antibody or antigen-binding fragment according to the present disclosure comprises a light chain antigen-binding region that comprises an L-CDR1 comprising any one of SEQ ID NOs: 46, 66, 106, 126, 146, 166, 186, 206, 226, 246, 266, 286, 306, 326, 346, 366, 386, 406, 426, 446, 466, 486, 506, 526, 546, and 566.

In particular embodiments, the isolated antibody or antigen-binding fragment according to the present disclosure comprises a light chain antigen-binding region that comprises an L-CDR2 comprising any one of SEQ ID NOs: 47, 67, 107, 127, 147, 167, 187, 207, 227, 247, 267, 287, 307, 327, 347, 367, 387, 407, 427, 447, 467, 487, 507, 527, 547, and 567.

In particular embodiments, the isolated antibody or antigen-binding fragment according to the present disclosure comprises:

i) a heavy chain antigen-binding region that comprises an H-CDR1 comprising SEQ ID NO: 42, an H-CDR2 comprising SEQ ID NO: 43, and an H-CDR3 comprising SEQ ID NO: 44 and a light chain antigen-binding region that comprises an L-CDR1 comprising SEQ ID NO: 46, an L-CDR2 comprising SEQ ID NO: 47, and an L-CDR3 comprising SEQ ID NO: 48; or ii) a heavy chain antigen-binding region that comprises an H-CDR1 comprising SEQ ID NO: 62, an H-CDR2 comprising SEQ ID NO: 63, and an H-CDR3 comprising SEQ ID NO: 64 and a light chain antigen-binding region that comprises an L-CDR1 comprising SEQ ID NO: 66, an L-CDR2 comprising SEQ ID NO: 67, and an L-CDR3 comprising SEQ ID NO: 68; or iii) a heavy chain antigen-binding region that comprises an H-CDR1 comprising SEQ ID NO: 102, an H-CDR2 comprising SEQ ID NO: 103, and an H-CDR3 comprising SEQ ID NO: 104 and a light chain antigen-binding region that comprises an L-CDR1 comprising SEQ ID NO: 106, an L-CDR2 comprising SEQ ID NO: 107, and an L-CDR3 comprising SEQ ID NO: 108; or iv) a heavy chain antigen-binding region that comprises an H-CDR1 comprising SEQ ID NO: 122, an H-CDR2 comprising SEQ ID NO: 123, and an H-CDR3 comprising SEQ ID NO: 124 and a light chain antigen-binding region that comprises an L-CDR1 comprising SEQ ID NO: 126, an L-CDR2 comprising SEQ ID NO: 127, and an L-CDR3 comprising SEQ ID NO: 128; or v) a heavy chain antigen-binding region that comprises an H-CDR1 comprising SEQ ID NO: 142, an H-CDR2 comprising SEQ ID NO: 143, and an H-CDR3 comprising SEQ ID NO: 144 and a light chain antigen-binding region that comprises an L-CDR1 comprising SEQ ID NO: 146, an L-CDR2 comprising SEQ ID NO: 147, and an L-CDR3 comprising SEQ ID NO: 148; or vi) a heavy chain antigen-binding region that comprises an H-CDR1 comprising SEQ ID NO: 162, an H-CDR2 comprising SEQ ID NO: 163, and an H-CDR3 comprising SEQ ID NO: 164 and a light chain antigen-binding region that comprises an L-CDR1 comprising SEQ ID NO: 166, an L-CDR2 comprising SEQ ID NO: 167, and an L-CDR3 comprising SEQ ID NO: 168; or vii) a heavy chain antigen-binding region that comprises an H-CDR1 comprising SEQ ID NO: 182, an H-CDR2 comprising SEQ ID NO: 183, and an H-CDR3 comprising SEQ ID NO: 184 and a light chain antigen-binding region that comprises an L-CDR1 comprising SEQ ID NO: 186, an L-CDR2 comprising SEQ ID NO: 187, and an L-CDR3 comprising SEQ ID NO: 188; or viii) a heavy chain antigen-binding region that comprises an H-CDR1 comprising SEQ ID NO: 202, an H-CDR2 comprising SEQ ID NO: 203, and an H-CDR3 comprising SEQ ID NO: 204 and a light chain antigen-binding region that comprises an L-CDR1 comprising SEQ ID NO: 206, an L-CDR2 comprising SEQ ID NO: 207, and an L-CDR3 comprising SEQ ID NO: 208; or ix) a heavy chain antigen-binding region that comprises an H-CDR1 comprising SEQ ID NO: 222, an H-CDR2 comprising SEQ ID NO: 223, and an H-CDR3 comprising SEQ ID NO: 224 and a light chain antigen-binding region that comprises an L-CDR1 comprising SEQ ID NO: 226, an L-CDR2 comprising SEQ ID NO: 227, and an L-CDR3 comprising SEQ ID NO: 228; or x) a heavy chain antigen-binding region that comprises an H-CDR1 comprising SEQ ID NO: 242, an H-CDR2 comprising SEQ ID NO: 243, and an H-CDR3 comprising SEQ ID NO: 244 and a light chain antigen-binding region that comprises an L-CDR1 comprising SEQ ID NO: 246, an L-CDR2 comprising SEQ ID NO: 247, and an L-CDR3 comprising SEQ ID NO: 248; or xi) a heavy chain antigen-binding region that comprises an H-CDR1 comprising SEQ ID NO: 262, an H-CDR2 comprising SEQ ID NO: 263, and an H-CDR3 comprising SEQ ID NO: 264 and a light chain antigen-binding region that comprises an L-CDR1 comprising SEQ ID NO: 266, an L-CDR2 comprising SEQ ID NO: 267, and an L-CDR3 comprising SEQ ID NO: 268; or xii) a heavy chain antigen-binding region that comprises an H-CDR1 comprising SEQ ID NO: 282, an H-CDR2 comprising SEQ ID NO: 283, and an H-CDR3 comprising SEQ ID NO: 284 and a light chain antigen-binding region that comprises an L-CDR1 comprising SEQ ID NO: 286, an L-CDR2 comprising SEQ ID NO: 287, and an L-CDR3 comprising SEQ ID NO: 288; or xiii) a heavy chain antigen-binding region that comprises an H-CDR1 comprising SEQ ID NO: 302, an H-CDR2 comprising SEQ ID NO: 303, and an H-CDR3 comprising SEQ ID NO: 304 and a light chain antigen-binding region that comprises an L-CDR1 comprising SEQ ID NO: 306, an L-CDR2 comprising SEQ ID NO: 307, and an L-CDR3 comprising SEQ ID NO: 308; or xiv) a heavy chain antigen-binding region that comprises an H-CDR1 comprising SEQ ID NO: 322, an H-CDR2 comprising SEQ ID NO: 323, and an H-CDR3 comprising SEQ ID NO: 324 and a light chain antigen-binding region that comprises an L-CDR1 comprising SEQ ID NO: 326, an L-CDR2 comprising SEQ ID NO: 327, and an L-CDR3 comprising SEQ ID NO: 328; or xv) a heavy chain antigen-binding region that comprises an H-CDR1 comprising SEQ ID NO: 342, an H-CDR2 comprising SEQ ID NO: 343, and an H-CDR3 comprising SEQ ID NO: 344 and a light chain antigen-binding region that comprises an L-CDR1 comprising SEQ ID NO: 346, an L-CDR2 comprising SEQ ID NO: 347, and an L-CDR3 comprising SEQ ID NO: 348; or xvi) a heavy chain antigen-binding region that comprises an H-CDR1 comprising SEQ ID NO: 362, an H-CDR2 comprising SEQ ID NO: 363, and an H-CDR3 comprising SEQ ID NO: 364 and a light chain antigen-binding region that comprises an L-CDR1 comprising SEQ ID NO: 366, an L-CDR2 comprising SEQ ID NO: 367, and an L-CDR3 comprising SEQ ID NO: 368; or xvii) a heavy chain antigen-binding region that comprises an H-CDR1 comprising SEQ ID NO: 382, an H-CDR2 comprising SEQ ID NO: 383, and an H-CDR3 comprising SEQ ID NO: 384 and a light chain antigen-binding region that comprises an L-CDR1 comprising SEQ ID NO: 386, an L-CDR2 comprising SEQ ID NO: 387, and an L-CDR3 comprising SEQ ID NO: 388; or xviii) a heavy chain antigen-binding region that comprises an H-CDR1 comprising SEQ ID NO: 402, an H-CDR2 comprising SEQ ID NO: 403, and an H-CDR3 comprising SEQ ID NO: 404 and a light chain antigen-binding region that comprises an L-CDR1 comprising SEQ ID NO: 406, an L-CDR2 comprising SEQ ID NO: 407, and an L-CDR3 comprising SEQ ID NO: 408; or xix) a heavy chain antigen-binding region that comprises an H-CDR1 comprising SEQ ID NO: 422, an H-CDR2 comprising SEQ ID NO: 423, and an H-CDR3 comprising SEQ ID NO: 424 and a light chain antigen-binding region that comprises an L-CDR1 comprising SEQ ID NO: 426, an L-CDR2 comprising SEQ ID NO: 427, and an L-CDR3 comprising SEQ ID NO: 428; or xx) a heavy chain antigen-binding region that comprises an H-CDR1 comprising SEQ ID NO: 442, an H-CDR2 comprising SEQ ID NO: 443, and an H-CDR3 comprising SEQ ID NO: 444 and a light chain antigen-binding region that comprises an L-CDR1 comprising SEQ ID NO: 446, an L-CDR2 comprising SEQ ID NO: 447, and an L-CDR3 comprising SEQ ID NO: 448; or xxi) a heavy chain antigen-binding region that comprises an H-CDR1 comprising SEQ ID NO: 462, an H-CDR2 comprising SEQ ID NO: 463, and an H-CDR3 comprising SEQ ID NO: 464 and a light chain antigen-binding region that comprises an L-CDR1 comprising SEQ ID NO: 466, an L-CDR2 comprising SEQ ID NO: 467, and an L-CDR3 comprising SEQ ID NO: 468; or xxii) a heavy chain antigen-binding region that comprises an H-CDR1 comprising SEQ ID NO: 482, an H-CDR2 comprising SEQ ID NO: 483, and an H-CDR3 comprising SEQ ID NO: 484 and a light chain antigen-binding region that comprises an L-CDR1 comprising SEQ ID NO: 486, an L-CDR2 comprising SEQ ID NO: 487, and an L-CDR3 comprising SEQ ID NO: 488; or xxiii) a heavy chain antigen-binding region that comprises an H-CDR1 comprising SEQ ID NO: 502, an H-CDR2 comprising SEQ ID NO: 503, and an H-CDR3 comprising SEQ ID NO: 504 and a light chain antigen-binding region that comprises an L-CDR1 comprising SEQ ID NO: 506, an L-CDR2 comprising SEQ ID NO: 507, and an L-CDR3 comprising SEQ ID NO: 508; or xxiv) a heavy chain antigen-binding region that comprises an H-CDR1 comprising SEQ ID NO: 522, an H-CDR2 comprising SEQ ID NO: 523, and an H-CDR3 comprising SEQ ID NO: 524 and a light chain antigen-binding region that comprises an L-CDR1 comprising SEQ ID NO: 526, an L-CDR2 comprising SEQ ID NO: 527, and an L-CDR3 comprising SEQ ID NO: 528; or xxv) a heavy chain antigen-binding region that comprises an H-CDR1 comprising SEQ ID NO: 542, an H-CDR2 comprising SEQ ID NO: 543, and an H-CDR3 comprising SEQ ID NO: 544 and a light chain antigen-binding region that comprises an L-CDR1 comprising SEQ ID NO: 546, an L-CDR2 comprising SEQ ID NO: 547, and an L-CDR3 comprising SEQ ID NO: 548; or xxvi) a heavy chain antigen-binding region that comprises an H-CDR1 comprising SEQ ID NO: 562, an H-CDR2 comprising SEQ ID NO: 563, and an H-CDR3 comprising SEQ ID NO: 564 and a light chain antigen-binding region that comprises an L-CDR1 comprising SEQ ID NO: 566, an L-CDR2 comprising SEQ ID NO: 567, and an L-CDR3 comprising SEQ ID NO: 568.

In particular embodiments, the isolated antibody or antigen-binding fragment according to the present disclosure comprises:

i) a variable heavy chain domain comprising SEQ ID NO: 41 and a variable light chain domain comprising SEQ ID NO: 45; or ii) a variable heavy chain domain comprising SEQ ID NO: 61 and a variable light chain domain comprising SEQ ID NO: 65; or iii) a variable heavy chain domain comprising SEQ ID NO: 101 and a variable light chain domain comprising SEQ ID NO: 105; or iv) a variable heavy chain domain comprising SEQ ID NO: 121 and a variable light chain domain comprising SEQ ID NO: 125; or v) a variable heavy chain domain comprising SEQ ID NO: 141 and a variable light chain domain comprising SEQ ID NO: 145; or vi) a variable heavy chain domain comprising SEQ ID NO: 161 and a variable light chain domain comprising SEQ ID NO: 165; or vii) a variable heavy chain domain comprising SEQ ID NO: 181 and a variable light chain domain comprising SEQ ID NO: 185; or viii) a variable heavy chain domain comprising SEQ ID NO: 201 and a variable light chain domain comprising SEQ ID NO: 205; or ix) a variable heavy chain domain comprising SEQ ID NO: 221 and a variable light chain domain comprising SEQ ID NO: 225; or x) a variable heavy chain domain comprising SEQ ID NO: 241 and a variable light chain domain comprising SEQ ID NO: 245; or xi) a variable heavy chain domain comprising SEQ ID NO: 261 and a variable light chain domain comprising SEQ ID NO: 265; or xii) a variable heavy chain domain comprising SEQ ID NO: 281 and a variable light chain domain comprising SEQ ID NO: 285; or xiii) a variable heavy chain domain comprising SEQ ID NO: 301 and a variable light chain domain comprising SEQ ID NO: 305; or xiv) a variable heavy chain domain comprising SEQ ID NO: 321 and a variable light chain domain comprising SEQ ID NO: 325; or
xv) a variable heavy chain domain comprising SEQ ID NO: 341 and a variable light chain domain comprising SEQ ID NO: 345; or
xvi) a variable heavy chain domain comprising SEQ ID NO: 361 and a variable light chain domain comprising SEQ ID NO: 365; or
xvii) a variable heavy chain domain comprising SEQ ID NO: 381 and a variable light chain domain comprising SEQ ID NO: 385; or
xviii) a variable heavy chain domain comprising SEQ ID NO: 401 and a variable light chain domain comprising SEQ ID NO: 405; or
xix) a variable heavy chain domain comprising SEQ ID NO: 421 and a variable light chain domain comprising SEQ ID NO: 425; or
xx) a variable heavy chain domain comprising SEQ ID NO: 441 and a variable light chain domain comprising SEQ ID NO: 445; or
xxi) a variable heavy chain domain comprising SEQ ID NO: 461 and a variable light chain domain comprising SEQ ID NO: 465; or
xxii) a variable heavy chain domain comprising SEQ ID NO: 481 and a variable light chain domain comprising SEQ ID NO: 485; or
xxiii) a variable heavy chain domain comprising SEQ ID NO: 501 and a variable light chain domain comprising SEQ ID NO: 505; or
xxiv) a variable heavy chain domain comprising SEQ ID NO: 521 and a variable light chain domain comprising SEQ ID NO: 525; or
xxv) a variable heavy chain domain comprising SEQ ID NO: 541 and a variable light chain domain comprising SEQ ID NO: 545; or
xxvi) a variable heavy chain domain comprising SEQ ID NO: 561 and a variable light chain domain comprising SEQ ID NO: 565.

In particular embodiments, the isolated antibody according to the present disclosure is an IgG antibody. In particular such embodiments, the isolated antibody according to the present disclosure is an IgG1, IgG2, IgG3 or an IgG4 antibody. Most particularly, the isolated antibody according to the present disclosure is an IgG1 or an IgG4 antibody.

In particular embodiments, the isolated antibody according to the present disclosure comprises:
i) a heavy chain comprising SEQ ID NO: 57 and a light chain comprising SEQ ID NO: 58; or
ii) a heavy chain comprising SEQ ID NO: 77 and a light chain comprising SEQ ID NO: 78; or
iii) a heavy chain comprising SEQ ID NO: 117 and a light chain comprising SEQ ID NO: 118; or
iv) a heavy chain comprising SEQ ID NO: 137 and a light chain comprising SEQ ID NO: 138; or
v) a heavy chain comprising SEQ ID NO: 157 and a light chain comprising SEQ ID NO: 158; or
vi) a heavy chain comprising SEQ ID NO: 177 and a light chain comprising SEQ ID NO: 178; or
vii) a heavy chain comprising SEQ ID NO: 197 and a light chain comprising SEQ ID NO: 198; or
viii) a heavy chain comprising SEQ ID NO: 217 and a light chain comprising SEQ ID NO: 218; or
ix) a heavy chain comprising SEQ ID NO: 237 and a light chain comprising SEQ ID NO: 238; or
x) a heavy chain comprising SEQ ID NO: 257 and a light chain comprising SEQ ID NO: 258; or
xi) a heavy chain comprising SEQ ID NO: 277 and a light chain comprising SEQ ID NO: 278; or
xii) a heavy chain comprising SEQ ID NO: 297 and a light chain comprising SEQ ID NO: 298; or
xiii) a heavy chain comprising SEQ ID NO: 317 and a light chain comprising SEQ ID NO: 318; or
xiv) a heavy chain comprising SEQ ID NO: 337 and a light chain comprising SEQ ID NO: 338; or
xv) a heavy chain comprising SEQ ID NO: 357 and a light chain comprising SEQ ID NO: 358; or
xvi) a heavy chain comprising SEQ ID NO: 377 and a light chain comprising SEQ ID NO: 378; or
xvii) a heavy chain comprising SEQ ID NO: 397 and a light chain comprising SEQ ID NO: 398; or
xviii) a heavy chain comprising SEQ ID NO: 417 and a light chain comprising SEQ ID NO: 418; or
xix) a heavy chain comprising SEQ ID NO: 437 and a light chain comprising SEQ ID NO: 438; or
xx) a heavy chain comprising SEQ ID NO: 457 and a light chain comprising SEQ ID NO: 458; or
xxi) a heavy chain comprising SEQ ID NO: 477 and a light chain comprising SEQ ID NO: 478; or
xxii) a heavy chain comprising SEQ ID NO: 497 and a light chain comprising SEQ ID NO: 498; or
xxiii) a heavy chain comprising SEQ ID NO: 517 and a light chain comprising SEQ ID NO: 518; or
xxiv) a heavy chain comprising SEQ ID NO: 537 and a light chain comprising SEQ ID NO: 538; or
xxv) a heavy chain comprising SEQ ID NO: 557 and a light chain comprising SEQ ID NO: 558; or
xxvi) a heavy chain comprising SEQ ID NO: 577 and a light chain comprising SEQ ID NO: 578.

In particular embodiments, the antigen-binding fragment according to the present disclosure is an scFv, Fab, Fab' fragment or a F(ab')2 fragment.

In particular embodiments, the isolated antibody or antigen-binding fragment according to the present disclosure is a monoclonal antibody or antigen-binding fragment thereof.

In particular embodiments, the isolated antibody or antigen-binding fragment according to the present disclosure is a human, humanized or chimeric antibody or antigen-binding fragment thereof, more particularly a fully human antibody or antigen-binding fragment thereof.

In particular embodiments, the isolated antibody or antigen-binding fragment according to the present disclosure is a monospecific antibody. In particular other embodiments, the isolated antibody or antigen-binding fragment according to the present disclosure is a multispecific antibody that binds to Sema3A and at least one further antigen, such as a bispecific, trispecific or tetraspecific antibody.

In another aspect the present disclosure relates to an isolated antibody or antigen-binding fragment thereof that competes with the isolated antibody or antigen-binding fragment according to the present disclosure for binding to human Sema3A.

In a further aspect, the present disclosure relates to an antibody conjugate, comprising the isolated antibody or antigen binding fragment according to the present disclosure. For example, an antibody could be conjugated to a cytotoxic agent, an immunotoxin, a toxophore or a radioisotope. Also provided are anti-Sema3A antibodies conjugated to a detectable marker. Preferred markers are a radiolabel, an enzyme, a chromophore or a fluorophore. The antibody may also be conjugated to high molecular weight molecules such as peptides or proteins, such as interleukins.

The ADC according to the present disclosure comprises an anti-Sema3A antibody conjugated to one or more cytotoxic agents, such as chemotherapeutic agents or drugs, growth inhibitory agents, toxins (e.g., protein toxins, enzymatically active toxins of bacterial, fungal, plant, human or animal origin, or fragments thereof), or radioactive isotopes.

In one embodiment, the ADC according to the present disclosure comprises an anti-Sema3A antibody as described herein conjugated to one or more drugs, including but not limited to a maytansinoid (see U.S. Pat. Nos. 5,208,020, 5,416,064 and European Patent EP0425235); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof; an anthracycline such as daunomycin or doxorubicin; methotrexate; vindesine; a taxane such as docetaxel, paclitaxel, larotaxel, tesetaxel, and ortataxel; a trichothecene; and CC1065.

In another embodiment, the ADC according to the present disclosure comprises an anti-Sema3A antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alphasarcin, *Aleurites fordii* proteins, dianthin proteins, *Phytolaca americana* proteins (P API, P APII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, the ACD according to the present disclosure comprises and anti-Sema3A antibody as described herein conjugated to a radioactive atom to form a radioconjugate. A variety of radioactive isotopes are available for the production of radioconjugates. Examples include 227Th, 225Ac, 211At, 131I, 125I, 90Y, 186Re, 188Re, 153Sm, 212Bi, 32P, 212Pb and radioactive isotopes of Lu. When the radioconjugate is used for detection, it may comprise a radioactive atom for scintigraphic studies, for example Tc99m, or a spin label for nuclear magnetic resonance (NMR) imaging, such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:12 7-131 (1992).

The ACD according to the present disclosure includes ADCs prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A)

Amino acid and nucleic acid sequences of preferred antibodies according to the present disclosure and three prior art antibodies are listed in Table 1 and Table 1A.

Peptide Variants

Antibodies or antigen-binding fragments of the disclosure are not limited to the specific peptide sequences provided herein. Rather, the disclosure also embodies variants of these polypeptides. With reference to the instant disclosure and conventionally available technologies and references, the skilled worker will be able to prepare, test and utilize functional variants of the antibodies disclosed herein, while appreciating these variants having the ability to bind to Sema3A fall within the scope of the present disclosure.

A variant can include, for example, an antibody that has at least one altered complementary determining region (CDR) (hyper-variable) and/or framework (FR) (variable) domain/position, vis-à-vis a peptide sequence disclosed herein.

By altering one or more amino acid residues in a CDR or FR region, the skilled worker routinely can generate mutated or diversified antibody sequences, which can be screened against the antigen, for new or improved properties, for example.

A further preferred embodiment of the disclosure is an antibody or antigen-binding fragment thereof in which the VH and VL sequences are selected as shown in Table 1 and Table 1A. The skilled worker can use the data in Table 1 and Table 1A to design peptide variants that are within the scope of the present disclosure. It is preferred that variants are constructed by changing amino acids within one or more CDR regions; a variant might also have one or more altered framework regions. For example, a peptide FR domain might be altered where there is a deviation in a residue compared to a germline sequence.

Alternatively, the skilled worker could make the same analysis by comparing the amino acid sequences disclosed herein to known sequences of the same class of such antibodies, using, for example, the procedure described by Knappik A., et al., JMB 2000, 296:57-86.

Furthermore, variants may be obtained by using one antibody as starting point for further optimization by diversifying one or more amino acid residues in the antibody, preferably amino acid residues in one or more CDRs, and by screening the resulting collection of antibody variants for variants with improved properties. Particularly preferred is diversification of one or more amino acid residues in CDR3 of VL and/or VH. Diversification can be done e.g. by synthesizing a collection of DNA molecules using trinucleotide mutagenesis (TRIM) technology (Virnekäs B. et al., Nucl. Acids Res. 1994, 22:5600.). Antibodies or antigen-binding fragments thereof include molecules with modifications/variations including but not limited to e.g. modifications leading to altered half-life (e.g. modification of the Fc part or attachment of further molecules such as PEG), altered binding affinity or altered ADCC or CDC activity.

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophane, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Glycosylation Variants

Where the antibody comprises an Fc region, the carbohydrate attached thereto may be altered. Native antibodies produced by mammalian cells typically comprise a branched, biantennary oligosaccharide that is generally attached by an N-linkage to Asn297 using Kabat EU numbering of the CH2 domain of the Fc region; see, e.g., Wright et al. Trends Biotechnol. 15:26-32 (1997).

In certain embodiments, an antibody provided herein is altered to increase or decrease the extent to which the antibody is glycosylated. Addition or deletion of glycosylation sites to an antibody may be conveniently accomplished by altering the expression system (e.g. host cell) and/or by altering the amino acid sequence such that one or more glycosylation sites is created or removed.

In one embodiment of this disclosure, aglycosyl antibodies having decreased effector function or antibody derivatives are prepared by expression in a prokaryotic host. Suitable prokaryotic hosts for include but are not limited to *E. coli, Bacillus subtilis, Salmonella typhimurium* and various species within the genera *Pseudomonas, Streptomyces,* and *Staphylococcus.*

In one embodiment, antibody variants are provided having decreased effector function, which are characterized by a modification at the conserved N-linked site in the CH2 domains of the Fc portion of said antibody. In one embodiment of present disclosure, the modification comprises a mutation at the heavy chain glycosylation site to prevent glycosylation at the site. Thus, in one preferred embodiment of this disclosure, the aglycosyl antibodies or antibody derivatives are prepared by mutation of the heavy chain glycosylation site, —i.e., mutation of N297 using Kabat EU numbering and expressed in an appropriate host cell.

In another embodiment of the present disclosure, aglycosyl antibodies or antibody derivatives have decreased effector function, wherein the modification at the conserved N-linked site in the CH2 domains of the Fc portion of said antibody or antibody derivative comprises the removal of the CH2 domain glycans, —i.e., deglycosylation. These aglycosyl antibodies may be generated by conventional methods and then deglycosylated enzymatically. Methods for enzymatic deglycosylation of antibodies are well known in the art (e.g. Winkelhake & Nicolson (1976), J Biol Chem. 251 (4): 1074-80).

In another embodiment of this disclosure, deglycosylation may be achieved using the glycosylation inhibitor tunicamycin (Nose & Wigzell (1983), Proc Natl Acad Sci USA, 80 (21): 6632-6). That is, the modification is the prevention of glycosylation at the conserved N-linked site in the CH2 domains of the Fc portion of said antibody.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function.

Examples of publications related to "defucosylated" or "fucose-deficient" antibody variants include: Okazaki et al. J Mol. Biol. 336:1239-1249 (2004); Yamane-Ohnuki et al. Biotech. Bioeng. 87:614 (2004).

Examples of cell lines capable of producing defucosylated antibodies include Lec13 CHO cells deficient in protein fucosylation (Ripka et al. Arch. Biochem. Biophys. 249: 533-545 (1986); and WO 2004/056312), and knockout cell lines, such as alpha-1,6-fucosyltransferase gene, FUT8, knockout CHO cells (see, e.g., Yamane-Ohnuki et al. Biotech. Bioeng. 87:614 (2004); Kanda, Y. et al., Biotechnol. Bioeng., 94 (4): 680-688 (2006)).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546.

Antibody variants with at least one galactose residue in the oligosaccharide attached to the Fc region are also provided. Such antibody variants may have improved CDC function. Such antibody variants are described, e.g., in WO1997/30087; WO1998/58964; and WO1999/22764.

FC Region Variants

In certain embodiments, one or more amino acid modifications (e.g. a substitution) may be introduced into the Fc region of an antibody (e.g., a human IgG1, IgG2, IgG3 or IgG4 Fc region) provided herein, thereby generating an Fc region variant.

In certain embodiments, the disclosure contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity) but retains FcRn binding ability. In some embodiments, alterations are made in the Fc region that result in altered (i.e., either improved or diminished) C1q binding and/or Complement Dependent Cytotoxicity (CDC).

In certain embodiments, the disclosure contemplates an antibody variant that possesses an increased or decreased half-live. Antibodies with increased half-lives and improved binding to the neonatal Fc receptor (FcRn), which is responsible for the transfer of maternal IgGs to the fetus (Guyer et al., J Immunol. 117:587 (1976) and Kim et al., J Immunol. 24:249 (1994)), are described in US2005/0014934 (Hinton et al.). Those antibodies comprise an Fc region with one or more substitutions therein which improve binding of the Fc region to FcRn.

Antibody Generation

An antibody of the disclosure may be derived from a recombinant antibody library that is based on amino acid sequences that have been isolated from the antibodies of a large number of healthy volunteers e.g. using the n-CoDeR® technology the fully human CDRs are recombined into new antibody molecules (Carlson & Söderlind, Expert Rev Mol Diagn. 2001 May; 1 (1): 102-8). Or alternatively for example antibody libraries as the fully human antibody phage display library described in Hoet R M et al., Nat Biotechnol 2005; 23 (3): 344-8) can be used to isolate Sema3A-specific antibodies. Antibodies or antibody fragments isolated from human antibody libraries are considered human antibodies or human antibody fragments herein.

Human antibodies may be further prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. For example immunization of genetically engineered mice inter alia immunization of hMAb mice (e.g. VelocImmune Mouse® or XENOMOUSE®) may be performed.

Further antibodies may be generated using the hybridoma technology (for example see Köhler and Milstein Nature. 1975 Aug. 7; 256 (5517): 495-7), resulting in for example murine, rat, or rabbit antibodies which can be converted into chimeric or humanized antibodies. Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Natl Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Examples are provided for the generation of antibodies using a recombinant antibody library.

DNA Molecules According to the Present Disclosure

The present disclosure also relates to an isolated nucleic acid sequence that encodes the antibody or antigen-binding fragment according to the present disclosure. The isolated nucleic acid sequence encoding the antibody or antigen-binding fragment according to the present disclosure can for instance be produced by techniques described in Sambrook et al., 1989, and Ausubel et al., 1989, or alternatively, by chemically synthesis. (e.g. techniques described in Oligonucleotide Synthesis (1984, Gait, ed., IRL Press, Oxford)). The DNA sequences and respective SEQ IDs used for the antibodies expressed are given in Table 1 and 1A. These sequences are optimized in certain cases for mammalian expression. DNA molecules of the disclosure are not limited to the sequences disclosed herein, but also include variants thereof. DNA variants within the disclosure may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 supra and Ausubel et al., 1995 (Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

Functionally Equivalent DNA Variants

Yet another class of DNA variants within the scope of the disclosure may be described with reference to the product they encode. These functionally equivalent polynucleotides are characterized by the fact that they encode the same peptide sequences due to the degeneracy of the genetic code.

It is recognized that variants of DNA molecules provided herein can be constructed in several different ways. For example, they may be constructed as completely synthetic DNAs. Methods of efficiently synthesizing oligonucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration (s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present disclosure further provides recombinant DNA constructs comprising one or more of the nucleotide sequences according to the present disclosure. The recombinant constructs of the present disclosure can be used in connection with a vector, such as a plasmid, phagemid, phage or viral vector, into which a DNA molecule encoding an antibody of the disclosure or antigen-binding fragment thereof or variant thereof is inserted.

Thus, in one aspect, the present disclosure relates to a vector comprising a nucleic acid sequence according to the present disclosure.

An antibody, antigen binding portion, or variant thereof provided herein can be prepared by recombinant expression of nucleic acid sequences encoding light and heavy chains or portions thereof in a host cell. To express an antibody, antigen binding portion, or variant thereof recombinantly a host cell can be transfected with one or more recombinant expression vectors carrying DNA fragments encoding the light and/or heavy chains or portions thereof such that the light and heavy chains are expressed in the host cell. Standard recombinant DNA methodologies are used to prepare and/or obtain nucleic acids encoding the heavy and light chains, incorporate these nucleic acids into recombinant expression vectors and introduce the vectors into host cells, such as those described in Sambrook, Fritsch and Maniatis (eds.), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al.

In addition, the nucleic acid sequences encoding variable regions of the heavy and/or light chains can be converted, for example, to nucleic acid sequences encoding full-length antibody chains, Fab fragments, or to scFv. The VL- or VH-encoding DNA fragment can be operatively linked, (such that the amino acid sequences encoded by the two DNA fragments are in-frame) to another DNA fragment encoding, for example, an antibody constant region or a flexible linker. The sequences of human heavy chain and light chain constant regions are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

To create a polynucleotide sequence that encodes a scFv, the VH- and VL-encoding nucleic acids can be operatively linked to another fragment encoding a flexible linker such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554).

To express the antibodies, antigen binding fragments thereof or variants thereof standard recombinant DNA expression methods can be used (see, for example, Goeddel; Gene Expression Technology. Methods in Enzymology 185, Academic Press, San Diego, Calif. (1990)). For example, DNA encoding the desired polypeptide can be inserted into an expression vector which is then transfected into a suitable host cell. Suitable host cells are prokaryotic and eukaryotic host cells. Examples for prokaryotic host cells are e.g. bacteria, examples for eukaryotic hosts cells are yeasts, insects and insect cells, plants and plant cells, transgenic animals, or mammalian cells. Introduction of the recombinant construct into the host cell can be carried out using standard techniques such as calcium phosphate transfection, DEAE dextran mediated transfection, electroporation, transduction or phage infection.

In some embodiments, the DNAs encoding the heavy and light chains are inserted into separate vectors. In other embodiments, the DNA encoding the heavy and light chains is inserted into the same vector. It is understood that the design of the expression vector, including the selection of regulatory sequences is affected by factors such as the choice of the host cell, the level of expression of protein desired and whether expression is constitutive or inducible.

Thus, in a further aspect, the present disclosure relates to an isolated cell expressing the antibody or antigen-binding fragment according to the present disclosure and/or comprising the nucleic acid according to the present disclosure or the vector according to the present disclosure.

The isolated cell can be virtually any cell for which expression vectors are available. The isolated cell can for example a higher eukaryotic host cell, such as a mammalian cell, a lower eukaryotic host cell, such as a yeast cell, and may be a prokaryotic cell, such as a bacterial cell.

In a further aspect, the present disclosure relates to a method of producing the isolated antibody or antigen-binding fragment according to the present disclosure comprising culturing of the cell according to the present disclosure. In particular embodiments, the cell according to the present disclosure is cultivated under suitable conditions for antibody expression and the antibody or antigen-binding fragment thereof is recovered. In particular embodiments, the antibody or antigen-binding fragment thereof is purified, particularly to at least 95% homogeneity by weight.

Bacterial Expression

Useful expression vectors for bacterial use are constructed by inserting a DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include but are not limited to *E. coli, Bacillus subtilis, Salmonella typhimurium* and various species within the genera *Pseudomonas, Streptomyces*, and *Staphylococcus*.

Bacterial vectors may be, for example, bacteriophage-, plasmid- or phagemid-based. These vectors can contain a selectable marker and a bacterial origin of replication derived from commercially available plasmids typically containing elements of the well-known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therefore, an embodiment of the present disclosure is an expression vector comprising a nucleic acid sequence encoding for the novel antibodies of the present disclosure.

Antibodies of the present disclosure or antigen-binding fragments thereof or variants thereof include naturally purified products, products of chemical synthetic procedures, and products produced by recombinant techniques from a prokaryotic host, including, for example, *E. coli, Bacillus subtilis, Salmonella typhimurium* and various species within the genera *Pseudomonas, Streptomyces*, and *Staphylococcus*, preferably, from *E. coli* cells.

Mammalian Expression

Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. Expression of the antibodies may be constitutive or regulated (e.g. inducible by addition or removal of small molecule inductors such as Tetracyclin in conjunction with Tet system). For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al., The recombinant expression vectors can also include origins of replication and selectable markers (see e.g., U.S. Pat. Nos. 4,399,216, 4,634,665 and 5,179,017). Suitable selectable markers include genes that confer resistance to drugs such as G418, puromycin, hygromycin, blasticidin, zeocin/bleomycin or methotrexate or selectable marker that exploit auxotrophies such as Glutamine Synthetase (Bebbington et al., Biotechnology (N Y). 1992 February; 10 (2): 169-75), on a host cell into which the vector has been introduced. For example, the dihydrofolate reductase (DHFR) gene confers resistance to methotrexate, neo gene confers resistance to G418, the bsd gene from *Aspergillus terreus* confers resistance to blasticidin, puromycin N-acetyl-transferase confers resistance to puromycin, the Sh ble gene product confers resitance to zeocin, and resistance to hygromycin is conferred by the *E. coli* hygromycin resistance gene (hyg or hph). Selectable markers like DHFR or Glutamine Synthetase are also useful for amplification techniques in conjunction with MTX and MSX.

Transfection of the expression vector into a host cell can be carried out using standard techniques such as electroporation, nucleofection, calcium-phosphate precipitation, lipofection, polycation-based transfection such as polyethylenimine (PEI)-based transfection and DEAE-dextran transfection.

Suitable mammalian host cells for expressing the antibodies, antigen binding fragments thereof or variants thereof provided herein include Chinese Hamster Ovary (CHO cells) such as CHO-K1, CHO-S, CHO-K1SV [including dhfr-CHO cells, described in Urlaub and Chasin, (1980) Proc. Natl. Acad. Sci. USA 77:4216-4220 and Urlaub et al., Cell. 1983 June; 33 (2):405-12, used with a DHFR selectable marker, e.g., as described in R. J. Kaufman and P. A. Sharp (1982) Mol. Biol. 159:601-621; and other knockout cells exemplified in Fan et al., Biotechnol Bioeng. 2012 April; 109 (4):1007-15], NS0 myeloma cells, COS cells, HEK293 cells, HKB11 cells, BHK21 cells, CAP cells, EB66 cells, and SP2 cells.

Expression might also be transient or semi-stable in expression systems such as HEK293, HEK293T, HEK293-EBNA, HEK293E, HEK293-6E, HEK293-Freestyle, HKB11, Expi293F, 293EBNALT75, CHO Freestyle, CHO-S, CHO-K1, CHO-K1SV, CHOEBNALT85, CHOS-XE, CHO-3E7 or CAP-T cells (for instance Durocher et al., Nucleic Acids Res. 2002 Jan. 15; 30 (2): E9).

In some embodiments, the expression vector is designed such that the expressed protein is secreted into the culture medium in which the host cells are grown. The antibodies, antigen binding fragments thereof or variants thereof can be recovered from the culture medium using standard protein purification methods.

Purification

Antibodies of the disclosure or antigen-binding fragments thereof or variants thereof can be recovered and purified from recombinant cell cultures by well-known methods including, but not limited to ammonium sulfate or ethanol precipitation, acid extraction, Protein A chromatography, Protein G chromatography, anion or cation exchange chromatography, phospho-cellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present disclosure or antigen-binding fragments thereof or variants thereof include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present disclosure can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20.

In preferred embodiments, the antibody is purified (1) to greater than 95% by weight of antibody as determined e.g. by the Lowry method, UV-Vis spectroscopy or by by SDS-Capillary Gel electrophoresis (for example on a Caliper LabChip GXII, GX 90 or Biorad Bioanalyzer device), and in further preferred embodiments more than 99% by weight, (2) to a degree sufficient to obtain at least 15 residues of N-terminal or internal amino acid sequence, or (3) to homogeneity by SDS-PAGE under reducing or non-reducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

Therapeutic Methods

Therapeutic methods involve administering to a subject in need of treatment a therapeutically effective amount of an antibody or an antigen-binding fragment thereof or a variant thereof contemplated by the disclosure. A "therapeutically effective" amount hereby is defined as the amount of an antibody or antigen-binding fragment thereof that is of sufficient quantity to decrease Sema3A activity in a subject-either as a single dose or according to a multiple dose regimen, alone or in combination with other agents, which leads to the alleviation of an adverse condition, yet which amount is toxicologically tolerable. The subject may be a human or non-human animal (e.g., rabbit, rat, mouse, dog, monkey or other lower-order primate).

Thus, in one aspect, the present disclosure relates to the isolated antibody or antigen-binding fragment according the present disclosure or to a conjugate comprising the isolated antibody or antigen-binding fragment according the present disclosure or to a pharmaceutical composition comprising the isolated antibody or antigen-binding fragment according the present disclosure for use as a medicament.

The isolated antibody or antigen-binding fragment according to the present disclosure can be used as a therapeutic or a diagnostic tool in a variety of Sema3A-associated disorders.

Thus, in a further aspect, the present disclosure relates to the isolated antibody or antigen-binding fragment according the present disclosure or to a conjugate comprising the isolated antibody or antigen-binding fragment according the present disclosure or to a pharmaceutical composition comprising the isolated antibody or antigen-binding fragment according the present disclosure for use in the treatment and/or prevention of renal diseases, in particular of acute and chronic kidney diseases, diabetic kidney diseases, Alport syndrome and of acute and chronic renal failure. The general terms 'renal disease' or 'kidney disease' describes a class of conditions in which the kidneys fail to filter and remove waste products from the blood. There are two major forms of kidney disease: acute kidney disease (acute kidney injury, AKI) and chronic kidney disease (CKD). The isolated antibody or antigen-binding fragment according to the present disclosure or a conjugate or pharmaceutical composition comprising the same may further be used for the treatment and/or prevention of sequelae of acute kidney injury arising from multiple insults such as ischemia-reperfusion injury, radiocontrast administration, cardiopulmonary bypass surgery, shock and sepsis. In the context of the present disclosure, the terms renal failure and renal insufficiency comprise both acute and chronic manifestations of renal insufficiency, as well as underlying or related kidney diseases such as renal hypoperfusion, intradialytic hypotension, obstructive uropathy, glomerulopathies, IgA nephropathy, glomerulonephritis, acute glomerulonephritis, glomerulosclerosis, tubulointerstitial diseases, nephropathic diseases such as primary and congenital kidney disease, nephritis, Alport syndrome, kidney inflammation, immunological kidney diseases such as kidney transplant rejection, immune complex-induced kidney diseases, nephropathy induced by toxic substances, contrast medium-induced nephropathy; minimal change glomerulonephritis (lipoid); Membranous glomerulonephritis; focal segmental glomerulosclerosis (FSGS); hemolytic uremic syndrome (HUS), amyloidosis, Goodpasture's syndrome, Wegener's granulomatosis, Purpura Schönlein-Henoch, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally increased blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions of glomeruli and arterioles, tubular dilatation, hyperphosphatemia and/or the need for dialysis. The present disclosure also relates to the isolated antibody or antigen-binding fragment according to the present disclosure or a conjugate or pharmaceutical composition comprising same for use in the treatment and/or prevention of sequelae of renal insufficiency, for example pulmonary edema, heart failure, uremia, anemia, electrolyte disturbances (e.g. hyperkaliemia, hyponatremia) and disturbances in bone and carbohydrate metabolism. The compounds according to the disclosure are also suitable for the treatment and/or prevention of polycystic kidney disease (PCKD) and of the syndrome of inadequate ADH secretion (SIADH).

Additionally, the isolated antibody or antigen-binding fragment according to the present disclosure or a conjugate or pharmaceutical composition comprising the same may be used for the treatment and/or prevention of vascular hyperpermeability, diabetic retinopathy, deterioration of the blood retinal barrier and consequent macular edema, preferably, age related macular edema, non-proliferative age-related macular edema and non-proliferative diabetic macular edema.

Further, the isolated antibody or antigen-binding fragment according to the present disclosure or a conjugate or pharmaceutical composition comprising same is suitable for the prevention or treatment of disease of the central or peripheral nervous system like neuropathic pain, spinal cord injury, multiple sclerosis, traumatic brain injury, brain edema or neurodegenerative diseases in which the neurodegenerative disease is Alzheimer's disease, Parkinson's disease, Huntington's disease, amyotrophic lateral sclerosis, progressive supranuclear paralysis, black substance degeneration, Shy-Drager syndrome, olivopontocerebellar atrophy or spinocerebellar degeneration.

Furthermore, the isolated antibody or antigen-binding fragment according to the present disclosure or a conjugate or pharmaceutical composition comprising the same may be useful for the treatment and/or prevention of cancer, wherein the cancer is intestinal cancer, colorectal cancer, lung cancer, breast cancer, brain cancer, melanoma, renal cell cancer, leukemia, lymphoma, T-cell lymphoma, stomach cancer, pancreatic cancer, cervical cancer, endometrial cancer, ovarian cancer, esophageal cancer, liver cancer, squamous cell carcinoma of the head and neck, skin cancer, urinary tract cancer, prostate cancer, choriocarcinoma, pharyngeal cancer or larynx cancer.

The disorders mentioned above have been well characterized in humans, but also exist with a similar etiology in other animals, including mammals, and can be treated by administering pharmaceutical compositions according to the present disclosure.

The antibody or the antigen-binding fragment according to the present disclosure or a variant thereof might be co-administered with known medicaments, and in some instances the antibody or antigen-binding fragment thereof might itself be modified. For example, an antibody or an antigen-binding fragment thereof or a variant thereof could be conjugated to a drug or to another peptide or protein to potentially further increase efficacy.

Antibodies of the present disclosure or antigen-binding fragments thereof or variants thereof may be administered as the sole pharmaceutical agent or in combination with one or more additional therapeutic agents where the combination causes no unacceptable adverse effects.

Thus, in a further aspect, the present disclosure relates to the isolated antibody or antigen-binding fragment according to the present disclosure or the conjugate according to the present disclosure or the pharmaceutical composition according to the present disclosure for use in simultaneous, separate, or sequential combination with one or more further therapeutically active compounds.

Non-limiting examples of therapeutically active compounds to be used in combination with the antibody or antigen-binding fragment according to the present disclosure are:

blood pressure lowering agents, for example and preferably from the group of calcium antagonists, angiotensin II antagonists, ACE inhibitors, NEP inhibitors, vasopeptidase inhibitors, endothelin antagonists, renin inhibitors, alpha-blockers, beta-blockers, mineralocorticoid receptor antagonists and diuretics;

antidiabetic agents (hypoglycemic or antihyperglycemic agents), such as for example and preferably insulin and derivatives, sulfonylureas, biguanides, thiazolidinediones, acarbose, DPP4 inhibitors, GLP-1 analogues, or SGLT inhibitors (gliflozins);

compounds inhibiting the signal transduction cascade, in particular tyrosine and/or serine/threonine kinase inhibitors, such as for example nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

anti-inflammatory drugs such as non-steroidal anti-inflammatory drugs (NSAIDs) including acetylsalicylic acid (aspirin), ibuprofen and naproxen, glucocorticoids such as for example and preferably prednison, prednisolon, methylprednisolon, triamcinolon, dexamethason, beclomethason, betamethason, flunisolid, budesonid or fluticason, or 5-aminosalicylic acid derivatives, leukotriene antagonists, TNF-alpha inhibitors and chemokine receptor antagonists such as CCR1, 2 and/or 5 inhibitors, NF-κB inhibitors and Nerf2 activators;

anti-fibrotic drugs such as TGFbeta antagonist, or microRNA-21 inhibitors;

organic nitrates and NO-donors, for example sodium nitroprusside, nitroglycerin, isosorbide mononitrate, isosorbide dinitrate, molsidomine or SIN-1, and inhalational NO;

compounds that inhibit the degradation of cyclic guanosine monophosphate (cGMP), for example inhibitors of phosphodiesterases (PDE) 1, 2, 5 and/or 9, in particular PDE-5 inhibitors such as sildenafil, vardenafil, tadalafil, udenafil, dasantafil, avanafil, mirodenafil, lodenafil, CTP-499 or PF-00489791;

calcium sensitizers, such as for example and preferably levosimendan;

antithrombotic agents, particularly selected from the group consisting of platelet aggregation inhibitors, anticoagulants and profibrinolytic substances;

agents, that stimulate NO- and heme-dependent as well as NO- and heme-indipendent the synthesis of cGMP, for example and with preference soluble guanylate cyclase (sGC) modulators, for example and with preference riociguat, cinaciguat, vericiguat or BAY 1101042;

fat metabolism altering agents, for example and preferably from the group of thyroid receptor agonists, cholesterol synthesis inhibitors, such as for example and preferably HMG-COA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein (a) antagonists.

In particular embodiments, the isolated antibody or antigen-binding fragment according to the present disclosure is administered in combination with a platelet aggregation inhibitor, particularly aspirin, clopidogrel, ticlopidine or dipyridamole.

In particular embodiments, the isolated antibody or antigen-binding fragment according to the present disclosure is administered in combination with a thrombin inhibitor, particularly ximelagatran, dabigatran, melagatran, bivalirudin or enoxaparin.

In particular embodiments, the isolated antibody or antigen-binding fragment according to the present disclosure is administered in combination with a GPIIb/IIIa antagonist, particularly tirofiban or abciximab.

In particular embodiments, the isolated antibody or antigen-binding fragment according to the present disclosure is administered in combination with a factor Xa inhibitor, particularly selected from rivaroxaban, apixaban, otamixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 and SSR-128428.

In particular embodiments, the isolated antibody or antigen-binding fragment according to the present disclosure is administered in combination with heparin or a low molecular weight (LMW) heparin derivative.

In particular embodiments, the isolated antibody or antigen-binding fragment according to the present disclosure is administered in combination with a vitamin K antagonist, particularly selected from coumarin.

Blood pressure lowering agents are particularly selected from the group consisting of calcium antagonists, angiotensin AII antagonists, ACE inhibitors, NEP inhibitors, vasopeptidase inhibitors, endothelin antagonists, renin inhibitors, alpha-blockers, beta-blockers, mineralocorticoid receptor antagonists and diuretics.

In particular embodiments, the isolated antibody or antigen-binding fragment according to the present disclosure is administered in combination with a calcium antagonist, particularly selected from nifedipine, amlodipine, verapamil and diltiazem.

In particular embodiments, the isolated antibody or antigen-binding fragment according to the present disclosure is administered in combination with an angiotensin AII receptor antagonist, particularly selected from the group consisting of losartan, candesartan, valsartan, telmisartan, irbesartan, olmesartan, eprosartan, embursartan and azilsartan.

In particular embodiments, the isolated antibody or antigen-binding fragment according to the present disclosure is administered in combination with an ACE inhibitor, particularly selected from the group consisting of enalapril, captopril, lisinopril, ramipril, delapril, fosinopril, quinopril, perindopril, benazepril and trandopril.

In particular embodiments, the isolated antibody or antigen-binding fragment according to the present disclosure is administered in combination with an endothelin antagonist, particularly selected from the group consisting of bosentan, darusentan, ambrisentan, tezosentan, sitaxsentan, avosentan, macitentan and atrasentan.

In particular embodiments, the isolated antibody or antigen-binding fragment according to the present disclosure is administered in combination with a renin inhibitor, particularly selected from the group consisting of aliskiren, SPP-600 and SPP-800.

In particular embodiments, the isolated antibody or antigen-binding fragment according to the present disclosure is administered in combination with a mineralocorticoid receptor antagonist, particularly selected from the group consisting of finerenone, spironolactone, canrenone, potassium canrenoate, eplerenone, esaxerenone (CS-3150), or apararenone (MT-3995), CS-3150, and MT-3995.

In particular embodiments, the isolated antibody or antigen-binding fragment according to the present disclosure is administered in combination with a diuretic, particularly selected from the group consisting of furosemide, bumetanide, piretanide, torsemide, bendroflumethiazide, chlorothiazide, hydrochlorothiazide, xipamide, indapamide, hydroflumethiazide, methyclothiazide, polythiazide, trichloromethiazide, chlorothalidone, metolazone, quinethazone, acetazolamide, dichlorophenamide, methazolamide, glycerine, isosorbide, mannitol, amiloride and triamterene.

Fat metabolism altering agents are particularly selected from the group consisting of CETP inhibitors, thyroid receptor agonists, cholesterol synthesis inhibitors such as HMG-CoA-reductase or squalene synthesis inhibitors, ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and lipoprotein (a) antagonists.

In particular embodiments, the isolated antibody or antigen-binding fragment according to the present disclosure is administered in combination with a Nerf2 activator, particularly selected from Bardoxolone methyl.

In particular embodiments, the isolated antibody or antigen-binding fragment according to the present disclosure is administered in combination with a thyroid receptor agonist, particularly selected from the group consisting of D-thyroxin, 3,5,3'-triiodothyronin (T3), CGS 23425 and axitirome (CGS 26214).

In particular embodiments, the isolated antibody or antigen-binding fragment according to the present disclosure is administered in combination with an HMG-COA-reductase inhibitor from the class of statins, particularly selected from the group consisting of lovastatin, simvastatin, pravastatin, fluvastatin, atorvastatin, rosuvastatin and pitavastatin.

In particular embodiments, the isolated antibody or antigen-binding fragment according to the present disclosure is administered in combination with a PPAR-gamma modulator, particularly selected from pioglitazone and rosiglitazone.

In particular embodiments, the isolated antibody or antigen-binding fragment according to the present disclosure is administered in combination with a PPAR-delta modulator, particularly selected from the group consisting of ASP1128, GW 501516 and BAY 68-5042.

In particular embodiments, the isolated antibody or antigen-binding fragment according to the present disclosure is administered in combination with a cholesterol absorption inhibitor, particularly selected from the group consisting of ezetimibe, tiqueside and pamaqueside.

In particular embodiments, the isolated antibody or antigen-binding fragment according to the present disclosure is administered in combination with a lipase inhibitor, particularly selected from orlistat.

In particular embodiments, the isolated antibody or antigen-binding fragment according to the present disclosure is administered in combination with a polymeric bile acid adsorber, particularly selected from the group consisting of cholestyramine, colestipol, colesolvam, CholestaGel and colestimide.

In particular embodiments, the isolated antibody or antigen-binding fragment according to the present disclosure is administered in combination with a bile acid reabsorption inhibitor, particularly selected from the group consisting of ASBT (IBAT) inhibitors such as AZD-7806, S-8921, AK-105, BARI-1741, SC-435 and SC-635.

In particular embodiments, the isolated antibody or antigen-binding fragment according to the present disclosure is administered in combination with a lipoprotein (a) antagonist, particularly selected from the group consisting of gemcabene calcium (CI-1027) and nicotinic acid.

In particular embodiments, the isolated antibody or antigen-binding fragment according to the present disclosure is administered in combination with a TGFbeta antagonist, particularly selected from pirfenidone and fresolimumab.

In particular embodiments, the isolated antibody or antigen-binding fragment according to the present disclosure is administered in combination with anti-microRNA-21 oligonucleotides, particularly selected from Lademirsen.

In particular embodiments, the isolated antibody or antigen-binding fragment according to the present disclosure is administered in combination with HIF-PH inhibitors, particularly selected from molidustat and roxadustat.

In particular embodiments, the isolated antibody or antigen-binding fragment according to the present disclosure is administered in combination with a CCR2 antagonist, particularly selected from CCX-140.

In particular embodiments, the isolated antibody or antigen-binding fragment according to the present disclosure is administered in combination with a TNFalpha antagonist, particularly selected from adalimumab.

In particular embodiments, the isolated antibody or antigen-binding fragment according to the present disclosure is administered in combination with a galectin-3 inhibitor, particularly selected from GCS-100.

In particular embodiments, the isolated antibody or antigen-binding fragment according to the present disclosure is administered in combination with a hepatocyte growth factor mimeticmimetics, particularly selected from Refanalin.

In particular embodiments, the isolated antibody or antigen-binding fragment according to the present disclosure is administered in combination with a p53 modulator, particularly selected from QPI-1002.

In particular embodiments, the isolated antibody or antigen-binding fragment according to the present disclosure is administered in combination with a NOX1/4 inhibitor, particularly selected from GKT-137831.

In particular embodiments, the isolated antibody or antigen-binding fragment according to the present disclosure is administered in combination with a medicament which affects the vitamin D metabolism, particularly selected from cholecalciferol and paracalcitol.

In particular embodiments, the isolated antibody or antigen-binding fragment according to the present disclosure is administered in combination with a cytostatic agent, particularly selected from cyclophosphamide.

In particular embodiments, the isolated antibody or antigen-binding fragment according to the present disclosure is administered in combination with anti-VEGF therapy, particularly selected from the group consisting of ranibizumab, bevacizumab and aflibercept.

In particular embodiments, the isolated antibody or antigen-binding fragment according to the present disclosure is administered in combination with an immunosuppressive agent, particularly selected from ciclosporin.

In particular embodiments, the isolated antibody or antigen-binding fragment according to the present disclosure is administered in combination with a phosphate binder, particularly selected from sevelamer and lanthanum carbonate.

In particular embodiments, the isolated antibody or antigen-binding fragment according to the present disclosure is administered in combination with a calcimimetic for therapy of hyperparathyroidism.

In particular embodiments, the isolated antibody or antigen-binding fragment according to the present disclosure is administered in combination with agents for iron deficit therapy, particularly selected from iron products.

In particular embodiments, the isolated antibody or antigen-binding fragment according to the present disclosure is administered in combination with agents for the therapy of hyperurikaemia, particularly selected from allopurinol and rasburicase.

In particular embodiments, the isolated antibody or antigen-binding fragment according to the present disclosure is administered in combination with glycoprotein hormone for the therapy of anaemia, particularly selected from erythropoietin.

In particular embodiments, the isolated antibody or antigen-binding fragment according to the present disclosure is administered in combination with biologics for immune therapy, particularly selected from the group consisting of abatacept, rituximab, eculizumab and belimumab.

In particular embodiments, the isolated antibody or antigen-binding fragment according to the present disclosure is administered in combination with Jak inhibitors, particularly selected from the group consisting of ruxolitinib, tofacitinib, baricitinib, CYT387, GSK2586184, lestaurtinib, pacritinib (SB1518) and TG101348.

In particular embodiments, the isolated antibody or antigen-binding fragment according to the present disclosure is administered in combination with prostacyclin analogs for therapy of microthrombi.

In particular embodiments, the isolated antibody or antigen-binding fragment according to the present disclosure is administered in combination with an alkali therapy, particularly selected from sodium bicarbonate.

In particular embodiments, the isolated antibody or antigen-binding fragment according to the present disclosure is administered in combination with an mTOR inhibitor, particularly selected from everolimus and rapamycin.

In particular embodiments, the isolated antibody or antigen-binding fragment according to the present disclosure is administered in combination with an NHE3 inhibitor, particularly selected from AZD1722.

In particular embodiments, the isolated antibody or antigen-binding fragment according to the present disclosure is administered in combination with an eNOS modulator, particularly selected from sapropterin.

In particular embodiments, the isolated antibody or antigen-binding fragment according to the present disclosure is administered in combination with a CTGF inhibitor, particularly selected from FG-3019.

In particular embodiments, the isolated antibody or antigen-binding fragment according to the present disclosure is administered in combination with one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), and positive-inotropic agents.

In particular embodiments, the isolated antibody or antigen-binding fragment according to the present disclosure is administered in combination with one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), positive-inotropic agents, anti-inflammatory agents, immunosuppressive agents, phosphate binders and antibodies which modulate vitamin D metabolism.

Combination therapy includes administration of a single pharmaceutical dosage formulation which comprises the antibody or antigen-binding fragment according to the present disclosure or a variant thereof and one or more additional therapeutic agents, as well as administration of the antibody or antigen-binding fragment according to the present disclosure and each additional therapeutic agent in its own separate pharmaceutical dosage formulation. For example, an antibody of the disclosure or an antigen-binding fragment thereof or a variant thereof and a therapeutic agent may be administered to the patient together in a single liquid composition, or each agent may be administered in separate dosage formulation.

Where separate dosage formulations are used, the antibody or antigen-binding fragment according to the present disclosure or the variant thereof and one or more additional therapeutic agents may be administered at essentially the same time (e.g., concurrently) or at separately staggered times (e.g., sequentially).

The antibody or the antigen-binding fragment according to the present disclosure or a variant thereof might be used in combination with surgical interventions, including but not limited to:

major cardiovascular surgeries e.g. coronary artery bypass grafting (CABG), heart valve repair or replacement, insertion of a pacemaker or an implantable cardioverter defibrillator (ICD), maze surgery, aneurysm repair, arotid artery surgery/endarterectomy and thrombectomy;

major non-cardiac surgeries e.g., thoracic, orthopedic urologic surgeries.

Diagnostic Methods

Furthermore, the antibody or antigen-binding fragment according to the present disclosure may be utilized, as such or in compositions, in research and diagnostics, or as analytical reference standards, and the like.

Anti-Sema3A antibodies or antigen-binding fragments thereof can be used for detecting the presence of Sema3A. Thus, in a further aspect, the present disclosure relates to the isolated antibody or antigen-binding fragment according to the present disclosure or the antibody conjugate according to the present disclosure for use as a diagnostic agent.

Pharmaceutical Compositions and Administration

In a further aspect, the present disclosure relates to a pharmaceutical composition comprising the isolated antibody or antigen-binding fragment according to the present disclosure or the antibody conjugate according to the present disclosure. To treat any of the foregoing disorders, pharmaceutical compositions for use in accordance with the present disclosure may be formulated in any conventional manner using one or more physiologically acceptable carriers, excipients, or auxiliaries. Further details on techniques for formulation and administration may be found in the latest edition of Remington's Pharmaceutical Sciences (Ed. Maack Publishing Co, Easton, Pa.).

The antibody or antigen-binding fragment according to the present disclosure can be administered by any suitable means, which can vary, depending on the type of disorder being treated. Possible administration routes include oral, parenteral, and topical administration. Methods of parenteral delivery include intra-arterial, intramuscular, subcutaneous, intramedullary, intrathecal, intraventricular, intravenous, intraperitoneal, or intranasal administration. In addition, the antibody or antigen-binding fragment according to the present disclosure may be administered by pulse infusion, with, e.g., declining doses of the antibody. Preferably, administration is by injections, most preferably intravenous or subcutaneous injections, depending in part on whether the administration is brief or prolonged. The amount to be administered will depend on a variety of factors such as the clinical symptoms, weight of the individual, whether other drugs are administered, and the like. The skilled artisan will recognize that the route of administration will vary depending on the disorder or condition to be treated.

The pharmaceutical composition according to the present disclosure comprises the antibody or antigen-binding fragment according to the present disclosure alone or in combination with at least one other agent, such as a stabilizing compound. The antibody or antigen-binding fragment according to the present disclosure may be administered in any sterile, biocompatible pharmaceutical carrier, including, but not limited to, saline, buffered saline, dextrose, and water. In particular embodiments, the pharmaceutical composition according to the present disclosure may comprise one or more further pharmaceutically active compounds, in particular one or more further pharmaceutically active compounds that are suitable to treat Sema3A associated disorders. Any of these agents can be administered to a patient alone, or in combination with other agents or drugs, in pharmaceutical compositions where it is mixed with excipient(s) or pharmaceutically acceptable carriers. In particular embodiments, the pharmaceutically acceptable carrier is pharmaceutically inert.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methylcellulose, hydroxypropylmethylcellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores can be provided with suitable coatings such as concentrated sugar solutions, which may also contain gum arabic, talc, polyvinyl pyrrolidone, carbopol gel, polyethylene glycol and/or titanium dioxide, lacquer solutions, and suitable organic solvents or solvent mixtures. Dyestuffs or pigments may be added to the tablets or dragee coatings for product identification or to characterize the quantity of active compound, i.e. dosage.

Pharmaceutical preparations that can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the disclosure may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present disclosure may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a salt and can be formed with acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine or phosphate or Tris, 0.1%-2% sucrose and/or 2%-7% mannitol at a pH range of 4.5 to 7.5 optionally comprising additional substances like polysorbate that is combined with buffer prior to use.

After pharmaceutical compositions comprising a compound of the disclosure formulated in an acceptable carrier have been prepared, they can be placed in an appropriate container and labeled for treatment of an indicated condition. For administration of anti-Sema3A antibodies or antigen-binding fragment thereof, such labeling would include amount, frequency and method of administration.

Therapeutically Effective Dose

The determination of an effective dose is well within the capability of those skilled in the art. Determining a therapeutically effective amount of the novel antibody of this disclosure or an antigen-binding fragment thereof or a variant thereof, largely will depend on particular patient characteristics, route of administration, and the nature of the disorder being treated. General guidance can be found, for example, in the publications of the International Conference on Harmonization and in REMINGTON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

For any compound, the therapeutically effective dose can be estimated initially either in cell culture assays, or in animal models, usually mice, rabbits, dogs, pigs or monkeys. The animal model is also used to achieve a desirable concentration range and route of administration. Such information can then be used to determine useful doses and routes for administration in humans.

A therapeutically effective dose refers to that amount of antibody or antigen-binding fragment thereof, that ameliorates the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Long acting pharmaceutical compositions might be administered for example every 3 to 4 days, every week, once every two weeks, or once every three weeks, depending on half-life and clearance rate of the particular formulation.

Normal dosage amounts may vary from 0.1 to 100,000 micrograms, up to a total dose of about 10 g, depending upon the route of administration. Guidance as to particular dosages and methods of delivery is provided in the literature. See U.S. Pat. Nos. 4,657,760; 5,206,344; or 5,225,212.

Kits

In a further aspect, the present disclosure relates to a kit comprising the isolated antibody or antigen-binding fragment according to the present disclosure or the conjugate according to the present disclosure and instructions for use. In particular embodiments, the kit comprises one or more containers filled with one or more of the ingredients of the aforementioned compositions of the disclosure. Associated with such container(s) can be a notice in the form prescribed by a governmental agency regulating the manufacture, use or sale of pharmaceuticals or biological products, reflecting approval by the agency of the manufacture, use or sale of the product for human administration.

DRAWINGS

FIG. 1A: Effects of Sema3A inhibition with TPP-15370 (grey bar), TPP-11489 (striped bar) and TPP-17755 (squared bar) on Sema3A-induced albumin excretion in mice. Shown are mean±S.D. (n=10). *, **:p<0.001 p<0.0001 vs. isotype control. Dunnett's post hoc test.

Figure 1B:
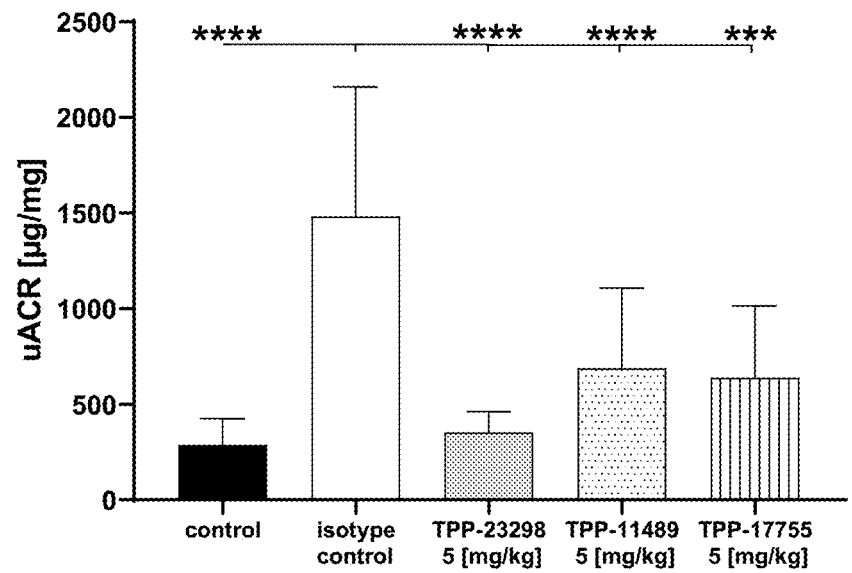

FIG. 1B: Effects of Sema3A inhibition with TPP-23298 (grey bars), TPP-11489 (dotted bar) and TPP-17755 (striped bar) on Sema3A-induced albumin excretion in mice. Shown are mean±S.D. (n=10). *, **:p<0.001 p<0.0001 vs. isotype control. Dunnett's post hoc test.

Figure 2A:
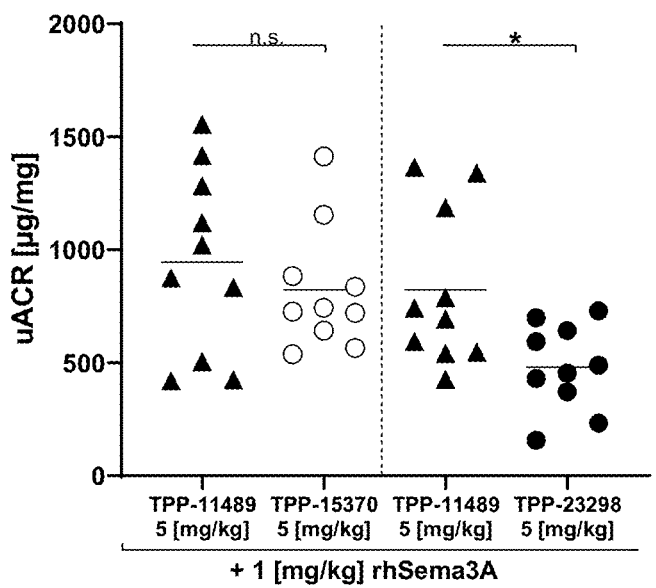

FIG. 2A: Sema3A induced albuminuria in mice after treatment with TPP-15370 (white circles) and TPP-23298 (black circles) in comparison to TPP-11489 (black triangles). The comparisons were performed in two separate experiments. Shown are mean values. (n=10). n.s.=statistically not significant vs. TPP-15370; *=p<0.05 vs. TPP-23298. Unpaired T-test.

Figure 2B:
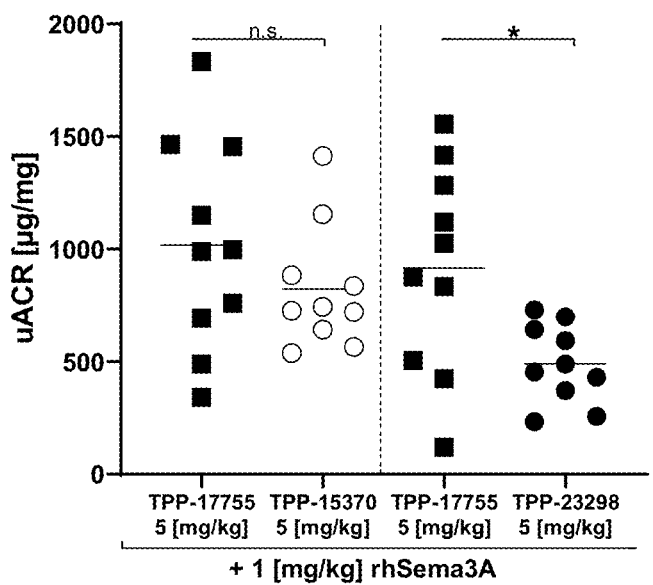

FIG. 2B: Sema3A induced albuminuria in mice after treatment with TPP-15370 (white circles) and TPP-23298 (black circles) in comparison to TPP-17755 (black squares). The comparisons were performed in two separate experiments. Shown are mean values. (n=10). n.s.=statistically not significant vs. TPP-15370; *=p<0.05 vs. TPP-23298. Unpaired T-test.

Figure 2C:
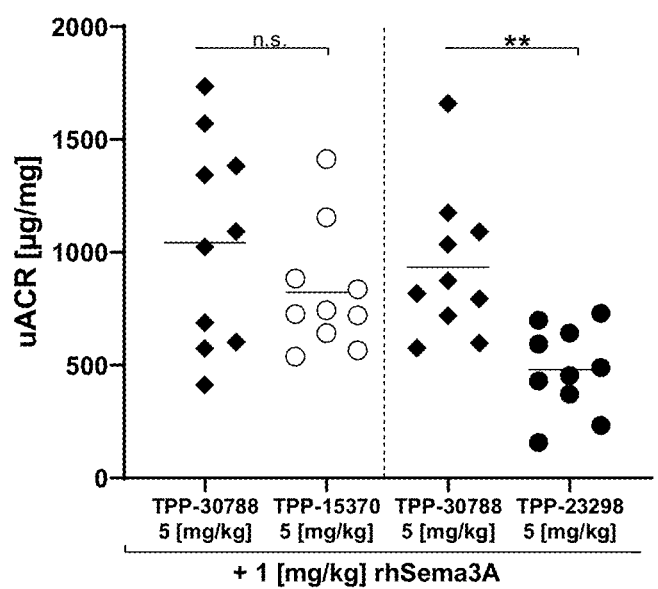

FIG. 2C: Sema3A induced albuminuria in mice after treatment with TPP-15370 (white circles) and TPP-23298 (black circles) in comparison to TPP-30788 (black rhombus). The comparisons were performed in two separate experiments. Shown are mean values. (n=10). n.s.=statistically not significant vs. TPP-15370; *=p<0.05 vs. TPP-23298. Unpaired T-test.

Figure 3A:
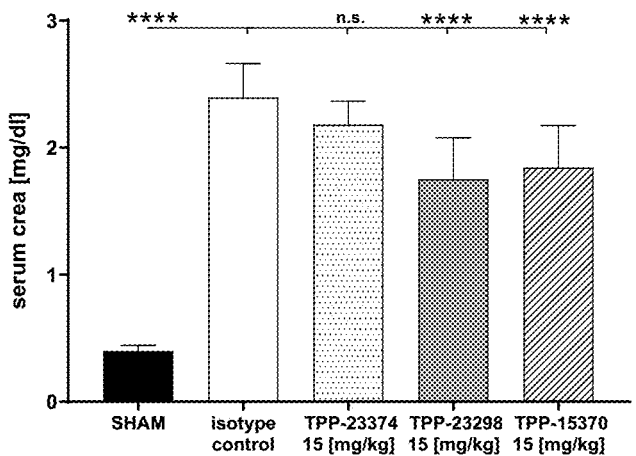
Figure 3B:
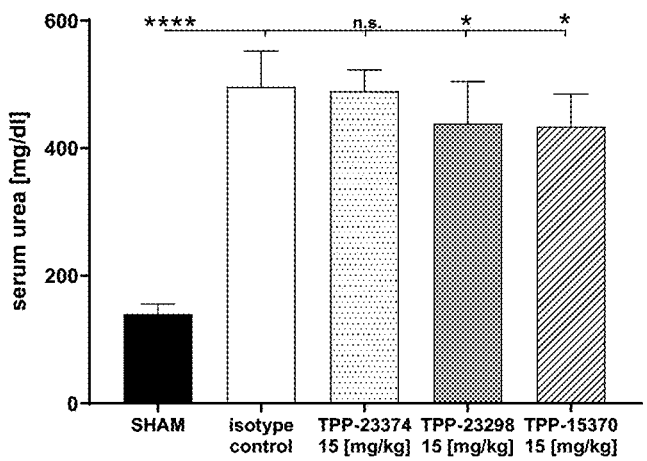
Figure 3C:
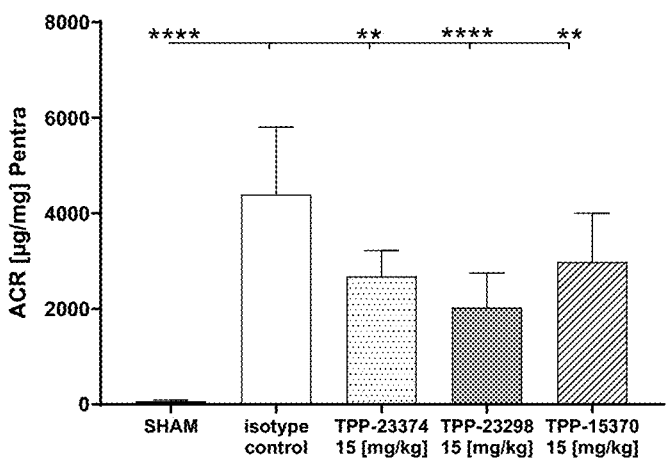

FIGS. 3A-3C: Effects of Sema3A inhibition with TPP-23374 (dotted bars) TPP-23298 (grey bars) and TPP-15370 (striped bars) on FIG. 3A: serum creatinine levels, FIG. 3B: serum urea levels and FIG. 3C: urinary albumin excretion after I/R injury in mice. Shown are mean±S.D. (n=8-10). *, , **:p<0.05, p<0.01, p<0.0001 vs. isotype control. Dunnett's post hoc test.

Figure 4A:
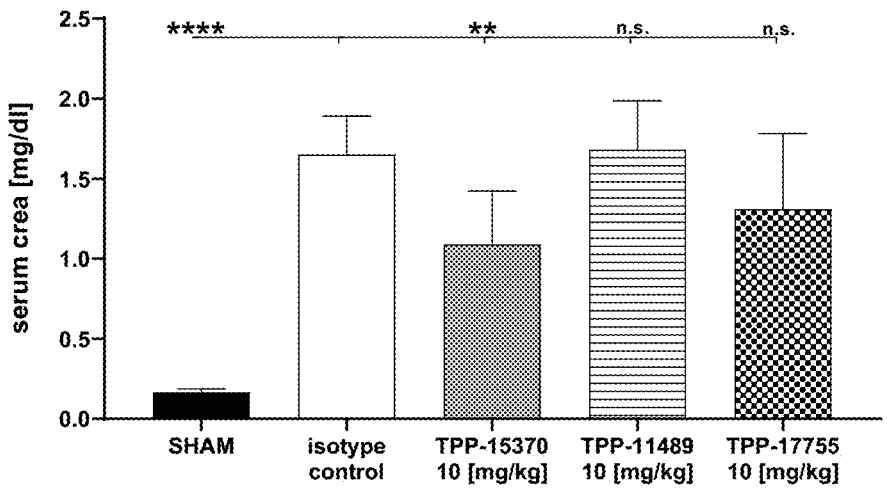
Figure 4B:
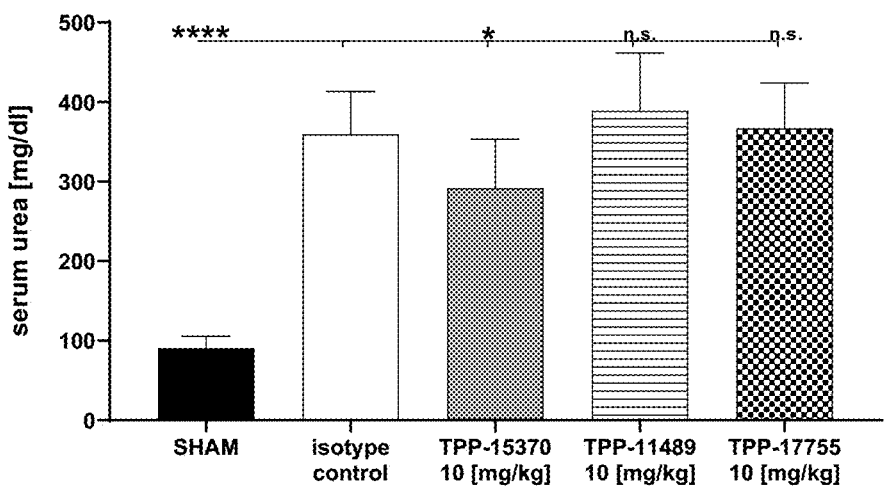
Figure 4C:
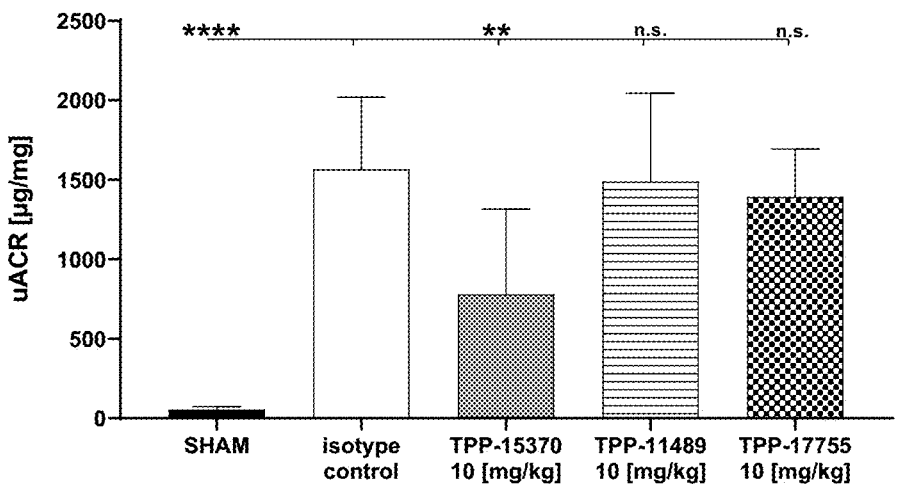

FIGS. 4A-4C: Effects of Sema3A inhibition with TPP-15370 (grey bars), TPP-11489 (striped bars) and TPP-17755 (squared bars) on FIG. 4A: serum creatinine levels, FIG. 4B: serum urea levels and FIG. 4C: urinary albumin excretion after I/R injury in mice. Shown are mean±S.D. (n=8-10). *, , **:p<0.05, p<0.01, p<0.0001 vs. isotype control. Dunnett's post hoc test.

Figure 5A:
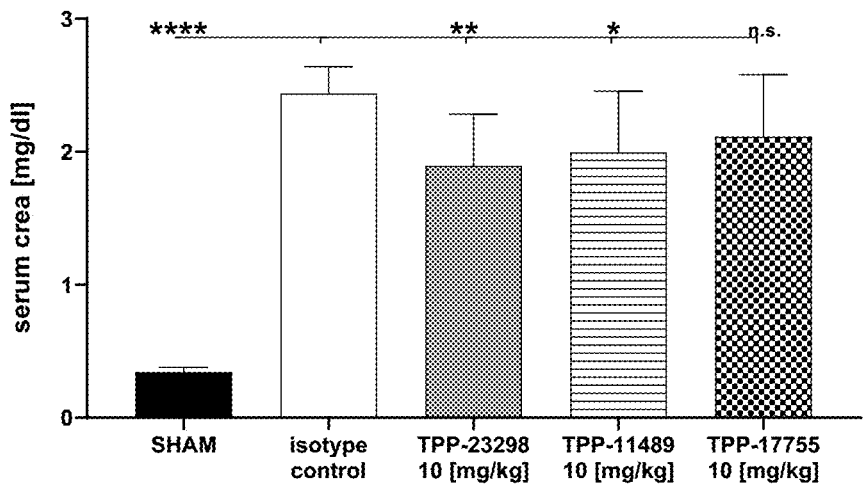
Figure 5B:
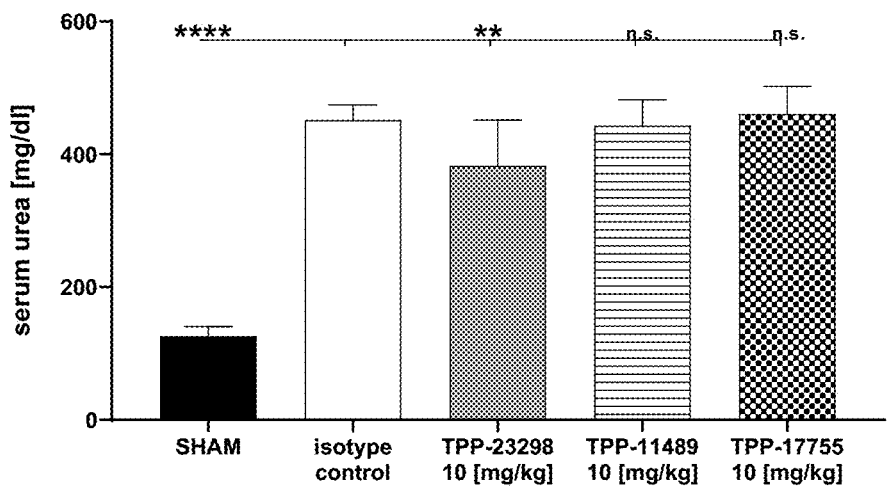
Figure 5C:
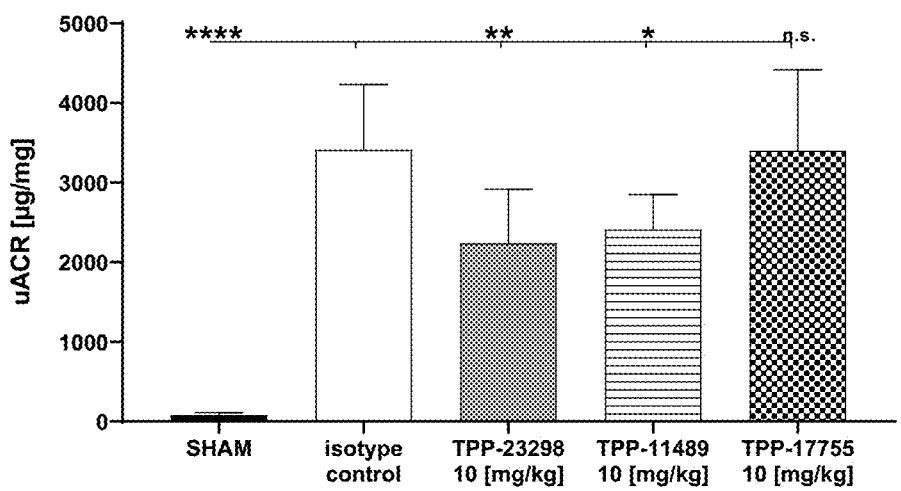
Figure 6A:
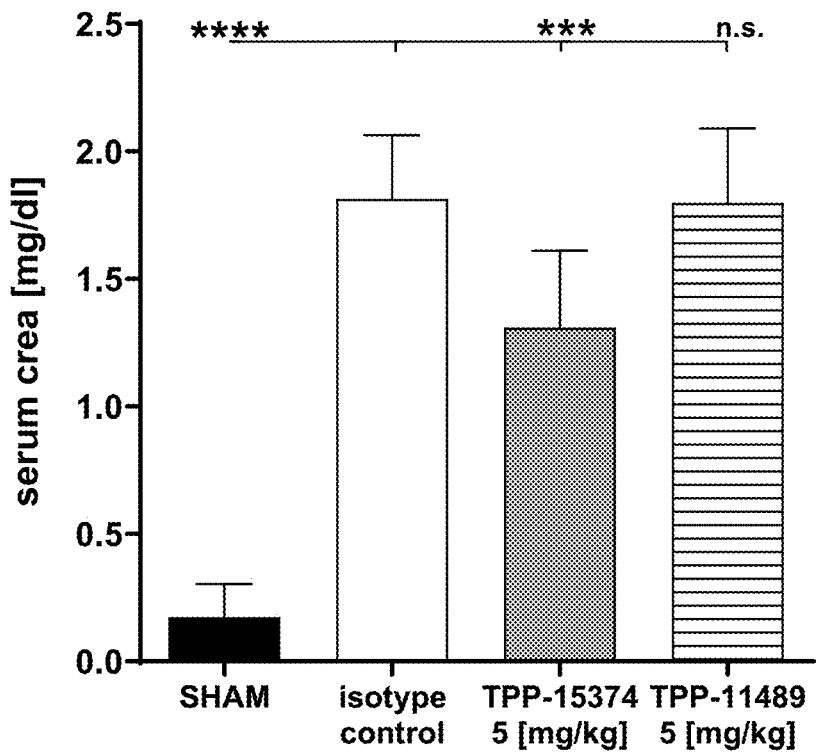
Figure 6B:
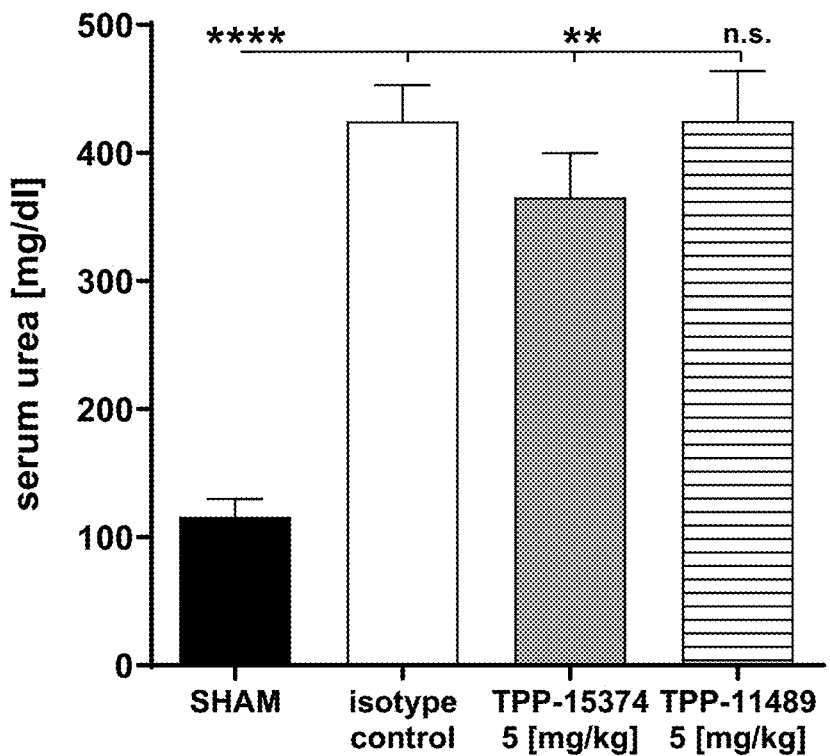
Figure 6C:
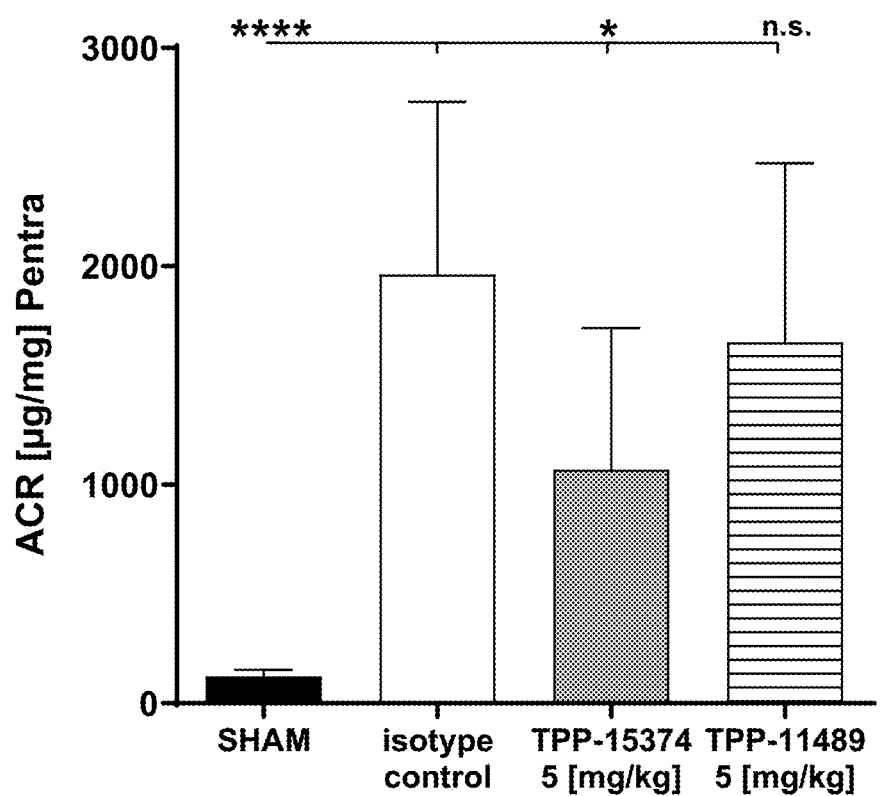

FIGS. 5A-5C: Effects of Sema3A inhibition with TPP-23298 (grey bars), TPP-11489 (striped bars) and TPP-17755 (squared bars) on FIG. 5A: serum creatinine levels, FIG. 5B: serum urea levels and FIG. 5C: urinary albumin excretion after I/R injury in mice. Shown are mean±S.D. (n=10-12) . *, , :p<0.05, p<0.01, p<0.0001 vs. isotype control. Dunnett's post hoc test FIGS. 6A-6C: Effects of Sema3A inhibition with TPP-15374 (grey bars), TPP-11489 (striped bars) on FIG. 6A: serum creatinine levels, FIG. 6B: serum urea levels and FIG. 6C**: urinary albumin excretion after I/R injury in mice. Shown are mean±S.D. (n=10-12). *, , *, ****:p<0.05, p<0.01, p<0.001 p<0.0001 vs. isotype control. Dunnett's post hoc test.

Figure 7:
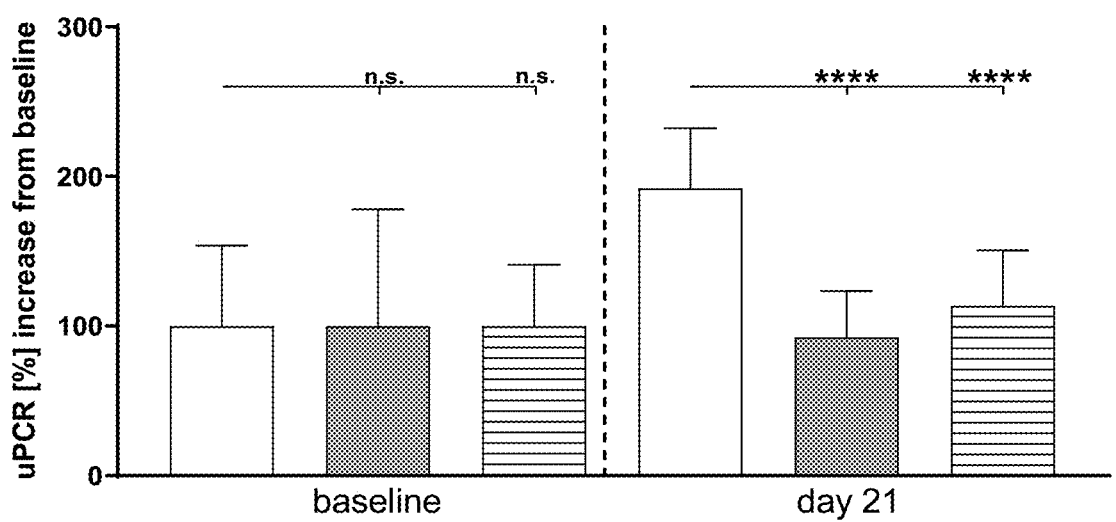
Figure 8A:
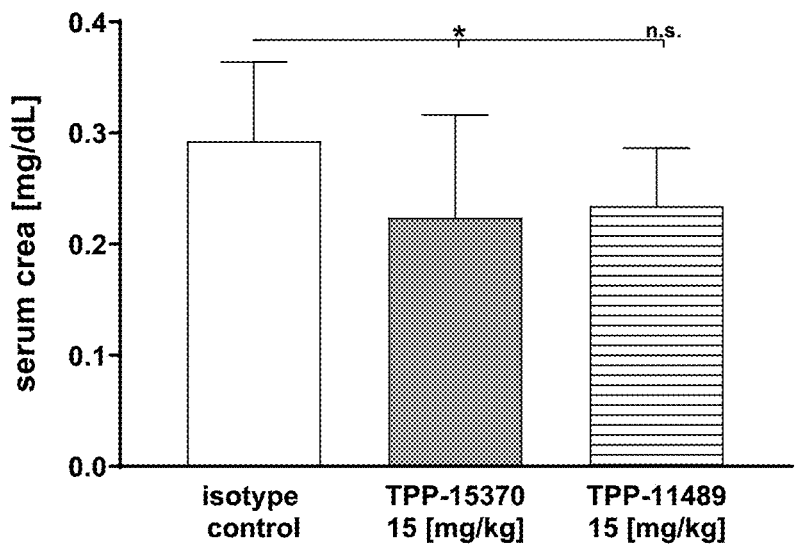
Figure 8B:
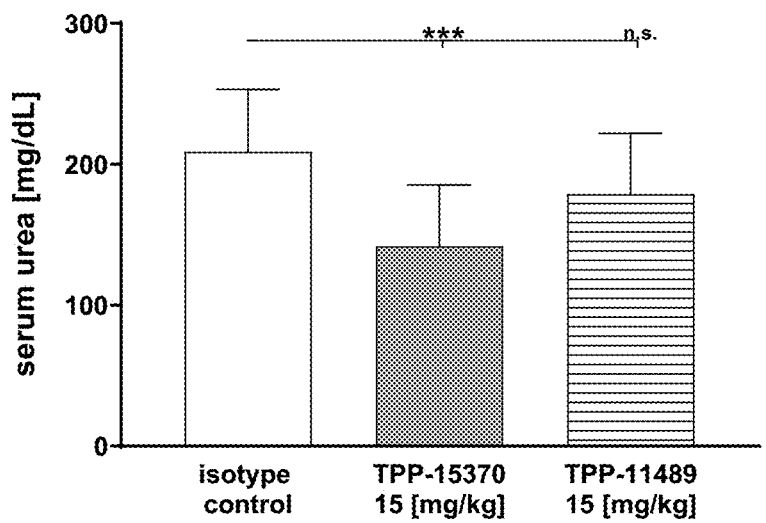
Figure 8C:
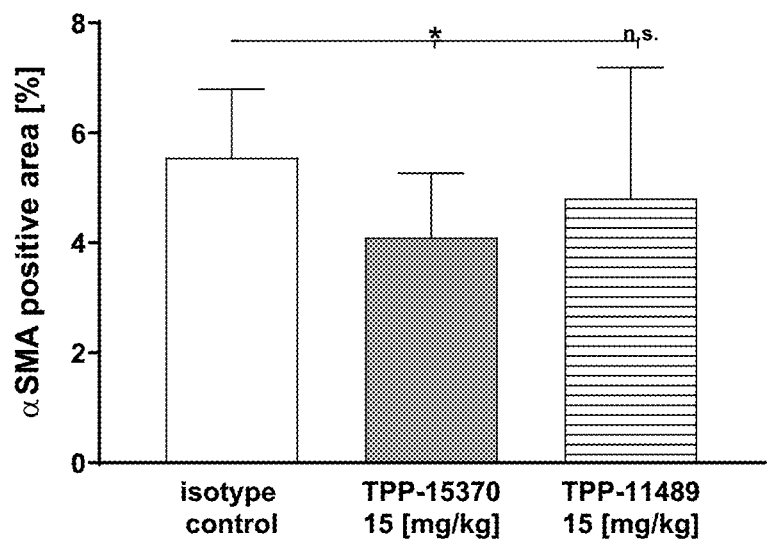
Figure 8D:
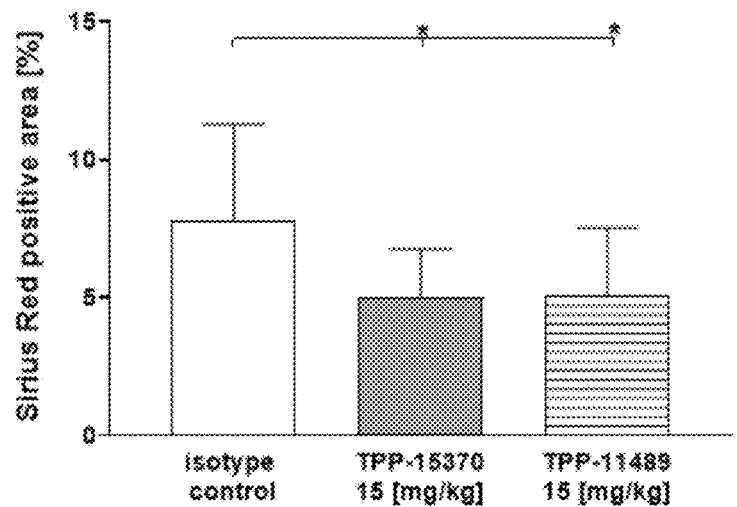

FIG. 7: Effects of Sema3A inhibition with TPP-15370 (grey bars), TPP-11489 (striped bars) on proteinuria in Alport mice. Shown are mean±S.D. (n=8-10). ****: p<0.0001 vs. isotype control. Dunnett's post hoc test.

Figure 9A:
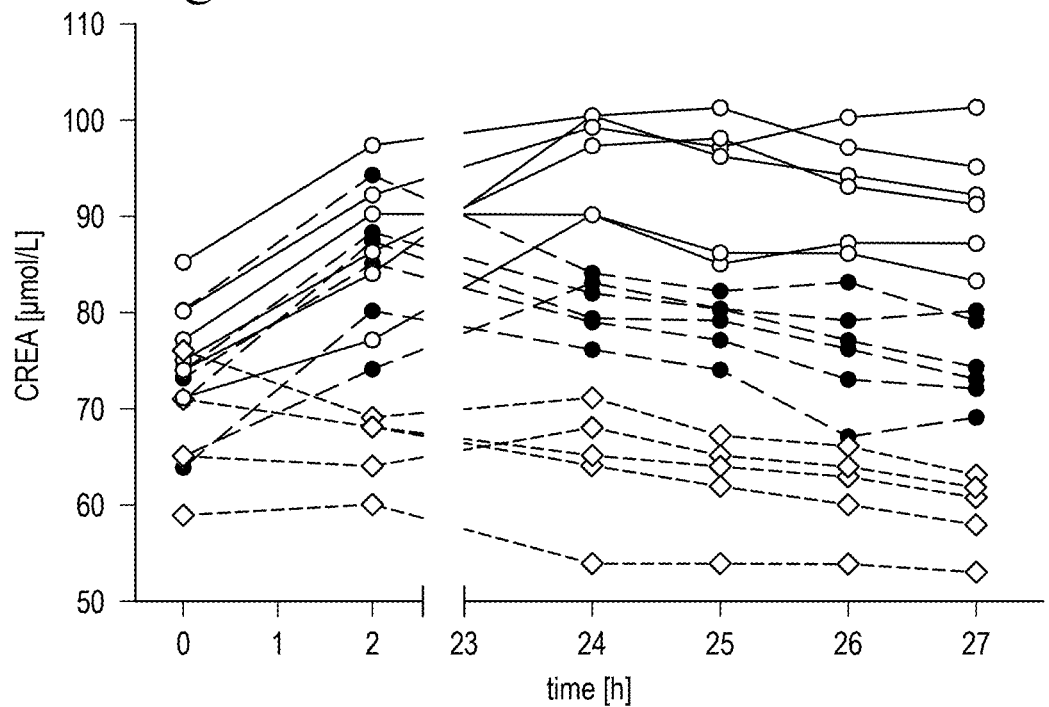
Figure 9B:
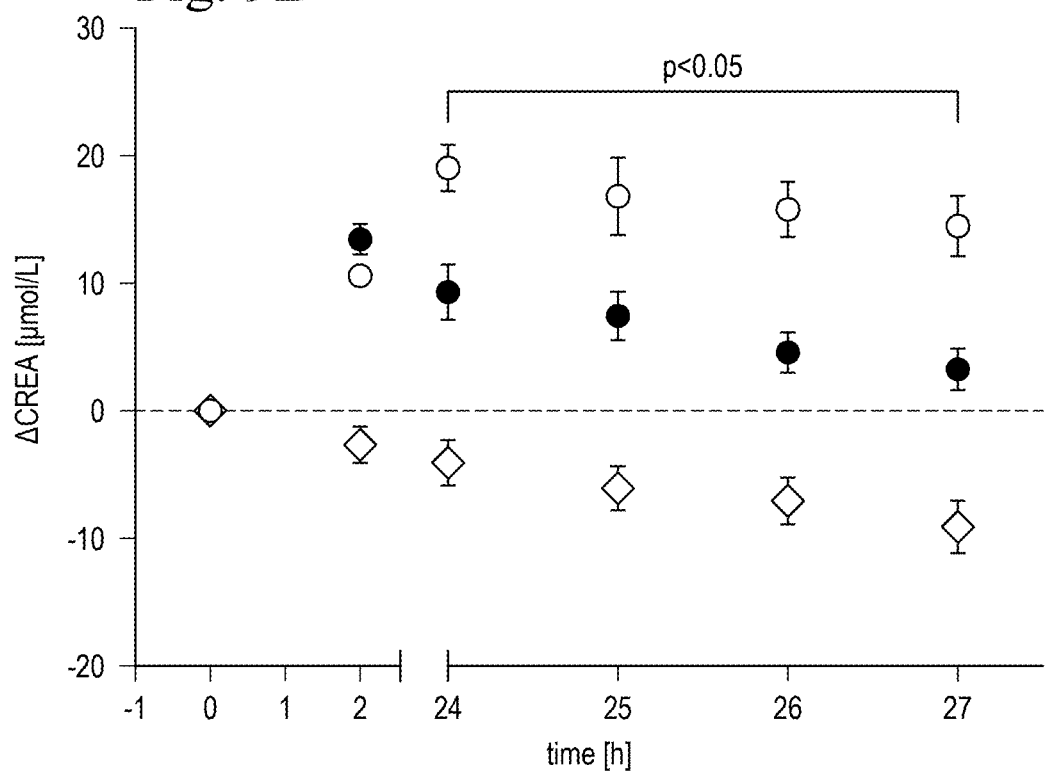
Figure 10C:
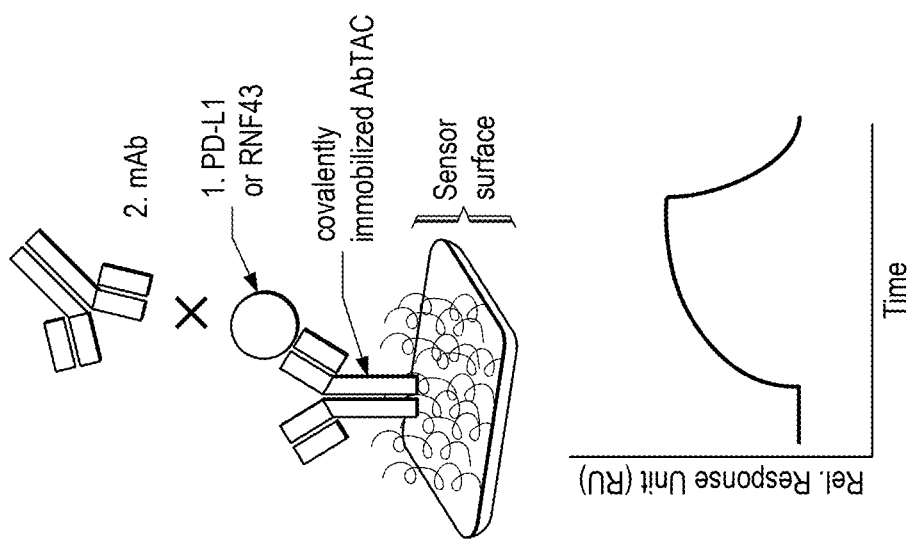
Figure 10B:
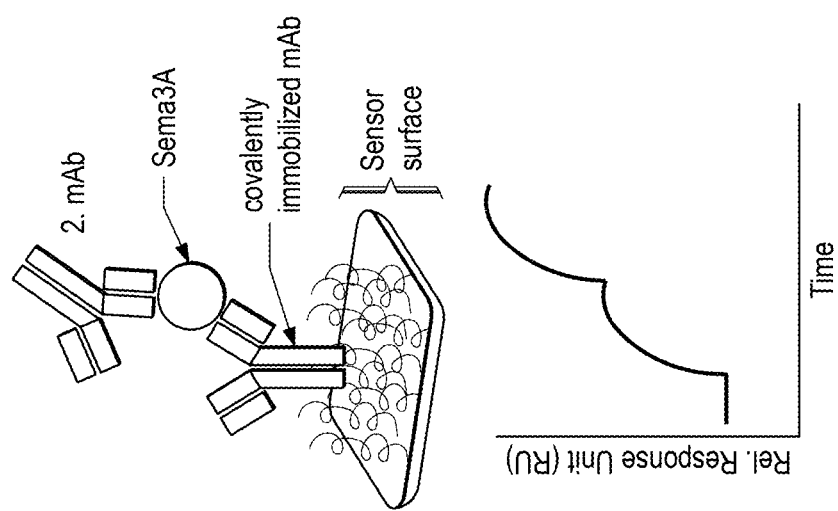
Figure 10A:
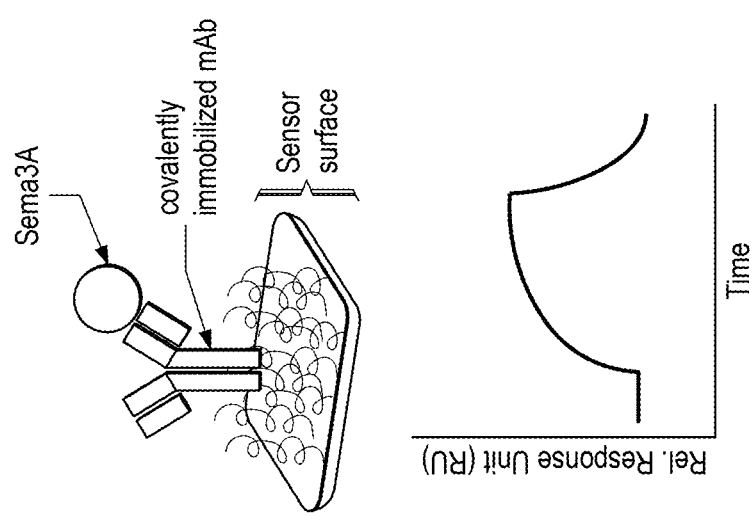

FIGS. 8A-8D: Effects of Sema3A inhibition with TPP-15370 (grey bars), TPP-11489 (striped bars)) on FIG. 8A: serum creatinine levels, FIG. 8B: serum urea levels and fibrosis FIG. 8C: myofibroblast and FIG. 8D: collagen deposition in Alport mice. Shown are mean±S.D. *, **:p<0.05, p<0.001, p<0.0001 vs. isotype control. Dunnett's post hoc test. (n=8-10). *, *, FIGS. 9A-9D: Effects of Sema3A inhibition with TPP-23298 in a single dose preventive setting in a unilateral kidney IRI model in pigs, 105 min of ischemia. TPP-23298 (FIG. 9A**; black dots) or control IgG (open circles) (10 mg/kg) were given 30 min before inflating the balloon in the left renal artery. Values from SHAM animals are indicated diamonds. Time course of plasma creatinine concentrations of individual animals (FIG. 9A), and time course of mean change of creatinine plasma concentrations versus base line values at start of experimentation (0 h) (FIG. 9B). Mean values of creatinine clearance for 24-27 h interval. Creatinine clearance side separated for left (damaged) and right (non-damaged) kidneys and kidneys from sham animals (FIG. 9C). Global creatinine clearance (FIG. 9D); means±SEM, p-value in (FIG. 9B) from t-test, */*** in (FIG. 9C) and FIG. 9D): p<0.05/0.001, one-way ANOVA versus corresponding control followed by Dunnett's multiple comparison FIGS. 10A-10C: Schematic representation of a sandwich-based epitope binning experiment using SPR (see also Example 5A): FIG. 10A) One antibody is immobilized to a SPR chip, Sema3A is injected, and the binding is monitored; FIG. 10B) A second (competitive) antibody is injected on to the complex of the immobilized mAb bound to Sema3A, and the binding is monitored; FIG. 10C) A second (non-competitive) antibody is injected on to the complex of the immobilized mAb bound to Sema3A, and the binding is monitored.

FIGS. 11A-11C: HRA image analysis steps: FIG. 11A) Fluorescence microscopy image of DAPI/CM cells; FIG. 11B) Identification of cells in the selected area; FIG. 11C) Calculation of cells-free region size (grey area).

FIG. 12: The percent inhibition of Sema3A in a HUVEC repulsion assay at an antibody concentration of 80 pM is shown (see Example 11). Each column represents one antibody in the following left to right order: TPP-23298 (black column), TPP-30788, TPP-TPP-30789, TPP-30790, and TPP-30791.

EXAMPLES

Example 1: Sema3A Sequences and Tool Generation the control of a CMV promoter and sequences contain a C-terminal FXa cleavage site followed by a 6× his-tag. Cell culture was performed using F17 medium (Life Technologies) supplemented with 0.1% pluronic F68 (Life Technologies) and 4 mM Glutamax (Life Technologies). 24 h post-transfection, 1% FCS ultra-low IgG (Life Technologies) and 0.5 mM valproic acid (Sigma Aldrich) were added. Cell supernatant was sterile filtered and subsequently purified or concentrated via crossflow filtration prior to purification.

Sema3A domains were purified using a two-step purification consisting of affinity and size exclusion chromatography. In brief, cell culture supernatant was loaded on to a $Ni^{2+}$-NTA column (GE Healthcare) connected to an Äkta Avant system (GE Healthcare). Column was equilibrated with 4 CV of 50 mM $NaH_2PO_4$, 300 mM NaCl, pH 8 and washed afterwards with 10 CV of running buffer until baseline was reached. Elution was carried out using 6 CV of running buffer containing 250 mM imidazole, pH 8.0. Fractions of the elution peak were unified, concentrated using a Vivaflow 200 Hydrosart membrane (cut-off 10 kDa, Sartorius) and subjected to size exclusion chromatography using a Superdex 200 column (GE Healthcare) connected to an Äkta Pure 25 system. The column was equilibrated and run in DPBS, pH 7.4. Fractions of the domain elution peak were unified and concentrated using a Vivaflow 200 Hydrosart membrane (cut-off 10 kDa, Sartorius). The final protein quality was assessed on an analytical size exclusion chromatography (Superdex 200) for purity and monodispersity as well as SDS-PAGE. Sema domains were aliquoted and snap frozen in liquid nitrogen and stored at −80° C. until further use.

Example 2: Antibody Generation from BioInvent Antibody Libraries

A fully human antibody phage display library (BioInvent n-CoDeR Fab lambda library) was used to isolate human monoclonal antibodies of the present disclosure by selection against recombinant human Sema3A (TPP-13211, R&D Systems) using the following protocol. Briefly, Immuno-

TABLE 2

Tools used in this disclosure

| TPP-No. | Protein | Bounderies [aa] | Uniprot ID | Catalog No. |
|---|---|---|---|---|
| TPP-13211 | Human Semaphorin3A-Fc (R&D Systems) | 26-771 | Q14563 | 1250-S3 |
| No TPP-No. | Human Semaphorin3G (Abnova) | 1-782 | Q9NS98 | H00056920-P01 |
| No TPP-No. | Human Semaphorin3F-Fc (R&D Systems) | 19-772 | Q13275 | 9878-S3 |
| TPP-13357 | Mouse Semaphorin3A-Fc (R&D Systems) | 21-747 | O08665 | 5926-S3 |
| TPP-19068 | Human Semaphorin3A - Sema Domain | 21-569 | Q14563 | Produced inhouse |
| TPP-19069 | Mouse Semaphorin3A - Sema Domain | 21-569 | O08665 | Produced inhouse |
| TPP-19122 | Cyno Semaphorin3A - Sema Domain | 21-569 | Q63548 | Produced inhouse |
| TPP-19120 | Rat Semaphorin3A - Sema Domain | 21-569 | E2QX94 | Produced inhouse |
| TPP-19121 | Dog Semaphorin3A - Sema Domain | 21-569 | A0A2K5VGJ0 | Produced inhouse |
| TPP-20176 | Pig Semaphorin3A - Sema Domain | 49-658 | A0A480WHT2 | Produced inhouse |

Sema3A domains were produced by mammalian cell culture using transiently transfected HEK293-6E cells (National Research Council Canada). All constructs were under tubes (Nunc) were coated for one hour at room temperature (RT) with the 100 µg of the target molecule (huSema3A) or an irrelevant Fc-containing off-target in 1 ml PBS (Phosphate Buffered Saline) with end-over-end rotation. The target and depletion antigen-coated immunotube as well as an empty immunotube were washed 4 times with PBS+ 0.05% Tween20 (PBST) and subsequently blocked using 3 ml of a 3% Milk powder in PBST solution for 1 h at RT with end-over-end rotation. An aliquot of the phage library was thawed and allowed to block in a solution of 3% milk powder in PBST for 1 h at RT with end-over-end rotation. The non-coated depletion immunotube was washed 3 times in 4 ml PBS before addition of the blocked phage library and incubation with end-over-end rotation for 30 min at RT. This step was repeated for the non-target antigen-coated depletion immunotube. The huSema3A-coated immunotube was washed 3 times in 4 ml PBS before addition of the depleted library and incubation for 90 min at room temperature with end-over-end rotation. After stringent washing (4 × with 4 ml PBST and 1 × with 4 ml PBS) Fab-expressing phages binding specifically to the coated target were eluted using 500 µl 100 nM TEA, 10 min incubation at room temperature followed by neutralization by addition of 500 µl Tris-HCl pH 7.5. 500 µl of eluted phage were used to infect *Escherichia coli* strain HB101. Subsequently the phages were amplified in *Escherichia coli* strain HB101 using M13KO7 Helper Phage (Invitrogen™). In two subsequent selection rounds the target concentration was decreased to 25 µg/ml. For a first qualitative assessment, 88 randomly picked Fab-expressing phage clones from each selection round were expressed in single wells and tested for binding to huSema3A compared to an irrelevant off-target. The clone pool from Round 3 in this example was found to contain a 60% positive hit rate and was chosen for further screening.

In a next step, the expression of soluble Fabs was enabled by bulk removal of the gene III fusion in this pool and 2208 single clones were picked for expression in *Escherichia coli* strain Top10 and evaluation of Fab-containing supernatants in a huSema3A binding ELISA. The VH and VL sequences for all 2208 clones was also determined using NGS methods. 154 distinct clones positive for binding to huSema3A were identified. These positive binding Fab fragments were tested in a confirmatory binding ELISA and were also evaluated for binding to mouse Sema3A-Fc (TPP-13357, R&D Systems) as well as specificity testing using an additional off target molecule, murine Sema3F (R&D Systems). Based on this analysis, 48 human/mouse cross-reactive Sema3A binding Fabs were prioritized. These Fab fragments were subsequently purified from 25 ml expression cultures using Capture Select CH1 matrix (LifeTechnologies), eluted using 12.5 mM Citric acid at pH 2.5 and finally buffer exchanged to PBS using a Zeba™ Spin desalting plate (ThermoFisher). A kinetic ranking was performed for all 48 purified Fab fragments by surface plasmon resonance (SPR), examining the binding to both human and mouse Sema3A and reformatted in to a full-length human IgG1 and again tested for binding in SPR (see Example 4).

Example 3: Sequence Optimization, Germlining & Affinity Maturation of Lead Antibodies TPP-15370 and TPP-15374

IgG1 antibodies TPP-15370 and TPP-15374 were subjected to lead optimization procedures aiming to (i) optimize its affinity, (ii) increase functional efficiency, (iii) reduce the risk of sequence-based immunogenicity and (iv) improve compatibility with downstream development processes.

Affinity maturation was done by a first single mutation gathering round followed by recombination of the most affinity- and potency-increasing amino acid exchanges in a germlined and sequence optimized antibody backbone.

For mutation gathering NNK (N=A or G or C or T, K=G or T) randomizations at the following individual amino acid positions were generated by site directed mutagenesis using synthetic oligonucleotides including NNK for codon-diversification. For TPP-15370 the following regions were analyzed for their effect on affinity: GFTFSSYGMH (residues 26 to 35 of VH SEQ ID NO: 41), WVSAIGTGGDTYYADSVMG (residues 47 to 65 of VH SEQ ID NO: 41), ARRDDYTSRDAFDV (residues 96 to 109 of VH SEQ ID NO:41), SGSSSNIGSNTVNWY (residues 23 to 37 of VL SEQ ID NO: 45), LLIYYDDLLPS (residues 47 to 57 of VL SEQ ID NO: 45), and AAWDDSLNGYVV (residues 90 to 101 of VL SEQ ID NO: 45).

For TPP-15374 the following regions were analyzed for their effect on affinity: GFTFSSYEMN (residues 26 to 35 of VH SEQ ID NO: 61), WVSGISWNSGSIGYADSVKG (residues 47 to 66 of VH SEQ ID NO: 61), ARSGYSSSWFDPDFDY (residues 97 to 112 of VH SEQ ID NO: 61), TGSSSNIGAGYDVHWY (residues 23 to 38 of VL SEQ ID NO: 65), LLIYGNSNRPS (residues 48 to 58 of VL SEQ ID NO: 65), and SSYAGSNPYV (residues 91 to 101 of VL SEQ ID NO: 65).

The resulting single NNK libraries were sequenced and about 1000 single amino acid exchange variants of TPP15370 and TPP-15374, respectively, were identified. They were expressed by transient transfection of mammalian cells and resulting expression supernatants were normalized in terms of antibody concentrations to be screened in surface plasmon resonance and competition ELISA.

For the germlining and sequence optimization process of TPP-15370 and TPP-15374 the closest germline families for light and heavy chain were selected and scrutinized for potential CMC relevant residues. Deviations from closest human germlines in CDR regions and FW regions and potential CMC relevant residues in CDR regions were adjusted by site directed mutagenesis and tested for in functional and biophysical assays (unspecific binding, temperature stability in DSC). The resulting single reversions and following combinatorial IgG variants were expressed by transient transfection of mammalian cells and resulting expression supernatants were normalized in terms of antibody concentrations to be screened in binding assays (SPR, competition ELISA) and functional assays. This led to germlined and sequence optimized molecules TPP-21565 for TPP-15370 and TPP-18533 for TPP-15374. TPP-21565 carries in comparison to TPP-15370 reversions L55R and R80Q in the light chain and G33A, H35S, M64K and V109Y in the heavy chain. TPP-18533 carries in comparison to TPP-15374 reversions A10V, T13A, S78T, R81Q, S82A in the light chain.

For the final recombination library of TPP-21565 eight single substitution variants that were shown in the NNK library screening step to exhibit improved affinity and functional efficiency were selected. Light chain mutations A90H, G98D, G98V, Y99I and V100P and heavy chain mutations S30Y, S35L and T53Y were recombined in one recombination library (continuous amino acid nomenclature, reference is TPP-21565 as defined by SEQ ID NOs: 121-VH and 125-VL).

For the final recombination library of TPP-18533 eleven single substitution variants that were shown in the NNK library screening step to exhibit improved affinity and functional efficiency were selected. Light chain mutations N28D, N53A, S91K, S91Q, A94E, S96I and S96P and heavy chain mutations T28D, S30D, S57W and G59Y were recombined in one recombination library (continuous amino acid nomenclature, reference is TPP-18533 as defined by SEQ ID NOs: 101-VH and 105-VL).

For TPP-18533 oligonucleotides were generated to introduce selected mutations or the corresponding wild type amino acid at each selected position. Library construction was performed using sequential rounds of overlap extension PCR. The final PCR product was ligated into a mammalian IgG4 (S228P) expression vector and variants were sequenced using massive-parallel sequencing techniques. For TPP-21565 the recombinatorial variants were designed as distinct clones and cloned into an IgG4 (S228P) containing expression plasmid.

More than 1000 unique combinatorial amino acid exchange variants of TPP-18533 and more than 100 unique combinatorial variants of TPP-21565 were generated in that way, expressed by transient transfection of mammalian cells, and resulting expression supernatants were normalized in terms of antibody concentrations to be screened in varying number in SPR, competition ELISA and functional assays. Based on the result in these assays, mutants were either categorized as 'improved' or 'non-improved'.

Table 1 and 1A lists i.a. preferred antibodies candidates according to the present disclosure that were selected in the combination library screening step as being most potent in terms of binding to Sema3A and in terms of antagonizing the Sema3A-dependent biological activity as well as the respective amino acid and nucleic acid sequences of antibodies according to the present disclosure.

Example 4: Determination of Affinity and Species Cross-Reactivity Using Surface Plasmon Resonance To assess the binding kinetics and affinity of anti-Sema3A antibodies as well as their species cross-reactivity profile, binding assays were conducted using surface plasmon resonance (SPR). Binding assays were performed on a Biacore T200 instrument or on a Biacore 8K+ instrument (Cytiva) at 25° C. using assay buffer HBS P+, 300 mM NaCl, 0.75 mM $CaCl_2$, 2.5 mM $MgCl_2$, 1 mg/ml BSA, 0.05% $NaN_3$. Antibodies were captured either via anti-human Fc IgGs ("Human antibody capture kit", Order No. BR100839, Cytiva) or in case of Fc-tagged analytes by anti-human Fab IgGs ("Human Fab capture kit", Order No. 28958325, Cytiva) covalently amine coupled to a Series S CM5 sensor chip (Cytiva). The amine coupling was carried out according to the manufacturer's instructions using 1-ethyl-3-(3-dimethylaminopropyl) carbodiimide hydrochloride (EDC), N-hydroxysuccinimide (NHS) and ethanolamine HCl, pH 8.5 ("Amine Coupling Kit" BR-1000-50, Cytiva.). For phage display hits Fc-tagged human and mouse Sema3A was used as analytes in a concentration range from 1.56-200 nM. Human, mouse, cynomolgus, rat, dog and pig monovalent Sema3A domain were used as analytes in a concentration series from 0.024-3.125 nM in multi cycle kinetics mode or in 100 nM for binding analysis only. The sensor surface was regenerated with glycine pH 2.0 after each antigen injection. Obtained sensorgrams were double referenced (subtraction of reference flow cell signal and buffer injection) and were fitted to a 1:1 Langmuir binding model to derive kinetic data using the Biacore T200 Evaluation software. Results are shown in Tables 3, 4 and 4a.

TABLE 3

Affinity of anti-Sema3A IgG1 antibodies derived from phage display hits determined by SPR using TPP-13211 and TPP-13357.

| Nomenclature | Mouse $K_D$ [M] | Human $K_D$ [M] |
|---|---|---|
| TPP-15355 | 4.0E−09 | 3.5E−09 |
| TPP-15356 | n.b. | 3.2E−09 |
| TPP-15357 | 1.0E−07 | 5.0E−08 |
| TPP-15358 | 3.1E−09 | 9.5E−10 |
| TPP-15359 | n.b. | 1.1E−08 |
| TPP-15360 | 1.1E−07 | 7.2E−09 |
| TPP-15361 | n.b. | 5.5E−09 |
| TPP-15362 | n.b. | n.b. |
| TPP-15363 | n.b. | 2.4E−09 |
| TPP-15364 | n.b. | 2.6E−09 |
| TPP-15365 | 2.4E−07 | 6.5E−08 |
| TPP-15366 | 1.4E−08 | 1.3E−08 |
| TPP-15367 | 5.4E−09 | 2.2E−09 |
| TPP-15368 | 8.2E−07 | 1.5E−07 |
| TPP-15369 | 4.1E−08 | 3.5E−08 |
| TPP-15370 | 3.2E−09 | 2.8E−09 |
| TPP-15371 | 7.4E−09 | 4.5E−09 |
| TPP-15372 | n.b. | 3.7E−09 |
| TPP-15373 | 2.0E−07 | 1.3E−07 |
| TPP-15374 | 1.8E−08 | 1.8E−08 |
| TPP-15375 | 5.8E−09 | 5.2E−09 |
| TPP-15376 | 8.4E−09 | 5.8E−09 |
| TPP-15377 | 3.3E−09 | 1.9E−09 |
| TPP-15378 | n.d. | 1.2E−08 |
| TPP-15379 | 4.3E−07 | 2.1E−07 |
| TPP-15380 | n.b. | n.b. |
| TPP-15381 | 9.9E−09 | 3.3E−09 |
| TPP-15382 | 2.5E−07 | 1.9E−07 |
| TPP-15383 | 5.3E−08 | 2.8E−08 |
| TPP-15384 | 9.6E−09 | 9.1E−09 |
| TPP-15385 | 8.5E−09 | 7.2E−09 |
| TPP-15386 | n.b. | n.b. |
| TPP-15387 | 1.6E−07 | 1.1E−07 |
| TPP-15388 | 1.7E−07 | 1.3E−08 |
| TPP-15389 | 4.2E−09 | 2.8E−09 |
| TPP-15390 | 9.8E−08 | 5.7E−08 |
| TPP-15391 | n.b. | 7.0E−09 |
| TPP-15392 | n.d. | n.d. |
| TPP-15393 | 5.9E−08 | 9.3E−09 |
| TPP-15394 | n.d. | n.d. |
| TPP-15395 | 1.1E−06 | 2.2E−07 |
| TPP-15396 | 6.2E−09 | 2.1E−09 |
| TPP-15397 | 2.7E−07 | 9.7E−09 |
| TPP-15398 | 8.5E−09 | 8.4E−09 |
| TPP-15399 | 1.9E−07 | 1.5E−07 |
| TPP-15400 | 4.9E−09 | 4.6E−09 |
| TPP-15401 | 7.6E−07 | 1.2E−08 | n.b. = no binding,
n.d. = not determinable

The majority of phage display hits bind to human and mouse dimeric Sema3A in the lower nanomolar range.

TABLE 4

Affinity of anti-Sema3A antibodies derived from TPP-15370 and TPP-15374 determined by SPR using TPP-19068, TPP-19069, TPP-19122, TPP-19120, TPP-19121, TPP-20176 as analytes as well as prior art antibodies (TPP-30972 was purified from HEK cell expression).

| Nomenclature | Mouse $K_D$ [M] | Pig $K_D$ [M] | Cyno $K_D$ [M] | Dog $K_D$ [M] | Human $K_D$ [M] | Rat $K_D$ [M] |
|---|---|---|---|---|---|---|
| TPP-11489 (Chiome) | 1.6E−07 | 1.0E−07 | 6.3E−08 | 5.0E−08 | 7.3E−08 | 3.3E−08 |
| TPP-17755 (Samsung) | 3.9E−09 | 4.0E−09 | 1.4E−08 | 7.5E−09 | 6.9E−09 | 5.4E−09 |
| TPP-30791 (BI clone IV) | 2.8E−11 | 2.9E−11 | 5.7E−11 | 7.8E−11 | 1.2E−11 | 1.7E−11 |
| TPP-30790 (BI clone III) | 4.0E−11 | 3.6E−11 | 7.7E−11 | 1.0E−10 | 1.5E−11 | 2.2E−11 |
| TPP-30789 (BI clone II) | 4.2E−11 | 3.9E−11 | 7.9E−11 | 1.1E−10 | 2.2E−11 | 2.6E−11 |
| TPP-30788 (BI clone I) | 4.3E−11 | 3.8E−11 | 7.8E−11 | 1.1E−10 | 1.8E−11 | 2.6E−11 |
| TPP-30792 (3H4 Univ Ramot) | no binding | no binding | no binding | no binding | no binding | no binding |
| TPP-15370 | 7.2E−09 | 9.0E−09 | 4.0E−08 | 2.2E−08 | 1.0E−08 | 1.4E−08 |
| TPP-23298 | 7.4E−11 | 6.7E−11 | 7.8E−11 | 7.0E−11 | 8.7E−11 | 3.0E−11 |
| TPP-23334 | 6.2E−11 | 1.4E−11 | 1.5E−11 | 8.4E−12 | 2.1E−11 | 5.6E−11 |
| TPP-23337 | 5.0E−11 | 1.1E−11 | 2.6E−11 | 4.5E−12 | 5.0E−11 | 1.1E−10 |
| TPP-23338 | 4.5E−11 | 4.6E−11 | 4.2E−11 | 5.3E−11 | 5.4E−11 | |
| TPP-23340 | 5.9E−11 | 6.2E−11 | 6.0E−11 | 5.8E−11 | 2.2E−11 | |
| TPP-23341 | 9.2E−11 | 8.6E−11 | 8.7E−11 | 8.4E−11 | 9.1E−11 | |
| TPP-23345 | 6.3E−11 | 5.5E−11 | 6.2E−11 | 4.6E−11 | 6.5E−11 | |
| TPP-23346 | 6.4E−11 | 5.8E−11 | 6.1E−11 | 6.1E−11 | 7.2E−11 | |
| TPP-23347 | 5.5E−11 | 5.3E−11 | 5.4E−11 | 5.1E−11 | 6.0E−11 | |
| TPP-23373 | 8.3E−11 | 7.8E−11 | 7.2E−11 | 1.0E−10 | 1.1E−10 | |
| TPP-23374 | 1.6E−11 | below 3 pM | below 3 pM | 7.3E−12 | 8.1E−12 | 3.3E−12 |
| TPP-23375 | 4.2E−11 | 4.7E−11 | 4.5E−11 | 4.5E−11 | 5.3E−11 | |
| TPP-15374 | 8.3E−09 | 7.2E−09 | 4.6E−08 | 1.9E−08 | 1.5E−08 | 9.8E−09 |
| TPP-18533 | 8.1E−09 | | 6.4E−09 | | 8.7E−09 | |
| TPP-25497 | | | | | 5.2E−11 | |
| TPP-25256 | | | | | 4.9E−11 | |
| TPP-25255 | | | | | 5.1E−11 | |
| TPP-25257 | | | | | 5.3E−11 | |
| TPP-25248 | | | | | 5.0E−11 | |
| TPP-25064 | | | | | 4.9E−11 | |
| TPP-26111 | | | | | 5.2E−11 | |
| TPP-25224 | | | | | 4.9E−11 | |
| TPP-25448 | | | | | 5.3E−11 | |
| TPP-25655 | | | | | 4.9E−11 | |

All derivative antibodies of TPP-15370 and TPP-15374 have a significantly increased affinity to the Sema3A domain in the lower picomolar range compared to their parental antibodies as well as to most prior art antibodies.

TABLE 4a

Affinity of anti-Sema3A IgG1 antibodies determined by SPR using 100 nM TPP-19068 (human) in a binding experiment.

| Nomenclature | Human $K_D$ [M] |
|---|---|
| TPP-23298 | 1.3E−10 |
| TPP-17755 (Samsung) | 6.2E−09 |
| TPP-11489 (Chiome) | n.d. |
| TPP-30788 (BI clone I) | 9.8E−11 |
| TPP-31357 (Fab of 3H4 Univ Ramot) | 3.5E−10 | n.d. = not determinable due to multiphasic behaviour

In contrast to the full length 3H4 IgG1 (TPP-30792) which showed no binding in SPR to Sema3A molecules, the Fab variant of TPP-30792, TPP-31357 shows binding to human Sema3A, but with less affinity as TPP-23298.

Example 5: Determination of Binding Activity Using Surface Plasmon Resonance To assess the binding activity of anti-Sema3A antibodies binding assays were conducted using surface plasmon resonance (SPR). Binding assays were performed on a Biacore T200 instrument (Cytiva) at 25° C. using assay buffer HBS P+, 300 mM NaCl, 0.75 mM $CaCl_2$, 2.5 mM $MgCl_2$, 1 mg/ml BSA, 0.05% $NaN_3$. Antibodies were captured via anti-human Fc IgGs ("Human antibody capture kit", Order No. BR100839, Cytiva) covalently amine coupled to a Series S CM5 sensor chip (Cytiva). The amine coupling was carried out according to the manufacturer's instructions using 1-ethyl-3-(3-dimethylaminopropyl) carbodiimide hydrochloride (EDC), N-hydroxysuccinimide (NHS) and ethanolamine HCl, pH 8.5 ("Amine Coupling Kit" BR-1000-50, Cytiva.). Human, mouse, cynomolgus, rat, dog and pig monovalent Sema3A domain were used as analytes in a concentration series from 0.024-3.125 nM in multi cycle kinetics mode. The sensor surface was regenerated with glycine pH 2.0 after each antigen injection. Obtained sensorgrams were double referenced (subtraction of reference flow cell signal and buffer injection) and were fitted to a 1:1 Langmuir binding model using the Biacore T200 Evaluation software obtaining the experimental fitted $R_{Max}$ value. To calculate the binding activity first the theoretical $R_{Max}$ needs to be calculated according to equation 1:

$$R_{Max} = \frac{R_{Ligand} * Mr_{Analyte} * Valency_{Ligand}}{Mr_{Ligand}}$$

Equation 1: Theoretical calculation of $R_{Max}$. $R_{Ligand}$=Ligand Level in RU, Mr=molecular weight, $Valency_{Ligand}$=number of binding sites per antibody molecule, here 2

Binding activity was determined by dividing the experimental determined $R_{Max}$ by the theoretical calculated $R_{Max}$ according to equation 2:

$$\text{Activity in \%} = \frac{R_{Max\,experimental}}{R_{Max\,theoretical}} * 100$$

Equation 2: Calculation of binding activity in %

TABLE 5

Summary of ligand levels after capture, experimental, theoretical and binding activity of tested antibodies

| Ligand | Analyte | Ligand Level [RU] | Experimental Rmax [RU] | Theoretical Rmax [RU] | Binding Activity [%] |
|---|---|---|---|---|---|
| TPP-11489 (Chiome) | Rat | 798 | 212 | 681 | 31 |
| TPP-15370 | Sema3A | 53 | 51 | 45 | 113 |
| TPP-15374 | domain | 53 | 42 | 45 | 94 |
| TPP-17755 (Samsung) | | 54 | 26 | 46 | 56 |
| TPP-23298 | | 46 | 42 | 39 | 108 |
| TPP-30791 (BI clone IV) | | 46 | 42 | 39 | 109 |
| TPP-30790 (BI clone III) | | 62 | 50 | 53 | 94 |
| TPP-30789 (BI clone II) | | 50 | 44 | 42 | 104 |
| TPP-30788 (BI clone I) | | 46 | 43 | 40 | 109 |
| TPP-11489 (Chiome) | Dog | 797 | 148 | 680 | 22 |
| TPP-15370 | Sema3A | 53 | 51 | 45 | 114 |
| TPP-15374 | domain | 53 | 44 | 45 | 98 |
| TPP-17755 (Samsung) | | 54 | 25 | 46 | 55 |
| TPP-23298 | | 45 | 42 | 39 | 107 |
| TPP-30791 (BI clone IV) | | 47 | 43 | 40 | 106 |
| TPP-30790 (BI clone III) | | 61 | 48 | 52 | 92 |
| TPP-30789 (BI clone II) | | 50 | 44 | 43 | 102 |
| TPP-30788 (BI clone I) | | 47 | 42 | 40 | 106 |
| TPP-11489 (Chiome) | Pig | 801 | 525 | 684 | 77 |
| TPP-15370 | Sema3A | 53 | 50 | 45 | 111 |
| TPP-15374 | domain | 53 | 47 | 45 | 103 |
| TPP-17755 (Samsung) | | 54 | 28 | 46 | 60 |
| TPP-23298 | | 46 | 42 | 39 | 107 |
| TPP-30791 (BI clone IV) | | 49 | 44 | 42 | 105 |
| TPP-30790 (BI clone III) | | 61 | 48 | 52 | 92 |
| TPP-30789 (BI clone II) | | 51 | 45 | 43 | 103 |
| TPP-30788 (BI clone I) | | 47 | 43 | 40 | 107 |
| TPP-11489 (Chiome) | Cyno | 800 | 85 | 682 | 13 |
| TPP-15370 | Sema3A | 53 | 63 | 45 | 139 |
| TPP-15374 | domain | 53 | 47 | 45 | 104 |
| TPP-17755 (Samsung) | | 53 | 24 | 45 | 53 |
| TPP-23298 | | 46 | 41 | 39 | 106 |
| TPP-30791 (BI clone IV) | | 47 | 43 | 40 | 107 |
| TPP-30790 (BI clone III) | | 62 | 48 | 52 | 92 |
| TPP-30789 (BI clone II) | | 50 | 44 | 42 | 103 |
| TPP-30788 (BI clone I) | | 47 | 43 | 40 | 107 |
| TPP-11489 (Chiome) | Human | 798 | 257 | 681 | 38 |
| TPP-15370 | Sema3A | 53 | 51 | 45 | 112 |
| TPP-15374 | domain | 53 | 45 | 45 | 101 |
| TPP-17755 (Samsung) | | 54 | 25 | 46 | 55 |
| TPP-23298 | | 46 | 42 | 39 | 107 |
| TPP-30791 (BI clone IV) | | 48 | 44 | 41 | 107 |
| TPP-30790 (BI clone III) | | 61 | 48 | 52 | 93 |
| TPP-30789 (BI clone II) | | 49 | 45 | 42 | 106 |
| TPP-30788 (BI clone I) | | 47 | 43 | 40 | 107 |
| TPP-11489 (Chiome) | Mouse | 796 | 803 | 680 | 118 |
| TPP-15370 | Sema3A | 53 | 50 | 45 | 111 |
| TPP-15374 | domain | 53 | 48 | 45 | 106 |
| TPP-17755 (Samsung) | | 54 | 26 | 46 | 57 |
| TPP-23298 | | 46 | 42 | 39 | 108 |
| TPP-30791 (BI clone IV) | | 47 | 43 | 40 | 107 |
| TPP-30790 (BI clone III) | | 62 | 49 | 52 | 93 |
| TPP-30789 (BI clone II) | | 51 | 45 | 43 | 103 |
| TPP-30788 (BI clone I) | | 47 | 43 | 40 | 108 |

The binding activity calculated in the SPR experiment is a measure of the activity of the surface-attached ligand. As can be seen from Table 5, TPP-15370, TPP-15374, TPP-23298 and TPPs 30788-30791 are able to bind to all tested Sema3A domains with around 100% activity meaning all binding regions are fully able to bind. Prior art antibody TPP-17755 only reaches an activity level of 50-60% depending on the species. Prior art antibody TPP-11489 shows an even more reduced level of below 50%, except for mouse and pig where it is higher. Strikingly, to reach such an activity level, the ligand level of TPP-11489 needs to be over 10-fold higher as compared to the other antibodies pointing in general to a much lower binding activity as compared to TPP-15370, TPP-15374 and TPP-23298.

Example 6: Competition ELISA

For screening in a competition ELISA setup, human Sema3a (TPP-13211) was coated onto 384-well plates (Greiner bio-one, 781077) with a concentration of 0.5 µg/ml in coating buffer (Carbonate-Basis pH 9.6, Candor 121125) over night at 10° C. After washing the plates 3 times with 50 µl PBS 0.05% Tween the plates were blocked with 50 µl Smart Block® (Candor 113500) for 1 h at 20° C. and washed again 3 times as described.

Subsequently, 20 µl of pre-mixed antibody solution was added to the plates and incubate for 18 h at 10° C. For the pre-mixed antibody solution, for each well, one biotinylated, parental antibody being either TPP-15370 or TPP-15374 was mixed in a ratio 1:1, 1:5 or 5:1 with an antibody containing one or more amino acid variations within its CDR regions (recombination variants) and not containing any biotin tag. As additional controls an isotype control antibody not demonstrating any binding to human Sema3A was also used as competition antibody. The total concentration of the added antibody solution was 0.25 µg/ml. During the incubation time the antibodies bound to the plates in a competitive manner as they compete for the same epitope on the human Sema3A protein.

After subsequent washing with 50 µl PBS 0.05% Tween for 3 times, 20 µl of a Streptavidin-HRP solution (R&D Systems, DY998, 1:200 in PBS 0.05% Tween 10% Smart Block) were added and incubated for 1 h and 20° C. followed by subsequent washing 3 times with 50 µl PBS 0.05% Tween and addition of 20 µl Amplex Red solution (Invitrogen A12222, 1:1000 in NaP-buffer 50 mM pH7.6 with 1:10000 of 30% H2O2). After a final incubation for 20 min at 20° C. the signal was determined using an emission wavelength of 595 nm and excitation of 530 nm. Due to the biotinylation of the parental antibodies TPP-15370 and TPP-15374 only the binding of these variants can be detected. Hence, competition with an antibody variant demonstrating superior binding shows a lower binding signal in comparison to e.g. competition of the parental antibody with a non-bioinylated version of itself.

In total, 103 recombination variants of TPP-15370 and 1136 recombination variants for TPP-15374 were measured. For analysis, and to allow for correction of plate-to-plate variations, the ELISA raw values were normalized to the value of the competition with the isotype control antibody TPP-9809.

Table 6 lists the values for the competition ELISA for selected recombination variants of TPP-15370 and TPP-15374. Depicted are the ratios vs. the isotype control antibody TPP-9809 in the measurement with a 1 to 5 or a 1 to 1 ratio, respectively.

Experiments were performed on a Biacore T200 instrument (Cytiva) at 25° C. using assay buffer HBS P+, 300 mM NaCl, 0.75 mM CaCl$_2$), 2.5 mM MgCl$_2$, 1 mg/ml BSA, 0.05% NaN$_3$. Antibodies were covalently amine coupled to a Series S CM5 sensor chip (Cytiva). The amine coupling was carried out according to the manufacturer's instructions using 1-ethyl-3-(3-dimethylaminopropyl) carbodiimide hydrochloride (EDC), N-hydroxysuccinimide (NHS) and ethanolamine HCl, pH 8.5 ("Amine Coupling Kit" BR-1000-50, Cytiva.). Human, monovalent Sema3A domain was used as first analyte in a concentration of 200 nM followed by a second injection of the competitor antibody. This setup was performed with all possible combinations. The sensor surface was regenerated with glycine pH 2.0 after each antigen injection. Table 6a shows the binning results.

TABLE 6

Values for the competition ELISA for recombination variants of TPP-15374 and TPP-15370. Depicted are the ratios vs. the isotype control antibody for selected recombination variants, respectively, when normalized to the isotype control antibody TPP-9809 in the measurement with a 1 to 5 or a 1 to 1 ratio, respectively

| | TPP-15374 family | | | TPP-15370 family | |
|---|---|---|---|---|---|
| TPP Number | VAL norm to TPP-9809 (1 to 5 ratio) | VAL norm to TPP-9809 (1 to 1 ratio) | TPP Number | VAL norm to TPP-9809 (1 to 5 ratio) | VAL norm to TPP-9809 (1 to 1 ratio) |
| TPP-15374 | 0.41 | 0.69 | TPP-15370 | 0.54 | 0.67 |
| TPP-9809 | 1.00 | 1.00 | TPP-9809 | 1.00 | 1.00 |
| TPP-25497 | 0.26 | 0.39 | TPP-23298 | 0.09 | 0.18 |
| TPP-25256 | 0.15 | 0.41 | TPP-23334 | 0.11 | 0.28 |
| TPP-25255 | 0.17 | 0.37 | TPP-23337 | 0.14 | 0.27 |
| TPP-25257 | 0.18 | 0.36 | TPP-23338 | | 0.33 |
| TPP-25248 | 0.20 | 0.36 | TPP-23340 | | 0.40 |
| TPP-25064 | 0.19 | 0.48 | TPP-23341 | 0.18 | 0.38 |
| TPP-26111 | 0.18 | 0.49 | TPP-23345 | 0.08 | 0.27 |
| TPP-25224 | 0.17 | 0.43 | TPP-23346 | 0.13 | 0.22 |
| TPP-25448 | 0.19 | 0.47 | TPP-23347 | 0.16 | 0.30 |
| TPP-25655 | 0.23 | 0.39 | TPP-23373 | 0.20 | 0.35 |
| | | | TPP-23374 | 0.08 | 0.19 |
| | | | TPP-23375 | 0.16 | 0.30 |

Example 5a: Epitope Binning Using Surface Plasmon Resonance (SPR)

An epitope binning experiment was performed to determine the epitope bins of anti-Sema3A antibodies using SPR by employing a classical sandwich approach. In this experiment, one antibody is immobilized to a SPR chip, Sema3A is injected, and the binding is monitored (FIG. 10A). After successful binding of Sema3A to the first antibody, a second antibody is injected on to the complex of the immobilized mAb bound to Sema3A and the additional binding is monitored (FIG. 10B and FIG. 10C). If the second antibody competes with the first antibody for the binding to Sema3A than no additional binding signal is detected after injection of the second antibody, showing that the two antibodies bind to the same or very adjacent Sema3A epitope (FIG. 10C). If the second antibody does not compete with the first antibody for the binding to Sema3A than an additional binding signal is detected after injection of the second antibody, showing that the two antibodies bind to different Sema3A epitopes (FIG. 10B).

TABLE 6a

Matrix view of the epitope binning results (+ = additional binding, − = no additional binding)

| First antibody/ second antibody | TPP-30788 (BI Clone I) | TPP-23298 | TPP-17755 (Samsung) |
|---|---|---|---|
| TPP-30788 (BI Clone I) | | + | + |
| TPP-23298 | + | | − |
| TPP-17755 (Samsung) | + | − | |

"+" means injection of second antibody resulted in additional binding signal showing that the two tested antibodies bind to two different Sema3A epitopes
"−" means injection of second antibody did not resulted in additional binding signal showing that the two tested antibodies compete for binding to overlapping or adjacent epitopes Sema3A epitopes The binning experiment strongly points to another epitope for TPP-23298 compared to TPP-30788 (BI clone I) meaning that both antibodies target an independent/different epitope on Sema3A, whereas TPP-23298 might have overlapping or adjacent epitopes with TPP-17755 (Samsung).

Example 7: Assessment of Binding to Off-Targets

To assess the specificity of an anti-Sema3A mAb (TPP-15370, parental mAb) an off-target screen using Retrogenix technology was conducted. For primary screening, 5484 expression vectors, encoding both ZsGreen1 and a full-length human plasma membrane protein or a cell-surface tethered human secreted protein, were arrayed in duplicate across 16 microarray slides. Human HEK293 cells were used for reverse transfection/expression.

The test antibody was added to each slide after cell fixation giving a final concentration of 20 µg/ml. Detection of binding was performed by using the same AF647 anti-hIgG Fc detection antibody as used in the Pre-screen. Two replicate slides were screened for each of the 16 slide-sets. Hits were classified as 'strong, medium, weak or very weak', depending on the intensity of the duplicate spots.

Following a screen for binding against fixed HEK293 cells expressing 5484 human plasma membrane proteins and human secreted proteins, Retrogenix's technology identified no specific off-target interactions for test antibody TPP-15370. Binding to Sema3A—its primary target—was observed. These data indicate high specificity of TPP-15370 for its primary target.

Example 8: Selectivity of Anti-Sema3A mAbs

Semaphorin proteins can be subdivided in five classes occurring in vertebrates (class 3-7). To assess the selectivity profile of parental anti-Sema3A mAbs TPP-15370 and TPP-15374 in the Semaphorin 3 class (Sema3A-G) an ELISA assay was conducted using Sema3A, Sema3B, Sema3C, Sema3D, Sema3E, and Sema3F molecules from R&D Systems. Both antibodies showed no binding to Sema3B, Sema3C, Sema3D, Sema3E and Sema3F.

Because Sema3G has been recently identified as kidney protective (PMID: 27180624), it was important to test whether the antibodies do not bind to Sema3G. For the assessment of binding selectivity to Sema3A vs Sema3G, 1 nM recombinant human Sema3A-Fc chimera (R&D Systems) or recombinant human GST-Sema3G (Abnova) were coated on Maxisorb plates, incubated with antibodies in a dose-response curve from 0.00015-10 µg/ml, and the binding of antibodies quantified using HRP coupled anti-human antiserum and chemiluminescent substrate.

TABLE 7

Off-target ELISA values for testing of Sema3G as off-target

| Antibody | EC50 [nM] Coating: SEMA3A | EC50 [nM] Coating: SEMA3G | Selectivity Score SEMA3G/SEMA3A |
|---|---|---|---|
| TPP-23298 | 1.6 | >66667 | >41666 |
| TPP-23334 | 9.2 | >66667 | >7220 |
| TPP-23337 | 15.5 | >66667 | >4308 |
| TPP-23338 | 9.6 | >66667 | >6949 |
| TPP-23340 | 12.3 | >66667 | >5435 |
| TPP-23341 | 21.3 | >66667 | >3133 |
| TPP-23347 | 8.4 | >66667 | >7918 |
| TPP-23373 | 17.6 | >66667 | >3786 |
| TPP-23374 | 6.1 | >66667 | >10951 |
| TPP-23375 | 7.7 | >66667 | >8651 |
| TPP-11489 (Chiome) | Weak binding (EC50 not determinable) | >66667 | n.d. |
| TPP-17755 (Samsung) | Slight dose-response (not determinable) | >66667 | n.d. |
| TPP-30791 (BI clone IV) | 0.08 | >66667 | >833337 |
| TPP-30790 (BI clone III) | 0.08 | >66667 | >833337 |
| TPP-30789 (BI clone II) | 0.10 | >66667 | >666670 |
| TPP-30788 (BI clone I) | 0.15 | >66667 | >444446 |

All tested antibodies of the present disclosure as well as prior art antibodies do not bind to kidney protective Sema3G, as shown in Table 7.

Sema3A is a secreted protein that contains two furin cleavage sites and is present in an active an inactive cleaved form. In the in vivo situation Sema3A exists in both forms side by side. To test if anti-Sema3A antibodies are able to differentiate between the inactive and active form and to test how antibodies perform in binding to active Sema3A (resembled by full-length Sema3A (TPP-13211) in contrast to a inactive version as it only contains the Sema3A domain (resembled by cleaved Sema3A TPP-19068), an ELISA assay was performed. As readout out the ELISA signals of the tested antibody to the active Sema3A has been divided by the ELISA signals of the tested antibody to the inactive Sema3A.

TABLE 7a

Ratio for binding of anti-Sema3A antibodies to active vs. inactive Sema3A as determined by ELISA

| Antibody | Ratio ELISA binding TPP-13211/TPP-19068* |
|---|---|
| TPP-23298 | 0.66 ± 0.14 |
| TPP-30788 (BI clone I) | 0.19 ± 0.03 |
| TPP-30789 (BI clone II) | 0.20 ± 0.07 |
| TPP-30790 (BI clone III) | 0.19 ± 0.03 |
| TPP-30791 (BI clone IV) | 0.21 ± 0.004 |

*A Ratio ELISA binding TPP-13211/TPP-19068 below 1 shows a higher binding activity to active Sema3A.

A Ratio ELISA binding TPP-13211/TPP-19068 above 1 shows a higher binding activity to inactive Sema3A.

The binding analysis as shown in Table 7a clearly showed that the antibody of the present disclosure (TPP-23298) shows increased binding to active Sema3A than TPP-30788-TPP-30791 (BI clones) presumably since they target a different epitope indicating a higher selectivity for active Sema3A.

Example 9: In Vitro Efficacy in a Mesangial Cell Migration Assay

A confluent monolayer of human primary mesangial cells was generated by seeding cells in serum-containing culture medium into image lock plates for 24 hours. After switching to serum-free culture medium, scratch wounds were created using the WoundMaker tool, after which the cells were treated with 1 nM recombinant human Sema3A-Fc chimera (R&D Systems) in the absence or presence of inhibitory antibodies. The cells were imaged in the Incucyte and after 24 hrs the extent of wound closure was assessed using the Incucyte Integrated Cell Migration Analysis software module.

TABLE 8

EC50 values for phage display hits and recombination variants in the MCM assay

| Antibody | EC50 [nM] |
|---|---|
| TPP-15051 (Chiome) | 42.87 |
| TPP-15354 | 31.87 |
| TPP-15355 | >200 |
| TPP-15356 | >200 |
| TPP-15357 | 158.13 |
| TPP-15358 | >200 |
| TPP-15359 | >200 |

TABLE 8-continued

EC50 values for phage display hits and
recombination variants in the MCM assay

| Antibody | EC50 [nM] |
|---|---|
| TPP-15360 | 37.47 |
| TPP-15361 | 118.67 |
| TPP-15362 | >200 |
| TPP-15363 | >200 |
| TPP-15364 | >200 |
| TPP-15365 | >200 |
| TPP-15366 | 2.27 |
| TPP-15367 | 148.07 |
| TPP-15368 | >200 |
| TPP-15369 | 45.47 |
| TPP-15370 | 4.13 |
| TPP-15371 | >200 |
| TPP-15372 | 86.87 |
| TPP-15373 | 123.53 |
| TPP-15374 | 5.07 |
| TPP-15375 | >200 |
| TPP-15376 | >200 |
| TPP-15377 | >200 |
| TPP-15378 | 67.00 |
| TPP-15379 | >200 |
| TPP-15380 | 125.53 |
| TPP-15381 | >200 |
| TPP-15382 | 199.87 |
| TPP-15384 | 1.60 |
| TPP-15385 | 1.20 |
| TPP-15386 | >200 |
| TPP-15387 | >200 |
| TPP-15388 | >200 |
| TPP-15389 | 103.60 |
| TPP-15390 | >200 |
| TPP-15391 | >200 |
| TPP-15392 | 62.53 |
| TPP-15393 | 131.93 |
| TPP-15394 | >200 |
| TPP-15395 | >200 |
| TPP-15396 | 82.67 |
| TPP-15397 | >200 |
| TPP-15398 | 6.00 |
| TPP-15399 | 197.13 |
| TPP-15400 | 4.73 |
| TPP-15401 | >200 |
| TPP-17755 (Samsung) | 11.33 |
| TPP-23298 | 0.40 |
| TPP-23334 | 0.67 |
| TPP-23337 | 0.33 |
| TPP-23338 | 0.60 |
| TPP-23340 | 0.87 |
| TPP-23341 | 0.90 |
| TPP-23345 | 0.93 |
| TPP-23346 | 1.27 |
| TPP-23347 | 0.67 |
| TPP-23373 | 0.63 |
| TPP-23374 | 0.30 |
| TPP-23375 | 1.03 |
| TPP-30788 (BI clone I) | 1.43 |

We identified antibodies with potencies in the three-digit picomolar range in the human Mesangial Cell Migration Assay, which is considerably more potent than the prior art antibodies, as shown in Table 8.

Example 10: In Vitro Efficacy in a Growth Cone Collapse Assay

In the direction of determining the potency of the antibodies against Sema3A induced cytoskeletal collapse, a growth cone collapse assay was used similarly as described (PMID: 12077190) with a few modifications. In brief, mouse dorsal root ganglion (DRG) neurons were isolated from E13 C57Bl/6J mouse embryos, cultured on poly-L-lysine and laminin-coated 96-wells with Neurobasal medium+100 ng/ml NGF+B-27+10% FCS. After 20 hours, the cells were treated for 1 hour with 10 nM recombinant human Sema3A-Fc chimera (RnD Systems) in the absence or presence of inhibitory antibodies followed by PFA fixation and staining with Alexa488-phalloidin. The extent of growth cone collapse was assessed using immunofluorescence microscopy via actin growth cone area/shape/texture for more than 100 growth cones per well.

TABLE 9

EC50 values for phage display hits and
recombination variants in the GCC assay

| Antibody | EC50 (nM) |
|---|---|
| TPP-15051 (Chiome) | 243.40 |
| TPP-15354 | 67.73 |
| TPP-15355 | >200 |
| TPP-15356 | >200 |
| TPP-15357 | 50.73 |
| TPP-15358 | >200 |
| TPP-15359 | >200 |
| TPP-15360 | 31.07 |
| TPP-15361 | >200 |
| TPP-15362 | >200 |
| TPP-15363 | >200 |
| TPP-15364 | >200 |
| TPP-15365 | 142.87 |
| TPP-15366 | 4.13 |
| TPP-15367 | 170.87 |
| TPP-15368 | >200 |
| TPP-15369 | 76.60 |
| TPP-15370 | 4.33 |
| TPP-15371 | >200 |
| TPP-15372 | 109.47 |
| TPP-15373 | >200 |
| TPP-15374 | 8.13 |
| TPP-15375 | >200 |
| TPP-15376 | >200 |
| TPP-15377 | >200 |
| TPP-15378 | 138.60 |
| TPP-15379 | >200 |
| TPP-15380 | 135.40 |
| TPP-15381 | >200 |
| TPP-15382 | >200 |
| TPP-15384 | 18.80 |
| TPP-15385 | 6.00 |
| TPP-15386 | >200 |
| TPP-15387 | >200 |
| TPP-15388 | >200 |
| TPP-15389 | 160.67 |
| TPP-15390 | >200 |
| TPP-15391 | >200 |
| TPP-15392 | >200 |
| TPP-15393 | >200 |
| TPP-15394 | >200 |
| TPP-15395 | 66.47 |
| TPP-15396 | 180.80 |
| TPP-15397 | >200 |
| TPP-15398 | 12.00 |
| TPP-15399 | >200 |
| TPP-15400 | 25.73 |
| TPP-15401 | >200 |
| TPP17755 (Samsung) | 52.67 |
| TPP-23298 | 2.40 |
| TPP-23334 | 2.24 |
| TPP-23337 | 2.12 |
| TPP-23374 | 2.19 |

The identified antibodies also show potencies in the single digit nanomolar range in the murine Growth Cone Collapse Assay, again considerably more potent than the tested prior art antibodies (two- to three-digit nanomolar potency), as shown in Table 9.

Example 11: In Vitro Efficacy in a HUVEC Repulsion Assay

Recombinant human Sema3A-Fc chimera (R&D Systems) is not identical to Sema3A in human biofluids because it contains several mutated amino acids and an extra protein fragment at its carboxy-terminus. Furthermore, the above described assays (human Mesangial Cell Migration Assay and murine Growth Cone Collapse Assay) use Sema3A in homogenous distribution, which is in contrast to the gradient distribution described for Sema3A in tissues. We hypothesized that these differences could result in a different potency of the antibodies towards recombinant versus endogenous protein. Therefore, we adapted an assay using a gradient of human wild-type Sema3A as agonist (PMID: 17569671). In brief, in this HUVEC repulsion assay, human embryonic kidney 293 cells (HEK293) cells expressing human Sema3A of the sequence of SEQ ID NO: 600, were seeded on a confluent monolayer of human umbilical vein endothelial cells (HUVEC) in EGM-2 medium in the absence or presence of inhibitory antibodies, cultured for 72 hours, fixed, stained with DAPI and the extent of cell repulsion assessed by immunofluorescence microscopy (measurement of cell free areas). Consequently, the substrate human Sema3A exists in excess.

Based on immunofluorescence microscopy images of the DAPI/CM stained cells (CM=HCS CellMask™ Stain, stains the whole cell in order to define the total cell area) data analysis is performed as follows: Cells are identified based on the DAPI/CM signals (FIG. 11B). The cell area for analysis is defined and selected. In this area the cell-free region is calculated (FIG. 11C). Percent inhibition is calculated based on the "cell free-region" that is induced by Sema3A in the antibody-treated wells in comparison to the isotype-treated wells. Percent inhibition is plotted over antibody concentration and EC-50 values of the respective antibodies are calculated.

In detail the following steps are performed for the data analysis:
1. Four fields are imaged per well which corresponds to 80% of the well area. All of these fields stitched together are used for the detection of the cells via the DAPI/CM fluorescence.
2. The "cell area" is calculated based on the DAPI/CM area.
3. The "cell-free region" is calculated based on the "total area" subtracted by the "cell area".
4. Percent inhibition is calculated based on the "cell free-region" that is induced by Sema3A in the antibody-treated wells vs the isotype-treated wells.
5. The software GraphPad Prism is used to determine the EC50 values using nonlinear regression (Variable slope model=four-parameter dose-response curve).

TABLE 10

EC50 values for selected antibodies in the repulsion assay, first experiment

| Antibody | EC50 (pM) |
| --- | --- |
| TPP-15370 | 800 |
| TPP-23298 | 80 |
| TPP-23334 | 120 |
| TPP-23337 | 170 |
| TPP-23340 | 180 |
| TPP-23341 | 113 |
| TPP-23373 | 180 |

TABLE 10-continued

EC50 values for selected antibodies in the repulsion assay, first experiment

| Antibody | EC50 (pM) |
| --- | --- |
| TPP-23374 | 77 |
| TPP-23375 | 123 |

TABLE 10a

EC50 values for TPP-23298 in the repulsion assay in a second experiment to compare to prior art antibodies

| Antibody | EC50 (pM) |
| --- | --- |
| TPP-23298 | 54 |
| TPP-30788 (BI clone I) | 104 |
| TPP-30789 (BI clone II) | 165 |
| TPP-30790 (BI clone III) | 121 |
| TPP-30791 (BI clone IV) | 221 |
| TPP-17755 (Samsung) | 2794 |
| TPP-11489 (Chiome) | >20000 |

The potency distinction to the prior art antibodies in the human Mesangial Cell Migration Assay and murine Growth Cone Collapse Assay above, is even more pronounced in this HUVEC Repulsion Assay that uses a gradient of native wt Sema3A (mixture of processed inactive and undigested active Sema3A) as shown in Table 10 and 10a. The improved potency in HUVEC repulsion assay in comparison to TPP-17755, to TPP-11489, to TPP-30788, to TPP-30789, TPP-30790, or to TPP-30791 is quantified measuring the picomolar activity as shown by the corresponding EC-50 values. While TPP-23298 shows two-digit picomolar activities, prior art antibody potencies of TPP-17755, TPP-11489, TPP-30788, TPP-30789, TPP-30790, or TPP-30791, are in the three-digit picomolar or even nanomolar range.

As an alternative illustration of the results, the improved potency in HUVEC repulsion assay is quantified by measuring the cell-free region at a specified concentration of 80 pM of the respective antibodies. TPP-23298 shows a higher percent inhibition of Sema3A than to TPP-30788, to TPP-30789, TPP-30790, or to TPP-30791 (FIG. 12).

Analyzing the data from both assays displayed in table 10 and 10a TPP-23298 shows the highest potency against cellular Sema3A induced HUVEC repulsion. The BI Antibodies TPP-30788, TPP-30798, TPP-30790 and TPP-30791 exhibited slightly higher EC50 values (2-5-fold). The Samsung Antibody TPP-17755 has a significantly lower potency than the TPP-23298 (50-fold). The Chiome Antibody TPP-11489 did only show inhibitory activity at the highest tested concentrations resulting in a predicted EC50 value >400-fold above antibody according to the present disclosure.

That shows that under conditions, that resembles a native environment without any spiked exogenous, recombinant semaphorin3A, the antibodies according to the present disclosure inhibit Sema3A-induced cell repulsion with the strongest activity, as shown in Table 10 and 10a.

Example 12: In Vivo Assay for Detecting Protective Renal Effects: Inhibition of Sema3a-Induced Albuminuria in Mice Sema3A inhibitors decrease urinary albumin excretion induced via systemic injection of recombinant Sema3A. The beneficial effect of the compounds on albuminuria reduction were investigated in a Sema3A-induced albuminuria model as follows:

Male C57B1/6 mice (8- to 10-wk-old) purchased from Taconic were injected intravenously with anti-Sema3A antibodies. Thirty minutes after antibody application albuminuria was induced by intravenous injection of human recombinant Sema3A (1.0 mg/kg, R&D Systems). Animals were placed into metabolic cages and urine was collected for 4 h. Urinary creatinine was measured via clinical biochemistry analyzer (Pentra400). For the assessment of urinary albumin, a mouse specific Albumin ELISA (Abcam) was used according to manufacturer's protocol. Both urinary creatinine and albumin were used to calculate urinary albumin to creatine ratio (ACR). Differences between groups were analyzed by one-way ANOVA with Dunnett's corrections for multiple comparisons. Statistical significance is defined as $p<0.05$. All statistical analyses were done using GraphPad Prism 8.

Table 11-15a show dose-response experiments with TPP-15370, TPP-15374, TPP-11489, TPP-17755, TPP-30788 and TPP-23298 in the Sema3A-induced albuminuria model in mice. Effects on albuminuria reduction with TPP-15370, TPP-23298 in comparison to TPP-11489 and/or TPP-17755 and/or TPP-30788 are shown in FIGS. 1A-2C.

The antibodies according to the present disclosure reduce Sema3A-induced urinary Albumin excretion.

TABLE 11

Dose-response of Sema3A-induced albuminuria reduction after treatment with TPP-15370

| | urinary albumin to creatinine ratio [μg/mg] |
|---|---|
| control; Mean ± SD | 345.30 ± 102.15**** |
| 15 [mg/kg] isotype control; Mean ± SD | 1392.80 ± 350.70 |
| 1 [mg/kg] TPP-15370; Mean ± SD | 1030.80 ± 216.27** |
| 5 [mg/kg] TPP-15370; Mean ± SD | 693.84 ± 203.18**** |
| 15 [mg/kg] TPP-15370; Mean ± SD | 273.10 ± 146.02**** |

8-10 animal/group, One-way ANOVA with Dunnett's corrections for multiple comparisons,
*//*/****= significant with $p < 0.05/0.01/0.001/0.0001$ vs isotype control

TABLE 12

Dose-response of Sema3A-induced albuminuria reduction after treatment with TPP-15374

| | urinary albumin to creatinine ratio [μg/mg] |
|---|---|
| Control; Mean ± SD | 226.40 ± 65.50**** |
| 15 [mg/kg] isotype control; Mean ± SD | 1061.43 ± 216.47 |
| 1 [mg/kg] TPP-15374; Mean ± SD | 782.60 ± 122.43** |
| 5 [mg/kg] TPP-15374; Mean ± SD | 690.19 ± 190.27**** |
| 15 [mg/kg] TPP-15374; Mean ± SD | 592.87 ± 123.93**** |

8-10 animal/group, One-way ANOVA with Dunnett's corrections for multiple comparisons,
*//*/****= significant with $p < 0.05/0.01/0.001/0.0001$ vs isotype control

TABLE 13

Dose-response of Sema3A-induced albuminuria reduction after treatment with TPP-23298

| | urinary albumin to creatinine ratio [μg/mg] |
|---|---|
| Control; Mean ± SD | 345.30 ± 102.15**** |
| 15 [mg/kg] isotype control; Mean ± SD | 1281.65 ± 447.14 |
| 1 [mg/kg] TPP-23298; Mean ± SD | 623.37 ± 240.41**** |

TABLE 13-continued

Dose-response of Sema3A-induced albuminuria reduction after treatment with TPP-23298

| | urinary albumin to creatinine ratio [μg/mg] |
|---|---|
| 5 [mg/kg] TPP-23298; Mean ± SD | 471.07 ± 164.97**** |
| 15 [mg/kg] TPP-23298; Mean ± SD | 320.60 ++± 166.36**** |

8-10 animal/group, One-way ANOVA with Dunnett's corrections for multiple comparisons,
*//*/****= significant with $p < 0.05/0.01/0.001/0.0001$ vs isotype control

TABLE 14

Dose-response of Sema3A-induced albuminuria reduction after treatment with TPP-11489

| | urinary albumin to creatinine ratio [μg/mg] |
|---|---|
| Control; Mean ± SD | 237.23 ± 92.61**** |
| 15 [mg/kg] isotype control; Mean ± SD | 1404.81 ± 411.55 |
| 1 [mg/kg] TPP-11489; Mean ± SD | 1204.81 ± 426.64 |
| 5 [mg/kg] TPP-11489; Mean ± SD | 664.02 ± 228.96**** |
| 15 [mg/kg] TPP-11489; Mean ± SD | 572.42 ± 211.05**** |

8-10 animal/group, One-way ANOVA with Dunnett's corrections for multiple comparisons,
*//*/****= significant with $p < 0.05/0.01/0.001/0.0001$ vs isotype control

TABLE 15

Dose-response of Sema3A-induced albuminuria reduction after treatment with TPP-17755

| | urinary albumin to creatinine ratio [μg/mg] |
|---|---|
| Control; Mean ± SD | 298.02 ± 91.06**** |
| 15 [mg/kg] isotype control; Mean ± SD | 1053.75 ± 162.28 |
| 1 [mg/kg] TPP-17755; Mean ± SD | 932.57 ± 221.09 |
| 5 [mg/kg] TPP-17755; Mean ± SD | 823.11 ± 196.93* |
| 15 [mg/kg] TPP-17755; Mean ± SD | 711.09 ± 181.65*** |

8-10 animal/group, One-way ANOVA with Dunnett's corrections for multiple comparisons,
*//*/****= significant with $p < 0.05/0.01/0.001/0.0001$ vs isotype control

TABLE 15a

Dose-response of Sema3A-induced albuminuria reduction after treatment with TPP-30788

| | urinary albumin to creatinine ratio [μg/mg] |
|---|---|
| Control; Mean ± SD | 266.67 ± 115.66**** |
| 15 [mg/kg] isotype control; Mean ± SD | 1546.59 ± 312.43 |
| 1 [mg/kg] TPP-30788; Mean ± SD | 1234.13 ± 353.48 |
| 5 [mg/kg] TPP-30788; Mean ± SD | 958.30 ± 196.93*** |
| 15 [mg/kg] TPP-30788; Mean ± SD | 841.46 ± 438.51**** |

8-10 animal/group, One-way ANOVA with Dunnett's corrections for multiple comparisons,
*//*/****= significant with $p < 0.05/0.01/0.001/0.0001$ vs isotype control

Example 13: In Vivo Assay for Detecting Protective Renal Effects: Acute Ischemia/Reperfusion Injury (I/RI) Model in Mice Unilaterally nephrectomized mice may benefit from treatment with Sema3A inhibitors after ischemia reperfusion injury. The beneficial effect of Sema3A antibodies on kidney function was investigated in a kidney ischemia-reperfusion injury model in mice as follows:

Laboratory bred male C57B1/6J mice 6-8 weeks old were obtained from Charles River. Mice were maintained under standard laboratory conditions, 12-hour light-dark cycles with access to normal chow and drinking water at libitum. For the ischemia reperfusion injury model, a total of 8-10 was used in each control and experimental group.

Animals were anesthetized with continuous inhaled isoflurane. Right nephrectomy was performed through a right flank incision 7 days before the ischemic procedures in the contralateral kidneys. One-hour before the initiation of renal ischemia antibodies and adequate isotype control were administrated to mice via i.v. injection. Mice were anesthetized and a left flank incision was made. Renal vessels were exposed by dissection of the left renal pedicle. Non-traumatic vascular clamps were used to stop blood flow (artery and vein) during 25 min (mice) of ischemia. Reperfusion was established by removing the clamps. The abdominal wall (muscular layer and skin) was closed with 5.0 polypropylene sutures. Temgesic® (Buprenorphin, 0.025 mg/kg s.c.) was applied as an analgesic.

Urine of each animal was collected in metabolic cages over night before sacrifice at 24 h post ischemia. Urinary creatinine was measured by a clinical biochemistry analyzer (Pentra400). For the assessment of urinary albumin, a mouse specific Albumin Kit (Hitachi) was used within the Pentra analyzer. Both urinary creatinine and albumin were used to determine Albuminuria (albumin/creatinine ratio). Upon sacrifice, blood samples were obtained under terminal anesthesia. After centrifugation of the blood samples, serum was isolated. Both serum creatinine and serum urea were measured via clinical biochemistry analyzer (Pentra 400). Differences between groups were analyzed by one-way ANOVA with Dunnett's corrections for multiple comparisons. Statistical significance is defined as p<0.05. All statistical analyses were done using GraphPad Prism 8.

Table 16-20 show dose-response experiments with TPP-15370, TPP-15374, TPP-11489, TPP-17755 and TPP-23298 in an acute renal ischemia/reperfusion injury model in mice. FIGS. 3A-3C show the efficacy of TPP-23374, TPP-23298 and TPP-15370 after treatment with 15 mg/kg in the I/RI model. Treatment effects with TPP-15370, TPP-23298 and TPP-15374 in comparison to TPP-11489 and/or TPP-17755 are shown in FIGS. 4A-6C.

The antibodies attenuated ischemia/reperfusion induced kidney damage by reducing serum creatinine and serum urea (surrogates for glomerular filtration rate) and excretion of urinary albumin.

TABLE 16

Dose-response of TPP-15370 in mouse I/R injury model

|  | serum creatinine [mg/dl] | serum urea [mg/dl] | urinary albumin to creatinine ratio [μg/mg] |
|---|---|---|---|
| SHAM Mean ± SD | 0.34 ± 0.05**** | 102.78 ± 9.45**** | 58.50 ± 19.22**** |
| 15 [mg/kg] isotype control Mean ± SD | 1.72 ± 0.30 | 385.63 ± 41.69 | 1699.47 ± 461.60 |
| 1 [mg/kg] TPP-15370 Mean ± SD | 1.61 ± 0.52 | 396.51 ± 86.91 | 1165.37 ± 445.50** |
| 5 [mg/kg] TPP-15370 Mean ± SD | 1.22 ± 0.32* | 297.92 ± 70.02** | 705.21 ± 192.26** |

TABLE 16-continued

Dose-response of TPP-15370 in mouse I/R injury model

|  | serum creatinine [mg/dl] | serum urea [mg/dl] | urinary albumin to creatinine ratio [μg/mg] |
|---|---|---|---|
| 15 [mg/kg] TPP-15370 Mean ± SD | 0.89 ± 0.27**** | 261.95 ± 27.76*** | 554.52 ± 133.99**** |

8-10 animal/group, One-way ANOVA with Dunnett's corrections for multiple comparisons,
*//*/****= significant with p < 0.05/0.01/0.001/0.0001 vs isotype control

TABLE 17

Dose-response of TPP-15374 in mouse I/R injury model

|  | serum creatinine [mg/dl] | serum urea [mg/dl] | urinary albumin to creatinine ratio [μg/mg] |
|---|---|---|---|
| SHAM Mean ± SD | 0.26 ± 0.02**** | 113.90 ± 29.95**** | 39.36 ± 10.19**** |
| 15 [mg/kg] isotype control Mean ± SD | 2.09 ± 0.19 | 494.52 ± 29.75 | 3942.50 ± 1790.29 |
| 1 [mg/kg] TPP-15374 Mean ± SD | 1.84 ± 0.39 | 478.10 ± 66.55 | 2774.43 ± 946.18 |
| 5 [mg/kg] TPP-15374 Mean ± SD | 1.66 ± 0.32* | 416.49 ± 98.47* | 2195.95 ± 900.56* |
| 15 [mg/kg] TPP-15374 Mean ± SD | 1.43 ± 0.34**** | 389.02 ± 5128** | 1495.88 ± 560.06** |

8-10 animal/group, One-way ANOVA with Dunnett's corrections for multiple comparisons,
*//*/****= significant with p < 0.05/0.01/0.001/0.0001 vs isotype control

TABLE 18

Dose-response of TPP-11489 in mouse I/R injury model

|  | serum creatinine [mg/dl] | serum urea [mg/dl] | urinary albumin to creatinine ratio [μg/mg] |
|---|---|---|---|
| SHAM Mean ± SD | 0.22 ± 0.02**** | 57.64 ± 14.62**** | 27.87 ± 13.55**** |
| 15 [mg/kg] isotype control Mean ± SD | 1.99 ± 0.29 | 410.18 ± 39.80 | 1569.47 ± 277.70 |
| 1 [mg/kg] TPP-11489 Mean ± SD | 2.00 ± 0.12 | 453.84 ± 26.54 | 1600.96 ± 338.48 |
| 5 [mg/kg] TPP-11489 Mean ± SD | 1.92 ± 0.16 | 416.87 ± 49.81 | 1437.08 ± 323.46 |
| 15 [mg/kg] TPP-11489 Mean ± SD | 1.68 ± 0.42* | 367.67 ± 39.32 | 1186.32 ± 366.49* |

8-10 animal/group, One-way ANOVA with Dunnett's corrections for multiple comparisons,
/*/****= significant with p < 0.05/0.01/0.001/0.0001 vs isotype control

TABLE 19

Dose-response of TPP-17755 antibody in mouse I/R injury model

| | serum creatinine [mg/dl] | serum urea [mg/dl] | urinary albumin to creatinine ratio [µg/mg] |
|---|---|---|---|
| SHAM Mean ± SD | 0.21 ± 0.06**** | 91.20 ± 34.20**** | 75.45 ± 42.78**** |
| 15 [mg/kg] isotype control Mean ± SD | 1.75 ± 0.30 | 444.25 ± 64.25 | 1791.23 ± 543.46 |
| 1 [mg/kg] TPP-17755 Mean ± SD | 1.74 ± 0.27 | 430.30 ± 75.96 | 1659.08 ± 577.99 |
| 5 [mg/kg] TPP-17755 Mean ± SD | 1.84 ± 0.24 | 439.83 ± 73.68 | 1661.14 ± 460.41 |
| 15 [mg/kg] TPP-17755 Mean ± SD | 1.31 ± 0.37** | 346.62 ± 78.14** | 1351.64 ± 795.59 |

8-10 animal/group, One-way ANOVA with Dunnett's corrections for multiple comparisons,
*//*/****= significant with p < 0.05/0.01/0.001/0.0001 vs isotype control

TABLE 20

Dose-response of TPP-23298 antibody in mouse I/R injury model

| | serum creatinine [mg/dl] | serum urea [mg/dl] | urinary albumin to creatinine ratio [µg/mg] |
|---|---|---|---|
| SHAM Mean ± SD | 0.26 ± 0.04**** | 115.80 ± 6.76**** | 71.05 ± 865.39**** |
| 15 [mg/kg] isotype control Mean ± SD | 2.53 ± 0.15 | 498.92 ± 45.45 | 3968.71 ± 453.52 |
| 1 [mg/kg] TPP-23298 Mean ± SD | 2.38 ± 0.22 | 482.06 ± 25.84 | 2383.77 ± 1111.94** |
| 5 [mg/kg] TPP-23298 Mean ± SD | 2.20 ± 0.36* | 425.64 ± 58.85* | 1966.11 ± 677.69**** |
| 15 [mg/kg] TPP-23298 Mean ± SD | 2.02 ± 0.28*** | 422.79 ± 71.44** | 1949.56 ± 700.58**** |

8-10 animal/group, One-way ANOVA with Dunnett's corrections for multiple comparisons. One-way ANOVA with Dunnett's corrections for multiple comparisons,
*//*/****= significant with p < 0.05/0.01/0.001/0.0001 vs isotype control

Example 14: In Vivo Assay for Detecting Protective Renal Effects: Alport Syndrome Model (Col4α3 Deficient Mice)

The phenotype of Alport mice is similar to that of Alport patients, including characteristic thickening and splitting of the glomerular basement membrane as well as strong proteinuria. Alport mice may benefit from treatment with Sema3A inhibitors due to increased Sema3A expression in kidneys of those mice. The beneficial effect of Sema3A blocking antibodies on kidney function was investigated in the Alport mouse model as follows: A colony of knockout Col4α3 (129-Col4α3<tm1Dec>/J) mice (Jackson Laboratory, USA) was established by mating heterozygous animals within the breeding facilities at Bayer A G, Wuppertal, Germany. Male and female homozygous and wild-type Col4α3 mice at an age of 4-5 weeks were obtained from the animal breeding facilities at Bayer A G and used for this study.

The homozygous mice (HOM) were randomized into groups (n=10 each group) according to their age and gender. Mice were dosed once weekly with isotype control and TPP-15370 and TPP-23298. TPP-11489 was administered biweekly. Urine of each animal was collected in metabolic cages once weekly starting before initiation of treatment. Urinary creatinine as well as total protein was measured by a clinical biochemistry analyzer (Pentra400). Both urinary creatinine and albumin were used to determine proteinuria (protein/creatinine ratio). Upon sacrifice at day 21 or day 28 post treatment start, blood samples were obtained under terminal anesthesia. After centrifugation of the blood samples, serum was isolated. Both serum creatinine and serum urea were measured via clinical biochemistry analyzer (Pentra 400).

Kidneys were collected and divided in two parts. One part was snap-frozen in liquid nitrogen for mRNA analysis. The other part was stored in Davidson's fixative for the preparation of histological sections. Total RNA was isolated from parts of harvested kidneys. Kidney tissue was homogenized, and RNA was obtained and transcribed to cDNA. Using TaqMan real time PCR renal mRNA expression of pro-fibrotic markers was analyzed in kidney tissues. For the assessment of fibrosis on the protein level paraffin tissue sections were stained with alpha-smooth muscle actin (αSMA) and Sirius Red/Fast Green Collagen staining using standard procedures.

Quantitative measurements of alpha-smooth muscle actin (αSMA)-positive as well as Sirius Red (Collagen) positive areas within the kidneys were obtained by computer image analysis using the Axio Scan Z1 (Zeiss) microscope and the Zen software.

All data are expressed as means±S.D. Differences between groups were analyzed by one-way ANOVA with Dunnett's corrections for multiple comparisons. Statistical significance was defined as p<0.05. All statistical analyses were done using GraphPad Prism 8.

Tables 21A-21C and 22A-22C show effects on proteinuria, kidney function and kidney fibrosis obtained after treatment with TPP-15370 and TPP-23298 in the Alport model. Effects after treatment with TPP-15370 in comparison to TPP-11489 on proteinuria, kidney function and kidney fibrosis are displayed in FIGS. 7 and 8A-8D.

The antibodies according to the present disclosure stopped the progression of kidney disease in a mouse model of Alport syndrome. The antibodies according to the present disclosure reduced the excretion of urinary protein, reduced creatinine and serum urea (surrogates for glomerular filtration rate) as well as fibrosis quantified via myofibroblasts staining and collagen deposition.

TABLE 21A

Effects of TPP-15370 on proteinuria progression in Alport mouse model

| | urinary protein to creatinine ratio [%] increase from baseline | | | |
|---|---|---|---|---|
| | baseline | day 7 | day 14 | day 21 |
| HOM 15 [mg/kg] isotype control Mean ± SD | 100.00 ± 53.71 | 118.65 ± 47.18 | 167.49 ± 55.77 | 192.03 ± 40.23 |
| HOM 5 [mg/kg] TPP-15370 Mean ± SD | 100.00 ± 54.02 | 114.61 ± 50.48 | 149.35 ± 95.41 | 164.92 ± 47.18 |

TABLE 21A-continued

Effects of TPP-15370 on proteinuria progression in Alport mouse model

| | urinary protein to creatinine ratio [%] increase from baseline | | | |
|---|---|---|---|---|
| | baseline | day 7 | day 14 | day 21 |
| HOM 15 [mg/kg] TPP-15370 Mean ± SD | 100.00 ± 65.59 | 114.61 ± 50.48 | 95.41 ± 52.50** | 93.04 ± 31.26**** |

10 animal/group, data are expressed as relative means ± SD percentage values calculated vs. baseline (set to 100). Differences between groups were analyzed by one-way ANOVA with Dunnett's corrections for multiple comparisons. Statistical significance was defined as $p \leq 0.05$.

TABLE 21B

Effects of TPP-15370 on functional parameters at day 21 in Alport mouse model

| | serum creatinine [mg/dl] | serum urea [mg/dl] |
|---|---|---|
| HOM 15 [mg/kg] isotype control Mean ± SD | 0.71 ± 0.26 | 380.61 ± 120.28 |
| HOM 5 [mg/kg] TPP-15370 Mean ± SD | 0.39 ± 0.16** | 255.25 ± 56.80** |
| HOM 15 [mg/kg] TPP-15370 Mean ± SD | 0.44 ± 0.21** | 256.71 ± 95.03** |

10-15 animal/group, One-way ANOVA with Dunnett's corrections for multiple comparisons. One-way ANOVA with Dunnett's corrections for multiple comparisons, /*/**** = significant with $p < 0.05/0.01/0.001/0.0001$ vs isotype control

TABLE 21C

| Effects of TPP-15370 on fibrosis at day 28 in Alport mouse model | | |
|---|---|---|
| | Myofibroblasts % aSMA reduction | Collagen % Sirius Red reduction |
| HOM 15 [mg/kg] isotype control Mean ± SD | 100.00 ± 53.53 | 100.00 ± 47.78 |
| HOM 5 [mg/kg] TPP-15370 Mean ± SD | 50.18 ± 21.00** | 80.08 ± 51.58 |
| HOM 15 [mg/kg] TPP-15370 Mean ± SD | 54.86 ± 17.60** | 100.26 ± 50.97 |

10-15 animal/group, One-way ANOVA with Dunnett's corrections for multiple comparisons. One-way ANOVA with Dunnett's corrections for multiple comparisons, /*/**** = significant with $p < 0.05/0.01/0.001/0.0001$ vs isotype control

TABLE 22A

Effects of TPP-23298 on proteinuria progression in Alport mouse model

| | urinary protein to creatinine ratio [%] increase from baseline | | | |
|---|---|---|---|---|
| | baseline | day 14 | day 21 | day 28 |
| HOM 15 [mg/kg] isotype control Mean ± SD | 100.00 ± 70.94 | 185.29 ± 88.09 | 228.62 ± 160.68 | 283.62 ± 77.37 |
| HOM 5 [mg/kg] TPP-23298 Mean ± SD | 100.00 ± 55.72 | 148.01 ± 77.13 | 155.25 ± 61.60 | 151.82 ± 45.84**** |
| HOM 15 [mg/kg] TPP-23298 Mean ± SD | 100.00 ± 56.02 | 154.58 ± 91.21 | 120.54 ± 37.21**** | 125.71 ± 34.25**** |

10 animal/group, data are expressed as relative means ± SD percentage values calculated vs. baseline (set to 100). Differences between groups were analyzed by one-way ANOVA with Dunnett's corrections for multiple comparisons. Statistical significance was defined as $p \leq 0.05$.

TABLE 22B

Effects of TPP-23298 on functional parameters at day 28 in Alport mouse model

| | serum creatinine [mg/dl] | serum urea [mg/dl] |
|---|---|---|
| HOM 15 [mg/kg] isotype control Mean ± SD | 0.29 ± 0.07 | 208.89 ± 0.07 |
| HOM 5 [mg/kg] TPP-23298 Mean ± SD | 0.22 ± 0.09* | 175.54 ± 0.03 |
| HOM 15 [mg/kg] TPP-23298 Mean ± SD | 0.19 ± 0.03*** | 141.84 ± 0.03*** |

10-15 animal/group, One-way ANOVA with Dunnett's corrections for multiple comparisons. One-way ANOVA with Dunnett's corrections for multiple comparisons, /*/**** = significant with $p < 0.05/0.01/0.001/0.0001$ vs isotype control

TABLE 22C

| Effects of TPP-23298 on fibrosis at day 28 in Alport mouse model | | |
|---|---|---|
| | Myofibroblasts % αSMA positive area | Collagen % Sirius Red positive area |
| HOM 15 [mg/kg] isotype control Mean ± SD | 100.00 ± 53.53 | 100.00 ± 47.78 |
| HOM 5 [mg/kg] TPP-23298 Mean ± SD | 50.18 ± 21.00** | 80.08 ± 51.58 |
| HOM 15 [mg/kg] TPP-23298 Mean ± SD | 54.86 ± 17.60** | 100.26 ± 50.97 |

10-15 animal/group, One-way ANOVA with Dunnett's corrections for multiple comparisons. One-way ANOVA with Dunnett's corrections for multiple comparisons, /*/**** = significant with $p < 0.05/0.01/0.001/0.0001$ vs isotype control

Example 15: In Vivo Away for Detecting Protective Renal Effects: Unilateral Kidney IRI Model in Pig TPP-23298 was tested in a minimal invasive, unilateral kidney artery balloon-catheter occlusion model in adult minipigs with a post-reperfusion follow-up of about 24 hours. Female Göttingen mini pigs of a body weight range 14 to 17 kg (Ellegaard, Denmark) were used for the experiments. Animals were randomly assigned to experimental groups.

TPP-23298 was administered in a blinded, controlled study to 6 animals in comparison to 6 matched IgG-treated controls. Animals which were subjected to all treatment procedures without kidney artery occlusion and received phosphate buffered saline vehicle only served as sham treated reference group.

TPP-23298 was administered at weight adjusted doses in a final volume of 1 ml/kg phosphate buffered saline as a bolus by slow intravenous injection before start of kidney artery occlusion (preventive setting).

For the intervention on day 1 of experimentation pigs were anesthetized by a combination of Propofol and Fentanyl and artificially ventilated over an oro-tracheal tube under muscular relaxation by Pancuronium. Volume was continuously substituted by continuous infusion of Ringer lactate solution. Before starting surgery, antibiotic and thrombosis prophylaxis were provided by administration of Enrofloxacin i.m. and Heparin i.v., respectively. Blood pressure and heart rate were monitored with a non-invasive veterinary device equipped with a foreleg cuff.

All following interventions were performed under strictly aseptic conditions. A catheter was tunneled subcutaneously through the dorsal neck skin to a jugular vein for drug administration. A sheath was placed into the—preferably left—femoral artery and fixed, through which a hockey-stick catheter with a balloon catheter inside was advanced upstream into the abdominal aorta and inserted with its tip into the orifice of the left or right kidney artery. The balloon catheter was then protruded, and the balloon was inflated to interrupt blood flow to the kidney. Correct positioning of the balloon was controlled by Doppler ultrasound using a commercial ultrasound diagnostic apparatus. Plasma samples were collected at baseline and 2 h after start of ischemia.

Kidney ischemia was relieved exactly at pre-defined time points after start of occlusion (ranging from 90 to 120 min) by deflating the balloon and withdrawing the catheter and the sheath. After vascular suture and wound closure animals were re-awakened from anesthesia and after onset of spontaneous breathing extubated.

About 22 to 23 hours after the kidney artery occlusion animals were re-anesthetized by a combination of Ketaset/Dormicum and Pancuronium and artificially ventilated as described. Blood pressure and heart rate were invasively monitored via a carotid artery catheter. Volume substitution was provided at a flow rate of 10 ml/kg/h Ringer Lactate intravenously. Via a small incision in the lower abdomen both ureters were dissected on the urinary bladder wall and catheters were inserted to collect urine side separately for volume determination and urinalysis. Recordings and sample collections were started when all parameters were stable, which was typically the case 24 hours after occlusion. Blood samples were collected at baseline and every hour for three hours (24-27 h interval). In parallel urine was collected for three intervals of 1 h.

After urine volume flow ($V_U$) and urinary creatinine concentrations ($[Crea]_U$) were determined creatinine clearance ($CL_{Crea}$) was calculated side separately according to the standard formula $CL_{Crea}=V_U*[Crea]_U/[Crea]_{Pl}$ in which $[Crea]_{Pl}$ stands for plasma creatinine concentration. Global $CL_{Crea}$ was calculated by adding $CL_{Crea}$ of left and right kidney of each animal.

The results are depicted in FIGS. 9A-9D. TPP-23298 when administered in a preventive manner 30 min before occlusion prevented deterioration of ischemia/reperfusion-induced creatinine clearance significantly in this experimental setting after a unilateral kidney artery occlusion of 105 min.

Example 16: Expression Titer of Anti-Sema3A Antibodies in Mammalian Cell Culture HEK293-6E cells were transfected with pTT5 plasmids coding for the heavy and light chain of anti-Sema3A antibodies or with the Fab fragment of TPP-30792 (TPP-31357). Two days prior to transfection, HEK293-6E cells were split to a density of 5×10^5 cells/mL in FreeStyle™ F17 Expression Medium (Gibco, A1383501) with 0.1% Pluronic F68 (Gibco, 24040032) and 4 mM GlutaMax (Gibco, 35050061) in a shake flask, making up 90% of the desired expression volume. HEK293-6E cells were cultivated at 37° C., 5% $CO_2$ shaking at 75 rpm.

For transfection, the DNA and polyethylenimine (Polysciences, 29366) are mixed in FreeStyle™ F17 Expression Medium (Gibco, A1383501) with 4 mM GlutaMax (Gibco, 35050061) making up 10% of the final expression volume. The solution is incubated for 10 minutes and added to the shake flask.

24 hours after transfection, 1% (v/v) ultra-low IgG FBS (Gibco, 16250078) and 0.05% (v/v) 1N valproic acid (Sigma, P4543) are added to the shake flask.

The cell viability and density are monitored every day starting 4 days post transfection, the supernatant is harvested by centrifugation and sterile filtration when the viability is determined to be 70%. To determine the production titer, 100 µL of the harvested supernatant are loaded to a 0.1 mL Poros A affinity column (Thermo Scientific, 2100100) via HPLC-system (Agilent, 1100 HPLC system) using 50 mM sodium phosphate (Sigma, S0751, S9763), 150 mM NaCl (Sigma, S6546), 5% 2-propanol (sigma, 34863), pH 7.2 as running buffer. Subsequently, the protein is eluted using 12 mM HCl (Sigma, H9892), 150 mM NaCl, 5% 2-propanol pH 2. A calibration curve from 5 µg/mL to 150 µg/mL is set up using a protein of known size and is applied to the Poros A column via HPLC-system as well. Taking the size and extinction coefficient of the protein in the supernatant into consideration, the exact titer can be calculated using the standard curve. Expression in CHO is similar to HEK cells except that plasmid pTT22AKT was used for TPP-30792.

TABLE 23

Expression Titer of anti-Sema3A antibodies in mammalian cells in mg/L

| | Titer [mg/L] |
|---|---|
| TPP-23298 | 203.6 |
| TPP-17755 (Samsung) | 277.0 |
| TPP-11489 (Chiome) | 132.0 |
| TPP-30791 (BI clone IV) | 333.0 |
| TPP-30790 (BI clone III) | 160.9 |
| TPP-30789 (BI clone II) | 187.6 |
| TPP-30788 (BI clone I) | 240.2 |
| TPP-30792 (3H4 Univ Ramot) | 3.0 (HEK), 3.2 (CHO) |
| TPP-31357 (Fab of TPP-30792) | Not determined |

The antibody of the present disclosure as well as all prior art antibodies except TPP-30792 can be produced with high titers in mammalian cells, as shown in Table 23. TPP-30792 could not be expressed in a significant amount in either HEK or CHO cells. In total 125 µg of TPP-30792 could be purified out of 4.5 liters of HEK293 cell culture. Similarly, the Fab fragment of TPP30792 (TPP-31357) yielded only 200 µg purified Fab out of 5 liters HEK293 cell culture.

Example 17: Analysis of CMC Parameter Stability and Solubility of Anti-Sema3A Antibodies It is known that high concentrated protein solutions of more than 50 mg/ml usually exhibit also higher viscosities compared to lower concentrated protein solutions. Increased viscosity negatively affects the deliverability of the protein solutions especially in low application volumes and it may increase the injection time and pain at the site of injection. In addition to that, high viscosity impacts high-scale protein production in the industry. Thus, reducing viscosity of high concentrated protein solutions while maintaining stability for a long shelf life is i.a. important for the therapeutical in vivo setting.

Proteins in high concentrated solutions are often less stable than in diluted solutions, since the proteins tend to aggregate and may reversibly self-associate at higher concentrations. Aggregation may negatively impact structural integrity and therefore also the amount of functional, bioavailable protein in the therapeutical in vivo setting. This further complicates delivery by injection.

Solubility of proteins is another important quality criterion. Increased solubility of the isolated protein allows for the preparation of highly concentrated solutions required for the therapeutical in vivo setting.

Thus, providing a high concentrated protein solution with reduced viscosity and increased stability and solubility is beneficial for therapeutic applicability of therapeutic molecules.

To assess the CMC (Chemistry, Manufacturing, Control) parameters stability, solubility and viscosity of anti-Sema3A antibodies for potential therapeutic use, antibodies TPP-23289 and TPP-30788 (BI clone I) were diluted in PBS to 25 mg/ml and incubated at 700 rpm and 40° C. for two weeks. While antibodies are usually stored at 4°–10° C. for short-term or frozen at ≤−18° C. or ≥−81° C. for long term an exposure of mammalian antibodies to temperatures higher than ≥40° C. (mammalian average body temperature is 36° C.-39° C.) resembles a thermal stress condition. In this thermal stress condition accelerated protein stability/stress stability is tested. Analysis of stability was assessed by size-exclusion chromatography using a Superdex 200 column (Cytiva) coupled to an Äkta system (Cytiva) in PBS buffer as well as capillary gel electrophoresis using a Caliper system (Perkin Elmer). Changes in profile were calculated as percentage to non-stressed starting material. Solubility was determined by concentrating anti-Sema3A antibodies using an Amicon spin filter (Millipore) with a cut-off of 30 kDa in PBS buffer. The solubility was determined at 90% recovery from the concentrator and protein concentration was measured using Absorption at UV280 nm.

TABLE 24

Overview of CMC parameters for TPP-23298 and TPP-30788; SEC = size-exclusion chromatography, cGE = capillary gel electrophoresis

| CMC Parameter | Method | Analysis | TPP-23298 | TPP-30788 (BI clone I) |
|---|---|---|---|---|
| Stability at 40° C. | SEC* | Δ % monomer | 1 | −5.5 |
|  | cGE** | Δ % LC ± HC | <1 | −4.7 |
| Solubility | concentrator | mg/ml at 90% recovery | 225 | 105 |
|  | SEC* | Δ % monomer | <1 | <1 |
| Viscosity | Viscosizer | cP | 5.1 (150 mg/ml) | 5.3 (127 mg/ml) |

*SEC = Size exclusion chromatography;
**cGE = capillary gel electrophoresis

Stability, solubility and viscosity are critical CMC parameters for therapeutic molecules as described above. The structural integrity after a thermal stress condition, like exposure to 40° C., or concentrating step is analyzed via SEC and/or cGE to see the effect of the applied stress on the structural integrity. Less than 1% change after the applied stress compared to the start points to a stable molecule whereas deviations >1% points to instabilities in the molecule. TPP-23289 shows a much higher solubility in PBS compared to TPP-30788 by a factor >2 which is very beneficial for e.g. enabling low application volume. Furthermore, TPP-23298 is more stable and more resistant to heat stress than TPP-30788 and is less viscous in PBS buffer.

TABLE 1

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-11489 | Chiome Prior Art (hIgG1) | VH | PRT | SEQ ID NO: 1 |
| TPP-11489 | Chiome Prior Art (hIgG1) | HCDR1 | PRT | SEQ ID NO: 2 |
| TPP-11489 | Chiome Prior Art (hIgG1) | HCDR2 | PRT | SEQ ID NO: 3 |
| TPP-11489 | Chiome Prior Art (hIgG1) | HCDR3 | PRT | SEQ ID NO: 4 |
| TPP-11489 | Chiome Prior Art (hIgG1) | VL | PRT | SEQ ID NO: 5 |
| TPP-11489 | Chiome Prior Art (hIgG1) | LCDR1 | PRT | SEQ ID NO: 6 |
| TPP-11489 | Chiome Prior Art (hIgG1) | LCDR2 | PRT | SEQ ID NO: 7 |
| TPP-11489 | Chiome Prior Art (hIgG1) | LCDR3 | PRT | SEQ ID NO: 8 |
| TPP-11489 | Chiome Prior Art (hIgG1) | VH | DNA | SEQ ID NO: 9 |
| TPP-11489 | Chiome Prior Art (hIgG1) | HCDR1 | DNA | SEQ ID NO: 10 |
| TPP-11489 | Chiome Prior Art (hIgG1) | HCDR2 | DNA | SEQ ID NO: 11 |
| TPP-11489 | Chiome Prior Art (hIgG1) | HCDR3 | DNA | SEQ ID NO: 12 |
| TPP-11489 | Chiome Prior Art (hIgG1) | VL | DNA | SEQ ID NO: 13 |
| TPP-11489 | Chiome Prior Art (hIgG1) | LCDR1 | DNA | SEQ ID NO: 14 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-11489 | Chiome Prior Art (hIgG1) | LCDR2 | DNA | SEQ ID NO: 15 |
| TPP-11489 | Chiome Prior Art (hIgG1) | LCDR3 | DNA | SEQ ID NO: 16 |
| TPP-11489 | Chiome Prior Art (hIgG1) | Heavy Chain | PRT | SEQ ID NO: 17 |
| TPP-11489 | Chiome Prior Art (hIgG1) | Light Chain | PRT | SEQ ID NO: 18 |
| TPP-11489 | Chiome Prior Art (hIgG1) | Heavy Chain | DNA | SEQ ID NO: 19 |
| TPP-11489 | Chiome Prior Art (hIgG1) | Light Chain | DNA | SEQ ID NO: 20 |
| TPP-15051 | Chiome Prior Art (mIgG1) | VH | PRT | SEQ ID NO: 21 |
| TPP-15051 | Chiome Prior Art (mIgG1) | HCDR1 | PRT | SEQ ID NO: 22 |
| TPP-15051 | Chiome Prior Art (mIgG1) | HCDR2 | PRT | SEQ ID NO: 23 |
| TPP-15051 | Chiome Prior Art (mIgG1) | HCDR3 | PRT | SEQ ID NO: 24 |
| TPP-15051 | Chiome Prior Art (mIgG1) | VL | PRT | SEQ ID NO: 25 |
| TPP-15051 | Chiome Prior Art (mIgG1) | LCDR1 | PRT | SEQ ID NO: 26 |
| TPP-15051 | Chiome Prior Art (mIgG1) | LCDR2 | PRT | SEQ ID NO: 27 |
| TPP-15051 | Chiome Prior Art (mIgG1) | LCDR3 | PRT | SEQ ID NO: 28 |
| TPP-15051 | Chiome Prior Art (mIgG1) | VH | DNA | SEQ ID NO: 29 |
| TPP-15051 | Chiome Prior Art (mIgG1) | HCDR1 | DNA | SEQ ID NO: 30 |
| TPP-15051 | Chiome Prior Art (mIgG1) | HCDR2 | DNA | SEQ ID NO: 31 |
| TPP-15051 | Chiome Prior Art (mIgG1) | HCDR3 | DNA | SEQ ID NO: 32 |
| TPP-15051 | Chiome Prior Art (mIgG1) | VL | DNA | SEQ ID NO: 33 |
| TPP-15051 | Chiome Prior Art (mIgG1) | LCDR1 | DNA | SEQ ID NO: 34 |
| TPP-15051 | Chiome Prior Art (mIgG1) | LCDR2 | DNA | SEQ ID NO: 35 |
| TPP-15051 | Chiome Prior Art (mIgG1) | LCDR3 | DNA | SEQ ID NO: 36 |
| TPP-15051 | Chiome Prior Art (mIgG1) | Heavy Chain | PRT | SEQ ID NO: 37 |
| TPP-15051 | Chiome Prior Art (mIgG1) | Light Chain | PRT | SEQ ID NO: 38 |
| TPP-15051 | Chiome Prior Art (mIgG1) | Heavy Chain | DNA | SEQ ID NO: 39 |
| TPP-15051 | Chiome Prior Art (mIgG1) | Light Chain | DNA | SEQ ID NO: 40 |
| TPP-15370 | IgG1, hit from panning | VH | PRT | SEQ ID NO: 41 |
| TPP-15370 | IgG1, hit from panning | HCDR1 | PRT | SEQ ID NO: 42 |
| TPP-15370 | IgG1, hit from panning | HCDR2 | PRT | SEQ ID NO: 43 |
| TPP-15370 | IgG1, hit from panning | HCDR3 | PRT | SEQ ID NO: 44 |
| TPP-15370 | IgG1, hit from panning | VL | PRT | SEQ ID NO: 45 |
| TPP-15370 | IgG1, hit from panning | LCDR1 | PRT | SEQ ID NO: 46 |
| TPP-15370 | IgG1, hit from panning | LCDR2 | PRT | SEQ ID NO: 47 |
| TPP-15370 | IgG1, hit from panning | LCDR3 | PRT | SEQ ID NO: 48 |
| TPP-15370 | IgG1, hit from panning | VH | DNA | SEQ ID NO: 49 |
| TPP-15370 | IgG1, hit from panning | HCDR1 | DNA | SEQ ID NO: 50 |
| TPP-15370 | IgG1, hit from panning | HCDR2 | DNA | SEQ ID NO: 51 |
| TPP-15370 | IgG1, hit from panning | HCDR3 | DNA | SEQ ID NO: 52 |
| TPP-15370 | IgG1, hit from panning | VL | DNA | SEQ ID NO: 53 |
| TPP-15370 | IgG1, hit from panning | LCDR1 | DNA | SEQ ID NO: 54 |
| TPP-15370 | IgG1, hit from panning | LCDR2 | DNA | SEQ ID NO: 55 |
| TPP-15370 | IgG1, hit from panning | LCDR3 | DNA | SEQ ID NO: 56 |
| TPP-15370 | IgG1, hit from panning | Heavy Chain | PRT | SEQ ID NO: 57 |
| TPP-15370 | IgG1, hit from panning | Light Chain | PRT | SEQ ID NO: 58 |
| TPP-15370 | IgG1, hit from panning | Heavy Chain | DNA | SEQ ID NO: 59 |
| TPP-15370 | IgG1, hit from panning | Light Chain | DNA | SEQ ID NO: 60 |
| TPP-15374 | IgG1, hit from panning | VH | PRT | SEQ ID NO: 61 |
| TPP-15374 | IgG1, hit from panning | HCDR1 | PRT | SEQ ID NO: 62 |
| TPP-15374 | IgG1, hit from panning | HCDR2 | PRT | SEQ ID NO: 63 |
| TPP-15374 | IgG1, hit from panning | HCDR3 | PRT | SEQ ID NO: 64 |
| TPP-15374 | IgG1, hit from panning | VL | PRT | SEQ ID NO: 65 |
| TPP-15374 | IgG1, hit from panning | LCDR1 | PRT | SEQ ID NO: 66 |
| TPP-15374 | IgG1, hit from panning | LCDR2 | PRT | SEQ ID NO: 67 |
| TPP-15374 | IgG1, hit from panning | LCDR3 | PRT | SEQ ID NO: 68 |
| TPP-15374 | IgG1, hit from panning | VH | DNA | SEQ ID NO: 69 |
| TPP-15374 | IgG1, hit from panning | HCDR1 | DNA | SEQ ID NO: 70 |
| TPP-15374 | IgG1, hit from panning | HCDR2 | DNA | SEQ ID NO: 71 |
| TPP-15374 | IgG1, hit from panning | HCDR3 | DNA | SEQ ID NO: 72 |
| TPP-15374 | IgG1, hit from panning | VL | DNA | SEQ ID NO: 73 |
| TPP-15374 | IgG1, hit from panning | LCDR1 | DNA | SEQ ID NO: 74 |
| TPP-15374 | IgG1, hit from panning | LCDR2 | DNA | SEQ ID NO: 75 |
| TPP-15374 | IgG1, hit from panning | LCDR3 | DNA | SEQ ID NO: 76 |
| TPP-15374 | IgG1, hit from panning | Heavy Chain | PRT | SEQ ID NO: 77 |
| TPP-15374 | IgG1, hit from panning | Light Chain | PRT | SEQ ID NO: 78 |
| TPP-15374 | IgG1, hit from panning | Heavy Chain | DNA | SEQ ID NO: 79 |
| TPP-15374 | IgG1, hit from panning | Light Chain | DNA | SEQ ID NO: 80 |
| TPP-17755 | Samsung Prior Art F11 | VH | PRT | SEQ ID NO: 81 |
| TPP-17755 | Samsung Prior Art F11 | HCDR1 | PRT | SEQ ID NO: 82 |
| TPP-17755 | Samsung Prior Art F11 | HCDR2 | PRT | SEQ ID NO: 83 |
| TPP-17755 | Samsung Prior Art F11 | HCDR3 | PRT | SEQ ID NO: 84 |
| TPP-17755 | Samsung Prior Art F11 | VL | PRT | SEQ ID NO: 85 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
| --- | --- | --- | --- | --- |
| TPP-17755 | Samsung Prior Art F11 | LCDR1 | PRT | SEQ ID NO: 86 |
| TPP-17755 | Samsung Prior Art F11 | LCDR2 | PRT | SEQ ID NO: 87 |
| TPP-17755 | Samsung Prior Art F11 | LCDR3 | PRT | SEQ ID NO: 88 |
| TPP-17755 | Samsung Prior Art F11 | VH | DNA | SEQ ID NO: 89 |
| TPP-17755 | Samsung Prior Art F11 | HCDR1 | DNA | SEQ ID NO: 90 |
| TPP-17755 | Samsung Prior Art F11 | HCDR2 | DNA | SEQ ID NO: 91 |
| TPP-17755 | Samsung Prior Art F11 | HCDR3 | DNA | SEQ ID NO: 92 |
| TPP-17755 | Samsung Prior Art F11 | VL | DNA | SEQ ID NO: 93 |
| TPP-17755 | Samsung Prior Art F11 | LCDR1 | DNA | SEQ ID NO: 94 |
| TPP-17755 | Samsung Prior Art F11 | LCDR2 | DNA | SEQ ID NO: 95 |
| TPP-17755 | Samsung Prior Art F11 | LCDR3 | DNA | SEQ ID NO: 96 |
| TPP-17755 | Samsung Prior Art F11 | Heavy Chain | PRT | SEQ ID NO: 97 |
| TPP-17755 | Samsung Prior Art F11 | Light Chain | PRT | SEQ ID NO: 98 |
| TPP-17755 | Samsung Prior Art F11 | Heavy Chain | DNA | SEQ ID NO: 99 |
| TPP-17755 | Samsung Prior Art F11 | Light Chain | DNA | SEQ ID NO: 100 |
| TPP-18533 | germline IgG1 of TPP-15374 | VH | PRT | SEQ ID NO: 101 |
| TPP-18533 | germline IgG1 of TPP-15374 | HCDR1 | PRT | SEQ ID NO: 102 |
| TPP-18533 | germline IgG1 of TPP-15374 | HCDR2 | PRT | SEQ ID NO: 103 |
| TPP-18533 | germline IgG1 of TPP-15374 | HCDR3 | PRT | SEQ ID NO: 104 |
| TPP-18533 | germline IgG1 of TPP-15374 | VL | PRT | SEQ ID NO: 105 |
| TPP-18533 | germline IgG1 of TPP-15374 | LCDR1 | PRT | SEQ ID NO: 106 |
| TPP-18533 | germline IgG1 of TPP-15374 | LCDR2 | PRT | SEQ ID NO: 107 |
| TPP-18533 | germline IgG1 of TPP-15374 | LCDR3 | PRT | SEQ ID NO: 108 |
| TPP-18533 | germline IgG1 of TPP-15374 | VH | DNA | SEQ ID NO: 109 |
| TPP-18533 | germline IgG1 of TPP-15374 | HCDR1 | DNA | SEQ ID NO: 110 |
| TPP-18533 | germline IgG1 of TPP-15374 | HCDR2 | DNA | SEQ ID NO: 111 |
| TPP-18533 | germline IgG1 of TPP-15374 | HCDR3 | DNA | SEQ ID NO: 112 |
| TPP-18533 | germline IgG1 of TPP-15374 | VL | DNA | SEQ ID NO: 113 |
| TPP-18533 | germline IgG1 of TPP-15374 | LCDR1 | DNA | SEQ ID NO: 114 |
| TPP-18533 | germline IgG1 of TPP-15374 | LCDR2 | DNA | SEQ ID NO: 115 |
| TPP-18533 | germline IgG1 of TPP-15374 | LCDR3 | DNA | SEQ ID NO: 116 |
| TPP-18533 | germline IgG1 of TPP-15374 | Heavy Chain | PRT | SEQ ID NO: 117 |
| TPP-18533 | germline IgG1 of TPP-15374 | Light Chain | PRT | SEQ ID NO: 118 |
| TPP-18533 | germline IgG1 of TPP-15374 | Heavy Chain | DNA | SEQ ID NO: 119 |
| TPP-18533 | germline IgG1 of TPP-15374 | Light Chain | DNA | SEQ ID NO: 120 |
| TPP-21565 | germline IgG1 of TPP-15370 | VH | PRT | SEQ ID NO: 121 |
| TPP-21565 | germline IgG1 of TPP-15370 | HCDR1 | PRT | SEQ ID NO: 122 |
| TPP-21565 | germline IgG1 of TPP-15370 | HCDR2 | PRT | SEQ ID NO: 123 |
| TPP-21565 | germline IgG1 of TPP-15370 | HCDR3 | PRT | SEQ ID NO: 124 |
| TPP-21565 | germline IgG1 of TPP-15370 | VL | PRT | SEQ ID NO: 125 |
| TPP-21565 | germline IgG1 of TPP-15370 | LCDR1 | PRT | SEQ ID NO: 126 |
| TPP-21565 | germline IgG1 of TPP-15370 | LCDR2 | PRT | SEQ ID NO: 127 |
| TPP-21565 | germline IgG1 of TPP-15370 | LCDR3 | PRT | SEQ ID NO: 128 |
| TPP-21565 | germline IgG1 of TPP-15370 | VH | DNA | SEQ ID NO: 129 |
| TPP-21565 | germline IgG1 of TPP-15370 | HCDR1 | DNA | SEQ ID NO: 130 |
| TPP-21565 | germline IgG1 of TPP-15370 | HCDR2 | DNA | SEQ ID NO: 131 |
| TPP-21565 | germline IgG1 of TPP-15370 | HCDR3 | DNA | SEQ ID NO: 132 |
| TPP-21565 | germline IgG1 of TPP-15370 | VL | DNA | SEQ ID NO: 133 |
| TPP-21565 | germline IgG1 of TPP-15370 | LCDR1 | DNA | SEQ ID NO: 134 |
| TPP-21565 | germline IgG1 of TPP-15370 | LCDR2 | DNA | SEQ ID NO: 135 |
| TPP-21565 | germline IgG1 of TPP-15370 | LCDR3 | DNA | SEQ ID NO: 136 |
| TPP-21565 | germline IgG1 of TPP-15370 | Heavy Chain | PRT | SEQ ID NO: 137 |
| TPP-21565 | germline IgG1 of TPP-15370 | Light Chain | PRT | SEQ ID NO: 138 |
| TPP-21565 | germline IgG1 of TPP-15370 | Heavy Chain | DNA | SEQ ID NO: 139 |
| TPP-21565 | germline IgG1 of TPP-15370 | Light Chain | DNA | SEQ ID NO: 140 |
| TPP-23298 | Recombi Variant of TPP-15370 | VH | PRT | SEQ ID NO: 141 |
| TPP-23298 | Recombi Variant of TPP-15370 | HCDR1 | PRT | SEQ ID NO: 142 |
| TPP-23298 | Recombi Variant of TPP-15370 | HCDR2 | PRT | SEQ ID NO: 143 |
| TPP-23298 | Recombi Variant of TPP-15370 | HCDR3 | PRT | SEQ ID NO: 144 |
| TPP-23298 | Recombi Variant of TPP-15370 | VL | PRT | SEQ ID NO: 145 |
| TPP-23298 | Recombi Variant of TPP-15370 | LCDR1 | PRT | SEQ ID NO: 146 |
| TPP-23298 | Recombi Variant of TPP-15370 | LCDR2 | PRT | SEQ ID NO: 147 |
| TPP-23298 | Recombi Variant of TPP-15370 | LCDR3 | PRT | SEQ ID NO: 148 |
| TPP-23298 | Recombi Variant of TPP-15370 | VH | DNA | SEQ ID NO: 149 |
| TPP-23298 | Recombi Variant of TPP-15370 | HCDR1 | DNA | SEQ ID NO: 150 |
| TPP-23298 | Recombi Variant of TPP-15370 | HCDR2 | DNA | SEQ ID NO: 151 |
| TPP-23298 | Recombi Variant of TPP-15370 | HCDR3 | DNA | SEQ ID NO: 152 |
| TPP-23298 | Recombi Variant of TPP-15370 | VL | DNA | SEQ ID NO: 153 |
| TPP-23298 | Recombi Variant of TPP-15370 | LCDR1 | DNA | SEQ ID NO: 154 |
| TPP-23298 | Recombi Variant of TPP-15370 | LCDR2 | DNA | SEQ ID NO: 155 |
| TPP-23298 | Recombi Variant of TPP-15370 | LCDR3 | DNA | SEQ ID NO: 156 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-23298 | Recombi Variant of TPP-15370 | Heavy Chain | PRT | SEQ ID NO: 157 |
| TPP-23298 | Recombi Variant of TPP-15370 | Light Chain | PRT | SEQ ID NO: 158 |
| TPP-23298 | Recombi Variant of TPP-15370 | Heavy Chain | DNA | SEQ ID NO: 159 |
| TPP-23298 | Recombi Variant of TPP-15370 | Light Chain | DNA | SEQ ID NO: 160 |
| TPP-23334 | Recombi Variant of TPP-15370 | VH | PRT | SEQ ID NO: 161 |
| TPP-23334 | Recombi Variant of TPP-15370 | HCDR1 | PRT | SEQ ID NO: 162 |
| TPP-23334 | Recombi Variant of TPP-15370 | HCDR2 | PRT | SEQ ID NO: 163 |
| TPP-23334 | Recombi Variant of TPP-15370 | HCDR3 | PRT | SEQ ID NO: 164 |
| TPP-23334 | Recombi Variant of TPP-15370 | VL | PRT | SEQ ID NO: 165 |
| TPP-23334 | Recombi Variant of TPP-15370 | LCDR1 | PRT | SEQ ID NO: 166 |
| TPP-23334 | Recombi Variant of TPP-15370 | LCDR2 | PRT | SEQ ID NO: 167 |
| TPP-23334 | Recombi Variant of TPP-15370 | LCDR3 | PRT | SEQ ID NO: 168 |
| TPP-23334 | Recombi Variant of TPP-15370 | VH | DNA | SEQ ID NO: 169 |
| TPP-23334 | Recombi Variant of TPP-15370 | HCDR1 | DNA | SEQ ID NO: 170 |
| TPP-23334 | Recombi Variant of TPP-15370 | HCDR2 | DNA | SEQ ID NO: 171 |
| TPP-23334 | Recombi Variant of TPP-15370 | HCDR3 | DNA | SEQ ID NO: 172 |
| TPP-23334 | Recombi Variant of TPP-15370 | VL | DNA | SEQ ID NO: 173 |
| TPP-23334 | Recombi Variant of TPP-15370 | LCDR1 | DNA | SEQ ID NO: 174 |
| TPP-23334 | Recombi Variant of TPP-15370 | LCDR2 | DNA | SEQ ID NO: 175 |
| TPP-23334 | Recombi Variant of TPP-15370 | LCDR3 | DNA | SEQ ID NO: 176 |
| TPP-23334 | Recombi Variant of TPP-15370 | Heavy Chain | PRT | SEQ ID NO: 177 |
| TPP-23334 | Recombi Variant of TPP-15370 | Light Chain | PRT | SEQ ID NO: 178 |
| TPP-23334 | Recombi Variant of TPP-15370 | Heavy Chain | DNA | SEQ ID NO: 179 |
| TPP-23334 | Recombi Variant of TPP-15370 | Light Chain | DNA | SEQ ID NO: 180 |
| TPP-23337 | Recombi Variant of TPP-15370 | VH | PRT | SEQ ID NO: 181 |
| TPP-23337 | Recombi Variant of TPP-15370 | HCDR1 | PRT | SEQ ID NO: 182 |
| TPP-23337 | Recombi Variant of TPP-15370 | HCDR2 | PRT | SEQ ID NO: 183 |
| TPP-23337 | Recombi Variant of TPP-15370 | HCDR3 | PRT | SEQ ID NO: 184 |
| TPP-23337 | Recombi Variant of TPP-15370 | VL | PRT | SEQ ID NO: 185 |
| TPP-23337 | Recombi Variant of TPP-15370 | LCDR1 | PRT | SEQ ID NO: 186 |
| TPP-23337 | Recombi Variant of TPP-15370 | LCDR2 | PRT | SEQ ID NO: 187 |
| TPP-23337 | Recombi Variant of TPP-15370 | LCDR3 | PRT | SEQ ID NO: 188 |
| TPP-23337 | Recombi Variant of TPP-15370 | VH | DNA | SEQ ID NO: 189 |
| TPP-23337 | Recombi Variant of TPP-15370 | HCDR1 | DNA | SEQ ID NO: 190 |
| TPP-23337 | Recombi Variant of TPP-15370 | HCDR2 | DNA | SEQ ID NO: 191 |
| TPP-23337 | Recombi Variant of TPP-15370 | HCDR3 | DNA | SEQ ID NO: 192 |
| TPP-23337 | Recombi Variant of TPP-15370 | VL | DNA | SEQ ID NO: 193 |
| TPP-23337 | Recombi Variant of TPP-15370 | LCDR1 | DNA | SEQ ID NO: 194 |
| TPP-23337 | Recombi Variant of TPP-15370 | LCDR2 | DNA | SEQ ID NO: 195 |
| TPP-23337 | Recombi Variant of TPP-15370 | LCDR3 | DNA | SEQ ID NO: 196 |
| TPP-23337 | Recombi Variant of TPP-15370 | Heavy Chain | PRT | SEQ ID NO: 197 |
| TPP-23337 | Recombi Variant of TPP-15370 | Light Chain | PRT | SEQ ID NO: 198 |
| TPP-23337 | Recombi Variant of TPP-15370 | Heavy Chain | DNA | SEQ ID NO: 199 |
| TPP-23337 | Recombi Variant of TPP-15370 | Light Chain | DNA | SEQ ID NO: 200 |
| TPP-23338 | Recombi Variant of TPP-15370 | VH | PRT | SEQ ID NO: 201 |
| TPP-23338 | Recombi Variant of TPP-15370 | HCDR1 | PRT | SEQ ID NO: 202 |
| TPP-23338 | Recombi Variant of TPP-15370 | HCDR2 | PRT | SEQ ID NO: 203 |
| TPP-23338 | Recombi Variant of TPP-15370 | HCDR3 | PRT | SEQ ID NO: 204 |
| TPP-23338 | Recombi Variant of TPP-15370 | VL | PRT | SEQ ID NO: 205 |
| TPP-23338 | Recombi Variant of TPP-15370 | LCDR1 | PRT | SEQ ID NO: 206 |
| TPP-23338 | Recombi Variant of TPP-15370 | LCDR2 | PRT | SEQ ID NO: 207 |
| TPP-23338 | Recombi Variant of TPP-15370 | LCDR3 | PRT | SEQ ID NO: 208 |
| TPP-23338 | Recombi Variant of TPP-15370 | VH | DNA | SEQ ID NO: 209 |
| TPP-23338 | Recombi Variant of TPP-15370 | HCDR1 | DNA | SEQ ID NO: 210 |
| TPP-23338 | Recombi Variant of TPP-15370 | HCDR2 | DNA | SEQ ID NO: 211 |
| TPP-23338 | Recombi Variant of TPP-15370 | HCDR3 | DNA | SEQ ID NO: 212 |
| TPP-23338 | Recombi Variant of TPP-15370 | VL | DNA | SEQ ID NO: 213 |
| TPP-23338 | Recombi Variant of TPP-15370 | LCDR1 | DNA | SEQ ID NO: 214 |
| TPP-23338 | Recombi Variant of TPP-15370 | LCDR2 | DNA | SEQ ID NO: 215 |
| TPP-23338 | Recombi Variant of TPP-15370 | LCDR3 | DNA | SEQ ID NO: 216 |
| TPP-23338 | Recombi Variant of TPP-15370 | Heavy Chain | PRT | SEQ ID NO: 217 |
| TPP-23338 | Recombi Variant of TPP-15370 | Light Chain | PRT | SEQ ID NO: 218 |
| TPP-23338 | Recombi Variant of TPP-15370 | Heavy Chain | DNA | SEQ ID NO: 219 |
| TPP-23338 | Recombi Variant of TPP-15370 | Light Chain | DNA | SEQ ID NO: 220 |
| TPP-23340 | Recombi Variant of TPP-15370 | VH | PRT | SEQ ID NO: 221 |
| TPP-23340 | Recombi Variant of TPP-15370 | HCDR1 | PRT | SEQ ID NO: 222 |
| TPP-23340 | Recombi Variant of TPP-15370 | HCDR2 | PRT | SEQ ID NO: 223 |
| TPP-23340 | Recombi Variant of TPP-15370 | HCDR3 | PRT | SEQ ID NO: 224 |
| TPP-23340 | Recombi Variant of TPP-15370 | VL | PRT | SEQ ID NO: 225 |
| TPP-23340 | Recombi Variant of TPP-15370 | LCDR1 | PRT | SEQ ID NO: 226 |
| TPP-23340 | Recombi Variant of TPP-15370 | LCDR2 | PRT | SEQ ID NO: 227 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-23340 | Recombi Variant of TPP-15370 | LCDR3 | PRT | SEQ ID NO: 228 |
| TPP-23340 | Recombi Variant of TPP-15370 | VH | DNA | SEQ ID NO: 229 |
| TPP-23340 | Recombi Variant of TPP-15370 | HCDR1 | DNA | SEQ ID NO: 230 |
| TPP-23340 | Recombi Variant of TPP-15370 | HCDR2 | DNA | SEQ ID NO: 231 |
| TPP-23340 | Recombi Variant of TPP-15370 | HCDR3 | DNA | SEQ ID NO: 232 |
| TPP-23340 | Recombi Variant of TPP-15370 | VL | DNA | SEQ ID NO: 233 |
| TPP-23340 | Recombi Variant of TPP-15370 | LCDR1 | DNA | SEQ ID NO: 234 |
| TPP-23340 | Recombi Variant of TPP-15370 | LCDR2 | DNA | SEQ ID NO: 235 |
| TPP-23340 | Recombi Variant of TPP-15370 | LCDR3 | DNA | SEQ ID NO: 236 |
| TPP-23340 | Recombi Variant of TPP-15370 | Heavy Chain | PRT | SEQ ID NO: 237 |
| TPP-23340 | Recombi Variant of TPP-15370 | Light Chain | PRT | SEQ ID NO: 238 |
| TPP-23340 | Recombi Variant of TPP-15370 | Heavy Chain | DNA | SEQ ID NO: 239 |
| TPP-23340 | Recombi Variant of TPP-15370 | Light Chain | DNA | SEQ ID NO: 240 |
| TPP-23341 | Recombi Variant of TPP-15370 | VH | PRT | SEQ ID NO: 241 |
| TPP-23341 | Recombi Variant of TPP-15370 | HCDR1 | PRT | SEQ ID NO: 242 |
| TPP-23341 | Recombi Variant of TPP-15370 | HCDR2 | PRT | SEQ ID NO: 243 |
| TPP-23341 | Recombi Variant of TPP-15370 | HCDR3 | PRT | SEQ ID NO: 244 |
| TPP-23341 | Recombi Variant of TPP-15370 | VL | PRT | SEQ ID NO: 245 |
| TPP-23341 | Recombi Variant of TPP-15370 | LCDR1 | PRT | SEQ ID NO: 246 |
| TPP-23341 | Recombi Variant of TPP-15370 | LCDR2 | PRT | SEQ ID NO: 247 |
| TPP-23341 | Recombi Variant of TPP-15370 | LCDR3 | PRT | SEQ ID NO: 248 |
| TPP-23341 | Recombi Variant of TPP-15370 | VH | DNA | SEQ ID NO: 249 |
| TPP-23341 | Recombi Variant of TPP-15370 | HCDR1 | DNA | SEQ ID NO: 250 |
| TPP-23341 | Recombi Variant of TPP-15370 | HCDR2 | DNA | SEQ ID NO: 251 |
| TPP-23341 | Recombi Variant of TPP-15370 | HCDR3 | DNA | SEQ ID NO: 252 |
| TPP-23341 | Recombi Variant of TPP-15370 | VL | DNA | SEQ ID NO: 253 |
| TPP-23341 | Recombi Variant of TPP-15370 | LCDR1 | DNA | SEQ ID NO: 254 |
| TPP-23341 | Recombi Variant of TPP-15370 | LCDR2 | DNA | SEQ ID NO: 255 |
| TPP-23341 | Recombi Variant of TPP-15370 | LCDR3 | DNA | SEQ ID NO: 256 |
| TPP-23341 | Recombi Variant of TPP-15370 | Heavy Chain | PRT | SEQ ID NO: 257 |
| TPP-23341 | Recombi Variant of TPP-15370 | Light Chain | PRT | SEQ ID NO: 258 |
| TPP-23341 | Recombi Variant of TPP-15370 | Heavy Chain | DNA | SEQ ID NO: 259 |
| TPP-23341 | Recombi Variant of TPP-15370 | Light Chain | DNA | SEQ ID NO: 260 |
| TPP-23345 | Recombi Variant of TPP-15370 | VH | PRT | SEQ ID NO: 261 |
| TPP-23345 | Recombi Variant of TPP-15370 | HCDR1 | PRT | SEQ ID NO: 262 |
| TPP-23345 | Recombi Variant of TPP-15370 | HCDR2 | PRT | SEQ ID NO: 263 |
| TPP-23345 | Recombi Variant of TPP-15370 | HCDR3 | PRT | SEQ ID NO: 264 |
| TPP-23345 | Recombi Variant of TPP-15370 | VL | PRT | SEQ ID NO: 265 |
| TPP-23345 | Recombi Variant of TPP-15370 | LCDR1 | PRT | SEQ ID NO: 266 |
| TPP-23345 | Recombi Variant of TPP-15370 | LCDR2 | PRT | SEQ ID NO: 267 |
| TPP-23345 | Recombi Variant of TPP-15370 | LCDR3 | PRT | SEQ ID NO: 268 |
| TPP-23345 | Recombi Variant of TPP-15370 | VH | DNA | SEQ ID NO: 269 |
| TPP-23345 | Recombi Variant of TPP-15370 | HCDR1 | DNA | SEQ ID NO: 270 |
| TPP-23345 | Recombi Variant of TPP-15370 | HCDR2 | DNA | SEQ ID NO: 271 |
| TPP-23345 | Recombi Variant of TPP-15370 | HCDR3 | DNA | SEQ ID NO: 272 |
| TPP-23345 | Recombi Variant of TPP-15370 | VL | DNA | SEQ ID NO: 273 |
| TPP-23345 | Recombi Variant of TPP-15370 | LCDR1 | DNA | SEQ ID NO: 274 |
| TPP-23345 | Recombi Variant of TPP-15370 | LCDR2 | DNA | SEQ ID NO: 275 |
| TPP-23345 | Recombi Variant of TPP-15370 | LCDR3 | DNA | SEQ ID NO: 276 |
| TPP-23345 | Recombi Variant of TPP-15370 | Heavy Chain | PRT | SEQ ID NO: 277 |
| TPP-23345 | Recombi Variant of TPP-15370 | Light Chain | PRT | SEQ ID NO: 278 |
| TPP-23345 | Recombi Variant of TPP-15370 | Heavy Chain | DNA | SEQ ID NO: 279 |
| TPP-23345 | Recombi Variant of TPP-15370 | Light Chain | DNA | SEQ ID NO: 280 |
| TPP-23346 | Recombi Variant of TPP-15370 | VH | PRT | SEQ ID NO: 281 |
| TPP-23346 | Recombi Variant of TPP-15370 | HCDR1 | PRT | SEQ ID NO: 282 |
| TPP-23346 | Recombi Variant of TPP-15370 | HCDR2 | PRT | SEQ ID NO: 283 |
| TPP-23346 | Recombi Variant of TPP-15370 | HCDR3 | PRT | SEQ ID NO: 284 |
| TPP-23346 | Recombi Variant of TPP-15370 | VL | PRT | SEQ ID NO: 285 |
| TPP-23346 | Recombi Variant of TPP-15370 | LCDR1 | PRT | SEQ ID NO: 286 |
| TPP-23346 | Recombi Variant of TPP-15370 | LCDR2 | PRT | SEQ ID NO: 287 |
| TPP-23346 | Recombi Variant of TPP-15370 | LCDR3 | PRT | SEQ ID NO: 288 |
| TPP-23346 | Recombi Variant of TPP-15370 | VH | DNA | SEQ ID NO: 289 |
| TPP-23346 | Recombi Variant of TPP-15370 | HCDR1 | DNA | SEQ ID NO: 290 |
| TPP-23346 | Recombi Variant of TPP-15370 | HCDR2 | DNA | SEQ ID NO: 291 |
| TPP-23346 | Recombi Variant of TPP-15370 | HCDR3 | DNA | SEQ ID NO: 292 |
| TPP-23346 | Recombi Variant of TPP-15370 | VL | DNA | SEQ ID NO: 293 |
| TPP-23346 | Recombi Variant of TPP-15370 | LCDR1 | DNA | SEQ ID NO: 294 |
| TPP-23346 | Recombi Variant of TPP-15370 | LCDR2 | DNA | SEQ ID NO: 295 |
| TPP-23346 | Recombi Variant of TPP-15370 | LCDR3 | DNA | SEQ ID NO: 296 |
| TPP-23346 | Recombi Variant of TPP-15370 | Heavy Chain | PRT | SEQ ID NO: 297 |
| TPP-23346 | Recombi Variant of TPP-15370 | Light Chain | PRT | SEQ ID NO: 298 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-23346 | Recombi Variant of TPP-15370 | Heavy Chain | DNA | SEQ ID NO: 299 |
| TPP-23346 | Recombi Variant of TPP-15370 | Light Chain | DNA | SEQ ID NO: 300 |
| TPP-23347 | Recombi Variant of TPP-15370 | VH | PRT | SEQ ID NO: 301 |
| TPP-23347 | Recombi Variant of TPP-15370 | HCDR1 | PRT | SEQ ID NO: 302 |
| TPP-23347 | Recombi Variant of TPP-15370 | HCDR2 | PRT | SEQ ID NO: 303 |
| TPP-23347 | Recombi Variant of TPP-15370 | HCDR3 | PRT | SEQ ID NO: 304 |
| TPP-23347 | Recombi Variant of TPP-15370 | VL | PRT | SEQ ID NO: 305 |
| TPP-23347 | Recombi Variant of TPP-15370 | LCDR1 | PRT | SEQ ID NO: 306 |
| TPP-23347 | Recombi Variant of TPP-15370 | LCDR2 | PRT | SEQ ID NO: 307 |
| TPP-23347 | Recombi Variant of TPP-15370 | LCDR3 | PRT | SEQ ID NO: 308 |
| TPP-23347 | Recombi Variant of TPP-15370 | VH | DNA | SEQ ID NO: 309 |
| TPP-23347 | Recombi Variant of TPP-15370 | HCDR1 | DNA | SEQ ID NO: 310 |
| TPP-23347 | Recombi Variant of TPP-15370 | HCDR2 | DNA | SEQ ID NO: 311 |
| TPP-23347 | Recombi Variant of TPP-15370 | HCDR3 | DNA | SEQ ID NO: 312 |
| TPP-23347 | Recombi Variant of TPP-15370 | VL | DNA | SEQ ID NO: 313 |
| TPP-23347 | Recombi Variant of TPP-15370 | LCDR1 | DNA | SEQ ID NO: 314 |
| TPP-23347 | Recombi Variant of TPP-15370 | LCDR2 | DNA | SEQ ID NO: 315 |
| TPP-23347 | Recombi Variant of TPP-15370 | LCDR3 | DNA | SEQ ID NO: 316 |
| TPP-23347 | Recombi Variant of TPP-15370 | Heavy Chain | PRT | SEQ ID NO: 317 |
| TPP-23347 | Recombi Variant of TPP-15370 | Light Chain | PRT | SEQ ID NO: 318 |
| TPP-23347 | Recombi Variant of TPP-15370 | Heavy Chain | DNA | SEQ ID NO: 319 |
| TPP-23347 | Recombi Variant of TPP-15370 | Light Chain | DNA | SEQ ID NO: 320 |
| TPP-23373 | Recombi Variant of TPP-15370 | VH | PRT | SEQ ID NO: 321 |
| TPP-23373 | Recombi Variant of TPP-15370 | HCDR1 | PRT | SEQ ID NO: 322 |
| TPP-23373 | Recombi Variant of TPP-15370 | HCDR2 | PRT | SEQ ID NO: 323 |
| TPP-23373 | Recombi Variant of TPP-15370 | HCDR3 | PRT | SEQ ID NO: 324 |
| TPP-23373 | Recombi Variant of TPP-15370 | VL | PRT | SEQ ID NO: 325 |
| TPP-23373 | Recombi Variant of TPP-15370 | LCDR1 | PRT | SEQ ID NO: 326 |
| TPP-23373 | Recombi Variant of TPP-15370 | LCDR2 | PRT | SEQ ID NO: 327 |
| TPP-23373 | Recombi Variant of TPP-15370 | LCDR3 | PRT | SEQ ID NO: 328 |
| TPP-23373 | Recombi Variant of TPP-15370 | VH | DNA | SEQ ID NO: 329 |
| TPP-23373 | Recombi Variant of TPP-15370 | HCDR1 | DNA | SEQ ID NO: 330 |
| TPP-23373 | Recombi Variant of TPP-15370 | HCDR2 | DNA | SEQ ID NO: 331 |
| TPP-23373 | Recombi Variant of TPP-15370 | HCDR3 | DNA | SEQ ID NO: 332 |
| TPP-23373 | Recombi Variant of TPP-15370 | VL | DNA | SEQ ID NO: 333 |
| TPP-23373 | Recombi Variant of TPP-15370 | LCDR1 | DNA | SEQ ID NO: 334 |
| TPP-23373 | Recombi Variant of TPP-15370 | LCDR2 | DNA | SEQ ID NO: 335 |
| TPP-23373 | Recombi Variant of TPP-15370 | LCDR3 | DNA | SEQ ID NO: 336 |
| TPP-23373 | Recombi Variant of TPP-15370 | Heavy Chain | PRT | SEQ ID NO: 337 |
| TPP-23373 | Recombi Variant of TPP-15370 | Light Chain | PRT | SEQ ID NO: 338 |
| TPP-23373 | Recombi Variant of TPP-15370 | Heavy Chain | DNA | SEQ ID NO: 339 |
| TPP-23373 | Recombi Variant of TPP-15370 | Light Chain | DNA | SEQ ID NO: 340 |
| TPP-23374 | Recombi Variant of TPP-15370 | VH | PRT | SEQ ID NO: 341 |
| TPP-23374 | Recombi Variant of TPP-15370 | HCDR1 | PRT | SEQ ID NO: 342 |
| TPP-23374 | Recombi Variant of TPP-15370 | HCDR2 | PRT | SEQ ID NO: 343 |
| TPP-23374 | Recombi Variant of TPP-15370 | HCDR3 | PRT | SEQ ID NO: 344 |
| TPP-23374 | Recombi Variant of TPP-15370 | VL | PRT | SEQ ID NO: 345 |
| TPP-23374 | Recombi Variant of TPP-15370 | LCDR1 | PRT | SEQ ID NO: 346 |
| TPP-23374 | Recombi Variant of TPP-15370 | LCDR2 | PRT | SEQ ID NO: 347 |
| TPP-23374 | Recombi Variant of TPP-15370 | LCDR3 | PRT | SEQ ID NO: 348 |
| TPP-23374 | Recombi Variant of TPP-15370 | VH | DNA | SEQ ID NO: 349 |
| TPP-23374 | Recombi Variant of TPP-15370 | HCDR1 | DNA | SEQ ID NO: 350 |
| TPP-23374 | Recombi Variant of TPP-15370 | HCDR2 | DNA | SEQ ID NO: 351 |
| TPP-23374 | Recombi Variant of TPP-15370 | HCDR3 | DNA | SEQ ID NO: 352 |
| TPP-23374 | Recombi Variant of TPP-15370 | VL | DNA | SEQ ID NO: 353 |
| TPP-23374 | Recombi Variant of TPP-15370 | LCDR1 | DNA | SEQ ID NO: 354 |
| TPP-23374 | Recombi Variant of TPP-15370 | LCDR2 | DNA | SEQ ID NO: 355 |
| TPP-23374 | Recombi Variant of TPP-15370 | LCDR3 | DNA | SEQ ID NO: 356 |
| TPP-23374 | Recombi Variant of TPP-15370 | Heavy Chain | PRT | SEQ ID NO: 357 |
| TPP-23374 | Recombi Variant of TPP-15370 | Light Chain | PRT | SEQ ID NO: 358 |
| TPP-23374 | Recombi Variant of TPP-15370 | Heavy Chain | DNA | SEQ ID NO: 359 |
| TPP-23374 | Recombi Variant of TPP-15370 | Light Chain | DNA | SEQ ID NO: 360 |
| TPP-23375 | Recombi Variant of TPP-15370 | VH | PRT | SEQ ID NO: 361 |
| TPP-23375 | Recombi Variant of TPP-15370 | HCDR1 | PRT | SEQ ID NO: 362 |
| TPP-23375 | Recombi Variant of TPP-15370 | HCDR2 | PRT | SEQ ID NO: 363 |
| TPP-23375 | Recombi Variant of TPP-15370 | HCDR3 | PRT | SEQ ID NO: 364 |
| TPP-23375 | Recombi Variant of TPP-15370 | VL | PRT | SEQ ID NO: 365 |
| TPP-23375 | Recombi Variant of TPP-15370 | LCDR1 | PRT | SEQ ID NO: 366 |
| TPP-23375 | Recombi Variant of TPP-15370 | LCDR2 | PRT | SEQ ID NO: 367 |
| TPP-23375 | Recombi Variant of TPP-15370 | LCDR3 | PRT | SEQ ID NO: 368 |
| TPP-23375 | Recombi Variant of TPP-15370 | VH | DNA | SEQ ID NO: 369 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-23375 | Recombi Variant of TPP-15370 | HCDR1 | DNA | SEQ ID NO: 370 |
| TPP-23375 | Recombi Variant of TPP-15370 | HCDR2 | DNA | SEQ ID NO: 371 |
| TPP-23375 | Recombi Variant of TPP-15370 | HCDR3 | DNA | SEQ ID NO: 372 |
| TPP-23375 | Recombi Variant of TPP-15370 | VL | DNA | SEQ ID NO: 373 |
| TPP-23375 | Recombi Variant of TPP-15370 | LCDR1 | DNA | SEQ ID NO: 374 |
| TPP-23375 | Recombi Variant of TPP-15370 | LCDR2 | DNA | SEQ ID NO: 375 |
| TPP-23375 | Recombi Variant of TPP-15370 | LCDR3 | DNA | SEQ ID NO: 376 |
| TPP-23375 | Recombi Variant of TPP-15370 | Heavy Chain | PRT | SEQ ID NO: 377 |
| TPP-23375 | Recombi Variant of TPP-15370 | Light Chain | PRT | SEQ ID NO: 378 |
| TPP-23375 | Recombi Variant of TPP-15370 | Heavy Chain | DNA | SEQ ID NO: 379 |
| TPP-23375 | Recombi Variant of TPP-15370 | Light Chain | DNA | SEQ ID NO: 380 |
| TPP-25064 | Recombi Variant of TPP-15374 | VH | PRT | SEQ ID NO: 381 |
| TPP-25064 | Recombi Variant of TPP-15374 | HCDR1 | PRT | SEQ ID NO: 382 |
| TPP-25064 | Recombi Variant of TPP-15374 | HCDR2 | PRT | SEQ ID NO: 383 |
| TPP-25064 | Recombi Variant of TPP-15374 | HCDR3 | PRT | SEQ ID NO: 384 |
| TPP-25064 | Recombi Variant of TPP-15374 | VL | PRT | SEQ ID NO: 385 |
| TPP-25064 | Recombi Variant of TPP-15374 | LCDR1 | PRT | SEQ ID NO: 386 |
| TPP-25064 | Recombi Variant of TPP-15374 | LCDR2 | PRT | SEQ ID NO: 387 |
| TPP-25064 | Recombi Variant of TPP-15374 | LCDR3 | PRT | SEQ ID NO: 388 |
| TPP-25064 | Recombi Variant of TPP-15374 | VH | DNA | SEQ ID NO: 389 |
| TPP-25064 | Recombi Variant of TPP-15374 | HCDR1 | DNA | SEQ ID NO: 390 |
| TPP-25064 | Recombi Variant of TPP-15374 | HCDR2 | DNA | SEQ ID NO: 391 |
| TPP-25064 | Recombi Variant of TPP-15374 | HCDR3 | DNA | SEQ ID NO: 392 |
| TPP-25064 | Recombi Variant of TPP-15374 | VL | DNA | SEQ ID NO: 393 |
| TPP-25064 | Recombi Variant of TPP-15374 | LCDR1 | DNA | SEQ ID NO: 394 |
| TPP-25064 | Recombi Variant of TPP-15374 | LCDR2 | DNA | SEQ ID NO: 395 |
| TPP-25064 | Recombi Variant of TPP-15374 | LCDR3 | DNA | SEQ ID NO: 396 |
| TPP-25064 | Recombi Variant of TPP-15374 | Heavy Chain | PRT | SEQ ID NO: 397 |
| TPP-25064 | Recombi Variant of TPP-15374 | Light Chain | PRT | SEQ ID NO: 398 |
| TPP-25064 | Recombi Variant of TPP-15374 | Heavy Chain | DNA | SEQ ID NO: 399 |
| TPP-25064 | Recombi Variant of TPP-15374 | Light Chain | DNA | SEQ ID NO: 400 |
| TPP-25224 | Recombi Variant of TPP-15374 | VH | PRT | SEQ ID NO: 401 |
| TPP-25224 | Recombi Variant of TPP-15374 | HCDR1 | PRT | SEQ ID NO: 402 |
| TPP-25224 | Recombi Variant of TPP-15374 | HCDR2 | PRT | SEQ ID NO: 403 |
| TPP-25224 | Recombi Variant of TPP-15374 | HCDR3 | PRT | SEQ ID NO: 404 |
| TPP-25224 | Recombi Variant of TPP-15374 | VL | PRT | SEQ ID NO: 405 |
| TPP-25224 | Recombi Variant of TPP-15374 | LCDR1 | PRT | SEQ ID NO: 406 |
| TPP-25224 | Recombi Variant of TPP-15374 | LCDR2 | PRT | SEQ ID NO: 407 |
| TPP-25224 | Recombi Variant of TPP-15374 | LCDR3 | PRT | SEQ ID NO: 408 |
| TPP-25224 | Recombi Variant of TPP-15374 | VH | DNA | SEQ ID NO: 409 |
| TPP-25224 | Recombi Variant of TPP-15374 | HCDR1 | DNA | SEQ ID NO: 410 |
| TPP-25224 | Recombi Variant of TPP-15374 | HCDR2 | DNA | SEQ ID NO: 411 |
| TPP-25224 | Recombi Variant of TPP-15374 | HCDR3 | DNA | SEQ ID NO: 412 |
| TPP-25224 | Recombi Variant of TPP-15374 | VL | DNA | SEQ ID NO: 413 |
| TPP-25224 | Recombi Variant of TPP-15374 | LCDR1 | DNA | SEQ ID NO: 414 |
| TPP-25224 | Recombi Variant of TPP-15374 | LCDR2 | DNA | SEQ ID NO: 415 |
| TPP-25224 | Recombi Variant of TPP-15374 | LCDR3 | DNA | SEQ ID NO: 416 |
| TPP-25224 | Recombi Variant of TPP-15374 | Heavy Chain | PRT | SEQ ID NO: 417 |
| TPP-25224 | Recombi Variant of TPP-15374 | Light Chain | PRT | SEQ ID NO: 418 |
| TPP-25224 | Recombi Variant of TPP-15374 | Heavy Chain | DNA | SEQ ID NO: 419 |
| TPP-25224 | Recombi Variant of TPP-15374 | Light Chain | DNA | SEQ ID NO: 420 |
| TPP-25248 | Recombi Variant of TPP-15374 | VH | PRT | SEQ ID NO: 421 |
| TPP-25248 | Recombi Variant of TPP-15374 | HCDR1 | PRT | SEQ ID NO: 422 |
| TPP-25248 | Recombi Variant of TPP-15374 | HCDR2 | PRT | SEQ ID NO: 423 |
| TPP-25248 | Recombi Variant of TPP-15374 | HCDR3 | PRT | SEQ ID NO: 424 |
| TPP-25248 | Recombi Variant of TPP-15374 | VL | PRT | SEQ ID NO: 425 |
| TPP-25248 | Recombi Variant of TPP-15374 | LCDR1 | PRT | SEQ ID NO: 426 |
| TPP-25248 | Recombi Variant of TPP-15374 | LCDR2 | PRT | SEQ ID NO: 427 |
| TPP-25248 | Recombi Variant of TPP-15374 | LCDR3 | PRT | SEQ ID NO: 428 |
| TPP-25248 | Recombi Variant of TPP-15374 | VH | DNA | SEQ ID NO: 429 |
| TPP-25248 | Recombi Variant of TPP-15374 | HCDR1 | DNA | SEQ ID NO: 430 |
| TPP-25248 | Recombi Variant of TPP-15374 | HCDR2 | DNA | SEQ ID NO: 431 |
| TPP-25248 | Recombi Variant of TPP-15374 | HCDR3 | DNA | SEQ ID NO: 432 |
| TPP-25248 | Recombi Variant of TPP-15374 | VL | DNA | SEQ ID NO: 433 |
| TPP-25248 | Recombi Variant of TPP-15374 | LCDR1 | DNA | SEQ ID NO: 434 |
| TPP-25248 | Recombi Variant of TPP-15374 | LCDR2 | DNA | SEQ ID NO: 435 |
| TPP-25248 | Recombi Variant of TPP-15374 | LCDR3 | DNA | SEQ ID NO: 436 |
| TPP-25248 | Recombi Variant of TPP-15374 | Heavy Chain | PRT | SEQ ID NO: 437 |
| TPP-25248 | Recombi Variant of TPP-15374 | Light Chain | PRT | SEQ ID NO: 438 |
| TPP-25248 | Recombi Variant of TPP-15374 | Heavy Chain | DNA | SEQ ID NO: 439 |
| TPP-25248 | Recombi Variant of TPP-15374 | Light Chain | DNA | SEQ ID NO: 440 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-25255 | Recombi Variant of TPP-15374 | VH | PRT | SEQ ID NO: 441 |
| TPP-25255 | Recombi Variant of TPP-15374 | HCDR1 | PRT | SEQ ID NO: 442 |
| TPP-25255 | Recombi Variant of TPP-15374 | HCDR2 | PRT | SEQ ID NO: 443 |
| TPP-25255 | Recombi Variant of TPP-15374 | HCDR3 | PRT | SEQ ID NO: 444 |
| TPP-25255 | Recombi Variant of TPP-15374 | VL | PRT | SEQ ID NO: 445 |
| TPP-25255 | Recombi Variant of TPP-15374 | LCDR1 | PRT | SEQ ID NO: 446 |
| TPP-25255 | Recombi Variant of TPP-15374 | LCDR2 | PRT | SEQ ID NO: 447 |
| TPP-25255 | Recombi Variant of TPP-15374 | LCDR3 | PRT | SEQ ID NO: 448 |
| TPP-25255 | Recombi Variant of TPP-15374 | VH | DNA | SEQ ID NO: 449 |
| TPP-25255 | Recombi Variant of TPP-15374 | HCDR1 | DNA | SEQ ID NO: 450 |
| TPP-25255 | Recombi Variant of TPP-15374 | HCDR2 | DNA | SEQ ID NO: 451 |
| TPP-25255 | Recombi Variant of TPP-15374 | HCDR3 | DNA | SEQ ID NO: 452 |
| TPP-25255 | Recombi Variant of TPP-15374 | VL | DNA | SEQ ID NO: 453 |
| TPP-25255 | Recombi Variant of TPP-15374 | LCDR1 | DNA | SEQ ID NO: 454 |
| TPP-25255 | Recombi Variant of TPP-15374 | LCDR2 | DNA | SEQ ID NO: 455 |
| TPP-25255 | Recombi Variant of TPP-15374 | LCDR3 | DNA | SEQ ID NO: 456 |
| TPP-25255 | Recombi Variant of TPP-15374 | Heavy Chain | PRT | SEQ ID NO: 457 |
| TPP-25255 | Recombi Variant of TPP-15374 | Light Chain | PRT | SEQ ID NO: 458 |
| TPP-25255 | Recombi Variant of TPP-15374 | Heavy Chain | DNA | SEQ ID NO: 459 |
| TPP-25255 | Recombi Variant of TPP-15374 | Light Chain | DNA | SEQ ID NO: 460 |
| TPP-25256 | Recombi Variant of TPP-15374 | VH | PRT | SEQ ID NO: 461 |
| TPP-25256 | Recombi Variant of TPP-15374 | HCDR1 | PRT | SEQ ID NO: 462 |
| TPP-25256 | Recombi Variant of TPP-15374 | HCDR2 | PRT | SEQ ID NO: 463 |
| TPP-25256 | Recombi Variant of TPP-15374 | HCDR3 | PRT | SEQ ID NO: 464 |
| TPP-25256 | Recombi Variant of TPP-15374 | VL | PRT | SEQ ID NO: 465 |
| TPP-25256 | Recombi Variant of TPP-15374 | LCDR1 | PRT | SEQ ID NO: 466 |
| TPP-25256 | Recombi Variant of TPP-15374 | LCDR2 | PRT | SEQ ID NO: 467 |
| TPP-25256 | Recombi Variant of TPP-15374 | LCDR3 | PRT | SEQ ID NO: 468 |
| TPP-25256 | Recombi Variant of TPP-15374 | VH | DNA | SEQ ID NO: 469 |
| TPP-25256 | Recombi Variant of TPP-15374 | HCDR1 | DNA | SEQ ID NO: 470 |
| TPP-25256 | Recombi Variant of TPP-15374 | HCDR2 | DNA | SEQ ID NO: 471 |
| TPP-25256 | Recombi Variant of TPP-15374 | HCDR3 | DNA | SEQ ID NO: 472 |
| TPP-25256 | Recombi Variant of TPP-15374 | VL | DNA | SEQ ID NO: 473 |
| TPP-25256 | Recombi Variant of TPP-15374 | LCDR1 | DNA | SEQ ID NO: 474 |
| TPP-25256 | Recombi Variant of TPP-15374 | LCDR2 | DNA | SEQ ID NO: 475 |
| TPP-25256 | Recombi Variant of TPP-15374 | LCDR3 | DNA | SEQ ID NO: 476 |
| TPP-25256 | Recombi Variant of TPP-15374 | Heavy Chain | PRT | SEQ ID NO: 477 |
| TPP-25256 | Recombi Variant of TPP-15374 | Light Chain | PRT | SEQ ID NO: 478 |
| TPP-25256 | Recombi Variant of TPP-15374 | Heavy Chain | DNA | SEQ ID NO: 479 |
| TPP-25256 | Recombi Variant of TPP-15374 | Light Chain | DNA | SEQ ID NO: 480 |
| TPP-25257 | Recombi Variant of TPP-15374 | VH | PRT | SEQ ID NO: 481 |
| TPP-25257 | Recombi Variant of TPP-15374 | HCDR1 | PRT | SEQ ID NO: 482 |
| TPP-25257 | Recombi Variant of TPP-15374 | HCDR2 | PRT | SEQ ID NO: 483 |
| TPP-25257 | Recombi Variant of TPP-15374 | HCDR3 | PRT | SEQ ID NO: 484 |
| TPP-25257 | Recombi Variant of TPP-15374 | VL | PRT | SEQ ID NO: 485 |
| TPP-25257 | Recombi Variant of TPP-15374 | LCDR1 | PRT | SEQ ID NO: 486 |
| TPP-25257 | Recombi Variant of TPP-15374 | LCDR2 | PRT | SEQ ID NO: 487 |
| TPP-25257 | Recombi Variant of TPP-15374 | LCDR3 | PRT | SEQ ID NO: 488 |
| TPP-25257 | Recombi Variant of TPP-15374 | VH | DNA | SEQ ID NO: 489 |
| TPP-25257 | Recombi Variant of TPP-15374 | HCDR1 | DNA | SEQ ID NO: 490 |
| TPP-25257 | Recombi Variant of TPP-15374 | HCDR2 | DNA | SEQ ID NO: 491 |
| TPP-25257 | Recombi Variant of TPP-15374 | HCDR3 | DNA | SEQ ID NO: 492 |
| TPP-25257 | Recombi Variant of TPP-15374 | VL | DNA | SEQ ID NO: 493 |
| TPP-25257 | Recombi Variant of TPP-15374 | LCDR1 | DNA | SEQ ID NO: 494 |
| TPP-25257 | Recombi Variant of TPP-15374 | LCDR2 | DNA | SEQ ID NO: 495 |
| TPP-25257 | Recombi Variant of TPP-15374 | LCDR3 | DNA | SEQ ID NO: 496 |
| TPP-25257 | Recombi Variant of TPP-15374 | Heavy Chain | PRT | SEQ ID NO: 497 |
| TPP-25257 | Recombi Variant of TPP-15374 | Light Chain | PRT | SEQ ID NO: 498 |
| TPP-25257 | Recombi Variant of TPP-15374 | Heavy Chain | DNA | SEQ ID NO: 499 |
| TPP-25257 | Recombi Variant of TPP-15374 | Light Chain | DNA | SEQ ID NO: 500 |
| TPP-25448 | Recombi Variant of TPP-15374 | VH | PRT | SEQ ID NO: 501 |
| TPP-25448 | Recombi Variant of TPP-15374 | HCDR1 | PRT | SEQ ID NO: 502 |
| TPP-25448 | Recombi Variant of TPP-15374 | HCDR2 | PRT | SEQ ID NO: 503 |
| TPP-25448 | Recombi Variant of TPP-15374 | HCDR3 | PRT | SEQ ID NO: 504 |
| TPP-25448 | Recombi Variant of TPP-15374 | VL | PRT | SEQ ID NO: 505 |
| TPP-25448 | Recombi Variant of TPP-15374 | LCDR1 | PRT | SEQ ID NO: 506 |
| TPP-25448 | Recombi Variant of TPP-15374 | LCDR2 | PRT | SEQ ID NO: 507 |
| TPP-25448 | Recombi Variant of TPP-15374 | LCDR3 | PRT | SEQ ID NO: 508 |
| TPP-25448 | Recombi Variant of TPP-15374 | VH | DNA | SEQ ID NO: 509 |
| TPP-25448 | Recombi Variant of TPP-15374 | HCDR1 | DNA | SEQ ID NO: 510 |
| TPP-25448 | Recombi Variant of TPP-15374 | HCDR2 | DNA | SEQ ID NO: 511 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-25448 | Recombi Variant of TPP-15374 | HCDR3 | DNA | SEQ ID NO: 512 |
| TPP-25448 | Recombi Variant of TPP-15374 | VL | DNA | SEQ ID NO: 513 |
| TPP-25448 | Recombi Variant of TPP-15374 | LCDR1 | DNA | SEQ ID NO: 514 |
| TPP-25448 | Recombi Variant of TPP-15374 | LCDR2 | DNA | SEQ ID NO: 515 |
| TPP-25448 | Recombi Variant of TPP-15374 | LCDR3 | DNA | SEQ ID NO: 516 |
| TPP-25448 | Recombi Variant of TPP-15374 | Heavy Chain | PRT | SEQ ID NO: 517 |
| TPP-25448 | Recombi Variant of TPP-15374 | Light Chain | PRT | SEQ ID NO: 518 |
| TPP-25448 | Recombi Variant of TPP-15374 | Heavy Chain | DNA | SEQ ID NO: 519 |
| TPP-25448 | Recombi Variant of TPP-15374 | Light Chain | DNA | SEQ ID NO: 520 |
| TPP-25497 | Recombi Variant of TPP-15374 | VH | PRT | SEQ ID NO: 521 |
| TPP-25497 | Recombi Variant of TPP-15374 | HCDR1 | PRT | SEQ ID NO: 522 |
| TPP-25497 | Recombi Variant of TPP-15374 | HCDR2 | PRT | SEQ ID NO: 523 |
| TPP-25497 | Recombi Variant of TPP-15374 | HCDR3 | PRT | SEQ ID NO: 524 |
| TPP-25497 | Recombi Variant of TPP-15374 | VL | PRT | SEQ ID NO: 525 |
| TPP-25497 | Recombi Variant of TPP-15374 | LCDR1 | PRT | SEQ ID NO: 526 |
| TPP-25497 | Recombi Variant of TPP-15374 | LCDR2 | PRT | SEQ ID NO: 527 |
| TPP-25497 | Recombi Variant of TPP-15374 | LCDR3 | PRT | SEQ ID NO: 528 |
| TPP-25497 | Recombi Variant of TPP-15374 | VH | DNA | SEQ ID NO: 529 |
| TPP-25497 | Recombi Variant of TPP-15374 | HCDR1 | DNA | SEQ ID NO: 530 |
| TPP-25497 | Recombi Variant of TPP-15374 | HCDR2 | DNA | SEQ ID NO: 531 |
| TPP-25497 | Recombi Variant of TPP-15374 | HCDR3 | DNA | SEQ ID NO: 532 |
| TPP-25497 | Recombi Variant of TPP-15374 | VL | DNA | SEQ ID NO: 533 |
| TPP-25497 | Recombi Variant of TPP-15374 | LCDR1 | DNA | SEQ ID NO: 534 |
| TPP-25497 | Recombi Variant of TPP-15374 | LCDR2 | DNA | SEQ ID NO: 535 |
| TPP-25497 | Recombi Variant of TPP-15374 | LCDR3 | DNA | SEQ ID NO: 536 |
| TPP-25497 | Recombi Variant of TPP-15374 | Heavy Chain | PRT | SEQ ID NO: 537 |
| TPP-25497 | Recombi Variant of TPP-15374 | Light Chain | PRT | SEQ ID NO: 538 |
| TPP-25497 | Recombi Variant of TPP-15374 | Heavy Chain | DNA | SEQ ID NO: 539 |
| TPP-25497 | Recombi Variant of TPP-15374 | Light Chain | DNA | SEQ ID NO: 540 |
| TPP-25655 | Recombi Variant of TPP-15374 | VH | PRT | SEQ ID NO: 541 |
| TPP-25655 | Recombi Variant of TPP-15374 | HCDR1 | PRT | SEQ ID NO: 542 |
| TPP-25655 | Recombi Variant of TPP-15374 | HCDR2 | PRT | SEQ ID NO: 543 |
| TPP-25655 | Recombi Variant of TPP-15374 | HCDR3 | PRT | SEQ ID NO: 544 |
| TPP-25655 | Recombi Variant of TPP-15374 | VL | PRT | SEQ ID NO: 545 |
| TPP-25655 | Recombi Variant of TPP-15374 | LCDR1 | PRT | SEQ ID NO: 546 |
| TPP-25655 | Recombi Variant of TPP-15374 | LCDR2 | PRT | SEQ ID NO: 547 |
| TPP-25655 | Recombi Variant of TPP-15374 | LCDR3 | PRT | SEQ ID NO: 548 |
| TPP-25655 | Recombi Variant of TPP-15374 | VH | DNA | SEQ ID NO: 549 |
| TPP-25655 | Recombi Variant of TPP-15374 | HCDR1 | DNA | SEQ ID NO: 550 |
| TPP-25655 | Recombi Variant of TPP-15374 | HCDR2 | DNA | SEQ ID NO: 551 |
| TPP-25655 | Recombi Variant of TPP-15374 | HCDR3 | DNA | SEQ ID NO: 552 |
| TPP-25655 | Recombi Variant of TPP-15374 | VL | DNA | SEQ ID NO: 553 |
| TPP-25655 | Recombi Variant of TPP-15374 | LCDR1 | DNA | SEQ ID NO: 554 |
| TPP-25655 | Recombi Variant of TPP-15374 | LCDR2 | DNA | SEQ ID NO: 555 |
| TPP-25655 | Recombi Variant of TPP-15374 | LCDR3 | DNA | SEQ ID NO: 556 |
| TPP-25655 | Recombi Variant of TPP-15374 | Heavy Chain | PRT | SEQ ID NO: 557 |
| TPP-25655 | Recombi Variant of TPP-15374 | Light Chain | PRT | SEQ ID NO: 558 |
| TPP-25655 | Recombi Variant of TPP-15374 | Heavy Chain | DNA | SEQ ID NO: 559 |
| TPP-25655 | Recombi Variant of TPP-15374 | Light Chain | DNA | SEQ ID NO: 560 |
| TPP-26111 | Recombi Variant of TPP-15374 | VH | PRT | SEQ ID NO: 561 |
| TPP-26111 | Recombi Variant of TPP-15374 | HCDR1 | PRT | SEQ ID NO: 562 |
| TPP-26111 | Recombi Variant of TPP-15374 | HCDR2 | PRT | SEQ ID NO: 563 |
| TPP-26111 | Recombi Variant of TPP-15374 | HCDR3 | PRT | SEQ ID NO: 564 |
| TPP-26111 | Recombi Variant of TPP-15374 | VL | PRT | SEQ ID NO: 565 |
| TPP-26111 | Recombi Variant of TPP-15374 | LCDR1 | PRT | SEQ ID NO: 566 |
| TPP-26111 | Recombi Variant of TPP-15374 | LCDR2 | PRT | SEQ ID NO: 567 |
| TPP-26111 | Recombi Variant of TPP-15374 | LCDR3 | PRT | SEQ ID NO: 568 |
| TPP-26111 | Recombi Variant of TPP-15374 | VH | DNA | SEQ ID NO: 569 |
| TPP-26111 | Recombi Variant of TPP-15374 | HCDR1 | DNA | SEQ ID NO: 570 |
| TPP-26111 | Recombi Variant of TPP-15374 | HCDR2 | DNA | SEQ ID NO: 571 |
| TPP-26111 | Recombi Variant of TPP-15374 | HCDR3 | DNA | SEQ ID NO: 572 |
| TPP-26111 | Recombi Variant of TPP-15374 | VL | DNA | SEQ ID NO: 573 |
| TPP-26111 | Recombi Variant of TPP-15374 | LCDR1 | DNA | SEQ ID NO: 574 |
| TPP-26111 | Recombi Variant of TPP-15374 | LCDR2 | DNA | SEQ ID NO: 575 |
| TPP-26111 | Recombi Variant of TPP-15374 | LCDR3 | DNA | SEQ ID NO: 576 |
| TPP-26111 | Recombi Variant of TPP-15374 | Heavy Chain | PRT | SEQ ID NO: 577 |
| TPP-26111 | Recombi Variant of TPP-15374 | Light Chain | PRT | SEQ ID NO: 578 |
| TPP-26111 | Recombi Variant of TPP-15374 | Heavy Chain | DNA | SEQ ID NO: 579 |
| TPP-26111 | Recombi Variant of TPP-15374 | Light Chain | DNA | SEQ ID NO: 580 |
| TPP-13211 | huSema3a_FXaFc | Chain 1 | PRT | SEQ ID NO: 581 |
| TPP-19068 | human Sema3a_FXaHis6 | Chain 1 | PRT | SEQ ID NO: 582 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-19069 | mouse Sema3a_FXaHis6 | Chain 1 | PRT | SEQ ID NO: 583 |
| TPP-19120 | rat-Sema3a_FXaHis6 | Chain 1 | PRT | SEQ ID NO: 584 |
| TPP-19121 | dog-Sema3a_FXaHis6 | Chain 1 | PRT | SEQ ID NO: 585 |
| TPP-19122 | cyno-Sema3a_FXaHis6 | Chain 1 | PRT | SEQ ID NO: 586 |
| TPP-20176 | pigSema3A_FXaHis6 | Chain 1 | PRT | SEQ ID NO: 587 |
| TPP-30788 | Böhringer (BI) Clone I | VH | PRT | SEQ ID NO: 800 |
| TPP-30788 | Böhringer (BI) Clone I | HCDR1 | PRT | SEQ ID NO: 801 |
| TPP-30788 | Böhringer (BI) Clone I | HCDR2 | PRT | SEQ ID NO: 802 |
| TPP-30788 | Böhringer (BI) Clone I | HCDR3 | PRT | SEQ ID NO: 803 |
| TPP-30788 | Böhringer (BI) Clone I | VL | PRT | SEQ ID NO: 804 |
| TPP-30788 | Böhringer (BI) Clone I | LCDR1 | PRT | SEQ ID NO: 805 |
| TPP-30788 | Böhringer (BI) Clone I | LCDR2 | PRT | SEQ ID NO: 806 |
| TPP-30788 | Böhringer (BI) Clone I | LCDR3 | PRT | SEQ ID NO: 807 |
| TPP-30788 | Böhringer (BI) Clone I | VH | DNA | SEQ ID NO: 808 |
| TPP-30788 | Böhringer (BI) Clone I | VL | DNA | SEQ ID NO: 809 |
| TPP-30788 | Böhringer (BI) Clone I | Heavy Chain | PRT | SEQ ID NO: 810 |
| TPP-30788 | Böhringer (BI) Clone I | Light Chain | PRT | SEQ ID NO: 811 |
| TPP-30788 | Böhringer (BI) Clone I | Heavy Chain | DNA | SEQ ID NO: 812 |
| TPP-30788 | Böhringer (BI) Clone I | Light Chain | DNA | SEQ ID NO: 813 |
| TPP-30789 | Böhringer (BI) Clone II | VH | PRT | SEQ ID NO: 814 |
| TPP-30789 | Böhringer (BI) Clone II | HCDR1 | PRT | SEQ ID NO: 815 |
| TPP-30789 | Böhringer (BI) Clone II | HCDR2 | PRT | SEQ ID NO: 816 |
| TPP-30789 | Böhringer (BI) Clone II | HCDR3 | PRT | SEQ ID NO: 817 |
| TPP-30789 | Böhringer (BI) Clone II | VL | PRT | SEQ ID NO: 818 |
| TPP-30789 | Böhringer (BI) Clone II | LCDR1 | PRT | SEQ ID NO: 819 |
| TPP-30789 | Böhringer (BI) Clone II | LCDR2 | PRT | SEQ ID NO: 820 |
| TPP-30789 | Böhringer (BI) Clone II | LCDR3 | PRT | SEQ ID NO: 821 |
| TPP-30789 | Böhringer (BI) Clone II | VH | DNA | SEQ ID NO: 822 |
| TPP-30789 | Böhringer (BI) Clone II | VL | DNA | SEQ ID NO: 823 |
| TPP-30789 | Böhringer (BI) Clone II | Heavy Chain | PRT | SEQ ID NO: 824 |
| TPP-30789 | Böhringer (BI) Clone II | Light Chain | PRT | SEQ ID NO: 825 |
| TPP-30789 | Böhringer (BI) Clone II | Heavy Chain | DNA | SEQ ID NO: 826 |
| TPP-30789 | Böhringer (BI) Clone II | Light Chain | DNA | SEQ ID NO: 827 |
| TPP-30790 | Böhringer (BI) Clone III | VH | PRT | SEQ ID NO: 828 |
| TPP-30790 | Böhringer (BI) Clone III | HCDR1 | PRT | SEQ ID NO: 829 |
| TPP-30790 | Böhringer (BI) Clone III | HCDR2 | PRT | SEQ ID NO: 830 |
| TPP-30790 | Böhringer (BI) Clone III | HCDR3 | PRT | SEQ ID NO: 831 |
| TPP-30790 | Böhringer (BI) Clone III | VL | PRT | SEQ ID NO: 832 |
| TPP-30790 | Böhringer (BI) Clone III | LCDR1 | PRT | SEQ ID NO: 833 |
| TPP-30790 | Böhringer (BI) Clone III | LCDR2 | PRT | SEQ ID NO: 834 |
| TPP-30790 | Böhringer (BI) Clone III | LCDR3 | PRT | SEQ ID NO: 835 |
| TPP-30790 | Böhringer (BI) Clone III | VH | DNA | SEQ ID NO: 836 |
| TPP-30790 | Böhringer (BI) Clone III | VL | DNA | SEQ ID NO: 837 |
| TPP-30790 | Böhringer (BI) Clone III | Heavy Chain | PRT | SEQ ID NO: 838 |
| TPP-30790 | Böhringer (BI) Clone III | Light Chain | PRT | SEQ ID NO: 839 |
| TPP-30790 | Böhringer (BI) Clone III | Heavy Chain | DNA | SEQ ID NO: 840 |
| TPP-30790 | Böhringer (BI) Clone III | Light Chain | DNA | SEQ ID NO: 841 |
| TPP-30791 | Böhringer (BI) Clone IV | VH | PRT | SEQ ID NO: 842 |
| TPP-30791 | Böhringer (BI) Clone IV | HCDR1 | PRT | SEQ ID NO: 843 |
| TPP-30791 | Böhringer (BI) Clone IV | HCDR2 | PRT | SEQ ID NO: 844 |
| TPP-30791 | Böhringer (BI) Clone IV | HCDR3 | PRT | SEQ ID NO: 845 |
| TPP-30791 | Böhringer (BI) Clone IV | VL | PRT | SEQ ID NO: 846 |
| TPP-30791 | Böhringer (BI) Clone IV | LCDR1 | PRT | SEQ ID NO: 847 |
| TPP-30791 | Böhringer (BI) Clone IV | LCDR2 | PRT | SEQ ID NO: 848 |
| TPP-30791 | Böhringer (BI) Clone IV | LCDR3 | PRT | SEQ ID NO: 849 |
| TPP-30791 | Böhringer (BI) Clone IV | VH | DNA | SEQ ID NO: 850 |
| TPP-30791 | Böhringer (BI) Clone IV | VL | DNA | SEQ ID NO: 851 |
| TPP-30791 | Böhringer (BI) Clone IV | Heavy Chain | PRT | SEQ ID NO: 852 |
| TPP-30791 | Böhringer (BI) Clone IV | Light Chain | PRT | SEQ ID NO: 853 |
| TPP-30791 | Böhringer (BI) Clone IV | Heavy Chain | DNA | SEQ ID NO: 854 |
| TPP-30791 | Böhringer (BI) Clone IV | Light Chain | DNA | SEQ ID NO: 855 |
| TPP-30792 | 3H4 (Ramot) Clon I | VH | PRT | SEQ ID NO: 856 |
| TPP-30792 | 3H4 (Ramot) Clon I | HCDR1 | PRT | SEQ ID NO: 857 |
| TPP-30792 | 3H4 (Ramot) Clon I | HCDR2 | PRT | SEQ ID NO: 858 |
| TPP-30792 | 3H4 (Ramot) Clon I | HCDR3 | PRT | SEQ ID NO: 859 |
| TPP-30792 | 3H4 (Ramot) Clon I | VL | PRT | SEQ ID NO: 860 |
| TPP-30792 | 3H4 (Ramot) Clon I | LCDR1 | PRT | SEQ ID NO: 861 |
| TPP-30792 | 3H4 (Ramot) Clon I | LCDR2 | PRT | SEQ ID NO: 862 |
| TPP-30792 | 3H4 (Ramot) Clon I | LCDR3 | PRT | SEQ ID NO: 863 |
| TPP-30792 | 3H4 (Ramot) Clon I | VH | DNA | SEQ ID NO: 864 |
| TPP-30792 | 3H4 (Ramot) Clon I | VL | DNA | SEQ ID NO: 865 |

TABLE 1-continued

Amino acid sequences and nucleic acid sequences of preferred antibodies according
to the present disclosure and of three prior art antibodies. TPP-11489 corresponds
to Chiome antibody Humanized-2 derived of clone No. 4-2 strain (WO 2014/123186);
TPP-15051 respresents a murine IgG1 variant thereof. TPP-30788-TPP-30791 corresponds
to Böhringer Ingelheim antibody (BI) Clone I-IV (WO 2020/225400). TPP-
30792 corresponds to University Ramot antibody clone I (WO 2020/261281).

| TPP ID | Antibody Description | Sequence Region | Sequence Type | SEQ ID |
|---|---|---|---|---|
| TPP-30792 | 3H4 (Ramot) Clon I | Heavy Chain | PRT | SEQ ID NO: 866 |
| TPP-30792 | 3H4 (Ramot) Clon I | Light Chain | PRT | SEQ ID NO: 867 |
| TPP-30792 | 3H4 (Ramot) Clon I | Heavy Chain | DNA | SEQ ID NO: 868 |
| TPP-30792 | 3H4 (Ramot) Clon I | Light Chain | DNA | SEQ ID NO: 869 |
| TPP-31357 | Fab of 3H4 Univ Ramot | VH | PRT | SEQ ID NO: 870 |
| TPP-31357 | Fab of 3H4 Univ Ramot | HCDR1 | PRT | SEQ ID NO: 871 |
| TPP-31357 | Fab of 3H4 Univ Ramot | HCDR2 | PRT | SEQ ID NO: 872 |
| TPP-31357 | Fab of 3H4 Univ Ramot | HCDR3 | PRT | SEQ ID NO: 873 |
| TPP-31357 | Fab of 3H4 Univ Ramot | VL | PRT | SEQ ID NO: 874 |
| TPP-31357 | Fab of 3H4 Univ Ramot | LCDR1 | PRT | SEQ ID NO: 875 |
| TPP-31357 | Fab of 3H4 Univ Ramot | LCDR2 | PRT | SEQ ID NO: 876 |
| TPP-31357 | Fab of 3H4 Univ Ramot | LCDR3 | PRT | SEQ ID NO: 877 |
| TPP-31357 | Fab of 3H4 Univ Ramot | VH | DNA | SEQ ID NO: 878 |
| TPP-31357 | Fab of 3H4 Univ Ramot | VL | DNA | SEQ ID NO: 879 |
| TPP-31357 | Fab of 3H4 Univ Ramot | Heavy Chain | PRT | SEQ ID NO: 880 |
| TPP-31357 | Fab of 3H4 Univ Ramot | Light Chain | PRT | SEQ ID NO: 881 |
| TPP-31357 | Fab of 3H4 Univ Ramot | Heavy Chain | DNA | SEQ ID NO: 882 |
| TPP-31357 | Fab of 3H4 Univ Ramot | Light Chain | DNA | SEQ ID NO: 883 |

TABLE 1A

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 1 | PRT | EVQLLESGGGLVQPGGSLRLSCAASGFTFSSYPMGWVRQAPGKGLEWV AGIDDDGDSDTRYAPAVKGRATISRDNSKNTVYLQMNSLRAEDTAVYY CAKHTGIGANSAGSIDAWGQGTLVTVSS |
| 2 | PRT | SYPMG |
| 3 | PRT | GIDDDGDSDTRYAPAVKG |
| 4 | PRT | HTGIGANSAGSIDA |
| 5 | PRT | SYELTQPPSVSVSPGQTARITCSGGGSYTGSYYYGWYQQKPGQAPVTVI YYNNKRPSDIPERFSGSLSGTTNTLTISGVQAEDEADYYCGSADNSGDAF GTGTKVTVL |
| 6 | PRT | SGGGSYTGSYYYG |
| 7 | PRT | YNNKRPS |
| 8 | PRT | GSADNSGDA |
| 9 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ATCCTATGGGCTGGGTCCGACAGGCCCCTGGCAAAGGACTTGAATGG GTGGCCGGCATCGACGACGATGGCGATAGCGATACAAGATACGCCC CTGCCGTGAAGGGCAGAGCCACCATCTCCAGAGACAACAGCAAGAA CACCGTGTACCTGCAGATGAACAGCCTGAGAGCCGAGGACACCGCC GTGTACTATTGTGCCAAGCACACAGGCATCGGCGCCAATTCTGCCGG CTCTATTGATGCCTGGGGCCAGGGAACACTGGTCACAGTTTCTTCA |
| 10 | DNA | AGCTATCCTATGGGC |
| 11 | DNA | GGCATCGACGACGATGGCGATAGCGATACAAGATACGCCCCTGCCGT GAAGGGC |
| 12 | DNA | CACACAGGCATCGGCGCCAATTCTGCCGGCTCTATTGATGCC |
| 13 | DNA | AGCTATGAGCTGACACAGCCTCCAAGCGTGTCCGTGTCTCCTGGACA GACCGCCAGAATCACATGTAGCGGCGGAGGCAGCTACACCGGCAGC |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from *Homo sapiens* (SEQ ID 581, 582), *Mus Musculus*
(SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| | | TACTACTATGGCTGGTATCAGCAGAAGCCCGGACAGGCCCCTGTGAC<br>CGTGATCTACTACAACAACAAGCGGCCCAGCGACATCCCCGAGAGAT<br>TTTCTGGCTCTCTGAGCGGCACCACCAACACACTGACAATCTCTGGC<br>GTGCAGGCCGAGGACGAGGCCGATTACTATTGTGGCAGCGCCGATAA<br>TAGCGGCGACGCCTTTGGCACCGGCACCAAAGTTACAGTGCTA |
| 14 | DNA | AGCGGCGGAGGCAGCTACACCGGCAGCTACTACTATGGC |
| 15 | DNA | TACAACAACAAGCGGCCCAGC |
| 16 | DNA | GGCAGCGCCGATAATAGCGGCGACGCC |
| 17 | PRT | EVQLLESGGGLVQPGGSLRLSCAASGFTFSSYPMGWVRQAPGKGLEWV<br>AGIDDDGDSDTRYAPAVKGRATISRDNSKNTVYLQMNSLRAEDTAVYY<br>CAKHTGIGANSAGSIDAWGQGTLVTVSSASTKGPSVFPLAPSSKSTSGGT<br>AALGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPG |
| 18 | PRT | SYELTQPPSVSVSPGQTARITCSGGGSYTGSYYYGWYQQKPGQAPVTVI<br>YYNNKRPSDIPERFSGSLSGTTNTLTISGVQAEDEADYYCGSADNSGDAF<br>GTGTKVTVLGQPKAAPSVTLFPPSSEELQANKATLVCLISDFYPGAVTVA<br>WKADSSPVKAGVETTTPSKQSNNKYAASSYLSLTPEQWKSHRSYSCQV<br>THEGSTVEKTVAPTECS |
| 19 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ATCCTATGGGCTGGGTCCGACAGGCCCCTGGCAAAGGACTTGAATGG<br>GTGGCCGGCATCGACGACGATGGCGATAGCGATACAAGATACGCCC<br>CTGCCGTGAAGGGCAGAGCCACCATCTCCAGAGACAACAGCAAGAA<br>CACCGTGTACCTGCAGATGAACAGCCTGAGAGCCGAGGACACCGCC<br>GTGTACTATTGTGCCAAGCACACAGGCATCGGCGCCAATTCTGCCGG<br>CTCTATTGATGCCTGGGGCCAGGGAACACTGGTTACAGTTTCTTCAG<br>CCAGCACCAAGGGCCCCAGCGTGTTCCCTCTGGCCCCTAGCAGCAAG<br>AGCACATCTGGCGGAACAGCCGCCCTGGGCTGCCTCGTGAAGGACTA<br>CTTTCCCGAGCCCGTGACCGTGTCCTGGAACTCTGGCGCTCTGACAA<br>GCGGCGTGCACACCTTTCCAGCCGTGCTGCAGAGCAGCGGCCTGTAC<br>TCTCTGAGCAGCGTCGTGACAGTGCCCAGCAGCTCTCTGGGCACCCA<br>GACCTACATCTGCAACGTGAACCACAAGCCCAGCAACACCAAGGTG<br>GACAAGAAGGTGGAACCCAAGAGCTGCGACAAGACCCACACCTGTC<br>CCCCTTGTCCTGCCCCCGAACTGCTGGGAGGCCCTTCCGTGTTCCTGT<br>TCCCCCCAAAGCCCAAGGACACCCTGATGATCAGCCGGACCCCCGAA<br>GTGACCTGCGTGGTGGTGGATGTGTCCCACGAGGACCCTGAAGTGAA<br>GTTCAATTGGTACGTGGACGGCGTGGAAGTGCACAACGCCAAGACCA<br>AGCCTAGAGAGGAACAGTACAACAGCACCTACCGGGTGGTGTCCGT<br>GCTGACAGTGCTGCACCAGGACTGGCTGAACGGCAAAGAGTACAAG<br>TGCAAGGTGTCCAACAAGGCCCTGCCTGCCCCCATCGAGAAAACCAT<br>CAGCAAGGCCAAGGGCCAGCCCCGCGAACCCCAGGTGTACACACTG<br>CCCCCAAGCAGGGACGAGCTGACCAAGAACCAGGTGTCCCTGACCTG<br>TCTCGTGAAAGGCTTCTACCCCTCCGATATCGCCGTGGAATGGGAGA<br>GCAACGGCCAGCCCGAGAACAACTACAAGACCACCCCCCCTGTGCTG<br>GACAGCGACGGCTCATTCTTCCTGTACAGCAAGCTGACCGTGGACAA<br>GTCCCGGTGGCAGCAGGGCAACGTGTTCAGCTGCAGCGTGATGCACG<br>AGGCCCTGCACAACCACTACACCCAGAAGTCCCTGAGCCTGAGCCCT<br>GGC |
| 20 | DNA | AGCTATGAGCTGACACAGCCTCCAAGCGTGTCCGTGTCTCCTGGACA<br>GACCGCCAGAATCACATGTAGCGGCGGAGGCAGCTACACCGGCAGC<br>TACTACTATGGCTGGTATCAGCAGAAGCCCGGACAGGCCCCTGTGAC<br>CGTGATCTACTACAACAACAAGCGGCCCAGCGACATCCCCGAGAGAT<br>TTTCTGGCTCTCTGAGCGGCACCACCAACACACTGACAATCTCTGGC<br>GTGCAGGCCGAGGACGAGGCCGATTACTATTGTGGCAGCGCCGATAA<br>TAGCGGCGACGCCTTTGGCACCGGCACCAAAGTTACAGTGCTAGGCC<br>AGCCTAAAGCCGCCCCTAGCGTGACCCTGTTCCCTCCAAGCAGCGAG<br>GAACTGCAGGCCAACAAGGCCACCCTCGTGTGCCTGATCAGCGACTT<br>CTATCCTGGCGCCGTGACCGTGGCCTGGAAGGCCGATAGCTCTCCTG<br>TGAAGGCCGGCGTGGAAACCACCACCCCTAGCAAGCAGAGCAACAA |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
|  |  | CAAATACGCCGCCAGCAGCTACCTGAGCCTGACCCCCGAGCAGTGGA AGTCCCACAGATCCTACAGCTGCCAAGTGACCCACGAGGGCAGCACC GTGGAAAAGACAGTGGCCCCTACCGAGTGCAGC |
| 21 | PRT | EVQLLESGGGLVQPGGSLRLSCAASGFTFSSYPMGWVRQAPGKGLEWV AGIDDDGDSDTRYAPAVKGRATISRDNSKNTVYLQMNSLRAEDTAVYY CAKHTGIGANSAGSIDAWGQGTLVTVSS |
| 22 | PRT | SYPMG |
| 23 | PRT | GIDDDGDSDTRYAPAVKG |
| 24 | PRT | HTGIGANSAGSIDA |
| 25 | PRT | SYELTQPPSVSVSPGQTARITCSGGGSYTGSYYYGWYQQKPGQAPVTVI YYNNKRPSDIPERFSGSLSGTTNTLTISGVQAEDEADYYCGSADNSGDAF GTGTKVTVL |
| 26 | PRT | SGGGSYTGSYYYG |
| 27 | PRT | YNNKRPS |
| 28 | PRT | GSADNSGDA |
| 29 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ATCCTATGGGCTGGGTCCGACAGGCCCCTGGCAAAGGACTTGAATGG GTGGCCGGCATCGACGACGATGGCGATAGCGATACAAGATACGCCC CTGCCGTGAAGGGCAGAGCCACCATCTCCAGAGACAACAGCAAGAA CACCGTGTACCTGCAGATGAACAGCCTGAGAGCCGAGGACACCGCC GTGTACTATTGTGCCAAGCACACAGGCATCGGCGCCAATTCTGCCGG CTCTATTGATGCCTGGGGCCAGGGAACACTGGTCACAGTTTCTTCA |
| 30 | DNA | AGCTATCCTATGGGC |
| 31 | DNA | GGCATCGACGACGATGGCGATAGCGATACAAGATACGCCCCTGCCGT GAAGGGC |
| 32 | DNA | CACACAGGCATCGGCGCCAATTCTGCCGGCTCTATTGATGCC |
| 33 | DNA | AGCTATGAGCTGACACAGCCTCCAAGCGTGTCCGTGTCTCCTGGACA GACCGCCAGAATCACATGTAGCGGCGGAGGCAGCTACACCGGCAGC TACTACTATGGCTGGTATCAGCAGAAGCCCGGACAGGCCCCTGTGAC CGTGATCTACTACAACAACAAGCGGCCCAGCGACATCCCCGAGAGAT TTTCTGGCTCTCTGAGCGGCACCACCAACACACTGACAATCTCTGGC GTGCAGGCCGAGGACGAGGCCGATTACTATTGTGGCAGCGCCGATAA TAGCGGCGACGCCTTTGGCACCGGCACCAAAGTTACAGTGCTA |
| 34 | DNA | AGCGGCGGAGGCAGCTACACCGGCAGCTACTACTATGGC |
| 35 | DNA | TACAACAACAAGCGGCCCAGC |
| 36 | DNA | GGCAGCGCCGATAATAGCGGCGACGCC |
| 37 | PRT | EVQLLESGGGLVQPGGSLRLSCAASGFTFSSYPMGWVRQAPGKGLEWV AGIDDDGDSDTRYAPAVKGRATISRDNSKNTVYLQMNSLRAEDTAVYY CAKHTGIGANSAGSIDAWGQGTLVTVSSAKTTPPSVYPLAPGSAAQTNS MVTLGCLVKGYFPEPVTVTWNSGSLSSGVHTFPAVLQSDLYTLSSSVTV PSSTWPSETVTCNVAHPASSTKVDKKIVPRDCGCKPCICTVPEVSSVFIFP PKPKDVLTITLTPKVTCVVVDISKDDPEVQFSWFVDDVEVHTAQTQPRE EQFNSTFRSVSELPIMHQDWLNGKEFKCRVNSAAFPAPIEKTISKTKGRP KAPQVYTIPPPKEQMAKDKVSLTCMITDFFPEDITVEWQWNGQPAENYK NTQPIMDTDGSYFVYSKLNVQKSNWEAGNTFTCSVLHEGLHNHHTEKS LSHSPGK |
| 38 | PRT | SYELTQPPSVSVSPGQTARITCSGGGSYTGSYYYGWYQQKPGQAPVTVI YYNNKRPSDIPERFSGSLSGTTNTLTISGVQAEDEADYYCGSADNSGDAF GTGTKVTVLGQPKSSPSVTLFPPSSEELETNKATLVCTITDFYPGVVTVD WKVDGTPVTQGMETTQPSKQSNNKYMASSYLTLTARAWERHSSYSCQ VTHEGHTVEKSLSRADCS |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 39 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ATCCTATGGGCTGGGTCCGACAGGCCCCTGGCAAAGGACTTGAATGG<br>GTGGCCGGCATCGACGACGATGGCGATAGCGATACAAGATACGCCC<br>CTGCCGTGAAGGGCAGAGCCACCATCTCCAGAGACAACAGCAAGAA<br>CACCGTGTACCTGCAGATGAACAGCCTGAGAGCCGAGGACACCGCC<br>GTGTACTATTGTGCCAAGCACACAGGCATCGGCGCCAATTCTGCCGG<br>CTCTATTGATGCCTGGGGCCAGGGAACACTGGTCACAGTTTCTTCAG<br>CCAAGACCACCCCCCCCAGCGTGTACCCTCTGGCTCCTGGATCTGCC<br>GCCCAGACCAACAGCATGGTCACCCTGGGCTGCCTCGTGAAGGGCTA<br>CTTCCCTGAGCCTGTGACCGTGACCTGGAACAGCGGCTCTCTGTCTAG<br>CGGCGTGCACACCTTTCCAGCCGTGCTGCAGAGCGACCTGTACACCC<br>TGAGCAGCAGCGTGACCGTGCCTAGCAGCACCTGGCCTAGCGAGACA<br>GTGACCTGCAACGTGGCCCACCCTGCCAGCAGCACAAAGGTGGACA<br>AGAAAATCGTGCCCCGGGACTGCGGCTGCAAGCCCTGTATCTGTACC<br>GTGCCCGAGGTGTCCAGCGTGTTCATCTTCCCACCCAAGCCCAAGGA<br>CGTGCTGACCATCACCCTGACCCCCAAAGTGACCTGTGTGGTGGTGG<br>ACATCAGCAAGGACGACCCCGAGGTGCAGTTCAGTTGGTTCGTGGAC<br>GACGTGGAAGTGCACACAGCCCAGACCCAGCCCAGAGAGGAACAGT<br>TCAACAGCACCTTCAGAAGCGTGTCCGAGCTGCCCATCATGCACCAG<br>GACTGGCTGAACGGCAAAGAGTTCAAGTGCAGAGTGAACAGCGCCG<br>CCTTCCCTGCCCCCATCGAGAAAACCATCTCCAAGACCAAGGGCAGA<br>CCCAAGGCCCCTCAGGTGTACACAATCCCCCCACCCAAAGAACAGAT<br>GGCCAAGGACAAGGTGTCCCTGACCTGCATGATCACCGATTTCTTCC<br>CAGAGGACATCACCGTGGAATGGCAGTGGAACGGCCAGCCCGCCGA<br>GAACTACAAGAACACCCAGCCTATCATGGACACCGACGGCAGCTACT<br>TCGTGTACAGCAAGCTGAACGTGCAGAAGTCCAACTGGGAGGCCGG<br>CAACACCTTCACCTGTAGCGTGCTGCACGAGGGCCTGCACAATCACC<br>ACACCGAGAAGTCCCTGTCCCACAGCCCTGGCAAG |
| 40 | DNA | AGCTATGAGCTGACACAGCCTCCAAGCGTGTCCGTGTCTCCTGGACA<br>GACCGCCAGAATCACATGTAGCGGCGGAGGCAGCTACACCGGCAGC<br>TACTACTATGGCTGGTATCAGCAGAAGCCCGACAGGCCCCTGTGAC<br>CGTGATCTACTACAACAACAAGCGGCCCAGCGACATCCCCGAGAGAT<br>TTTCTGGCTCTCTGAGCGGCACCACCAACACACTGACAATCTCTGGC<br>GTGCAGGCCGAGGACGAGGCCGATTACTATTGTGGCAGCGCCGATAA<br>TAGCGGCGACGCCTTTGGCACCGGCACCAAAGTTACAGTGCTAGGCC<br>AGCCCAAGAGCAGCCCTAGCGTGACCCTGTTCCCTCCAAGCAGCGAG<br>GAACTGGAAACAAACAAGGCCACCCTCGTGTGCACCATCACCGACTT<br>CTACCCCGGCGTCGTGACCGTGGACTGGAAGGTGGACGGCACCCCAG<br>TGACCCAGGGCATGGAAACCACCCAGCCCAGCAAGCAGAGCAACAA<br>CAAGTACATGGCCAGCAGCTACCTGACCCTGACCGCCAGAGCCTGGG<br>AGAGACACAGCTCCTACAGCTGCCAAGTGACCCACGAGGGCCACAC<br>CGTGGAAAAGAGCCTGAGCAGAGCCGACTGCAGC |
| 41 | PRT | EVQLLESGGGLVQPGGSLRLSCAASGFTFSSYGMHWVRQAPGKGLEWV<br>SAIGTGGDTYYADSVMGRFTISRDNSKNTLYLQMNSLRAEDTAVYYCA<br>RRDDYTSRDAFDVWGQGTLVTVSS |
| 42 | PRT | SYGMH |
| 43 | PRT | AIGTGGDTYYADSVMG |
| 44 | PRT | RDDYTSRDAFDV |
| 45 | PRT | QSVLTQPPSASGTPGQRVTISCSGSSSNIGSNTVNWYQQLPGTAPKLLIYY<br>DDLLPSGVPDRFSGSKSGTSASLAISGLRSEDEADYYCAAWDDSLNGYV<br>VFGGGTKLTVL |
| 46 | PRT | SGSSSNIGSNTVN |
| 47 | PRT | YDDLLPS |
| 48 | PRT | AAWDDSLNGYVV |
| 49 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ATGGCATGCACTGGGTCCGACAGGCCCCTGGCAAAGGACTTGAATGG<br>GTGGTCGCCATCGGCACAGGCGGCGATACCTACTATGCCGATAGCGT<br>GATGGGCAGATTCACCATCAGCCGGGACAACAGCAAGAACACCCTG<br>TACCTGCAGATGAACAGCCTGAGAGCCGAGGACACCGCCGTGTACTA |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
|  |  | TTGCGCCAGAAGGGACGACTACACCAGCAGGGATGCCTTCGATGTGT<br>GGGGCCAGGGAACACTGGTTACCGTTTCTTCA |
| 50 | DNA | AGCTATGGCATGCAC |
| 51 | DNA | GCCATCGGCACAGGCGGCGATACCTACTATGCCGATAGCGTGATGGG<br>C |
| 52 | DNA | AGGGACGACTACACCAGCAGGGATGCCTTCGATGTG |
| 53 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCTGCCTAGCGGCGTGCCCGATAGAT<br>TTTCTGGCAGCAAGAGCGGCACAAGCGCCAGCCTGGCTATCTCTGGA<br>CTGAGATCTGAGGACGAGGCCGACTACTATTGCGCCGCCTGGGACGA<br>TAGCCTGAACGGCTATGTGGTTTTCGGCGGAGGCACCAAGCTGACCG<br>TGCTA |
| 54 | DNA | AGCGGCAGCAGCTCCAACATCGGCAGCAACACCGTGAAC |
| 55 | DNA | TACGACGACCTGCTGCCTAGC |
| 56 | DNA | GCCGCCTGGGACGATAGCCTGAACGGCTATGTGGTT |
| 57 | PRT | EVQLLESGGGLVQPGGSLRLSCAASGFTFSSYGMHWVRQAPGKGLEWV<br>SAIGTGGDTYYADSVMGRFTISRDNSKNTLYLQMNSLRAEDTAVYYCA<br>RRDDYTSRDAFDVWGQGTLVTVSSASTKGPSVFPLAPSSKSTSGGTAAL<br>GCLVKDYFPEPVTVSWNSGALTSGVHTFPAVLQSSGLYSLSSVVTVPSSS<br>LGTQTYICNVNHKPSNTKVDKKVEPKSCDKTHTCPPCPAPELLGGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISKA<br>KGQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHY<br>TQKSLSLSPG |
| 58 | PRT | QSVLTQPPSASGTPGQRVTISCSGSSSNIGSNTVNWYQQLPGTAPKLLIYY<br>DDLLPSGVPDRFSGSKSGTSASLAISGLRSEDEADYYCAAWDDSLNGYV<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 59 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ATGGCATGCACTGGGTCCGACAGGCCCCTGGCAAAGGACTTGAATGG<br>GTGTCCGCCATCGGCACAGGCGGCGATACCTACTATGCCGATAGCGT<br>GATGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGATGCCTTCGATGTGT<br>GGGGCCAGGGAACACTGGTTACCGTTTCTTCAGCCAGCACCAAGGGC<br>CCCAGCGTGTTCCCTCTGGCCCCTAGCAGCAAGAGCACATCTGGCGG<br>AACAGCCGCCCTGGGCTGCCTCGTGAAGGACTACTTTCCCGAGCCCG<br>TGACCGTGTCCTGGAACTCTGGCGCTCTGACAAGCGGCGTGCACACC<br>TTTCCAGCCGTGCTGCAGAGCAGCGGCCTGTACTCTCTGAGCAGCGT<br>CGTGACAGTGCCCAGCAGCTCTCTGGGCACCCAGACCTACATCTGCA<br>ACGTGAACCACAAGCCCAGCAACACCAAGGTGGACAAGAAGGTGGA<br>ACCCAAGAGCTGCGACAAGACCCACACCTGTCCCCCTTGTCCTGCCC<br>CCGAACTGCTGGGAGGCCCTTCCGTGTTCCTGTTCCCCCCAAAGCCCA<br>AGGACACCCTGATGATCAGCCGGACCCCCGAAGTGACCTGCGTGGTG<br>GTGGATGTGTCCCACGAGGACCCTGAAGTGAAGTTCAATTGGTACGT<br>GGACGGCGTGGAAGTGCACAACGCCAAGACCAAGCCTAGAGAGGAA<br>CAGTACAACAGCACCTACCGGGTGGTGTCCGTGCTGACAGTGCTGCA<br>CCAGGACTGGCTGAACGGCAAAGAGTACAAGTGCAAGGTGTCCAAC<br>AAGGCCCTGCCTGCCCCCATCGAGAAAACCATCAGCAAGGCCAAGG<br>GCCAGCCCCGCGAACCCCAGGTGTACACACTGCCCCCAAGCAGGGAC<br>GAGCTGACCAAGAACCAGGTGTCCCTGACCTGTCTCGTGAAAGGCTT<br>CTACCCCTCCGATATCGCCGTGGAATGGGAGAGCAACGGCCAGCCCG<br>AGAACAACTACAAGACCACCCCCCCTGTGCTGGACAGCGACGGCTCA<br>TTCTTCCTGTACAGCAAGCTGACCGTGGACAAGTCCCGGTGGCAGCA<br>GGGCAACGTGTTCAGCTGCAGCGTGATGCACGAGGCCCTGCACAACC<br>ACTACACCCAGAAGTCCCTGAGCCTGAGCCCTGGC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 60 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCTGCCTAGCGGCGTGCCCGATAGAT TTTCTGGCAGCAAGAGCGGCACAAGCGCCAGCCTGGCTATCTCTGGA CTGAGATCTGAGGACGAGGCCGACTACTATTGCGCCGCCTGGGACGA TAGCCTGAACGGCTATGTGGTTTTCGGCGGAGGCACCAAGCTGACCG TGCTAGGCCAGCCTAAAGCCGCCCCTAGCGTGACCCTGTTCCCTCCA AGCAGCGAGGAACTGCAGGCCAACAAGGCCACCCTCGTGTGCCTGAT CAGCGACTTCTATCCTGGCGCCGTGACCGTGGCCTGGAAGGCCGATA GCTCTCCTGTGAAGGCCGGCGTGGAAACCACCACCCCTAGCAAGCAG AGCAACAACAAATACGCCGCCAGCAGCTACCTGAGCCTGACCCCCGA GCAGTGGAAGTCCCACAGATCCTACAGCTGCCAAGTGACCCACGAGG GCAGCACCGTGGAAAAGACAGTGGCCCCTACCGAGTGCAGC |
| 61 | PRT | EVQLLESGGGLVQPGGSLRLSCAASGFTFSSYEMNWVRQAPGKGLEWV SGISWNSGSIGYADSVKGRFTISRDNSKNTLYLQMNSLRAEDTAVYYCA RSGYSSSWFDPDFDYWGQGTLVTVSS |
| 62 | PRT | SYEMN |
| 63 | PRT | GISWNSGSIGYADSVKG |
| 64 | PRT | SGYSSSWFDPDFDY |
| 65 | PRT | QSVLTQPPSASGTPGQRVTISCTGSSSNIGAGYDVHWYQQLPGTAPKLLI YGNSNRPSGVPDRFSGSKSGTSASLAISGLRSEDEADYYCSSYAGSNPYV VFGGGTKLTVL |
| 66 | PRT | TGSSSNIGAGYDVH |
| 67 | PRT | GNSNRPS |
| 68 | PRT | SSYAGSNPYVV |
| 69 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGAGATGAACTGGGTCCGACAGGCCCCTGGCAAAGGCCTTGAATG GGTGTCCGGCATCAGCTGGAATAGCGGCTCTATCGGCTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCA |
| 70 | DNA | AGCTACGAGATGAAC |
| 71 | DNA | GGCATCAGCTGGAATAGCGGCTCTATCGGCTACGCCGACAGCGTGAA GGGC |
| 72 | DNA | AGCGGCTACAGCAGCTCTTGGTTTGACCCCGACTTCGACTAT |
| 73 | DNA | CAGTCTGTTCTGACACAGCCTCCTAGCGCCTCTGGCACACCTGGACA GAGAGTGACCATCAGCTGTACCGGCAGCAGCTCCAATATCGGAGCCG GCTATGACGTGCACTGGTATCAGCAGCTGCCTGGCACAGCCCCTAAA CTGCTGATCTACGGCAACAGCAACAGACCCAGCGGCGTGCCCGATAG ATTTTCCGGCTCTAAGAGCGGCACAAGCGCCAGCCTGGCTATCTCTG GACTGAGATCTGAGGACGAGGCCGACTACTACTGCAGCAGCTATGCC GGCAGCAACCCCTACGTTGTGTTTGGCGGAGGCACCAAGCTGACCGT TCTA |
| 74 | DNA | ACCGGCAGCAGCTCCAATATCGGAGCCGGCTATGACGTGCAC |
| 75 | DNA | GGCAACAGCAACAGACCCAGC |
| 76 | DNA | AGCAGCTATGCCGGCAGCAACCCCTACGTTGTG |
| 77 | PRT | EVQLLESGGGLVQPGGSLRLSCAASGFTFSSYEMNWVRQAPGKGLEWV SGISWNSGSIGYADSVKGRFTISRDNSKNTLYLQMNSLRAEDTAVYYCA RSGYSSSWFDPDFDYWGQGTLVTVSSASTKGPSVFPLAPSSKSTSGGTA ALGCLVKDYFPEPVTVSWNSGALTSGVHTFPAVLQSSGLYSLSSVVTVP |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
|  |  | SSSLGTQTYICNVNHKPSNTKVDKKVEPKSCDKTHTCPPCPAPELLGGPS<br>VFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPG |
| 78 | PRT | QSVLTQPPSASGTPGQRVTISCTGSSSNIGAGYDVHWYQQLPGTAPKLLI<br>YGNSNRPSGVPDRFSGSKSGTSASLAISGLRSEDEADYYCSSYAGSNPYV<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 79 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGAGATGAACTGGGTCCGACAGGCCCCTGGCAAAGGCCTTGAATG<br>GGTGTCCGGCATCAGCTGGAATAGCGGCTCTATCGGCTACGCCGACA<br>GCGTGAAGGGCAGATTCACCATCAGCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCAGCCAG<br>CACCAAGGGCCCCAGCGTGTTCCCTCTGGCCCCTAGCAGCAAGAGCA<br>CATCTGGCGGAACAGCCGCCCTGGGCTGCCTCGTGAAGGACTACTTT<br>CCCGAGCCCGTGACCGTGTCCTGGAACTCTGGCGCTCTGACAAGCGG<br>CGTGCACACCTTTCCAGCCGTGCTGCAGAGCAGCGGCCTGTACTCTCT<br>GAGCAGCGTCGTGACAGTGCCCAGCAGCTCTCTGGGCACCCAGACCT<br>ACATCTGCAACGTGAACCACAAGCCCAGCAACACCAAGGTGGACAA<br>GAAGGTGGAACCCAAGAGCTGCGACAAGACCCACACCTGTCCCCCTT<br>GTCCTGCCCCCGAACTGCTGGGAGGCCCTTCCGTGTTCCTGTTCCCCC<br>CAAAGCCCAAGGACACCCTGATGATCAGCCGGACCCCCGAAGTGAC<br>CTGCGTGGTGGTGGATGTGTCCCACGAGGACCCTGAAGTGAAGTTCA<br>ATTGGTACGTGGACGGCGTGGAAGTGCACAACGCCAAGACCAAGCC<br>TAGAGAGGAACAGTACAACAGCACCTACCGGGTGGTGTCCGTGCTGA<br>CAGTGCTGCACCAGGACTGGCTGAACGGCAAAGAGTACAAGTGCAA<br>GGTGTCCAACAAGGCCCTGCCTGCCCCCATCGAGAAAACCATCAGCA<br>AGGCCAAGGGCCAGCCCCGCGAACCCCAGGTGTACACACTGCCCCCA<br>AGCAGGGACGAGCTGACCAAGAACCAGGTGTCCCTGACCTGTCTCGT<br>GAAAGGCTTCTACCCCTCCGATATCGCCGTGGAATGGGAGAGCAACG<br>GCCAGCCCGAGAACAACTACAAGACCACCCCCCCTGTGCTGGACAGC<br>GACGGCTCATTCTTCCTGTACAGCAAGCTGACCGTGGACAAGTCCCG<br>GTGGCAGCAGGGCAACGTGTTCAGCTGCAGCGTGATGCACGAGGCCC<br>TGCACAACCACTACACCCAGAAGTCCCTGAGCCTGAGCCCTGGC |
| 80 | DNA | CAGTCTGTTCTGACACAGCCTCCTAGCGCCTCTGGCACACCTGGACA<br>GAGAGTGACCATCAGCTGTACCGGCAGCAGCTCCAATATCGGAGCG<br>GCTATGACGTGCACTGGTATCAGCAGCTGCCTGGCACAGCCCCTAAA<br>CTGCTGATCTACGGCAACAGCAACAGACCCAGCGGCGTGCCCGATAG<br>ATTTTCCGGCTCTAAGAGCGGCACAAGCGCCAGCCTGGCTATCTCTG<br>GACTGAGATCTGAGGACGAGGCCGACTACTACTGCAGCAGCTATGCC<br>GGCAGCAACCCCTACGTTGTGTTTGGCGGAGGCACCAAGCTGACCGT<br>TCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 81 | PRT | EVQLLESGGGLVQTGGSLRLSCAASGFTFSDYAMSWVRQAPGKGLEWV<br>SWIYYDSGSKYYADSVKGRFTISRDNSKNTLYLQMNSLRAEDTAVYYC<br>AKLNGDFDYWGQGTLVTVSS |
| 82 | PRT | DYAMS |
| 83 | PRT | WIYYDSGSKYYADSVKG |
| 84 | PRT | LNGDFDY |
| 85 | PRT | QSVLTQPPSASGTPGQRVTISCSGSSSNIGNNDVSWYQQLPGTAPKLLIY<br>ADSHRPSGVPDRFSGSKSGTSASLAISGLRSEDEADYYCGAWDSSLGY<br>VFGGGTKLTVL |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
| --- | --- | --- |
| 86 | PRT | SGSSSNIGNNDVS |
| 87 | PRT | ADSHRPS |
| 88 | PRT | GAWDSSLSGYV |
| 89 | DNA | GAAGTTCAGCTGCTGGAATCTGGCGGCGGACTGGTTCAAACAGGCGG<br>CTCTCTGAGACTGAGCTGTGCCGCCTCTGGCTTCACCTTCAGCGATTA<br>CGCCATGAGCTGGGTCCGACAGGCCCCTGGAAAAGGCCTTGAATGGG<br>TGTCCTGGATCTACTACGACAGCGGCAGCAAGTACTACGCCGACAGC<br>GTGAAGGGCAGATTCACCATCAGCCGGGACAACAGCAAGAACACCC<br>TGTACCTGCAGATGAACAGCCTGAGAGCCGAGGACACCGCCGTGTAC<br>TATTGCGCCAAGCTGAACGGCGACTTCGACTATTGGGGCCAGGGCAC<br>ACTGGTCACAGTCTCTTCA |
| 90 | DNA | GATTACGCCATGAGC |
| 91 | DNA | TGGATCTACTACGACAGCGGCAGCAAGTACTACGCCGACAGCGTGAA<br>GGGC |
| 92 | DNA | CTGAACGGCGACTTCGACTAT |
| 93 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAAC<br>AACGACGTGTCCTGGTATCAGCAGCTGCCTGGCACAGCCCCTAAACT<br>GCTGATCTACGCCGACAGCCACAGACCTAGCGGCGTGCCAGATAGAT<br>TCAGCGGCTCTAAGAGCGGCACATCTGCCAGCCTGGCCATCTCTGGA<br>CTGAGATCTGAGGACGAGGCCGACTACTATTGCGGCGCCTGGGATTC<br>TAGCCTGAGCGGCTATGTTTTTGGCGGAGGCACCAAGCTGACCGTGC<br>TA |
| 94 | DNA | AGCGGCAGCAGCTCCAACATCGGCAACAACGACGTGTCC |
| 95 | DNA | GCCGACAGCCACAGACCTAGC |
| 96 | DNA | GGCGCCTGGGATTCTAGCCTGAGCGGCTATGTT |
| 97 | PRT | EVQLLESGGGLVQTGGSLRLSCAASGFTFSDYAMSWVRQAPGKGLEWV<br>SWIYYDSGSKYYADSVKGRFTISRDNSKNTLYLQMNSLRAEDTAVYYC<br>AKLNGDFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLPPK<br>PKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQK<br>SLSLSPG |
| 98 | PRT | QSVLTQPPSASGTPGQRVTISCSGSSSNIGNNDVSWYQQLPGTAPKLLIY<br>ADSHRPSGVPDRFSGSKSGTSASLAISGLRSEDEADYYCGAWDSSLSGY<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 99 | DNA | GAAGTTCAGCTGCTGGAATCTGGCGGCGGACTGGTTCAAACAGGCGG<br>CTCTCTGAGACTGAGCTGTGCCGCCTCTGGCTTCACCTTCAGCGATTA<br>CGCCATGAGCTGGGTCCGACAGGCCCCTGGAAAAGGCCTTGAATGGG<br>TGTCCTGGATCTACTACGACAGCGGCAGCAAGTACTACGCCGACAGC<br>GTGAAGGGCAGATTCACCATCAGCCGGGACAACAGCAAGAACACCC<br>TGTACCTGCAGATGAACAGCCTGAGAGCCGAGGACACCGCCGTGTAC<br>TATTGCGCCAAGCTGAACGGCGACTTCGACTATTGGGGCCAGGGCAC<br>ACTGGTCACAGTCTCTTCAGCCAGCACCAAGGGCCCCAGCGTGTTCC<br>CTCTGGCCCCTAGCAGCAAGAGCACATCTGGCGGAACAGCCGCCCTG<br>GGCTGCCTCGTGAAGGACTACTTTCCCGAGCCCGTGACCGTGTCCTG<br>GAACTCTGGCGCTCTGACAAGCGGCGTGCACACCTTTCCAGCCGTGC<br>TGCAGAGCAGCGGCCTGTACTCTCTGAGCAGCGTCGTGACAGTGCCC<br>AGCAGCTCTCTGGGCACCCAGACCTACATCTGCAACGTGAACCACAA<br>GCCCAGCAACACCAAGGTGGACAAGAAGGTGGAACCCAAGAGCTGC<br>GACAAGACCCACACCTGTCCCCCTTGTCCTGCCCCCGAACTGCTGGG<br>AGGCCCTTCCGTGTTCCTGTTCCCCCCAAAGCCCAAGGACACCCTGAT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | GATCAGCCGGACCCCCGAAGTGACCTGCGTGGTGGTGGATGTGTCCC ACGAGGACCCTGAAGTGAAGTTCAATTGGTACGTGGACGGCGTGGA AGTGCACAACGCCAAGACCAAGCCTAGAGAGGAACAGTACAACAGC ACCTACCGGGTGGTGTCCGTGCTGACAGTGCTGCACCAGGACTGGCT GAACGGCAAAGAGTACAAGTGCAAGGTGTCCAACAAGGCCCTGCCT GCCCCCATCGAGAAACCATCAGCAAGGCCAAGGGCCAGCCCCGCG AACCCCAGGTGTACACACTGCCCCCAAGCAGGGACGAGCTGACCAA GAACCAGGTGTCCCTGACCTGTCTCGTGAAAGGCTTCTACCCCTCCG ATATCGCCGTGGAATGGGAGAGCAACGGCCAGCCCGAGAACAACTA CAAGACCACCCCCCCTGTGCTGGACAGCGACGGCTCATTCTTCCTGT ACAGCAAGCTGACCGTGGACAAGTCCCGGTGGCAGCAGGGCAACGT GTTCAGCTGCAGCGTGATGCACGAGGCCCTGCACAACCACTACACCC AGAAGTCCCTGAGCCTGAGCCCTGGC |
| 100 | DNA | CAGTCTGTTCTGACACAGCCTCCTAGCGCCTCTGGCACACCTGGACA GAGAGTGACCATCAGCTGTAGCGGCAGCAGCTCCAACATCGGCAAC AACGACGTGTCCTGGTATCAGCAGCTGCCTGGCACAGCCCCTAAACT GCTGATCTACGCCGACAGCCACAGACCTAGCGGCGTGCCAGATAGAT TCAGCGGCTCTAAGAGCGGCACATCTGCCAGCCTGGCCATCTCTGGA CTGGAGATCGAGGACGAGGCCGACTACTATTGCGGCGCCTGGGATTC TAGCCTGAGCGGCTATGTTTTTGGCGGAGGCACCAAGCTGACCGTGC TAGGCCAGCCTAAAGCCGCCCCTAGCGTGACCCTGTTCCCTCCAAGC AGCGAGGAACTGCAGGCCAACAAGGCCACCCTCGTGTGCCTGATCAG CGACTTCTATCCTGGCGCCGTGACCGTGGCCTGGAAGGCCGATAGCT CTCCTGTGAAGGCCGGCGTGGAAACCACCACCCCTAGCAAGCAGAGC AACAACAAATACGCCGCCAGCAGCTACCTGAGCCTGACCCCCGAGCA GTGGAAGTCCCACAGATCCTACAGCTGCCAAGTGACCCACGAGGGCA GCACCGTGGAAAAGACAGTGGCCCCTACCGAGTGCAGC |
| 101 | PRT | EVQLLESGGGLVQPGGSLRLSCAASGFTFSSYEMNWVRQAPGKGLEWV SGISWNSGSIGYADSVKGRFTISRDNSKNTLYLQMNSLRAEDTAVYYCA RSGYSSSWFDPDFDYWGQGTLVTVSS |
| 102 | PRT | SYEMN |
| 103 | PRT | GISWNSGSIGYADSVKG |
| 104 | PRT | SGYSSSWFDPDFDY |
| 105 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCSSYAGSNPY VVFGGGTKLTVL |
| 106 | PRT | TGSSSNIGAGYDVH |
| 107 | PRT | GNSNRPS |
| 108 | PRT | SSYAGSNPYVV |
| 109 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGAGATGAACTGGGTCCGACAGGCCCCTGGCAAAGGCCTTGAATG GGTGTCCGGCATCAGCTGGAATAGCGGCTCTATCGGCTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCA |
| 110 | DNA | AGCTACGAGATGAAC |
| 111 | DNA | GGCATCAGCTGGAATAGCGGCTCTATCGGCTACGCCGACAGCGTGAA GGGC |
| 112 | DNA | AGCGGCTACAGCAGCTCTTGGTTTGACCCCGACTTCGACTAT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 113 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTTCTAGCTACGCCG GCAGCAACCCCTACGTGGTGTTTGGCGGAGGCACCAAGCTGACAGTT CTA |
| 114 | DNA | ACAGGCAGCAGCTCCAATATCGGAGCCGGCTATGACGTGCAC |
| 115 | DNA | GGCAACAGCAACAGACCCAGC |
| 116 | DNA | TCTAGCTACGCCGGCAGCAACCCCTACGTGGTG |
| 117 | PRT | EVQLLESGGGLVQPGGSLRLSCAASGFTFSSYEMNWVRQAPGKGLEWV SGISWNSGSIGYADSVKGRFTISRDNSKNTLYLQMNSLRAEDTAVYYCA RSGYSSSWFDPDFDYWGQGTLVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPG |
| 118 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCSSYAGSNPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |
| 119 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGAGATGAACTGGGTCCGACAGGCCCCTGGCAAAGGCCTTGAATG GGTGTCCGGCATCAGCTGGAATAGCGGCTCTATCGGCTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGC |
| 120 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTTCTAGCTACGCCG GCAGCAACCCCTACGTGGTGTTTGGCGGAGGCACCAAGCTGACAGTT CTAGGCCAGCCTAAAGCCGCCCCTAGCGTGACCCTGTTCCCTCCAAG CAGCGAGGAACTGCAGGCCAACAAGGCCACCCTCGTGTGCCTGATCA |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
|  |  | GCGACTTCTATCCTGGCGCCGTGACCGTGGCCTGGAAGGCCGATAGC<br>TCTCCTGTGAAGGCCGGCGTGGAAACCACCACCCCTAGCAAGCAGAG<br>CAACAACAAATACGCCGCCAGCAGCTACCTGAGCCTGACCCCCGAGC<br>AGTGGAAGTCCCACAGATCCTACAGCTGCCAAGTGACCCACGAGGGC<br>AGCACCGTGGAAAAGACAGTGGCCCCTACCGAGTGCAGC |
| 121 | PRT | EVQLLESGGGLVQPGGSLRLSCAASGFTFSSYAMSWVRQAPGKGLEWV<br>SAIGTGGDTYYADSVKGRFTISRDNSKNTLYLQMNSLRAEDTAVYYCA<br>RRDDYTSRDAFDYWGQGTLVTVSS |
| 122 | PRT | SYAMS |
| 123 | PRT | AIGTGGDTYYADSVKG |
| 124 | PRT | RDDYTSRDAFDY |
| 125 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNGYV<br>VFGGGTKLTVL |
| 126 | PRT | SGSSSNIGSNTVN |
| 127 | PRT | YDDLRPS |
| 128 | PRT | AAWDDSLNGYVV |
| 129 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATTGGCACAGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCA |
| 130 | DNA | AGCTACGCCATGAGC |
| 131 | DNA | GCCATTGGCACAGGCGGCGATACCTACTACGCCGACTCTGTGAAGGG<br>C |
| 132 | DNA | AGGGACGACTACACCAGCAGGGACGCCTTCGATTAT |
| 133 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGGCTATGTTGTTTTCGGCGGAGGCACCAAGCTGACCG<br>TTCTA |
| 134 | DNA | AGCGGCAGCAGCTCCAACATCGGCAGCAACACCGTGAAC |
| 135 | DNA | TACGACGACCTGCGGCCTAGC |
| 136 | DNA | GCCGCCTGGGACGACAGCCTGAACGGCTATGTTGTT |
| 137 | PRT | EVQLLESGGGLVQPGGSLRLSCAASGFTFSSYAMSWVRQAPGKGLEWV<br>SAIGTGGDTYYADSVKGRFTISRDNSKNTLYLQMNSLRAEDTAVYYCA<br>RRDDYTSRDAFDYWGQGTLVTVSSASTKGPSVFPLAPSSKSTSGGTAAL<br>GCLVKDYFPEPVTVSWNSGALTSGVHTFPAVLQSSGLYSLSSVVTVPSSS<br>LGTQTYICNVNHKPSNTKVDKKVEPKSCDKTHTCPPCPAPELLGGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISKA<br>KGQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHY<br>TQKSLSLSPG |
| 138 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNGYV<br>VFGGGTKLTVLGQPKAAPSVTLFPPSSEELQANKATLVCLISDFYPGAVT |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | VAWKADSSPVKAGVETTTPSKQSNNKYAASSYLSLTPEQWKSHRSYSC QVTHEGSTVEKTVAPTECS |
| 139 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGCCATGAGCTGGGTCCGACAGGCTCCTGGCAAAGGCCTTGAATGG GTGTCCGCCATTGGCACAGGCGGCGATACCTACTACGCCGACTCTGT GAAGGGCAGATTCACCATCAGCCGGGACAACAGCAAGAACACCCTG TACCTGCAGATGAACAGCCTGAGAGCCGAGGACACCGCCGTGTACTA TTGCGCCAGAAGGGACGACTACACCAGCAGGGACGCCTTCGATTATT GGGGCCAGGGCACACTGGTCACCGTTTCTTCAGCCAGCACCAAGGGC CCCAGCGTGTTCCCTCTGGCCCCTAGCAGCAAGAGCACATCTGGCGG AACAGCCGCCCTGGGCTGCCTCGTGAAGGACTACTTTCCCGAGCCCG TGACCGTGTCCTGGAACTCTGGCGCTCTGACAAGCGGCGTGCACACC TTTCCAGCCGTGCTGCAGAGCAGCGGCCTGTACTCTCTGAGCAGCGT CGTGACAGTGCCCAGCAGCTCTCTGGGCACCCAGACCTACATCTGCA ACGTGAACCACAAGCCCAGCAACACCAAGGTGGACAAGAAGGTGGA ACCCAAGAGCTGCGACAAGACCCACACCTGTCCCCCTTGTCCTGCCC CCGAACTGCTGGGAGGCCCTTCCGTGTTCCTGTTCCCCCCAAAGCCCA AGGACACCCTGATGATCAGCCGGACCCCCGAAGTGACCTGCGTGGTG GTGGATGTGTCCCACGAGGACCCTGAAGTGAAGTTCAATTGGTACGT GGACGGCGTGGAAGTGCACAACGCCAAGACCAAGCCTAGAGAGGAA CAGTACAACAGCACCTACCGGGTGGTGTCCGTGCTGACAGTGCTGCA CCAGGACTGGCTGAACGGCAAAGAGTACAAGTGCAAGGTGTCCAAC AAGGCCCTGCCTGCCCCCATCGAGAAAACCATCAGCAAGGCCAAGG GCCAGCCCCGCGAACCCCAGGTGTACACACTGCCCCCAAGCAGGGAC GAGCTGACCAAGAACCAGGTGTCCCTGACCTGTCTCGTGAAAGGCTT CTACCCCTCCGATATCGCCGTGGAATGGGAGAGCAACGGCCAGCCCG AGAACAACTACAAGACCACCCCCCCTGTGCTGGACAGCGACGGCTCA TTCTTCCTGTACAGCAAGCTGACCGTGGACAAGTCCCGGTGGCAGCA GGGCAACGTGTTCAGCTGCAGCGTGATGCACGAGGCCCTGCACAACC ACTACACCCAGAAGTCCCTGAGCCTGAGCCCTGGC |
| 140 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGGCTATGTTGTTTTCGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 141 | PRT | EVQLLESGGGLVQPGGSLRLSCAASGFTFYSYAMSWVRQAPGKGLEWV SAIGTGGDTYYADSVKGRFTISRDNSKNTLYLQMNSLRAEDTAVYYCA RRDDYTSRDAFDYWGQGTLVTVSS |
| 142 | PRT | SYAMS |
| 143 | PRT | AIGTGGDTYYADSVKG |
| 144 | PRT | RDDYTSRDAFDY |
| 145 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNDYV VFGGGTKLTVL |
| 146 | PRT | SGSSSNIGSNTVN |
| 147 | PRT | YDDLRPS |
| 148 | PRT | AAWDDSLNDYVV |
| 149 | DNA | GAAGTTCAGCTGCTGGAATCTGGCGGCGGACTGGTTCAACCTGGCGG ATCTCTGAGACTGAGCTGTGCCGCCAGCGCGGCTTCACCTTTTACAGCTA CGCCATGAGCTGGGTCCGACAGGCCCCTGGAAAAGGCCTTGAATGGG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
| --- | --- | --- |
|  |  | TGTCCGCCATCGGCACAGGCGGCGATACCTACTATGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCCAGAAGGGACGACTACACCAGCAGGGACGCCTTCGATTATTG<br>GGGCCAGGGCACACTGGTCACCGTTTCTTCA |
| 150 | DNA | AGCTACGCCATGAGC |
| 151 | DNA | GCCATCGGCACAGGCGGCGATACCTACTATGCCGACTCTGTGAAGGG<br>C |
| 152 | DNA | AGGGACGACTACACCAGCAGGGACGCCTTCGATTAT |
| 153 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGACTACGTTGTGTTTGGCGGAGGCACCAAGCTGACCG<br>TTCTA |
| 154 | DNA | AGCGGCAGCAGCTCCAACATCGGCAGCAACACCGTGAAC |
| 155 | DNA | TACGACGACCTGCGGCCTAGC |
| 156 | DNA | GCCGCCTGGGACGACAGCCTGAACGACTACGTTGTG |
| 157 | PRT | EVQLLESGGGLVQPGGSLRLSCAASGFTFYSYAMSWVRQAPGKGLEWV<br>SAIGTGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLFPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 158 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNDYV<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 159 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGAGCTGGGTCCGACAGGCCCCTGGAAAAGGCCTTGAATGGG<br>TGTCCGCCATCGGCACAGGCGGCGATACCTACTATGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCCAGAAGGGACGACTACACCAGCAGGGACGCCTTCGATTATTG<br>GGGCCAGGGCACACTGGTCACCGTTTCTTCAGCCAGCACCAAGGGCC<br>CCAGCGTGTTCCCTCTGGCCCCTTGTAGCAGAAGCACCAGCGAGTCT<br>ACAGCCGCCCTGGGCTGCCTCGTGAAGGACTACTTTCCCGAGCCCGT<br>GACCGTGTCCTGGAACTCTGGCGCTCTGACAAGCGGCGTGCACACCT<br>TTCCAGCCGTGCTGCAGAGCAGCGGCCTGTACTCTCTGAGCAGCGTC<br>GTGACAGTGCCCAGCAGCAGCTGGGCACCAAGACCTACACCTGTAA<br>CGTGGACCACAAGCCCAGCAACACCAAGGTGGACAAGCGGGTGGAA<br>TCTAAGTACGGCCCTCCCTGCCCTCCTTGCCCAGCCCCTGAATTCTG<br>GGCGGACCCTCCGTGTTCCTGTTCCCCCCAAAGCCCAAGGACACCCT<br>GATGATCAGCCGGACCCCCGAAGTGACCTGCGTGGTGGTGGATGTGT<br>CCCAGGAAGATCCCGAGGTGCAGTTCAATTGGTACGTGGACGGCGTG<br>GAAGTGCACAACGCCAAGACCAAGCCCAGAGAGGAACAGTTCAACA<br>GCACCTACCGGGTGGTGTCCGTGCTGACAGTGCTGCACCAGGACTGG<br>CTGAACGGCAAAGAGTACAAGTGCAAGGTGTCCAACAAGGGCCTGC<br>CCAGCTCCATCGAGAAAACCATCAGCAAGGCCAAGGGCCAGCCCCG<br>CGAACCCCAGGTGTACACACTGCCTCCAAGCCAGGAAGAGATGACC<br>AAGAACCAGGTGTCCCTGACCTGTCTCGTGAAAGGCTTCTACCCCTC<br>CGATATCGCCGTGGAATGGGAGAGCAACGGCCAGCCCGAGAACAAC<br>TACAAGACCACCCCCCCCGTGCTGGACAGCGACGGCTCATTCTTCCT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| | | GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 160 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGACTACGTTGTGTTTGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 161 | PRT | EVQLLESGGGLVQPGGSLRLSCAASGFTFSSYAMSWVRQAPGKGLEWV SAIGYGGDTYYADSVKGRFTISRDNSKNTLYLQMNSLRAEDTAVYYCA RRDDYTSRDAFDYWGQGTLVTVSS |
| 162 | PRT | SYAMS |
| 163 | PRT | AIGYGGDTYYADSVKG |
| 164 | PRT | RDDYTSRDAFDY |
| 165 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNDIV VFGGGTKLTVL |
| 166 | PRT | SGSSSNIGSNTVN |
| 167 | PRT | YDDLRPS |
| 168 | PRT | AAWDDSLNDIVV |
| 169 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGCCATGAGCTGGGTCCGACAGGCTCCTGGCAAAGGCCTTGAATGG GTGTCCGCCATCGGCTATGGCGGCGATACCTACTACGCCGACTCTGT GAAGGGCAGATTCACCATCAGCCGGGACAACAGCAAGAACACCCTG TACCTGCAGATGAACAGCCTGAGAGCCGAGGACACCGCCGTGTACTA TTGCGCCAGAAGGGACGACTACACCAGCAGGGACGCCTTCGATTATT GGGGCCAGGGCACACTGGTCACCGTTTCTTCA |
| 170 | DNA | AGCTACGCCATGAGC |
| 171 | DNA | GCCATCGGCTATGGCGGCGATACCTACTACGCCGACTCTGTGAAGGG C |
| 172 | DNA | AGGGACGACTACACCAGCAGGGACGCCTTCGATTAT |
| 173 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGACATCGTTGTTTTCGGCGGAGGCACCAAGCTGACCG TTCTA |
| 174 | DNA | AGCGGCAGCAGCTCCAACATCGGCAGCAACACCGTGAAC |
| 175 | DNA | TACGACGACCTGCGGCCTAGC |
| 176 | DNA | GCCGCCTGGGACGACAGCCTGAACGACATCGTTGTT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 177 | PRT | EVQLLESGGGLVQPGGSLRLSCAASGFTFSSYAMSWVRQAPGKGLEWV SAIGYGGDTYYADSVKGRFTISRDNSKNTLYLQMNSLRAEDTAVYYCA RRDDYTSRDAFDYWGQGTLVTVSSASTKGPSVFPLAPCSRSTSESTAAL GCLVKDYFPEPVTVSWNSGALTSGVHTFPAVLQSSGLYSLSSVVTVPSSS LGTKTYTCNVDHKPSNTKVDKRVESKYGPPCPPCPAPEFLGGPSVFLFPP KPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQK SLSLSLGK |
| 178 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNDIV VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 179 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGCCATGAGCTGGGTCCGACAGGCTCCTGGCAAAGGCCTTGAATGG GTGTCCGCCATCGGCTATGGCGGCGATACCTACTACGCCGACTCTGT GAAGGGCAGATTCACCATCAGCCGGGACAACAGCAAGAACACCCTG TACCTGCAGATGAACAGCCTGAGAGCCGAGGACACCGCCGTGTACTA TTGCGCCAGAAGGGACGACTACACCAGCAGGGACGCCTTCGATTATT GGGGCCAGGGCACACTGGTCACCGTTTCTTCAGCCAGCACCAAGGGC CCCAGCGTGTTCCCTCTGGCCCCTTGTAGCAGAAGCACCAGCGAGTC TACAGCCGCCCTGGGCTGCCTCGTGAAGGACTACTTTCCCGAGCCCG TGACCGTGTCCTGGAACTCTGGCGCTCTGACAAGCGGCGTGCACACC TTTCCAGCCGTGCTGCAGAGCAGCGGCCTGTACTCTCTGAGCAGCGT CGTGACAGTGCCCAGCAGCAGCCTGGGCACCAAGACCTACACCTGTA ACGTGGACCACAAGCCCAGCAACACCAAGGTGGACAAGCGGGTGGA ATCTAAGTACGGCCCTCCCTGCCCTCCTTGCCCAGCCCCTGAATTTCT GGGCGGACCCTCCGTGTTCCTGTTCCCCCCAAAGCCCAAGGACACCC TGATGATCAGCCGGACCCCCGAAGTGACCTGCGTGGTGGTGGATGTG TCCCAGGAAGATCCCGAGGTGCAGTTCAATTGGTACGTGGACGGCGT GGAAGTGCACAACGCCAAGACCAAGCCCAGAGAGGAACAGTTCAAC AGCACCTACCGGGTGGTGTCCGTGCTGACAGTGCTGCACCAGGACTG GCTGAACGGCAAAGAGTACAAGTGCAAGGTGTCCAACAAGGGCCTG CCCAGCTCCATCGAGAAAACCATCAGCAAGGCCAAGGGCCAGCCCC GCGAACCCCAGGTGTACACACTGCCTCCAAGCCAGGAAGAGATGAC CAAGAACCAGGTGTCCCTGACCTGTCTCGTGAAAGGCTTCTACCCCT CCGATATCGCCGTGGAATGGGAGAGCAACGGCCAGCCCGAGAACAA CTACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 180 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGACATCGTTGTTTTCGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 181 | PRT | EVQLLESGGGLVQPGGSLRLSCAASGFTFSSYAMSWVRQAPGKGLEWV SAIGYGGDTYYADSVKGRFTISRDNSKNTLYLQMNSLRAEDTAVYYCA RRDDYTSRDAFDYWGQGTLVTVSS |
| 182 | PRT | SYAMS |
| 183 | PRT | AIGYGGDTYYADSVKG |
| 184 | PRT | RDDYTSRDAFDY |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 185 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNVYP VFGGGTKLTVL |
| 186 | PRT | SGSSSNIGSNTVN |
| 187 | PRT | YDDLRPS |
| 188 | PRT | AAWDDSLNVYPV |
| 189 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGCCATGAGCTGGGTCCGACAGGCTCCTGGCAAAGGCCTTGAATGG GTGTCCGCCATCGGCTATGGCGGCGATACCTACTACGCCGACTCTGT GAAGGGCAGATTCACCATCAGCCGGGACAACAGCAAGAACACCCTG TACCTGCAGATGAACAGCCTGAGAGCCGAGGACACCGCCGTGTACTA TTGCGCCAGAAGGGACGACTACACCAGCAGGGACGCCTTCGATTATT GGGGCCAGGGCACACTGGTCACCGTTTCTTCA |
| 190 | DNA | AGCTACGCCATGAGC |
| 191 | DNA | GCCATCGGCTATGGCGGCGATACCTACTACGCCGACTCTGTGAAGGG C |
| 192 | DNA | AGGGACGACTACACCAGCAGGGACGCCTTCGATTAT |
| 193 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGTGTACCCTGTTTTTGGCGGAGGCACCAAGCTGACCG TTCTA |
| 194 | DNA | AGCGGCAGCAGCTCCAACATCGGCAGCAACACCGTGAAC |
| 195 | DNA | TACGACGACCTGCGGCCTAGC |
| 196 | DNA | GCCGCCTGGGACGACAGCCTGAACGTGTACCCTGTT |
| 197 | PRT | EVQLLESGGGLVQPGGSLRLSCAASGFTFSSYAMSWVRQAPGKGLEWV SAIGYGGDTYYADSVKGRFTISRDNSKNTLYLQMNSLRAEDTAVYYCA RRDDYTSRDAFDYWGQGTLVTVSSASTKGPSVFPLAPCSRSTSESTAAL GCLVKDYFPEPVTVSWNSGALTSGVHTFPAVLQSSGLYSLSSVVTVPSSS LGTKTYTCNVDHKPSNTKVDKRVESKYGPPCPPCPAPEFLGGPSVFLFPP KPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQK SLSLSLGK |
| 198 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNVYP VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 199 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGCCATGAGCTGGGTCCGACAGGCTCCTGGCAAAGGCCTTGAATGG GTGTCCGCCATCGGCTATGGCGGCGATACCTACTACGCCGACTCTGT GAAGGGCAGATTCACCATCAGCCGGGACAACAGCAAGAACACCCTG TACCTGCAGATGAACAGCCTGAGAGCCGAGGACACCGCCGTGTACTA TTGCGCCAGAAGGGACGACTACACCAGCAGGGACGCCTTCGATTATT GGGGCCAGGGCACACTGGTCACCGTTTCTTCAGCCAGCACCAAGGGC CCCAGCGTGTTCCCTCTGGCCCCTTGTAGCAGAAGCACCAGCGAGTC TACAGCCGCCCTGGGCTGCCTCGTGAAGGACTACTTTCCCGAGCCCG TGACCGTGTCCTGGAACTCTGGCGCTCTGACAAGCGGCGTGCACACC TTTCCAGCCGTGCTGCAGAGCAGCGGCCTGTACTCTCTGAGCAGCGT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | CGTGACAGTGCCCAGCAGCAGCCTGGGCACCAAGACCTACACCTGTA |
| | | ACGTGGACCACAAGCCCAGCAACACCAAGGTGGACAAGCGGGTGGA |
| | | ATCTAAGTACGGCCCTCCCTGCCCTCCTTGCCCAGCCCCTGAATTCT |
| | | GGGCGGACCCTCCGTGTTCCTGTTCCCCCCAAAGCCCAAGGACACCC |
| | | TGATGATCAGCCGGACCCCCGAAGTGACCTGCGTGGTGGTGGATGTG |
| | | TCCCAGGAAGATCCCGAGGTGCAGTTCAATTGGTACGTGGACGGCGT |
| | | GGAAGTGCACAACGCCAAGACCAAGCCCAGAGAGGAACAGTTCAAC |
| | | AGCACCTACCGGGTGGTGTCCGTGCTGACAGTGCTGCACCAGGACTG |
| | | GCTGAACGGCAAAGAGTACAAGTGCAAGGTGTCCAACAAGGGCCTG |
| | | CCCAGCTCCATCGAGAAAACCATCAGCAAGGCCAAGGGCCAGCCCC |
| | | GCGAACCCCAGGTGTACACACTGCCTCCAAGCCAGGAAGAGATGAC |
| | | CAAGAACCAGGTGTCCCTGACCTGTCTCGTGAAAGGCTTCTACCCCT |
| | | CCGATATCGCCGTGGAATGGGAGAGCAACGGCCAGCCCGAGAACAA |
| | | CTACAAGACCACCCCCCCTGTGCTGGACAGCGACGGCTCATTCTTCCT |
| | | GTACAGCAGACTGACCGTGGACAAGAGCCGGTGGCAGGAAGGCAAC |
| | | GTGTTCAGCTGCAGCGTGATGCACGAGGCCCTGCACAACCACTACAC |
| | | CCAGAAGTCCCTGTCTCTGAGCCTGGGCAAG |
| 200 | DNA | CAGTCTGTTCTGACACAGCCTCCTAGCGCCTCTGGCACACCTGGACA |
| | | GAGAGTGACCATCAGCTGTAGCGGCAGCAGCTCCAACATCGGCAGC |
| | | AACACCGTGAACTGGTATCAGCAGCTGCCTGGCACAGCCCCTAAACT |
| | | GCTGATCTACTACGACGACCTGCGGCCTAGCGGCGTGCCAGATAGAT |
| | | TTTCTGGCAGCAAGAGCGGCACCTCTGCCAGCCTGGCTATTTCTGGA |
| | | CTGCAGAGCGAGGACGAGGCCGACTATTATTGTGCCGCCTGGGACGA |
| | | CAGCCTGAACGTGTACCCTGTTTTTGGCGGAGGCACCAAGCTGACCG |
| | | TTCTAGGCCAGCCTAAAGCCGCCCCTAGCGTGACCCTGTTCCCTCCAA |
| | | GCAGCGAGGAACTGCAGGCCAACAAGGCCACCCTCGTGTGCCTGATC |
| | | AGCGACTTCTATCCTGGCGCCGTGACCGTGGCCTGGAAGGCCGATAG |
| | | CTCTCCTGTGAAGGCCGGCGTGGAAACCACCACCCCTAGCAAGCAGA |
| | | GCAACAACAAATACGCCGCCAGCAGCTACCTGAGCCTGACCCCCGAG |
| | | CAGTGGAAGTCCCACAGATCCTACAGCTGCCAAGTGACCCACGAGGG |
| | | CAGCACCGTGGAAAAGACAGTGGCCCCTACCGAGTGCAGC |
| 201 | PRT | EVQLLESGGGLVQPGGSLRLSCAASGFTFSSYAMSWVRQAPGKGLEWV |
| | | SAIGYGGDTYYADSVKGRFTISRDNSKNTLYLQMNSLRAEDTAVYYCA |
| | | RRDDYTSRDAFDYWGQGTLVTVSS |
| 202 | PRT | SYAMS |
| 203 | PRT | AIGYGGDTYYADSVKG |
| 204 | PRT | RDDYTSRDAFDY |
| 205 | PRT | QSVLTQPPSASGTPGQRVTISCSGSSSNIGSNTVNWYQQLPGTAPKLLIYY |
| | | DDLRPSGVPDRFSGSKSGTSASLAISGLQSEDEADYYCHAWDDSLNDIV |
| | | VFGGGTKLTVL |
| 206 | PRT | SGSSSNIGSNTVN |
| 207 | PRT | YDDLRPS |
| 208 | PRT | HAWDDSLNDIVV |
| 209 | DNA | GAAGTTCAGCTGCTGGAATCTGGCGGCGGACTGGTTCAACCTGGCGG |
| | | ATCTCTGAGACTGAGCTGTGCCGCCAGCGGCTTCACCTTTAGCAGCT |
| | | ACGCCATGAGCTGGGTCCGACAGGCTCCTGGCAAAGGCCTTGAATGG |
| | | GTGTCCGCCATCGGCTATGGCGGCGATACCTACTACGCCGACTCTGT |
| | | GAAGGGCAGATTCACCATCAGCCGGGACAACAGCAAGAACACCCTG |
| | | TACCTGCAGATGAACAGCCTGAGAGCCGAGGACACCGCCGTGTACTA |
| | | TTGCGCCAGAAGGGACGACTACACCAGCAGGGACGCCTTCGATTATT |
| | | GGGGCCAGGGCACACTGGTCACCGTTTCTTCA |
| 210 | DNA | AGCTACGCCATGAGC |
| 211 | DNA | GCCATCGGCTATGGCGGCGATACCTACTACGCCGACTCTGTGAAGGG<br>C |
| 212 | DNA | AGGGACGACTACACCAGCAGGGACGCCTTCGATTAT |
| 213 | DNA | CAGTCTGTTCTGACACAGCCTCCTAGCGCCTCTGGCACACCTGGACA |
| | | GAGAGTGACCATCAGCTGTAGCGGCAGCAGCTCCAACATCGGCAGC |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGACATCGTGGTTTTTGGCGGAGGCACCAAGCTGACCG<br>TTCTA |
| 214 | DNA | AGCGGCAGCAGCTCCAACATCGGCAGCAACACCGTGAAC |
| 215 | DNA | TACGACGACCTGCGGCCTAGC |
| 216 | DNA | CACGCCTGGGACGACAGCCTGAACGACATCGTGGTT |
| 217 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLFPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 218 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNDIV<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 219 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACTACACCAGCAGGGACGCCTTCGATTATT<br>GGGGCCAGGGCACACTGGTCACCGTTTCTTCAGCCAGCACCAAGGGC<br>CCCAGCGTGTTCCCTCTGGCCCCTTGTAGCAGAAGCACCAGCGAGTC<br>TACAGCCGCCCTGGGCTGCCTCGTGAAGGACTACTTTCCCGAGCCCG<br>TGACCGTGTCCTGGAACTCTGGCGCTCTGACAAGCGGCGTGCACACC<br>TTTCCAGCCGTGCTGCAGAGCAGCGGCCTGTACTCTCTGAGCAGCGT<br>CGTGACAGTGCCCAGCAGCAGCCTGGGCACCAAGACCTACACCTGTA<br>ACGTGGACCACAAGCCCAGCAACACCAAGGTGGACAAGCGGGTGGA<br>ATCTAAGTACGGCCCTCCCTGCCCTCCTTGCCCAGCCCCTGAATTTCT<br>GGGCGGACCCTCCGTGTTCCTGTTCCCCCCAAAGCCCAAGGACACCC<br>TGATGATCAGCCGGACCCCCGAAGTGACCTGCGTGGTGGTGGATGTG<br>TCCCAGGAAGATCCCGAGGTGCAGTTCAATTGGTACGTGGACGGCGT<br>GGAAGTGCACAACGCCAAGACCAAGCCCAGAGAGGAACAGTTCAAC<br>AGCACCTACCGGGTGGTGTCCGTGCTGACAGTGCTGCACCAGGACTG<br>GCTGAACGGCAAAGAGTACAAGTGCAAGGTGTCCAACAAGGGCCTG<br>CCCAGCTCCATCGAGAAAACCATCAGCAAGGCCAAGGGCCAGCCCC<br>GCGAACCCCAGGTGTACACACTGCCTCCAAGCCAGGAAGAGATGAC<br>CAAGAACCAGGTGTCCCTGACCTGTCTCGTGAAAGGCTTCTACCCCT<br>CCGATATCGCCGTGGAATGGGAGAGCAACGGCCAGCCCGAGAACAA<br>CTACAAGACCACCCCCCCTGTGCTGGACAGCGACGGCTCATTCTTCCT<br>GTACAGCAGACTGACCGTGGACAAGAGCCGGTGGCAGGAAGGCAAC<br>GTGTTCAGCTGCAGCGTGATGCACGAGGCCCTGCACAACCACTACAC<br>CCAGAAGTCCCTGTCTCTGAGCCTGGGCAAG |
| 220 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGACATCGTGGTTTTTGGCGGAGGCACCAAGCTGACCG<br>TTCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
| --- | --- | --- |
| | | GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 221 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSS |
| 222 | PRT | SYAMS |
| 223 | PRT | AIGYGGDTYYADSVKG |
| 224 | PRT | RDDYTSRDAFDY |
| 225 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNDYP<br>VFGGGTKLTVL |
| 226 | PRT | SGSSSNIGSNTVN |
| 227 | PRT | YDDLRPS |
| 228 | PRT | HAWDDSLNDYPV |
| 229 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCA |
| 230 | DNA | AGCTACGCCATGAGC |
| 231 | DNA | GCCATCGGCTATGGCGGCGATACCTACTACGCCGACTCTGTGAAGGG<br>C |
| 232 | DNA | AGGGACGACTACACCAGCAGGGACGCCTTCGATTAT |
| 233 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGACTACCCTGTTTTTGGCGGAGGCACCAAGCTGACCG<br>TTCTA |
| 234 | DNA | AGCGGCAGCAGCTCCAACATCGGCAGCAACACCGTGAAC |
| 235 | DNA | TACGACGACCTGCGGCCTAGC |
| 236 | DNA | CACGCCTGGGACGACAGCCTGAACGACTACCCTGTT |
| 237 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLFPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 238 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNDYP<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 239 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACTACACCAGCAGGGACGCCTTCGATTATT<br>GGGGCCAGGGCACACTGGTCACCGTTTCTTCAGCCAGCACCAAGGGC<br>CCCAGCGTGTTCCCTCTGGCCCCTTGTAGCAGAAGCACCAGCGAGTC<br>TACAGCCGCCCTGGGCTGCCTCGTGAAGGACTACTTTCCCGAGCCCG<br>TGACCGTGTCCTGGAACTCTGGCGCTCTGACAAGCGGCGTGCACACC<br>TTTCCAGCCGTGCTGCAGAGCAGCGGCCTGTACTCTCTGAGCAGCGT<br>CGTGACAGTGCCCAGCAGCAGCCTGGGCACCAAGACCTACACCTGTA<br>ACGTGGACCACAAGCCCAGCAACACCAAGGTGGACAAGCGGGTGGA<br>ATCTAAGTACGGCCCTCCCTGCCCTCCTTGCCCAGCCCTGAATTTCT<br>GGGCGGACCCTCCGTGTTCCTGTTCCCCCCAAAGCCCAAGGACACCC<br>TGATGATCAGCCGGACCCCCGAAGTGACCTGCGTGGTGGTGGATGTG<br>TCCCAGGAAGATCCCGAGGTGCAGTTCAATTGGTACGTGGACGGCGT<br>GGAAGTGCACAACGCCAAGACCAAGCCCAGAGAGGAACAGTTCAAC<br>AGCACCTACCGGGTGGTGTCCGTGCTGACAGTGCTGCACCAGGACTG<br>GCTGAACGGCAAAGAGTACAAGTGCAAGGTGTCCAACAAGGGCCTG<br>CCCAGCTCCATCGAGAAAACCATCAGCAAGGCCAAGGGCCAGCCCC<br>GCGAACCCCAGGTGTACACACTGCCTCCAAGCCAGGAAGAGATGAC<br>CAAGAACCAGGTGTCCCTGACCTGTCTCGTGAAAGGCTTCTACCCCT<br>CCGATATCGCCGTGGAATGGGAGAGCAACGGCCAGCCCGAGAACAA<br>CTACAAGACCACCCCCCCTGTGCTGGACAGCGACGGCTCATTCTTCCT<br>GTACAGCAGACTGACCGTGGACAAGAGCCGGTGGCAGGAAGGCAAC<br>GTGTTCAGCTGCAGCGTGATGCACGAGGCCCTGCACAACCACTACAC<br>CCAGAAGTCCCTGTCTCTGAGCCTGGGCAAG |
| 240 | DNA | CAGTCTGTTCTGACACAGCCTCCTAGCGCCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGACTACCCTGTTTTTGGCGGAGGCACCAAGCTGACCG<br>TTCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 241 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSS |
| 242 | PRT | SYAMS |
| 243 | PRT | AIGYGGDTYYADSVKG |
| 244 | PRT | RDDYTSRDAFDY |
| 245 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNVYP<br>VFGGGTKLTVL |
| 246 | PRT | SGSSSNIGSNTVN |
| 247 | PRT | YDDLRPS |
| 248 | PRT | HAWDDSLNVYPV |
| 249 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCA |
| 250 | DNA | AGCTACGCCATGAGC |
| 251 | DNA | GCCATCGGCTATGGCGGCGATACCTACTACGCCGACTCTGTGAAGGG<br>C |
| 252 | DNA | AGGGACGACTACACCAGCAGGGACGCCTTCGATTAT |
| 253 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGTGTACCCTGTTTTTGGCGGAGGCACCAAGCTGACCG<br>TTCTA |
| 254 | DNA | AGCGGCAGCAGCTCCAACATCGGCAGCAACACCGTGAAC |
| 255 | DNA | TACGACGACCTGCGGCCTAGC |
| 256 | DNA | CACGCCTGGGACGACAGCCTGAACGTGTACCCTGTT |
| 257 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLFPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 258 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNVYP<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 259 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCAGCCAGCACCAAGGGC<br>CCCAGCGTGTTCCCTCTGGCCCCTTGTAGCAGAAGCACCAGCGAGTC<br>TACAGCCGCCCTGGGCTGCCTCGTGAAGGACTACTTTCCCGAGCCCG<br>TGACCGTGTCCTGGAACTCTGGCGCTCTGACAAGCGGCGTGCACACC<br>TTTCCAGCCGTGCTGCAGAGCAGCGGCCTGTACTCTCTGAGCAGCGT<br>CGTGACAGTGCCCAGCAGCAGCCTGGGCACCAAGACCTACACCTGTA<br>ACGTGGACCACAAGCCCAGCAACACCAAGGTGGACAAGCGGGTGGA<br>ATCTAAGTACGGCCCTCCCTGCCCTCCTTGCCCAGCCCCTGAATTTCT<br>GGGCGGACCCTCCGTGTTCCTGTTCCCCCCAAAGCCCAAGGACACCC<br>TGATGATCAGCCGGACCCCCGAAGTGACCTGCGTGGTGGTGGATGTG<br>TCCCAGGAAGATCCCGAGGTGCAGTTCAATTGGTACGTGGACGGCGT<br>GGAAGTGCACAACGCCAAGACCAAGCCCAGAGAGGAACAGTTCAAC<br>AGCACCTACCGGGTGGTGTCCGTGCTGACAGTGCTGCACCAGGACTG<br>GCTGAACGGCAAAGAGTACAAGTGCAAGGTGTCCAACAAGGGCCTG<br>CCCAGCTCCATCGAGAAAACCATCAGCAAGGCCAAGGGCCAGCCCC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
|  |  | GCGAACCCCAGGTGTACACACTGCCTCCAAGCCAGGAAGAGATGAC<br>CAAGAACCAGGTGTCCCTGACCTGTCTCGTGAAAGGCTTCTACCCCT<br>CCGATATCGCCGTGGAATGGGAGAGCAACGGCCAGCCCGAGAACAA<br>CTACAAGACCACCCCCCCTGTGCTGGACAGCGACGGCTCATTCTTCCT<br>GTACAGCAGACTGACCGTGGACAAGAGCCGGTGGCAGGAAGGCAAC<br>GTGTTCAGCTGCAGCGTGATGCACGAGGCCCTGCACAACCACTACAC<br>CCAGAAGTCCCTGTCTCTGAGCCTGGGCAAG |
| 260 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGTGTACCCTGTTTTTGGCGGAGGCACCAAGCTGACCG<br>TTCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 261 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSS |
| 262 | PRT | SYAMS |
| 263 | PRT | AIGYGGDTYYADSVKG |
| 264 | PRT | RDDYTSRDAFDY |
| 265 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNVIPV<br>FGGGTKLTVL |
| 266 | PRT | SGSSSNIGSNTVN |
| 267 | PRT | YDDLRPS |
| 268 | PRT | HAWDDSLNVIPV |
| 269 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCA |
| 270 | DNA | AGCTACGCCATGAGC |
| 271 | DNA | GCCATCGGCTATGGCGGCGATACCTACTACGCCGACTCTGTGAAGGG<br>C |
| 272 | DNA | AGGGACGACTACACCAGCAGGGACGCCTTCGATTAT |
| 273 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGTGATCCCTGTTTTTGGCGGAGGCACCAAGCTGACCG<br>TTCTA |
| 274 | DNA | AGCGGCAGCAGCTCCAACATCGGCAGCAACACCGTGAAC |
| 275 | DNA | TACGACGACCTGCGGCCTAGC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 276 | DNA | CACGCCTGGGACGACAGCCTGAACGTGATCCCTGTT |
| 277 | PRT | EVQLLESGGGLVQPGGSLRLSCAASGFTFSSYAMSWVRQAPGKGLEWV SAIGYGGDTYYADSVKGRFTISRDNSKNTLYLQMNSLRAEDTAVYYCA RRDDYTSRDAFDYWGQGTLVTVSSASTKGPSVFPLAPCSRSTSESTAAL GCLVKDYFPEPVTVSWNSGALTSGVHTFPAVLQSSGLYSLSSVVTVPSSS LGTKTYTCNVDHKPSNTKVDKRVESKYGPPCPPCPAPEFLGGPSVFLFPP KPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQK SLSLSLGK |
| 278 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCHAWDDSLNVIPV FGGGTKLTVLGQPKAAPSVTLFPPSSEELQANKATLVCLISDFYPGAVTV AWKADSSPVKAGVETTTPSKQSNNKYAASSYLSLTPEQWKSHRSYSCQ VTHEGSTVEKTVAPTECS |
| 279 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGCCATGAGCTGGGTCCGACAGGCTCCTGGCAAAGGCCTTGAATGG GTGTCCGCCATCGGCTATGGCGGCGATACCTACTACGCCGACTCTGT GAAGGGCAGATTCACCATCAGCCGGGACAACAGCAAGAACACCCTG TACCTGCAGATGAACAGCCTGAGAGCCGAGGACACCGCCGTGTACTA TTGCGCCAGAAGGGACGACTACACCAGCAGGGACGCCTTCGATTATT GGGGCCAGGGCACACTGGTCACCGTTTCTTCAGCCAGCACCAAGGGC CCCAGCGTGTTCCCTCTGGCCCCTTGTAGCAGAAGCACCAGCGAGTC TACAGCCGCCCTGGGCTGCCTCGTGAAGGACTACTTTCCCGAGCCCG TGACCGTGTCCTGGAACTCTGGCGCTCTGACAAGCGGCGTGCACACC TTTCCAGCCGTGCTGCAGAGCAGCGGCCTGTACTCTCTGAGCAGCGT CGTGACAGTGCCCAGCAGCAGCCTGGGCACCAAGACCTACACCTGTA ACGTGGACCACAAGCCCAGCAACACCAAGGTGGACAAGCGGGTGGA ATCTAAGTACGGCCCTCCCTGCCCTCCTTGCCCAGCCCCTGAATTTCT GGGCGGACCCTCCGTGTTCCTGTTCCCCCCAAAGCCCAAGGACACCC TGATGATCAGCCGGACCCCCGAAGTGACCTGCGTGGTGGTGGATGTG TCCCAGGAAGATCCCGAGGTGCAGTTCAATTGGTACGTGGACGGCGT GGAAGTGCACAACGCCAAGACCAAGCCCAGAGAGGAACAGTTCAAC AGCACCTACCGGGTGGTGTCCGTGCTGACAGTGCTGCACCAGGACTG GCTGAACGGCAAAGAGTACAAGTGCAAGGTGTCCAACAAGGGCCTG CCCAGCTCCATCGAGAAAACCATCAGCAAGGCCAAGGGCCAGCCCC GCGAACCCCAGGTGTACACACTGCCTCCAAGCCAGGAAGAGATGAC CAAGAACCAGGTGTCCCTGACCTGTCTCGTGAAAGGCTTCTACCCCT CCGATATCGCCGTGGAATGGGAGAGCAACGGCCAGCCCGAGAACAA CTACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 280 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTACTATTGTCACGCCTGGGACGA CAGCCTGAACGTGATCCCTGTTTTTGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 281 | PRT | EVQLLESGGGLVQPGGSLRLSCAASGFTFYSYAMLWVRQAPGKGLEWV SAIGTGGDTYYADSVKGRFTISRDNSKNTLYLQMNSLRAEDTAVYYCA RRDDYTSRDAFDYWGQGTLVTVSS |
| 282 | PRT | SYAML |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
| --- | --- | --- |
| 283 | PRT | AIGTGGDTYYADSVKG |
| 284 | PRT | RDDYTSRDAFDY |
| 285 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNDYV VFGGGTKLTVL |
| 286 | PRT | SGSSSNIGSNTVN |
| 287 | PRT | YDDLRPS |
| 288 | PRT | AAWDDSLNDYVV |
| 289 | DNA | GAAGTTCAGCTGCTGGAATCTGGCGGCGGACTGGTTCAACCTGGCGG ATCTCTGAGACTGAGCTGTGCCGCCAGCGGCTTCACCTTTTACAGCTA CGCCATGCTGTGGGTCCGACAGGCCCCTGGAAAAGGCCTTGAATGGG TGTCCGCCATCGGCACAGGCGGCGATACCTACTATGCCGACTCTGTG AAGGGCAGATTCACCATCAGCCGGGACAACAGCAAGAACACCCTGT ACCTGCAGATGAACAGCCTGAGAGCCGAGGACACCGCCGTGTACTAT TGCGCCAGAAGGGACGACTACACCAGCAGGGACGCCTTCGATTATTG GGGCCAGGGCACACTGGTCACCGTTTCTTCA |
| 290 | DNA | AGCTACGCCATGCTG |
| 291 | DNA | GCCATCGGCACAGGCGGCGATACCTACTATGCCGACTCTGTGAAGGG C |
| 292 | DNA | AGGGACGACTACACCAGCAGGGACGCCTTCGATTAT |
| 293 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGACTACGTTGTGTTTGGCGGAGGCACCAAGCTGACCG TTCTA |
| 294 | DNA | AGCGGCAGCAGCTCCAACATCGGCAGCAACACCGTGAAC |
| 295 | DNA | TACGACGACCTGCGGCCTAGC |
| 296 | DNA | GCCGCCTGGGACGACAGCCTGAACGACTACGTTGTG |
| 297 | PRT | EVQLLESGGGLVQPGGSLRLSCAASGFTFYSYAMLWVRQAPGKGLEWV SAIGTGGDTYYADSVKGRFTISRDNSKNTLYLQMNSLRAEDTAVYYCA RRDDYTSRDAFDYWGQGTLVTVSSASTKGPSVFPLAPCSRSTSESTAAL GCLVKDYFPEPVTVSWNSGALTSGVHTFPAVLQSSGLYSLSSVVTVPSSS LGTKTYTCNVDHKPSNTKVDKRVESKYGPPCPPCPAPEFLGGPSVFLFPP KPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQK SLSLSLGK |
| 298 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNDYV VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 299 | DNA | GAAGTTCAGCTGCTGGAATCTGGCGGCGGACTGGTTCAACCTGGCGG ATCTCTGAGACTGAGCTGTGCCGCCAGCGGCTTCACCTTTTACAGCTA CGCCATGCTGTGGGTCCGACAGGCCCCTGGAAAAGGCCTTGAATGGG TGTCCGCCATCGGCACAGGCGGCGATACCTACTATGCCGACTCTGTG AAGGGCAGATTCACCATCAGCCGGGACAACAGCAAGAACACCCTGT ACCTGCAGATGAACAGCCTGAGAGCCGAGGACACCGCCGTGTACTAT TGCGCCAGAAGGGACGACTACACCAGCAGGGACGCCTTCGATTATTG GGGCCAGGGCACACTGGTCACCGTTTCTTCAGCCAGCACCAAGGGCC CCAGCGTGTTCCCTCTGGCCCCCTTGTAGCAGAAGCACCAGCGAGTCT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | ACAGCCGCCCTGGGCTGCCTCGTGAAGGACTACTTTCCCGAGCCCGT GACCGTGTCCTGGAACTCTGGCGCTCTGACAAGCGGCGTGCACACCT TTCCAGCCGTGCTGCAGAGCAGCGGCCTGTACTCTCTGAGCAGCGTC GTGACAGTGCCCAGCAGCAGCCTGGGCACCAAGACCTACACCTGTAA CGTGGACCACAAGCCCAGCAACACCAAGGTGGACAAGCGGGTGGAA TCTAAGTACGGCCCTCCCTGCCCTCCTTGCCCAGCCCCTGAATTTCTG GGCGGACCCTCCGTGTTCCTGTTCCCCCCAAAGCCCAAGGACACCCT GATGATCAGCCGGACCCCCGAAGTGACCTGCGTGGTGGTGGATGTGT CCCAGGAAGATCCCGAGGTGCAGTTCAATTGGTACGTGGACGGCGTG GAAGTGCACAACGCCAAGACCAAGCCCAGAGAGGAACAGTTCAACA GCACCTACCGGGTGGTGTCCGTGCTGACAGTGCTGCACCAGGACTGG CTGAACGGCAAAGAGTACAAGTGCAAGGTGTCCAACAAGGGCCTGC CCAGCTCCATCGAGAAAACCATCAGCAAGGCCAAGGGCCAGCCCCG CGAACCCCAGGTGTACACACTGCCCTCCAAGCCAGGAAGAGATGACC AAGAACCAGGTGTCCCTGACCTGTCTCGTGAAAGGCTTCTACCCCTC CGATATCGCCGTGGAATGGGAGAGCAACGGCCAGCCCGAGAACAAC TACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 300 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGACTACGTTGTGTTTGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 301 | PRT | EVQLLESGGGLVQPGGSLRLSCAASGFTFYSYAMLWVRQAPGKGLEWV SAIGTGGDTYYADSVKGRFTISRDNSKNTLYLQMNSLRAEDTAVYYCA RRDDYTSRDAFDYWGQGTLVTVSS |
| 302 | PRT | SYAML |
| 303 | PRT | AIGTGGDTYYADSVKG |
| 304 | PRT | RDDYTSRDAFDY |
| 305 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNVYV VFGGGTKLTVL |
| 306 | PRT | SGSSSNIGSNTVN |
| 307 | PRT | YDDLRPS |
| 308 | PRT | AAWDDSLNVYVV |
| 309 | DNA | GAAGTTCAGCTGCTGGAATCTGGCGGCGGACTGGTTCAACCTGGCGG ATCTCTGAGACTGAGCTGTGCCGCCAGCGGCTTCACCTTTTACAGCTA CGCCATGCTGTGGGTCCGACAGGCCCCTGGAAAAGGCCTTGAATGGG TGTCCGCCATCGGCACAGGCGGCGATACCTACTATGCCGACTCTGTG AAGGGCAGATTCACCATCAGCCGGGACAACAGCAAGAACACCCTGT ACCTGCAGATGAACAGCCTGAGAGCCGAGGACACCGCCGTGTACTAT TGCGCCAGAAGGGACGACTACACCAGCAGGGACGCCTTCGATTATTG GGGCCAGGGCACACTGGTCACCGTTTCTTCA |
| 310 | DNA | AGCTACGCCATGCTG |
| 311 | DNA | GCCATCGGCACAGGCGGCGATACCTACTATGCCGACTCTGTGAAGGG C |
| 312 | DNA | AGGGACGACTACACCAGCAGGGACGCCTTCGATTAT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 313 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGTGTACGTTGTGTTTGGCGGAGGCACCAAGCTGACCG TTCTA |
| 314 | DNA | AGCGGCAGCAGCTCCAACATCGGCAGCAACACCGTGAAC |
| 315 | DNA | TACGACGACCTGCGGCCTAGC |
| 316 | DNA | GCCGCCTGGGACGACAGCCTGAACGTGTACGTTGTG |
| 317 | PRT | EVQLLESGGGLVQPGGSLRLSCAASGFTFYSYAMLWVRQAPGKGLEWV SAIGTGGDTYYADSVKGRFTISRDNSKNTLYLQMNSLRAEDTAVYYCA RRDDYTSRDAFDYWGQGTLVTVSSASTKGPSVFPLAPCSRSTSESTAAL GCLVKDYFPEPVTVSWNSGALTSGVHTFPAVLQSSGLYSLSSVVTVPSSS LGTKTYTCNVDHKPSNTKVDKRVESKYGPPCPPCPAPEFLGGPSVFLFPP KPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQK SLSLSLGK |
| 318 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNVYV VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 319 | DNA | GAAGTTCAGCTGCTGGAATCTGGCGGCGGACTGGTTCAACCTGGCGG ATCTCTGAGACTGAGCTGTGCCGCCAGCGGCTTCACCTTTTACAGCTA CGCCATGCTGTGGGTCCGACAGGCCCCTGGAAAAGGCCTTGAATGGG TGTCCGCCATCGGCACAGGCGGCGATACCTACTATGCCGACTCTGTG AAGGGCAGATTCACCATCAGCCGGGACAACAGCAAGAACACCCTGT ACCTGCAGATGAACAGCCTGAGAGCCGAGGACACCGCCGTGTACTAT TGCCGCCAGAAGGGACGACTACACCAGCAGGGACGCCTTCGATTATTG GGGCCAGGGCACACTGGTCACCGTTTCTTCAGCCAGCACCAAGGGCC CCAGCGTGTTCCCTCTGGCCCCTTGTAGCAGAAGCACCAGCGAGTCT ACAGCCGCCCTGGGCTGCCTCGTGAAGGACTACTTTCCCGAGCCCGT GACCGTGTCCTGGAACTCTGGCGCTCTGACAAGCGGCGTGCACACCT TTCCAGCCGTGCTGCAGAGCAGCGGCCTGTACTCTCTGAGCAGCGTC GTGACAGTGCCCAGCAGCAGCCTGGGCACCAAGACCTACACCTGTAA CGTGGACCACAAGCCCAGCAACACCAAGGTGGACAAGCGGGTGGAA TCTAAGTACGGCCCTCCCTGCCCTCCTTGCCCAGCCCCTGAATTTCTG GGCGGACCCTCCGTGTTCCTGTTCCCCCCAAAGCCCAAGGACACCCT GATGATCAGCCGGACCCCCGAAGTGACCTGCGTGGTGGTGGATGTGT CCCAGGAAGATCCCGAGGTGCAGTTCAATTGGTACGTGGACGGCGTG GAAGTGCACAACGCCAAGACCAAGCCCAGAGAGGAACAGTTCAACA GCACCTACCGGGTGGTGTCCGTGCTGACAGTGCTGCACCAGGACTGG CTGAACGGCAAAGAGTACAAGTGCAAGGTGTCCAACAAGGGCCTGC CCAGCTCCATCGAGAAAACCATCAGCAAGGCCAAGGGCCAGCCCCG CGAACCCCAGGTGTACACACTGCCTCCAAGCCAGGAAGAGATGACC AAGAACCAGGTGTCCCTGACCTGTCTCGTGAAAGGCTTCTACCCCTC CGATATCGCCGTGGAATGGGAGAGCAACGGCCAGCCCGAGAACAAC TACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 320 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGTGTACGTTGTGTTTGGCGGAGGCACCAAGCTGACCG TTCTAGGCCAGCCTAAAGCCGCCCCTAGCGTGACCCTGTTCCCTCCAA |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from *Homo sapiens* (SEQ ID 581, 582), *Mus Musculus*
(SEQ ID 583), *Rattus norvegicus* (SEQ ID 584), *Canis lupus familiaris* (SEQ ID 585), *Macaca
fascicularis* (SEQ ID 586), *Sus scrofa* (SEQ ID 587).

| SEQ ID No | SEQ Type | SEQUENCE |
|---|---|---|
| | | GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 321 | PRT | EVQLLESGGGLVQPGGSLRLSCAASGFTFYSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSS |
| 322 | PRT | SYAMS |
| 323 | PRT | AIGYGGDTYYADSVKG |
| 324 | PRT | RDDYTSRDAFDY |
| 325 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNVYP<br>VFGGGTKLTVL |
| 326 | PRT | SGSSSNIGSNTVN |
| 327 | PRT | YDDLRPS |
| 328 | PRT | HAWDDSLNVYPV |
| 329 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGAGCTGGGTCCGACAGGCCCCTGGAAAAGGCCTTGAATGGG<br>TGTCCGCCATCGGCTATGGCGGCGATACCTACTACGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCCAGAAGGGACGACTACACCAGCAGGGACGCCTTCGATTATTG<br>GGGCCAGGGCACACTGGTCACCGTTTCTTCA |
| 330 | DNA | AGCTACGCCATGAGC |
| 331 | DNA | GCCATCGGCTATGGCGGCGATACCTACTACGCCGACTCTGTGAAGGG<br>C |
| 332 | DNA | AGGGACGACTACACCAGCAGGGACGCCTTCGATTAT |
| 333 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGTGTACCCTGTTTTTGGCGGAGGCACCAAGCTGACCG<br>TTCTA |
| 334 | DNA | AGCGGCAGCAGCTCCAACATCGGCAGCAACACCGTGAAC |
| 335 | DNA | TACGACGACCTGCGGCCTAGC |
| 336 | DNA | CACGCCTGGGACGACAGCCTGAACGTGTACCCTGTT |
| 337 | PRT | EVQLLESGGGLVQPGGSLRLSCAASGFTFYSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLFPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 338 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNVYP |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| | | VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 339 | DNA | GAAGTTCAGCTGCTGGAATCTGGCGGCGGACTGGTTCAACCTGGCGG ATCTCTGAGACTGAGCTGTGCCGCCAGCGGCTTCACCTTTTACAGCTA CGCCATGAGCTGGGTCCGACAGGCCCCTGGAAAAGGCCTTGAATGGG TGTCCGCCATCGGCTATGGCGGCGATACCTACTACGCCGACTCTGTG AAGGGCAGATTCACCATCAGCCGGGACAACAGCAAGAACACCCTGT ACCTGCAGATGAACAGCCTGAGAGCCGAGGACACCGCCGTGTACTAT TGCGCCAGAAGGGACGACTACACCAGCAGGGACGCCTTCGATTATTG GGGCCAGGGCACACTGGTCACCGTTTCTTCAGCCAGCACCAAGGGCC CCAGCGTGTTCCCTCTGGCCCCTTGTAGCAGAAGCACCAGCGAGTCT ACAGCCGCCCTGGGCTGCCTCGTGAAGGACTACTTTCCCGAGCCCGT GACCGTGTCCTGGAACTCTGGCGCTCTGACAAGCGGCGTGCACACCT TTCCAGCCGTGCTGCAGAGCAGCGGCCTGTACTCTCTGAGCAGCGTC GTGACAGTGCCCAGCAGCAGCCTGGGCACCAAGACCTACACCTGTAA CGTGGACCACAAGCCCAGCAACACCAAGGTGGACAAGCGGGTGGAA TCTAAGTACGGCCCTCCCTGCCCTCCTTGCCCAGCCCCTGAATTTCTG GGCGGACCCTCCGTGTTCCTGTTCCCCCCAAAGCCCAAGGACACCCT GATGATCAGCCGGACCCCCGAAGTGACCTGCGTGGTGGTGGATGTGT CCCAGGAAGATCCCGAGGTGCAGTTCAATTGGTACGTGGACGGCGTG GAAGTGCACAACGCCAAGACCAAGCCCAGAGAGGAACAGTTCAACA GCACCTACCGGGTGGTGTCCGTGCTGACAGTGCTGCACCAGGACTGG CTGAACGGCAAAGAGTACAAGTGCAAGGTGTCCAACAAGGGCCTGC CCAGCTCCATCGAGAAAACCATCAGCAAGGCCAAGGGCCAGCCCCG CGAACCCCAGGTGTACACACTGCCTCCAAGCCAGGAAGAGATGACC AAGAACCAGGTGTCCCTGACCTGTCTCGTGAAAGGCTTCTACCCCTC CGATATCGCCGTGGAATGGGAGAGCAACGGCCAGCCCGAGAACAAC TACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 340 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTACTATTGTGCACGCCTGGGACGA CAGCCTGAACGTGTACCCTGTTTTTGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 341 | PRT | EVQLLESGGGLVQPGGSLRLSCAASGFTFYSYAMSWVRQAPGKGLEWV SAIGYGGDTYYADSVKGRFTISRDNSKNTLYLQMNSLRAEDTAVYYCA RRDDYTSRDAFDYWGQGTLVTVSS |
| 342 | PRT | SYAMS |
| 343 | PRT | AIGYGGDTYYADSVKG |
| 344 | PRT | RDDYTSRDAFDY |
| 345 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNDIPV FGGGTKLTVL |
| 346 | PRT | SGSSSNIGSNTVN |
| 347 | PRT | YDDLRPS |
| 348 | PRT | AAWDDSLNDIPV |
| 349 | DNA | GAAGTTCAGCTGCTGGAATCTGGCGGCGGACTGGTTCAACCTGGCGG ATCTCTGAGACTGAGCTGTGCCGCCAGCGGCTTCACCTTTTACAGCTA |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | CGCCATGAGCTGGGTCCGACAGGCCCCTGGAAAAGGCCTTGAATGGG<br>TGTCCGCCATCGGCTATGGCGGCGATACCTACTACGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCCAGAAGGGACGACTACACCAGCAGGGACGCCTTCGATTATTG<br>GGGCCAGGGCACACTGGTCACCGTTTCTTCA |
| 350 | DNA | AGCTACGCCATGAGC |
| 351 | DNA | GCCATCGGCTATGGCGGCGATACCTACTACGCCGACTCTGTGAAGGG<br>C |
| 352 | DNA | AGGGACGACTACACCAGCAGGGACGCCTTCGATTAT |
| 353 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGACATCCCTGTTTTTGGCGGAGGCACCAAGCTGACCG<br>TTCTA |
| 354 | DNA | AGCGGCAGCAGCTCCAACATCGGCAGCAACACCGTGAAC |
| 355 | DNA | TACGACGACCTGCGGCCTAGC |
| 356 | DNA | GCCGCCTGGGACGACAGCCTGAACGACATCCCTGTT |
| 357 | PRT | EVQLLESGGGLVQPGGSLRLSCAASGFTFYSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLFPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 358 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNDIPV<br>FGGGTKLTVLGQPKAAPSVTLFPPSSEELQANKATLVCLISDFYPGAVTV<br>AWKADSSPVKAGVETTTPSKQSNNKYAASSYLSLTPEQWKSHRSYSCQ<br>VTHEGSTVEKTVAPTECS |
| 359 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGAGCTGGGTCCGACAGGCCCCTGGAAAAGGCCTTGAATGGG<br>TGTCCGCCATCGGCTATGGCGGCGATACCTACTACGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCCAGAAGGGACGACTACACCAGCAGGGACGCCTTCGATTATTG<br>GGGCCAGGGCACACTGGTCACCGTTTCTTCAGCCAGCACCAAGGGCC<br>CCAGCGTGTTCCCTCTGGCCCCTTGTAGCAGAAGCACCAGCGAGTCT<br>ACAGCCGCCCTGGGCTGCCTCGTGAAGGACTACTTTCCCGAGCCCGT<br>GACCGTGTCCTGGAACTCTGGCGCTCTGACAAGCGGCGTGCACACCT<br>TTCCAGCCGTGCTGCAGAGCAGCGGCCTGTACTCTCTGAGCAGCGTC<br>GTGACAGTGCCCAGCAGCAGCCTGGGCACCAAGACCTACACCTGTAA<br>CGTGGACCACAAGCCCAGCAACACCAAGGTGGACAAGCGGGTGGAA<br>TCTAAGTACGGCCCTCCCTGCCCTCCTTGCCCAGCCCCTGAATTTCTG<br>GGCGGACCCTCCGTGTTCCTGTTCCCCCCAAAGCCCAAGGACACCCT<br>GATGATCAGCCGGACCCCCGAAGTGACCTGCGTGGTGGTGGATGTGT<br>CCCAGGAAGATCCCGAGGTGCAGTTCAATTGGTACGTGGACGGCGTG<br>GAAGTGCACAACGCCAAGACCAAGCCCAGAGAGGAACAGTTCAACA<br>GCACCTACCGGGTGGTGTCCGTGCTGACAGTGCTGCACCAGGACTGG<br>CTGAACGGCAAAGAGTACAAGTGCAAGGTGTCCAACAAGGGCCTGC<br>CCAGCTCCATCGAGAAAACCATCAGCAAGGCCAAGGGCCAGCCCCG<br>CGAACCCCAGGTGTACACACTGCCTCCAAGCCAGGAAGAGATGACC<br>AAGAACCAGGTGTCCCTGACCTGTCTCGTGAAAGGCTTCTACCCCTC<br>CGATATCGCCGTGGAATGGGAGAGCAACGGCCAGCCCGAGAACAAC |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | TACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 360 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGACATCCCTGTTTTTGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 361 | PRT | EVQLLESGGGLVQPGGSLRLSCAASGFTFYSYAMSWVRQAPGKGLEWV SAIGYGGDTYYADSVKGRFTISRDNSKNTLYLQMNSLRAEDTAVYYCA RRDDYTSRDAFDYWGQGTLVTVSS |
| 362 | PRT | SYAMS |
| 363 | PRT | AIGYGGDTYYADSVKG |
| 364 | PRT | RDDYTSRDAFDY |
| 365 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNVIPV FGGGTKLTVL |
| 366 | PRT | SGSSSNIGSNTVN |
| 367 | PRT | YDDLRPS |
| 368 | PRT | AAWDDSLNVIPV |
| 369 | DNA | GAAGTTCAGCTGCTGGAATCTGGCGGCGGACTGGTTCAACCTGGCGG ATCTCTGAGACTGAGCTGTGCCGCCAGCGGCTTCACCTTTTACAGCTA CGCCATGAGCTGGGTCCGACAGGCCCCTGGAAAAGGCCTTGAATGGG TGTCCGCCATCGGCTATGGCGGCGATACCTACTACGCCGACTCTGTG AAGGGCAGATTCACCATCAGCCGGGACAACAGCAAGAACACCCTGT ACCTGCAGATGAACAGCCTGAGAGCCGAGGACACCGCCGTGTACTAT TGCGCCAGAAGGGACGACTACACCAGCAGGGACGCCTTCGATTATTG GGGCCAGGGCACACTGGTCACCGTTTCTTCA |
| 370 | DNA | AGCTACGCCATGAGC |
| 371 | DNA | GCCATCGGCTATGGCGGCGATACCTACTACGCCGACTCTGTGAAGGG C |
| 372 | DNA | AGGGACGACTACACCAGCAGGGACGCCTTCGATTAT |
| 373 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGTGATCCCTGTTTTTGGCGGAGGCACCAAGCTGACCG TTCTA |
| 374 | DNA | AGCGGCAGCAGCTCCAACATCGGCAGCAACACCGTGAAC |
| 375 | DNA | TACGACGACCTGCGGCCTAGC |
| 376 | DNA | GCCGCCTGGGACGACAGCCTGAACGTGATCCCTGTT |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 377 | PRT | EVQLLESGGGLVQPGGSLRLSCAASGFTFYSYAMSWVRQAPGKGLEWV SAIGYGGDTYYADSVKGRFTISRDNSKNTLYLQMNSLRAEDTAVYYCA RRDDYTSRDAFDYWGQGTLVTVSSASTKGPSVFPLAPCSRSTSESTAAL GCLVKDYFPEPVTVSWNSGALTSGVHTFPAVLQSSGLYSLSSVVTVPSSS LGTKTYTCNVDHKPSNTKVDKRVESKYGPPCPPCPAPEFLGGPSVFLFPP KPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQK SLSLSLGK |
| 378 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNVIPV FGGGTKLTVLGQPKAAPSVTLFPPSSEELQANKATLVCLISDFYPGAVTV AWKADSSPVKAGVETTTPSKQSNNKYAASSYLSLTPEQWKSHRSYSCQ VTHEGSTVEKTVAPTECS |
| 379 | DNA | GAAGTTCAGCTGCTGGAATCTGGCGGCGGACTGGTTCAACCTGGCGG ATCTCTGAGACTGAGCTGTGCCGCCAGCGGCTTCACCTTTTACAGCTA CGCCATGAGCTGGGTCCGACAGGCCCCTGGAAAAGGCCTTGAATGGG TGTCCGCCATCGGCTATGGCGGCGATACCTACTACGCCGACTCTGTG AAGGGCAGATTCACCATCAGCCGGGACAACAGCAAGAACACCCTGT ACCTGCAGATGAACAGCCTGAGAGCCGAGGACACCGCCGTGTACTAT TGCGCCAGAAGGGACGACTACACCAGCAGGGACGCCTTCGATTATTG GGGCCAGGGCACACTGGTCACCGTTTCTTCAGCCAGCACCAAGGGCC CCAGCGTGTTCCCTCTGGCCCCTTGTAGCAGAAGCACCAGCGAGTCT ACAGCCGCCCTGGGCTGCCTCGTGAAGGACTACTTTCCCGAGCCCGT GACCGTGTCCTGGAACTCTGGCGCTCTGACAAGCGGCGTGCACACCT TTCCAGCCGTGCTGCAGAGCAGCGGCCTGTACTCTCTGAGCAGCGTC GTGACAGTGCCCAGCAGCAGCCTGGGCACCAAGACCTACACCTGTAA CGTGGACCACAAGCCCAGCAACACCAAGGTGGACAAGCGGGTGGAA TCTAAGTACGGCCCTCCCTGCCCTCCTTGCCCAGCCCCTGAATTTCTG GGCGGACCCTCCGTGTTCCTGTTCCCCCCAAAGCCCAAGGACACCCT GATGATCAGCCGGACCCCCGAAGTGACCTGCGTGGTGGTGGATGTGT CCCAGGAAGATCCCGAGGTGCAGTTCAATTGGTACGTGGACGGCGTG GAAGTGCACAACGCCAAGACCAAGCCCAGAGAGGAACAGTTCAACA GCACCTACCGGGTGGTGTCCGTGCTGACAGTGCTGCACCAGGACTGG CTGAACGGCAAAGAGTACAAGTGCAAGGTGTCCAACAAGGGCCTGC CCAGCTCCATCGAGAAAACCATCAGCAAGGCCAAGGGCCAGCCCCG CGAACCCCAGGTGTACACACTGCCTCCAAGCCAGGAAGAGATGACC AAGAACCAGGTGTCCCTGACCTGTCTCGTGAAAGGCTTCTACCCCTC CGATATCGCCGTGGAATGGGAGAGCAACGGCCAGCCCGAGAACAAC TACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 380 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGTGATCCCTGTTTTTGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 381 | PRT | EVQLLESGGGLVQPGGSLRLSCAASGFTFDSYEMNWVRQAPGKGLEWV SGISWNSGWIDYADSVKGRFTISRDNSKNTLYLQMNSLRAEDTAVYYC ARSGYSSSWFDPDFDYWGQGTLVTVSS |
| 382 | PRT | SYEMN |
| 383 | PRT | GISWNSGWIDYADSVKG |
| 384 | PRT | SGYSSSWFDPDFDY |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 385 | PRT | QSVLTQPPSVSGAPGQRVTISCTGSSSDIGAGYDVHWYQQLPGTAPKLLI YGNSNRPSGVPDRFSGSKSGTSASLAITGLQAEDEADYYCSSYAGPNPY VVFGGGTKLTVL |
| 386 | PRT | TGSSSDIGAGYDVH |
| 387 | PRT | GNSNRPS |
| 388 | PRT | SSYAGPNPYVV |
| 389 | DNA | GAAGTTCAGCTGCTGGAATCTGGCGGCGGACTGGTTCAACCTGGCGG ATCTCTGAGACTGAGCTGTGCCGCCAGCGGCTTCACCTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCA |
| 390 | DNA | AGCTACGAGATGAAC |
| 391 | DNA | GGCATCAGCTGGAATAGCGGCTGGATCGACTACGCCGACAGCGTGA AGGGC |
| 392 | DNA | AGCGGCTACAGCAGCTCTTGGTTTGACCCCGACTTCGACTAT |
| 393 | DNA | CAGTCTGTTCTGACACAGCCTCCATCTGTGTCTGGCGCCCCTGGACAG AGAGTGACCATCAGCTGTACAGGCAGCAGCTCCGATATTGGCGCCGG ATACGACGTGCACTGGTATCAGCAACTGCCTGGCACAGCCCCTAAGC TGCTGATCTACGGCAACAGCAACAGACCTAGCGGCGTGCCCGATAGA TTCAGCGGCTCTAAGTCTGGCACAAGCGCCAGCCTGGCCATTACTGG ACTGCAGGCCGAAGATGAGGCCGACTACTACTGCAGCAGCTACGCTG GCCCCAATCCTTACGTGGTGTTTGGCGGCGGAACAAAGCTGACCGTT CTA |
| 394 | DNA | ACAGGCAGCAGCTCCGATATTGGCGCCGGATACGACGTGCAC |
| 395 | DNA | GGCAACAGCAACAGACCTAGC |
| 396 | DNA | AGCAGCTACGCTGGCCCCAATCCTTACGTGGTG |
| 397 | PRT | EVQLLESGGGLVQPGGSLRLSCAASGFTFDSYEMNWVRQAPGKGLEWV SGISWNSGWIDYADSVKGRFTISRDNSKNTLYLQMNSLRAEDTAVYYC ARSGYSSSWFDPDFDYWGQGTLVTVSSASTKGPSVFPLAPSSKSTSGGT AALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK |
| 398 | PRT | QSVLTQPPSVSGAPGQRVTISCTGSSSDIGAGYDVHWYQQLPGTAPKLLI YGNSNRPSGVPDRFSGSKSGTSASLAITGLQAEDEADYYCSSYAGPNPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |
| 399 | DNA | GAAGTTCAGCTGCTGGAATCTGGCGGCGGACTGGTTCAACCTGGCGG ATCTCTGAGACTGAGCTGTGCCGCCAGCGGCTTCACCTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCGGCGCTCTGACAAGCGG CGTGCACACCTTTCCAGCCGTGCTGCAGAGCAGCGGCCTGTACTCTCT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | GAGCAGCGTCGTGACAGTGCCCAGCAGCTCTCTGGGCACCCAGACCT<br>ACATCTGCAACGTGAACCACAAGCCCAGCAACACCAAGGTGGACAA<br>GAAGGTGGAACCCAAGAGCTGCGACAAGACCCACACCTGTCCCCCTT<br>GTCCTGCCCCCGAACTGCTGGGAGGCCCTTCCGTGTTCCTGTTCCCCC<br>CAAAGCCCAAGGACACCCTGATGATCAGCCGGACCCCCGAAGTGAC<br>CTGCGTGGTGGTGGATGTGTCCCACGAGGACCCTGAAGTGAAGTTCA<br>ATTGGTACGTGGACGGCGTGGAAGTGCACAACGCCAAGACCAAGCC<br>TAGAGAGGAACAGTACAACAGCACCTACCGGGTGGTGTCCGTGCTGA<br>CAGTGCTGCACCAGGACTGGCTGAACGGCAAAGAGTACAAGTGCAA<br>GGTGTCCAACAAGGCCCTGCCTGCCCCCATCGAGAAAACCATCAGCA<br>AGGCCAAGGGCCAGCCCCGCGAACCCCAGGTGTACACACTGCCCCCA<br>AGCAGGGACGAGCTGACCAAGAACCAGGTGTCCCTGACCTGTCTCGT<br>GAAAGGCTTCTACCCCTCCGATATCGCCGTGGAATGGGAGAGCAACG<br>GCCAGCCCGAGAACAACTACAAGACCACCCCCCCTGTGCTGGACAGC<br>GACGGCTCATTCTTCCTGTACAGCAAGCTGACCGTGGACAAGTCCCG<br>GTGGCAGCAGGGCAACGTGTTCAGCTGCAGCGTGATGCACGAGGCCC<br>TGCACAACCACTACACCCAGAAGTCCCTGAGCCTGAGCCCTGGCAAG |
| 400 | DNA | CAGTCTGTTCTGACACAGCCTCCATCTGTGTCTGGCGCCCCTGGACAG<br>AGAGTGACCATCAGCTGTACAGGCAGCAGCTCCGATATTGGCGCCGG<br>ATACGACGTGCACTGGTATCAGCAACTGCCTGGCACAGCCCCTAAGC<br>TGCTGATCTACGGCAACAGCAACAGACCTAGCGGCGTGCCCGATAGA<br>TTCAGCGGCTCTAAGTCTGGCACAAGCGCCAGCCTGGCCATTACTGG<br>ACTGCAGGCCGAAGATGAGGCCGACTACTACTGCAGCAGCTACGCTG<br>GCCCCAATCCTTACGTGGTGTTTGGCGGCGGAACAAAGCTGACCGTT<br>CTAGGCCAGCCTAAAGCCGCCCCTAGCGTGACCCTGTTCCCTCCAAG<br>CAGCGAGGAACTGCAGGCCAACAAGGCCACCCTCGTGTGCCTGATCA<br>GCGACTTCTATCCTGGCGCCGTGACCGTGGCCTGGAAGGCCGATAGC<br>TCTCCTGTGAAGGCCGGCGTGGAAACCACCACCCCTAGCAAGCAGAG<br>CAACAACAAATACGCCGCCAGCAGCTACCTGAGCCTGACCCCCGAGC<br>AGTGGAAGTCCCACAGATCCTACAGCTGCAAGTGACCCACGAGGGC<br>AGCACCGTGGAAAAGACAGTGGCCCCTACCGAGTGCAGC |
| 401 | PRT | EVQLLESGGGLVQPGGSLRLSCAASGFTFDSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSS |
| 402 | PRT | SYEMN |
| 403 | PRT | GISWNSGWIDYADSVKG |
| 404 | PRT | SGYSSSWFDPDFDY |
| 405 | PRT | QSVLTQPPSVSGAPGQRVTISCTGSSSNIGAGYDVHWYQQLPGTAPKLLI<br>YGNSNRPSGVPDRFSGSKSGTSASLAITGLQAEDEADYYCQSYAGINPY<br>VVFGGGTKLTVL |
| 406 | PRT | TGSSSNIGAGYDVH |
| 407 | PRT | GNSNRPS |
| 408 | PRT | QSYAGINPYVV |
| 409 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTCGATAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |
| 410 | DNA | AGCTACGAGATGAAC |
| 411 | DNA | GGCATCAGCTGGAATAGCGGCTGGATCGACTACGCCGACAGCGTGA<br>AGGGC |
| 412 | DNA | AGCGGCTACAGCAGCTCTTGGTTTGACCCCGACTTCGACTAT |
| 413 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTCAGAGCTACGCCG GCATCAACCCCTACGTGGTGTTTGGCGGAGGCACCAAGCTGACAGTT CTA |
| 414 | DNA | ACAGGCAGCAGCTCCAATATCGGAGCCGGCTATGACGTGCAC |
| 415 | DNA | GGCAACAGCAACAGACCCAGC |
| 416 | DNA | CAGAGCTACGCCGGCATCAACCCCTACGTGGTG |
| 417 | PRT | EVQLLESGGGLVQPGGSLRLSCAASGFTFDSYEMNWVRQAPGKGLEWV SGISWNSGWIDYADSVKGRFTISRDNSKNTLYLQMNSLRAEDTAVYYC ARSGYSSSWFDPDFDYWGQGTLVTVSSASTKGPSVFPLAPSSKSTSGGT AALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK |
| 418 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGINPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |
| 419 | DNA | GAAGTTCAGCTGCTGGAATCTGGCGGCGGACTGGTTCAACCTGGCGG ATCTCTGAGACTGAGCTGTGCCGCCAGCGGCTTCACCTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGCAAG |
| 420 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTCAGAGCTACGCCG GCATCAACCCCTACGTGGTGTTTGGCGGAGGCACCAAGCTGACAGTT CTAGGCCAGCCTAAAGCCGCCCCTAGCGTGACCCTGTTCCCTCCAAG CAGCGAGGAACTGCAGGCCAACAAGGCCACCCTCGTGTGCCTGATCA GCGACTTCTATCCTGGCGCCGTGACCGTGGCCTGGAAGGCCGATAGC TCTCCTGTGAAGGCCGGCGTGGAAACCACCACCCCTAGCAAGCAGAG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | CAACAACAAATACGCCGCCAGCAGCTACCTGAGCCTGACCCCCGAGC AGTGGAAGTCCCACAGATCCTACAGCTGCCAAGTGACCCACGAGGGC AGCACCGTGGAAAAGACAGTGGCCCCTACCGAGTGCAGC |
| 421 | PRT | EVQLLESGGGLVQPGGSLRLSCAASGFDFSSYEMNWVRQAPGKGLEWV SGISWNSGWIGYADSVKGRFTISRDNSKNTLYLQMNSLRAEDTAVYYC ARSGYSSSWFDPDFDYWGQGTLVTVSS |
| 422 | PRT | SYEMN |
| 423 | PRT | GISWNSGWIGYADSVKG |
| 424 | PRT | SGYSSSWFDPDFDY |
| 425 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGPNPY VVFGGGTKLTVL |
| 426 | PRT | TGSSSNIGAGYDVH |
| 427 | PRT | GNSNRPS |
| 428 | PRT | QSYAGPNPYVV |
| 429 | DNA | GAAGTTCAGCTGCTGGAATCTGGCGGCGGACTGGTTCAACCTGGCGG ATCTCTGAGACTGAGCTGTGCCGCCAGCGGCTTCGATTTCAGCAGCT ACGAGATGAACTGGGTCCGACAGGCCCCTGGCAAAGGCCTTGAATG GGTGTCCGGCATCAGCTGGAATAGCGGCTGGATCGGCTACGCCGATA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCA |
| 430 | DNA | AGCTACGAGATGAAC |
| 431 | DNA | GGCATCAGCTGGAATAGCGGCTGGATCGGCTACGCCGATAGCGTGAA GGGC |
| 432 | DNA | AGCGGCTACAGCAGCTCTTGGTTTGACCCCGACTTCGACTAT |
| 433 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTCAGTCTTACGCTG GCCCCAATCCTTACGTGGTGTTTGGCGGCGGAACAAAGCTGACCGTT CTA |
| 434 | DNA | ACAGGCAGCAGCTCCAATATCGGAGCCGGCTATGACGTGCAC |
| 435 | DNA | GGCAACAGCAACAGACCCAGC |
| 436 | DNA | CAGTCTTACGCTGGCCCCAATCCTTACGTGGTG |
| 437 | PRT | EVQLLESGGGLVQPGGSLRLSCAASGFDFSSYEMNWVRQAPGKGLEWV SGISWNSGWIGYADSVKGRFTISRDNSKNTLYLQMNSLRAEDTAVYYC ARSGYSSSWFDPDFDYWGQGTLVTVSSASTKGPSVFPLAPSSKSTSGGT AALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK |
| 438 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGPNPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 439 | DNA | GAAGTTCAGCTGCTGGAATCTGGCGGCGGACTGGTTCAACCTGGCGG<br>ATCTCTGAGACTGAGCTGTGCCGCCAGCGGCTTCGATTTCAGCAGCT<br>ACGAGATGAACTGGGTCCGACAGGCCCCTGGCAAAGGCCTTGAATG<br>GGTGTCCGGCATCAGCTGGAATAGCGGCTGGATCGGCTACGCCGATA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCAGCCAG<br>CACCAAGGGCCCCAGCGTGTTCCCTCTGGCCCCTAGCAGCAAGAGCA<br>CATCTGGCGGAACAGCCGCCCTGGGCTGCCTCGTGAAGGACTACTTT<br>CCCGAGCCCGTGACCGTGTCCTGGAACTCTGGCGCTCTGACAAGCGG<br>CGTGCACACCTTTCCAGCCGTGCTGCAGAGCAGCGGCCTGTACTCTCT<br>GAGCAGCGTCGTGACAGTGCCCAGCAGCTCTCTGGGCACCCAGACCT<br>ACATCTGCAACGTGAACCACAAGCCCAGCAACACCAAGGTGGACAA<br>GAAGGTGGAACCCAAGAGCTGCGACAAGACCCACACCTGTCCCCCTT<br>GTCCTGCCCCCGAACTGCTGGGAGGCCCTTCCGTGTTCCTGTTCCCCC<br>CAAAGCCCAAGGACACCCTGATGATCAGCCGGACCCCCGAAGTGAC<br>CTGCGTGGTGGTGGATGTGTCCCACGAGGACCCTGAAGTGAAGTTCA<br>ATTGGTACGTGGACGGCGTGGAAGTGCACAACGCCAAGACCAAGCC<br>TAGAGAGGAACAGTACAACAGCACCTACCGGGTGGTGTCCGTGCTGA<br>CAGTGCTGCACCAGGACTGGCTGAACGGCAAAGAGTACAAGTGCAA<br>GGTGTCCAACAAGGCCCTGCCTGCCCCCATCGAGAAAACCATCAGCA<br>AGGCCAAGGGCCAGCCCCGCGAACCCCAGGTGTACACACTGCCCCCA<br>AGCAGGGACGAGCTGACCAAGAACCAGGTGTCCCTGACCTGTCTCGT<br>GAAAGGCTTCTACCCCTCCGATATCGCCGTGGAATGGGAGAGCAACG<br>GCCAGCCCGAGAACAACTACAAGACCACCCCCCCTGTGCTGGACAGC<br>GACGGCTCATTCTTCCTGTACAGCAAGCTGACCGTGGACAAGTCCCG<br>GTGGCAGCAGGGCAACGTGTTCAGCTGCAGCGTGATGCACGAGGCCC<br>TGCACAACCACTACACCCAGAAGTCCCTGAGCCTGAGCCCTGGCAAG |
| 440 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTCAGTCTTACGCTG<br>GCCCCAATCCTTACGTGGTGTTTGGCGGCGGAACAAAGCTGACCGTT<br>CTAGGCCAGCCTAAAGCCGCCCCTAGCGTGACCCTGTTCCCTCCAAG<br>CAGCGAGGAACTGCAGGCCAACAAGGCCACCCTCGTGTGCCTGATCA<br>GCGACTTCTATCCTGGCGCCGTGACCGTGGCCTGGAAGGCCGATAGC<br>TCTCCTGTGAAGGCCGGCGTGGAAACCACCACCCCTAGCAAGCAGAG<br>CAACAACAAATACGCCGCCAGCAGCTACCTGAGCCTGACCCCCGAGC<br>AGTGGAAGTCCCACAGATCCTACAGCTGCCAAGTGACCCACGAGGGC<br>AGCACCGTGAAAAGACAGTGGCCCCTACCGAGTGCAGC |
| 441 | PRT | EVQLLESGGGLVQPGGSLRLSCAASGFDFSSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSS |
| 442 | PRT | SYEMN |
| 443 | PRT | GISWNSGWIDYADSVKG |
| 444 | PRT | SGYSSSWFDPDFDY |
| 445 | PRT | QSVLTQPPSVSGAPGQRVTISCTGSSSNIGAGYDVHWYQQLPGTAPKLLI<br>YGNSNRPSGVPDRFSGSKSGTSASLAITGLQAEDEADYYCQSYAGPNPY<br>VVFGGGTKLTVL |
| 446 | PRT | TGSSSNIGAGYDVH |
| 447 | PRT | GNSNRPS |
| 448 | PRT | QSYAGPNPYVV |
| 449 | DNA | GAAGTTCAGCTGCTGGAATCTGGCGGCGGACTGGTTCAACCTGGCGG<br>ATCTCTGAGACTGAGCTGTGCCGCCAGCGGCTTCGATTTCAGCAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
| --- | --- | --- |
| | | CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCA |
| 450 | DNA | AGCTACGAGATGAAC |
| 451 | DNA | GGCATCAGCTGGAATAGCGGCTGGATCGACTACGCCGACAGCGTGA AGGGC |
| 452 | DNA | AGCGGCTACAGCAGCTCTTGGTTTGACCCCGACTTCGACTAT |
| 453 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTCAGTCTTACGCTG GCCCCAATCCTTACGTGGTGTTTGGCGGCGGAACAAAGCTGACCGTT CTA |
| 454 | DNA | ACAGGCAGCAGCTCCAATATCGGAGCCGGCTATGACGTGCAC |
| 455 | DNA | GGCAACAGCAACAGACCCAGC |
| 456 | DNA | CAGTCTTACGCTGGCCCCAATCCTTACGTGGTG |
| 457 | PRT | EVQLLESGGGLVQPGGSLRLSCAASGFDFSSYEMNWVRQAPGKGLEWV SGISWNSGWIDYADSVKGRFTISRDNSKNTLYLQMNSLRAEDTAVYYC ARSGYSSSWFDPDFDYWGQGTLVTVSSASTKGPSVFPLAPSSKSTSGGT AALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK |
| 458 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGPNPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |
| 459 | DNA | GAAGTTCAGCTGCTGGAATCTGGCGGCGGACTGGTTCAACCTGGCGG ATCTCTGAGACTGAGCTGTGCCGCCAGCGGCTTCGATTTCAGCAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
| --- | --- | --- |
| | | AGCAGGGACGAGCTGACCAAGAACCAGGTGTCCCTGACCTGTCTCGT<br>GAAAGGCTTCTACCCCTCCGATATCGCCGTGGAATGGGAGAGCAACG<br>GCCAGCCCGAGAACAACTACAAGACCACCCCCCCTGTGCTGGACAGC<br>GACGGCTCATTCTTCCTGTACAGCAAGCTGACCGTGGACAAGTCCCG<br>GTGGCAGCAGGGCAACGTGTTCAGCTGCAGCGTGATGCACGAGGCCC<br>TGCACAACCACTACACCCAGAAGTCCCTGAGCCTGAGCCCTGGCAAG |
| 460 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTCAGTCTTACGCTG<br>GCCCCAATCCTTACGTGGTGTTTGGCGGCGGAACAAAGCTGACCGTT<br>CTAGGCCAGCCTAAAGCCGCCCCTAGCGTGACCCTGTTCCCTCCAAG<br>CAGCGAGGAACTGCAGGCCAACAAGGCCACCCTCGTGTGCCTGATCA<br>GCGACTTCTATCCTGGCGCCGTGACCGTGGCCTGGAAGGCCGATAGC<br>TCTCCTGTGAAGGCCGGCGTGGAAACCACCACCCCTAGCAAGCAGAG<br>CAACAACAAATACGCCGCCAGCAGCTACCTGAGCCTGACCCCCGAGC<br>AGTGGAAGTCCCACAGATCCTACAGCTGCCAAGTGACCCACGAGGGC<br>AGCACCGTGAAAAGACAGTGGCCCCTACCGAGTGCAGC |
| 461 | PRT | EVQLLESGGGLVQPGGSLRLSCAASGFTFDSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSS |
| 462 | PRT | SYEMN |
| 463 | PRT | GISWNSGWIDYADSVKG |
| 464 | PRT | SGYSSSWFDPDFDY |
| 465 | PRT | QSVLTQPPSVSGAPGQRVTISCTGSSSNIGAGYDVHWYQQLPGTAPKLLI<br>YGNSNRPSGVPDRFSGSKSGTSASLAITGLQAEDEADYYCQSYAGPNPY<br>VVFGGGTKLTVL |
| 466 | PRT | TGSSSNIGAGYDVH |
| 467 | PRT | GNSNRPS |
| 468 | PRT | QSYAGPNPYVV |
| 469 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTCGATAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |
| 470 | DNA | AGCTACGAGATGAAC |
| 471 | DNA | GGCATCAGCTGGAATAGCGGCTGGATCGACTACGCCGACAGCGTGA<br>AGGGC |
| 472 | DNA | AGCGGCTACAGCAGCTCTTGGTTTGACCCCGACTTCGACTAT |
| 473 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTCAGTCTTACGCTG<br>GCCCCAATCCTTACGTGGTGTTTGGCGGCGGAACAAAGCTGACCGTT<br>CTA |
| 474 | DNA | ACAGGCAGCAGCTCCAATATCGGAGCCGGCTATGACGTGCAC |
| 475 | DNA | GGCAACAGCAACAGACCCAGC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 476 | DNA | CAGTCTTACGCTGGCCCCAATCCTTACGTGGTG |
| 477 | PRT | EVQLLESGGGLVQPGGSLRLSCAASGFTFDSYEMNWVRQAPGKGLEWV SGISWNSGWIDYADSVKGRFTISRDNSKNTLYLQMNSLRAEDTAVYYC ARSGYSSSWFDPDFDYWGQGTLVTVSSASTKGPSVFPLAPSSKSTSGGT AALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK |
| 478 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGPNPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |
| 479 | DNA | GAAGTTCAGCTGCTGGAATCTGGCGGCGGACTGGTTCAACCTGGCGG ATCTCTGAGACTGAGCTGTGCCGCCAGCGGCTTCACCTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGCAAG |
| 480 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTCAGTCTTACGCTG GCCCCAATCCTTACGTGGTGTTTGGCGGCGGAACAAAGCTGACCGTT CTAGGCCAGCCTAAAGCCGCCCCTAGCGTGACCCTGTTCCCTCCAAG CAGCGAGGAACTGCAGGCCAACAAGGCCACCCTCGTGTGCCTGATCA GCGACTTCTATCCTGGCGCCGTGACCGTGGCCTGGAAGGCCGATAGC TCTCCTGTGAAGGCCGGCGTGGAAACCACCACCCCTAGCAAGCAGAG CAACAACAAATACGCCGCCAGCAGCTACCTGAGCCTGACCCCCGAGC AGTGGAAGTCCCACAGATCCTACAGCTGCCAAGTGACCCACGAGGGC AGCACCGTGGAAAAGACAGTGGCCCCTACCGAGTGCAGC |
| 481 | PRT | EVQLLESGGGLVQPGGSLRLSCAASGFDFDSYEMNWVRQAPGKGLEW VSGISWNSGWIDYADSVKGRFTISRDNSKNTLYLQMNSLRAEDTAVYY CARSGYSSSWFDPDFDYWGQGTLVTVSS |
| 482 | PRT | SYEMN |
| 483 | PRT | GISWNSGWIDYADSVKG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| 484 | PRT | SGYSSSWFDPDFDY |
| 485 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGPNPY VVFGGGTKLTVL |
| 486 | PRT | TGSSSNIGAGYDVH |
| 487 | PRT | GNSNRPS |
| 488 | PRT | QSYAGPNPYVV |
| 489 | DNA | GAAGTTCAGCTGCTGGAATCTGGCGGCGGACTGGTTCAACCTGGCGG ATCTCTGAGACTGAGCTGTGCCGCCAGCGGCTTCGACTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCA |
| 490 | DNA | AGCTACGAGATGAAC |
| 491 | DNA | GGCATCAGCTGGAATAGCGGCTGGATCGACTACGCCGACAGCGTGA AGGGC |
| 492 | DNA | AGCGGCTACAGCAGCTCTTGGTTTGACCCCGACTTCGACTAT |
| 493 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTCAGTCTTACGCTG GCCCCAATCCTTACGTGGTGTTTGGCGGCGGAACAAAGCTGACCGTT CTA |
| 494 | DNA | ACAGGCAGCAGCTCCAATATCGGAGCCGGCTATGACGTGCAC |
| 495 | DNA | GGCAACAGCAACAGACCCAGC |
| 496 | DNA | CAGTCTTACGCTGGCCCCAATCCTTACGTGGTG |
| 497 | PRT | EVQLLESGGGLVQPGGSLRLSCAASGFDFDSYEMNWVRQAPGKGLEW VSGISWNSGWIDYADSVKGRFTISRDNSKNTLYLQMNSLRAEDTAVYY CARSGYSSSWFDPDFDYWGQGTLVTVSSASTKGPSVFPLAPSSKSTSGG TAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEAL HNHYTQKSLSLSPGK |
| 498 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGPNPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |
| 499 | DNA | GAAGTTCAGCTGCTGGAATCTGGCGGCGGACTGGTTCAACCTGGCGG ATCTCTGAGACTGAGCTGTGCCGCCAGCGGCTTCGACTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | CCCGAGCCCGTGACCGTGTCCTGGAACTCTGGCGCTCTGACAAGCGG<br>CGTGCACACCTTTCCAGCCGTGCTGCAGAGCAGCGGCCTGTACTCTCT<br>GAGCAGCGTCGTGACAGTGCCCAGCAGCTCTCTGGGCACCCAGACCT<br>ACATCTGCAACGTGAACCACAAGCCCAGCAACACCAAGGTGGACAA<br>GAAGGTGGAACCCAAGAGCTGCGACAAGACCCACACCTGTCCCCCTT<br>GTCCTGCCCCCGAACTGCTGGGAGGCCCTTCCGTGTTCCTGTTCCCCC<br>CAAAGCCCAAGGACACCCTGATGATCAGCCGGACCCCCGAAGTGAC<br>CTGCGTGGTGGTGGATGTGTCCCACGAGGACCCTGAAGTGAAGTTCA<br>ATTGGTACGTGGACGGCGTGGAAGTGCACAACGCCAAGACCAAGCC<br>TAGAGAGGAACAGTACAACAGCACCTACCGGGTGGTGTCCGTGCTGA<br>CAGTGCTGCACCAGGACTGGCTGAACGGCAAAGAGTACAAGTGCAA<br>GGTGTCCAACAAGGCCCTGCCTGCCCCCATCGAGAAAACCATCAGCA<br>AGGCCAAGGGCCAGCCCCGCGAACCCCAGGTGTACACACTGCCCCCA<br>AGCAGGGACGAGCTGACCAAGAACCAGGTGTCCCTGACCTGTCTCGT<br>GAAAGGCTTCTACCCCTCCGATATCGCCGTGGAATGGGAGAGCAACG<br>GCCAGCCCGAGAACAACTACAAGACCACCCCCCCTGTGCTGGACAGC<br>GACGGCTCATTCTTCCTGTACAGCAAGCTGACCGTGGACAAGTCCCG<br>GTGGCAGCAGGGCAACGTGTTCAGCTGCAGCGTGATGCACGAGGCCC<br>TGCACAACCACTACACCCAGAAGTCCCTGAGCCTGAGCCCTGGCAAG |
| 500 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTCAGTCTTACGCTG<br>GCCCCAATCCTTACGTGGTGTTTGGCGGCGGAACAAAGCTGACCGTT<br>CTAGGCCAGCCTAAAGCCGCCCCTAGCGTGACCCTGTTCCCTCCAAG<br>CAGCGAGGAACTGCAGGCCAACAAGGCCACCCTCGTGTGCCTGATCA<br>GCGACTTCTATCCTGGCGCCGTGACCGTGGCCTGGAAGGCCGATAGC<br>TCTCCTGTGAAGGCCGGCGTGGAAACCACCACCCCTAGCAAGCAGAG<br>CAACAACAAATACGCCGCCAGCAGCTACCTGAGCCTGACCCCCGAGC<br>AGTGGAAGTCCCACAGATCCTACAGCTGCCAAGTGACCCACGAGGGC<br>AGCACCGTGGAAAAGACAGTGGCCCCTACCGAGTGCAGC |
| 501 | PRT | EVQLLESGGGLVQPGGSLRLSCAASGFTFDSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSS |
| 502 | PRT | SYEMN |
| 503 | PRT | GISWNSGWIDYADSVKG |
| 504 | PRT | SGYSSSWFDPDFDY |
| 505 | PRT | QSVLTQPPSVSGAPGQRVTISCTGSSSDIGAGYDVHWYQQLPGTAPKLLI<br>YGNSNRPSGVPDRFSGSKSGTSASLAITGLQAEDEADYYCQSYAGINPY<br>VVFGGGTKLTVL |
| 506 | PRT | TGSSSDIGAGYDVH |
| 507 | PRT | GNSNRPS |
| 508 | PRT | QSYAGINPYVV |
| 509 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTCGATAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |
| 510 | DNA | AGCTACGAGATGAAC |
| 511 | DNA | GGCATCAGCTGGAATAGCGGCTGGATCGACTACGCCGACAGCGTGA<br>AGGGC |
| 512 | DNA | AGCGGCTACAGCAGCTCTTGGTTTGACCCCGACTTCGACTAT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 513 | DNA | CAGTCTGTTCTGACACAGCCTCCATCTGTGTCTGGCGCCCCTGGACAG<br>AGAGTGACCATCAGCTGTACAGGCAGCAGCTCCGATATTGGCGCCGG<br>ATACGACGTGCACTGGTATCAGCAACTGCCTGGCACAGCCCCTAAGC<br>TGCTGATCTACGGCAACAGCAACAGACCTAGCGGCGTGCCCGATAGA<br>TTCAGCGGCTCTAAGTCTGGCACAAGCGCCAGCCTGGCCATTACTGG<br>ACTGCAGGCCGAAGATGAGGCCGACTACTACTGTCAGAGCTACGCCG<br>GCATCAACCCCTACGTGGTGTTTGGCGGAGGCACCAAGCTGACAGTT<br>CTA |
| 514 | DNA | ACAGGCAGCAGCTCCGATATTGGCGCCGGATACGACGTGCAC |
| 515 | DNA | GGCAACAGCAACAGACCTAGC |
| 516 | DNA | CAGAGCTACGCCGGCATCAACCCCTACGTGGTG |
| 517 | PRT | EVQLLESGGGLVQPGGSLRLSCAASGFTFDSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSSASTKGPSVFPLAPSSKSTSGGT<br>AALGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPGK |
| 518 | PRT | QSVLTQPPSVSGAPGQRVTISCTGSSSDIGAGYDVHWYQQLPGTAPKLLI<br>YGNSNRPSGVPDRFSGSKSGTSASLAITGLQAEDEADYYCQSYAGINPY<br>VVFGGGTKLTVLGQPKAAPSVTLFPPSSEELQANKATLVCLISDFYPGAV<br>TVAWKADSSPVKAGVETTTPSKQSNNKYAASSYLSLTPEQWKSHRSYS<br>CQVTHEGSTVEKTVAPTECS |
| 519 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTCGATAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCAGCCAG<br>CACCAAGGGCCCCAGCGTGTTCCCTCTGGCCCCTAGCAGCAAGAGCA<br>CATCTGGCGGAACAGCCGCCCTGGGCTGCCTCGTGAAGGACTACTTT<br>CCCGAGCCCGTGACCGTGTCCTGGAACTCTGGCGCTCTGACAAGCGG<br>CGTGCACACCTTTCCAGCCGTGCTGCAGAGCAGCGGCCTGTACTCTCT<br>GAGCAGCGTCGTGACAGTGCCCAGCAGCTCTCTGGGCACCCAGACCT<br>ACATCTGCAACGTGAACCACAAGCCCAGCAACACCAAGGTGGACAA<br>GAAGGTGGAACCCAAGAGCTGCGACAAGACCCACACCTGTCCCCCTT<br>GTCCTGCCCCCGAACTGCTGGGAGGCCCTTCCGTGTTCCTGTTCCCCC<br>CAAAGCCCAAGGACACCCTGATGATCAGCCGGACCCCCGAAGTGAC<br>CTGCGTGGTGGTGGATGTGTCCCACGAGGACCCTGAAGTGAAGTTCA<br>ATTGGTACGTGGACGGCGTGGAAGTGCACAACGCCAAGACCAAGCC<br>TAGAGAGGAACAGTACAACAGCACCTACCGGGTGGTGTCCGTGCTGA<br>CAGTGCTGCACCAGGACTGGCTGAACGGCAAAGAGTACAAGTGCAA<br>GGTGTCCAACAAGGCCCTGCCTGCCCCCATCGAGAAAACCATCAGCA<br>AGGCCAAGGGCCAGCCCCGCGAACCCCAGGTGTACACACTGCCCCCA<br>AGCAGGGACGAGCTGACCAAGAACCAGGTGTCCCTGACCTGTCTCGT<br>GAAAGGCTTCTACCCCTCCGATATCGCCGTGGAATGGGAGAGCAACG<br>GCCAGCCCGAGAACAACTACAAGACCACCCCCCCTGTGCTGGACAGC<br>GACGGCTCATTCTTCCTGTACAGCAAGCTGACCGTGGACAAGTCCCG<br>GTGGCAGCAGGGCAACGTGTTCAGCTGCAGCGTGATGCACGAGGCCC<br>TGCACAACCACTACACCCAGAAGTCCCTGAGCCTGAGCCCTGGCAAG |
| 520 | DNA | CAGTCTGTTCTGACACAGCCTCCATCTGTGTCTGGCGCCCCTGGACAG<br>AGAGTGACCATCAGCTGTACAGGCAGCAGCTCCGATATTGGCGCCGG<br>ATACGACGTGCACTGGTATCAGCAACTGCCTGGCACAGCCCCTAAGC<br>TGCTGATCTACGGCAACAGCAACAGACCTAGCGGCGTGCCCGATAGA<br>TTCAGCGGCTCTAAGTCTGGCACAAGCGCCAGCCTGGCCATTACTGG<br>ACTGCAGGCCGAAGATGAGGCCGACTACTACTGTCAGAGCTACGCCG<br>GCATCAACCCCTACGTGGTGTTTGGCGGAGGCACCAAGCTGACAGTT<br>CTAGGCCAGCCTAAAGCCGCCCCTAGCGTGACCCTGTTCCCTCCAAG<br>CAGCGAGGAACTGCAGGCCAACAAGGCCACCCTCGTGTGCCTGATCA |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
|  |  | GCGACTTCTATCCTGGCGCCGTGACCGTGGCCTGGAAGGCCGATAGC<br>TCTCCTGTGAAGGCCGGCGTGGAAACCACCACCCCTAGCAAGCAGAG<br>CAACAACAAATACGCCGCCAGCAGCTACCTGAGCCTGACCCCCGAGC<br>AGTGGAAGTCCCACAGATCCTACAGCTGCCAAGTGACCCACGAGGGC<br>AGCACCGTGGAAAAGACAGTGGCCCCTACCGAGTGCAGC |
| 521 | PRT | EVQLLESGGGLVQPGGSLRLSCAASGFDFDSYEMNWVRQAPGKGLEW<br>VSGISWNSGWIDYADSVKGRFTISRDNSKNTLYLQMNSLRAEDTAVYY<br>CARSGYSSSWFDPDFDYWGQGTLVTVSS |
| 522 | PRT | SYEMN |
| 523 | PRT | GISWNSGWIDYADSVKG |
| 524 | PRT | SGYSSSWFDPDFDY |
| 525 | PRT | QSVLTQPPSVSGAPGQRVTISCTGSSSDIGAGYDVHWYQQLPGTAPKLLI<br>YGNSNRPSGVPDRFSGSKSGTSASLAITGLQAEDEADYYCSSYEGINPYV<br>VFGGGTKLTVL |
| 526 | PRT | TGSSSDIGAGYDVH |
| 527 | PRT | GNSNRPS |
| 528 | PRT | SSYEGINPYVV |
| 529 | DNA | GAAGTTCAGCTGCTGGAATCTGGCGGCGGACTGGTTCAACCTGGCGG<br>ATCTCTGAGACTGAGCTGTGCCGCCAGCGGCTTCGACTTCGATAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |
| 530 | DNA | AGCTACGAGATGAAC |
| 531 | DNA | GGCATCAGCTGGAATAGCGGCTGGATCGACTACGCCGACAGCGTGA<br>AGGGC |
| 532 | DNA | AGCGGCTACAGCAGCTCTTGGTTTGACCCCGACTTCGACTAT |
| 533 | DNA | CAGTCTGTTCTGACACAGCCTCCATCTGTGTCTGGCGCCCCTGGACAG<br>AGAGTGACCATCAGCTGTACAGGCAGCAGCTCCGATATTGGCGCCGG<br>ATACGACGTGCACTGGTATCAGCAACTGCCTGGCACAGCCCCTAAGC<br>TGCTGATCTACGGCAACAGCAACAGACCTAGCGGCGTGCCCGATAGA<br>TTCAGCGGCTCTAAGTCTGGCACAAGCGCCAGCCTGGCCATTACTGG<br>ACTGCAGGCCGAAGATGAGGCCGACTACTACTGCAGCAGCTACGAG<br>GGCATCAACCCCTACGTGGTGTTTGGCGGCGGAACAAAGCTGACCGT<br>TCTA |
| 534 | DNA | ACAGGCAGCAGCTCCGATATTGGCGCCGGATACGACGTGCAC |
| 535 | DNA | GGCAACAGCAACAGACCTAGC |
| 536 | DNA | AGCAGCTACGAGGGCATCAACCCCTACGTGGTG |
| 537 | PRT | EVQLLESGGGLVQPGGSLRLSCAASGFDFDSYEMNWVRQAPGKGLEW<br>VSGISWNSGWIDYADSVKGRFTISRDNSKNTLYLQMNSLRAEDTAVYY<br>CARSGYSSSWFDPDFDYWGQGTLVTVSSASTKGPSVFPLAPSSKSTSGG<br>TAALGCLVKDYFPEPVTVSWNSGALTSGVHTFPAVLQSSGLYSLSSVVT<br>VPSSSLGTQTYICNVNHKPSNTKVDKKVEPKSCDKTHTCPPCPAPELLGG<br>PSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEK<br>TISKAKGQPREPQVYTLPPSRDELTKNQVSLTCLVKGFYPSDIAVEWESN<br>GQPENNYKTTPPVLDSDGSFFLYSKLTVDKSRWQQGNVFSCSVMHEAL<br>HNHYTQKSLSLSPGK |
| 538 | PRT | QSVLTQPPSVSGAPGQRVTISCTGSSSDIGAGYDVHWYQQLPGTAPKLLI<br>YGNSNRPSGVPDRFSGSKSGTSASLAITGLQAEDEADYYCSSYEGINPYV<br>VFGGGTKLTVLGQPKAAPSVTLFPPSSEELQANKATLVCLISDFYPGAVT |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from *Homo sapiens* (SEQ ID 581, 582), *Mus Musculus*
(SEQ ID 583), *Rattus norvegicus* (SEQ ID 584), *Canis lupus familiaris* (SEQ ID 585), *Macaca
fascicularis* (SEQ ID 586), *Sus scrofa* (SEQ ID 587).

| SEQ ID No | SEQ Type | SEQUENCE |
|---|---|---|
| | | VAWKADSSPVKAGVETTTPSKQSNNKYAASSYLSLTPEQWKSHRSYSC QVTHEGSTVEKTVAPTECS |
| 539 | DNA | GAAGTTCAGCTGCTGGAATCTGGCGGCGGACTGGTTCAACCTGGCGG ATCTCTGAGACTGAGCTGTGCCGCCAGCGGCTTCGACTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGCAAG |
| 540 | DNA | CAGTCTGTTCTGACACAGCCTCCATCTGTGTCTGGCGCCCCTGGACAG AGAGTGACCATCAGCTGTACAGGCAGCAGCTCCGATATTGGCGCCGG ATACGACGTGCACTGGTATCAGCAACTGCCTGGCACAGCCCCTAAGC TGCTGATCTACGGCAACAGCAACAGACCTAGCGGCGTGCCCGATAGA TTCAGCGGCTCTAAGTCTGGCACAAGCGCCAGCCTGGCCATTACTGG ACTGCAGGCCGAAGATGAGGCCGACTACTACTGCAGCAGCTACGAG GGCATCAACCCCTACGTGGTGTTTGGCGGCGGAACAAAGCTGACCGT TCTTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 541 | PRT | EVQLLESGGGLVQPGGSLRLSCAASGFDFSSYEMNWVRQAPGKGLEWV SGISWNSGWIDYADSVKGRFTISRDNSKNTLYLQMNSLRAEDTAVYYC ARSGYSSSWFDPDFDYWGQGTLVTVSS |
| 542 | PRT | SYEMN |
| 543 | PRT | GISWNSGWIDYADSVKG |
| 544 | PRT | SGYSSSWFDPDFDY |
| 545 | PRT | QSVLTQPPSVSGAPGQRVTISCTGSSSNIGAGYDVHWYQQLPGTAPKLLI YGASNRPSGVPDRFSGSKSGTSASLAITGLQAEDEADYYCSSYEGPNPYV VFGGGTKLTVL |
| 546 | PRT | TGSSSNIGAGYDVH |
| 547 | PRT | GASNRPS |
| 548 | PRT | SSYEGPNPYVV |
| 549 | DNA | GAAGTTCAGCTGCTGGAATCTGGCGGCGGACTGGTTCAACCTGGCGG ATCTCTGAGACTGAGCTGTGCCGCCAGCGGCTTCGATTTCAGCAGCT ACGAGATGAACTGGGTCCGACAGGCCCCTGGCAAAGGCCTTGAATG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| | | GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCA |
| 550 | DNA | AGCTACGAGATGAAC |
| 551 | DNA | GGCATCAGCTGGAATAGCGGCTGGATCGACTACGCCGACAGCGTGA AGGGC |
| 552 | DNA | AGCGGCTACAGCAGCTCTTGGTTTGACCCCGACTTCGACTAT |
| 553 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCGCCAGCAATAGACCTAGCGGCGTGCCCGATAGA TTCAGCGGCTCTAAGTCTGGCACAAGCGCCAGCCTGGCCATTACTGG ACTGCAGGCCGAAGATGAGGCCGACTACTACTGCAGCAGCTACGAG GGCCCCAATCCTTACGTGGTGTTTGGCGGCGGAACAAAGCTGACCGT TCTA |
| 554 | DNA | ACAGGCAGCAGCTCCAATATCGGAGCCGGCTATGACGTGCAC |
| 555 | DNA | GGCGCCAGCAATAGACCTAGC |
| 556 | DNA | AGCAGCTACGAGGGCCCCAATCCTTACGTGGTG |
| 557 | PRT | EVQLLESGGGLVQPGGSLRLSCAASGFDFSSYEMNWVRQAPGKGLEWV SGISWNSGWIDYADSVKGRFTISRDNSKNTLYLQMNSLRAEDTAVYYC ARSGYSSSWFDPDFDYWGQGTLVTVSSASTKGPSVFPLAPSSKSTSGGT AALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK |
| 558 | PRT | QSVLTQPPSVSGAPGQRVTISCTGSSSNIGAGYDVHWYQQLPGTAPKLLI YGASNRPSGVPDRFSGSKSGTSASLAITGLQAEDEADYYCSSYEGPNPYV VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 559 | DNA | GAAGTTCAGCTGCTGGAATCTGGCGGCGGACTGGTTCAACCTGGCGG ATCTCTGAGACTGAGCTGTGCCGCCAGCGGCTTCGATTTCAGCAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
|  |  | GACGGCTCATTCTTCCTGTACAGCAAGCTGACCGTGGACAAGTCCCG<br>GTGGCAGCAGGGCAACGTGTTCAGCTGCAGCGTGATGCACGAGGCCC<br>TGCACAACCACTACACCCAGAAGTCCCTGAGCCTGAGCCCTGGCAAG |
| 560 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCGCCAGCAATAGACCTAGCGGCGTGCCCGATAGA<br>TTCAGCGGCTCTAAGTCTGGCACAAGCGCCAGCCTGGCCATTACTGG<br>ACTGCAGGCCGAAGATGAGGCCGACTACTACTGCAGCAGCTACGAG<br>GGCCCCAATCCTTACGTGGTGTTTGGCGGCGGAACAAAGCTGACCGT<br>TCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 561 | PRT | EVQLLESGGGLVQPGGSLRLSCAASGFTFDSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSS |
| 562 | PRT | SYEMN |
| 563 | PRT | GISWNSGWIDYADSVKG |
| 564 | PRT | SGYSSSWFDPDFDY |
| 565 | PRT | QSVLTQPPSVSGAPGQRVTISCTGSSSNIGAGYDVHWYQQLPGTAPKLLI<br>YGNSNRPSGVPDRFSGSKSGTSASLAITGLQAEDEADYYCSSYAGPNPY<br>VVFGGGTKLTVL |
| 566 | PRT | TGSSSNIGAGYDVH |
| 567 | PRT | GNSNRPS |
| 568 | PRT | SSYAGPNPYVV |
| 569 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTCGATAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |
| 570 | DNA | AGCTACGAGATGAAC |
| 571 | DNA | GGCATCAGCTGGAATAGCGGCTGGATCGACTACGCCGACAGCGTGA<br>AGGGC |
| 572 | DNA | AGCGGCTACAGCAGCTCTTGGTTTGACCCCGACTTCGACTAT |
| 573 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTAGCTCTTACGCTG<br>GCCCCAATCCTTACGTGGTGTTTGGCGGCGGAACAAAGCTGACCGTT<br>CTA |
| 574 | DNA | ACAGGCAGCAGCTCCAATATCGGAGCCGGCTATGACGTGCAC |
| 575 | DNA | GGCAACAGCAACAGACCCAGC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 576 | DNA | AGCTCTTACGCTGGCCCCAATCCTTACGTGGTG |
| 577 | PRT | EVQLLESGGGLVQPGGSLRLSCAASGFTFDSYEMNWVRQAPGKGLEWV SGISWNSGWIDYADSVKGRFTISRDNSKNTLYLQMNSLRAEDTAVYYC ARSGYSSSWFDPDFDYWGQGTLVTVSSASTKGPSVFPLAPSSKSTSGGT AALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK |
| 578 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCSSYAGPNPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |
| 579 | DNA | GAAGTTCAGCTGCTGGAATCTGGCGGCGGACTGGTTCAACCTGGCGG ATCTCTGAGACTGAGCTGTGCCGCCAGCGGCTTCACCTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGCAAG |
| 580 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTAGCTCTTACGCTG GCCCCAATCCTTACGTGGTGTTTGGCGGCGGAACAAAGCTGACCGTT CTAGGCCAGCCTAAAGCCGCCCCTAGCGTGACCCTGTTCCCTCCAAG CAGCGAGGAACTGCAGGCCAACAAGGCCACCCTCGTGTGCCTGATCA GCGACTTCTATCCTGGCGCCGTGACCGTGGCCTGGAAGGCCGATAGC TCTCCTGTGAAGGCCGGCGTGGAAACCACCACCCCTAGCAAGCAGAG CAACAACAAATACGCCGCCAGCAGCTACCTGAGCCTGACCCCCGAGC AGTGGAAGTCCCACAGATCCTACAGCTGCCAAGTGACCCACGAGGGC AGCACCGTGGAAAAGACAGTGGCCCCTACCGAGTGCAGC |
| 581 | PRT | HHHHHHKNNVPRLKLSYKEMLESNNVITFNGLANSSSYHTFLLDEERSR LYVGAKDHIFSFDLVNIKDFQKIVWPVSYTRRDECKWAGKDILKECANF IKVLKAYNQTHLYACGTGAFHPICTYIEIGHHPEDNIFKLENSHFENGRG KSPYDPKLLTASLLIDGELYSGTAADFMGRDPAIFRTLGHHHPIRTEQHD SRWLNDPKFISAHLISESDNPEDDKVYFFFRENAIDGEHSGKATHARIGQI CKNDFGGHRSLVNKWTTFLKARLICSVPGPNGIDTHFDELQDVFLMNFK DPKNPVVYGVFTTSSNIFKGSAVCMYSMSDVRRVFLGPYAHRDGPNYQ |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| | | WVPYQGRVPYPRPGTCPSKTFGGFDSTKDLPDDVITFARSHPAMYNPVF<br>PMNNRPIVIKTDVNYQFTQIVVDRVDAEDGQYDVMFIGTDVGTVLKVV<br>SIPKETWYDLEEVLLEEMTVFREPTAISAMELSTKQQQLYIGSTAGVAQL<br>PLHRCDIYGKACAECCLARDPYCAWDGSACSRYFPTAKRATRAQDIRN<br>GDPLTHCSDLHHDNHHGHSPEERIIYGVENSSTFLECSPKSQRALVYWQF<br>QRRNEERKEEIRVDDHIIRTDQGLLLRSLQQKDSGNYLCHAVEHGFIQTL<br>LKVTLEVIDTEHLEELLHKDDDGDGSKTKEMSNSMTPSQKVWYRDFMQ<br>LINHPNLNTMDEFCEQVWKRDRKQRRQRPGHTPGNSNKWKHLQENKK<br>GRNRRTHEFERAPRSVDIEGRMDPKSCDKTHTCPPCPAPELLGGPSVFLF<br>PPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPGK |
| 582 | PRT | NYQNGKNNVPRLKLSYKEMLESNNVITFNGLANSSSYHTFLLDEERSRL<br>YVGAKDHIFSFDLVNIKDFQKIVWPVSYTRRDECKWAGKDILKECANFI<br>KVLKAYNQTHLYACGTGAFHPICTYIEIGHHPEDNIFKLENSHFENGRGK<br>SPYDPKLLTASLLIDGELYSGTAADFMGRDFAIFRTLGHHHPIRTEQHDS<br>RWLNDPKFISAHLISESDNPEDDKVYFFFRENAIDGEHSGKATHARIGQI<br>CKNDFGGHRSLVNKWTTFLKARLICSVPGPNGIDTHFDELQDVFLMNFKD<br>PKNPVVYGVFTTSSNIFKGSAVCMYSMSDVRRVFLGPYAHRDGPNYQW<br>VPYQGRVPYPRPGTCPSKTFGGFDSTKDLPDDVITFARSHPAMYNPVFP<br>MNNRPIVIKTDVNYQFTQIVVDRVDAEDGQYDVMFIGTDVGTVLKVVSI<br>PKETWYDLEEVLLEEMTVFREPTAISAMELSTKQQQLYIGSTAGVAQLP<br>LHRCDIYGKACAECCLARDPYCAWDGSACSRYFPTAKARTRAQDIRNG<br>DPLTHCSDGGIEGRMDHHHHHH |
| 583 | PRT | NYANGKNNVPRLKLSYKEMLESNNVITFNGLANSSSYHTFLLDEERSRL<br>YVGAKDHIFSFNLVNIKDFQKIVWPVSYTRRDECKWAGKDILKECANFI<br>KVLEAYNQTHLYACGTGAFHPICTYIEVGHHPEDNIFKLQDSHFENGRG<br>KSPYDPKLLTASLLIDGELYSGTAADFMGRDFAIFRTLGHHHPIRTEQHD<br>SRWLNDPRFISAHLIPESDNPEDDKVYFFFRENAIDGEHSGKATHARIGQI<br>CKNDFGGHRSLVNKWTTFLKARLICSVPGPNGIDTHFDELQDVFLMNSK<br>DPKNPIVYGVFTTSSNIFKGSAVCMYSMSDVRRVFLGPYAHRDGPNYQ<br>WVPYQGRVPYPRPGTCPSKTFGGFDSTKDLPDDVITFARSHPAMYNPVF<br>PINNRPIMIKTDVNYQFTQIVVDRVDAEDGQYDVMFIGTDVGTVLKVVS<br>VPKETWHDLEEILLEEMTVFREPTTISAMELSTKQQQLYIGSTAGVAQLP<br>LHRCDIYGKACAECCLARDPYCAWDGSSCSRYFPTAKARTRAQDIRNG<br>DPLTHCSDGGIEGRMDHHHHHH |
| 584 | PRT | NYANGKNNVPRLKLSYKEMLESNNVITFNGLANSSSYHTFLLDEERSRL<br>YVGAKDHIFSFNLVNIKDFQKIVWPVSYTRRDECKWAGKDILKECANFI<br>KVLKAYNQTHLYACGTGAFHPICTYIEVGHHPEDNIFKLQDSHFENGRG<br>KSPYDPKLLTASLLIDGELYSGTAADFMGRDFAIFRTLGHHHPIRTEQHD<br>SRWLNDPRFISAHLIPESDNPEDDKVYFFFRENAIDGEHSGKATHARIGQI<br>CKNDFGGHRSLVNKWTTFLKARLICSVPGPNGIDTHFDELQDVFLMNSK<br>DPKNPIVYGVFTTSSNIFKGSAVCMYSMSDVRRVFLGPYAHRDGPNYQ<br>WVPYQGRVPYPRPGTCPSKTFGGFDSTKDLPDDVITFARSHPAMYNPVF<br>PINNRPIMIKTDVNYQFTQIVVDRVDAEDGQYDVMFIGTDVGTVLKVVS<br>VPKETWHDLEEVLLEEMTVFREPTTISAMELSTKQQQLYIGSTAGVAQL<br>PLHRCDIYGKACAECCLARDPYCAWDGSSCSRYFPTAKARTRAQDIRNG<br>DPLTHCSDGGIEGRMDHHHHHH |
| 585 | PRT | NYQNGKNNVPRLKLSYKEMLESNSVITFNGLANSSSYHTFLLDEERSRL<br>YVGAKDHIFSFNLVNIKDFQKIVWPVSYTRRDECKWAGKDIQKECANFI<br>KVLKAYNQTHLYACGTGAFHPICTYIEIGHHPEDNIFKLEDSHFENGRGK<br>SPYDPKLLTASLLIDGELYSGTAADFMGRDFAIFRTLGHHHPIRTEQHDS<br>RWLNDPRFISAHLIPESDNPEDDKVYFFFRENAIDGEHTGKATHARIGQIC<br>KNDFGGHRSLVNKWTTFLKARLICSVPGPNGIDTHFDELQDVFLMNSKD<br>PKNPIVYGVFTTSSNIFKGSAVCMYSMSDVRRVFLGPYAHRDGPNYQW<br>VPYQGRVPYPRPGTCPSKTFGGFDSTKDLPDDVITFARSHPAMYNPVFPI<br>NNRPIMIKTDVNYQFTQIVVDRVDAEDGQYDVMFIGTDVGTVLKVVSIP<br>KETWHDLEEVLLEEMTVFREPTPISAMELSTKQHQLYAGSPAGLAQLPL<br>QRCAAYGRACAECCLARDPYCAWDGAACSRYFPAAKARTRAQDIRNG<br>DPLTHCSDGGIEGRMDHHHHHH |
| 586 | PRT | NYQNGKNNVPRLKLSYKEMLESNNVITFNGLANSSSYHTFLLDEERSRL<br>YVGAKDHIFSFNLVNIKDFQKIVWPVSYTRRDECKWAGKDILKECANFI<br>KVLKAYNQTHLYACGTGAFHPICTYIEIGHHPEDNIFKLENSHFENGRGK<br>SPYDPKLLTASLLIDGELYSGTAADFMGRDFAIFRTLGHHHPIRTEQHDS |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
|  |  | RWLNDPRFISAHLIPESDNPEDDKVYFFFRENAIDGEHSGKATHARIGQIC KNDFGGHRSLVNKWTTFLKARLICSVPGPNGIDTHFDELQDVFLMNFKD PKNPIVYGVFTTSSNIFKGSAVCMYSMSDVRRVFLGPYAHRDGPNYQW VPYQGRVPYPRPGTCPSKTFGGFDSTKDLPDDVITFARSHPAMYNPVFPI NNRPIMIKTDVNYQFTQIVVDRVDAEDGQYDVMFIGTDVGTVLKVVSIP KETWHDLEEVLLEEMTVFREPTTISAMELSTKQQQLYIGSTAGIAQLPLH RCDIYGKACAECCLARDPYCAWDGSSCSRYFPTAKARTRAQDIRNGDPL THCSDGGIEGRMDHHHHHH |
| 587 | PRT | NYQNGKNNVPRLKLSYKEMLESNNVITFNGLANSSSYHTFLLDEERSRL YVGAKDHIFSFNLVNIKDFQKIVWPVSYTRRDECKWAGKDILKECANFI KVLKAYNQTHLYACGTGAFHPICTYIEIGHHPEDNIFKLEDSHFENGRGK SPYDPKLLTASLLIDGELYSGTAADFMGRDFAIFRTLGHHHPIRTEQHDS RWLNDPRFISAHLIPESDNPEDDKVYFFFRENAIDGEHTGKATHARIGQIC KNDFGGHRSLVNKWTTFLKARLICSVPGPNGIDTHFDELQDVFLMNSKD PKNPVVYGVFTTSSNIFKGSAVCMYSMSDVRRVFLGPYAHRDGPNYQW VPYQGRVPYPRPGTCPSKTFGGFDSTKDLPDDVITFARSHPAMYNPVFPI NNRPIMIKTDVNYQFTQIVVDRVDAEDGQYDVMFIGTDVGTVLKVVSIP KETWHDLEEVLLEEMTVFREPTTISAMELSTKQQQLYVGSAAGVAQLPL HRCDIYGKACAECCLARDPYCAWDGSSCSRYFPTAKARTRAQDIRNGD PLTHCSDGGIEGRMDHHHHHH |
| 800 | PRT | EVQLVESGGGLVQPGGSLRLSCAASGFTFSSYYMSWVRQAPGKGLEWV STIIKSGGYAYYPDSVKDRFTISRDNSKNTLYLQMSSLRAEDTAVYYCVR GGQGAMDYWGQGTTVTVSS |
| 801 | PRT | SYYMS |
| 802 | PRT | TIIKSGGYAYYPDSVKD |
| 803 | PRT | GGQGAMDY |
| 804 | PRT | EIVLTQSPATLSLSPGERATLSCRASQSIGDYLHWYQQKPGQAPRLLIKY ASQSISGIPARFSGSGSGTDFTLTITSLEPEDFAVYYCQQGYSFPYTFGGG TKLEIK |
| 805 | PRT | RASQSIGDYLH |
| 806 | PRT | YASQSIS |
| 807 | PRT | QQGYSFPYT |
| 808 | DNA | GAAGTGCAGCTGGTGGAATCTGGCGGAGGACTGGTTCAACCTGGCGG CTCTCTGAGACTGTCTTGTGCCGCCAGCGGCTTCACCTTCAGCAGCTA CTACATGAGCTGGGTCCGACAGGCCCCTGGCAAAGGACTTGAATGGG TGTCCACCATCATCAAGAGCGGCGGCTACGCCTACTATCCCGACAGC GTGAAGGACCGGTTCACCATCTCCAGAGACAACAGCAAGAACACCCT GTACCTGCAGATGAGCAGCCTGAGAGCCGAGGATACCGCCGTGTACT ACTGTGTTAGAGGCGGACAGGGCGCCATGGATTATTGGGGCCAGGG AACCACAGTGACCGTGTCATCA |
| 809 | DNA | GAGATTGTGCTGACACAGTCTCCCGCCACACTGTCTCTTAGCCCTGGC GAAAGAGCCACACTGAGCTGTAGAGCCAGCCAGAGCATCGGCGATT ACCTGCACTGGTATCAGCAGAAGCCTGGACAGGCCCCTCGGCTGCTG ATTAAGTACGCCAGCCAGTCCATCAGCGGCATCCCTGCCAGATTTTCT GGCAGCGGCTCTGGCACCGATTTCACCCTGACCATCACCAGCCTGGA ACCTGAGGACTTCGCCGTGTACTACTGCCAGCAGGGCTACAGCTTCC CCTACACATTTGGCGGAGGCACCAAGCTGGAAATCAAA |
| 810 | PRT | EVQLVESGGGLVQPGGSLRLSCAASGFTFSSYYMSWVRQAPGKGLEWV STIIKSGGYAYYPDSVKDRFTISRDNSKNTLYLQMSSLRAEDTAVYYCVR GGQGAMDYWGQGTTVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPGK |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 811 | PRT | EIVLTQSPATLSLSPGERATLSCRASQSIGDYLHWYQQKPGQAPRLLIKY ASQSISGIPARFSGSGSGTDFTLTITSLEPEDFAVYYCQQGYSFPYTFGGG TKLEIKRTVAAPSVFIFPPSDEQLKSGTASVVCLLNNFYPREAKVQWKVD NALQSGNSQESVTEQDSKDSTYSLSSTLTLSKADYEKHKVYACEVTHQG LSSPVTKSFNRGEC |
| 812 | DNA | GAAGTGCAGCTGGTGGAATCTGGCGGAGGACTGGTTCAACCTGGCGG CTCTCTGAGACTGTCTTGTGCCGCCAGCGGCTTCACCTTCAGCAGCTA CTACATGAGCTGGGTCCGACAGGCCCCTGGCAAAGGACTTGAATGGG TGTCCACCATCATCAAGAGCGGCGGCTACGCCTACTATCCCGACAGC GTGAAGGACCGGTTCACCATCTCCAGAGACAACAGCAAGAACACCCT GTACCTGCAGATGAGCAGCCTGAGAGCCGAGGATACCGCCGTGTACT ACTGTGTTAGAGGCGGACAGGGCGCCATGGATTATTGGGGCCAGGG AACCACAGTGACCGTGTCATCAGCCAGCACCAAGGGCCCCAGCGTGT TCCCTCTGGCCCCTAGCAGCAAGAGCACATCTGGCGGAACAGCCGCC CTGGGCTGCCTCGTGAAGGACTACTTTCCCGAGCCCGTGACCGTGTC CTGGAACTCTGGCGCTCTGACAAGCGGCGTGCACACCTTTCCAGCCG TGCTGCAGAGCAGCGGCCTGTACTCTCTGAGCAGCGTCGTGACAGTG CCCAGCAGCTCTCTGGGCACCCAGACCTACATCTGCAACGTGAACCA CAAGCCCAGCAACACCAAGGTGGACAAGAAGGTGGAACCCAAGAGC TGCGACAAGACCCACACCTGTCCCCCTTGTCCTGCCCCCGAACTGCTG GGAGGCCCTTCCGTGTTCCTGTTCCCCCCAAAGCCCAAGGACACCCT GATGATCAGCCGGACCCCCGAAGTGACCTGCGTGGTGGTGGATGTGT CCCACGAGGACCCTGAAGTGAAGTTCAATTGGTACGTGGACGGCGTG GAAGTGCACAACGCCAAGACCAAGCCTAGAGAGGAACAGTACAACA GCACCTACCGGGTGGTGTCCGTGCTGACAGTGCTGCACCAGGACTGG CTGAACGGCAAAGAGTACAAGTGCAAGGTGTCCAACAAGGCCCTGC CTGCCCCCATCGAGAAAACCATCAGCAAGGCCAAGGGCCAGCCCCG CGAACCCCAGGTGTACACACTGCCCCCAAGCAGGGACGAGCTGACC AAGAACCAGGTGTCCCTGACCTGTCTCGTGAAAGGCTTCTACCCCTC CGATATCGCCGTGGAATGGGAGAGCAACGGCCAGCCCGAGAACAAC TACAAGACCACCCCCCCTGTGCTGGACAGCGACGGCTCATTCTTCCT GTACAGCAAGCTGACCGTGGACAAGTCCCGGTGGCAGCAGGGCAAC GTGTTCAGCTGCAGCGTGATGCACGAGGCCCTGCACAACCACTACAC CCAGAAGTCCCTGAGCCTGAGCCCTGGCAAG |
| 813 | DNA | GAGATTGTGCTGACACAGTCTCCCGCCACACTGTCTCTTAGCCCTGGC GAAAGAGCCACACTGAGCTGTAGAGCCAGCCAGAGCATCGGCGATT ACCTGCACTGGTATCAGAAGCCTGGACAGGCCCCTCGGCTGCTG ATTAAGTACGCCAGCCAGTCCATCAGCGGCATCCCTGCCAGATTTTCT GGCAGCGGCTCTGGCACCGATTTCACCCTGACCATCACCAGCCTGGA ACCTGAGGACTTCGCCGTGTACTACTGCCAGCAGGGCTACAGCTTCC CCTACACATTTGGCGGAGGCACCAAGCTGGAAATCAAACGAACCGTG GCCGCTCCCAGCGTGTTCATCTTCCCACCTAGCGACGAGCAGCTGAA GTCCGGCACAGCCTCTGTCGTGTGCCTGCTGAACAACTTCTACCCCCG CGAGGCCAAGGTGCAGTGGAAGGTGGACAATGCCCTGCAGAGCGGC AACAGCCAGGAAAGCGTGACCGAGCAGGACAGCAAGGACTCCACCT ACAGCCTGAGCAGCACCCTGACCCTGAGCAAGGCCGACTACGAGAA GCACAAGGTGTACGCCTGCGAAGTGACCCACCAGGGCCTGTCTAGCC CCGTGACCAAGAGCTTCAACCGGGGCGAGTGT |
| 814 | PRT | EVQLVESGGGLVQPGGSLRLSCAASGFPFSSYYMSWVRQAPGKGLEWV STIIKSGGYAYYPDSVKDRFTISRDNSKNTLYLQMSSLRAEDTAVYYCVR GGQGAMDYWGQGTTVTVSS |
| 815 | PRT | SYYMS |
| 816 | PRT | TIIKSGGYAYYPDSVKD |
| 817 | PRT | GGQGAMDY |
| 818 | PRT | EIVLTQSPATLSLSPGERATLSCRASQSIGDYLHWYQQKPGQAPRLLIKY ASQSISGIPARFSGSGSGTDFTLTITSLEPEDFAVYYCQQGYSFPYTFGGG TKLEIK |
| 819 | PRT | RASQSIGDYLH |
| 820 | PRT | YASQSIS |
| 821 | PRT | QQGYSFPYT |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 822 | DNA | GAAGTGCAGCTGGTGGAATCTGGCGGAGGACTGGTTCAACCTGGCGG<br>CTCTCTGAGACTGTCTTGTGCCGCCTCTGGCTTCCCATTCAGCAGCTA<br>CTACATGAGCTGGGTCCGACAGGCCCCTGGCAAAGGACTTGAATGGG<br>TGTCCACCATCATCAAGAGCGGCGGCTACGCCTACTATCCCGACAGC<br>GTGAAGGACCGGTTCACCATCAGCCGGGACAACAGCAAGAACACCC<br>TGTACCTGCAGATGAGCAGCCTGAGAGCCGAGGATACCGCCGTGTAC<br>TACTGTGTTAGAGGCGGACAGGGCGCCATGGATTATTGGGGCCAGGG<br>AACCACAGTGACCGTGTCATCA |
| 823 | DNA | GAGATTGTGCTGACACAGTCTCCCGCCACACTGTCTCTTAGCCCTGGC<br>GAAAGAGCCACACTGAGCTGTAGAGCCAGCCAGAGCATCGGCGATT<br>ACCTGCACTGGTATCAGCAGAAGCCTGGACAGGCCCCTCGGCTGCTG<br>ATTAAGTACGCCAGCCAGTCCATCAGCGGCATCCCTGCCAGATTTTCT<br>GGCAGCGGCTCTGGCACCGATTTCACCCTGACCATCACCAGCCTGGA<br>ACCTGAGGACTTCGCCGTGTACTACTGCCAGCAGGGCTACAGCTTCC<br>CCTACACATTTGGCGGAGGCACCAAGCTGGAAATCAAA |
| 824 | PRT | EVQLVESGGGLVQPGGSLRLSCAASGFPFSSYYMSWVRQAPGKGLEWV<br>STIIKSGGYAYYPDSVKDRFTISRDNSKNTLYLQMSSLRAEDTAVYYCVR<br>GGQGAMDYWGQGTTVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLPPPK<br>PKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNY<br>KTTPPVLDSDGSFFLYSKLTVDKSRWQQGNVFSCSVMHEALHNHYTQK<br>SLSLSPGK |
| 825 | PRT | EIVLTQSPATLSLSPGERATLSCRASQSIGDYLHWYQQKPGQAPRLLIKY<br>ASQSISGIPARFSGSGSGTDFTLTITSLEPEDFAVYYCQQGYSFPYTFGGG<br>TKLEIKRTVAAPSVFIFPPSDEQLKSGTASVVCLLNNFYPREAKVQWKVD<br>NALQSGNSQESVTEQDSKDSTYSLSSTLTLSKADYEKHKVYACEVTHQG<br>LSSPVTKSFNRGEC |
| 826 | DNA | GAAGTGCAGCTGGTGGAATCTGGCGGAGGACTGGTTCAACCTGGCGG<br>CTCTCTGAGACTGTCTTGTGCCGCCTCTGGCTTCCCATTCAGCAGCTA<br>CTACATGAGCTGGGTCCGACAGGCCCCTGGCAAAGGACTTGAATGGG<br>TGTCCACCATCATCAAGAGCGGCGGCTACGCCTACTATCCCGACAGC<br>GTGAAGGACCGGTTCACCATCAGCCGGGACAACAGCAAGAACACCC<br>TGTACCTGCAGATGAGCAGCCTGAGAGCCGAGGATACCGCCGTGTAC<br>TACTGTGTTAGAGGCGGACAGGGCGCCATGGATTATTGGGGCCAGGG<br>AACCACAGTGACCGTGTCATCAGCCAGCACCAAGGGCCCCAGCGTGT<br>TCCCTCTGGCCCCTAGCAGCAAGAGCACATCTGGCGGAACAGCCGCC<br>CTGGGCTGCCTCGTGAAGGACTACTTTCCCGAGCCCGTGACCGTGTC<br>CTGGAACTCTGGCGCTCTGACAAGCGGCGTGCACACCTTTCCAGCCG<br>TGCTGCAGAGCAGCGGCCTGTACTCTCTGAGCAGCGTCGTGACAGTG<br>CCCAGCAGCTCTCTGGGCACCCAGACCTACATCTGCAACGTGAACCA<br>CAAGCCCAGCAACACCAAGGTGGACAAGAAGGTGGAACCCAAGAGC<br>TGCGACAAGACCCACACCTGTCCCCCTTGTCCTGCCCCCGAACTGCTG<br>GGAGGCCCCTTCCGTGTTCCTGTTCCCCCCAAAGCCCAAGGACACCCT<br>GATGATCAGCCGGACCCCCGAAGTGACCTGCGTGGTGGTGGATGTGT<br>CCCACGAGGACCCTGAAGTGAAGTTCAATTGGTACGTGGACGGCGTG<br>GAAGTGCACAACGCCAAGACCAAGCCTAGAGAGGAACAGTACAACA<br>GCACCTACCGGGTGGTGTCCGTGCTGACAGTGCTGCACCAGGACTGG<br>CTGAACGGCAAAGAGTACAAGTGCAAGGTGTCCAACAAGGCCCTGC<br>CTGCCCCCATCGAGAAAACCATCAGCAAGGCCAAGGGCCAGCCCCG<br>CGAACCCCAGGTGTACACACTGCCCCCAAGCAGGGACGAGCTGACC<br>AAGAACCAGGTGTCCCTGACCTGTCTCGTGAAAGGCTTCTACCCCTC<br>CGATATCGCCGTGGAATGGGAGAGCAACGGCCAGCCCGAGAACAAC<br>TACAAGACCACCCCCCCTGTGCTGGACAGCGACGGCTCATTCTTCCT<br>GTACAGCAAGCTGACCGTGGACAAGTCCCGGTGGCAGCAGGGCAAC<br>GTGTTCAGCTGCAGCGTGATGCACGAGGCCCTGCACAACCACTACAC<br>CCAGAAGTCCCTGAGCCTGAGCCCTGGCAAG |
| 827 | DNA | GAGATTGTGCTGACACAGTCTCCCGCCACACTGTCTCTTAGCCCTGGC<br>GAAAGAGCCACACTGAGCTGTAGAGCCAGCCAGAGCATCGGCGATT<br>ACCTGCACTGGTATCAGCAGAAGCCTGGACAGGCCCCTCGGCTGCTG<br>ATTAAGTACGCCAGCCAGTCCATCAGCGGCATCCCTGCCAGATTTTCT<br>GGCAGCGGCTCTGGCACCGATTTCACCCTGACCATCACCAGCCTGGA<br>ACCTGAGGACTTCGCCGTGTACTACTGCCAGCAGGGCTACAGCTTCC<br>CCTACACATTTGGCGGAGGCACCAAGCTGGAAATCAAACGAACCGTG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
|  |  | GCCGCTCCCAGCGTGTTCATCTTCCCACCTAGCGACGAGCAGCTGAA
GTCCGGCACAGCCTCTGTCGTGTGCCTGCTGAACAACTTCTACCCCG
CGAGGCCAAGGTGCAGTGGAAGGTGGACAATGCCCTGCAGAGCGGC
AACAGCCAGGAAAGCGTGACCGAGCAGGACAGCAAGGACTCCACCT
ACAGCCTGAGCAGCACCCTGACCCTGAGCAAGGCCGACTACGAGAA
GCACAAGGTGTACGCCTGCGAAGTGACCCACCAGGGCCTGTCTAGCC
CCGTGACCAAGAGCTTCAACCGGGGCGAGTGT |
| 828 | PRT | EVQLVESGGGLVQLGGSLRLSCAASGFTFSSYYMSWVRQAPGKGLEWV
STIIKSGGYAYYPDSVKDRFTISRDNSKNTLYLQMNSLRAEDTAVYYCV
KGGQGAMDYWGQGTTVTVSS |
| 829 | PRT | SYYMS |
| 830 | PRT | TIIKSGGYAYYPDSVKD |
| 831 | PRT | GGQGAMDY |
| 832 | PRT | EIVLTQSPATLSLSPGERATLSCRASQSIGDYLHWYQQKPGQAPRLLIYY
ASQSISGIPARFSGSGSGTDFTLTISSLEPEDFAVYYCQQGYSFPYTFGGGT
KLEIK |
| 833 | PRT | RASQSIGDYLH |
| 834 | PRT | YASQSIS |
| 835 | PRT | QQGYSFPYT |
| 836 | DNA | GAAGTGCAGCTGGTGGAATCTGGCGGAGGACTGGTTCAGCTCGGCGG
ATCTCTGAGACTGTCTTGTGCCGCCAGCGGCTTCACCTTCAGCAGCTA
CTACATGAGCTGGGTCCGACAGGCCCTGGCAAAGGACTTGAATGGG
TGTCCACCATCATCAAGAGCGGCGGCTACGCCTACTATCCCGACAGC
GTGAAGGACCGGTTCACCATCTCCAGAGACAACAGCAAGAACACCCT
GTACCTGCAGATGAACAGCCTGAGAGCCGAGGACACCGCCGTGTACT
ACTGTGTGAAAGGTGGACAGGGCGCCATGGACTATTGGGGCCAGGG
AACAACAGTGACCGTGTCCTCA |
| 837 | DNA | GAGATTGTGCTGACACAGTCTCCCGCCACACTGTCTCTTAGCCCTGGC
GAAAGAGCCACACTGAGCTGTAGAGCCAGCCAGAGCATCGGCGATT
ACCTGCACTGGTATCAGCAGAAGCCTGGACAGGCCCCTCGGCTGCTG
ATCTACTATGCCAGCCAGTCCATCAGCGGCATCCCCGCCAGATTTCT
GGCAGCGGCTCTGGCACCGATTTCACCCTGACCATAAGCAGCCTGGA
ACCTGAGGACTTCGCCGTGTACTACTGCCAGCAGGGCTACAGCTTCC
CCTACACATTTGGCGGAGGCACCAAGCTGGAAATCAAA |
| 838 | PRT | EVQLVESGGGLVQLGGSLRLSCAASGFTFSSYYMSWVRQAPGKGLEWV
STIIKSGGYAYYPDSVKDRFTISRDNSKNTLYLQMNSLRAEDTAVYYCV
KGGQGAMDYWGQGTTVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQ
KSLSLSPGK |
| 839 | PRT | EIVLTQSPATLSLSPGERATLSCRASQSIGDYLHWYQQKPGQAPRLLIYY
ASQSISGIPARFSGSGSGTDFTLTISSLEPEDFAVYYCQQGYSFPYTFGGGT
KLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQG
LSSPVTKSFNRGEC |
| 840 | DNA | GAAGTGCAGCTGGTGGAATCTGGCGGAGGACTGGTTCAGCTCGGCGG
ATCTCTGAGACTGTCTTGTGCCGCCAGCGGCTTCACCTTCAGCAGCTA
CTACATGAGCTGGGTCCGACAGGCCCTGGCAAAGGACTTGAATGGG
TGTCCACCATCATCAAGAGCGGCGGCTACGCCTACTATCCCGACAGC
GTGAAGGACCGGTTCACCATCTCCAGAGACAACAGCAAGAACACCCT
GTACCTGCAGATGAACAGCCTGAGAGCCGAGGACACCGCCGTGTACT
ACTGTGTGAAAGGTGGACAGGGCGCCATGGACTATTGGGGCCAGGG
AACAACAGTGACCGTGTCCTCAGCCAGCACCAAGGGCCCCAGCGTGT
TCCCTCTGGCCCCTAGCAGCAAGAGCACATCTGGCGGAACAGCCGCC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | CTGGGCTGCCTCGTGAAGGACTACTTTCCCGAGCCCGTGACCGTGTC CTGGAACTCTGGCGCTCTGACAAGCGGCGTGCACACCTTTCCAGCCG TGCTGCAGAGCAGCGGCCTGTACTCTCTGAGCAGCGTCGTGACAGTG CCCAGCAGCTCTCTGGGCACCCAGACCTACATCTGCAACGTGAACCA CAAGCCCAGCAACACCAAGGTGGACAAGAAGGTGGAACCCAAGAGC TGCGACAAGACCCACACCTGTCCCCCTTGTCCTGCCCCCGAACTGCTG GGAGGCCCTTCCGTGTTCCTGTTCCCCCCAAAGCCCAAGGACACCCT GATGATCAGCCGGACCCCCGAAGTGACCTGCGTGGTGGTGGATGTGT CCCACGAGGACCCTGAAGTGAAGTTCAATTGGTACGTGGACGGCGTG GAAGTGCACAACGCCAAGACCAAGCCTAGAGAGGAACAGTACAACA GCACCTACCGGGTGGTGTCCGTGCTGACAGTGCTGCACCAGGACTGG CTGAACGGCAAAGAGTACAAGTGCAAGGTGTCCAACAAGGCCCTGC CTGCCCCCATCGAGAAAACCATCAGCAAGGCCAAGGGCCAGCCCCG CGAACCCCAGGTGTACACACTGCCCCCAAGCAGGGACGAGCTGACC AAGAACCAGGTGTCCCTGACCTGTCTCGTGAAAGGCTTCTACCCCTC CGATATCGCCGTGGAATGGGAGAGCAACGGCCAGCCCGAGAACAAC TACAAGACCACCCCCCCTGTGCTGGACAGCGACGGCTCATTCTTCCT GTACAGCAAGCTGACCGTGGACAAGTCCCGGTGGCAGCAGGGCAAC GTGTTCAGCTGCAGCGTGATGCACGAGGCCCTGCACAACCACTACAC CCAGAAGTCCCTGAGCCTGAGCCCTGGCAAG |
| 841 | DNA | GAGATTGTGCTGACACAGTCTCCCGCCACACTGTCTCTTAGCCCTGGC GAAAGAGCCACACTGAGCTGTAGAGCCAGCCAGAGCATCGGCGATT ACCTGCACTGGTATCAGCAGAAGCCTGGACAGGCCCCTCGGCTGCTG ATCTACTATGCCAGCCAGTCCATCAGCGGCATCCCCGCCAGATTTTCT GGCAGCGGCTCTGGCACCGATTTCACCCTGACCATAAGCAGCCTGGA ACCTGAGGACTTCGCCGTGTACTACTGCCAGCAGGGCTACAGCTTCC CCTACACATTTGGCGGAGGCACCAAGCTGGAAATCAAACGAACCGTG GCCGCTCCCAGCGTGTTCATCTTCCCACCTAGCGACGAGCAGCTGAA GTCCGGCACAGCCTCTGTCGTGTGCCTGCTGAACAACTTCTACCCCCG CGAGGCCAAGGTGCAGTGGAAGGTGGACAATGCCCTGCAGAGCGGC AACAGCCAGGAAAGCGTGACCGAGCAGGACAGCAAGGACTCCACCT ACAGCCTGAGCAGCACCCTGACCCTGAGCAAGGCCGACTACGAGAA GCACAAGGTGTACGCCTGCGAAGTGACCCACCAGGGCCTGTCTAGCC CCGTGACCAAGAGCTTCAACCGGGGCGAGTGT |
| 842 | PRT | EVQLVESGGGLLQLGGSLRLSCAASGFTFSSYYMSWVRQAPGKGLEWV STIIKSGGYAYYPDSVKDRFTISRDNSKNTLNLQMNSLRAEDTAVYYCV KGGQGAMDYWGQGTTVTVSS |
| 843 | PRT | SYYMS |
| 844 | PRT | TIIKSGGYAYYPDSVKD |
| 845 | PRT | GGQGAMDY |
| 846 | PRT | EIVLTQSPATLSLSPGERATLSCRASQSIGDYLHWYQQKPGQAPRLLIKY ASQSISGIPARFSGSGSGTDFTLTISSLEPEDFAVYYCQQGYSFPYTFGGGT KLEIK |
| 847 | PRT | RASQSIGDYLH |
| 848 | PRT | YASQSIS |
| 849 | PRT | QQGYSFPYT |
| 850 | DNA | GAAGTGCAGCTGGTGGAATCTGGCGGAGGACTGCTGCAGCTTGGCGG ATCTCTGAGACTGTCTTGTGCCGCCAGCGGCTTCACCTTCAGCAGCTA CTACATGAGCTGGGTCCGACAGGCCCCTGGCAAAGGACTTGAATGGG TGTCCACCATCATCAAGAGCGGCGGCTACGCCTACTATCCCGACAGC GTGAAGGACCGGTTCACCATCTCCAGAGACAACAGCAAGAACACCCT GAACCTGCAGATGAACAGCCTGAGAGCCGAGGACACCGCCGTGTAC TACTGTGTGAAAGGTGGACAGGGCGCCATGGACTATTGGGGCCAGG GAACAACAGTGACCGTGTCCTCA |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| 851 | DNA | GAGATTGTGCTGACACAGTCTCCCGCCACACTGTCTCTTAGCCCTGGC<br>GAAAGAGCCACACTGAGCTGTAGAGCCAGCCAGAGCATCGGCGATT<br>ACCTGCACTGGTATCAGCAGAAGCCTGGACAGGCCCCTCGGCTGCTG<br>ATTAAGTACGCCAGCCAGTCCATCAGCGGCATCCCTGCCAGATTTTCT<br>GGCAGCGGCTCTGGCACCGATTTCACCCTGACCATAAGCAGCCTGGA<br>ACCTGAGGACTTCGCCGTGTACTACTGCCAGCAGGGCTACAGCTTCC<br>CCTACACATTTGGCGGAGGCACCAAGCTGGAAATCAAA |
| 852 | PRT | EVQLVESGGGLLQLGGSLRLSCAASGFTFSSYYMSWVRQAPGKGLEWV<br>STIIKSGGYAYYPDSVKDRFTISRDNSKNTLNLQMNSLRAEDTAVYYCV<br>KGGGQGAMDYWGQGTTVTVSSASTKGPSVFPLAPSSKSTSGGTAALGCL<br>VKDYFPEPVTVSWNSGALTSGVHTFPAVLQSSGLYSLSSVVTVPSSSLGT<br>QTYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENN<br>YKTTPPVLDSDGSFFLYSKLTVDKSRWQQGNVFSCSVMHEALHNHYTQ<br>KSLSLSPGK |
| 853 | PRT | EIVLTQSPATLSLSPGERATLSCRASQSIGDYLHWYQQKPGQAPRLLIKY<br>ASQSISGIPARFSGSGSGTDFTLTISSLEPEDFAVYYCQQGYSFPYTFGGGT<br>KLEIKRTVAAPSVFIFPPSDEQLKSGTASVVCLLNNFYPREAKVQWKVD<br>NALQSGNSQESVTEQDSKDSTYSLSSTLTLSKADYEKHKVYACEVTHQG<br>LSSPVTKSFNRGEC |
| 854 | DNA | GAAGTGCAGCTGGTGGAATCTGGCGGAGGACTGCTGCAGCTTGGCGG<br>ATCTCTGAGACTGTCTTGTGCCGCCAGCGGCTTCACCTTCAGCAGCTA<br>CTACATGAGCTGGGTCCGACAGGCCCCTGGCAAAGGACTTGAATGGG<br>TGTCCACCATCATCAAGAGCGGCGGCTACGCCTACTATCCCGACAGC<br>GTGAAGGACCGGTTCACCATCTCCAGAGACAACAGCAAGAACACCCT<br>GAACCTGCAGATGAACAGCCTGAGAGCCGAGGACACCGCCGTGTAC<br>TACTGTGTGAAAGGTGGACAGGGCGCCATGGACTATTGGGGCCAGG<br>GAACAACAGTGACCGTGTCCTCAGCCAGCACCAAGGGCCCCAGCGTG<br>TTCCCTCTGGCCCCTAGCAGCAAGAGCACATCTGGCGGAACAGCCGC<br>CCTGGGCTGCCTCGTGAAGGACTACTTTCCCGAGCCCGTGACCGTGT<br>CCTGGAACTCTGGCGCTCTGACAAGCGGCGTGCACACCTTTCCAGCC<br>GTGCTGCAGAGCAGCGGCCTGTACTCTCTGAGCAGCGTCGTGACAGT<br>GCCCAGCAGCTCTCTGGGCACCCAGACCTACATCTGCAACGTGAACC<br>ACAAGCCCAGCAACACCAAGGTGGACAAGAAGGTGGAACCCAAGAG<br>CTGCGACAAGACCCACACCTGTCCCCCTTGTCCTGCCCCCGAACTGCT<br>GGGAGGCCCTTCCGTGTTCCTGTTCCCCCCAAAGCCCAAGGACACCC<br>TGATGATCAGCCGGACCCCCGAAGTGACCTGCGTGGTGGTGGATGTG<br>TCCCACGAGGACCCTGAAGTGAAGTTCAATTGGTACGTGGACGGCGT<br>GGAAGTGCACAACGCCAAGACCAAGCCTAGAGAGGAACAGTACAAC<br>AGCACCTACCGGGTGGTGTCCGTGCTGACAGTGCTGCACCAGGACTG<br>GCTGAACGGCAAAGAGTACAAGTGCAAGGTGTCCAACAAGGCCCTG<br>CCTGCCCCCATCGAGAAAACCATCAGCAAGGCCAAGGGCCAGCCCC<br>GCGAACCCCAGGTGTACACACTGCCCCCAAGCAGGGACGAGCTGAC<br>CAAGAACCAGGTGTCCCTGACCTGTCTCGTGAAAGGCTTCTACCCCT<br>CCGATATCGCCGTGGAATGGGAGAGCAACGGCCAGCCCGAGAACAA<br>CTACAAGACCACCCCCCCTGTGCTGGACAGCGACGGCTCATTCTTCCT<br>GTACAGCAAGCTGACCGTGGACAAGTCCCGGTGGCAGCAGGGCAAC<br>GTGTTCAGCTGCAGCGTGATGCACGAGGCCCTGCACAACCACTACAC<br>CCAGAAGTCCCTGAGCCTGAGCCCTGGCAAG |
| 855 | DNA | GAGATTGTGCTGACACAGTCTCCCGCCACACTGTCTCTTAGCCCTGGC<br>GAAAGAGCCACACTGAGCTGTAGAGCCAGCCAGAGCATCGGCGATT<br>ACCTGCACTGGTATCAGCAGAAGCCTGGACAGGCCCCTCGGCTGCTG<br>ATTAAGTACGCCAGCCAGTCCATCAGCGGCATCCCTGCCAGATTTTCT<br>GGCAGCGGCTCTGGCACCGATTTCACCCTGACCATAAGCAGCCTGGA<br>ACCTGAGGACTTCGCCGTGTACTACTGCCAGCAGGGCTACAGCTTCC<br>CCTACACATTTGGCGGAGGCACCAAGCTGGAAATCAAACGAACCGTG<br>GCCGCTCCCAGCGTGTTCATCTTCCCACCTAGCGACGAGCAGCTGAA<br>GTCCGGCACAGCCTCTGTCGTGTGCCTGCTGAACAACTTCTACCCCCG<br>CGAGGCCAAGGTGCAGTGGAAGGTGGACAATGCCCTGCAGAGCGGC<br>AACAGCCAGGAAAGCGTGACCGAGCAGGACAGCAAGGACTCCACCT<br>ACAGCCTGAGCAGCACCCTGACCCTGAGCAAGGCCGACTACGAGAA<br>GCACAAGGTGTACGCCTGCGAAGTGACCCACCAGGGCCTGTCTAGCC<br>CCGTGACCAAGAGCTTCAACCGGGGCGAGTGT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 856 | PRT | EVQLLESGGGLVQPGGSLRLSCAASGFTFRSYAVHWVRQAPGKGLEWV SSTEGSGVGTSYTDSVKGRFTISRDNSKNTLYLQMNSLRAEDTAVYYCA RMLGGGNPLDYLDYWGQGTLVTVSS |
| 857 | PRT | SYAVH |
| 858 | PRT | STEGSGVGTSYTDSVKG |
| 859 | PRT | MLGGGNPLDYLDY |
| 860 | PRT | QSVLTQPPSASGTPGQRVTISCSGSSSNLGEGYDVHWYQQLPGKAPKLLI YYSDFRPSGVSDRFSGSKSGTSASLAISGLQSEDEADYYCAAWDDSLSSQ VFGGGTQVTVL |
| 861 | PRT | SGSSSNLGEGYDVH |
| 862 | PRT | YSDFRPS |
| 863 | PRT | AAWDDSLSSQV |
| 864 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGAAGCT ATGCCGTGCACTGGGTCCGACAGGCCCCTGGAAAAGGACTGGAATG GGTGTCCAGCACCGAAGGCTCTGGCGTGGGCACAAGCTACACCGATT CTGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAATGCTCGGCGGAGGCAACCCTCTGGACTACCTG GATTATTGGGGCCAGGGCACCCTGGTCACAGTCTCTTCA |
| 865 | DNA | CAGTCTGTTCTGACACAGCCTCCTAGCGCCTCTGGCACACCTGGACA GAGAGTGACCATCAGCTGTAGCGGCAGCAGCTCCAATCTCGGCGAGG GCTATGACGTGCACTGGTATCAGCAGCTGCCTGGCAAGGCCCCTAAA CTGCTGATCTACTACAGCGACTTCAGACCCAGCGGCGTGTCCGATAG ATTCAGCGGCTCTAAGAGCGGCACATCTGCCAGCCTGGCCATCTCTG GACTGCAGAGCGAAGATGAGGCCGACTACTATTGCGCCGCCTGGGAT GATAGCCTGAGCAGCCAAGTTTTTGGCGGCGGAACCCAAGTGACCGT GCTA |
| 866 | PRT | EVQLLESGGGLVQPGGSLRLSCAASGFTFRSYAVHWVRQAPGKGLEWV SSTEGSGVGTSYTDSVKGRFTISRDNSKNTLYLQMNSLRAEDTAVYYCA RMLGGGNPLDYLDYWGQGTLVTVSSASTKGPSVFPLAPSSKSTSGGTAA LGCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK |
| 867 | PRT | QSVLTQPPSASGTPGQRVTISCSGSSSNLGEGYDVHWYQQLPGKAPKLLI YYSDFRPSGVSDRFSGSKSGTSASLAISGLQSEDEADYYCAAWDDSLSSQ VFGGGTQVTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 868 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGAAGCT ATGCCGTGCACTGGGTCCGACAGGCCCCTGGAAAAGGACTGGAATG GGTGTCCAGCACCGAAGGCTCTGGCGTGGGCACAAGCTACACCGATT CTGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAATGCTCGGCGGAGGCAACCCTCTGGACTACCTG GATTATTGGGGCCAGGGCACCCTGGTCACAGTCTCTTCAGCCAGCAC CAAGGGCCCCAGCGTGTTCCCTCTGGCCCCTAGCAGCAAGAGCACAT CTGGCGGAACAGCCGCCCTGGGCTGCCTCGTGAAGGACTACTTTCCC GAGCCCGTGACCGTGTCCTGGAACTCTGGCGCTCTGACAAGCGGCGT GCACACCTTTCCAGCCGTGCTGCAGAGCAGCGGCCTGTACTCTCTGA GCAGCGTCGTGACAGTGCCCAGCAGCTCTCTGGGCACCCAGACCTAC ATCTGCAACGTGAACCACAAGCCCAGCAACACCAAGGTGGACAAGA AGGTGGAACCCAAGAGCTGCGACAAGCCCACACCTGTCCCCCTTGT CCTGCCCCCGAACTGCTGGGAGGCCCTTCCGTGTTCCTGTTCCCCCCA |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | AAGCCCAAGGACACCCTGATGATCAGCCGGACCCCCGAAGTGACCTG |
| | | CGTGGTGGTGGATGTGTCCCACGAGGACCCTGAAGTGAAGTTCAATT |
| | | GGTACGTGGACGGCGTGGAAGTGCACAACGCCAAGACCAAGCCTAG |
| | | AGAGGAACAGTACAACAGCACCTACCGGGTGGTGTCCGTGCTGACA |
| | | GTGCTGCACCAGGACTGGCTGAACGGCAAAGAGTACAAGTGCAAGG |
| | | TGTCCAACAAGGCCCTGCCCTGCCCCATCGAGAAAACCATCAGCAAG |
| | | GCCAAGGGCCAGCCCCGCGAACCCCAGGTGTACACACTGCCCCCAAG |
| | | CAGGGACGAGCTGACCAAGAACCAGGTGTCCCTGACCTGTCTCGTGA |
| | | AAGGCTTCTACCCCTCCGATATCGCCGTGGAATGGGAGAGCAACGGC |
| | | CAGCCCGAGAACAACTACAAGACCACCCCCCCTGTGCTGGACAGCGA |
| | | CGGCTCATTCTTCCTGTACAGCAAGCTGACCGTGGACAAGTCCCGGT |
| | | GGCAGCAGGGCAACGTGTTCAGCTGCAGCGTGATGCACGAGGCCCTG |
| | | CACAACCACTACACCCAGAAGTCCCTGAGCCTGAGCCCTGGCAAG |
| 869 | DNA | CAGTCTGTTCTGACACAGCCTCCTAGCGCCTCTGGCACACCTGGACA |
| | | GAGAGTGACCATCAGCTGTAGCGGCAGCAGCTCCAATCTCGGCGAGG |
| | | GCTATGACGTGCACTGGTATCAGCAGCTGCCTGGCAAGGCCCCTAAA |
| | | CTGCTGATCTACTACAGCGACTTCAGACCCAGCGGCGTGTCCGATAG |
| | | ATTCAGCGGCTCTAAGAGCGGCACATCTGCCAGCCTGGCCATCTCTG |
| | | GACTGCAGAGCGAAGATGAGGCCGACTACTATTGCGCCGCCTGGGAT |
| | | GATAGCCTGAGCAGCCAAGTTTTTGGCGGCGGAACCCAAGTGACCGT |
| | | GCTAGGCCAGCCTAAAGCCGCCCCTAGCGTGACCCTGTTCCCTCCAA |
| | | GCAGCGAGGAACTGCAGGCCAACAAGGCCACCCTCGTGTGCCTGATC |
| | | AGCGACTTCTATCCTGGCGCCGTGACCGTGGCCTGGAAGGCCGATAG |
| | | CTCTCCTGTGAAGGCCGGCGTGGAAACCACCACCCCTAGCAAGCAGA |
| | | GCAACAACAAATACGCCGCCAGCAGCTACCTGAGCCTGACCCCCGAG |
| | | CAGTGGAAGTCCCACAGATCCTACAGCTGCCAAGTGACCCACGAGGG |
| | | CAGCACCGTGGAAAAGACAGTGGCCCCTACCGAGTGCAGC |
| 870 | PRT | EVQLLESGGGLVQPGGSLRLSCAASGFTFRSYAVHWVRQAPGKGLEWV |
| | | SSTEGSGVGTSYTDSVKGRFTISRDNSKNTLYLQMNSLRAEDTAVYYCA |
| | | RMLGGGNPLDYLDYWGQGTLVTVSS |
| 871 | PRT | SYAVH |
| 872 | PRT | STEGSGVGTSYTDSVKG |
| 873 | PRT | MLGGGNPLDYLDY |
| 874 | PRT | QSVLTQPPSASGTPGQRVTISCSGSSSNLGEGYDVHWYQQLPGKAPKLLI |
| | | YYSDFRPSGVSDRFSGSKSGTSASLAISGLQSEDEADYYCAAWDDSLSSQ |
| | | VFGGGTQVTVL |
| 875 | PRT | SGSSSNLGEGYDVH |
| 876 | PRT | YSDFRPS |
| 877 | PRT | AAWDDSLSSQV |
| 878 | DNA | GAAGTTCAGCTGCTGGAATCTGGCGGCGGACTGGTTCAACCTGGCGG |
| | | ATCTCTGAGACTGAGCTGTGCCGCCAGCGGCTTCACCTTTAGAAGCT |
| | | ATGCCGTGCACTGGGTCCGACAGGCCCCTGGAAAAGGACTGGAATG |
| | | GGTGTCCAGCACCGAAGGCTCTGGCGTGGGCACAAGCTACACCGATT |
| | | CTGTGAAGGGCAGATTCACCATCAGCCGGGACAACAGCAAGAACAC |
| | | CCTGTACCTGCAGATGAACAGCCTGAGAGCCGAGGACACCGCCGTGT |
| | | ACTACTGTGCCAGAATGCTCGGCGGAGGCAACCCTCTGGACTACCTG |
| | | GATTATTGGGGCCAGGGCACCCTGGTCACAGTCTCTTCA |
| 879 | DNA | CAGTCTGTTCTGACACAGCCTCCTAGCGCCTCTGGCACACCTGGACA |
| | | GAGAGTGACCATCAGCTGTAGCGGCAGCAGCTCCAATCTCGGCGAGG |
| | | GCTATGACGTGCACTGGTATCAGCAGCTGCCTGGCAAGGCCCCTAAA |
| | | CTGCTGATCTACTACAGCGACTTCAGACCCAGCGGCGTGTCCGATAG |
| | | ATTCAGCGGCTCTAAGAGCGGCACATCTGCCAGCCTGGCCATCTCTG |
| | | GACTGCAGAGCGAAGATGAGGCCGACTACTATTGCGCCGCCTGGGAT |
| | | GATAGCCTGAGCAGCCAAGTTTTTGGCGGCGGAACCCAAGTGACCGT |
| | | GCTA |
| 880 | PRT | EVQLLESGGGLVQPGGSLRLSCAASGFTFRSYAVHWVRQAPGKGLEWV |
| | | SSTEGSGVGTSYTDSVKGRFTISRDNSKNTLYLQMNSLRAEDTAVYYCA |
| | | RMLGGGNPLDYLDYWGQGTLVTVSSASTKGPSVFPLAPSSKSTSGGTAA |
| | | LGCLVKDYFPEPVTVSWNSGALTSGVHTFPAVLQSSGLYSLSSVVTVPSS |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| | | SLGTQTYICNVNHKPSNTKVDKKVEPKSCAAGSEQKLISEEDLSGSAAA HHHHHH |
| 881 | PRT | QSVLTQPPSASGTPGQRVTISCSGSSSNLGEGYDVHWYQQLPGKAPKLLI YYSDFRPSGVSDRFSGSKSGTSASLAISGLQSEDEADYYCAAWDDSLSSQ VFGGGTQVTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 882 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGAAGCT ATGCCGTGCACTGGGTCCGACAGGCCCCTGGAAAAGGACTGGAATG GGTGTCCAGCACCGAAGGCTCTGGCGTGGGCACAAGCTACACCGATT CTGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAATGCTCGGCGGAGGCAACCCTCTGGACTACCTG GATTATTGGGGCCAGGGCACCCTGGTCACAGTCTCTTCAGCCTCCAC CAAGGGCCCATCGGTGTTCCCCCTGGCACCCTCCTCCAAGAGCACCT CTGGGGGCACAGCGGCCCTGGGCTGCCTGGTCAAGGACTACTTCCCC GAACCGGTGACGGTGTCGTGGAACTCAGGCGCCCTGACCAGCGGCGT GCACACCTTCCCGGCTGTCCTACAGTCCTCAGGACTCTACTCCCTCAG CAGCGTGGTGACCGTGCCCTCAGCAGCTTGGGCACCCAGACCTACA TCTGCAACGTGAATCACAAGCCCAGCAACACCAAGGTGGACAAGAA AGTTGAGCCCAAATCTTGTGCAGCGGGTTCTGAACAAAAACTCATCT CAGAAGAGGATCTGTCTGGATCAGCGGCCGCCCATCATCATCATCAT CAT |
| 883 | DNA | CAGTCTGTTCTGACACAGCCTCCTAGCGCCTCTGGCACACCTGGACA GAGAGTGACCATCAGCTGTAGCGGCAGCAGCTCCAATCTCGGCGAGG GCTATGACGTGCACTGGTATCAGCAGCTGCCTGGCAAGGCCCCTAAA CTGCTGATCTACTACAGCGACTTCAGACCCAGCGGCGTGTCCGATAG ATTCAGCGGCTCTAAGAGCGGCACATCTGCCAGCCTGGCCATCTCTG GACTGCAGAGCGAAGATGAGGCCGACTACTATTGCGCCGCCTGGGAT GATAGCCTGAGCAGCCAAGTTTTTGGCGGCGGAACCCAAGTGACCGT GCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 884 | PRT | NYQNGKNNVPRLKLSYKEMLESNNVITFNGLANSSSYHTFLLDEERSRL YVGAKDHIFSFNLVNIKDFQKIAWPVSYTRRDECKWAGKDILRECANFI KVLKVYNQTHLYACGTGAFHPICTYVGIGHHPEDNIFKLEDSHFENGRG KSPYDPKLLTASLLIDGELYSGTAADFMGRDFAIFRTLGQHHPIRTEQHD SRWLNDPRFISAHLIPESDNPEDDKVYFFFRENAIDGEHSGKATHARIGQI CKNDFGGHRSLVNKWTTFLKARLICSVPGPNGIDTHFDELQDVFLMNSK DPKNPIVYGVFTTSSNIFRGSAVCMYSMSDVRRVFLGPYAHRDGPNYQ WVPFQGRVPYPRPGTCPSKTFGGFESTKDLPDDVITFARSHPAMYNPVFP INNRPIMVKTDVNYQFTQIVVDRVDAEDGQYDVMFIGTDVGTVLKVVSI PKETWHDLEEVLLEEMTVFREPTTISAMELSTKQQQLYVGSAAGVAQLP LHRCDIYGKACAECCLARDPYCAWDGSSCSRYFPTAKRRTRRQDIRNG DPLTHCSDGGIEGRMDHHHHHH |
| 885 | DNA | AACTATCAGAACGGCAAGAACAACGTGCCCCGGCTGAAGCTGAGCT ACAAAGAGATGCTGGAAAGCAACAACGTGATCACCTTCAACGGCCT GGCCAACAGCAGCAGCTACCACACCTTTCTGCTGGACGAGGAACGGT CCAGACTGTACGTGGGAGCCAAGGACCACATCTTCAGCTTCAACCTG GTCAACATCAAGGACTTCCAGAAAATCGCCTGGCCTGTGTCCTACAC CAGACGGGATGAGTGTAAATGGGCCGGCAAGGACATCCTGAGAGAG TGCGCCAACTTCATCAAGGTGCTGAAGGTGTACAATCAGACCCACCT GTACGCCTGTGGCACCGGCGCTTTTCACCCTATCTGTACCTATGTCGG CATCGGCCACCATCCTGAGGACAATATCTTCAAGCTCGAGGACAGCC ACTTCGAGAACGGCAGAGGCAAGAGCCCCTACGATCCCAAACTGCTG ACAGCCTCTCTGCTGATCGACGGCGAGCTGTATTCTGGCACAGCCGC CGATTTCATGGGCAGAGACTTCGCCATCTTCAGAACCCTGGGCCAGC ATCACCCCATCAGAACCGAGCAGCACGACAGCAGATGGCTGAACGA CCCCAGATTCATCAGCGCCCATCTGATCCCCGAGAGCGACAACCCCG AGGACGACAAGGTGTACTTCTTCTTCCGGGAAAACGCCATCGACGGG GAGCACTCTGGAAAAGCCACACACGCCAGAATCGGCCAGATCTGCA |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | AGAACGACTTCGGCGGCCACAGATCCCTCGTGAACAAGTGGACCACC TTCCTGAAGGCCCGGCTGATCTGTTCTGTGCCCGGACCTAATGGCATC GATACCCACTTCGACGAGCTGCAGGACGTGTTCCTGATGAACAGCAA GGACCCCAAGAATCCCATCGTGTACGGCGTGTTCACCACCAGCAGCA ACATCTTTAGAGGCAGCGCCGTGTGCATGTACAGCATGTCCGATGTG CGGAGAGTGTTTCTGGGCCCCTACGCTCACAGAGATGGCCCCAATTA TCAGTGGGTGCCATTCCAGGGCAGAGTGCCCTATCCTAGACCTGGCA CCTGTCCTAGCAAGACCTTTGGCGGCTTCGAGAGCACCAAGGACCTG CCTGACGATGTGATTACCTTCGCCAGATCTCACCCCGCCATGTACAAC CCTGTGTTCCCCATCAACAACAGGCCCATCATGGTCAAGACCGACGT GAACTACCAGTTCACCCAGATCGTGGTGGACAGAGTGGATGCCGAGG ACGGCCAGTACGACGTGATGTTCATCGGCACCGATGTGGGCACCGTG CTGAAAGTGGTGTCTATCCCCAAAGAGACATGGCACGACCTGGAAGA GGTGCTGCTGGAAGAGATGACCGTGTTCAGAGAGCCCACCACCATCT CCGCCATGGAACTGAGCACAAAACAGCAACAGCTGTATGTGGGCTCC GCCGCTGGTGTTGCTCAACTGCCTCTGCACAGATGCGACATCTACGG CAAAGCCTGCGCCGAGTGTTGCCTGGCCAGAGATCCTTACTGTGCCT GGGATGGCAGCAGCTGCAGCAGATACTTTCCCACCGCCAAGCGGAG AACCAGACGGCAGGATATCAGAAACGGCGACCCTCTGACACACTGC AGCGACGGTGGCATCGAGGGCCGCATGGATCATCATCATCACCATCA T |

What is claimed is:

1. An isolated antibody or antigen-binding fragment thereof which binds to human Semaphorin 3A (Sema3A), wherein said isolated antibody or antigen-binding fragment thereof comprises:
   a heavy chain antigen-binding region that comprises an H-CDR1 comprising SEQ ID NO: 42, an H-CDR2 comprising SEQ ID NO: 43, and an H-CDR3 comprising SEQ ID NO: 44 and a light chain antigen-binding region that comprises an L-CDR1 comprising SEQ ID NO: 46, an L-CDR2 comprising SEQ ID NO: 47, and an L-CDR3 comprising SEQ ID NO: 48; or
   a heavy chain antigen-binding region that comprises an H-CDR1 comprising SEQ ID NO: 62, an H-CDR2 comprising SEQ ID NO: 63, and an H-CDR3 comprising SEQ ID NO: 64 and a light chain antigen-binding region that comprises an L-CDR1 comprising SEQ ID NO: 66, an L-CDR2 comprising SEQ ID NO: 67, and an L-CDR3 comprising SEQ ID NO: 68; or
   a heavy chain antigen-binding region that comprises an H-CDR1 comprising SEQ ID NO: 102, an H-CDR2 comprising SEQ ID NO: 103, and an H-CDR3 comprising SEQ ID NO: 104 and a light chain antigen-binding region that comprises an L-CDR1 comprising SEQ ID NO: 106, an L-CDR2 comprising SEQ ID NO: 107, and an L-CDR3 comprising SEQ ID NO: 108; or
   a heavy chain antigen-binding region that comprises an H-CDR1 comprising SEQ ID NO: 122, an H-CDR2 comprising SEQ ID NO: 123, and an H-CDR3 comprising SEQ ID NO: 124 and a light chain antigen-binding region that comprises an L-CDR1 comprising SEQ ID NO: 126, an L-CDR2 comprising SEQ ID NO: 127, and an L-CDR3 comprising SEQ ID NO: 128; or
   a heavy chain antigen-binding region that comprises an H-CDR1 comprising SEQ ID NO: 162, an H-CDR2 comprising SEQ ID NO: 163, and an H-CDR3 comprising SEQ ID NO: 164 and a light chain antigen-binding region that comprises an L-CDR1 comprising SEQ ID NO: 166, an L-CDR2 comprising SEQ ID NO: 167, and an L-CDR3 comprising SEQ ID NO: 168; or
   a heavy chain antigen-binding region that comprises an H-CDR1 comprising SEQ ID NO: 182, an H-CDR2 comprising SEQ ID NO: 183, and an H-CDR3 comprising SEQ ID NO: 184 and a light chain antigen-binding region that comprises an L-CDR1 comprising SEQ ID NO: 186, an L-CDR2 comprising SEQ ID NO: 187, and an L-CDR3 comprising SEQ ID NO: 188; or
   a heavy chain antigen-binding region that comprises an H-CDR1 comprising SEQ ID NO: 342, an H-CDR2 comprising SEQ ID NO: 343, and an H-CDR3 comprising SEQ ID NO: 344 and a light chain antigen-binding region that comprises an L-CDR1 comprising SEQ ID NO: 346, an L-CDR2 comprising SEQ ID NO: 347, and an L-CDR3 comprising SEQ ID NO: 348.

2. The isolated antibody or antigen-binding fragment according to claim 1, comprising:
   a variable heavy chain domain that is at least 98% identical to SEQ ID NO: 41 and a variable light chain domain that is at least 98%, identical to SEQ ID NO: 45; or
   a variable heavy chain domain that is at least 98% identical to SEQ ID NO: 61 and a variable light chain domain that is at least 98%, identical to SEQ ID NO: 65; or
   a variable heavy chain domain that is at least 98% identical to SEQ ID NO: 101 and a variable light chain domain that is at least 98%, identical to SEQ ID NO: 105; or
   a variable heavy chain domain that is at least 98% identical to SEQ ID NO: 121 and a variable light chain domain that is at least 98%, identical to SEQ ID NO: 125; or
   a variable heavy chain domain that is at least 98% identical to SEQ ID NO: 161 and a variable light chain domain that is at least 98%, identical to SEQ ID NO: 165;

a variable heavy chain domain that is at least 98% identical to SEQ ID NO: 181 and a variable light chain domain that is at least 98%, identical to SEQ ID NO: 185; or a variable heavy chain domain that is at least 98% identical to SEQ ID NO: 341 and a variable light chain domain that is at least 98%, identical to SEQ ID NO: 345.

3. The isolated antibody or antigen-binding fragment according to claim 1, comprising:

a variable heavy chain domain comprising SEQ ID NO: 41 and a variable light chain domain comprising SEQ ID NO: 45; or a variable heavy chain domain comprising SEQ ID NO: 61 and a variable light chain domain comprising SEQ ID NO: 65; or a variable heavy chain domain comprising SEQ ID NO: 101 and a variable light chain domain comprising SEQ ID NO: 105; or a variable heavy chain domain comprising SEQ ID NO: 121 and a variable light chain domain comprising SEQ ID NO: 125; or a variable heavy chain domain comprising SEQ ID NO: 161 and a variable light chain domain comprising SEQ ID NO: 165; or a variable heavy chain domain comprising SEQ ID NO: 181 and a variable light chain domain comprising SEQ ID NO: 185; or a variable heavy chain domain comprising SEQ ID NO: 341 and a variable light chain domain comprising SEQ ID NO: 345.

4. The isolated antibody according to claim 1, wherein said isolated antibody is an IgG1 or an IgG4 antibody.

5. The isolated antibody according to claim 1, comprising:

a heavy chain comprising SEQ ID NO: 57 and a light chain comprising SEQ ID NO: 58; or a heavy chain comprising SEQ ID NO: 77 and a light chain comprising SEQ ID NO: 78; or a heavy chain comprising SEQ ID NO: 117 and a light chain comprising SEQ ID NO: 118; or a heavy chain comprising SEQ ID NO: 137 and a light chain comprising SEQ ID NO: 138; or a heavy chain comprising SEQ ID NO: 177 and a light chain comprising SEQ ID NO: 178; or a heavy chain comprising SEQ ID NO: 197 and a light chain comprising SEQ ID NO: 198; or a heavy chain comprising SEQ ID NO: 357 and a light chain comprising SEQ ID NO: 358.

6. The antigen-binding fragment according to claim 1, which is an scFv, Fab, Fab' fragment or a F(ab')2 fragment.

7. The isolated antibody or antigen-binding fragment according to claim 1, which is a monoclonal antibody or antigen-binding fragment thereof.

8. The isolated antibody or antigen-binding fragment according to claim 1, which is a human, humanized, or chimeric antibody or antigen-binding fragment thereof.

9. An antibody conjugate, comprising the isolated antibody or antigen binding fragment according to claim 1.

10. A pharmaceutical composition comprising the isolated antibody or antigen-binding fragment according to claim 1 or an antibody conjugate comprising the isolated antibody or antigen binding fragment according to claim 1.

11. A kit comprising the isolated antibody or antigen-binding fragment according to claim 1 or an antibody conjugate comprising the isolated antibody or antigen binding fragment according to claim 1 or a pharmaceutical composition comprising the isolated antibody or antigen-binding fragment of claim 1; and instructions for use.

* * * * *

SEQUENCE LISTING

<160> NUMBER OF SEQ ID NOS: 885

<210> SEQ ID NO 1
<211> LENGTH: 124
<212> TYPE: PRT
<213> ORGANISM: Artificial Sequence
<220> FEATURE:
<223> OTHER INFORMATION: antibody sequence

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Gly Trp Val Arg Gln Ala Pro Gly Lys Gly Leu Glu Trp Val
        35                  40                  45

Ala Gly Ile Asp Asp Asp Gly Asp Ser Asp Thr Arg Tyr Ala Pro Ala
    50                  55                  60

Val Lys Gly Arg Ala Thr Ile Ser Arg Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Lys His Thr Gly Ile Gly Ala Asn Ser Ala Gly Ser Ile Asp
            100                 105                 110

Ala Trp Gly Gln Gly Thr Leu Val Thr Val Ser Ser
        115                 120

<210> SEQ ID NO 2
<211> LENGTH: 5
<212> TYPE: PRT
<213> ORGANISM: Artificial Sequence
<220> FEATURE:
<223> OTHER INFORMATION: antibody sequence

```
<400> SEQUENCE: 2

Ser Tyr Pro Met Gly
1               5

<210> SEQ ID NO 3
<211> LENGTH: 18
<212> TYPE: PRT
<213> ORGANISM: Artificial Sequence
<220> FEATURE:
<223> OTHER INFORMATION: antibody sequence

<400> SEQUENCE: 3

Gly Ile Asp Asp Asp Gly Asp Ser Asp Thr Arg Tyr Ala Pro Ala Val
1               5                   10                  15

Lys Gly

<210> SEQ ID NO 4
<211> LENGTH: 14
<212> TYPE: PRT
<213> ORGANISM: Artificial Sequence
<220> FEATURE:
<223> OTHER INFORMATION: antibody sequence

<400> SEQUENCE: 4

His Thr Gly Ile Gly Ala Asn Ser Ala Gly Ser Ile Asp Ala
1               5                   10

<210> SEQ ID NO 5
<211> LENGTH: 108
<212> TYPE: PRT
<213> ORGANISM: Artificial Sequence
<220> FEATURE:
<223> OTHER INFORMATION: antibody sequence

<400> SEQUENCE: 5

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Thr Gly Ser Tyr
                20                  25                  30

Tyr Tyr Gly Trp Tyr Gln Gln Lys Pro Gly Gln Ala Pro Val Thr Val
                35                  40                  45

Ile Tyr Tyr Asn Asn Lys Arg Pro Ser Asp Ile Pro Glu Arg Phe Ser
                50                  55                  60

Gly Ser Leu Ser Gly Thr Thr Asn Thr Leu Thr Ile Ser Gly Val Gln
65                  70                  75                  80

Ala Glu Asp Glu Ala Asp Tyr Tyr Cys Gly Ser Ala Asp Asn Ser Gly
                85                  90                  95

Asp Ala Phe Gly Thr Gly Thr Lys Val Thr Val Leu
                100                 105

<210> SEQ ID NO 6
<211> LENGTH: 13
<212> TYPE: PRT
<213> ORGANISM: Artificial Sequence
<220> FEATURE:
<223> OTHER INFORMATION: antibody sequence

<400> SEQUENCE: 6

Ser Gly Gly Gly Ser Tyr Thr Gly Ser Tyr Tyr Tyr Gly
1               5                   10
```

```
<210> SEQ ID NO 7
<211> LENGTH: 7
<212> TYPE: PRT
<213> ORGANISM: Artificial Sequence
<220> FEATURE:
<223> OTHER INFORMATION: antibody sequence

<400> SEQUENCE: 7

Tyr Asn Asn Lys Arg Pro Ser
1               5

<210> SEQ ID NO 8
<211> LENGTH: 9
<212> TYPE: PRT
<213> ORGANISM: Artificial Sequence
<220> FEATURE:
<223> OTHER INFORMATION: antibody sequence

<400> SEQUENCE: 8

Gly Ser Ala Asp Asn Ser Gly Asp Ala
1               5

<210> SEQ ID NO 9
<211> LENGTH: 372
<212> TYPE: DNA
<213> ORGANISM: Artificial Sequence
<220> FEATURE:
<223> OTHER INFORMATION: antibody sequence

<400> SEQUENCE: 9
gaagttcagc tgctggaatc tgcggcgga  ctggttcaac ctggcggatc tctgagactg      60
agctgtgccg ccagcggctt cacctttagc agctatccta tgggctgggt ccgacaggcc    120
cctggcaaag gacttgaatg ggtggccggc atcgacgacg atggcgatag cgatacaaga    180
tacgcccctg ccgtgaaggg cagagccacc atctccagag acaacagcaa gaacaccgtg    240
tacctgcaga tgaacagcct gagagccgag gacaccgccg tgtactattg tgccaagcac    300
acaggcatcg gcgccaattc tgccggctct attgatgcct ggggccaggg aacactggtc    360
acagtttctt ca                                                        372

<210> SEQ ID NO 10
<211> LENGTH: 15
<212> TYPE: DNA
<213> ORGANISM: Artificial Sequence
<220> FEATURE:
<223> OTHER INFORMATION: antibody sequence

<400> SEQUENCE: 10
agctatccta tgggc                                                       15

<210> SEQ ID NO 11
<211> LENGTH: 54
<212> TYPE: DNA
<213> ORGANISM: Artificial Sequence
<220> FEATURE:
<223> OTHER INFORMATION: antibody sequence

<400> SEQUENCE: 11
ggcatcgacg acgatggcga tagcgataca agatacgccc ctgccgtgaa gggc            54

<210> SEQ ID NO 12
<211> LENGTH: 42
<212> TYPE: DNA
<213> ORGANISM: Artificial Sequence
<220> FEATURE:
```

<223> OTHER INFORMATION: antibody sequence

<400> SEQUENCE: 12
cacacaggca tcggcgccaa ttctgccggc tctattgatg cc        42

<210> SEQ ID NO 13
<211> LENGTH: 324
<212> TYPE: DNA
<213> ORGANISM: Artificial Sequence
<220> FEATURE:
<223> OTHER INFORMATION: antibody sequence

<400> SEQUENCE: 13
agctatgagc tgacacagcc tccaagcgtg tccgtgtctc tggacagac cgccagaatc    60
acatgtagcg gcggaggcag ctacaccggc agctactact atggctggta tcagcagaag  120
cccggacagg cccctgtgac cgtgatctac tacaacaaca gcggcccag cgacatcccc   180
gagagatttt ctggctctct gagcggcacc accaacacac tgacaatctc tggcgtgcag  240
gccgaggacg aggccgatta ctattgtggc agcgccgata atagcggcga cgcctttggc  300
accggcacca aagttacagt gcta                                         324

<210> SEQ ID NO 14
<211> LENGTH: 39
<212> TYPE: DNA
<213> ORGANISM: Artificial Sequence
<220> FEATURE:
<223> OTHER INFORMATION: antibody sequence

<400> SEQUENCE: 14
agcggcggag gcagctacac cggcagctac tactatggc        39

<210> SEQ ID NO 15
<211> LENGTH: 21
<212> TYPE: DNA
<213> ORGANISM: Artificial Sequence
<220> FEATURE:
<223> OTHER INFORMATION: antibody sequence

<400> SEQUENCE: 15
tacaacaaca gcggcccag c        21

<210> SEQ ID NO 16
<211> LENGTH: 27
<212> TYPE: DNA
<213> ORGANISM: Artificial Sequence
<220> FEATURE:
<223> OTHER INFORMATION: antibody sequence

<400> SEQUENCE: 16
ggcagcgccg ataatagcgg cgacgcc        27

<210> SEQ ID NO 17
<211> LENGTH: 453
<212> TYPE: PRT
<213> ORGANISM: Artificial Sequence
<220> FEATURE:
<223> OTHER INFORMATION: antibody sequence

<400> SEQUENCE: 17

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30

```
Pro Met Gly Trp Val Arg Gln Ala Pro Gly Lys Gly Leu Glu Trp Val
            35                  40                  45

Ala Gly Ile Asp Asp Asp Gly Asp Ser Asp Thr Arg Tyr Ala Pro Ala
 50                  55                  60

Val Lys Gly Arg Ala Thr Ile Ser Arg Asp Asn Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Lys His Thr Gly Ile Gly Ala Asn Ser Ala Gly Ser Ile Asp
                100                 105                 110

Ala Trp Gly Gln Gly Thr Leu Val Thr Val Ser Ser Ala Ser Thr Lys
                115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445
```

Ser Leu Ser Pro Gly
    450

<210> SEQ ID NO 18
<211> LENGTH: 214
<212> TYPE: PRT
<213> ORGANISM: Artificial Sequence
<220> FEATURE:
<223> OTHER INFORMATION: antibody sequence

<400> SEQUENCE: 18

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Thr Gly Ser Tyr
            20                  25                  30

Tyr Tyr Gly Trp Tyr Gln Gln Lys Pro Gly Gln Ala Pro Val Thr Val
        35                  40                  45

Ile Tyr Tyr Asn Asn Lys Arg Pro Ser Asp Ile Pro Glu Arg Phe Ser
    50                  55                  60

Gly Ser Leu Ser Gly Thr Thr Asn Thr Leu Thr Ile Ser Gly Val Gln
65                  70                  75                  80

Ala Glu Asp Glu Ala Asp Tyr Tyr Cys Gly Ser Ala Asp Asn Ser Gly
                85                  90                  95

Asp Ala Phe Gly Thr Gly Thr Lys Val Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 19
<211> LENGTH: 1359
<212> TYPE: DNA
<213> ORGANISM: Artificial Sequence
<220> FEATURE:
<223> OTHER INFORMATION: antibody sequence

<400> SEQUENCE: 19
gaagttcagc tgctggaatc tggcggcgga ctggttcaac tggcggatc tctgagactg      60 agctgtgccg ccagcggctt cacctttagc agctatccta tgggctgggt ccgacaggcc    120
cctggcaaag gacttgaatg ggtggccggc atcgacgacg atggcgatag cgatacaaga    180
tacgcccctg ccgtgaaggg cagagccacc atctccagag acaacagcaa gaacaccgtg    240
tacctgcaga tgaacagcct gagagccgag gacaccgccg tgtactattg tccaagcac     300 acaggcatcg cgccaattc tgccggctct attgatgcct ggggccaggg aacactggtc    360
acagtttctt cagccagcac caagggcccc agcgtgttcc ctctggcccc tagcagcaag    420

| | |
|---|---|
| agcacatctg gcggaacagc cgccctgggc tgcctcgtga aggactactt tcccgagccc | 480 |
| gtgaccgtgt cctggaactc tggcgctctg acaagcggcg tgcacacctt ccagccgtg | 540 |
| ctgcagagca gcggcctgta ctctctgagc agcgtcgtga cagtgcccag cagctctctg | 600 |
| ggcacccaga cctacatctg caacgtgaac cacaagccca gcaacaccaa ggtggacaag | 660 |
| aaggtggaac ccaagagctg cgacaagacc cacacctgtc ccccttgtcc tgcccccgaa | 720 |
| ctgctgggag gcccttccgt gttcctgttc cccccaaagc ccaaggacac cctgatgatc | 780 |
| agccggaccc ccgaagtgac ctgcgtggtg gtggatgtgt cccacgagga ccctgaagtg | 840 |
| aagttcaatt ggtacgtgga cggcgtggaa gtgcacaacg ccaagaccaa gcctagagag | 900 |
| gaacagtaca acagcaccta ccgggtggtg tccgtgctga cagtgctgca ccaggactgg | 960 |
| ctgaacggca agagtacaa gtgcaaggtg tccaacaagg ccctgcctgc ccccatcgag | 1020 |
| aaaaccatca gcaaggccaa gggccagccc cgcgaacccc aggtgtacac actgccccca | 1080 |
| agcagggacg agctgaccaa gaaccaggtg tccctgacct gtctcgtgaa aggcttctac | 1140 |
| ccctccgata tcgccgtgga atgggagagc aacggccagc cgagaacaa ctacaagacc | 1200 |
| accccccctg tgctggacag cgacggctca ttcttcctgt acagcaagct gaccgtggac | 1260 |
| aagtcccggt ggcagcaggg caacgtgttc agctgcagcg tgatgcacga ggccctgcac | 1320 |
| aaccactaca cccagaagtc cctgagcctg agccctggc | 1359 |

<210> SEQ ID NO 20
<211> LENGTH: 642
<212> TYPE: DNA
<213> ORGANISM: Artificial Sequence
<220> FEATURE:
<223> OTHER INFORMATION: antibody sequence

<400> SEQUENCE: 20

| | |
|---|---|
| agctatgagc tgacacagcc tccaagcgtg tccgtgtctc ctggacagac cgccagaatc | 60 |
| acatgtagcg gcggaggcag ctacaccggc agctactact atggctggta tcagcagaag | 120 |
| cccggacagg cccctgtgac cgtgatctac tacaacaaca gcggcccag cgacatcccc | 180 |
| gagagatttt ctggctctct gagcggcacc accaacacac tgacaatctc tggcgtgcag | 240 |
| gccgaggacg aggccgatta ctattgtggc agcgccgata tagcggcga cgccttggc | 300 |
| accggcacca agttacagt gctaggccag cctaaagccg cccctagcgt gaccctgttc | 360 |
| cctccaagca gcgaggaact gcaggccaac aaggccaccc tcgtgtgcct gatcagcgac | 420 |
| ttctatcctg gcgccgtgac cgtggcctgg aaggccgata gctctcctgt gaaggccggc | 480 |
| gtggaaacca ccacccctag caagcagagc aacaacaaat acgccgccag cagctacctg | 540 |
| agcctgaccc ccgagcagtg gaagtcccac agatcctaca gctgccaagt gacccacgag | 600 |
| ggcagcaccg tggaaaagac agtggcccct accgagtgca gc | 642 |

<210> SEQ ID NO 21
<211> LENGTH: 124
<212> TYPE: PRT
<213> ORGANISM: Artificial Sequence
<220> FEATURE:
<223> OTHER INFORMATION: antibody sequence

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Pro Met Gly Trp Val Arg Gln Ala Pro Gly Lys Gly Leu Glu Trp Val
        35                  40                  45

Ala Gly Ile Asp Asp Asp Gly Asp Ser Asp Thr Arg Tyr Ala Pro Ala
    50                  55                  60

Val Lys Gly Arg Ala Thr Ile Ser Arg Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Lys His Thr Gly Ile Gly Ala Asn Ser Ala Gly Ser Ile Asp
                100                 105                 110

Ala Trp Gly Gln Gly Thr Leu Val Thr Val Ser Ser
        115                 120
```

<210> SEQ ID NO 22
<211> LENGTH: 5
<212> TYPE: PRT
<213> ORGANISM: Artificial Sequence
<220> FEATURE:
<223> OTHER INFORMATION: antibody sequence

<400> SEQUENCE: 22

```
Ser Tyr Pro Met Gly
1               5
```

<210> SEQ ID NO 23
<211> LENGTH: 18
<212> TYPE: PRT
<213> ORGANISM: Artificial Sequence
<220> FEATURE:
<223> OTHER INFORMATION: antibody sequence

<400> SEQUENCE: 23

```
Gly Ile Asp Asp Asp Gly Asp Ser Asp Thr Arg Tyr Ala Pro Ala Val
1               5                   10                  15

Lys Gly
```

<210> SEQ ID NO 24
<211> LENGTH: 14
<212> TYPE: PRT
<213> ORGANISM: Artificial Sequence
<220> FEATURE:
<223> OTHER INFORMATION: antibody sequence

<400> SEQUENCE: 24

```
His Thr Gly Ile Gly Ala Asn Ser Ala Gly Ser Ile Asp Ala
1               5                   10
```

<210> SEQ ID NO 25
<211> LENGTH: 108
<212> TYPE: PRT
<213> ORGANISM: Artificial Sequence
<220> FEATURE:
<223> OTHER INFORMATION: antibody sequence

<400> SEQUENCE: 25

```
Ser Tyr Glu Leu Thr Gln Pro Pro Ser Val Ser Val Ser Pro Gly Gln
1               5                   10                  15

Thr Ala Arg Ile Thr Cys Ser Gly Gly Gly Tyr Thr Gly Ser Tyr Tyr
            20                  25                  30

Tyr Tyr Gly Trp Tyr Gln Gln Lys Pro Gly Gln Ala Pro Val Thr Val
        35                  40                  45
```

```
Ile Tyr Tyr Asn Asn Lys Arg Pro Ser Asp Ile Pro Glu Arg Phe Ser
 50                  55                  60
Gly Ser Leu Ser Gly Thr Thr Asn Thr Leu Thr Ile Ser Gly Val Gln
 65                  70                  75                  80
Ala Glu Asp Glu Ala Asp Tyr Tyr Cys Gly Ser Ala Asp Asn Ser Gly
                 85                  90                  95
Asp Ala Phe Gly Thr Gly Thr Lys Val Thr Val Leu
            100                 105
```

<210> SEQ ID NO 26
<211> LENGTH: 13
<212> TYPE: PRT
<213> ORGANISM: Artificial Sequence
<220> FEATURE:
<223> OTHER INFORMATION: antibody sequence

<400> SEQUENCE: 26

```
Ser Gly Gly Gly Ser Tyr Thr Gly Ser Tyr Tyr Tyr Gly
 1               5                  10
```

<210> SEQ ID NO 27
<211> LENGTH: 7
<212> TYPE: PRT
<213> ORGANISM: Artificial Sequence
<220> FEATURE:
<223> OTHER INFORMATION: antibody sequence

<400> SEQUENCE: 27

```
Tyr Asn Asn Lys Arg Pro Ser
 1               5
```

<210> SEQ ID NO 28
<211> LENGTH: 9
<212> TYPE: PRT
<213> ORGANISM: Artificial Sequence
<220> FEATURE:
<223> OTHER INFORMATION: antibody sequence

<400> SEQUENCE: 28

```
Gly Ser Ala Asp Asn Ser Gly Asp Ala
 1               5
```

<210> SEQ ID NO 29
<211> LENGTH: 372
<212> TYPE: DNA
<213> ORGANISM: Artificial Sequence
<220> FEATURE:
<223> OTHER INFORMATION: antibody sequence

<400> SEQUENCE: 29

```
gaagttcagc tgctggaatc tggcggcgga ctggttcaac tggcggatct tctgagactg      60
agctgtgccg ccagcggctt cacctttagc agctatccta tgggctgggt ccgacaggcc     120
cctggcaaag acttgaatg gtggccggc atcgacgacg atggcgatag cgatacaaga       180
tacgcccctg ccgtgaaggg cagagccacc atctccagag acaacagcaa gaacaccgtg     240
tacctgcaga tgaacagcct gagagccgag gacaccgccg tgtactattg tgccaagcac     300
acaggcatcg cgccaattc tgccggctct attgatgcct ggggccaggg aacactggtc     360
acagtttctt ca                                                         372
```

<210> SEQ ID NO 30
<211> LENGTH: 15
<212> TYPE: DNA

```
<213> ORGANISM: Artificial Sequence
<220> FEATURE:
<223> OTHER INFORMATION: antibody sequence

<400> SEQUENCE: 30
agctatccta tgggc                                                     15

<210> SEQ ID NO 31
<211> LENGTH: 54
<212> TYPE: DNA
<213> ORGANISM: Artificial Sequence
<220> FEATURE:
<223> OTHER INFORMATION: antibody sequence

<400> SEQUENCE: 31
ggcatcgacg acgatggcga tagcgataca agatacgccc ctgccgtgaa gggc          54

<210> SEQ ID NO 32
<211> LENGTH: 42
<212> TYPE: DNA
<213> ORGANISM: Artificial Sequence
<220> FEATURE:
<223> OTHER INFORMATION: antibody sequence

<400> SEQUENCE: 32
cacacaggca tcggcgccaa ttctgccggc tctattgatg cc                       42

<210> SEQ ID NO 33
<211> LENGTH: 324
<212> TYPE: DNA
<213> ORGANISM: Artificial Sequence
<220> FEATURE:
<223> OTHER INFORMATION: antibody sequence

<400> SEQUENCE: 33
agctatgagc tgacacagcc tccaagcgtg tccgtgtctc ctggacagac cgccagaatc    60
acatgtagcg gcgaggcag ctacaccggc agctactact atggctggta tcagcagaag    120
cccggacagg cccctgtgac cgtgatctac tacaacaaca gcggcccag cgacatcccc    180 gagagatttt ctggctctct gagcggcacc accaacacac tgacaatctc tggcgtgcag   240
gccgaggacg aggccgatta ctattgtggc agcgccgata atagcggcga cgcctttggc   300
accggcacca aagttacagt gcta                                          324

<210> SEQ ID NO 34
<211> LENGTH: 39
<212> TYPE: DNA
<213> ORGANISM: Artificial Sequence
<220> FEATURE:
<223> OTHER INFORMATION: antibody sequence

<400> SEQUENCE: 34
agcggcggag gcagctacac cggcagctac tactatggc                           39

<210> SEQ ID NO 35
<211> LENGTH: 21
<212> TYPE: DNA
<213> ORGANISM: Artificial Sequence
<220> FEATURE:
<223> OTHER INFORMATION: antibody sequence

<400> SEQUENCE: 35
tacaacaaca gcggcccag c                                               21
```

<210> SEQ ID NO 36
<211> LENGTH: 27
<212> TYPE: DNA
<213> ORGANISM: Artificial Sequence
<220> FEATURE:
<223> OTHER INFORMATION: antibody sequence

<400> SEQUENCE: 36
ggcagcgccg ataatagcgg cgacgcc        27

<210> SEQ ID NO 37
<211> LENGTH: 448
<212> TYPE: PRT
<213> ORGANISM: Artificial Sequence
<220> FEATURE:
<223> OTHER INFORMATION: antibody sequence

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Gly Trp Val Arg Gln Ala Pro Gly Lys Gly Leu Glu Trp Val
        35                  40                  45

Ala Gly Ile Asp Asp Gly Asp Ser Asp Thr Arg Tyr Ala Pro Ala
    50                  55                  60

Val Lys Gly Arg Ala Thr Ile Ser Arg Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Lys His Thr Gly Ile Gly Ala Asn Ser Ala Gly Ser Ile Asp
            100                 105                 110

Ala Trp Gly Gln Gly Thr Leu Val Thr Val Ser Ser Ala Lys Thr Thr
        115                 120                 125

Pro Pro Ser Val Tyr Pro Leu Ala Pro Gly Ser Ala Ala Gln Thr Asn
    130                 135                 140

Ser Met Val Thr Leu Gly Cys Leu Val Lys Gly Tyr Phe Pro Glu Pro
145                 150                 155                 160

Val Thr Val Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Pro Ser Ser Thr Trp Pro Ser Glu Thr Val Thr Cys Asn Val
        195                 200                 205

Ala His Pro Ala Ser Ser Thr Lys Val Asp Lys Ile Val Pro Arg
    210                 215                 220

Asp Cys Gly Cys Lys Pro Cys Ile Cys Thr Val Pro Glu Val Ser Ser
225                 230                 235                 240

Val Phe Ile Phe Pro Pro Lys Pro Lys Asp Val Leu Thr Ile Thr Leu
                245                 250                 255

Thr Pro Lys Val Thr Cys Val Val Asp Ile Ser Lys Asp Asp Pro
            260                 265                 270

Glu Val Gln Phe Ser Trp Phe Val Asp Asp Val Glu Val His Thr Ala
        275                 280                 285

Gln Thr Gln Pro Arg Glu Glu Gln Phe Asn Ser Thr Phe Arg Ser Val
    290                 295                 300

Ser Glu Leu Pro Ile Met His Gln Asp Trp Leu Asn Gly Lys Glu Phe

```
             305                 310                 315                 320
Lys Cys Arg Val Asn Ser Ala Ala Phe Pro Ala Pro Ile Glu Lys Thr
                    325                 330                 335

Ile Ser Lys Thr Lys Gly Arg Pro Lys Ala Pro Gln Val Tyr Thr Ile
                    340                 345                 350

Pro Pro Pro Lys Glu Gln Met Ala Lys Asp Lys Val Ser Leu Thr Cys
                    355                 360                 365

Met Ile Thr Asp Phe Phe Pro Glu Asp Ile Thr Val Glu Trp Gln Trp
                    370                 375                 380

Asn Gly Gln Pro Ala Glu Asn Tyr Lys Asn Thr Gln Pro Ile Met Asp
385                 390                 395                 400

Thr Asp Gly Ser Tyr Phe Val Tyr Ser Lys Leu Asn Val Gln Lys Ser
                    405                 410                 415

Asn Trp Glu Ala Gly Asn Thr Phe Thr Cys Ser Val Leu His Glu Gly
                    420                 425                 430

Leu His Asn His His Thr Glu Lys Ser Leu Ser His Ser Pro Gly Lys
                    435                 440                 445
```

<210> SEQ ID NO 38
<211> LENGTH: 214
<212> TYPE: PRT
<213> ORGANISM: Artificial Sequence
<220> FEATURE:
<223> OTHER INFORMATION: antibody sequence

<400> SEQUENCE: 38

```
Ser Tyr Glu Leu Thr Gln Pro Pro Ser Val Ser Val Ser Pro Gly Gln
1               5                   10                  15

Thr Ala Arg Ile Thr Cys Ser Gly Gly Gly Ser Tyr Thr Gly Ser Tyr
                20                  25                  30

Tyr Tyr Gly Trp Tyr Gln Gln Lys Pro Gly Gln Ala Pro Val Thr Val
                35                  40                  45

Ile Tyr Tyr Asn Asn Lys Arg Pro Ser Asp Ile Pro Glu Arg Phe Ser
            50                  55                  60

Gly Ser Leu Ser Gly Thr Thr Asn Thr Leu Thr Ile Ser Gly Val Gln
65                  70                  75                  80

Ala Glu Asp Glu Ala Asp Tyr Tyr Cys Gly Ser Ala Asp Asn Ser Gly
                85                  90                  95

Asp Ala Phe Gly Thr Gly Thr Lys Val Thr Val Leu Gly Gln Pro Lys
                100                 105                 110

Ser Ser Pro Ser Val Thr Leu Phe Pro Pro Ser Ser Glu Glu Leu Glu
            115                 120                 125

Thr Asn Lys Ala Thr Leu Val Cys Thr Ile Thr Asp Phe Tyr Pro Gly
        130                 135                 140

Val Val Thr Val Asp Trp Lys Val Asp Gly Thr Pro Val Thr Gln Gly
145                 150                 155                 160

Met Glu Thr Thr Gln Pro Ser Lys Gln Ser Asn Asn Lys Tyr Met Ala
                165                 170                 175

Ser Ser Tyr Leu Thr Leu Thr Ala Arg Ala Trp Glu Arg His Ser Ser
                180                 185                 190

Tyr Ser Cys Gln Val Thr His Glu Gly His Thr Val Glu Lys Ser Leu
            195                 200                 205

Ser Arg Ala Asp Cys Ser
        210
```

<210> SEQ ID NO 39
<211> LENGTH: 1344
<212> TYPE: DNA
<213> ORGANISM: Artificial Sequence
<220> FEATURE:
<223> OTHER INFORMATION: antibody sequence

<400> SEQUENCE: 39

| | |
|---|---:|
| gaagttcagc tgctggaatc tggcggcgga ctggttcaac ctggcggatc tctgagactg | 60 |
| agctgtgccg ccagcggctt cacctttagc agctatccta tgggctgggt ccgacaggcc | 120 |
| cctggcaaag gacttgaatg ggtggccggc atcgacgacg atggcgatag cgatacaaga | 180 |
| tacgccctg ccgtgaaggg cagagccacc atctccagag acaacagcaa gaacaccgtg | 240 |
| tacctgcaga tgaacagcct gagagccgag gacaccgccg tgtactattg tgccaagcac | 300 |
| acaggcatcg cgccaattc tgccggctct attgatgcct ggggccaggg aacactggtc | 360 |
| acagtttctt cagccaagac caccccccc agcgtgtacc ctctggctcc tggatctgcc | 420 |
| gcccagacca acagcatggt caccctgggc tgcctcgtga agggctactt ccctgagcct | 480 |
| gtgaccgtga cctggaacag cggctctctg tctagcggcg tgcacacctt ccagccgtg | 540 |
| ctgcagagcg acctgtacac cctgagcagc agcgtgaccg tgcctagcag cacctggcct | 600 |
| agcgagacag tgacctgcaa cgtggcccac cctgccagca gcacaaaggt ggacaagaaa | 660 |
| atcgtgcccc gggactgcgg ctgcaagccc tgtatctgta ccgtgcccga ggtgtccagc | 720 |
| gtgttcatct cccacccaa gcccaaggac gtgctgacca tcaccctgac ccccaaagtg | 780 |
| acctgtgtgg tggtggacat cagcaaggac gaccccgagg tgcagttcag ttggttcgtg | 840 |
| gacgacgtgg aagtgcacac agcccagacc cagcccagag aggaacagtt caacagcacc | 900 |
| ttcagaagcg tgtccgagct gcccatcatg caccaggact ggctgaacgg caaagagttc | 960 |
| aagtgcagag tgaacagcgc cgccttccct gcccccatcg agaaaaccat ctccaagacc | 1020 |
| aagggcagac ccaaggcccc tcaggtgtac acaatccccc acccaaaga acagatggcc | 1080 |
| aaggacaagg tgtccctgac ctgcatgatc accgatttct cccagagga catcaccgtg | 1140 |
| gaatggcagt ggaacggcca gcccgccgag aactacaaga acacccagcc tatcatggac | 1200 |
| accgacggca gctacttcgt gtacagcaag ctgaacgtgc agaagtccaa ctgggaggcc | 1260 |
| ggcaacacct tcacctgtag cgtgctgcac gagggcctgc acaatcacca caccgagaag | 1320 |
| tccctgtccc acagccctgg caag | 1344 |

<210> SEQ ID NO 40
<211> LENGTH: 642
<212> TYPE: DNA
<213> ORGANISM: Artificial Sequence
<220> FEATURE:
<223> OTHER INFORMATION: antibody sequence

<400> SEQUENCE: 40

| | |
|---|---:|
| agctatgagc tgacacagcc tccaagcgtg tccgtgtctc tggacagac cgccagaatc | 60 |
| acatgtagcg gcggaggcag ctacaccggc agctactact atggctggta tcagcagaag | 120 |
| cccggacagg cccctgtgac cgtgatctac tacaacaaca gcggcccag cgacatcccc | 180 |
| gagagatttt ctggctctct gagcggcacc accaacacac tgacaatctc tggcgtgcag | 240 |
| gccgaggacg aggccgatta ctattgtggc agcgccgata tagcggcga cgcctttggc | 300 |
| accggcacca agttacagt gctaggccag cccaagagca gccctagcgt gaccctgttc | 360 |
| cctccaagca gcgaggaact ggaaacaaac aaggccaccc tcgtgtgcac catcaccgac | 420 |

```
ttctaccccg gcgtcgtgac cgtggactgg aaggtggacg gcaccccagt gacccagggc        480
atggaaacca cccagcccag caagcagagc aacaacaagt acatggccag cagctacctg        540
accctgaccg ccagagcctg ggagagacac agctcctaca gctgccaagt gacccacgag        600
ggccacaccg tggaaaagag cctgagcaga gccgactgca gc                          642
```

```
<210> SEQ ID NO 41
<211> LENGTH: 120
<212> TYPE: PRT
<213> ORGANISM: Artificial Sequence
<220> FEATURE:
<223> OTHER INFORMATION: antibody sequence

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Gly Thr Gly Gly Asp Thr Tyr Tyr Ala Asp Ser Val Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Val Trp Gly Gln
            100                 105                 110

Gly Thr Leu Val Thr Val Ser Ser
        115                 120

<210> SEQ ID NO 42
<211> LENGTH: 5
<212> TYPE: PRT
<213> ORGANISM: Artificial Sequence
<220> FEATURE:
<223> OTHER INFORMATION: antibody sequence

<400> SEQUENCE: 42

Ser Tyr Gly Met His
1               5

<210> SEQ ID NO 43
<211> LENGTH: 16
<212> TYPE: PRT
<213> ORGANISM: Artificial Sequence
<220> FEATURE:
<223> OTHER INFORMATION: antibody sequence

<400> SEQUENCE: 43

Ala Ile Gly Thr Gly Gly Asp Thr Tyr Tyr Ala Asp Ser Val Met Gly
1               5                   10                  15

<210> SEQ ID NO 44
<211> LENGTH: 12
<212> TYPE: PRT
<213> ORGANISM: Artificial Sequence
<220> FEATURE:
<223> OTHER INFORMATION: antibody sequence

<400> SEQUENCE: 44

Arg Asp Asp Tyr Thr Ser Arg Asp Ala Phe Asp Val
```

<210> SEQ ID NO 45
<211> LENGTH: 111
<212> TYPE: PRT
<213> ORGANISM: Artificial Sequence
<220> FEATURE:
<223> OTHER INFORMATION: antibody sequence

<400> SEQUENCE: 45

Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
                20                  25                  30
Thr Val Asn Trp Tyr Gln Gln Leu Pro Gly Thr Ala Pro Lys Leu Leu
            35                  40                  45
Ile Tyr Tyr Asp Asp Leu Leu Pro Ser Gly Val Pro Asp Arg Phe Ser
        50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Ala Trp Asp Asp Ser Leu
                85                  90                  95
Asn Gly Tyr Val Val Phe Gly Gly Gly Thr Lys Leu Thr Val Leu
            100                 105                 110

<210> SEQ ID NO 46
<211> LENGTH: 13
<212> TYPE: PRT
<213> ORGANISM: Artificial Sequence
<220> FEATURE:
<223> OTHER INFORMATION: antibody sequence

<400> SEQUENCE: 46

Ser Gly Ser Ser Ser Asn Ile Gly Ser Asn Thr Val Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: antibody sequence

<400> SEQUENCE: 47

Tyr Asp Asp Leu Leu Pro Ser
1               5

<210> SEQ ID NO 48
<211> LENGTH: 12
<212> TYPE: PRT
<213> ORGANISM: Artificial Sequence
<220> FEATURE:
<223> OTHER INFORMATION: antibody sequence

<400> SEQUENCE: 48

Ala Ala Trp Asp Asp Ser Leu Asn Gly Tyr Val Val
1               5                   10

<210> SEQ ID NO 49
<211> LENGTH: 360
<212> TYPE: DNA
<213> ORGANISM: Artificial Sequence
<220> FEATURE:
<223> OTHER INFORMATION: antibody sequence

<400> SEQUENCE: 49

```
gaagttcagc tgctggaatc tggcggcgga ctggttcaac ctggcggatc tctgagactg    60
agctgtgccg ccagcggctt cacctttagc agctatggca tgcactgggt ccgacaggcc   120
cctggcaaag gacttgaatg ggtgtccgcc atcggcacag gcggcgatac ctactatgcc   180
gatagcgtga tgggcagatt caccatcagc cgggacaaca gcaagaacac cctgtacctg   240
cagatgaaca gcctgagagc cgaggacacc gccgtgtact attgcgccag aagggacgac   300
tacaccagca gggatgcctt cgatgtgtgg ggccagggaa cactggttac cgtttcttca   360
```

<210> SEQ ID NO 50
<211> LENGTH: 15
<212> TYPE: DNA
<213> ORGANISM: Artificial Sequence
<220> FEATURE:
<223> OTHER INFORMATION: antibody sequence

<400> SEQUENCE: 50

```
agctatggca tgcac                                                     15
```

<210> SEQ ID NO 51
<211> LENGTH: 48
<212> TYPE: DNA
<213> ORGANISM: Artificial Sequence
<220> FEATURE:
<223> OTHER INFORMATION: antibody sequence

<400> SEQUENCE: 51

```
gccatcggca caggcggcga tacctactat gccgatagcg tgatgggc                 48
```

<210> SEQ ID NO 52
<211> LENGTH: 36
<212> TYPE: DNA
<213> ORGANISM: Artificial Sequence
<220> FEATURE:
<223> OTHER INFORMATION: antibody sequence

<400> SEQUENCE: 52

```
agggacgact acaccagcag ggatgccttc gatgtg                              36
```

<210> SEQ ID NO 53
<211> LENGTH: 333
<212> TYPE: DNA
<213> ORGANISM: Artificial Sequence
<220> FEATURE:
<223> OTHER INFORMATION: antibody sequence

<400> SEQUENCE: 53

```
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgctgcctag cggcgtgccc   180
gatagatttt ctggcagcaa gagcggcaca agcgccagcc tggctatctc tggactgaga   240
tctgaggacg aggccgacta ctattgcgcc gcctgggacg atagcctgaa cggctatgtg   300
gttttcggcg gaggcaccaa gctgaccgtg cta                                 333
```

<210> SEQ ID NO 54
<211> LENGTH: 39
<212> TYPE: DNA
<213> ORGANISM: Artificial Sequence
<220> FEATURE:

<223> OTHER INFORMATION: antibody sequence

<400> SEQUENCE: 54
agcggcagca gctccaacat cggcagcaac accgtgaac						39

<210> SEQ ID NO 55
<211> LENGTH: 21
<212> TYPE: DNA
<213> ORGANISM: Artificial Sequence
<220> FEATURE:
<223> OTHER INFORMATION: antibody sequence

<400> SEQUENCE: 55
tacgacgacc tgctgcctag c							21

<210> SEQ ID NO 56
<211> LENGTH: 36
<212> TYPE: DNA
<213> ORGANISM: Artificial Sequence
<220> FEATURE:
<223> OTHER INFORMATION: antibody sequence

<400> SEQUENCE: 56
gccgcctggg acgatagcct gaacggctat gtggtt					36

<210> SEQ ID NO 57
<211> LENGTH: 449
<212> TYPE: PRT
<213> ORGANISM: Artificial Sequence
<220> FEATURE:
<223> OTHER INFORMATION: antibody sequence

<400> SEQUENCE: 57

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Gly Thr Gly Gly Asp Thr Tyr Tyr Ala Asp Ser Val Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly

<210> SEQ ID NO 58
<211> LENGTH: 217
<212> TYPE: PRT
<213> ORGANISM: Artificial Sequence
<220> FEATURE:
<223> OTHER INFORMATION: antibody sequence

<400> SEQUENCE: 58

Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
                20                  25                  30
Thr Val Asn Trp Tyr Gln Gln Leu Pro Gly Thr Ala Pro Lys Leu Leu
                35                  40                  45
Ile Tyr Tyr Asp Asp Leu Leu Pro Ser Gly Val Pro Asp Arg Phe Ser
            50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Ala Trp Asp Asp Ser Leu
                85                  90                  95
Asn Gly Tyr Val Val Phe Gly Gly Gly Thr Lys Leu Thr Val Leu Gly
                100                 105                 110
Gln Pro Lys Ala Ala Pro Ser Val Thr Leu Phe Pro Pro Ser Ser Glu
```

```
              115                 120                 125
Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
                195                 200                 205

Lys Thr Val Ala Pro Thr Glu Cys Ser
    210                 215

<210> SEQ ID NO 59
<211> LENGTH: 1347
<212> TYPE: DNA
<213> ORGANISM: Artificial Sequence
<220> FEATURE:
<223> OTHER INFORMATION: antibody sequence

<400> SEQUENCE: 59
gaagttcagc tgctggaatc tggcggcgga ctggttcaac ctggcggatc tctgagactg      60
agctgtgccg ccagcggctt cacctttagc agctatggca tgcactgggt ccgacaggcc     120
cctggcaaag acttgaatg gtgtccgcc atcggcacag gcggcgatac ctactatgcc      180
gatagcgtga tggcagatt caccatcagc cgggacaaca gcaagaacac cctgtacctg     240
cagatgaaca gcctgagagc cgaggacacc gccgtgtact attgcgccag aagggacgac     300
tacaccagca gggatgcctt cgatgtgtgg ggccagggaa cactggttac cgtttcttca     360
gccagcacca agggcccag cgtgttccct ctggccccta gcagcaagag cacatctggc     420
ggaacagccg ccctgggctg cctcgtgaag gactactttc ccgagcccgt gaccgtgtcc     480
tggaactctg gcgctctgac aagcggcgtg cacacctttc agccgtgct gcagagcagc     540 ggcctgtact ctctgagcag cgtcgtgaca gtgcccagca gctctctggg cacccagacc     600
tacatctgca acgtgaacca caagcccagc aacaccaagg tggacaagaa ggtggaaccc     660
aagagctgcg acaagaccca cacctgtccc ccttgtcctg cccccgaact gctgggaggc     720
ccttccgtgt tcctgttccc cccaaagccc aaggacaccc tgatgatcag ccggacccc     780 gaagtgacct gcgtggtggt ggatgtgtcc cacgaggacc ctgaagtgaa gttcaattgg     840
tacgtggacg gcgtggaagt gcacaacgcc aagaccaagc ctagagagga acagtacaac     900
agcacctacc gggtggtgtc cgtgctgaca gtgctgcacc aggactggct gaacggcaaa     960
gagtacaagt gcaaggtgtc caacaaggcc ctgcctgccc ccatcgagaa aaccatcagc    1020
aaggccaagg gccagccccg cgaacccag gtgtacacac tgcccccaag cagggacgag    1080
ctgaccaaga accaggtgtc cctgacctgt ctcgtgaaag gcttctaccc ctccgatatc    1140
gccgtggaat gggagagcaa cggccagccc gagaacaact acaagaccac ccccctgtg    1200 ctggacagcg acggctcatt cttcctgtac agcaagctga ccgtggacaa gtccggtgg    1260 cagcagggca acgtgttcag ctgcagcgtg atgcacgagg ccctgcacaa ccactacacc    1320
cagaagtccc tgagcctgag ccctggc                                       1347

<210> SEQ ID NO 60
<211> LENGTH: 651
```

<212> TYPE: DNA
<213> ORGANISM: Artificial Sequence
<220> FEATURE:
<223> OTHER INFORMATION: antibody sequence

<400> SEQUENCE: 60

```
cagtctgttc tgacacagcc tcctagcgcc tctggcacac ctggacagag agtgaccatc      60
agctgtagcg gcagcagctc aacatcggc agcaacaccg tgaactggta tcagcagctg     120
cctggcacag ccctaaact gctgatctac tacgacgacc tgctgcctag cggcgtgccc     180
gatagatttt ctggcagcaa gagcggcaca agcgccagcc tggctatctc tggactgaga    240
tctgaggacg aggccgacta ctattgcgcc gcctgggacg atagcctgaa cggctatgtg    300
gttttcggcg gaggcaccaa gctgaccgtg ctaggccagc ctaaagccgc ccctagcgtg    360
accctgttcc ctccaagcag cgaggaactg caggccaaca ggccaccct cgtgtgcctg     420
atcagcgact tctatcctgg cgccgtgacc gtggcctgga aggccgatag ctctcctgtg    480
aaggccggcg tggaaaccac caccctagc aagcagagca caacaaata cgccgccagc     540
agctacctga gcctgacccc cgagcagtgg aagtcccaca gatcctacag ctgccaagtg    600
acccacgagg gcagcaccgt ggaaaagaca gtggccccta ccgagtgcag c             651
```

<210> SEQ ID NO 61
<211> LENGTH: 123
<212> TYPE: PRT
<213> ORGANISM: Artificial Sequence
<220> FEATURE:
<223> OTHER INFORMATION: antibody sequence

<400> SEQUENCE: 61

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Glu Met Asn Trp Val Arg Gln Ala Pro Gly Lys Gly Leu Glu Trp Val
        35                  40                  45
Ser Gly Ile Ser Trp Asn Ser Gly Ser Ile Gly Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Gly Tyr Ser Ser Ser Trp Phe Asp Pro Asp Phe Asp Tyr
            100                 105                 110
Trp Gly Gln Gly Thr Leu Val Thr Val Ser Ser
        115                 120
```

<210> SEQ ID NO 62
<211> LENGTH: 5
<212> TYPE: PRT
<213> ORGANISM: Artificial Sequence
<220> FEATURE:
<223> OTHER INFORMATION: antibody sequence

<400> SEQUENCE: 62

```
Ser Tyr Glu Met Asn
1               5
```

<210> SEQ ID NO 63
<211> LENGTH: 17

```
<212> TYPE: PRT
<213> ORGANISM: Artificial Sequence
<220> FEATURE:
<223> OTHER INFORMATION: antibody sequence

<400> SEQUENCE: 63

Gly Ile Ser Trp Asn Ser Gly Ser Ile Gly Tyr Ala Asp Ser Val Lys
1               5                   10                  15
Gly

<210> SEQ ID NO 64
<211> LENGTH: 14
<212> TYPE: PRT
<213> ORGANISM: Artificial Sequence
<220> FEATURE:
<223> OTHER INFORMATION: antibody sequence

<400> SEQUENCE: 64

Ser Gly Tyr Ser Ser Ser Trp Phe Asp Pro Asp Phe Asp Tyr
1               5                   10

<210> SEQ ID NO 65
<211> LENGTH: 111
<212> TYPE: PRT
<213> ORGANISM: Artificial Sequence
<220> FEATURE:
<223> OTHER INFORMATION: antibody sequence

<400> SEQUENCE: 65

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ser Ser Tyr Ala Gly Ser
                85                  90                  95

Asn Pro Tyr Val Val Phe Gly Gly Gly Thr Lys Leu Thr Val Leu
            100                 105                 110

<210> SEQ ID NO 66
<211> LENGTH: 14
<212> TYPE: PRT
<213> ORGANISM: Artificial Sequence
<220> FEATURE:
<223> OTHER INFORMATION: antibody sequence

<400> SEQUENCE: 66

Thr Gly Ser Ser Ser Asn Ile Gly Ala Gly Tyr Asp Val His
1               5                   10

<210> SEQ ID NO 67
<211> LENGTH: 7
<212> TYPE: PRT
<213> ORGANISM: Artificial Sequence
<220> FEATURE:
<223> OTHER INFORMATION: antibody sequence

<400> SEQUENCE: 67
```

Gly Asn Ser Asn Arg Pro Ser
1               5

<210> SEQ ID NO 68
<211> LENGTH: 11
<212> TYPE: PRT
<213> ORGANISM: Artificial Sequence
<220> FEATURE:
<223> OTHER INFORMATION: antibody sequence

<400> SEQUENCE: 68

Ser Ser Tyr Ala Gly Ser Asn Pro Tyr Val Val
1               5                   10

<210> SEQ ID NO 69
<211> LENGTH: 369
<212> TYPE: DNA
<213> ORGANISM: Artificial Sequence
<220> FEATURE:
<223> OTHER INFORMATION: antibody sequence

<400> SEQUENCE: 69

```
gaagttcagc tgctggaatc tggcggcgga ctggttcaac ctggcggatc tctgagactg    60
agctgtgccg ccagcggctt cacctttagc agctacgaga tgaactgggt ccgacaggcc   120
cctggcaaag ccttgaatg gtgtccggc atcagctgga atagcggctc tatcggctac     180
gccgacagcg tgaagggcag attcaccatc agccgggaca cagcaagaa caccctgtac    240
ctgcagatga acagcctgag agccgaggac accgccgtgt actactgtgc cagaagcggc   300
tacagcagct cttggtttga ccccgacttc gactattggg gccagggcac actggtcaca   360
gtctcttca                                                           369
```

<210> SEQ ID NO 70
<211> LENGTH: 15
<212> TYPE: DNA
<213> ORGANISM: Artificial Sequence
<220> FEATURE:
<223> OTHER INFORMATION: antibody sequence

<400> SEQUENCE: 70
agctacgaga tgaac    15

<210> SEQ ID NO 71
<211> LENGTH: 51
<212> TYPE: DNA
<213> ORGANISM: Artificial Sequence
<220> FEATURE:
<223> OTHER INFORMATION: antibody sequence

<400> SEQUENCE: 71
ggcatcagct ggaatagcgg ctctatcggc tacgccgaca gcgtgaaggg c    51

<210> SEQ ID NO 72
<211> LENGTH: 42
<212> TYPE: DNA
<213> ORGANISM: Artificial Sequence
<220> FEATURE:
<223> OTHER INFORMATION: antibody sequence

<400> SEQUENCE: 72
agcggctaca gcagctcttg gtttgacccc gacttcgact at    42

<210> SEQ ID NO 73
<211> LENGTH: 333

```
<212> TYPE: DNA
<213> ORGANISM: Artificial Sequence
<220> FEATURE:
<223> OTHER INFORMATION: antibody sequence

<400> SEQUENCE: 73
cagtctgttc tgacacagcc tcctagcgcc tctggcacac ctggacagag agtgaccatc     60
agctgtaccg gcagcagctc aatatcgga gccggctatg acgtgcactg gtatcagcag    120
ctgcctggca gcccctaa actgctgatc tacggcaaca gcaacagacc cagcggcgtg     180
cccgatagat tttccggctc taagagcggc acaagcgcca gcctggctat ctctggactg    240
agatctgagg acgaggccga ctactactgc agcagctatg ccggcagcaa ccctacgtt    300 gtgtttggcg gaggcaccaa gctgaccgtt cta                                 333

<210> SEQ ID NO 74
<211> LENGTH: 42
<212> TYPE: DNA
<213> ORGANISM: Artificial Sequence
<220> FEATURE:
<223> OTHER INFORMATION: antibody sequence

<400> SEQUENCE: 74
accggcagca gctccaatat cggagccggc tatgacgtgc ac                        42

<210> SEQ ID NO 75
<211> LENGTH: 21
<212> TYPE: DNA
<213> ORGANISM: Artificial Sequence
<220> FEATURE:
<223> OTHER INFORMATION: antibody sequence

<400> SEQUENCE: 75
ggcaacagca acagacccag c                                               21

<210> SEQ ID NO 76
<211> LENGTH: 33
<212> TYPE: DNA
<213> ORGANISM: Artificial Sequence
<220> FEATURE:
<223> OTHER INFORMATION: antibody sequence

<400> SEQUENCE: 76
agcagctatg ccggcagcaa ccctacgtt gtg                                   33

<210> SEQ ID NO 77
<211> LENGTH: 452
<212> TYPE: PRT
<213> ORGANISM: Artificial Sequence
<220> FEATURE:
<223> OTHER INFORMATION: antibody sequence

<400> SEQUENCE: 77
```

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Ser Gly Tyr Ser Ser Trp Phe Asp Pro Asp Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 78
<211> LENGTH: 217
<212> TYPE: PRT
<213> ORGANISM: Artificial Sequence
<220> FEATURE:
```

<223> OTHER INFORMATION: antibody sequence

<400> SEQUENCE: 78

| | | | | | | | | | | | | | | |
|---|---|---|---|---|---|---|---|---|---|---|---|---|---|---|
| Gln | Ser | Val | Leu | Thr | Gln | Pro | Pro | Ser | Ala | Ser | Gly | Thr | Pro | Gly | Gln |
| 1 | | | | 5 | | | | | 10 | | | | | 15 |
| Arg | Val | Thr | Ile | Ser | Cys | Thr | Gly | Ser | Ser | Ser | Asn | Ile | Gly | Ala | Gly |
| | | | 20 | | | | | 25 | | | | | 30 | | |
| Tyr | Asp | Val | His | Trp | Tyr | Gln | Gln | Leu | Pro | Gly | Thr | Ala | Pro | Lys | Leu |
| | | | 35 | | | | | 40 | | | | | 45 | | |
| Leu | Ile | Tyr | Gly | Asn | Ser | Asn | Arg | Pro | Ser | Gly | Val | Pro | Asp | Arg | Phe |
| | 50 | | | | | 55 | | | | | 60 | | | | |
| Ser | Gly | Ser | Lys | Ser | Gly | Thr | Ser | Ala | Ser | Leu | Ala | Ile | Ser | Gly | Leu |
| 65 | | | | | 70 | | | | | 75 | | | | | 80 |
| Arg | Ser | Glu | Asp | Glu | Ala | Asp | Tyr | Tyr | Cys | Ser | Ser | Tyr | Ala | Gly | Ser |
| | | | | 85 | | | | | 90 | | | | | 95 | |
| Asn | Pro | Tyr | Val | Val | Phe | Gly | Gly | Gly | Thr | Lys | Leu | Thr | Val | Leu | Gly |
| | | | 100 | | | | | 105 | | | | | 110 | | |
| Gln | Pro | Lys | Ala | Ala | Pro | Ser | Val | Thr | Leu | Phe | Pro | Pro | Ser | Ser | Glu |
| | | | 115 | | | | | 120 | | | | | 125 | | |
| Glu | Leu | Gln | Ala | Asn | Lys | Ala | Thr | Leu | Val | Cys | Leu | Ile | Ser | Asp | Phe |
| | 130 | | | | | 135 | | | | | 140 | | | | |
| Tyr | Pro | Gly | Ala | Val | Thr | Val | Ala | Trp | Lys | Ala | Asp | Ser | Ser | Pro | Val |
| 145 | | | | | 150 | | | | | 155 | | | | | 160 |
| Lys | Ala | Gly | Val | Glu | Thr | Thr | Thr | Pro | Ser | Lys | Gln | Ser | Asn | Asn | Lys |
| | | | | 165 | | | | | 170 | | | | | 175 | |
| Tyr | Ala | Ala | Ser | Ser | Tyr | Leu | Ser | Leu | Thr | Pro | Glu | Gln | Trp | Lys | Ser |
| | | | 180 | | | | | 185 | | | | | 190 | | |
| His | Arg | Ser | Tyr | Ser | Cys | Gln | Val | Thr | His | Glu | Gly | Ser | Thr | Val | Glu |
| | | | 195 | | | | | 200 | | | | | 205 | | |
| Lys | Thr | Val | Ala | Pro | Thr | Glu | Cys | Ser | | | | | | | |
| | 210 | | | | | 215 | | | | | | | | | |

<210> SEQ ID NO 79
<211> LENGTH: 1356
<212> TYPE: DNA
<213> ORGANISM: Artificial Sequence
<220> FEATURE:
<223> OTHER INFORMATION: antibody sequence

<400> SEQUENCE: 79

| | | | | |
|---|---|---|---|---|
| gaagttcagc tgctggaatc tggcggcgga ctggttcaac tggcggatc tctgagactg | 60 |
| agctgtgccg ccagcggctt cacctttagc agctacgaga tgaactgggt ccgacaggcc | 120 |
| cctggcaaag gccttgaatg ggtgtccggc atcagctgga atagcggctc tatcggctac | 180 |
| gccgacagcg tgaagggcag attcaccatc agccgggaca cagcaagaa caccctgtac | 240 |
| ctgcagatga acagcctgag agccgaggac accgccgtgt actactgtgc agaagcggc | 300 |
| tacagcagct cttggtttga ccccgacttc gactattggg gccagggcac actggtcaca | 360 |
| gtctcttcag ccagcaccaa gggccccagc gtgttccctc tggcccctag cagcaagagc | 420 |
| acatctggcg gaacagccgc cctgggctgc ctcgtgaagg actactttcc cgagcccgtg | 480 |
| accgtgtcct ggaactctgg cgctctgaca agcggcgtgc acacctttcc agccgtgctg | 540 |
| cagagcagcg gcctgtactc tctgagcagc gtcgtgacag tgcccagcag ctctctgggc | 600 |
| acccagacct acatctgcaa cgtgaaccac aagcccagca caccaaggt ggacaagaag | 660 |
| gtggaaccca gagctgcga caagacccac acctgtcccc cttgtcctgc ccccgaactg | 720 |

```
ctgggaggcc cttccgtgtt cctgttcccc ccaaagccca aggacaccct gatgatcagc    780 cggaccccg aagtgacctg cgtggtggtg gatgtgtccc acgaggaccc tgaagtgaag     840
ttcaattggt acgtggacgg cgtggaagtg cacaacgcca agaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa   1020
accatcagca aggccaaggg ccagccccgc gaacccagg tgtacacact gcccccaagc    1080
agggacgagc tgaccaagaa ccaggtgtcc ctgacctgtc tcgtgaaagg cttctacccc   1140
tccgatatcg ccgtggaatg ggagagcaac ggccagcccg agaacaacta caagaccacc   1200 cccctgtgc tggacagcga cggctcattc ttcctgtaca gcaagctgac cgtggacaag    1260
tcccggtggc agcagggcaa cgtgttcagc tgcagcgtga tgcacgaggc cctgcacaac   1320
cactacaccc agaagtccct gagcctgagc cctggc                             1356
```

<210> SEQ ID NO 80
<211> LENGTH: 651
<212> TYPE: DNA
<213> ORGANISM: Artificial Sequence
<220> FEATURE:
<223> OTHER INFORMATION: antibody sequence

<400> SEQUENCE: 80

```
cagtctgttc tgacacagcc tcctagcgcc tctggcacac tggacagag agtgaccatc     60 agctgtaccg gcagcagctc caatatcgga gccggctatg acgtgcactg gtatcagcag   120
ctgcctggca cagcccctaa actgctgatc tacggcaaca gcaacagacc cagcggcgtg   180
cccgatagat ttccggctc taagagcggc acaagcgcca gcctggctat ctctggactg    240
agatctgagg acgaggccga ctactactgc agcagctatg ccggcagcaa ccctacgtt    300 gtgtttggcg gaggcaccaa gctgaccgtt ctaggccagc ctaaagccgc ccctagcgtg   360
accctgttcc ctccaagcag cgaggaactg caggccaaca aggccaccct cgtgtgcctg   420
atcagcgact tctatcctgg cgccgtgacc gtggcctgga aggccgatag ctctcctgtg   480
aaggccggcg tggaaaccac cacccctagc aagcagagca caacaaata cgccgccagc   540 agctacctga gcctgacccc cgagcagtgg aagtcccaca gatcctacag ctgccaagtg   600
acccacgagg gcagcaccgt ggaaaagaca gtggccccta ccgagtgcag c            651
```

<210> SEQ ID NO 81
<211> LENGTH: 116
<212> TYPE: PRT
<213> ORGANISM: Artificial Sequence
<220> FEATURE:
<223> OTHER INFORMATION: antibody sequence

<400> SEQUENCE: 81

```
Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Trp Ile Tyr Tyr Asp Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Leu Asn Gly Asp Phe Asp Tyr Trp Gly Gln Gly Thr Leu Val
            100                 105                 110

Thr Val Ser Ser
        115

<210> SEQ ID NO 82
<211> LENGTH: 5
<212> TYPE: PRT
<213> ORGANISM: Artificial Sequence
<220> FEATURE:
<223> OTHER INFORMATION: antibody sequence

<400> SEQUENCE: 82

Asp Tyr Ala Met Ser
1               5

<210> SEQ ID NO 83
<211> LENGTH: 17
<212> TYPE: PRT
<213> ORGANISM: Artificial Sequence
<220> FEATURE:
<223> OTHER INFORMATION: antibody sequence

<400> SEQUENCE: 83

Trp Ile Tyr Tyr Asp Ser Gly Ser Lys Tyr Tyr Ala Asp Ser Val Lys
1               5                   10                  15

Gly

<210> SEQ ID NO 84
<211> LENGTH: 7
<212> TYPE: PRT
<213> ORGANISM: Artificial Sequence
<220> FEATURE:
<223> OTHER INFORMATION: antibody sequence

<400> SEQUENCE: 84

Leu Asn Gly Asp Phe Asp Tyr
1               5

<210> SEQ ID NO 85
<211> LENGTH: 110
<212> TYPE: PRT
<213> ORGANISM: Artificial Sequence
<220> FEATURE:
<223> OTHER INFORMATION: antibody sequence

<400> SEQUENCE: 85

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Asp Val Ser Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65              70                  75                  80

Ser Glu Asp Glu Ala Asp Tyr Tyr Cys Gly Ala Trp Asp Ser Ser Leu
                85                  90                  95
```

Ser Gly Tyr Val Phe Gly Gly Gly Thr Lys Leu Thr Val Leu
            100                 105                 110

<210> SEQ ID NO 86
<211> LENGTH: 13
<212> TYPE: PRT
<213> ORGANISM: Artificial Sequence
<220> FEATURE:
<223> OTHER INFORMATION: antibody sequence

<400> SEQUENCE: 86

Ser Gly Ser Ser Ser Asn Ile Gly Asn Asn Asp Val Ser
1               5                   10

<210> SEQ ID NO 87
<211> LENGTH: 7
<212> TYPE: PRT
<213> ORGANISM: Artificial Sequence
<220> FEATURE:
<223> OTHER INFORMATION: antibody sequence

<400> SEQUENCE: 87

Ala Asp Ser His Arg Pro Ser
1               5

<210> SEQ ID NO 88
<211> LENGTH: 11
<212> TYPE: PRT
<213> ORGANISM: Artificial Sequence
<220> FEATURE:
<223> OTHER INFORMATION: antibody sequence

<400> SEQUENCE: 88

Gly Ala Trp Asp Ser Ser Leu Ser Gly Tyr Val
1               5                   10

<210> SEQ ID NO 89
<211> LENGTH: 348
<212> TYPE: DNA
<213> ORGANISM: Artificial Sequence
<220> FEATURE:
<223> OTHER INFORMATION: antibody sequence

<400> SEQUENCE: 89
gaagttcagc tgctggaatc tggcggcgga ctggttcaaa caggcggctc tctgagactg      60
agctgtgccg cctctggctt caccttcagc gattacgcca tgagctgggt ccgacaggcc     120
cctggaaaag gccttgaatg ggtgtcctgg atctactacg acagcggcag caagtactac     180
gccgacagcg tgaagggcag attcaccatc agccgggaca cagcaagaa cacccctgtac     240 ctgcagatga acagcctgag agccgaggac accgccgtgt actattgcgc caagctgaac     300
ggcgacttcg actattgggg ccagggcaca ctggtcacag tctcttca                  348

<210> SEQ ID NO 90
<211> LENGTH: 15
<212> TYPE: DNA
<213> ORGANISM: Artificial Sequence
<220> FEATURE:
<223> OTHER INFORMATION: antibody sequence

<400> SEQUENCE: 90
gattacgcca tgagc                                                       15

<210> SEQ ID NO 91
<211> LENGTH: 51

```
<212> TYPE: DNA
<213> ORGANISM: Artificial Sequence
<220> FEATURE:
<223> OTHER INFORMATION: antibody sequence

<400> SEQUENCE: 91
tggatctact acgacagcgg cagcaagtac tacgccgaca gcgtgaaggg c        51

<210> SEQ ID NO 92
<211> LENGTH: 21
<212> TYPE: DNA
<213> ORGANISM: Artificial Sequence
<220> FEATURE:
<223> OTHER INFORMATION: antibody sequence

<400> SEQUENCE: 92
ctgaacggcg acttcgacta t                                          21

<210> SEQ ID NO 93
<211> LENGTH: 330
<212> TYPE: DNA
<213> ORGANISM: Artificial Sequence
<220> FEATURE:
<223> OTHER INFORMATION: antibody sequence

<400> SEQUENCE: 93
cagtctgttc tgacacagcc tcctagcgcc tctggcacac ctggacagag agtgaccatc    60
agctgtagcg gcagcagctc caacatcggc aacaacgacg tgtcctggta tcagcagctg   120
cctggcacag cccctaaact gctgatctac gccgacagcc acagacctag cggcgtgcca   180
gatagattca gcggctctaa gagcggcaca tctgccagcc tggccatctc tggactgaga   240
tctgaggacg aggccgacta ctattgcggc gcctgggatt ctagcctgag cggctatgtt   300
tttggcggag gcaccaagct gaccgtgcta                                   330

<210> SEQ ID NO 94
<211> LENGTH: 39
<212> TYPE: DNA
<213> ORGANISM: Artificial Sequence
<220> FEATURE:
<223> OTHER INFORMATION: antibody sequence

<400> SEQUENCE: 94
agcggcagca gctccaacat cggcaacaac gacgtgtcc                        39

<210> SEQ ID NO 95
<211> LENGTH: 21
<212> TYPE: DNA
<213> ORGANISM: Artificial Sequence
<220> FEATURE:
<223> OTHER INFORMATION: antibody sequence

<400> SEQUENCE: 95
gccgacagcc acagacctag c                                          21

<210> SEQ ID NO 96
<211> LENGTH: 33
<212> TYPE: DNA
<213> ORGANISM: Artificial Sequence
<220> FEATURE:
<223> OTHER INFORMATION: antibody sequence

<400> SEQUENCE: 96
ggcgcctggg attctagcct gagcggctat gtt                             33
```

```
<210> SEQ ID NO 97
<211> LENGTH: 445
<212> TYPE: PRT
<213> ORGANISM: Artificial Sequence
<220> FEATURE:
<223> OTHER INFORMATION: antibody sequence

<400> SEQUENCE: 97

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Trp Ile Tyr Tyr Asp Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asn Gly Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly
            435                 440                 445
```

<210> SEQ ID NO 98
<211> LENGTH: 216
<212> TYPE: PRT
<213> ORGANISM: Artificial Sequence
<220> FEATURE:
<223> OTHER INFORMATION: antibody sequence

<400> SEQUENCE: 98

```
Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Asn Asn
                20                  25                  30
Asp Val Ser Trp Tyr Gln Gln Leu Pro Gly Thr Ala Pro Lys Leu Leu
            35                  40                  45
Ile Tyr Ala Asp Ser His Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Gly Ala Trp Asp Ser Ser Leu
                85                  90                  95
Ser Gly Tyr Val Phe Gly Gly Gly Thr Lys Leu Thr Val Leu Gly Gln
                100                 105                 110
Pro Lys Ala Ala Pro Ser Val Thr Leu Phe Pro Pro Ser Ser Glu Glu
            115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
                180                 185                 190
Arg Ser Tyr Ser Cys Gln Val Thr His Glu Gly Ser Thr Val Glu Lys
            195                 200                 205
Thr Val Ala Pro Thr Glu Cys Ser
    210                 215
```

<210> SEQ ID NO 99
<211> LENGTH: 1335
<212> TYPE: DNA
<213> ORGANISM: Artificial Sequence
<220> FEATURE:
<223> OTHER INFORMATION: antibody sequence

<400> SEQUENCE: 99

```
gaagttcagc tgctggaatc tggcggcgga ctggttcaaa caggcggctc tctgagactg    60
```

```
agctgtgccg cctctggctt caccttcagc gattacgcca tgagctgggt ccgacaggcc    120
cctggaaaag gccttgaatg ggtgtcctgg atctactacg acagcggcag caagtactac    180
gccgacagcg tgaagggcag attcaccatc agccgggaca cagcaagaa caccctgtac    240
ctgcagatga acagcctgag agccgaggac accgccgtgt actattgcgc caagctgaac    300
ggcgacttcg actattgggg ccagggcaca ctggtcacag tctcttcagc cagcaccaag    360
ggccccagcg tgttccctct ggccctagc agcaagagca catctggcgg aacagccgcc    420
ctgggctgcc tcgtgaagga ctactttccc gagcccgtga ccgtgtcctg gaactctggc    480
gctctgacaa gcggcgtgca cacctttcca gccgtgctgc agagcagcgg cctgtactct    540
ctgagcagcg tcgtgacagt gcccagcagc tctctgggca cccagaccta catctgcaac    600
gtgaaccaca gcccagcaa caccaaggtg gacaagaagg tggaacccaa gagctgcgac    660
aagacccaca cctgtccccc ttgtcctgcc cccgaactgc tgggaggccc ttccgtgttc    720
ctgttccccc caaagcccaa ggacaccctg atgatcagcc ggacccccga agtgacctgc    780
gtggtggtgg atgtgtccca cgaggaccct gaagtgaagt tcaattggta cgtggacggc    840
gtggaagtgc acaacgccaa gaccaagcct agagaggaac agtacaacag cacctaccgg    900
gtggtgtccg tgctgacagt gctgcaccag gactggctga acggcaaaga gtacaagtgc    960
aaggtgtcca acaaggccct gcctgccccc atcgagaaaa ccatcagcaa ggccaagggc   1020
cagccccgcg aacccaggt gtacacactg ccccaagca gggacgagct gaccaagaac    1080
caggtgtccc tgacctgtct cgtgaaaggc ttctaccccc tccgatatcgc cgtggaatgg   1140
gagagcaacg gccagcccga gaacaactac aagaccaccc cccctgtgct ggacagcgac   1200
ggctcattct tcctgtacag caagctgacc gtggacaagt cccggtggca gcagggcaac   1260
gtgttcagct gcagcgtgat gcacgaggcc ctgcacaacc actacaccca gaagtccctg   1320
agcctgagcc ctggc                                                    1335

<210> SEQ ID NO 100
<211> LENGTH: 648
<212> TYPE: DNA
<213> ORGANISM: Artificial Sequence
<220> FEATURE:
<223> OTHER INFORMATION: antibody sequence

<400> SEQUENCE: 100
cagtctgttc tgacacagcc tcctagcgcc tctggcacac tggacagag agtgaccatc     60
agctgtagcg gcagcagctc caacatcggc aacaacgacg tgtcctggta tcagcagctg   120
cctggcacag cccctaaact gctgatctac gccgacagcc acagacctag cggcgtgcca   180
gatagattca gcggctctaa gagcggcaca tctgccagcc tggccatctc tggactgaga   240
tctgaggacg aggccgacta ctattgcggc gcctgggatt ctagcctgag cggctatgtt   300
tttggcggag gcaccaagct gaccgtgcta ggccagccta agccgcccc tagcgtgacc   360
ctgttccctc caagcagcga ggaactgcag gccaacaagg ccaccctcgt gtgcctgatc   420
agcgacttct atcctggcgc cgtgaccgtg gcctggaagg ccgatagctc tcctgtgaag   480
gccggcgtgg aaaccaccac ccctagcaag cagagcaaca caaatacgc cgccagcagc   540
tacctgagcc tgacccccga gcagtggaag tcccacagat cctacagctg ccaagtgacc   600
cacgagggca gcaccgtgga aaagacagtg gcccctaccg agtgcagc                648

<210> SEQ ID NO 101
<211> LENGTH: 123
```

<212> TYPE: PRT
<213> ORGANISM: Artificial Sequence
<220> FEATURE:
<223> OTHER INFORMATION: antibody sequence

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser
        115                 120

<210> SEQ ID NO 102
<211> LENGTH: 5
<212> TYPE: PRT
<213> ORGANISM: Artificial Sequence
<220> FEATURE:
<223> OTHER INFORMATION: antibody sequence

<400> SEQUENCE: 102

Ser Tyr Glu Met Asn
1               5

<210> SEQ ID NO 103
<211> LENGTH: 17
<212> TYPE: PRT
<213> ORGANISM: Artificial Sequence
<220> FEATURE:
<223> OTHER INFORMATION: antibody sequence

<400> SEQUENCE: 103

Gly Ile Ser Trp Asn Ser Gly Ser Ile Gly Tyr Ala Asp Ser Val Lys
1               5                   10                  15

Gly

<210> SEQ ID NO 104
<211> LENGTH: 14
<212> TYPE: PRT
<213> ORGANISM: Artificial Sequence
<220> FEATURE:
<223> OTHER INFORMATION: antibody sequence

<400> SEQUENCE: 104

Ser Gly Tyr Ser Ser Ser Trp Phe Asp Pro Asp Phe Asp Tyr
1               5                   10

<210> SEQ ID NO 105
<211> LENGTH: 111
<212> TYPE: PRT
<213> ORGANISM: Artificial Sequence
<220> FEATURE:
<223> OTHER INFORMATION: antibody sequence

<400> SEQUENCE: 105

Gln Ser Val Leu Thr Gln Pro Pro Ser Val Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Ala Gly Ser
                85                  90                  95

Asn Pro Tyr Val Val Phe Gly Gly Gly Thr Lys Leu Thr Val Leu
            100                 105                 110

<210> SEQ ID NO 106
<211> LENGTH: 14
<212> TYPE: PRT
<213> ORGANISM: Artificial Sequence
<220> FEATURE:
<223> OTHER INFORMATION: antibody sequence

<400> SEQUENCE: 106

Thr Gly Ser Ser Ser Asn Ile Gly Ala Gly Tyr Asp Val His
1               5                   10

<210> SEQ ID NO 107
<211> LENGTH: 7
<212> TYPE: PRT
<213> ORGANISM: Artificial Sequence
<220> FEATURE:
<223> OTHER INFORMATION: antibody sequence

<400> SEQUENCE: 107

Gly Asn Ser Asn Arg Pro Ser
1               5

<210> SEQ ID NO 108
<211> LENGTH: 11
<212> TYPE: PRT
<213> ORGANISM: Artificial Sequence
<220> FEATURE:
<223> OTHER INFORMATION: antibody sequence

<400> SEQUENCE: 108

Ser Ser Tyr Ala Gly Ser Asn Pro Tyr Val Val
1               5                   10

<210> SEQ ID NO 109
<211> LENGTH: 369
<212> TYPE: DNA
<213> ORGANISM: Artificial Sequence
<220> FEATURE:
<223> OTHER INFORMATION: antibody sequence

<400> SEQUENCE: 109
gaagttcagc tgctggaatc tggcggcgga ctggttcaac ctggcggatc tctgagactg    60
agctgtgccg ccagcggctt cacctttagc agctacgaga tgaactgggt ccgacaggcc   120
cctggcaaag gccttgaatg gtgtccggc atcagctgga atagcggctc tatcggctac   180

```
gccgacagcg tgaagggcag attcaccatc agccgggaca acagcaagaa caccctgtac    240
ctgcagatga acagcctgag agccgaggac accgccgtgt actactgtgc cagaagcggc    300
tacagcagct cttggtttga ccccgacttc gactattggg gccagggcac actggtcaca    360
gtctcttca                                                            369
```

<210> SEQ ID NO 110
<211> LENGTH: 15
<212> TYPE: DNA
<213> ORGANISM: Artificial Sequence
<220> FEATURE:
<223> OTHER INFORMATION: antibody sequence

<400> SEQUENCE: 110

```
agctacgaga tgaac                                                      15
```

<210> SEQ ID NO 111
<211> LENGTH: 51
<212> TYPE: DNA
<213> ORGANISM: Artificial Sequence
<220> FEATURE:
<223> OTHER INFORMATION: antibody sequence

<400> SEQUENCE: 111

```
ggcatcagct ggaatagcgg ctctatcggc tacgccgaca gcgtgaaggg c               51
```

<210> SEQ ID NO 112
<211> LENGTH: 42
<212> TYPE: DNA
<213> ORGANISM: Artificial Sequence
<220> FEATURE:
<223> OTHER INFORMATION: antibody sequence

<400> SEQUENCE: 112

```
agcggctaca gcagctcttg gtttgacccc gacttcgact at                         42
```

<210> SEQ ID NO 113
<211> LENGTH: 333
<212> TYPE: DNA
<213> ORGANISM: Artificial Sequence
<220> FEATURE:
<223> OTHER INFORMATION: antibody sequence

<400> SEQUENCE: 113

```
cagtctgttc tgacacagcc tccatctgtg tctggcgccc tggacagag agtgaccatc      60 agctgtacag gcagcagctc caatatcgga gccggctatg acgtgcactg gtatcagcag    120
ctgcctggca gcccctaa actgctgatc tacggcaaca gcaacagacc cagcggcgtg      180
cccgatagat tttccggctc taagagcggc acaagcgcca gcctggctat tactggactg    240
caggccgagg acgaggccga ctactactgt tctagctacg ccggcagcaa cccctacgtg    300
gtgtttggcg gaggcaccaa gctgacagtt cta                                  333
```

<210> SEQ ID NO 114
<211> LENGTH: 42
<212> TYPE: DNA
<213> ORGANISM: Artificial Sequence
<220> FEATURE:
<223> OTHER INFORMATION: antibody sequence

<400> SEQUENCE: 114

```
acaggcagca gctccaatat cggagccggc tatgacgtgc ac                        42
```

```
<210> SEQ ID NO 115
<211> LENGTH: 21
<212> TYPE: DNA
<213> ORGANISM: Artificial Sequence
<220> FEATURE:
<223> OTHER INFORMATION: antibody sequence

<400> SEQUENCE: 115
ggcaacagca acagacccag c                                              21

<210> SEQ ID NO 116
<211> LENGTH: 33
<212> TYPE: DNA
<213> ORGANISM: Artificial Sequence
<220> FEATURE:
<223> OTHER INFORMATION: antibody sequence

<400> SEQUENCE: 116
tctagctacg ccggcagcaa ccccctacgtg gtg                                33

<210> SEQ ID NO 117
<211> LENGTH: 452
<212> TYPE: PRT
<213> ORGANISM: Artificial Sequence
<220> FEATURE:
<223> OTHER INFORMATION: antibody sequence

<400> SEQUENCE: 117
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr

```
            245                 250                 255
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly
            450

<210> SEQ ID NO 118
<211> LENGTH: 217
<212> TYPE: PRT
<213> ORGANISM: Artificial Sequence
<220> FEATURE:
<223> OTHER INFORMATION: antibody sequence

<400> SEQUENCE: 118

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Ala Gly Ser
                85                  90                  95

Asn Pro Tyr Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
        130                 135                 140

Tyr Pro Gly Ala Val Thr Val Ala Trp Lys Ala Asp Ser Ser Pro Val
```

```
                145                 150                 155                 160
Lys Ala Gly Val Glu Thr Thr Thr Pro Ser Lys Gln Ser Asn Asn Lys
                    165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                    195                 200                 205

Lys Thr Val Ala Pro Thr Glu Cys Ser
            210                 215
```

<210> SEQ ID NO 119
<211> LENGTH: 1356
<212> TYPE: DNA
<213> ORGANISM: Artificial Sequence
<220> FEATURE:
<223> OTHER INFORMATION: antibody sequence

<400> SEQUENCE: 119

| | | | | | | |
|---|---|---|---|---|---|---|
| gaagttcagc | tgctggaatc | tggcggcgga | ctggttcaac | ctggcggatc | tctgagactg | 60 |
| agctgtgccg | ccagcggctt | cacctttagc | agctacgaga | tgaactgggt | ccgacaggcc | 120 |
| cctggcaaag | ccttgaatg | gtgtccggc | atcagctgga | atagcggctc | tatcggctac | 180 |
| gccgacagcg | tgaagggcag | attcaccatc | agccgggaca | acagcaagaa | caccctgtac | 240 |
| ctgcagatga | acagcctgag | agccgaggac | accgccgtgt | actactgtgc | cagaagcggc | 300 |
| tacagcagct | cttggtttga | ccccgacttc | gactattggg | gccagggcac | actggtcaca | 360 |
| gtctcttcag | ccagcaccaa | gggccccagc | gtgttccctc | tggcccctag | cagcaagagc | 420 |
| acatctggcg | gaacagccgc | cctgggctgc | ctcgtgaagg | actactttcc | cgagcccgtg | 480 |
| accgtgtcct | ggaactctgg | cgctctgaca | agcggcgtgc | acacctttcc | agccgtgctg | 540 |
| cagagcagcg | gcctgtactc | tctgagcagc | gtcgtgacag | tgcccagcag | ctctctgggc | 600 |
| acccagacct | acatctgcaa | cgtgaaccac | aagcccagca | acaccaaggt | ggacaagaag | 660 |
| gtggaaccca | gagctgcga | caagacccac | acctgtcccc | cttgtcctgc | cccgaactg | 720 |
| ctgggaggcc | cttccgtgtt | cctgttcccc | ccaaagccca | aggacaccct | gatgatcagc | 780 |
| cggaccccg | aagtgacctg | cgtggtggtg | gatgtgtccc | acgaggaccc | tgaagtgaag | 840 |
| ttcaattggt | acgtggacgg | cgtggaagtg | cacaacgcca | agaccaagcc | tagagaggaa | 900 |
| cagtacaaca | gcacctaccg | ggtggtgtcc | gtgctgacag | tgctgcacca | ggactggctg | 960 |
| aacggcaaag | agtacaagtg | caaggtgtcc | aacaaggccc | tgcctgcccc | catcgagaaa | 1020 |
| accatcagca | aggccaaggg | ccagccccgc | gaaccccagg | tgtacacact | gcccccaagc | 1080 |
| agggacgagc | tgaccaagaa | ccaggtgtcc | ctgacctgtc | tcgtgaaagg | cttctacccc | 1140 |
| tccgatatcg | ccgtggaatg | ggagagcaac | ggccagcccg | agaacaacta | caagaccacc | 1200 |
| cccctgtgc | tggacagcga | cggctcattc | ttcctgtaca | gcaagctgac | cgtggacaag | 1260 |
| tcccggtggc | agcagggcaa | cgtgttcagc | tgcagcgtga | tgcacgaggc | cctgcacaac | 1320 |
| cactacaccc | agaagtccct | gagcctgagc | cctggc | | | 1356 |

<210> SEQ ID NO 120
<211> LENGTH: 651
<212> TYPE: DNA
<213> ORGANISM: Artificial Sequence
<220> FEATURE:
<223> OTHER INFORMATION: antibody sequence

<400> SEQUENCE: 120

```
cagtctgttc tgacacagcc tccatctgtg tctggcgccc ctggacagag agtgaccatc    60
agctgtacag gcagcagctc caatatcgga gccggctatg acgtgcactg gtatcagcag   120
ctgcctggca cagcccctaa actgctgatc tacggcaaca gcaacagacc cagcggcgtg   180
cccgatagat tttccggctc taagagcggc acaagcgcca gcctggctat tactggactg   240
caggccgagg acgaggccga ctactactgt tctagctacg ccggcagcaa ccctacgtg    300 gtgtttggcg gaggcaccaa gctgacagtt ctaggccagc ctaaagccgc ccctagcgtg   360
accctgttcc ctccaagcag cgaggaactg caggccaaca aggccaccct cgtgtgcctg   420
atcagcgact ctatcctgg cgccgtgacc gtggcctgga aggccgatag ctctcctgtg    480
aaggccggcg tggaaaccac caccc ctagc aagcagagca acaacaaata cgccgccagc   540
agctacctga gcctgacccc cgagcagtgg aagtcccaca gatcctacag ctgccaagtg   600
acccacgagg gcagcaccgt ggaaaagaca gtggccccta ccgagtgcag c            651
```

<210> SEQ ID NO 121
<211> LENGTH: 120
<212> TYPE: PRT
<213> ORGANISM: Artificial Sequence
<220> FEATURE:
<223> OTHER INFORMATION: antibody sequence

<400> SEQUENCE: 121

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Thr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser
        115                 120
```

<210> SEQ ID NO 122
<211> LENGTH: 5
<212> TYPE: PRT
<213> ORGANISM: Artificial Sequence
<220> FEATURE:
<223> OTHER INFORMATION: antibody sequence

<400> SEQUENCE: 122

```
Ser Tyr Ala Met Ser
 1               5
```

<210> SEQ ID NO 123
<211> LENGTH: 16
<212> TYPE: PRT
<213> ORGANISM: Artificial Sequence
<220> FEATURE:
<223> OTHER INFORMATION: antibody sequence

<400> SEQUENCE: 123

```
Ala Ile Gly Thr Gly Gly Asp Thr Tyr Tyr Ala Asp Ser Val Lys Gly
1               5                   10                  15

<210> SEQ ID NO 124
<211> LENGTH: 12
<212> TYPE: PRT
<213> ORGANISM: Artificial Sequence
<220> FEATURE:
<223> OTHER INFORMATION: antibody sequence

<400> SEQUENCE: 124

Arg Asp Asp Tyr Thr Ser Arg Asp Ala Phe Asp Tyr
1               5                   10

<210> SEQ ID NO 125
<211> LENGTH: 111
<212> TYPE: PRT
<213> ORGANISM: Artificial Sequence
<220> FEATURE:
<223> OTHER INFORMATION: antibody sequence

<400> SEQUENCE: 125

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Val Phe Gly Gly Gly Thr Lys Leu Thr Val Leu
            100                 105                 110

<210> SEQ ID NO 126
<211> LENGTH: 13
<212> TYPE: PRT
<213> ORGANISM: Artificial Sequence
<220> FEATURE:
<223> OTHER INFORMATION: antibody sequence

<400> SEQUENCE: 126

Ser Gly Ser Ser Ser Asn Ile Gly Ser Asn Thr Val Asn
1               5                   10

<210> SEQ ID NO 127
<211> LENGTH: 7
<212> TYPE: PRT
<213> ORGANISM: Artificial Sequence
<220> FEATURE:
<223> OTHER INFORMATION: antibody sequence

<400> SEQUENCE: 127

Tyr Asp Asp Leu Arg Pro Ser
1               5

<210> SEQ ID NO 128
<211> LENGTH: 12
<212> TYPE: PRT
<213> ORGANISM: Artificial Sequence
```

<220> FEATURE:
<223> OTHER INFORMATION: antibody sequence

<400> SEQUENCE: 128

Ala Ala Trp Asp Asp Ser Leu Asn Gly Tyr Val Val
1               5                   10

<210> SEQ ID NO 129
<211> LENGTH: 360
<212> TYPE: DNA
<213> ORGANISM: Artificial Sequence
<220> FEATURE:
<223> OTHER INFORMATION: antibody sequence

<400> SEQUENCE: 129

```
gaagttcagc tgctggaatc tggcggcgga ctggttcaac ctggcggatc tctgagactg    60
agctgtgccg ccagcggctt cacctttagc agctacgcca tgagctgggt ccgacaggct   120
cctggcaaag ccttgaatg gtgtccgcc attggcacag cggcgatac ctactacgcc      180 gactctgtga aggcagatt caccatcagc cgggacaaca gcaagaacac cctgtacctg    240
cagatgaaca gcctgagagc cgaggacacc gccgtgtact attgcgccag aagggacgac   300
tacaccagca gggacgcctt cgattattgg ggccagggca cactggtcac cgtttcttca   360
```

<210> SEQ ID NO 130
<211> LENGTH: 15
<212> TYPE: DNA
<213> ORGANISM: Artificial Sequence
<220> FEATURE:
<223> OTHER INFORMATION: antibody sequence

<400> SEQUENCE: 130
agctacgcca tgagc                                                     15

<210> SEQ ID NO 131
<211> LENGTH: 48
<212> TYPE: DNA
<213> ORGANISM: Artificial Sequence
<220> FEATURE:
<223> OTHER INFORMATION: antibody sequence

<400> SEQUENCE: 131
gccattggca caggcggcga tacctactac gccgactctg tgaagggc                 48

<210> SEQ ID NO 132
<211> LENGTH: 36
<212> TYPE: DNA
<213> ORGANISM: Artificial Sequence
<220> FEATURE:
<223> OTHER INFORMATION: antibody sequence

<400> SEQUENCE: 132
agggacgact acaccagcag ggacgccttc gattat                              36

<210> SEQ ID NO 133
<211> LENGTH: 333
<212> TYPE: DNA
<213> ORGANISM: Artificial Sequence
<220> FEATURE:
<223> OTHER INFORMATION: antibody sequence

<400> SEQUENCE: 133

```
cagtctgttc tgacacagcc tcctagcgcc tctggcacac tggacagag agtgaccatc    60 agctgtagcg gcagcagctc caacatcggc agcaacaccg tgaactggta tcagcagctg   120
```
cctggcacag cccctaaact gctgatctac tacgacgacc tgcggcctag cggcgtgcca    180
gatagatttt ctggcagcaa gagcggcacc tctgccagcc tggctatttc tggactgcag    240
agcgaggacg aggccgacta ttattgtgcc gcctgggacg acagcctgaa cggctatgtt    300
gttttcggcg aggcaccaa gctgaccgtt cta                                  333

<210> SEQ ID NO 134
<211> LENGTH: 39
<212> TYPE: DNA
<213> ORGANISM: Artificial Sequence
<220> FEATURE:
<223> OTHER INFORMATION: antibody sequence

<400> SEQUENCE: 134
agcggcagca gctccaacat cggcagcaac accgtgaac                            39

<210> SEQ ID NO 135
<211> LENGTH: 21
<212> TYPE: DNA
<213> ORGANISM: Artificial Sequence
<220> FEATURE:
<223> OTHER INFORMATION: antibody sequence

<400> SEQUENCE: 135
tacgacgacc tgcggcctag c                                               21

<210> SEQ ID NO 136
<211> LENGTH: 36
<212> TYPE: DNA
<213> ORGANISM: Artificial Sequence
<220> FEATURE:
<223> OTHER INFORMATION: antibody sequence

<400> SEQUENCE: 136
gccgcctggg acgacagcct gaacggctat gttgtt                               36

<210> SEQ ID NO 137
<211> LENGTH: 449
<212> TYPE: PRT
<213> ORGANISM: Artificial Sequence
<220> FEATURE:
<223> OTHER INFORMATION: antibody sequence

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Thr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

```
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 138
<211> LENGTH: 217
<212> TYPE: PRT
<213> ORGANISM: Artificial Sequence
<220> FEATURE:
<223> OTHER INFORMATION: antibody sequence

<400> SEQUENCE: 138

Gln Ser Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ser Asn
            20                  25                  30
Thr Val Asn Trp Tyr Gln Gln Leu Pro Gly Thr Ala Pro Lys Leu Leu
```

```
                35                  40                  45
Ile Tyr Tyr Asp Asp Leu Arg Pro Ser Gly Val Pro Asp Arg Phe Ser
     50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Ser Leu
                 85                  90                  95

Asn Gly Tyr Val Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
                115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
        210                 215

<210> SEQ ID NO 139
<211> LENGTH: 1347
<212> TYPE: DNA
<213> ORGANISM: Artificial Sequence
<220> FEATURE:
<223> OTHER INFORMATION: antibody sequence

<400> SEQUENCE: 139
gaagttcagc tgctggaatc tggcggcgga ctggttcaac tggcggatc tctgagactg     60 agctgtgccg ccagcggctt cacctttagc agctacgcca tgagctgggt ccgacaggct    120
cctggcaaag gccttgaatg ggtgtccgcc attggcacag cggcgatac ctactacgcc     180 gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360
gccagcacca agggccccag cgtgttccct ctggccccta gcagcaagag cacatctggc    420
ggaacagccg ccctgggctg cctcgtgaag gactactttc ccgagcccgt gaccgtgtcc    480
tggaactctg gcgctctgac aagcggcgtg cacacctttc cagccgtgct gcagagcagc    540
ggcctgtact ctctgagcag cgtcgtgaca gtgcccagca gctctctggg cacccagacc    600
tacatctgca acgtgaacca caagcccagc aacaccaagg tggacaagaa ggtgaacccc    660
aagagctgcg acaagaccca cacctgtccc ccttgtcctg cccccgaact gctgggaggc    720
ccttccgtgt tcctgttccc cccaaagccc aaggacaccc tgatgatcag ccggaccccc    780
gaagtgacct gcgtggtggt ggatgtgtcc acgaggacc tgaagtgaa gttcaattgg     840 tacgtggacg gcgtggaagt gcacaacgcc aagaccaagc tagagagga acagtacaac    900 agcacctacc gggtggtgtc cgtgctgaca gtgctgcacc aggactggct gaacggcaaa    960
gagtacaagt gcaaggtgtc caacaaggcc ctgcctgccc catcgagaa aaccatcagc   1020
```

```
aaggccaagg gccagccccg cgaaccccag gtgtacacac tgcccccaag cagggacgag    1080
ctgaccaaga accaggtgtc cctgacctgt ctcgtgaaag gcttctaccc ctccgatatc    1140
gccgtggaat gggagagcaa cggccagccc gagaacaact acaagaccac ccccctgtg     1200 ctggacagcg acggctcatt cttcctgtac agcaagctga ccgtggacaa gtcccggtgg    1260
cagcagggca acgtgttcag ctgcagcgtg atgcacgagg ccctgcacaa ccactacacc    1320
cagaagtccc tgagcctgag ccctggc                                        1347
```

<210> SEQ ID NO 140
<211> LENGTH: 651
<212> TYPE: DNA
<213> ORGANISM: Artificial Sequence
<220> FEATURE:
<223> OTHER INFORMATION: antibody sequence

<400> SEQUENCE: 140

```
cagtctgttc tgacacagcc tcctagcgcc tctggcacac ctggacagag agtgaccatc      60
agctgtagcg gcagcagctc caacatcggc agcaacaccg tgaactggta tcagcagctg     120
cctggcacag cccctaaact gctgatctac tacgacgacc tgcggcctag cggcgtgcca     180
gatagatttt ctggcagcaa gagcggcacc tctgccagcc tggctatttc tggactgcag     240
agcgaggacg aggccgacta ttattgtgcc gcctgggacg acagcctgaa cggctatgtt     300
gttttcggcg gaggcaccaa gctgaccgtt ctaggccagc ctaaagccgc cctagcgtg      360 accctgttcc ctccaagcag cgaggaactg caggccaaca aggccaccct cgtgtgcctg     420
atcagcgact tctatcctgg cgccgtgacc gtggcctgga aggccgatag ctctcctgtg     480
aaggccggcg tggaaaccac caccctagc aagcagagca acaacaaata cgccgccagc      540
agctacctga gctgacccc cgagcagtgg aagtcccaca gatcctacag ctgccaagtg      600
acccacgagg gcagcaccgt ggaaaagaca gtggccccta ccgagtgcag c              651
```

<210> SEQ ID NO 141
<211> LENGTH: 120
<212> TYPE: PRT
<213> ORGANISM: Artificial Sequence
<220> FEATURE:
<223> OTHER INFORMATION: antibody sequence

<400> SEQUENCE: 141

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Tyr Ser Tyr
            20                  25                  30

Ala Met Ser Trp Val Arg Gln Ala Pro Gly Lys Gly Leu Glu Trp Val
        35                  40                  45

Ser Ala Ile Gly Thr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser
        115                 120
```

```
<210> SEQ ID NO 142
<211> LENGTH: 5
<212> TYPE: PRT
<213> ORGANISM: Artificial Sequence
<220> FEATURE:
<223> OTHER INFORMATION: antibody sequence

<400> SEQUENCE: 142

Ser Tyr Ala Met Ser
1               5

<210> SEQ ID NO 143
<211> LENGTH: 16
<212> TYPE: PRT
<213> ORGANISM: Artificial Sequence
<220> FEATURE:
<223> OTHER INFORMATION: antibody sequence

<400> SEQUENCE: 143

Ala Ile Gly Thr Gly Gly Asp Thr Tyr Tyr Ala Asp Ser Val Lys Gly
1               5                   10                  15

<210> SEQ ID NO 144
<211> LENGTH: 12
<212> TYPE: PRT
<213> ORGANISM: Artificial Sequence
<220> FEATURE:
<223> OTHER INFORMATION: antibody sequence

<400> SEQUENCE: 144

Arg Asp Asp Tyr Thr Ser Arg Asp Ala Phe Asp Tyr
1               5                   10

<210> SEQ ID NO 145
<211> LENGTH: 111
<212> TYPE: PRT
<213> ORGANISM: Artificial Sequence
<220> FEATURE:
<223> OTHER INFORMATION: antibody sequence

<400> SEQUENCE: 145

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
                35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Asp Tyr Val Val Phe Gly Gly Gly Thr Lys Leu Thr Val Leu
                100                 105                 110

<210> SEQ ID NO 146
<211> LENGTH: 13
<212> TYPE: PRT
<213> ORGANISM: Artificial Sequence
<220> FEATURE:
<223> OTHER INFORMATION: antibody sequence

<400> SEQUENCE: 146
```

Ser Gly Ser Ser Ser Asn Ile Gly Ser Asn Thr Val Asn
1               5                   10

<210> SEQ ID NO 147
<211> LENGTH: 7
<212> TYPE: PRT
<213> ORGANISM: Artificial Sequence
<220> FEATURE:
<223> OTHER INFORMATION: antibody sequence

<400> SEQUENCE: 147

Tyr Asp Asp Leu Arg Pro Ser
1               5

<210> SEQ ID NO 148
<211> LENGTH: 12
<212> TYPE: PRT
<213> ORGANISM: Artificial Sequence
<220> FEATURE:
<223> OTHER INFORMATION: antibody sequence

<400> SEQUENCE: 148

Ala Ala Trp Asp Asp Ser Leu Asn Asp Tyr Val Val
1               5                   10

<210> SEQ ID NO 149
<211> LENGTH: 360
<212> TYPE: DNA
<213> ORGANISM: Artificial Sequence
<220> FEATURE:
<223> OTHER INFORMATION: antibody sequence

<400> SEQUENCE: 149

```
gaagttcagc tgctggaatc tggcggcgga ctggttcaac ctggcggatc tctgagactg      60
agctgtgccg ccagcggctt cacctttTac agctacgcca tgagctgggt ccgacaggcc     120
cctggaaaag gccttgaatg ggtgtccgcc atcggcacag gcggcgatac ctactatgcc     180
gactctgtga agggcagatt caccatcagc cggacaacag caagaacac cctgtacctg      240
cagatgaaca gcctgagagc cgaggacacc gccgtgtact attgcgccag aagggacgac     300
tacaccagca gggacgcctt cgattattgg ggccagggca cactggtcac cgtttcttca     360
```

<210> SEQ ID NO 150
<211> LENGTH: 15
<212> TYPE: DNA
<213> ORGANISM: Artificial Sequence
<220> FEATURE:
<223> OTHER INFORMATION: antibody sequence

<400> SEQUENCE: 150

```
agctacgcca tgagc                                                       15
```

<210> SEQ ID NO 151
<211> LENGTH: 48
<212> TYPE: DNA
<213> ORGANISM: Artificial Sequence
<220> FEATURE:
<223> OTHER INFORMATION: antibody sequence

<400> SEQUENCE: 151

```
gccatcggca caggcggcga tacctactat gccgactctg tgaagggc                   48
```

<210> SEQ ID NO 152
<211> LENGTH: 36
<212> TYPE: DNA

```
<213> ORGANISM: Artificial Sequence
<220> FEATURE:
<223> OTHER INFORMATION: antibody sequence

<400> SEQUENCE: 152
agggacgact acaccagcag ggacgccttc gattat                               36

<210> SEQ ID NO 153
<211> LENGTH: 333
<212> TYPE: DNA
<213> ORGANISM: Artificial Sequence
<220> FEATURE:
<223> OTHER INFORMATION: antibody sequence

<400> SEQUENCE: 153
cagtctgttc tgacacagcc tcctagcgcc tctggcacac ctggacagag agtgaccatc      60
agctgtagcg gcagcagctc caacatcggc agcaacaccg tgaactggta tcagcagctg    120
cctggcacag cccctaaact gctgatctac tacgacgacc tgcggcctag cggcgtgcca    180
gatagatttt ctggcagcaa gagcggcacc tctgccagcc tggctatttc tggactgcag    240
agcgaggacg aggccgacta ttattgtgcc gcctgggacg acagcctgaa cgactacgtt    300
gtgtttggcg gaggcaccaa gctgaccgtt cta                                 333

<210> SEQ ID NO 154
<211> LENGTH: 39
<212> TYPE: DNA
<213> ORGANISM: Artificial Sequence
<220> FEATURE:
<223> OTHER INFORMATION: antibody sequence

<400> SEQUENCE: 154
agcggcagca gctccaacat cggcagcaac accgtgaac                            39

<210> SEQ ID NO 155
<211> LENGTH: 21
<212> TYPE: DNA
<213> ORGANISM: Artificial Sequence
<220> FEATURE:
<223> OTHER INFORMATION: antibody sequence

<400> SEQUENCE: 155
tacgacgacc tgcggcctag c                                               21

<210> SEQ ID NO 156
<211> LENGTH: 36
<212> TYPE: DNA
<213> ORGANISM: Artificial Sequence
<220> FEATURE:
<223> OTHER INFORMATION: antibody sequence

<400> SEQUENCE: 156
gccgcctggg acgacagcct gaacgactac gttgtg                               36

<210> SEQ ID NO 157
<211> LENGTH: 447
<212> TYPE: PRT
<213> ORGANISM: Artificial Sequence
<220> FEATURE:
<223> OTHER INFORMATION: antibody sequence

<400> SEQUENCE: 157

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Tyr Ser Tyr
             20                  25                  30

Ala Met Ser Trp Val Arg Gln Ala Pro Gly Lys Gly Leu Glu Trp Val
         35                  40                  45

Ser Ala Ile Gly Thr Gly Gly Asp Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly Lys
```

<210> SEQ ID NO 158
<211> LENGTH: 217
<212> TYPE: PRT
<213> ORGANISM: Artificial Sequence
<220> FEATURE:
<223> OTHER INFORMATION: antibody sequence

<400> SEQUENCE: 158

```
Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Thr Val Asn Trp Tyr Gln Gln Leu Pro Gly Thr Ala Pro Lys Leu Leu
        35                  40                  45
Ile Tyr Tyr Asp Asp Leu Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Asn Asp Tyr Val Val Phe Gly Gly Gly Thr Lys Leu Thr Val Leu Gly
            100                 105                 110
Gln Pro Lys Ala Ala Pro Ser Val Thr Leu Phe Pro Pro Ser Ser Glu
        115                 120                 125
Glu Leu Gln Ala Asn Lys Ala Thr Leu Val Cys Leu Ile Ser Asp Phe
    130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Cys Ser
    210                 215
```

<210> SEQ ID NO 159
<211> LENGTH: 1341
<212> TYPE: DNA
<213> ORGANISM: Artificial Sequence
<220> FEATURE:
<223> OTHER INFORMATION: antibody sequence

<400> SEQUENCE: 159

```
gaagttcagc tgctggaatc tggcggcgga ctggttcaac tggcggatc tctgagactg    60
agctgtgccg ccagcggctt cacctttac agctacgcca tgagctgggt ccgacaggcc    120
cctggaaaag gccttgaatg ggtgtccgcc atcggcacag gcggcgatac ctactatgcc    180
gactctgtga agggcagatt caccatcagc cggacaacag caagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360
gccagcacca agggccccag cgtgttccct ctggcccctt gtagcagaag caccagcgag    420
tctacagccg ccctgggctg cctcgtgaag gactactttc ccgagcccgt gaccgtgtcc    480
```

```
tggaactctg gcgctctgac aagcggcgtg cacacctttc cagccgtgct gcagagcagc      540
ggcctgtact ctctgagcag cgtcgtgaca gtgcccagca gcagcctggg caccaagacc      600
tacacctgta acgtggacca caagcccagc aacaccaagg tggacaagcg ggtggaatct      660
aagtacggcc ctcccctgcc ctccttgccca gcccctgaat ttctgggcgg accctccgtg      720
ttcctgttcc ccccaaagcc caaggacacc ctgatgatca gccggacccc cgaagtgacc      780
tgcgtggtgg tggatgtgtc ccaggaagat cccgaggtgc agttcaattg gtacgtggac      840
ggcgtggaag tgcacaacgc caagaccaag cccagagagg aacagttcaa cagcacctac      900
cgggtggtgt ccgtgctgac agtgctgcac caggactggc tgaacggcaa agagtacaag      960
tgcaaggtgt ccaacaaggg cctgcccagc tccatcgaga aaaccatcag caaggccaag      1020
ggccagcccc gcgaaccccca ggtgtacaca ctgcctccaa gccaggaaga gatgaccaag      1080
aaccaggtgt ccctgacctg tctcgtgaaa ggcttctacc cctccgatat cgccgtggaa      1140
tgggagagca acggccagcc cgagaacaac tacaagacca cccccctgt gctggacagc       1200 gacggctcat tcttcctgta cagcagactg accgtggaca gagccggtg caggaaggc       1260 aacgtgttca gctgcagcgt gatgcacgag gccctgcaca accactacac ccagaagtcc      1320
ctgtctctga gcctgggcaa g                                                 1341
```

<210> SEQ ID NO 160
<211> LENGTH: 651
<212> TYPE: DNA
<213> ORGANISM: Artificial Sequence
<220> FEATURE:
<223> OTHER INFORMATION: antibody sequence

<400> SEQUENCE: 160

```
cagtctgttc tgacacagcc tcctagcgcc tctggcacac ctggacagag agtgaccatc       60
agctgtagcg gcagcagctc caacatcggc agcaacaccg tgaactggta tcagcagctg      120
cctggcacag cccctaaact gctgatctac tacgacgacc tgcggcctag cggcgtgcca      180
gatagatttt ctggcagcaa gagcggcacc tctgccagcc tggctatttc tggactgcag      240
agcgaggacg aggccgacta ttattgtgcc gcctgggacg acagcctgaa cgactacgtt      300
gtgtttggcg gaggcaccaa gctgaccgtt ctaggccagc ctaaagccgc ccctagcgtg      360
accctgttcc ctccaagcag cgaggaactg caggccaaca aggccaccct cgtgtgcctg      420
atcagcgact tctatcctgg cgccgtgacc gtggcctgga aggccgatag ctctcctgtg      480
aaggccggcg tggaaaccac cacccctagc aagcagagca caacaaata cgccgccagc      540 agctacctga gcctgacccc cgagcagtgg aagtcccaca gatcctacag ctgccaagtg      600
acccacgagg gcagcaccgt ggaaaagaca gtggccccta ccgagtgcag c               651
```

<210> SEQ ID NO 161
<211> LENGTH: 120
<212> TYPE: PRT
<213> ORGANISM: Artificial Sequence
<220> FEATURE:
<223> OTHER INFORMATION: antibody sequence

<400> SEQUENCE: 161

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Ser Trp Val Arg Gln Ala Pro Gly Lys Gly Leu Glu Trp Val
            35                  40                  45
Ser Ala Ile Gly Tyr Gly Gly Asp Thr Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Arg Asp Asp Tyr Thr Ser Arg Asp Ala Phe Asp Tyr Trp Gly Gln
                100                 105                 110
Gly Thr Leu Val Thr Val Ser Ser
        115                 120

<210> SEQ ID NO 162
<211> LENGTH: 5
<212> TYPE: PRT
<213> ORGANISM: Artificial Sequence
<220> FEATURE:
<223> OTHER INFORMATION: antibody sequence

<400> SEQUENCE: 162

Ser Tyr Ala Met Ser
 1               5

<210> SEQ ID NO 163
<211> LENGTH: 16
<212> TYPE: PRT
<213> ORGANISM: Artificial Sequence
<220> FEATURE:
<223> OTHER INFORMATION: antibody sequence

<400> SEQUENCE: 163

Ala Ile Gly Tyr Gly Gly Asp Thr Tyr Tyr Ala Asp Ser Val Lys Gly
 1               5                  10                  15

<210> SEQ ID NO 164
<211> LENGTH: 12
<212> TYPE: PRT
<213> ORGANISM: Artificial Sequence
<220> FEATURE:
<223> OTHER INFORMATION: antibody sequence

<400> SEQUENCE: 164

Arg Asp Asp Tyr Thr Ser Arg Asp Ala Phe Asp Tyr
 1               5                  10

<210> SEQ ID NO 165
<211> LENGTH: 111
<212> TYPE: PRT
<213> ORGANISM: Artificial Sequence
<220> FEATURE:
<223> OTHER INFORMATION: antibody sequence

<400> SEQUENCE: 165

Gln Ser Val Leu Thr Gln Pro Pro Ser Ala Ser Gly Thr Pro Gly Gln
 1               5                  10                  15
Arg Val Thr Ile Ser Cys Ser Gly Ser Ser Ser Asn Ile Gly Ser Asn
                 20                  25                  30
Thr Val Asn Trp Tyr Gln Gln Leu Pro Gly Thr Ala Pro Lys Leu Leu
            35                  40                  45
Ile Tyr Tyr Asp Asp Leu Arg Pro Ser Gly Val Pro Asp Arg Phe Ser
 50                  55                  60

```
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Asp Ile Val Val Phe Gly Gly Gly Thr Lys Leu Thr Val Leu
            100                 105                 110

<210> SEQ ID NO 166
<211> LENGTH: 13
<212> TYPE: PRT
<213> ORGANISM: Artificial Sequence
<220> FEATURE:
<223> OTHER INFORMATION: antibody sequence

<400> SEQUENCE: 166

Ser Gly Ser Ser Ser Asn Ile Gly Ser Asn Thr Val Asn
1               5                   10

<210> SEQ ID NO 167
<211> LENGTH: 7
<212> TYPE: PRT
<213> ORGANISM: Artificial Sequence
<220> FEATURE:
<223> OTHER INFORMATION: antibody sequence

<400> SEQUENCE: 167

Tyr Asp Asp Leu Arg Pro Ser
1               5

<210> SEQ ID NO 168
<211> LENGTH: 12
<212> TYPE: PRT
<213> ORGANISM: Artificial Sequence
<220> FEATURE:
<223> OTHER INFORMATION: antibody sequence

<400> SEQUENCE: 168

Ala Ala Trp Asp Asp Ser Leu Asn Asp Ile Val Val
1               5                   10

<210> SEQ ID NO 169
<211> LENGTH: 360
<212> TYPE: DNA
<213> ORGANISM: Artificial Sequence
<220> FEATURE:
<223> OTHER INFORMATION: antibody sequence

<400> SEQUENCE: 169
gaagttcagc tgctggaatc tggcggcgga ctggttcaac ctggcggatc tctgagactg      60
agctgtgccg ccagcggctt cacctttagc agctacgcca tgagctgggt ccgacaggct     120
cctggcaaag gccttgaatg gctgtccgcc atcggctatg cggcgatac ctactacgcc     180 gactctgtga agggcagatt caccatcagc cgggacaaca gcaagaacac cctgtacctg     240
cagatgaaca gcctgagagc cgaggacacc gccgtgtact attgcgccag aagggacgac     300
tacaccagca gggacgcctt cgattattgg ggccagggca cactggtcac cgtttcttca     360

<210> SEQ ID NO 170
<211> LENGTH: 15
<212> TYPE: DNA
<213> ORGANISM: Artificial Sequence
<220> FEATURE:
<223> OTHER INFORMATION: antibody sequence

<400> SEQUENCE: 170
```

```
agctacgcca tgagc                                                          15

<210> SEQ ID NO 171
<211> LENGTH: 48
<212> TYPE: DNA
<213> ORGANISM: Artificial Sequence
<220> FEATURE:
<223> OTHER INFORMATION: antibody sequence

<400> SEQUENCE: 171
gccatcggct atggcggcga tacctactac gccgactctg tgaagggc                      48

<210> SEQ ID NO 172
<211> LENGTH: 36
<212> TYPE: DNA
<213> ORGANISM: Artificial Sequence
<220> FEATURE:
<223> OTHER INFORMATION: antibody sequence

<400> SEQUENCE: 172
agggacgact acaccagcag ggacgccttc gattat                                   36

<210> SEQ ID NO 173
<211> LENGTH: 333
<212> TYPE: DNA
<213> ORGANISM: Artificial Sequence
<220> FEATURE:
<223> OTHER INFORMATION: antibody sequence

<400> SEQUENCE: 173
cagtctgttc tgacacagcc tcctagcgcc tctggcacac ctggacagag agtgaccatc         60
agctgtagcg gcagcagctc caacatcggc agcaacaccg tgaactggta tcagcagctg        120
cctggcacag cccctaaact gctgatctac tacgacgacc tgcggcctag cggcgtgcca        180
gatagatttt ctggcagcaa gagcggcacc tctgccagcc tggctatttc tggactgcag        240
agcgaggacg aggccgacta ttattgtgcc gcctgggacg acagcctgaa cgacatcgtt        300
gttttcggcg gaggcaccaa gctgaccgtt cta                                     333

<210> SEQ ID NO 174
<211> LENGTH: 39
<212> TYPE: DNA
<213> ORGANISM: Artificial Sequence
<220> FEATURE:
<223> OTHER INFORMATION: antibody sequence

<400> SEQUENCE: 174
agcggcagca gctccaacat cggcagcaac accgtgaac                                39

<210> SEQ ID NO 175
<211> LENGTH: 21
<212> TYPE: DNA
<213> ORGANISM: Artificial Sequence
<220> FEATURE:
<223> OTHER INFORMATION: antibody sequence

<400> SEQUENCE: 175
tacgacgacc tgcggcctag c                                                   21

<210> SEQ ID NO 176
<211> LENGTH: 36
<212> TYPE: DNA
<213> ORGANISM: Artificial Sequence
<220> FEATURE:
```

<223> OTHER INFORMATION: antibody sequence

<400> SEQUENCE: 176
gccgcctggg acgacagcct gaacgacatc gttgtt                36

<210> SEQ ID NO 177
<211> LENGTH: 447
<212> TYPE: PRT
<213> ORGANISM: Artificial Sequence
<220> FEATURE:
<223> OTHER INFORMATION: antibody sequence

<400> SEQUENCE: 177

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335
```

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 178
<211> LENGTH: 217
<212> TYPE: PRT
<213> ORGANISM: Artificial Sequence
<220> FEATURE:
<223> OTHER INFORMATION: antibody sequence

<400> SEQUENCE: 178

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Asp Ile Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 179
<211> LENGTH: 1341
<212> TYPE: DNA
<213> ORGANISM: Artificial Sequence
<220> FEATURE:

<223> OTHER INFORMATION: antibody sequence

<400> SEQUENCE: 179

| | | | | | |
|---|---|---|---|---|---|
| gaagttcagc | tgctggaatc | tggcggcgga | ctggttcaac | ctggcggatc | tctgagactg | 60 |
| agctgtgccg | ccagcggctt | cacctttagc | agctacgcca | tgagctgggt | ccgacaggct | 120 |
| cctggcaaag | gccttgaatg | ggtgtccgcc | atcggctatg | gcggcgatac | ctactacgcc | 180 |
| gactctgtga | agggcagatt | caccatcagc | cgggacaaca | gcaagaacac | cctgtacctg | 240 |
| cagatgaaca | gcctgagagc | cgaggacacc | gccgtgtact | attgcgccag | aagggacgac | 300 |
| tacaccagca | gggacgcctt | cgattattgg | ggcagggca | cactggtcac | cgtttcttca | 360 |
| gccagcacca | agggcccag | cgtgttccct | ctggcccctt | gtagcagaag | caccagcgag | 420 |
| tctacagccg | ccctgggctg | cctcgtgaag | gactactttc | ccgagcccgt | gaccgtgtcc | 480 |
| tggaactctg | gcgctctgac | aagcggcgtg | cacacctttc | cagccgtgct | gcagagcagc | 540 |
| ggcctgtact | ctctgagcag | cgtcgtgaca | gtgcccagca | gcagcctggg | caccaagacc | 600 |
| tacacctgta | acgtggacca | caagcccagc | aacaccaagg | tggacaagcg | ggtggaatct | 660 |
| aagtacggcc | ctccctgccc | tccttgccca | gcccctgaat | ttctgggcgg | accctccgtg | 720 |
| ttcctgttcc | cccaaagcc | caaggacacc | ctgatgatca | gccggacccc | cgaagtgacc | 780 |
| tgcgtggtgg | tggatgtgtc | ccaggaagat | cccgaggtgc | agttcaattg | gtacgtggac | 840 |
| ggcgtggaag | tgcacaacgc | caagaccaag | cccagagagg | aacagttcaa | cagcacctac | 900 |
| cgggtggtgt | ccgtgctgac | agtgctgcac | caggactggc | tgaacggcaa | agagtacaag | 960 |
| tgcaaggtgt | ccaacaaggg | cctgcccagc | tccatcgaga | aaaccatcag | caaggccaag | 1020 |
| ggccagcccc | gcgaacccca | ggtgtacaca | ctgcctccaa | gccaggaaga | gatgaccaag | 1080 |
| aaccaggtgt | ccctgacctg | tctcgtgaaa | ggcttctacc | cctccgatat | cgccgtggaa | 1140 |
| tgggagagca | acggccagcc | cgagaacaac | tacaagacca | cccccctgt | gctggacagc | 1200 |
| gacggctcat | tcttcctgta | cagcagactg | accgtggaca | agagccggtg | gcaggaaggc | 1260 |
| aacgtgttca | gctgcagcgt | gatgcacgag | gccctgcaca | accactacac | ccagaagtcc | 1320 |
| ctgtctctga | gcctgggcaa | g | | | | 1341 |

<210> SEQ ID NO 180
<211> LENGTH: 651
<212> TYPE: DNA
<213> ORGANISM: Artificial Sequence
<220> FEATURE:
<223> OTHER INFORMATION: antibody sequence

<400> SEQUENCE: 180

| | | | | | |
|---|---|---|---|---|---|
| cagtctgttc | tgacacagcc | tcctagcgcc | tctggcacac | ctggacagag | agtgaccatc | 60 |
| agctgtagcg | gcagcagctc | caacatcggc | agcaacaccg | tgaactggta | tcagcagctg | 120 |
| cctggcacag | cccctaaact | gctgatctac | tacgacgacc | tgcggcctag | cggcgtgcca | 180 |
| gatagatttt | ctggcagcaa | gagcggcacc | tctgccagcc | tggctatttc | tggactgcag | 240 |
| agcgaggacg | aggccgacta | ttattgtgcc | gcctgggacg | acagcctgaa | cgacatcgtt | 300 |
| gttttcggcg | gaggcaccaa | gctgaccgtt | ctaggccagc | ctaaagccgc | cctagcgtg | 360 |
| accctgttcc | ctccaagcag | cgaggaactg | caggccaaca | aggccaccct | cgtgtgcctg | 420 |
| atcagcgact | tctatcctgg | cgccgtgacc | gtggcctgga | aggccgatag | ctctcctgtg | 480 |
| aaggccggcg | tggaaaccac | caccctagc | aagcagagca | acaacaaata | cgccgccagc | 540 |
| agctacctga | gcctgacccc | cgagcagtgg | aagtcccaca | gatcctacag | ctgccaagtg | 600 | acccacgagg gcagcaccgt ggaaaagaca gtggccccta ccgagtgcag c 651

<210> SEQ ID NO 181
<211> LENGTH: 120
<212> TYPE: PRT
<213> ORGANISM: Artificial Sequence
<220> FEATURE:
<223> OTHER INFORMATION: antibody sequence

<400> SEQUENCE: 181

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser
        115                 120

<210> SEQ ID NO 182
<211> LENGTH: 5
<212> TYPE: PRT
<213> ORGANISM: Artificial Sequence
<220> FEATURE:
<223> OTHER INFORMATION: antibody sequence

<400> SEQUENCE: 182

Ser Tyr Ala Met Ser
1               5

<210> SEQ ID NO 183
<211> LENGTH: 16
<212> TYPE: PRT
<213> ORGANISM: Artificial Sequence
<220> FEATURE:
<223> OTHER INFORMATION: antibody sequence

<400> SEQUENCE: 183

Ala Ile Gly Tyr Gly Gly Asp Thr Tyr Tyr Ala Asp Ser Val Lys Gly
1               5                   10                  15

<210> SEQ ID NO 184
<211> LENGTH: 12
<212> TYPE: PRT
<213> ORGANISM: Artificial Sequence
<220> FEATURE:
<223> OTHER INFORMATION: antibody sequence

<400> SEQUENCE: 184

Arg Asp Asp Tyr Thr Ser Arg Asp Ala Phe Asp Tyr
1               5                   10

<210> SEQ ID NO 185
<211> LENGTH: 111

```
<212> TYPE: PRT
<213> ORGANISM: Artificial Sequence
<220> FEATURE:
<223> OTHER INFORMATION: antibody sequence

<400> SEQUENCE: 185

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Val Tyr Pro Val Phe Gly Gly Gly Thr Lys Leu Thr Val Leu
            100                 105                 110

<210> SEQ ID NO 186
<211> LENGTH: 13
<212> TYPE: PRT
<213> ORGANISM: Artificial Sequence
<220> FEATURE:
<223> OTHER INFORMATION: antibody sequence

<400> SEQUENCE: 186

Ser Gly Ser Ser Ser Asn Ile Gly Ser Asn Thr Val Asn
1               5                   10

<210> SEQ ID NO 187
<211> LENGTH: 7
<212> TYPE: PRT
<213> ORGANISM: Artificial Sequence
<220> FEATURE:
<223> OTHER INFORMATION: antibody sequence

<400> SEQUENCE: 187

Tyr Asp Asp Leu Arg Pro Ser
1               5

<210> SEQ ID NO 188
<211> LENGTH: 12
<212> TYPE: PRT
<213> ORGANISM: Artificial Sequence
<220> FEATURE:
<223> OTHER INFORMATION: antibody sequence

<400> SEQUENCE: 188

Ala Ala Trp Asp Asp Ser Leu Asn Val Tyr Pro Val
1               5                   10

<210> SEQ ID NO 189
<211> LENGTH: 360
<212> TYPE: DNA
<213> ORGANISM: Artificial Sequence
<220> FEATURE:
<223> OTHER INFORMATION: antibody sequence

<400> SEQUENCE: 189
gaagttcagc tgctggaatc tggcggcgga ctggttcaac tggcggatc tctgagactg    60
```

```
agctgtgccg ccagcggctt cacctttagc agctacgcca tgagctgggt ccgacaggct    120
cctggcaaag gccttgaatg ggtgtccgcc atcggctatg gcggcgatac ctactacgcc    180
gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360
```

<210> SEQ ID NO 190
<211> LENGTH: 15
<212> TYPE: DNA
<213> ORGANISM: Artificial Sequence
<220> FEATURE:
<223> OTHER INFORMATION: antibody sequence

<400> SEQUENCE: 190

```
agctacgcca tgagc                                                      15
```

<210> SEQ ID NO 191
<211> LENGTH: 48
<212> TYPE: DNA
<213> ORGANISM: Artificial Sequence
<220> FEATURE:
<223> OTHER INFORMATION: antibody sequence

<400> SEQUENCE: 191

```
gccatcggct atggcggcga tacctactac gccgactctg tgaagggc                  48
```

<210> SEQ ID NO 192
<211> LENGTH: 36
<212> TYPE: DNA
<213> ORGANISM: Artificial Sequence
<220> FEATURE:
<223> OTHER INFORMATION: antibody sequence

<400> SEQUENCE: 192

```
agggacgact acaccagcag ggacgccttc gattat                               36
```

<210> SEQ ID NO 193
<211> LENGTH: 333
<212> TYPE: DNA
<213> ORGANISM: Artificial Sequence
<220> FEATURE:
<223> OTHER INFORMATION: antibody sequence

<400> SEQUENCE: 193

```
cagtctgttc tgacacagcc tcctagcgcc tctggcacac ctggacagag agtgaccatc    60
agctgtagcg gcagcagctc caacatcggc agcaacaccg tgaactggta tcagcagctg    120
cctggcacag cccctaaact gctgatctac tacgacgacc tgcggcctag cggcgtgcca    180
gatagatttt ctggcagcaa gagcggcacc tctgccagcc tggctatttc tggactgcag    240
agcgaggacg aggccgacta ttattgtgcc gcctgggacg acagcctgaa cgtgtaccct    300
gtttttggcg gaggcaccaa gctgaccgtt cta                                  333
```

<210> SEQ ID NO 194
<211> LENGTH: 39
<212> TYPE: DNA
<213> ORGANISM: Artificial Sequence
<220> FEATURE:
<223> OTHER INFORMATION: antibody sequence

<400> SEQUENCE: 194

```
agcggcagca gctccaacat cggcagcaac accgtgaac                            39
```

<210> SEQ ID NO 195
<211> LENGTH: 21
<212> TYPE: DNA
<213> ORGANISM: Artificial Sequence
<220> FEATURE:
<223> OTHER INFORMATION: antibody sequence

<400> SEQUENCE: 195
tacgacgacc tgcggcctag c                                          21

<210> SEQ ID NO 196
<211> LENGTH: 36
<212> TYPE: DNA
<213> ORGANISM: Artificial Sequence
<220> FEATURE:
<223> OTHER INFORMATION: antibody sequence

<400> SEQUENCE: 196
gccgcctggg acgacagcct gaacgtgtac cctgtt                          36

<210> SEQ ID NO 197
<211> LENGTH: 447
<212> TYPE: PRT
<213> ORGANISM: Artificial Sequence
<220> FEATURE:
<223> OTHER INFORMATION: antibody sequence

<400> SEQUENCE: 197

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 198
<211> LENGTH: 217
<212> TYPE: PRT
<213> ORGANISM: Artificial Sequence
<220> FEATURE:
<223> OTHER INFORMATION: antibody sequence

<400> SEQUENCE: 198

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Val Tyr Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
            165                 170                 175

Tyr Ala Ala Ser Ser Tyr Leu Ser Leu Thr Pro Glu Gln Trp Lys Ser
        180                 185                 190

His Arg Ser Tyr Ser Cys Gln Val Thr His Glu Gly Ser Thr Val Glu
    195                 200                 205

Lys Thr Val Ala Pro Thr Glu Cys Ser
    210                 215

<210> SEQ ID NO 199
<211> LENGTH: 1341
<212> TYPE: DNA
<213> ORGANISM: Artificial Sequence
<220> FEATURE:
<223> OTHER INFORMATION: antibody sequence

<400> SEQUENCE: 199
gaagttcagc tgctggaatc tggcggcgga ctggttcaac tggcggatc tctgagactg      60 agctgtgccg ccagcggctt cacctttagc agctacgcca tgagctgggt ccgacaggct    120
cctggcaaag ccttgaatg gtgtccgcc atcggctatg cggcgatac ctactacgcc       180 gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360
gccagcacca agggccccag cgtgttccct ctggccccct tgtagcagaag caccagcgag    420 tctacagccg cctgggctg cctcgtgaag gactactttc ccgagcccgt gaccgtgtcc    480
tggaactctg gcgctctgac aagcggcgtg cacaccttc cagccgtgct gcagagcagc    540
ggcctgtact ctctgagcag cgtcgtgaca gtgcccagca gcagctggg caccaagacc    600 tacacctgta acgtggacca caagcccagc aacaccaagg tggacaagcg ggtggaatct    660
aagtacggcc ctcccctgccc tccttgccca gcccctgaat ttctgggcgg accctccgtg    720
ttcctgttcc ccccaaagcc caaggacacc ctgatgatca gccggacccc cgaagtgacc    780
tgcgtggtgg tggatgtgtc ccaggaagat cccgaggtgc agttcaattg gtacgtggac    840
ggcgtggaag tgcacaacgc caagaccaag cccagagagg aacagttcaa cagcacctac    900
cgggtggtgt ccgtgctgac agtgctgcac caggactggc tgaacggcaa agagtacaag    960
tgcaaggtgt ccaacaaggg cctgcccagc tccatcgaga aaccatcag caaggccaag   1020 ggccagcccc gcgaaccca ggtgtacaca ctgcctccaa gccaggaaga gatgaccaag   1080
aaccaggtgt ccctgacctg tctcgtgaaa ggcttctacc cctccgatat cgccgtggaa   1140
tgggagagca acggccagcc cgagaacaac tacaagacca ccccccctgt gctggacagc   1200
gacggctcat tcttcctgta cagcagactg accgtggaca gagccggtg gcaggaaggc    1260 aacgtgttca gctgcagcgt gatgcacgag gccctgcaca accactacac ccagaagtcc    1320
ctgtctctga gcctgggcaa g                                              1341

<210> SEQ ID NO 200
<211> LENGTH: 651
<212> TYPE: DNA
<213> ORGANISM: Artificial Sequence
<220> FEATURE:
<223> OTHER INFORMATION: antibody sequence

<400> SEQUENCE: 200

```
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ttattgtgcc gcctgggacg acagcctgaa cgtgtaccct   300
gtttttggcg gaggcaccaa gctgaccgtt ctaggccagc ctaaagccgc cctagcgtg    360 accctgttcc ctccaagcag cgaggaactg caggccaaca aggccaccct cgtgtgcctg   420
atcagcgact ctatcctgg cgccgtgacc gtggcctgga aggccgatag ctctcctgtg    480
aaggccggcg tggaaaccac caccccctagc aagcagagca caacaaata cgccgccagc   540 agctacctga gcctgacccc cgagcagtgg aagtcccaca gatcctacag ctgccaagtg   600
acccacgagg gcagcaccgt ggaaaagaca gtggccccta ccgagtgcag c            651
```

<210> SEQ ID NO 201
<211> LENGTH: 120
<212> TYPE: PRT
<213> ORGANISM: Artificial Sequence
<220> FEATURE:
<223> OTHER INFORMATION: antibody sequence

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser
        115                 120

<210> SEQ ID NO 202
<211> LENGTH: 5
<212> TYPE: PRT
<213> ORGANISM: Artificial Sequence
<220> FEATURE:
<223> OTHER INFORMATION: antibody sequence

<400> SEQUENCE: 202

Ser Tyr Ala Met Ser
1               5

<210> SEQ ID NO 203
<211> LENGTH: 16
<212> TYPE: PRT
<213> ORGANISM: Artificial Sequence
<220> FEATURE:
<223> OTHER INFORMATION: antibody sequence

<400> SEQUENCE: 203

Ala Ile Gly Tyr Gly Gly Asp Thr Tyr Tyr Ala Asp Ser Val Lys Gly
1               5                   10                  15

<210> SEQ ID NO 204
<211> LENGTH: 12
<212> TYPE: PRT
<213> ORGANISM: Artificial Sequence
<220> FEATURE:
<223> OTHER INFORMATION: antibody sequence

<400> SEQUENCE: 204

Arg Asp Asp Tyr Thr Ser Arg Asp Ala Phe Asp Tyr
1               5                   10

<210> SEQ ID NO 205
<211> LENGTH: 111
<212> TYPE: PRT
<213> ORGANISM: Artificial Sequence
<220> FEATURE:
<223> OTHER INFORMATION: antibody sequence

<400> SEQUENCE: 205

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Tyr Asp Asp Leu Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys His Ala Trp Asp Ser Leu
                85                  90                  95

Asn Asp Ile Val Val Phe Gly Gly Gly Thr Lys Leu Thr Val Leu
            100                 105                 110

<210> SEQ ID NO 206
<211> LENGTH: 13
<212> TYPE: PRT
<213> ORGANISM: Artificial Sequence
<220> FEATURE:
<223> OTHER INFORMATION: antibody sequence

<400> SEQUENCE: 206

Ser Gly Ser Ser Ser Asn Ile Gly Ser Asn Thr Val Asn
1               5                   10

<210> SEQ ID NO 207
<211> LENGTH: 7
<212> TYPE: PRT
<213> ORGANISM: Artificial Sequence
<220> FEATURE:
<223> OTHER INFORMATION: antibody sequence

<400> SEQUENCE: 207

Tyr Asp Asp Leu Arg Pro Ser
1               5

<210> SEQ ID NO 208
<211> LENGTH: 12
<212> TYPE: PRT
<213> ORGANISM: Artificial Sequence
<220> FEATURE:

<223> OTHER INFORMATION: antibody sequence

<400> SEQUENCE: 208

His Ala Trp Asp Asp Ser Leu Asn Asp Ile Val Val
1               5                   10

<210> SEQ ID NO 209
<211> LENGTH: 360
<212> TYPE: DNA
<213> ORGANISM: Artificial Sequence
<220> FEATURE:
<223> OTHER INFORMATION: antibody sequence

<400> SEQUENCE: 209

```
gaagttcagc tgctggaatc tggcggcgga ctggttcaac ctggcggatc tctgagactg    60
agctgtgccg ccagcggctt cacctttagc agctacgcca tgagctgggt ccgacaggct   120
cctggcaaag ccttgaatg gtgtccgcc atcggctatg cggcgatac ctactacgcc     180
gactctgtga aggcagatt caccatcagc cgggacaaca gcaagaacac cctgtacctg   240
cagatgaaca gcctgagagc cgaggacacc gccgtgtact attgcgccag aagggacgac   300
tacaccagca gggacgcctt cgattattgg ggccagggca cactggtcac cgtttcttca   360
```

<210> SEQ ID NO 210
<211> LENGTH: 15
<212> TYPE: DNA
<213> ORGANISM: Artificial Sequence
<220> FEATURE:
<223> OTHER INFORMATION: antibody sequence

<400> SEQUENCE: 210

```
agctacgcca tgagc                                                     15
```

<210> SEQ ID NO 211
<211> LENGTH: 48
<212> TYPE: DNA
<213> ORGANISM: Artificial Sequence
<220> FEATURE:
<223> OTHER INFORMATION: antibody sequence

<400> SEQUENCE: 211

```
gccatcggct atgcggcga tacctactac gccgactctg tgaagggc                 48
```

<210> SEQ ID NO 212
<211> LENGTH: 36
<212> TYPE: DNA
<213> ORGANISM: Artificial Sequence
<220> FEATURE:
<223> OTHER INFORMATION: antibody sequence

<400> SEQUENCE: 212

```
agggacgact acaccagcag ggacgccttc gattat                             36
```

<210> SEQ ID NO 213
<211> LENGTH: 333
<212> TYPE: DNA
<213> ORGANISM: Artificial Sequence
<220> FEATURE:
<223> OTHER INFORMATION: antibody sequence

<400> SEQUENCE: 213

```
cagtctgttc tgacacagcc tcctagcgcc tctggcacac ctggacagag agtgaccatc    60
agctgtagcg gcagcagctc caacatcggc agcaacaccg tgaactggta tcagcagctg   120
```

```
cctggcacag cccctaaact gctgatctac tacgacgacc tgcggcctag cggcgtgcca    180
gatagatttt ctggcagcaa gagcggcacc tctgccagcc tggctatttc tggactgcag    240
agcgaggacg aggccgacta ctattgtcac gcctgggacg acagcctgaa cgacatcgtg    300
gtttttggcg gaggcaccaa gctgaccgtt cta                                 333
```

<210> SEQ ID NO 214
<211> LENGTH: 39
<212> TYPE: DNA
<213> ORGANISM: Artificial Sequence
<220> FEATURE:
<223> OTHER INFORMATION: antibody sequence

<400> SEQUENCE: 214

```
agcggcagca gctccaacat cggcagcaac accgtgaac                            39
```

<210> SEQ ID NO 215
<211> LENGTH: 21
<212> TYPE: DNA
<213> ORGANISM: Artificial Sequence
<220> FEATURE:
<223> OTHER INFORMATION: antibody sequence

<400> SEQUENCE: 215

```
tacgacgacc tgcggcctag c                                               21
```

<210> SEQ ID NO 216
<211> LENGTH: 36
<212> TYPE: DNA
<213> ORGANISM: Artificial Sequence
<220> FEATURE:
<223> OTHER INFORMATION: antibody sequence

<400> SEQUENCE: 216

```
cacgcctggg acgacagcct gaacgacatc gtggtt                               36
```

<210> SEQ ID NO 217
<211> LENGTH: 447
<212> TYPE: PRT
<213> ORGANISM: Artificial Sequence
<220> FEATURE:
<223> OTHER INFORMATION: antibody sequence

<400> SEQUENCE: 217

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala

```
                130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
                210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 218
<211> LENGTH: 217
<212> TYPE: PRT
<213> ORGANISM: Artificial Sequence
<220> FEATURE:
<223> OTHER INFORMATION: antibody sequence

<400> SEQUENCE: 218

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
                35                  40                  45

Ile Tyr Tyr Asp Asp Leu Arg Pro Ser Gly Val Pro Asp Arg Phe Ser
```

```
                50                  55                  60
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys His Ala Trp Asp Ser Ser Leu
                 85                  90                  95

Asn Asp Ile Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 219
<211> LENGTH: 1341
<212> TYPE: DNA
<213> ORGANISM: Artificial Sequence
<220> FEATURE:
<223> OTHER INFORMATION: antibody sequence

<400> SEQUENCE: 219
gaagttcagc tgctggaatc tggcggcgga ctggttcaac ctggcggatc tctgagactg      60
agctgtgccg ccagcggctt caccttagc agctacgcca tgagctgggt ccgacaggct     120
cctggcaaag ccttgaatg gtgtccgcc atcggctatg cggcgatac ctactacgcc      180
gactctgtga agggcagatt caccatcagc cgggacaaca gcaagaacac cctgtacctg     240
cagatgaaca gcctgagagc cgaggacacc gccgtgtact attgcgccag aagggacgac     300
tacaccagca gggacgcctt cgattattgg ggccagggca cactggtcac cgtttcttca     360
gccagcacca agggcccag cgtgttccct ctggcccctt gtagcagaag caccagcgag     420
tctacagccg ccctgggctg cctcgtgaag gactactttc ccgagcccgt gaccgtgtcc     480
tggaactctg gcgctctgac aagcggcgtg cacacctttc cagccgtgct gcagagcagc     540
ggcctgtact ctctgagcag cgtcgtgaca gtgcccagca gcagcctggg caccaagacc     600
tacacctgta acgtggacca caagcccagc aacaccaagg tggacaagcg ggtggaatct     660
aagtacggcc ctccctgccc tccttgccca gcccctgaat tctgggcgg accctccgtg      720
ttcctgttcc cccaaagcc caaggacacc ctgatgatca gccggacccc cgaagtgacc     780
tgcgtggtgg tggatgtgtc ccaggaagat cccgaggtgc agttcaattg gtacgtggac     840
ggcgtggaag tgcacaacgc caagaccaag cccagagagg aacagttcaa cagcacctac     900
cgggtggtgt ccgtgctgac agtgctgcac caggactggc tgaacggcaa agagtacaag     960
tgcaaggtgt ccaacaaggg cctgcccagc tccatcgaga aaaccatcag caaggccaag    1020
ggccagcccc gcgaacccca ggtgtacaca ctgcctccaa gccaggaaga gatgaccaag    1080
aaccaggtgt ccctgacctg tctcgtgaaa ggcttctacc cctccgatat cgccgtggaa    1140
```

```
tgggagagca acggccagcc cgagaacaac tacaagacca ccccccctgt gctggacagc    1200
gacggctcat tcttcctgta cagcagactg accgtggaca gagagccggtg caggaaggc    1260 aacgtgttca gctgcagcgt gatgcacgag gccctgcaca accactacac ccagaagtcc    1320
ctgtctctga gcctgggcaa g                                              1341
```

<210> SEQ ID NO 220
<211> LENGTH: 651
<212> TYPE: DNA
<213> ORGANISM: Artificial Sequence
<220> FEATURE:
<223> OTHER INFORMATION: antibody sequence

<400> SEQUENCE: 220

```
cagtctgttc tgacacagcc tcctagcgcc tctggcacac tggacagag agtgaccatc      60 agctgtagcg gcagcagctc aacatcggc agcaacaccg tgaactggta tcagcagctg    120
cctggcacag cccctaaact gctgatctac tacgacgacc tgcggcctag cggcgtgcca    180
gatagatttt ctggcagcaa gagcggcacc tctgccagcc tggctatttc tggactgcag    240
agcgaggacg aggccgacta ctattgtcac gcctgggacg acagcctgaa cgacatcgtg    300 gttttggcg gaggcaccaa gctgaccgtt ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac caccccctagc aagcagagca caacaaata cgccgccagc    540 agctacctga gcctgacccc cgagcagtgg aagtcccaca gatcctacag ctgccaagtg    600
acccacgagg gcagcaccgt ggaaaagaca gtggcccctcta ccgagtgcag c           651
```

<210> SEQ ID NO 221
<211> LENGTH: 120
<212> TYPE: PRT
<213> ORGANISM: Artificial Sequence
<220> FEATURE:
<223> OTHER INFORMATION: antibody sequence

<400> SEQUENCE: 221

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser
        115                 120
```

<210> SEQ ID NO 222
<211> LENGTH: 5
<212> TYPE: PRT

```
<213> ORGANISM: Artificial Sequence
<220> FEATURE:
<223> OTHER INFORMATION: antibody sequence

<400> SEQUENCE: 222

Ser Tyr Ala Met Ser
1               5

<210> SEQ ID NO 223
<211> LENGTH: 16
<212> TYPE: PRT
<213> ORGANISM: Artificial Sequence
<220> FEATURE:
<223> OTHER INFORMATION: antibody sequence

<400> SEQUENCE: 223

Ala Ile Gly Tyr Gly Gly Asp Thr Tyr Tyr Ala Asp Ser Val Lys Gly
1               5                   10                  15

<210> SEQ ID NO 224
<211> LENGTH: 12
<212> TYPE: PRT
<213> ORGANISM: Artificial Sequence
<220> FEATURE:
<223> OTHER INFORMATION: antibody sequence

<400> SEQUENCE: 224

Arg Asp Asp Tyr Thr Ser Arg Asp Ala Phe Asp Tyr
1               5                   10

<210> SEQ ID NO 225
<211> LENGTH: 111
<212> TYPE: PRT
<213> ORGANISM: Artificial Sequence
<220> FEATURE:
<223> OTHER INFORMATION: antibody sequence

<400> SEQUENCE: 225

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys His Ala Trp Asp Asp Ser Leu
                85                  90                  95

Asn Asp Tyr Pro Val Phe Gly Gly Gly Thr Lys Leu Thr Val Leu
            100                 105                 110

<210> SEQ ID NO 226
<211> LENGTH: 13
<212> TYPE: PRT
<213> ORGANISM: Artificial Sequence
<220> FEATURE:
<223> OTHER INFORMATION: antibody sequence

<400> SEQUENCE: 226

Ser Gly Ser Ser Ser Asn Ile Gly Ser Asn Thr Val Asn
1               5                   10
```

<210> SEQ ID NO 227
<211> LENGTH: 7
<212> TYPE: PRT
<213> ORGANISM: Artificial Sequence
<220> FEATURE:
<223> OTHER INFORMATION: antibody sequence

<400> SEQUENCE: 227

Tyr Asp Asp Leu Arg Pro Ser
1               5

<210> SEQ ID NO 228
<211> LENGTH: 12
<212> TYPE: PRT
<213> ORGANISM: Artificial Sequence
<220> FEATURE:
<223> OTHER INFORMATION: antibody sequence

<400> SEQUENCE: 228

His Ala Trp Asp Asp Ser Leu Asn Asp Tyr Pro Val
1               5                   10

<210> SEQ ID NO 229
<211> LENGTH: 360
<212> TYPE: DNA
<213> ORGANISM: Artificial Sequence
<220> FEATURE:
<223> OTHER INFORMATION: antibody sequence

<400> SEQUENCE: 229
gaagttcagc tgctggaatc tggcggcgga ctggttcaac ctggcggatc tctgagactg     60
agctgtgccg ccagcggctt caccttagc agctacgcca tgagctgggt ccgacaggct    120
cctggcaaag ccttgaatg ggtgtccgcc atcggctatg cggcgatac ctactacgcc    180 gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360

<210> SEQ ID NO 230
<211> LENGTH: 15
<212> TYPE: DNA
<213> ORGANISM: Artificial Sequence
<220> FEATURE:
<223> OTHER INFORMATION: antibody sequence

<400> SEQUENCE: 230
agctacgcca tgagc                                                      15

<210> SEQ ID NO 231
<211> LENGTH: 48
<212> TYPE: DNA
<213> ORGANISM: Artificial Sequence
<220> FEATURE:
<223> OTHER INFORMATION: antibody sequence

<400> SEQUENCE: 231
gccatcggct atgcggcga tacctactac gccgactctg tgaagggc                   48

<210> SEQ ID NO 232
<211> LENGTH: 36
<212> TYPE: DNA
<213> ORGANISM: Artificial Sequence
<220> FEATURE:
<223> OTHER INFORMATION: antibody sequence -continued

<400> SEQUENCE: 232
agggacgact acaccagcag ggacgccttc gattat                36

<210> SEQ ID NO 233
<211> LENGTH: 333
<212> TYPE: DNA
<213> ORGANISM: Artificial Sequence
<220> FEATURE:
<223> OTHER INFORMATION: antibody sequence

<400> SEQUENCE: 233
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ctattgtcac gcctgggacg acagcctgaa cgactaccct   300 gttttggcg gaggcaccaa gctgaccgtt cta                                 333

<210> SEQ ID NO 234
<211> LENGTH: 39
<212> TYPE: DNA
<213> ORGANISM: Artificial Sequence
<220> FEATURE:
<223> OTHER INFORMATION: antibody sequence

<400> SEQUENCE: 234
agcggcagca gctccaacat cggcagcaac accgtgaac                 39

<210> SEQ ID NO 235
<211> LENGTH: 21
<212> TYPE: DNA
<213> ORGANISM: Artificial Sequence
<220> FEATURE:
<223> OTHER INFORMATION: antibody sequence

<400> SEQUENCE: 235
tacgacgacc tgcggcctag c                                    21

<210> SEQ ID NO 236
<211> LENGTH: 36
<212> TYPE: DNA
<213> ORGANISM: Artificial Sequence
<220> FEATURE:
<223> OTHER INFORMATION: antibody sequence

<400> SEQUENCE: 236
cacgcctggg acgacagcct gaacgactac cctgtt                    36

<210> SEQ ID NO 237
<211> LENGTH: 447
<212> TYPE: PRT
<213> ORGANISM: Artificial Sequence
<220> FEATURE:
<223> OTHER INFORMATION: antibody sequence

<400> SEQUENCE: 237

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met Ser Trp Val Arg Gln Ala Pro Gly Lys Gly Leu Glu Trp Val
            35                  40                  45
Ser Ala Ile Gly Tyr Gly Asp Thr Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Arg Asp Asp Tyr Thr Ser Arg Asp Ala Phe Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
            195                 200                 205
Pro Ser Asn Thr Lys Val Asp Lys Arg Val Glu Ser Lys Tyr Gly Pro
            210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
            275                 280                 285
Thr Lys Pro Arg Glu Glu Gln Phe Asn Ser Thr Tyr Arg Val Val Ser
            290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
            435                 440                 445
```

<210> SEQ ID NO 238
<211> LENGTH: 217
<212> TYPE: PRT
<213> ORGANISM: Artificial Sequence
<220> FEATURE:
<223> OTHER INFORMATION: antibody sequence

<400> SEQUENCE: 238

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys His Ala Trp Asp Asp Ser Leu
                85                  90                  95

Asn Asp Tyr Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 239
<211> LENGTH: 1341
<212> TYPE: DNA
<213> ORGANISM: Artificial Sequence
<220> FEATURE:
<223> OTHER INFORMATION: antibody sequence

<400> SEQUENCE: 239

```
gaagttcagc tgctggaatc tggcggcgga ctggttcaac tggcggatc tctgagactg      60 agctgtgccg ccagcggctt cacctttagc agctacgcca tgagctgggt ccgacaggct    120
cctggcaaag gccttgaatg ggtgtccgcc atcggctatg cggcgatac ctactacgcc     180 gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360
gccagcacca agggcccag cgtgttccct ctggccccct tgtagcagaag caccagcgag    420 tctacagccg ccctgggctg cctcgtgaag gactactttc ccgagcccgt gaccgtgtcc    480
tggaactctg gcgctctgac aagcggcgtg cacacctttc agccgtgct gcagagcagc    540
```

```
ggcctgtact ctctgagcag cgtcgtgaca gtgcccagca gcagcctggg caccaagacc     600
tacacctgta acgtggacca caagcccagc aacaccaagg tggacaagcg ggtggaatct     660
aagtacggcc ctcccctgcc ctccttgccca gcccctgaat ttctgggcgg accctccgtg    720
ttcctgttcc ccccaaagcc caaggacacc ctgatgatca gccggacccc cgaagtgacc     780
tgcgtggtgg tggatgtgtc ccaggaagat cccgaggtgc agttcaattg gtacgtggac     840
ggcgtggaag tgcacaacgc caagaccaag cccagagagg aacagttcaa cagcacctac     900
cgggtggtgt ccgtgctgac agtgctgcac caggactggc tgaacggcaa agagtacaag     960
tgcaaggtgt ccaacaaggg cctgcccagc tccatcgaga aaaccatcag caaggccaag    1020
ggccagcccc gcgaaccccca ggtgtacaca ctgcctccaa gccaggaaga gatgaccaag    1080
aaccaggtgt ccctgacctg tctcgtgaaa ggcttctacc cctccgatat cgccgtggaa    1140
tgggagagca acggccagcc cgagaacaac tacaagacca ccccccctgt gctggacagc    1200
gacggctcat tcttcctgta cagcagactg accgtggaca gagccggtg caggaaggc     1260
aacgtgttca gctgcagcgt gatgcacgag gccctgcaca accactacac ccagaagtcc    1320
ctgtctctga gcctgggcaa g                                              1341
```

<210> SEQ ID NO 240
<211> LENGTH: 651
<212> TYPE: DNA
<213> ORGANISM: Artificial Sequence
<220> FEATURE:
<223> OTHER INFORMATION: antibody sequence

<400> SEQUENCE: 240

```
cagtctgttc tgacacagcc tcctagcgcc tctggcacac ctggacagag agtgaccatc      60
agctgtagcg gcagcagctc caacatcggc agcaacaccg tgaactggta tcagcagctg     120
cctggcacag cccctaaaact gctgatctac tacgacgacc tgcggcctag cggcgtgcca    180
gatagatttt ctggcagcaa gagcggcacc tctgccagcc tggctatttc tggactgcag    240
agcgaggacg aggccgacta ctattgtcac gcctgggacg acagcctgaa cgactaccct    300
gttttttggcg gaggcaccaa gctgaccgtt ctaggccagc ctaaagccgc ccctagcgtg    360
accctgttcc ctccaagcag cgaggaactg caggccaaca aggccaccct cgtgtgcctg    420
atcagcgact ctatcctgg cgccgtgacc gtggcctgga aggccgatag ctctcctgtg    480
aaggccggcg tggaaaccac caccccctagc aagcagagca caacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c             651
```

<210> SEQ ID NO 241
<211> LENGTH: 120
<212> TYPE: PRT
<213> ORGANISM: Artificial Sequence
<220> FEATURE:
<223> OTHER INFORMATION: antibody sequence

<400> SEQUENCE: 241

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Gly Tyr Gly Gly Asp Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Arg Asp Asp Tyr Thr Ser Arg Asp Ala Phe Asp Tyr Trp Gly Gln
                100                 105                 110

Gly Thr Leu Val Thr Val Ser Ser
            115                 120

<210> SEQ ID NO 242
<211> LENGTH: 5
<212> TYPE: PRT
<213> ORGANISM: Artificial Sequence
<220> FEATURE:
<223> OTHER INFORMATION: antibody sequence

<400> SEQUENCE: 242

Ser Tyr Ala Met Ser
 1               5

<210> SEQ ID NO 243
<211> LENGTH: 16
<212> TYPE: PRT
<213> ORGANISM: Artificial Sequence
<220> FEATURE:
<223> OTHER INFORMATION: antibody sequence

<400> SEQUENCE: 243

Ala Ile Gly Tyr Gly Gly Asp Thr Tyr Tyr Ala Asp Ser Val Lys Gly
 1               5                  10                  15

<210> SEQ ID NO 244
<211> LENGTH: 12
<212> TYPE: PRT
<213> ORGANISM: Artificial Sequence
<220> FEATURE:
<223> OTHER INFORMATION: antibody sequence

<400> SEQUENCE: 244

Arg Asp Asp Tyr Thr Ser Arg Asp Ala Phe Asp Tyr
 1               5                  10

<210> SEQ ID NO 245
<211> LENGTH: 111
<212> TYPE: PRT
<213> ORGANISM: Artificial Sequence
<220> FEATURE:
<223> OTHER INFORMATION: antibody sequence

<400> SEQUENCE: 245

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
                 20                  25                  30

Thr Val Asn Trp Tyr Gln Gln Leu Pro Gly Thr Ala Pro Lys Leu Leu
                 35                  40                  45

Ile Tyr Tyr Asp Asp Leu Arg Pro Ser Gly Val Pro Asp Arg Phe Ser
         50                  55                  60

Gly Ser Lys Ser Gly Thr Ser Ala Ser Leu Ala Ile Ser Gly Leu Gln
 65                  70                  75                  80
```

```
Ser Glu Asp Glu Ala Asp Tyr Tyr Cys His Ala Trp Asp Asp Ser Leu
            85                  90                  95

Asn Val Tyr Pro Val Phe Gly Gly Gly Thr Lys Leu Thr Val Leu
        100                 105                 110

<210> SEQ ID NO 246
<211> LENGTH: 13
<212> TYPE: PRT
<213> ORGANISM: Artificial Sequence
<220> FEATURE:
<223> OTHER INFORMATION: antibody sequence

<400> SEQUENCE: 246

Ser Gly Ser Ser Ser Asn Ile Gly Ser Asn Thr Val Asn
1               5                   10

<210> SEQ ID NO 247
<211> LENGTH: 7
<212> TYPE: PRT
<213> ORGANISM: Artificial Sequence
<220> FEATURE:
<223> OTHER INFORMATION: antibody sequence

<400> SEQUENCE: 247

Tyr Asp Asp Leu Arg Pro Ser
1               5

<210> SEQ ID NO 248
<211> LENGTH: 12
<212> TYPE: PRT
<213> ORGANISM: Artificial Sequence
<220> FEATURE:
<223> OTHER INFORMATION: antibody sequence

<400> SEQUENCE: 248

His Ala Trp Asp Asp Ser Leu Asn Val Tyr Pro Val
1               5                   10

<210> SEQ ID NO 249
<211> LENGTH: 360
<212> TYPE: DNA
<213> ORGANISM: Artificial Sequence
<220> FEATURE:
<223> OTHER INFORMATION: antibody sequence

<400> SEQUENCE: 249
gaagttcagc tgctggaatc tggcggcgga ctggttcaac ctggcggatc tctgagactg      60
agctgtgccg ccagcggctt cacctttagc agctacgcca tgagctgggt ccgacaggct     120
cctggcaaag ccttgaatg gtgtccgcc atcggctatg cggcgatac ctactacgcc        180 gactctgtga aggcagatt caccatcagc cggacaaca gcaagaacac cctgtacctg       240
cagatgaaca gcctgagagc cgaggacacc gccgtgtact attgcgccag aagggacgac    300
tacaccagca gggacgcctt cgattattgg ggccagggca cactggtcac cgtttcttca    360

<210> SEQ ID NO 250
<211> LENGTH: 15
<212> TYPE: DNA
<213> ORGANISM: Artificial Sequence
<220> FEATURE:
<223> OTHER INFORMATION: antibody sequence

<400> SEQUENCE: 250
agctacgcca tgagc                                                      15
```

<210> SEQ ID NO 251
<211> LENGTH: 48
<212> TYPE: DNA
<213> ORGANISM: Artificial Sequence
<220> FEATURE:
<223> OTHER INFORMATION: antibody sequence

<400> SEQUENCE: 251
gccatcggct atggcggcga tacctactac gccgactctg tgaagggc          48

<210> SEQ ID NO 252
<211> LENGTH: 36
<212> TYPE: DNA
<213> ORGANISM: Artificial Sequence
<220> FEATURE:
<223> OTHER INFORMATION: antibody sequence

<400> SEQUENCE: 252
agggacgact acaccagcag ggacgccttc gattat                       36

<210> SEQ ID NO 253
<211> LENGTH: 333
<212> TYPE: DNA
<213> ORGANISM: Artificial Sequence
<220> FEATURE:
<223> OTHER INFORMATION: antibody sequence

<400> SEQUENCE: 253
cagtctgttc tgacacagcc tcctagcgcc tctggcacac ctggacagag agtgaccatc    60
agctgtagcg gcagcagctc aacatcggc agcaacaccg tgaactggta tcagcagctg    120
cctggcacag ccctaaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ctattgtcac gcctgggacg acagcctgaa cgtgtaccct   300
gtttttggcg gaggcaccaa gctgaccgtt cta                              333

<210> SEQ ID NO 254
<211> LENGTH: 39
<212> TYPE: DNA
<213> ORGANISM: Artificial Sequence
<220> FEATURE:
<223> OTHER INFORMATION: antibody sequence

<400> SEQUENCE: 254
agcggcagca gctccaacat cggcagcaac accgtgaac                    39

<210> SEQ ID NO 255
<211> LENGTH: 21
<212> TYPE: DNA
<213> ORGANISM: Artificial Sequence
<220> FEATURE:
<223> OTHER INFORMATION: antibody sequence

<400> SEQUENCE: 255
tacgacgacc tgcggcctag c                                       21

<210> SEQ ID NO 256
<211> LENGTH: 36
<212> TYPE: DNA
<213> ORGANISM: Artificial Sequence
<220> FEATURE:
<223> OTHER INFORMATION: antibody sequence

<400> SEQUENCE: 256
cacgcctggg acgacagcct gaacgtgtac cctgtt                              36

<210> SEQ ID NO 257
<211> LENGTH: 447
<212> TYPE: PRT
<213> ORGANISM: Artificial Sequence
<220> FEATURE:
<223> OTHER INFORMATION: antibody sequence

<400> SEQUENCE: 257

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 258
<211> LENGTH: 217
<212> TYPE: PRT
<213> ORGANISM: Artificial Sequence
<220> FEATURE:
<223> OTHER INFORMATION: antibody sequence

<400> SEQUENCE: 258

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys His Ala Trp Asp Asp Ser Leu
                85                  90                  95

Asn Val Tyr Pro Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 259
<211> LENGTH: 1341
<212> TYPE: DNA
<213> ORGANISM: Artificial Sequence
<220> FEATURE:
<223> OTHER INFORMATION: antibody sequence

<400> SEQUENCE: 259

```
gaagttcagc tgctggaatc tggcggcgga ctggttcaac ctggcggatc tctgagactg      60
agctgtgccg ccagcggctt cacctttagc agctacgcca tgagctgggt ccgacaggct     120
cctggcaaag gccttgaatg ggtgtccgcc atcggctatg cggcgatac ctactacgcc      180 gactctgtga agggcagatt caccatcagc cgggacaaca gcaagaacac cctgtacctg     240
cagatgaaca gcctgagagc cgaggacacc gccgtgtact attgcgccag aagggacgac     300
tacaccagca gggacgcctt cgattattgg ggccagggca cactggtcac cgtttcttca     360
gccagcacca agggcccag cgtgttccct ctggccccttt gtagcagaag caccagcgag     420
tctacagccg ccctgggctg cctcgtgaag gactactttc ccgagcccgt gaccgtgtcc     480
tggaactctg gcgctctgac aagcggcgtg cacacctttc cagccgtgct gcagagcagc     540
ggcctgtact ctctgagcag cgtcgtgaca gtgccccagca gcagcctggg caccaagacc    600
tacacctgta acgtggacca caagcccagc aacaccaagg tggacaagcg ggtggaatct     660
aagtacggcc ctcccctgccc tccttgccca gcccctgaat ttctgggcgg acctccgtg    720 ttcctgttcc ccccaaagcc caaggacacc ctgatgatca gccggacccc cgaagtgacc    780
tgcgtggtgg tggatgtgtc ccaggaagat cccgaggtgc agttcaattg gtacgtggac    840
ggcgtggaag tgcacaacgc caagaccaag cccagagagg aacagttcaa cagcacctac    900
cgggtggtgt ccgtgctgac agtgctgcac caggactggc tgaacggcaa agagtacaag    960
tgcaaggtgt ccaacaaggg cctgcccagc tccatcgaga aaaccatcag caaggccaag    1020
ggccagcccc gcgaacccca ggtgtacaca ctgcctccaa gccaggaaga gatgaccaag    1080
aaccaggtgt ccctgacctg tctcgtgaaa ggcttctacc cctccgatat cgccgtggaa    1140
tgggagagca acggccagcc cgagaacaac tacaagacca cccccctgt gctggacagc     1200 gacggctcat tcttcctgta cagcagactg accgtggaca agagccggtg gcaggaaggc    1260
aacgtgttca gctgcagcgt gatgcacgag gccctgcaca accactacac ccagaagtcc    1320
ctgtctctga gcctgggcaa g                                              1341

<210> SEQ ID NO 260
<211> LENGTH: 651
<212> TYPE: DNA
<213> ORGANISM: Artificial Sequence
<220> FEATURE:
<223> OTHER INFORMATION: antibody sequence

<400> SEQUENCE: 260
cagtctgttc tgacacagcc tcctagcgcc tctggcacac ctggacagag agtgaccatc      60
agctgtagcg gcagcagctc caacatcggc agcaacaccg tgaactggta tcagcagctg     120
cctggcacag cccctaaact gctgatctac tacgacgacc tgcggcctag cggcgtgcca     180
gatagatttt ctggcagcaa gagcggcacc tctgccagcc tggctattcc tggactgcag    240
agcgaggacg aggccgacta ctattgtcac gcctgggacg acagcctgaa cgtgtaccct    300 gttttttggcg gaggcaccaa gctgaccgtt ctaggccagc ctaaagccgc ccctagcgtg    360
accctgttcc ctccaagcag cgaggaactg caggccaaca ggccacccct cgtgtgcctg    420
atcagcgact ctatcctgg cgccgtgacc gtggcctgga aggccgatag ctctcctgtg     480
aaggccggcg tggaaaccac caccccctagc aagcagagca caacaaata cgccgccagc    540 agctacctga gcctgacccc cgagcagtgg aagtcccaca gatcctacag ctgccaagtg    600
acccacgagg gcagcaccgt ggaaaagaca gtggccccta ccgagtgcag c            651
```

```
<210> SEQ ID NO 261
<211> LENGTH: 120
<212> TYPE: PRT
<213> ORGANISM: Artificial Sequence
<220> FEATURE:
<223> OTHER INFORMATION: antibody sequence

<400> SEQUENCE: 261

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser
        115                 120

<210> SEQ ID NO 262
<211> LENGTH: 5
<212> TYPE: PRT
<213> ORGANISM: Artificial Sequence
<220> FEATURE:
<223> OTHER INFORMATION: antibody sequence

<400> SEQUENCE: 262

Ser Tyr Ala Met Ser
1               5

<210> SEQ ID NO 263
<211> LENGTH: 16
<212> TYPE: PRT
<213> ORGANISM: Artificial Sequence
<220> FEATURE:
<223> OTHER INFORMATION: antibody sequence

<400> SEQUENCE: 263

Ala Ile Gly Tyr Gly Gly Asp Thr Tyr Tyr Ala Asp Ser Val Lys Gly
1               5                   10                  15

<210> SEQ ID NO 264
<211> LENGTH: 12
<212> TYPE: PRT
<213> ORGANISM: Artificial Sequence
<220> FEATURE:
<223> OTHER INFORMATION: antibody sequence

<400> SEQUENCE: 264

Arg Asp Asp Tyr Thr Ser Arg Asp Ala Phe Asp Tyr
1               5                   10

<210> SEQ ID NO 265
<211> LENGTH: 111
<212> TYPE: PRT
<213> ORGANISM: Artificial Sequence
<220> FEATURE:
```

<223> OTHER INFORMATION: antibody sequence

<400> SEQUENCE: 265

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys His Ala Trp Asp Asp Ser Leu
                85                  90                  95

Asn Val Ile Pro Val Phe Gly Gly Gly Thr Lys Leu Thr Val Leu
            100                 105                 110

<210> SEQ ID NO 266
<211> LENGTH: 13
<212> TYPE: PRT
<213> ORGANISM: Artificial Sequence
<220> FEATURE:
<223> OTHER INFORMATION: antibody sequence

<400> SEQUENCE: 266

Ser Gly Ser Ser Ser Asn Ile Gly Ser Asn Thr Val Asn
1               5                   10

<210> SEQ ID NO 267
<211> LENGTH: 7
<212> TYPE: PRT
<213> ORGANISM: Artificial Sequence
<220> FEATURE:
<223> OTHER INFORMATION: antibody sequence

<400> SEQUENCE: 267

Tyr Asp Asp Leu Arg Pro Ser
1               5

<210> SEQ ID NO 268
<211> LENGTH: 12
<212> TYPE: PRT
<213> ORGANISM: Artificial Sequence
<220> FEATURE:
<223> OTHER INFORMATION: antibody sequence

<400> SEQUENCE: 268

His Ala Trp Asp Asp Ser Leu Asn Val Ile Pro Val
1               5                   10

<210> SEQ ID NO 269
<211> LENGTH: 360
<212> TYPE: DNA
<213> ORGANISM: Artificial Sequence
<220> FEATURE:
<223> OTHER INFORMATION: antibody sequence

<400> SEQUENCE: 269
gaagttcagc tgctggaatc tggcggcgga ctggttcaac tggcggatc tctgagactg      60 agctgtgccg ccagcggctt cacctttagc agctacgcca tgagctgggt ccgacaggct    120
cctggcaaag gccttgaatg ggtgtccgcc atcggctatg cggcgatac ctactacgcc    180

```
gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360
```

```
<210> SEQ ID NO 270
<211> LENGTH: 15
<212> TYPE: DNA
<213> ORGANISM: Artificial Sequence
<220> FEATURE:
<223> OTHER INFORMATION: antibody sequence

<400> SEQUENCE: 270
agctacgcca tgagc                                                      15

<210> SEQ ID NO 271
<211> LENGTH: 48
<212> TYPE: DNA
<213> ORGANISM: Artificial Sequence
<220> FEATURE:
<223> OTHER INFORMATION: antibody sequence

<400> SEQUENCE: 271
gccatcggct atggcggcga tacctactac gccgactctg tgaagggc                  48

<210> SEQ ID NO 272
<211> LENGTH: 36
<212> TYPE: DNA
<213> ORGANISM: Artificial Sequence
<220> FEATURE:
<223> OTHER INFORMATION: antibody sequence

<400> SEQUENCE: 272
agggacgact acaccagcag ggacgccttc gattat                               36

<210> SEQ ID NO 273
<211> LENGTH: 333
<212> TYPE: DNA
<213> ORGANISM: Artificial Sequence
<220> FEATURE:
<223> OTHER INFORMATION: antibody sequence

<400> SEQUENCE: 273
cagtctgttc tgacacagcc tcctagcgcc tctggcacac tggacagag agtgaccatc      60 agctgtagcg gcagcagctc aacatcggc agcaacaccg tgaactggta tcagcagctg    120
cctggcacag cccctaaact gctgatctac tacgacgacc tgcggcctag cggcgtgcca    180
gatagatttt ctggcagcaa gagcggcacc tctgccagcc tggctatttc tggactgcag    240
agcgaggacg aggccgacta ctattgtcac gcctgggacg acagcctgaa cgtgatccct    300 gttttttggcg gaggcaccaa gctgaccgtt cta                                 333

<210> SEQ ID NO 274
<211> LENGTH: 39
<212> TYPE: DNA
<213> ORGANISM: Artificial Sequence
<220> FEATURE:
<223> OTHER INFORMATION: antibody sequence

<400> SEQUENCE: 274
agcggcagca gctccaacat cggcagcaac accgtgaac                            39

<210> SEQ ID NO 275
```

-continued

```
<211> LENGTH: 21
<212> TYPE: DNA
<213> ORGANISM: Artificial Sequence
<220> FEATURE:
<223> OTHER INFORMATION: antibody sequence

<400> SEQUENCE: 275
tacgacgacc tgcggcctag c                                              21

<210> SEQ ID NO 276
<211> LENGTH: 36
<212> TYPE: DNA
<213> ORGANISM: Artificial Sequence
<220> FEATURE:
<223> OTHER INFORMATION: antibody sequence

<400> SEQUENCE: 276
cacgcctggg acgacagcct gaacgtgatc cctgtt                              36

<210> SEQ ID NO 277
<211> LENGTH: 447
<212> TYPE: PRT
<213> ORGANISM: Artificial Sequence
<220> FEATURE:
<223> OTHER INFORMATION: antibody sequence

<400> SEQUENCE: 277
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

```
Pro Glu Val Thr Cys Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 278
<211> LENGTH: 217
<212> TYPE: PRT
<213> ORGANISM: Artificial Sequence
<220> FEATURE:
<223> OTHER INFORMATION: antibody sequence

<400> SEQUENCE: 278

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys His Ala Trp Asp Ser Leu
                85                  90                  95

Asn Val Ile Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175
```

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 279
<211> LENGTH: 1341
<212> TYPE: DNA
<213> ORGANISM: Artificial Sequence
<220> FEATURE:
<223> OTHER INFORMATION: antibody sequence

<400> SEQUENCE: 279

```
gaagttcagc tgctggaatc tggcggcgga ctggttcaac tggcggatc tctgagactg      60 agctgtgccg ccagcggctt cacctttagc agctacgcca tgagctgggt ccgacaggct    120
cctggcaaag gccttgaatg ggtgtccgcc atcggctatg cggcgatac ctactacgcc     180 gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360
gccagcacca agggccccag cgtgttccct ctggccccct tgtagcagaag caccagcgag    420 tctacagccg ccctgggctg cctcgtgaag gactactttc ccgagcccgt gaccgtgtcc    480
tggaactctg gcgctctgac aagcggcgtg cacacctttc cagccgtgct gcagagcagc    540
ggcctgtact ctctgagcag cgtcgtgaca gtgcccagca gcagcctggg caccaagacc    600
tacacctgta acgtggacca caagcccagc aacaccaagg tggacaagcg ggtggaatct    660
aagtacggcc ctcctgccc tccttgccca gcccctgaat tcctgggcgg accctccgtg    720
ttcctgttcc cccaaagcc aaggacacc ctgatgatca gccggaccc cgaagtgacc      780 tgcgtggtgg tggatgtgtc ccaggaagat cccgaggtgc agttcaattg gtacgtggac    840
ggcgtggaag tgcacaacgc caagaccaag cccagagagg aacagttcaa cagcacctac    900
cgggtggtgt ccgtgctgac agtgctgcac caggactggc tgaacggcaa agagtacaag    960
tgcaaggtgt ccaacaaggg cctgcccagc tccatcgaga aaccatcag caaggccaag    1020 ggccagcccc gcgaaccca ggtgtacaca ctgcctccaa gccaggaaga gatgaccaag    1080
aaccaggtgt ccctgacctg tctcgtgaaa ggcttctacc cctccgatat cgccgtggaa    1140
tgggagagca acggccagcc cgagaacaac tacaagacca ccccccctgt gctggacagc    1200
gacggctcat tcttcctgta cagcagactg accgtggaca gagccggtg gcaggaaggc    1260 aacgtgttca gctgcagcgt gatgcacgag gccctgcaca accactacac ccagaagtcc    1320
ctgtctctga gcctgggcaa g                                               1341
```

<210> SEQ ID NO 280
<211> LENGTH: 651
<212> TYPE: DNA
<213> ORGANISM: Artificial Sequence
<220> FEATURE:
<223> OTHER INFORMATION: antibody sequence

<400> SEQUENCE: 280

```
cagtctgttc tgacacagcc tcctagcgcc tctggcacac tggacagag agtgaccatc      60 agctgtagcg gcagcagctc caacatcggc agcaacaccg tgaactggta tcagcagctg    120
```

```
cctggcacag cccctaaact gctgatctac tacgacgacc tgcggcctag cggcgtgcca      180
gatagatttt ctggcagcaa gagcggcacc tctgccagcc tggctatttc tggactgcag      240
agcgaggacg aggccgacta ctattgtcac gcctgggacg acagcctgaa cgtgatccct      300
gtttttggcg gaggcaccaa gctgaccgtt ctaggccagc ctaaagccgc ccctagcgtg      360
accctgttcc ctccaagcag cgaggaactg caggccaaca aggccaccct cgtgtgcctg      420
atcagcgact tctatcctgg cgccgtgacc gtggcctgga aggccgatag ctctcctgtg      480
aaggccggcg tggaaaccac caccccctagc aagcagagca acaacaaata cgccgccagc      540
agctacctga gcctgacccc cgagcagtgg aagtcccaca gatcctacag ctgccaagtg      600
acccacgagg gcagcaccgt ggaaaagaca gtggccccta ccgagtgcag c               651
```

<210> SEQ ID NO 281
<211> LENGTH: 120
<212> TYPE: PRT
<213> ORGANISM: Artificial Sequence
<220> FEATURE:
<223> OTHER INFORMATION: antibody sequence

<400> SEQUENCE: 281

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Tyr
            20                  25                  30

Ala Met Leu Trp Val Arg Gln Ala Pro Gly Lys Gly Leu Glu Trp Val
        35                  40                  45

Ser Ala Ile Gly Thr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser
        115                 120
```

<210> SEQ ID NO 282
<211> LENGTH: 5
<212> TYPE: PRT
<213> ORGANISM: Artificial Sequence
<220> FEATURE:
<223> OTHER INFORMATION: antibody sequence

<400> SEQUENCE: 282

```
Ser Tyr Ala Met Leu
1               5
```

<210> SEQ ID NO 283
<211> LENGTH: 16
<212> TYPE: PRT
<213> ORGANISM: Artificial Sequence
<220> FEATURE:
<223> OTHER INFORMATION: antibody sequence

<400> SEQUENCE: 283

```
Ala Ile Gly Thr Gly Gly Asp Thr Tyr Tyr Ala Asp Ser Val Lys Gly
1               5                   10                  15
```

<210> SEQ ID NO 284
<211> LENGTH: 12
<212> TYPE: PRT
<213> ORGANISM: Artificial Sequence
<220> FEATURE:
<223> OTHER INFORMATION: antibody sequence

<400> SEQUENCE: 284

```
Arg Asp Asp Tyr Thr Ser Arg Asp Ala Phe Asp Tyr
1               5                   10
```

<210> SEQ ID NO 285
<211> LENGTH: 111
<212> TYPE: PRT
<213> ORGANISM: Artificial Sequence
<220> FEATURE:
<223> OTHER INFORMATION: antibody sequence

<400> SEQUENCE: 285

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Asp Tyr Val Val Phe Gly Gly Gly Thr Lys Leu Thr Val Leu
            100                 105                 110
```

<210> SEQ ID NO 286
<211> LENGTH: 13
<212> TYPE: PRT
<213> ORGANISM: Artificial Sequence
<220> FEATURE:
<223> OTHER INFORMATION: antibody sequence

<400> SEQUENCE: 286

```
Ser Gly Ser Ser Ser Asn Ile Gly Ser Asn Thr Val Asn
1               5                   10
```

<210> SEQ ID NO 287
<211> LENGTH: 7
<212> TYPE: PRT
<213> ORGANISM: Artificial Sequence
<220> FEATURE:
<223> OTHER INFORMATION: antibody sequence

<400> SEQUENCE: 287

```
Tyr Asp Asp Leu Arg Pro Ser
1               5
```

<210> SEQ ID NO 288
<211> LENGTH: 12
<212> TYPE: PRT
<213> ORGANISM: Artificial Sequence
<220> FEATURE:
<223> OTHER INFORMATION: antibody sequence

<400> SEQUENCE: 288

Ala Ala Trp Asp Asp Ser Leu Asn Asp Tyr Val Val
1               5                   10

<210> SEQ ID NO 289
<211> LENGTH: 360
<212> TYPE: DNA
<213> ORGANISM: Artificial Sequence
<220> FEATURE:
<223> OTHER INFORMATION: antibody sequence

<400> SEQUENCE: 289
gaagttcagc tgctggaatc tggcggcgga ctggttcaac ctggcggatc tctgagactg     60
agctgtgccg ccagcggctt cacctttac agctacgcca tgctgtgggt ccgacaggcc    120
cctggaaaag gccttgaatg ggtgtccgcc atcggcacag gcggcgatac ctactatgcc    180
gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360

<210> SEQ ID NO 290
<211> LENGTH: 15
<212> TYPE: DNA
<213> ORGANISM: Artificial Sequence
<220> FEATURE:
<223> OTHER INFORMATION: antibody sequence

<400> SEQUENCE: 290
agctacgcca tgctg                                                      15

<210> SEQ ID NO 291
<211> LENGTH: 48
<212> TYPE: DNA
<213> ORGANISM: Artificial Sequence
<220> FEATURE:
<223> OTHER INFORMATION: antibody sequence

<400> SEQUENCE: 291
gccatcggca caggcggcga tacctactat gccgactctg tgaagggc                  48

<210> SEQ ID NO 292
<211> LENGTH: 36
<212> TYPE: DNA
<213> ORGANISM: Artificial Sequence
<220> FEATURE:
<223> OTHER INFORMATION: antibody sequence

<400> SEQUENCE: 292
agggacgact acaccagcag ggacgccttc gattat                               36

<210> SEQ ID NO 293
<211> LENGTH: 333
<212> TYPE: DNA
<213> ORGANISM: Artificial Sequence
<220> FEATURE:
<223> OTHER INFORMATION: antibody sequence

<400> SEQUENCE: 293
cagtctgttc tgacacagcc tcctagcgcc tctggcacac ctggacagag agtgaccatc     60
agctgtagcg gcagcagctc caacatcggc agcaacaccg tgaactggta tcagcagctg    120
cctggcacag cccctaaact gctgatctac tacgacgacc tgcggcctag cggcgtgcca    180
gatagatttt ctggcagcaa gagcggcacc tctgccagcc tggctatttc tggactgcag    240

```
agcgaggacg aggccgacta ttattgtgcc gcctgggacg acagcctgaa cgactacgtt         300
gtgtttggcg gaggcaccaa gctgaccgtt cta                                      333
```

<210> SEQ ID NO 294
<211> LENGTH: 39
<212> TYPE: DNA
<213> ORGANISM: Artificial Sequence
<220> FEATURE:
<223> OTHER INFORMATION: antibody sequence

<400> SEQUENCE: 294

```
agcggcagca gctccaacat cggcagcaac accgtgaac                                 39
```

<210> SEQ ID NO 295
<211> LENGTH: 21
<212> TYPE: DNA
<213> ORGANISM: Artificial Sequence
<220> FEATURE:
<223> OTHER INFORMATION: antibody sequence

<400> SEQUENCE: 295

```
tacgacgacc tgcggcctag c                                                    21
```

<210> SEQ ID NO 296
<211> LENGTH: 36
<212> TYPE: DNA
<213> ORGANISM: Artificial Sequence
<220> FEATURE:
<223> OTHER INFORMATION: antibody sequence

<400> SEQUENCE: 296

```
gccgcctggg acgacagcct gaacgactac gttgtg                                    36
```

<210> SEQ ID NO 297
<211> LENGTH: 447
<212> TYPE: PRT
<213> ORGANISM: Artificial Sequence
<220> FEATURE:
<223> OTHER INFORMATION: antibody sequence

<400> SEQUENCE: 297

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Tyr
            20                  25                  30

Ala Met Leu Trp Val Arg Gln Ala Pro Gly Lys Gly Leu Glu Trp Val
        35                  40                  45

Ser Ala Ile Gly Thr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
```

```
            145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Lys Thr Tyr Thr Cys Asn Val Asp His Lys
                195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
                260                 265                 270
Val Gln Phe Asn Trp Tyr Val Asp Gly Val Glu Val His Asn Ala Lys
                275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Gln Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly Lys
                435                 440                 445

<210> SEQ ID NO 298
<211> LENGTH: 217
<212> TYPE: PRT
<213> ORGANISM: Artificial Sequence
<220> FEATURE:
<223> OTHER INFORMATION: antibody sequence

<400> SEQUENCE: 298

Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
                20                  25                  30
Thr Val Asn Trp Tyr Gln Gln Leu Pro Gly Thr Ala Pro Lys Leu Leu
                35                  40                  45
Ile Tyr Tyr Asp Asp Leu Arg Pro Ser Gly Val Pro Asp Arg Phe Ser
            50                  55                  60
Gly Ser Lys Ser Gly Thr Ser Ala Ser Leu Ala Ile Ser Gly Leu Gln
```

```
                65                  70                  75                  80
Ser Glu Asp Glu Ala Asp Tyr Tyr Cys Ala Ala Trp Asp Asp Ser Leu
                    85                  90                  95

Asn Asp Tyr Val Val Phe Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 299
<211> LENGTH: 1341
<212> TYPE: DNA
<213> ORGANISM: Artificial Sequence
<220> FEATURE:
<223> OTHER INFORMATION: antibody sequence

<400> SEQUENCE: 299
gaagttcagc tgctggaatc tggcggcgga ctggttcaac tggcggatc tctgagactg      60 agctgtgccg ccagcggctt cacctttta agctacgcca tgctgtgggt ccgacaggcc     120
cctggaaaag gccttgaatg ggtgtccgcc atcggcacag gcggcgatac ctactatgcc     180
gactctgtga agggcagatt caccatcagc cgggacaaca gcaagaacac cctgtacctg     240
cagatgaaca gcctgagagc cgaggacacc gccgtgtact attgcgccag aagggacgac     300
tacaccagca gggacgcctt cgattattgg ggccagggca cactggtcac cgtttcttca     360
gccagcacca agggcccag cgtgttccct ctggcccctt gtagcagaag caccagcgag     420
tctacagccg ccctgggctg cctcgtgaag gactactttc cgagcccgt gaccgtgtcc     480 tggaactctg gcgctctgac aagcggcgtg cacacctttc agccgtgct gcagagcagc     540 ggcctgtact ctctgagcag cgtcgtgaca gtgcccagca gcagcctggg caccaagacc     600
tacacctgta acgtggacca caagcccagc aacaccaagg tggacaagcg ggtggaatct     660
aagtacggcc ctccctgccc tccttgccca gcccctgaat tctgggcgg acctccgtg      720 ttcctgttcc ccccaaagcc caaggacacc ctgatgatca gccggacccc cgaagtgacc     780
tgcgtggtgg tggatgtgtc ccaggaagat cccgaggtgc agttcaattg gtacgtggac     840
ggcgtggaag tgcacaacgc caagaccaag cccagagagg aacagttcaa cagcacctac     900
cgggtggtgt ccgtgctgac agtgctgcac caggactggc tgaacggcaa agagtacaag     960
tgcaaggtgt ccaacaaggg cctgcccagc tccatcgaga aaaccatcag caaggccaag    1020
ggccagcccc gcgaaccccca ggtgtacaca ctgcctccaa gccaggaaga gatgaccaag    1080
aaccaggtgt ccctgacctg tctcgtgaaa ggcttctacc cctccgatat cgccgtggaa    1140
tgggagagca acggccagcc cgagaacaac tacaagacca ccccccctgt gctggacagc    1200
```

```
gacggctcat tcttcctgta cagcagactg accgtggaca agagccggtg gcaggaaggc    1260
aacgtgttca gctgcagcgt gatgcacgag gccctgcaca accactacac ccagaagtcc    1320
ctgtctctga gcctgggcaa g                                              1341
```

<210> SEQ ID NO 300
<211> LENGTH: 651
<212> TYPE: DNA
<213> ORGANISM: Artificial Sequence
<220> FEATURE:
<223> OTHER INFORMATION: antibody sequence

<400> SEQUENCE: 300

```
cagtctgttc tgacacagcc tcctagcgcc tctggcacac ctggacagag agtgaccatc     60
agctgtagcg gcagcagctc aacatcggc agcaacaccg tgaactggta tcagcagctg     120
cctggcacag cccctaaact gctgatctac tacgacgacc tgcggcctag cggcgtgcca    180
gatagatttt ctggcagcaa gagcggcacc tctgccagcc tggctatttc tggactgcag    240
agcgaggacg aggccgacta ttattgtgcc gcctgggacg acagcctgaa cgactacgtt    300
gtgtttggcg gaggcaccaa gctgaccgtt ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac caccccctagc aagcagagca caacaaata cgccgccagc    540 agctacctga gcctgacccc cgagcagtgg aagtcccaca gatcctacag ctgccaagtg    600
acccacgagg gcagcaccgt ggaaaagaca gtggccccta ccgagtgcag c             651
```

<210> SEQ ID NO 301
<211> LENGTH: 120
<212> TYPE: PRT
<213> ORGANISM: Artificial Sequence
<220> FEATURE:
<223> OTHER INFORMATION: antibody sequence

<400> SEQUENCE: 301

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Tyr
            20                  25                  30

Ala Met Leu Trp Val Arg Gln Ala Pro Gly Lys Gly Leu Glu Trp Val
        35                  40                  45

Ser Ala Ile Gly Thr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser
        115                 120
```

<210> SEQ ID NO 302
<211> LENGTH: 5
<212> TYPE: PRT
<213> ORGANISM: Artificial Sequence
<220> FEATURE:
<223> OTHER INFORMATION: antibody sequence

<400> SEQUENCE: 302

Ser Tyr Ala Met Leu
1               5

<210> SEQ ID NO 303
<211> LENGTH: 16
<212> TYPE: PRT
<213> ORGANISM: Artificial Sequence
<220> FEATURE:
<223> OTHER INFORMATION: antibody sequence

<400> SEQUENCE: 303

Ala Ile Gly Thr Gly Gly Asp Thr Tyr Tyr Ala Asp Ser Val Lys Gly
1               5                   10                  15

<210> SEQ ID NO 304
<211> LENGTH: 12
<212> TYPE: PRT
<213> ORGANISM: Artificial Sequence
<220> FEATURE:
<223> OTHER INFORMATION: antibody sequence

<400> SEQUENCE: 304

Arg Asp Asp Tyr Thr Ser Arg Asp Ala Phe Asp Tyr
1               5                   10

<210> SEQ ID NO 305
<211> LENGTH: 111
<212> TYPE: PRT
<213> ORGANISM: Artificial Sequence
<220> FEATURE:
<223> OTHER INFORMATION: antibody sequence

<400> SEQUENCE: 305

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Val Tyr Val Val Phe Gly Gly Gly Thr Lys Leu Thr Val Leu
            100                 105                 110

<210> SEQ ID NO 306
<211> LENGTH: 13
<212> TYPE: PRT
<213> ORGANISM: Artificial Sequence
<220> FEATURE:
<223> OTHER INFORMATION: antibody sequence

<400> SEQUENCE: 306

Ser Gly Ser Ser Ser Asn Ile Gly Ser Asn Thr Val Asn
1               5                   10

<210> SEQ ID NO 307
<211> LENGTH: 7

```
<212> TYPE: PRT
<213> ORGANISM: Artificial Sequence
<220> FEATURE:
<223> OTHER INFORMATION: antibody sequence

<400> SEQUENCE: 307

Tyr Asp Asp Leu Arg Pro Ser
1               5

<210> SEQ ID NO 308
<211> LENGTH: 12
<212> TYPE: PRT
<213> ORGANISM: Artificial Sequence
<220> FEATURE:
<223> OTHER INFORMATION: antibody sequence

<400> SEQUENCE: 308

Ala Ala Trp Asp Asp Ser Leu Asn Val Tyr Val Val
1               5                   10

<210> SEQ ID NO 309
<211> LENGTH: 360
<212> TYPE: DNA
<213> ORGANISM: Artificial Sequence
<220> FEATURE:
<223> OTHER INFORMATION: antibody sequence

<400> SEQUENCE: 309
gaagttcagc tgctggaatc tggcggcgga ctggttcaac ctggcggatc tctgagactg     60
agctgtgccg ccagcggctt caccttttac agctacgcca tgctgtgggt ccgacaggcc    120
cctggaaaag gccttgaatg ggtgtccgcc atcggcacag gcggcgatac ctactatgcc    180
gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360

<210> SEQ ID NO 310
<211> LENGTH: 15
<212> TYPE: DNA
<213> ORGANISM: Artificial Sequence
<220> FEATURE:
<223> OTHER INFORMATION: antibody sequence

<400> SEQUENCE: 310
agctacgcca tgctg                                                      15

<210> SEQ ID NO 311
<211> LENGTH: 48
<212> TYPE: DNA
<213> ORGANISM: Artificial Sequence
<220> FEATURE:
<223> OTHER INFORMATION: antibody sequence

<400> SEQUENCE: 311
gccatcggca caggcggcga tacctactat gccgactctg tgaagggc                  48

<210> SEQ ID NO 312
<211> LENGTH: 36
<212> TYPE: DNA
<213> ORGANISM: Artificial Sequence
<220> FEATURE:
<223> OTHER INFORMATION: antibody sequence

<400> SEQUENCE: 312
```
agggacgact acaccagcag ggacgccttc gattat                                    36

<210> SEQ ID NO 313
<211> LENGTH: 333
<212> TYPE: DNA
<213> ORGANISM: Artificial Sequence
<220> FEATURE:
<223> OTHER INFORMATION: antibody sequence

<400> SEQUENCE: 313
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ttattgtgcc gcctgggacg acagcctgaa cgtgtacgtt   300
gtgtttggcg gaggcaccaa gctgaccgtt cta                                333

<210> SEQ ID NO 314
<211> LENGTH: 39
<212> TYPE: DNA
<213> ORGANISM: Artificial Sequence
<220> FEATURE:
<223> OTHER INFORMATION: antibody sequence

<400> SEQUENCE: 314
agcggcagca gctccaacat cggcagcaac accgtgaac                            39

<210> SEQ ID NO 315
<211> LENGTH: 21
<212> TYPE: DNA
<213> ORGANISM: Artificial Sequence
<220> FEATURE:
<223> OTHER INFORMATION: antibody sequence

<400> SEQUENCE: 315
tacgacgacc tgcggcctag c                                               21

<210> SEQ ID NO 316
<211> LENGTH: 36
<212> TYPE: DNA
<213> ORGANISM: Artificial Sequence
<220> FEATURE:
<223> OTHER INFORMATION: antibody sequence

<400> SEQUENCE: 316
gccgcctggg acgacagcct gaacgtgtac gttgtg                               36

<210> SEQ ID NO 317
<211> LENGTH: 447
<212> TYPE: PRT
<213> ORGANISM: Artificial Sequence
<220> FEATURE:
<223> OTHER INFORMATION: antibody sequence

<400> SEQUENCE: 317

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Tyr
            20                  25                  30

Ala Met Leu Trp Val Arg Gln Ala Pro Gly Lys Gly Leu Glu Trp Val
        35                  40                  45

```
Ser Ala Ile Gly Thr Gly Gly Asp Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Arg Asp Asp Tyr Thr Ser Arg Asp Ala Phe Asp Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 318
<211> LENGTH: 217
<212> TYPE: PRT
```

<213> ORGANISM: Artificial Sequence
<220> FEATURE:
<223> OTHER INFORMATION: antibody sequence

<400> SEQUENCE: 318

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Val Tyr Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 319
<211> LENGTH: 1341
<212> TYPE: DNA
<213> ORGANISM: Artificial Sequence
<220> FEATURE:
<223> OTHER INFORMATION: antibody sequence

<400> SEQUENCE: 319

```
gaagttcagc tgctggaatc tggcggcgga ctggttcaac tggcggatc  tctgagactg    60
agctgtgccg ccagcggctt cacctttac  agctacgcca tgctgtgggt ccgacaggcc   120
cctggaaaag gccttgaatg ggtgtccgcc atcggcacag gcggcgatac ctactatgcc   180
gactctgtga agggcagatt caccatcagc cgggacaaca gcaagaacac cctgtacctg   240
cagatgaaca gcctgagagc cgaggacacc gccgtgtact attgcgccag aagggacgac   300
tacaccagca gggacgcctt cgattattgg ggccagggca cactggtcac cgtttcttca   360
gccagcacca agggcccag  cgtgttccct ctggccccct tgagcagaag caccagcgag   420
tctacagccg ccctgggctg cctcgtgaag gactactttc ccgagcccgt gaccgtgtcc   480
tggaactctg gcgctctgac aagcggcgtg cacacctttc cagccgtgct gcagagcagc   540
ggcctgtact ctctgagcag cgtcgtgaca gtgcccagca gcagcctggg caccaagacc   600
tacacctgta acgtggacca caagcccagc aacaccaagg tggacaagcg ggtggaatct   660
```

```
aagtacggcc ctccctgccc tccttgccca gccctgaat ttctgggcgg accctccgtg      720
ttcctgttcc ccccaaagcc caaggacacc ctgatgatca gccggacccc cgaagtgacc      780
tgcgtggtgg tggatgtgtc ccaggaagat cccgaggtgc agttcaattg gtacgtggac      840
ggcgtggaag tgcacaacgc caagaccaag cccagagagg aacagttcaa cagcacctac      900
cgggtggtgt ccgtgctgac agtgctgcac caggactggc tgaacggcaa agagtacaag      960
tgcaaggtgt ccaacaaggg cctgccagc tccatcgaga aaaccatcag caaggccaag     1020
ggccagcccc gcgaaccca ggtgtacaca ctgcctccaa gccaggaaga gatgaccaag     1080
aaccaggtgt ccctgacctg tctcgtgaaa ggcttctacc cctccgatat cgccgtggaa     1140
tgggagagca acggccagcc cgagaacaac tacaagacca ccccccctgt gctggacagc     1200
gacggctcat tcttcctgta cagcagactg accgtggaca gagccggtg gcaggaaggc     1260 aacgtgttca gctgcagcgt gatgcacgag gccctgcaca accactacac ccagaagtcc     1320
ctgtctctga gcctgggcaa g                                               1341
```

<210> SEQ ID NO 320
<211> LENGTH: 651
<212> TYPE: DNA
<213> ORGANISM: Artificial Sequence
<220> FEATURE:
<223> OTHER INFORMATION: antibody sequence

<400> SEQUENCE: 320

```
cagtctgttc tgacacagcc tcctagcgcc tctggcacac ctggacagag agtgaccatc      60
agctgtagcg gcagcagctc caacatcggc agcaacaccg tgaactggta tcagcagctg     120
cctggcacag cccctaaact gctgatctac tacgacgacc tgcggcctag cggcgtgcca     180
gatagatttt ctggcagcaa gagcggcacc tctgccagcc tggctatttc tggactgcag     240
agcgaggacg aggccgacta ttattgtgcc gcctgggacg acagcctgaa cgtgtacgtt     300
gtgtttggcg gaggcaccaa gctgaccgtt ctaggccagc ctaaagccgc ccctagcgtg     360
accctgttcc ctccaagcag cgaggaactg caggccaaca aggccaccct cgtgtgcctg     420
atcagcgact tctatcctgg cgccgtgacc gtggcctgga aggccgatag ctctcctgtg     480
aaggccggcg tggaaaccac caccccctagc aagcagagca caacaaata cgccgccagc     540 agctacctga gcctgacccc cgagcagtgg aagtcccaca gatcctacag ctgccaagtg     600
acccacgagg gcagcaccgt ggaaaagaca gtggcccta ccgagtgcag c                651
```

<210> SEQ ID NO 321
<211> LENGTH: 120
<212> TYPE: PRT
<213> ORGANISM: Artificial Sequence
<220> FEATURE:
<223> OTHER INFORMATION: antibody sequence

<400> SEQUENCE: 321

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60
```

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser
            115                 120

<210> SEQ ID NO 322
<211> LENGTH: 5
<212> TYPE: PRT
<213> ORGANISM: Artificial Sequence
<220> FEATURE:
<223> OTHER INFORMATION: antibody sequence

<400> SEQUENCE: 322

Ser Tyr Ala Met Ser
1               5

<210> SEQ ID NO 323
<211> LENGTH: 16
<212> TYPE: PRT
<213> ORGANISM: Artificial Sequence
<220> FEATURE:
<223> OTHER INFORMATION: antibody sequence

<400> SEQUENCE: 323

Ala Ile Gly Tyr Gly Gly Asp Thr Tyr Tyr Ala Asp Ser Val Lys Gly
1               5                   10                  15

<210> SEQ ID NO 324
<211> LENGTH: 12
<212> TYPE: PRT
<213> ORGANISM: Artificial Sequence
<220> FEATURE:
<223> OTHER INFORMATION: antibody sequence

<400> SEQUENCE: 324

Arg Asp Asp Tyr Thr Ser Arg Asp Ala Phe Asp Tyr
1               5                   10

<210> SEQ ID NO 325
<211> LENGTH: 111
<212> TYPE: PRT
<213> ORGANISM: Artificial Sequence
<220> FEATURE:
<223> OTHER INFORMATION: antibody sequence

<400> SEQUENCE: 325

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
                35                  40                  45

Ile Tyr Tyr Asp Asp Leu Arg Pro Ser Gly Val Pro Asp Arg Phe Ser
            50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys His Ala Trp Asp Asp Ser Leu
                85                  90                  95

Asn Val Tyr Pro Val Phe Gly Gly Gly Thr Lys Leu Thr Val Leu
            100                 105                 110

<210> SEQ ID NO 326
<211> LENGTH: 13
<212> TYPE: PRT
<213> ORGANISM: Artificial Sequence
<220> FEATURE:
<223> OTHER INFORMATION: antibody sequence

<400> SEQUENCE: 326

Ser Gly Ser Ser Ser Asn Ile Gly Ser Asn Thr Val Asn
1               5                   10

<210> SEQ ID NO 327
<211> LENGTH: 7
<212> TYPE: PRT
<213> ORGANISM: Artificial Sequence
<220> FEATURE:
<223> OTHER INFORMATION: antibody sequence

<400> SEQUENCE: 327

Tyr Asp Asp Leu Arg Pro Ser
1               5

<210> SEQ ID NO 328
<211> LENGTH: 12
<212> TYPE: PRT
<213> ORGANISM: Artificial Sequence
<220> FEATURE:
<223> OTHER INFORMATION: antibody sequence

<400> SEQUENCE: 328

His Ala Trp Asp Asp Ser Leu Asn Val Tyr Pro Val
1               5                   10

<210> SEQ ID NO 329
<211> LENGTH: 360
<212> TYPE: DNA
<213> ORGANISM: Artificial Sequence
<220> FEATURE:
<223> OTHER INFORMATION: antibody sequence

<400> SEQUENCE: 329
gaagttcagc tgctggaatc tggcggcgga ctggttcaac tggcggatc tctgagactg        60 agctgtgccg ccagcggctt cacctttac agctacgcca tgagctgggt ccgacaggcc       120
cctggaaaag gccttgaatg ggtgtccgcc atcggctatg cggcgatac ctactacgcc       180 gactctgtga agggcagatt caccatcagc cgggacaaca gcaagaacac cctgtacctg      240
cagatgaaca gcctgagagc cgaggacacc gccgtgtact attgcgccag aagggacgac      300
tacaccagca gggacgcctt cgattattgg ggccagggca cactggtcac cgtttcttca      360

<210> SEQ ID NO 330
<211> LENGTH: 15
<212> TYPE: DNA
<213> ORGANISM: Artificial Sequence
<220> FEATURE:
<223> OTHER INFORMATION: antibody sequence

<400> SEQUENCE: 330
agctacgcca tgagc                                                        15

<210> SEQ ID NO 331
<211> LENGTH: 48

```
<212> TYPE: DNA
<213> ORGANISM: Artificial Sequence
<220> FEATURE:
<223> OTHER INFORMATION: antibody sequence

<400> SEQUENCE: 331
gccatcggct atggcggcga tacctactac gccgactctg tgaagggc          48

<210> SEQ ID NO 332
<211> LENGTH: 36
<212> TYPE: DNA
<213> ORGANISM: Artificial Sequence
<220> FEATURE:
<223> OTHER INFORMATION: antibody sequence

<400> SEQUENCE: 332
agggacgact acaccagcag ggacgccttc gattat                       36

<210> SEQ ID NO 333
<211> LENGTH: 333
<212> TYPE: DNA
<213> ORGANISM: Artificial Sequence
<220> FEATURE:
<223> OTHER INFORMATION: antibody sequence

<400> SEQUENCE: 333
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ctattgtcac gcctgggacg acagcctgaa cgtgtaccct   300 gttttggcg gaggcaccaa gctgaccgtt cta                                 333

<210> SEQ ID NO 334
<211> LENGTH: 39
<212> TYPE: DNA
<213> ORGANISM: Artificial Sequence
<220> FEATURE:
<223> OTHER INFORMATION: antibody sequence

<400> SEQUENCE: 334
agcggcagca gctccaacat cggcagcaac accgtgaac                    39

<210> SEQ ID NO 335
<211> LENGTH: 21
<212> TYPE: DNA
<213> ORGANISM: Artificial Sequence
<220> FEATURE:
<223> OTHER INFORMATION: antibody sequence

<400> SEQUENCE: 335
tacgacgacc tgcggcctag c                                       21

<210> SEQ ID NO 336
<211> LENGTH: 36
<212> TYPE: DNA
<213> ORGANISM: Artificial Sequence
<220> FEATURE:
<223> OTHER INFORMATION: antibody sequence

<400> SEQUENCE: 336
cacgcctggg acgacagcct gaacgtgtac cctgtt                       36
```

```
<210> SEQ ID NO 337
<211> LENGTH: 447
<212> TYPE: PRT
<213> ORGANISM: Artificial Sequence
<220> FEATURE:
<223> OTHER INFORMATION: antibody sequence

<400> SEQUENCE: 337

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365
```

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 338
<211> LENGTH: 217
<212> TYPE: PRT
<213> ORGANISM: Artificial Sequence
<220> FEATURE:
<223> OTHER INFORMATION: antibody sequence

<400> SEQUENCE: 338

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys His Ala Trp Asp Asp Ser Leu
                85                  90                  95

Asn Val Tyr Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 339
<211> LENGTH: 1341
<212> TYPE: DNA
<213> ORGANISM: Artificial Sequence
<220> FEATURE:
<223> OTHER INFORMATION: antibody sequence

<400> SEQUENCE: 339
gaagttcagc tgctggaatc tggcggcgga ctggttcaac ctggcggatc tctgagactg    60

```
agctgtgccg ccagcggctt cacctttac agctacgcca tgagctgggt ccgacaggcc    120
cctggaaaag gccttgaatg ggtgtccgcc atcggctatg gcggcgatac ctactacgcc    180
gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360
gccagcacca agggccccag cgtgttccct ctggcccctt gtagcagaag caccagcgag    420
tctacagccg ccctgggctg cctcgtgaag gactactttc ccgagcccgt gaccgtgtcc    480
tggaactctg gcgctctgac aagcggcgtg cacacctttc cagccgtgct gcagagcagc    540
ggcctgtact ctctgagcag cgtcgtgaca gtgcccagca gcagcctggg caccaagacc    600
tacacctgta acgtggacca caagcccagc aacaccaagg tggacaagcg ggtggaatct    660
aagtacggcc ctccctgccc tccttgccca gcccctgaat tctgggcgg accctccgtg    720 ttcctgttcc ccccaaagcc caaggacacc ctgatgatca gccggacccc cgaagtgacc    780
tgcgtggtgg tggatgtgtc ccaggaagat cccgaggtgc agttcaattg gtacgtggac    840
ggcgtggaag tgcacaacgc caagaccaag cccagagagg aacagttcaa cagcacctac    900
cgggtggtgt ccgtgctgac agtgctgcac caggactggc tgaacggcaa agagtacaag    960
tgcaaggtgt ccaacaaggg cctgcccagc tccatcgaga aaccatcag caaggccaag   1020 ggccagcccc gcgaacccca ggtgtacaca ctgcctccaa gccaggaaga gatgaccaag   1080
aaccaggtgt ccctgacctg tctcgtgaaa ggcttctacc cctccgatat cgccgtggaa   1140
tgggagagca acggccagcc cgagaacaac tacaagacca ccccccctgt gctggacagc   1200
gacggctcat tcttcctgta cagcagactg accgtggaca gagccggtg gcaggaaggc   1260 aacgtgttca gctgcagcgt gatgcacgag gccctgcaca accactacac ccagaagtcc   1320
ctgtctctga gcctgggcaa g                                            1341

<210> SEQ ID NO 340
<211> LENGTH: 651
<212> TYPE: DNA
<213> ORGANISM: Artificial Sequence
<220> FEATURE:
<223> OTHER INFORMATION: antibody sequence

<400> SEQUENCE: 340
cagtctgttc tgacacagcc tcctagcgcc tctggcacac ctggacagag agtgaccatc     60
agctgtagcg gcagcagctc caacatcggc agcaacaccg tgaactggta tcagcagctg    120
cctggcacag cccctaaact gctgatctac tacgacgacc tgcggcctag cggcgtgcca    180
gatagatttt ctggcagcaa gagcggcacc tctgccagcc tggctatttc tggactgcag    240
agcgaggacg aggccgacta ctattgtcac gcctgggacg acagcctgaa cgtgtaccct    300 gttttggcg aggcaccaa gctgaccgtt ctaggccagc ctaaagccgc ccctagcgtg    360
accctgttcc ctccaagcag cgaggaactg caggccaaca aggccaccct cgtgtgcctg    420
atcagcgact ctatcctgg cgccgtgacc gtggcctgga aggccgatag ctctcctgtg    480
aaggccggcg tggaaaccac cacccctagc aagcagagca caacaaata cgccgccagc    540 agctacctga gcctgacccc cgagcagtgg aagtcccaca tcctacag ctgccaagtg    600 acccacgagg gcagcaccgt ggaaaagaca gtggccccta ccgagtgcag c            651

<210> SEQ ID NO 341
<211> LENGTH: 120
```

```
<212> TYPE: PRT
<213> ORGANISM: Artificial Sequence
<220> FEATURE:
<223> OTHER INFORMATION: antibody sequence

<400> SEQUENCE: 341

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser
        115                 120

<210> SEQ ID NO 342
<211> LENGTH: 5
<212> TYPE: PRT
<213> ORGANISM: Artificial Sequence
<220> FEATURE:
<223> OTHER INFORMATION: antibody sequence

<400> SEQUENCE: 342

Ser Tyr Ala Met Ser
1               5

<210> SEQ ID NO 343
<211> LENGTH: 16
<212> TYPE: PRT
<213> ORGANISM: Artificial Sequence
<220> FEATURE:
<223> OTHER INFORMATION: antibody sequence

<400> SEQUENCE: 343

Ala Ile Gly Tyr Gly Gly Asp Thr Tyr Tyr Ala Asp Ser Val Lys Gly
1               5                   10                  15

<210> SEQ ID NO 344
<211> LENGTH: 12
<212> TYPE: PRT
<213> ORGANISM: Artificial Sequence
<220> FEATURE:
<223> OTHER INFORMATION: antibody sequence

<400> SEQUENCE: 344

Arg Asp Asp Tyr Thr Ser Arg Asp Ala Phe Asp Tyr
1               5                   10

<210> SEQ ID NO 345
<211> LENGTH: 111
<212> TYPE: PRT
<213> ORGANISM: Artificial Sequence
<220> FEATURE:
<223> OTHER INFORMATION: antibody sequence

<400> SEQUENCE: 345
```

```
Gln Ser Val Leu Thr Gln Pro Pro Ser Ala Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Ser Leu
                85                  90                  95

Asn Asp Ile Pro Val Phe Gly Gly Gly Thr Lys Leu Thr Val Leu
            100                 105                 110
```

<210> SEQ ID NO 346
<211> LENGTH: 13
<212> TYPE: PRT
<213> ORGANISM: Artificial Sequence
<220> FEATURE:
<223> OTHER INFORMATION: antibody sequence

<400> SEQUENCE: 346

```
Ser Gly Ser Ser Asn Ile Gly Ser Asn Thr Val Asn
1               5                   10
```

<210> SEQ ID NO 347
<211> LENGTH: 7
<212> TYPE: PRT
<213> ORGANISM: Artificial Sequence
<220> FEATURE:
<223> OTHER INFORMATION: antibody sequence

<400> SEQUENCE: 347

```
Tyr Asp Asp Leu Arg Pro Ser
1               5
```

<210> SEQ ID NO 348
<211> LENGTH: 12
<212> TYPE: PRT
<213> ORGANISM: Artificial Sequence
<220> FEATURE:
<223> OTHER INFORMATION: antibody sequence

<400> SEQUENCE: 348

```
Ala Ala Trp Asp Asp Ser Leu Asn Asp Ile Pro Val
1               5                   10
```

<210> SEQ ID NO 349
<211> LENGTH: 360
<212> TYPE: DNA
<213> ORGANISM: Artificial Sequence
<220> FEATURE:
<223> OTHER INFORMATION: antibody sequence

<400> SEQUENCE: 349

```
gaagttcagc tgctggaatc tggcggcgga ctggttcaac tggcggatc tctgagactg    60 agctgtgccg ccagcggctt cacctttac agctacgcca tgagctgggt ccgacaggcc   120
cctggaaaag gccttgaatg ggtgtccgcc atcggctatg gcggcgatac ctactacgcc   180
gactctgtga aggcagatt caccatcagc cgggacaaca gcaagaacac cctgtacctg   240
```

```
cagatgaaca gcctgagagc cgaggacacc gccgtgtact attgcgccag aagggacgac    300
tacaccagca gggacgcctt cgattattgg ggccagggca cactggtcac cgtttcttca    360
```

<210> SEQ ID NO 350
<211> LENGTH: 15
<212> TYPE: DNA
<213> ORGANISM: Artificial Sequence
<220> FEATURE:
<223> OTHER INFORMATION: antibody sequence

<400> SEQUENCE: 350

```
agctacgcca tgagc                                                      15
```

<210> SEQ ID NO 351
<211> LENGTH: 48
<212> TYPE: DNA
<213> ORGANISM: Artificial Sequence
<220> FEATURE:
<223> OTHER INFORMATION: antibody sequence

<400> SEQUENCE: 351

```
gccatcggct atggcggcga tacctactac gccgactctg tgaagggc                  48
```

<210> SEQ ID NO 352
<211> LENGTH: 36
<212> TYPE: DNA
<213> ORGANISM: Artificial Sequence
<220> FEATURE:
<223> OTHER INFORMATION: antibody sequence

<400> SEQUENCE: 352

```
agggacgact acaccagcag ggacgccttc gattat                               36
```

<210> SEQ ID NO 353
<211> LENGTH: 333
<212> TYPE: DNA
<213> ORGANISM: Artificial Sequence
<220> FEATURE:
<223> OTHER INFORMATION: antibody sequence

<400> SEQUENCE: 353

```
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ttattgtgcc gcctgggacg acagcctgaa cgacatccct   300
gtttttggcg gaggcaccaa gctgaccgtt cta                                 333
```

<210> SEQ ID NO 354
<211> LENGTH: 39
<212> TYPE: DNA
<213> ORGANISM: Artificial Sequence
<220> FEATURE:
<223> OTHER INFORMATION: antibody sequence

<400> SEQUENCE: 354

```
agcggcagca gctccaacat cggcagcaac accgtgaac                            39
```

<210> SEQ ID NO 355
<211> LENGTH: 21
<212> TYPE: DNA
<213> ORGANISM: Artificial Sequence

```
<220> FEATURE:
<223> OTHER INFORMATION: antibody sequence

<400> SEQUENCE: 355
tacgacgacc tgcggcctag c                                              21

<210> SEQ ID NO 356
<211> LENGTH: 36
<212> TYPE: DNA
<213> ORGANISM: Artificial Sequence
<220> FEATURE:
<223> OTHER INFORMATION: antibody sequence

<400> SEQUENCE: 356
gccgcctggg acgacagcct gaacgacatc cctgtt                              36

<210> SEQ ID NO 357
<211> LENGTH: 447
<212> TYPE: PRT
<213> ORGANISM: Artificial Sequence
<220> FEATURE:
<223> OTHER INFORMATION: antibody sequence

<400> SEQUENCE: 357
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

```
Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
                435                 440                 445

<210> SEQ ID NO 358
<211> LENGTH: 217
<212> TYPE: PRT
<213> ORGANISM: Artificial Sequence
<220> FEATURE:
<223> OTHER INFORMATION: antibody sequence

<400> SEQUENCE: 358

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Asp Ile Pro Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190
```

His Arg Ser Tyr Ser Cys Gln Val Thr His Glu Gly Ser Thr Val Glu
    195                 200                 205

Lys Thr Val Ala Pro Thr Glu Cys Ser
    210                 215

<210> SEQ ID NO 359
<211> LENGTH: 1341
<212> TYPE: DNA
<213> ORGANISM: Artificial Sequence
<220> FEATURE:
<223> OTHER INFORMATION: antibody sequence

<400> SEQUENCE: 359

```
gaagttcagc tgctggaatc tggcggcgga ctggttcaac ctggcggatc tctgagactg      60
agctgtgccg ccagcggctt caccttttac agctacgcca tgagctgggt ccgacaggcc     120
cctggaaaag gccttgaatg gtgtccgcc atcggctatg gcggcgatac ctactacgcc      180
gactctgtga agggcagatt caccatcagc cgggacaaca gcaagaacac cctgtacctg     240
cagatgaaca gcctgagagc cgaggacacc gccgtgtact attgcgccag aagggacgac     300
tacaccagca gggacgcctt cgattattgg ggccagggca cactggtcac cgtttcttca     360
gccagcacca agggcccag cgtgttccct ctggcccctt gtagcagaag caccagcgag      420
tctacagccg ccctgggctg cctcgtgaag gactactttc ccgagcccgt gaccgtgtcc     480
tggaactctg gcgctctgac aagcggcgtg cacacctttc cagccgtgct gcagagcagc     540
ggcctgtact ctctgagcag cgtcgtgaca gtgcccagca gcagcctggg caccaagacc     600
tacacctgta acgtggacca caagcccagc aacaccaagg tggacaagcg ggtggaatct     660
aagtacggcc ctccctgccc tccttgccca gcccctgaat ttctgggcgg accctccgtg     720
ttcctgttcc ccccaaagcc caaggacacc ctgatgatca gccggacccc cgaagtgacc     780
tgcgtggtgg tggatgtgtc ccaggaagat cccgaggtgc agttcaattg gtacgtggac     840
ggcgtggaag tgcacaacgc caagaccaag cccagagagg aacagttcaa cagcacctac     900
cgggtggtgt ccgtgctgac agtgctgcac caggactggc tgaacggcaa agagtacaag     960
tgcaaggtgt ccaacaaggg cctgcccagc tccatcgaga aaaccatcag caaggccaag    1020
ggccagcccc gcgaacccca ggtgtacaca ctgcctccaa gccaggaaga tgatgaccaag   1080
aaccaggtgt ccctgacctg tctcgtgaaa ggcttctacc cctccgatat cgccgtggaa    1140
tgggagagca acggccagcc cgagaacaac tacaagacca cccccctgt gctggacagc     1200
gacggctcat tcttcctgta cagcagactg accgtggaca gagccggtg gcaggaaggc     1260
aacgtgttca gctgcagcgt gatgcacgag gccctgcaca accactacac ccagaagtcc    1320
ctgtctctga gcctgggcaa g                                              1341
```

<210> SEQ ID NO 360
<211> LENGTH: 651
<212> TYPE: DNA
<213> ORGANISM: Artificial Sequence
<220> FEATURE:
<223> OTHER INFORMATION: antibody sequence

<400> SEQUENCE: 360

```
cagtctgttc tgacacagcc tcctagcgcc tctggcacac tggacagag agtgaccatc       60
agctgtagcg gcagcagctc caacatcggc agcaacaccg tgaactggta tcagcagctg     120
cctggcacag cccctaaact gctgatctac tacgacacc tgcggcctag cggcgtgcca     180
```

```
gatagattt  ctggcagcaa  gagcggcacc  tctgccagcc  tggctatttc  tggactgcag      240
agcgaggacg  aggccgacta  ttattgtgcc  gcctgggacg  acagcctgaa  cgacatccct      300
gtttttggcg  gaggcaccaa  gctgaccgtt  ctaggccagc  ctaaagccgc  ccctagcgtg      360
accctgttcc  ctccaagcag  cgaggaactg  caggccaaca  aggccaccct  cgtgtgcctg      420
atcagcgact  tctatcctgg  cgccgtgacc  gtggcctgga  aggccgatag  ctctcctgtg      480
aaggccggcg  tggaaaccac  caccccctagc  aagcagagca  caacaaata   cgccgccagc      540 agctacctga  gcctgacccc  cgagcagtgg  aagtcccaca  gatcctacag  ctgccaagtg      600
acccacgagg  gcagcaccgt  ggaaaagaca  gtggcccta   ccgagtgcag  c              651
```

<210> SEQ ID NO 361
<211> LENGTH: 120
<212> TYPE: PRT
<213> ORGANISM: Artificial Sequence
<220> FEATURE:
<223> OTHER INFORMATION: antibody sequence

<400> SEQUENCE: 361

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser
        115                 120
```

<210> SEQ ID NO 362
<211> LENGTH: 5
<212> TYPE: PRT
<213> ORGANISM: Artificial Sequence
<220> FEATURE:
<223> OTHER INFORMATION: antibody sequence

<400> SEQUENCE: 362

```
Ser Tyr Ala Met Ser
1               5
```

<210> SEQ ID NO 363
<211> LENGTH: 16
<212> TYPE: PRT
<213> ORGANISM: Artificial Sequence
<220> FEATURE:
<223> OTHER INFORMATION: antibody sequence

<400> SEQUENCE: 363

```
Ala Ile Gly Tyr Gly Gly Asp Thr Tyr Tyr Ala Asp Ser Val Lys Gly
1               5                   10                  15
```

<210> SEQ ID NO 364
<211> LENGTH: 12

```
<212> TYPE: PRT
<213> ORGANISM: Artificial Sequence
<220> FEATURE:
<223> OTHER INFORMATION: antibody sequence

<400> SEQUENCE: 364

Arg Asp Asp Tyr Thr Ser Arg Asp Ala Phe Asp Tyr
1               5                   10

<210> SEQ ID NO 365
<211> LENGTH: 111
<212> TYPE: PRT
<213> ORGANISM: Artificial Sequence
<220> FEATURE:
<223> OTHER INFORMATION: antibody sequence

<400> SEQUENCE: 365

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Val Ile Pro Val Phe Gly Gly Gly Thr Lys Leu Thr Val Leu
            100                 105                 110

<210> SEQ ID NO 366
<211> LENGTH: 13
<212> TYPE: PRT
<213> ORGANISM: Artificial Sequence
<220> FEATURE:
<223> OTHER INFORMATION: antibody sequence

<400> SEQUENCE: 366

Ser Gly Ser Ser Ser Asn Ile Gly Ser Asn Thr Val Asn
1               5                   10

<210> SEQ ID NO 367
<211> LENGTH: 7
<212> TYPE: PRT
<213> ORGANISM: Artificial Sequence
<220> FEATURE:
<223> OTHER INFORMATION: antibody sequence

<400> SEQUENCE: 367

Tyr Asp Asp Leu Arg Pro Ser
1               5

<210> SEQ ID NO 368
<211> LENGTH: 12
<212> TYPE: PRT
<213> ORGANISM: Artificial Sequence
<220> FEATURE:
<223> OTHER INFORMATION: antibody sequence

<400> SEQUENCE: 368

Ala Ala Trp Asp Asp Ser Leu Asn Val Ile Pro Val
1               5                   10
```

<210> SEQ ID NO 369
<211> LENGTH: 360
<212> TYPE: DNA
<213> ORGANISM: Artificial Sequence
<220> FEATURE:
<223> OTHER INFORMATION: antibody sequence

<400> SEQUENCE: 369

```
gaagttcagc tgctggaatc tggcggcgga ctggttcaac ctggcggatc tctgagactg    60
agctgtgccg ccagcggctt caccttttac agctacgcca tgagctgggt ccgacaggcc   120
cctggaaaag gccttgaatg ggtgtccgcc atcggctatg gcggcgatac ctactacgcc   180
gactctgtga agggcagatt caccatcagc cgggacaaca gcaagaacac cctgtacctg   240
cagatgaaca gcctgagagc cgaggacacc gccgtgtact attgcgccag aagggacgac   300 taccaccagca gggacgcctt cgattattgg ggccagggca cactggtcac cgtttcttca   360
```

<210> SEQ ID NO 370
<211> LENGTH: 15
<212> TYPE: DNA
<213> ORGANISM: Artificial Sequence
<220> FEATURE:
<223> OTHER INFORMATION: antibody sequence

<400> SEQUENCE: 370

```
agctacgcca tgagc                                                      15
```

<210> SEQ ID NO 371
<211> LENGTH: 48
<212> TYPE: DNA
<213> ORGANISM: Artificial Sequence
<220> FEATURE:
<223> OTHER INFORMATION: antibody sequence

<400> SEQUENCE: 371

```
gccatcggct atggcggcga tacctactac gccgactctg tgaagggc                  48
```

<210> SEQ ID NO 372
<211> LENGTH: 36
<212> TYPE: DNA
<213> ORGANISM: Artificial Sequence
<220> FEATURE:
<223> OTHER INFORMATION: antibody sequence

<400> SEQUENCE: 372

```
agggacgact acaccagcag ggacgccttc gattat                               36
```

<210> SEQ ID NO 373
<211> LENGTH: 333
<212> TYPE: DNA
<213> ORGANISM: Artificial Sequence
<220> FEATURE:
<223> OTHER INFORMATION: antibody sequence

<400> SEQUENCE: 373

```
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ttattgtgcc gcctgggacg acagcctgaa cgtgatccct   300
```

```
gtttttggcg gaggcaccaa gctgaccgtt cta                            333
```

<210> SEQ ID NO 374
<211> LENGTH: 39
<212> TYPE: DNA
<213> ORGANISM: Artificial Sequence
<220> FEATURE:
<223> OTHER INFORMATION: antibody sequence

<400> SEQUENCE: 374

```
agcggcagca gctccaacat cggcagcaac accgtgaac                      39
```

<210> SEQ ID NO 375
<211> LENGTH: 21
<212> TYPE: DNA
<213> ORGANISM: Artificial Sequence
<220> FEATURE:
<223> OTHER INFORMATION: antibody sequence

<400> SEQUENCE: 375

```
tacgacgacc tgcggcctag c                                         21
```

<210> SEQ ID NO 376
<211> LENGTH: 36
<212> TYPE: DNA
<213> ORGANISM: Artificial Sequence
<220> FEATURE:
<223> OTHER INFORMATION: antibody sequence

<400> SEQUENCE: 376

```
gccgcctggg acgacagcct gaacgtgatc cctgtt                         36
```

<210> SEQ ID NO 377
<211> LENGTH: 447
<212> TYPE: PRT
<213> ORGANISM: Artificial Sequence
<220> FEATURE:
<223> OTHER INFORMATION: antibody sequence

<400> SEQUENCE: 377

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Ser Tyr
            20                  25                  30

Ala Met Ser Trp Val Arg Gln Ala Pro Gly Lys Gly Leu Glu Trp Val
        35                  40                  45

Ser Ala Ile Gly Tyr Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Asp Asp Tyr Thr Ser Arg Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val

```
                        165                 170                 175
Leu Gln Ser Ser Gly Leu Tyr Ser Leu Ser Ser Val Val Thr Val Pro
                    180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 378
<211> LENGTH: 217
<212> TYPE: PRT
<213> ORGANISM: Artificial Sequence
<220> FEATURE:
<223> OTHER INFORMATION: antibody sequence

<400> SEQUENCE: 378

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
```

|  |  |  | 85 |  |  | 90 |  |  |  | 95 |  |
|---|---|---|---|---|---|---|---|---|---|---|---|

Asn Val Ile Pro Val Phe Gly Gly Thr Lys Leu Thr Val Leu Gly
                                100                              105                                     110

Gln Pro Lys Ala Ala Pro Ser Val Thr Leu Phe Pro Pro Ser Ser Glu
                    115                              120                                 125

Glu Leu Gln Ala Asn Lys Ala Thr Leu Val Cys Leu Ile Ser Asp Phe
        130                              135                               140

Tyr Pro Gly Ala Val Thr Val Ala Trp Lys Ala Asp Ser Ser Pro Val
145                             150                               155                             160

Lys Ala Gly Val Glu Thr Thr Thr Pro Ser Lys Gln Ser Asn Asn Lys
                            165                             170                              175

Tyr Ala Ala Ser Ser Tyr Leu Ser Leu Thr Pro Glu Gln Trp Lys Ser
                    180                                185                             190

His Arg Ser Tyr Ser Cys Gln Val Thr His Glu Gly Ser Thr Val Glu
                195                              200                              205

Lys Thr Val Ala Pro Thr Glu Cys Ser
            210                              215

<210> SEQ ID NO 379
<211> LENGTH: 1341
<212> TYPE: DNA
<213> ORGANISM: Artificial Sequence
<220> FEATURE:
<223> OTHER INFORMATION: antibody sequence

<400> SEQUENCE: 379

```
gaagttcagc tgctggaatc tggcggcgga ctggttcaac tggcggatc tctgagactg     60
agctgtgccg ccagcggctt cacctttac agctacgcca tgagctgggt ccgacaggcc    120
cctggaaaag gccttgaatg gtgtccgcc atcggctatg cggcgatac ctactacgcc    180
gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360
gccagcacca agggcccag cgtgttccct ctggcccctt gtagcagaag caccagcgag    420
tctacagccg cctgggctg cctcgtgaag gactacttc ccgagcccgt gaccgtgtcc    480
tggaactctg gcgctctgac aagcggcgtg cacacctttc agccgtgct gcagagcagc    540
ggcctgtact ctctgagcag cgtcgtgaca gtgcccagca gcagcctggg caccaagacc    600
tacacctgta acgtggacca caagcccagc aacaccaagg tggacaagcg ggtggaatct    660
aagtacggcc ctcctgccc tccttgccca gcccctgaat tctgggcgg acctccgtg    720
ttcctgttcc ccccaaagcc caaggacacc ctgatgatca gccggacccc cgaagtgacc    780
tgcgtggtgg tggatgtgtc ccaggaagat cccgaggtgc agttcaattg gtacgtggac    840
ggcgtggaag tgcacaacgc caagaccaag cccagagagg aacagttcaa cagcacctac    900
cgggtggtgt ccgtgctgac agtgctgcac caggactggc tgaacggcaa agagtacaag    960
tgcaaggtgt ccaacaaggg cctgcccagc tccatcgaga aaaccatcag caaggccaag   1020
ggccagcccc gcgaaccca ggtgtacaca ctgcctccaa gccaggaaga gatgaccaag   1080
aaccaggtgt ccctgacctg tctcgtgaaa ggcttctacc cctccgatat cgccgtggaa   1140
tgggagagca acggccagcc cgagaacaac tacaagacca cccccctgt gctggacagc   1200
gacggctcat tcttcctgta cagcagctg accgtggaca gagccggtg caggaaggc   1260
aacgtgttca gctgcagcgt gatgcacgag gccctgcaca accactacac ccagaagtcc   1320
```
ctgtctctga gcctgggcaa g                                                    1341

<210> SEQ ID NO 380
<211> LENGTH: 651
<212> TYPE: DNA
<213> ORGANISM: Artificial Sequence
<220> FEATURE:
<223> OTHER INFORMATION: antibody sequence

<400> SEQUENCE: 380
cagtctgttc tgacacagcc tcctagcgcc tctggcacac ctggacagag agtgaccatc      60
agctgtagcg gcagcagctc aacatcggc agcaacaccg tgaactggta tcagcagctg     120
cctggcacag cccctaaact gctgatctac tacgacacc tgcggcctag cggcgtgcca     180
gatagatttt ctggcagcaa gagcggcacc tctgccagcc tggctatttc tggactgcag     240
agcgaggacg aggccgacta ttattgtgcc gcctgggacg acagcctgaa cgtgatccct     300
gttttttggcg aggcaccaa gctgaccgtt ctaggccagc ctaaagccgc ccctagcgtg     360
accctgttcc ctccaagcag cgaggaactg caggccaaca aggccaccct cgtgtgcctg     420
atcagcgact ctatcctgg cgccgtgacc gtggcctgga aggccgatag ctctcctgtg     480
aaggccggcg tggaaaccac caccctagc aagcagagca acaacaaata cgccgccagc     540
agctacctga gcctgacccc cgagcagtgg aagtcccaca gatcctacag ctgccaagtg     600
acccacgagg gcagcaccgt ggaaaagaca gtggccccta ccgagtgcag c             651

<210> SEQ ID NO 381
<211> LENGTH: 123
<212> TYPE: PRT
<213> ORGANISM: Artificial Sequence
<220> FEATURE:
<223> OTHER INFORMATION: antibody sequence

<400> SEQUENCE: 381

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser
        115                 120

<210> SEQ ID NO 382
<211> LENGTH: 5
<212> TYPE: PRT
<213> ORGANISM: Artificial Sequence
<220> FEATURE:
<223> OTHER INFORMATION: antibody sequence

<400> SEQUENCE: 382

```
Ser Tyr Glu Met Asn
1               5
```

\<210\> SEQ ID NO 383
\<211\> LENGTH: 17
\<212\> TYPE: PRT
\<213\> ORGANISM: Artificial Sequence
\<220\> FEATURE:
\<223\> OTHER INFORMATION: antibody sequence

\<400\> SEQUENCE: 383

```
Gly Ile Ser Trp Asn Ser Gly Trp Ile Asp Tyr Ala Asp Ser Val Lys
1               5                   10                  15

Gly
```

\<210\> SEQ ID NO 384
\<211\> LENGTH: 14
\<212\> TYPE: PRT
\<213\> ORGANISM: Artificial Sequence
\<220\> FEATURE:
\<223\> OTHER INFORMATION: antibody sequence

\<400\> SEQUENCE: 384

```
Ser Gly Tyr Ser Ser Trp Phe Asp Pro Asp Phe Asp Tyr
1               5                   10
```

\<210\> SEQ ID NO 385
\<211\> LENGTH: 111
\<212\> TYPE: PRT
\<213\> ORGANISM: Artificial Sequence
\<220\> FEATURE:
\<223\> OTHER INFORMATION: antibody sequence

\<400\> SEQUENCE: 385

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asp Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Ala Gly Pro
                85                  90                  95

Asn Pro Tyr Val Val Phe Gly Gly Gly Thr Lys Leu Thr Val Leu
            100                 105                 110
```

\<210\> SEQ ID NO 386
\<211\> LENGTH: 14
\<212\> TYPE: PRT
\<213\> ORGANISM: Artificial Sequence
\<220\> FEATURE:
\<223\> OTHER INFORMATION: antibody sequence

\<400\> SEQUENCE: 386

```
Thr Gly Ser Ser Ser Asp Ile Gly Ala Gly Tyr Asp Val His
1               5                   10
```

\<210\> SEQ ID NO 387
\<211\> LENGTH: 7
\<212\> TYPE: PRT

```
<213> ORGANISM: Artificial Sequence
<220> FEATURE:
<223> OTHER INFORMATION: antibody sequence

<400> SEQUENCE: 387

Gly Asn Ser Asn Arg Pro Ser
1               5

<210> SEQ ID NO 388
<211> LENGTH: 11
<212> TYPE: PRT
<213> ORGANISM: Artificial Sequence
<220> FEATURE:
<223> OTHER INFORMATION: antibody sequence

<400> SEQUENCE: 388

Ser Ser Tyr Ala Gly Pro Asn Pro Tyr Val Val
1               5                   10

<210> SEQ ID NO 389
<211> LENGTH: 369
<212> TYPE: DNA
<213> ORGANISM: Artificial Sequence
<220> FEATURE:
<223> OTHER INFORMATION: antibody sequence

<400> SEQUENCE: 389
gaagttcagc tgctggaatc tggcggcgga ctggttcaac ctggcggatc tctgagactg      60
agctgtgccg ccagcggctt caccttcgat agctacgaga tgaactgggt ccgacaggcc     120
cctggcaaag ccttgaatg ggtgtccggc atcagctgga atagcggctg gatcgactac     180
gccgacagcg tgaagggcag attcaccatc agccgggaca cagcaagaa caccctgtac     240 ctgcagatga acagcctgag agccgaggac accgccgtgt actactgtgc cagaagcggc     300
tacagcagct cttggtttga ccccgacttc gactattggg gccagggcac actggtcaca     360
gtctcttca                                                            369

<210> SEQ ID NO 390
<211> LENGTH: 15
<212> TYPE: DNA
<213> ORGANISM: Artificial Sequence
<220> FEATURE:
<223> OTHER INFORMATION: antibody sequence

<400> SEQUENCE: 390
agctacgaga tgaac                                                      15

<210> SEQ ID NO 391
<211> LENGTH: 51
<212> TYPE: DNA
<213> ORGANISM: Artificial Sequence
<220> FEATURE:
<223> OTHER INFORMATION: antibody sequence

<400> SEQUENCE: 391
ggcatcagct ggaatagcgg ctggatcgac tacgccgaca gcgtgaaggg c               51

<210> SEQ ID NO 392
<211> LENGTH: 42
<212> TYPE: DNA
<213> ORGANISM: Artificial Sequence
<220> FEATURE:
<223> OTHER INFORMATION: antibody sequence

<400> SEQUENCE: 392
```
agcggctaca gcagctcttg gtttgacccc gacttcgact at  42

<210> SEQ ID NO 393
<211> LENGTH: 333
<212> TYPE: DNA
<213> ORGANISM: Artificial Sequence
<220> FEATURE:
<223> OTHER INFORMATION: antibody sequence

<400> SEQUENCE: 393
cagtctgttc tgacacagcc tccatctgtg tctggcgccc ctggacagag agtgaccatc  60
agctgtacag gcagcagctc cgatattggc gccggatacg acgtgcactg gtatcagcaa  120
ctgcctggca gcccctaa gctgctgatc tacggcaaca gcaacagacc tagcggcgtg  180
cccgatagat tcagcggctc taagtctggc acaagcgcca gcctggccat tactggactg  240
caggccgaag atgaggccga ctactactgc agcagctacg ctggccccaa tccttacgtg  300
gtgtttggcg gcggaacaaa gctgaccgtt cta  333

<210> SEQ ID NO 394
<211> LENGTH: 42
<212> TYPE: DNA
<213> ORGANISM: Artificial Sequence
<220> FEATURE:
<223> OTHER INFORMATION: antibody sequence

<400> SEQUENCE: 394
acaggcagca gctccgatat tggcgccgga tacgacgtgc ac  42

<210> SEQ ID NO 395
<211> LENGTH: 21
<212> TYPE: DNA
<213> ORGANISM: Artificial Sequence
<220> FEATURE:
<223> OTHER INFORMATION: antibody sequence

<400> SEQUENCE: 395
ggcaacagca acagacctag c  21

<210> SEQ ID NO 396
<211> LENGTH: 33
<212> TYPE: DNA
<213> ORGANISM: Artificial Sequence
<220> FEATURE:
<223> OTHER INFORMATION: antibody sequence

<400> SEQUENCE: 396
agcagctacg ctggccccaa tccttacgtg gtg  33

<210> SEQ ID NO 397
<211> LENGTH: 453
<212> TYPE: PRT
<213> ORGANISM: Artificial Sequence
<220> FEATURE:
<223> OTHER INFORMATION: antibody sequence

<400> SEQUENCE: 397

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Glu Met Asn Trp Val Arg Gln Ala Pro Gly Lys Gly Leu Glu Trp Val
        35                  40                  45

-continued

Ser Gly Ile Ser Trp Asn Ser Gly Trp Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

```
<210> SEQ ID NO 398
<211> LENGTH: 217
<212> TYPE: PRT
<213> ORGANISM: Artificial Sequence
<220> FEATURE:
<223> OTHER INFORMATION: antibody sequence

<400> SEQUENCE: 398

Gln Ser Val Leu Thr Gln Pro Pro Ser Val Gly Ala Pro Gly Gln
1               5                   10                  15

Arg Val Thr Ile Ser Cys Thr Gly Ser Ser Asp Ile Gly Ala Gly
                20                  25                  30

Tyr Asp Val His Trp Tyr Gln Gln Leu Pro Gly Thr Ala Pro Lys Leu
                35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Ala Gly Pro
                85                  90                  95

Asn Pro Tyr Val Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
                115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
                210                 215

<210> SEQ ID NO 399
<211> LENGTH: 1359
<212> TYPE: DNA
<213> ORGANISM: Artificial Sequence
<220> FEATURE:
<223> OTHER INFORMATION: antibody sequence

<400> SEQUENCE: 399
gaagttcagc tgctggaatc tggcggcgga ctggttcaac tggcggatc tctgagactg      60 agctgtgccg ccagcggctt caccttcgat agctacgaga tgaactgggt ccgacaggcc     120
cctggcaaag gccttgaatg ggtgtccggc atcagctgga atagcggctg gatcgactac     180
gccgacagcg tgaagggcag attcaccatc agccgggaca cagcaagaa cacctgtac      240 ctgcagatga acagcctgag agccgaggac accgccgtgt actactgtgc cagaagcggc     300
tacagcagct cttggtttga ccccgacttc gactattggg ccagggcac actggtcaca     360 gtctcttcag ccagcaccaa gggcccagc gtgttccctc tggcccctag cagcaagagc     420
acatctggcg gaacagccgc cctggctgc ctcgtgaagg actactttcc cgagcccgtg     480
accgtgtcct ggaactctgg cgctctgaca agcggcgtgc acacctttcc agccgtgctg     540
```

-continued

```
cagagcagcg gcctgtactc tctgagcagc gtcgtgacag tgcccagcag ctctctgggc      600
acccagacct acatctgcaa cgtgaaccac aagcccagca acaccaaggt ggacaagaaa      660
gtggaaccca gagctgcgca agacccacc acctgtcccc cttgtcctgc ccccgaactg      720
ctgggaggcc cttccgtgtt cctgttcccc ccaaagccca aggacaccct gatgatcagc      780
cggacccccg aagtgacctg cgtggtggtg gatgtgtccc acgaggaccc tgaagtgaag      840
ttcaattggt acgtggacgg cgtggaagtg cacaacgcca agaccaagcc tagagaggaa      900
cagtacaaca gcacctaccg ggtggtgtcc gtgctgacag tgctgcacca ggactggctg      960
aacggcaaag agtacaagtg caaggtgtcc aacaaggccc tgcctgcccc catcgagaaa     1020
accatcagca aggccaaggg ccagccccgc gaaccccagg tgtacacact gcccccaagc     1080
agggacgagc tgaccaagaa ccaggtgtcc ctgacctgtc tcgtgaaagg cttctacccc     1140
tccgatatcg ccgtggaatg ggagagcaac ggccagcccg agaacaacta caagaccacc     1200 cccctgtgc tggacagcga cggctcattc ttcctgtaca gcaagctgac cgtgacaag      1260 tcccggtggc agcagggcaa cgtgttcagc tgcagcgtga tgcacgaggc cctgcacaac     1320
cactacaccc agaagtccct gagcctgagc cctggcaag                            1359
```

<210> SEQ ID NO 400
<211> LENGTH: 651
<212> TYPE: DNA
<213> ORGANISM: Artificial Sequence
<220> FEATURE:
<223> OTHER INFORMATION: antibody sequence

<400> SEQUENCE: 400

```
cagtctgttc tgacacagcc tccatctgtg tctggcgccc ctggacagag agtgaccatc       60
agctgtacag gcagcagctc cgatattggc gccggatacg acgtgcactg gtatcagcaa      120
ctgcctggca cagcccctaa gctgctgatc tacggcaaca gcaacagacc tagcggcgtg      180
cccgatagat tcagcggctc taagtctggc acaagcgcca gcctggccat tactggactg      240
caggccgaag atgaggccga ctactactgc agcagctacg ctggccccaa tccttacgtg      300
gtgtttggcg gcggaacaaa gctgaccgtt ctaggccagc ctaaagccgc cctagcgtg      360 accctgttcc ctccaagcag cgaggaactg caggccaaca ggccaccct cgtgtgcctg      420 atcagcgact tctatcctgg cgccgtgacc gtggcctgga aggccgatag ctctcctgtg      480
aaggccggcg tggaaaccac caccctagc aagcagagca caacaaata cgccgccagc      540 agctacctga gcctgacccc cgagcagtgg aagtcccaca gatcctacag ctgccaagtg      600
acccacgagg gcagcaccgt ggaaagaca gtggccccta ccgagtgcag c               651
```

<210> SEQ ID NO 401
<211> LENGTH: 123
<212> TYPE: PRT
<213> ORGANISM: Artificial Sequence
<220> FEATURE:
<223> OTHER INFORMATION: antibody sequence

<400> SEQUENCE: 401

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Glu Met Asn Trp Val Arg Gln Ala Pro Gly Lys Gly Leu Glu Trp Val
        35                  40                  45

```
Ser Gly Ile Ser Trp Asn Ser Gly Trp Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser
            115                 120
```

<210> SEQ ID NO 402
<211> LENGTH: 5
<212> TYPE: PRT
<213> ORGANISM: Artificial Sequence
<220> FEATURE:
<223> OTHER INFORMATION: antibody sequence

<400> SEQUENCE: 402

```
Ser Tyr Glu Met Asn
1               5
```

<210> SEQ ID NO 403
<211> LENGTH: 17
<212> TYPE: PRT
<213> ORGANISM: Artificial Sequence
<220> FEATURE:
<223> OTHER INFORMATION: antibody sequence

<400> SEQUENCE: 403

```
Gly Ile Ser Trp Asn Ser Gly Trp Ile Asp Tyr Ala Asp Ser Val Lys
1               5                   10                  15

Gly
```

<210> SEQ ID NO 404
<211> LENGTH: 14
<212> TYPE: PRT
<213> ORGANISM: Artificial Sequence
<220> FEATURE:
<223> OTHER INFORMATION: antibody sequence

<400> SEQUENCE: 404

```
Ser Gly Tyr Ser Ser Ser Trp Phe Asp Pro Asp Phe Asp Tyr
1               5                   10
```

<210> SEQ ID NO 405
<211> LENGTH: 111
<212> TYPE: PRT
<213> ORGANISM: Artificial Sequence
<220> FEATURE:
<223> OTHER INFORMATION: antibody sequence

<400> SEQUENCE: 405

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60
```

```
Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Ala Gly Ile
                 85                  90                  95

Asn Pro Tyr Val Val Phe Gly Gly Gly Thr Lys Leu Thr Val Leu
            100                 105                 110

<210> SEQ ID NO 406
<211> LENGTH: 14
<212> TYPE: PRT
<213> ORGANISM: Artificial Sequence
<220> FEATURE:
<223> OTHER INFORMATION: antibody sequence

<400> SEQUENCE: 406

Thr Gly Ser Ser Ser Asn Ile Gly Ala Gly Tyr Asp Val His
1               5                   10

<210> SEQ ID NO 407
<211> LENGTH: 7
<212> TYPE: PRT
<213> ORGANISM: Artificial Sequence
<220> FEATURE:
<223> OTHER INFORMATION: antibody sequence

<400> SEQUENCE: 407

Gly Asn Ser Asn Arg Pro Ser
1               5

<210> SEQ ID NO 408
<211> LENGTH: 11
<212> TYPE: PRT
<213> ORGANISM: Artificial Sequence
<220> FEATURE:
<223> OTHER INFORMATION: antibody sequence

<400> SEQUENCE: 408

Gln Ser Tyr Ala Gly Ile Asn Pro Tyr Val Val
1               5                   10

<210> SEQ ID NO 409
<211> LENGTH: 369
<212> TYPE: DNA
<213> ORGANISM: Artificial Sequence
<220> FEATURE:
<223> OTHER INFORMATION: antibody sequence

<400> SEQUENCE: 409
gaagttcagc tgctggaatc tgcggcgga ctggttcaac ctggcggatc tctgagactg      60
agctgtgccg ccagcggctt caccttcgat agctacgaga tgaactgggt ccgacaggcc    120
cctggcaaag gccttgaatg ggtgtccggc atcagctgga atagcggctg gatcgactac    180
gccgacagcg tgaagggcag attcaccatc agccgggaca cagcaagaa caccctgtac    240 ctgcagatga cagcctgag agccgaggac accgccgtgt actactgtgc cagaagcggc    300
tacagcagct cttggtttga ccccgacttc gactattggg ccagggcac actggtcaca    360 gtctcttca                                                            369

<210> SEQ ID NO 410
<211> LENGTH: 15
<212> TYPE: DNA
<213> ORGANISM: Artificial Sequence
<220> FEATURE:
<223> OTHER INFORMATION: antibody sequence
```

<400> SEQUENCE: 410
agctacgaga tgaac					15

<210> SEQ ID NO 411
<211> LENGTH: 51
<212> TYPE: DNA
<213> ORGANISM: Artificial Sequence
<220> FEATURE:
<223> OTHER INFORMATION: antibody sequence

<400> SEQUENCE: 411
ggcatcagct ggaatagcgg ctggatcgac tacgccgaca gcgtgaaggg c					51

<210> SEQ ID NO 412
<211> LENGTH: 42
<212> TYPE: DNA
<213> ORGANISM: Artificial Sequence
<220> FEATURE:
<223> OTHER INFORMATION: antibody sequence

<400> SEQUENCE: 412
agcggctaca gcagctcttg gtttgacccc gacttcgact at					42

<210> SEQ ID NO 413
<211> LENGTH: 333
<212> TYPE: DNA
<213> ORGANISM: Artificial Sequence
<220> FEATURE:
<223> OTHER INFORMATION: antibody sequence

<400> SEQUENCE: 413
cagtctgttc tgacacagcc tccatctgtg tctggcgccc ctggacagag agtgaccatc					60
agctgtacag gcagcagctc caatatcgga gccggctatg acgtgcactg gtatcagcag					120
ctgcctggca gcccctaa actgctgatc tacggcaaca gcaacagacc cagcggcgtg					180
cccgatagat tttccggctc taagagcggc acaagcgcca gcctggctat tactggactg					240
caggccgagg acgaggccga ctactactgt cagagctacg ccggcatcaa ccctacgtg					300
gtgtttggcg gaggcaccaa gctgacagtt cta					333

<210> SEQ ID NO 414
<211> LENGTH: 42
<212> TYPE: DNA
<213> ORGANISM: Artificial Sequence
<220> FEATURE:
<223> OTHER INFORMATION: antibody sequence

<400> SEQUENCE: 414
acaggcagca gctccaatat cggagccggc tatgacgtgc ac					42

<210> SEQ ID NO 415
<211> LENGTH: 21
<212> TYPE: DNA
<213> ORGANISM: Artificial Sequence
<220> FEATURE:
<223> OTHER INFORMATION: antibody sequence

<400> SEQUENCE: 415
ggcaacagca acagacccag c					21

<210> SEQ ID NO 416
<211> LENGTH: 33
<212> TYPE: DNA

<213> ORGANISM: Artificial Sequence
<220> FEATURE:
<223> OTHER INFORMATION: antibody sequence

<400> SEQUENCE: 416
cagagctacg ccggcatcaa ccccctacgtg gtg                                    33

<210> SEQ ID NO 417
<211> LENGTH: 453
<212> TYPE: PRT
<213> ORGANISM: Artificial Sequence
<220> FEATURE:
<223> OTHER INFORMATION: antibody sequence

<400> SEQUENCE: 417

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
```

```
                    325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Asp Glu Leu Thr Lys Asn Gln
            355                 360                 365
Val Ser Leu Thr Cys Leu Val Lys Gly Phe Tyr Pro Ser Asp Ile Ala
        370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450

<210> SEQ ID NO 418
<211> LENGTH: 217
<212> TYPE: PRT
<213> ORGANISM: Artificial Sequence
<220> FEATURE:
<223> OTHER INFORMATION: antibody sequence

<400> SEQUENCE: 418

Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Gly Asn Ser Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Ala Gly Ile
                85                  90                  95
Asn Pro Tyr Val Val Phe Gly Gly Gly Thr Lys Leu Thr Val Leu Gly
                100                 105                 110
Gln Pro Lys Ala Ala Pro Ser Val Thr Leu Phe Pro Pro Ser Ser Glu
            115                 120                 125
Glu Leu Gln Ala Asn Lys Ala Thr Leu Val Cys Leu Ile Ser Asp Phe
        130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Cys Ser
    210                 215
```

<210> SEQ ID NO 419
<211> LENGTH: 1359
<212> TYPE: DNA
<213> ORGANISM: Artificial Sequence
<220> FEATURE:
<223> OTHER INFORMATION: antibody sequence

<400> SEQUENCE: 419

```
gaagttcagc tgctggaatc tggcggcgga ctggttcaac ctggcggatc tctgagactg      60
agctgtgccg ccagcggctt caccttcgat agctacgaga tgaactgggt ccgacaggcc     120
cctggcaaag ccttgaatg gtgtccggca atcagctgga atagcggctg gatcgactac     180
gccgacagcg tgaagggcag attcaccatc agccgggaca cagcaagaa cacccctgtac     240
ctgcagatga cagcctgag agccgaggac accgccgtgt actactgtgc cagaagcggc     300
tacagcagct cttggtttga ccccgacttc gactattggg gccagggcac actggtcaca     360
gtctcttcag ccagcaccaa gggcccccagc gtgttccctc tggcccctag cagcaagagc     420
acatctggcg gaacagccgc cctgggctgc ctcgtgaagg actactttcc cgagcccgtg     480
accgtgtcct ggaactctgg cgctctgaca agcggcgtgc acacctttcc agccgtgctg     540
cagagcagcg gcctgtactc tctgagcagc gtcgtgacag tgcccagcag ctctctgggc     600
acccagacct acatctgcaa cgtgaaccac aagcccagca caccaaggt ggacaagaag     660
gtggaaccca gagctgcga caagacccac acctgtcccc cttgtcctgc cccgaactg     720
ctgggaggcc cttccgtgtt cctgttcccc ccaaagccca aggacaccct gatgatcagc     780
cggaccccg aagtgacctg cgtggtggtg gatgtgtccc acgaggaccc tgaagtgaag     840
ttcaattggt acgtggacgg cgtggaagtg cacaacgcca agaccaagcc tagagaggaa     900
cagtacaaca gcacctaccg ggtggtgtcc gtgctgacag tgctgcacca ggactggctg     960
aacggcaaag agtacaagtg caaggtgtcc aacaaggccc tgcctgcccc catcgagaaa    1020
accatcagca aggccaaggg ccagccccgc gaaccccagg tgtacacact gcccccaagc    1080
agggacgagc tgaccaagaa ccaggtgtcc ctgacctgtc tcgtgaaagg cttctacccc    1140
tccgatatcg ccgtggaatg ggagagcaac ggccagcccg agaacaacta caagaccacc    1200
cccctgtgc tggacagcga cggctcattc ttcctgtaca gcaagctgac cgtggacaag    1260
tcccggtggc agcagggcaa cgtgttcagc tgcagcgtga tgcacgaggc cctgcacaac    1320
cactacaccc agaagtccct gagcctgagc cctggcaag                          1359
```

<210> SEQ ID NO 420
<211> LENGTH: 651
<212> TYPE: DNA
<213> ORGANISM: Artificial Sequence
<220> FEATURE:
<223> OTHER INFORMATION: antibody sequence

<400> SEQUENCE: 420

```
cagtctgttc tgacacagcc tccatctgtg tctggcgccc ctggacagag agtgaccatc      60
agctgtacag gcagcagctc caatatcgga gccggctatg acgtgcactg gtatcagcag     120
ctgcctggca gccccctaa actgctgatc tacggcaaca gcaacagacc cagcggcgtg     180
cccgatagat tttccggctc taagagcggc acaagcgcca gcctggctat tactggactg     240
caggccgagg acgaggccga ctactactgt cagagctacg ccggcatcaa ccctacgtg     300
gtgtttggcg gaggcaccaa gctgacagtt ctaggccagc ctaaagccgc ccctagcgtg     360
acccctgttcc ctccaagcag cgaggaactg caggccaaca aggccaccct cgtgtgcctg     420
```

```
atcagcgact tctatcctgg cgccgtgacc gtggcctgga aggccgatag ctctcctgtg    480
aaggccggcg tggaaaccac caccccctagc aagcagagca acaacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c             651
```

```
<210> SEQ ID NO 421
<211> LENGTH: 123
<212> TYPE: PRT
<213> ORGANISM: Artificial Sequence
<220> FEATURE:
<223> OTHER INFORMATION: antibody sequence

<400> SEQUENCE: 421

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser
        115                 120
```

```
<210> SEQ ID NO 422
<211> LENGTH: 5
<212> TYPE: PRT
<213> ORGANISM: Artificial Sequence
<220> FEATURE:
<223> OTHER INFORMATION: antibody sequence

<400> SEQUENCE: 422

Ser Tyr Glu Met Asn
1               5
```

```
<210> SEQ ID NO 423
<211> LENGTH: 17
<212> TYPE: PRT
<213> ORGANISM: Artificial Sequence
<220> FEATURE:
<223> OTHER INFORMATION: antibody sequence

<400> SEQUENCE: 423

Gly Ile Ser Trp Asn Ser Gly Trp Ile Gly Tyr Ala Asp Ser Val Lys
1               5                   10                  15

Gly
```

```
<210> SEQ ID NO 424
<211> LENGTH: 14
<212> TYPE: PRT
<213> ORGANISM: Artificial Sequence
<220> FEATURE:
<223> OTHER INFORMATION: antibody sequence

<400> SEQUENCE: 424
```

Ser Gly Tyr Ser Ser Ser Trp Phe Asp Pro Asp Phe Asp Tyr
1               5                   10

<210> SEQ ID NO 425
<211> LENGTH: 111
<212> TYPE: PRT
<213> ORGANISM: Artificial Sequence
<220> FEATURE:
<223> OTHER INFORMATION: antibody sequence

<400> SEQUENCE: 425

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ala Gly Pro
                85                  90                  95

Asn Pro Tyr Val Val Phe Gly Gly Thr Lys Leu Thr Val Leu
            100                 105                 110

<210> SEQ ID NO 426
<211> LENGTH: 14
<212> TYPE: PRT
<213> ORGANISM: Artificial Sequence
<220> FEATURE:
<223> OTHER INFORMATION: antibody sequence

<400> SEQUENCE: 426

Thr Gly Ser Ser Ser Asn Ile Gly Ala Gly Tyr Asp Val His
1               5                   10

<210> SEQ ID NO 427
<211> LENGTH: 7
<212> TYPE: PRT
<213> ORGANISM: Artificial Sequence
<220> FEATURE:
<223> OTHER INFORMATION: antibody sequence

<400> SEQUENCE: 427

Gly Asn Ser Asn Arg Pro Ser
1               5

<210> SEQ ID NO 428
<211> LENGTH: 11
<212> TYPE: PRT
<213> ORGANISM: Artificial Sequence
<220> FEATURE:
<223> OTHER INFORMATION: antibody sequence

<400> SEQUENCE: 428

Gln Ser Tyr Ala Gly Pro Asn Pro Tyr Val Val
1               5                   10

<210> SEQ ID NO 429
<211> LENGTH: 369
<212> TYPE: DNA
<213> ORGANISM: Artificial Sequence -continued
<220> FEATURE:
<223> OTHER INFORMATION: antibody sequence

<400> SEQUENCE: 429

| gaagttcagc tgctggaatc tggcggcgga ctggttcaac ctggcggatc tctgagactg | 60 |
| agctgtgccg ccagcggctt cgatttcagc agctacgaga tgaactgggt ccgacaggcc | 120 |
| cctggcaaag gccttgaatg ggtgtccggc atcagctgga atagcggctg gatcggctac | 180 |
| gccgatagcg tgaagggcag attcaccatc agcgggaca acagcaagaa cacccctgtac | 240 |
| ctgcagatga acagcctgag agccgaggac accgccgtgt actactgtgc cagaagcggc | 300 |
| tacagcagct cttggtttga ccccgacttc gactattggg gccagggcac actggtcaca | 360 |
| gtctcttca | 369 |

<210> SEQ ID NO 430
<211> LENGTH: 15
<212> TYPE: DNA
<213> ORGANISM: Artificial Sequence
<220> FEATURE:
<223> OTHER INFORMATION: antibody sequence

<400> SEQUENCE: 430

| agctacgaga tgaac | 15 |

<210> SEQ ID NO 431
<211> LENGTH: 51
<212> TYPE: DNA
<213> ORGANISM: Artificial Sequence
<220> FEATURE:
<223> OTHER INFORMATION: antibody sequence

<400> SEQUENCE: 431

| ggcatcagct ggaatagcgg ctggatcggc tacgccgata gcgtgaaggg c | 51 |

<210> SEQ ID NO 432
<211> LENGTH: 42
<212> TYPE: DNA
<213> ORGANISM: Artificial Sequence
<220> FEATURE:
<223> OTHER INFORMATION: antibody sequence

<400> SEQUENCE: 432

| agcggctaca gcagctcttg gtttgacccc gacttcgact at | 42 |

<210> SEQ ID NO 433
<211> LENGTH: 333
<212> TYPE: DNA
<213> ORGANISM: Artificial Sequence
<220> FEATURE:
<223> OTHER INFORMATION: antibody sequence

<400> SEQUENCE: 433

| cagtctgttc tgacacagcc tccatctgtg tctggcgccc ctggacagag agtgaccatc | 60 |
| agctgtacag gcagcagctc caatatcgga gccggctatg acgtgcactg gtatcagcag | 120 |
| ctgcctggca gcccctaa actgctgatc tacggcaaca gcaacagacc cagcggcgtg | 180 |
| cccgatagat tttccggctc taagagcggc acaagcgcca gcctggctat tactggactg | 240 |
| caggccgagg acgaggccga ctactactgt cagtcttacg ctggccccaa tccttacgtg | 300 |
| gtgtttggcg gcggaacaaa gctgaccgtt cta | 333 |

<210> SEQ ID NO 434

```
<211> LENGTH: 42
<212> TYPE: DNA
<213> ORGANISM: Artificial Sequence
<220> FEATURE:
<223> OTHER INFORMATION: antibody sequence

<400> SEQUENCE: 434
acaggcagca gctccaatat cggagccggc tatgacgtgc ac        42

<210> SEQ ID NO 435
<211> LENGTH: 21
<212> TYPE: DNA
<213> ORGANISM: Artificial Sequence
<220> FEATURE:
<223> OTHER INFORMATION: antibody sequence

<400> SEQUENCE: 435
ggcaacagca acagacccag c                                21

<210> SEQ ID NO 436
<211> LENGTH: 33
<212> TYPE: DNA
<213> ORGANISM: Artificial Sequence
<220> FEATURE:
<223> OTHER INFORMATION: antibody sequence

<400> SEQUENCE: 436
cagtcttacg ctggccccaa tccttacgtg gtg                   33

<210> SEQ ID NO 437
<211> LENGTH: 453
<212> TYPE: PRT
<213> ORGANISM: Artificial Sequence
<220> FEATURE:
<223> OTHER INFORMATION: antibody sequence

<400> SEQUENCE: 437
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Trp Phe Asp Pro Asp Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

```
Thr Val Pro Ser Ser Leu Gly Thr Gln Thr Tyr Ile Cys Asn Val
            195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 438
<211> LENGTH: 217
<212> TYPE: PRT
<213> ORGANISM: Artificial Sequence
<220> FEATURE:
<223> OTHER INFORMATION: antibody sequence

<400> SEQUENCE: 438

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ala Gly Pro
                85                  90                  95
```

```
Asn Pro Tyr Val Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
            210                 215

<210> SEQ ID NO 439
<211> LENGTH: 1359
<212> TYPE: DNA
<213> ORGANISM: Artificial Sequence
<220> FEATURE:
<223> OTHER INFORMATION: antibody sequence

<400> SEQUENCE: 439
gaagttcagc tgctggaatc tggcggcgga ctggttcaac tggcggatc tctgagactg      60 agctgtgccg ccagcggctt cgatttcagc agctacgaga tgaactgggt ccgacaggcc    120
cctggcaaag ccttgaatg ggtgtccggc atcagctgga atagcggctg gatcggctac    180
gccgatagcg tgaagggcag attcaccatc agccgggaca cagcaagaa caccctgtac    240 ctgcagatga acagcctgag agccgaggac accgccgtgt actactgtgc cagaagcggc    300
tacagcagct cttggtttga ccccgacttc gactattggg gccagggcac actggtcaca    360
gtctcttcag ccagcaccaa gggccccagc gtgttccctc tggcccctag cagcaagagc    420
acatctggcg gaacagccgc cctgggctgc ctcgtgaagg actactttcc cgagcccgtg    480
accgtgtcct ggaactctgg cgctctgaca agcggcgtgc acaccttttc agccgtgctg    540
cagagcagcg gcctgtactc tctgagcagc gtcgtgacag tgcccagcag ctctctgggc    600
acccagacct acatctgcaa cgtgaaccac aagcccagca caccaaggt ggacaagaag    660 gtggaaccca gagctgcga caagacccac acctgtcccc cttgtcctgc ccccgaactg    720
ctgggaggcc cttccgtgtt cctgttcccc ccaaagccca aggacaccct gatgatcagc    780
cggacccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa   1020
accatcagca aggccaaggg ccagccccgc gaacccagg tgtacacact gcccccaagc   1080
agggacgagc tgaccaagaa ccaggtgtcc ctgacctgtc tcgtgaaagg cttctacccc   1140
tccgatatcg ccgtggaatg ggagagcaac ggccagcccg agaacaacta caagaccacc   1200 cccccctgtgc tggacagcga cggctcattc ttcctgtaca gcaagctgac cgtggacaag   1260
tcccggtggc agcagggcaa cgtgttcagc tgcagcgtga tgcacgaggc cctgcacaac   1320
```
cactacaccc agaagtccct gagcctgagc cctggcaag        1359

<210> SEQ ID NO 440
<211> LENGTH: 651
<212> TYPE: DNA
<213> ORGANISM: Artificial Sequence
<220> FEATURE:
<223> OTHER INFORMATION: antibody sequence

<400> SEQUENCE: 440
cagtctgttc tgacacagcc tccatctgtg tctggcgccc ctggacagag agtgaccatc        60
agctgtacag gcagcagctc caatatcgga gccggctatg acgtgcactg gtatcagcag       120
ctgcctggca gccccctaa actgctgatc tacggcaaca gcaacagacc cagcggcgtg        180
cccgatagat tttccggctc taagagcggc acaagcgcca gcctggctat tactggactg       240
caggccgagg acgaggccga ctactactgt cagtcttacg ctggcccaa tccttacgtg        300
gtgtttggcg gcggaacaaa gctgaccgtt ctaggccagc ctaaagccgc ccctagcgtg       360
accctgttcc ctccaagcag cgaggaactg caggccaaca aggccaccct cgtgtgcctg       420
atcagcgact tctatcctgg cgccgtgacc gtggcctgga aggccgatag ctctcctgtg       480
aaggccggcg tggaaaccac cacccctagc aagcagagca caacaaata cgccgccagc       540
agctacctga gcctgacccc cgagcagtgg aagtcccaca gatcctacag ctgccaagtg       600
acccacgagg cagcaccgt ggaaaagaca gtggccccta ccgagtgcag c                651

<210> SEQ ID NO 441
<211> LENGTH: 123
<212> TYPE: PRT
<213> ORGANISM: Artificial Sequence
<220> FEATURE:
<223> OTHER INFORMATION: antibody sequence

<400> SEQUENCE: 441

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Asp Phe Ser Ser Tyr
            20                  25                  30
Glu Met Asn Trp Val Arg Gln Ala Pro Gly Lys Gly Leu Glu Trp Val
        35                  40                  45
Ser Gly Ile Ser Trp Asn Ser Gly Trp Ile Asp Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Gly Tyr Ser Ser Trp Phe Asp Pro Asp Phe Asp Tyr
            100                 105                 110
Trp Gly Gln Gly Thr Leu Val Thr Val Ser Ser
        115                 120

<210> SEQ ID NO 442
<211> LENGTH: 5
<212> TYPE: PRT
<213> ORGANISM: Artificial Sequence
<220> FEATURE:
<223> OTHER INFORMATION: antibody sequence

<400> SEQUENCE: 442

Ser Tyr Glu Met Asn

<210> SEQ ID NO 443
<211> LENGTH: 17
<212> TYPE: PRT
<213> ORGANISM: Artificial Sequence
<220> FEATURE:
<223> OTHER INFORMATION: antibody sequence

<400> SEQUENCE: 443

Gly Ile Ser Trp Asn Ser Gly Trp Ile Asp Tyr Ala Asp Ser Val Lys
1               5                   10                  15
Gly

<210> SEQ ID NO 444
<211> LENGTH: 14
<212> TYPE: PRT
<213> ORGANISM: Artificial Sequence
<220> FEATURE:
<223> OTHER INFORMATION: antibody sequence

<400> SEQUENCE: 444

Ser Gly Tyr Ser Ser Ser Trp Phe Asp Pro Asp Phe Asp Tyr
1               5                   10

<210> SEQ ID NO 445
<211> LENGTH: 111
<212> TYPE: PRT
<213> ORGANISM: Artificial Sequence
<220> FEATURE:
<223> OTHER INFORMATION: antibody sequence

<400> SEQUENCE: 445

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ala Gly Pro
                85                  90                  95

Asn Pro Tyr Val Val Phe Gly Gly Gly Thr Lys Leu Thr Val Leu
            100                 105                 110

<210> SEQ ID NO 446
<211> LENGTH: 14
<212> TYPE: PRT
<213> ORGANISM: Artificial Sequence
<220> FEATURE:
<223> OTHER INFORMATION: antibody sequence

<400> SEQUENCE: 446

Thr Gly Ser Ser Ser Asn Ile Gly Ala Gly Tyr Asp Val His
1               5                   10

<210> SEQ ID NO 447
<211> LENGTH: 7
<212> TYPE: PRT
<213> ORGANISM: Artificial Sequence
<220> FEATURE:
<223> OTHER INFORMATION: antibody sequence

<400> SEQUENCE: 447

Gly Asn Ser Asn Arg Pro Ser
1               5

<210> SEQ ID NO 448
<211> LENGTH: 11
<212> TYPE: PRT
<213> ORGANISM: Artificial Sequence
<220> FEATURE:
<223> OTHER INFORMATION: antibody sequence

<400> SEQUENCE: 448

Gln Ser Tyr Ala Gly Pro Asn Pro Tyr Val Val
1               5                   10

<210> SEQ ID NO 449
<211> LENGTH: 369
<212> TYPE: DNA
<213> ORGANISM: Artificial Sequence
<220> FEATURE:
<223> OTHER INFORMATION: antibody sequence

<400> SEQUENCE: 449
gaagttcagc tgctggaatc tggcggcgga ctggttcaac ctggcggatc tctgagactg      60
agctgtgccg ccagcggctt cgatttcagc agctacgaga tgaactgggt ccgacaggcc     120
cctggcaaag gccttgaatg gtgtccggc atcagctgga atagcggctg gatcgactac      180
gccgacagcg tgaagggcag attcaccatc agccgggaca cagcaagaa caccctgtac      240 ctgcagatga acagcctgag agccgaggac accgccgtgt actactgtgc cagaagcggc     300
tacagcagct cttggtttga ccccgacttc gactattggg gccagggcac actggtcaca     360
gtctcttca                                                             369

<210> SEQ ID NO 450
<211> LENGTH: 15
<212> TYPE: DNA
<213> ORGANISM: Artificial Sequence
<220> FEATURE:
<223> OTHER INFORMATION: antibody sequence

<400> SEQUENCE: 450
agctacgaga tgaac                                                       15

<210> SEQ ID NO 451
<211> LENGTH: 51
<212> TYPE: DNA
<213> ORGANISM: Artificial Sequence
<220> FEATURE:
<223> OTHER INFORMATION: antibody sequence

<400> SEQUENCE: 451
ggcatcagct ggaatagcgg ctggatcgac tacgccgaca gcgtgaaggg c                51

<210> SEQ ID NO 452
<211> LENGTH: 42
<212> TYPE: DNA
<213> ORGANISM: Artificial Sequence
<220> FEATURE:
<223> OTHER INFORMATION: antibody sequence

<400> SEQUENCE: 452
agcggctaca gcagctcttg gtttgacccc gacttcgact at                              42

<210> SEQ ID NO 453
<211> LENGTH: 333
<212> TYPE: DNA
<213> ORGANISM: Artificial Sequence
<220> FEATURE:
<223> OTHER INFORMATION: antibody sequence

<400> SEQUENCE: 453
cagtctgttc tgacacagcc tccatctgtg tctggcgccc ctggacagag agtgaccatc      60
agctgtacag gcagcagctc caatatcgga gccggctatg acgtgcactg gtatcagcag     120
ctgcctggca gcccctaa actgctgatc tacggcaaca gcaacagacc cagcggcgtg      180
cccgatagat ttccggctc taagagcggc acaagcgcca gcctggctat tactggactg     240
caggccgagg acgaggccga ctactactgt cagtcttacg ctggccccaa tccttacgtg     300
gtgtttggcg gcggaacaaa gctgaccgtt cta                                  333

<210> SEQ ID NO 454
<211> LENGTH: 42
<212> TYPE: DNA
<213> ORGANISM: Artificial Sequence
<220> FEATURE:
<223> OTHER INFORMATION: antibody sequence

<400> SEQUENCE: 454
acaggcagca gctccaatat cggagccggc tatgacgtgc ac                              42

<210> SEQ ID NO 455
<211> LENGTH: 21
<212> TYPE: DNA
<213> ORGANISM: Artificial Sequence
<220> FEATURE:
<223> OTHER INFORMATION: antibody sequence

<400> SEQUENCE: 455
ggcaacagca acagacccag c                                                    21

<210> SEQ ID NO 456
<211> LENGTH: 33
<212> TYPE: DNA
<213> ORGANISM: Artificial Sequence
<220> FEATURE:
<223> OTHER INFORMATION: antibody sequence

<400> SEQUENCE: 456
cagtcttacg ctggccccaa tccttacgtg gtg                                       33

<210> SEQ ID NO 457
<211> LENGTH: 453
<212> TYPE: PRT
<213> ORGANISM: Artificial Sequence
<220> FEATURE:
<223> OTHER INFORMATION: antibody sequence

<400> SEQUENCE: 457

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Ser Ser Trp Phe Asp Pro Asp Phe Asp Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
450

<210> SEQ ID NO 458
<211> LENGTH: 217
<212> TYPE: PRT
<213> ORGANISM: Artificial Sequence
<220> FEATURE:
<223> OTHER INFORMATION: antibody sequence

<400> SEQUENCE: 458

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ala Gly Pro
                85                  90                  95

Asn Pro Tyr Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 459
<211> LENGTH: 1359
<212> TYPE: DNA
<213> ORGANISM: Artificial Sequence
<220> FEATURE:
<223> OTHER INFORMATION: antibody sequence

<400> SEQUENCE: 459

```
gaagttcagc tgctggaatc tggcggcgga ctggttcaac tggcggatc tctgagactg      60 agctgtgccg ccagcggctt cgatttcagc agctacgaga tgaactgggt ccgacaggcc    120
cctggcaaag gccttgaatg ggtgtccggc atcagctgga atagcggctg gatcgactac    180
gccgacagcg tgaagggcag attcaccatc agccgggaca acagcaagaa caccctgtac    240
ctgcagatga acagcctgag agccgaggac accgccgtgt actactgtgc cagaagcggc    300
tacagcagct cttggtttga ccccgacttc gactattggg gccagggcac actggtcaca    360
gtctcttcag ccagcaccaa gggcccage gtgttccctc tggcccctag cagcaagagc    420
acatctggcg gaacagccgc cctgggctgc ctcgtgaagg actactttcc cgagcccgtg    480
accgtgtcct ggaactctgg cgctctgaca agcggcgtgc acacctttcc agccgtgctg    540
```

-continued

```
cagagcagcg gcctgtactc tctgagcagc gtcgtgacag tgcccagcag ctctctgggc    600
acccagacct acatctgcaa cgtgaaccac aagcccagca acaccaaggt ggacaagaag    660
gtggaaccca agagctgcga caagacccac acctgtcccc cttgtcctgc ccccgaactg    720
ctgggaggcc cttccgtgtt cctgttcccc ccaaagccca aggacaccct gatgatcagc    780
cggacccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa   1020
accatcagca aggccaaggg ccagccccgc gaacccccagg tgtacacact gccccccaagc   1080 agggacgagc tgaccaagaa ccaggtgtcc ctgacctgtc tcgtgaaagg cttctacccc   1140
tccgatatcg ccgtggaatg ggagagcaac ggccagcccg agaacaacta caagaccacc   1200 cccctgtgc tggacagcga cggctcattc ttcctgtaca gcaagctgac cgtggacaag   1260 tccggtggc agcagggcaa cgtgttcagc tgcagcgtga tgcacgaggc cctgcacaac   1320
cactacaccc agaagtccct gagcctgagc cctggcaag                          1359
```

<210> SEQ ID NO 460
<211> LENGTH: 651
<212> TYPE: DNA
<213> ORGANISM: Artificial Sequence
<220> FEATURE:
<223> OTHER INFORMATION: antibody sequence

<400> SEQUENCE: 460

```
cagtctgttc tgacacagcc tccatctgtg tctggcgccc ctggacagag agtgaccatc     60
agctgtacag gcagcagctc caatatcgga gccggctatg acgtgcactg gtatcagcag    120
ctgcctggca cagcccctaa actgctgatc tacggcaaca gcaacagacc cagcggcgtg    180
cccgatagat tttccggctc taagagcggc acaagcgcca gcctggctat tactggactg    240
caggccgagg acgaggccga ctactactgt cagtcttacg ctggccccaa tccttacgtg    300
gtgtttggcg gcggaacaaa gctgaccgtt ctaggccagc ctaaagccgc ccctagcgtg    360
accctgttcc ctccaagcag cgaggaactg caggccaaca aggccaccct cgtgtgcctg    420
atcagcgact ctatcctgg cgccgtgacc gtggcctgga aggccgatag ctctcctgtg    480
aaggccggcg tggaaaccac caccccctagc aagcagagca acaacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c             651
```

<210> SEQ ID NO 461
<211> LENGTH: 123
<212> TYPE: PRT
<213> ORGANISM: Artificial Sequence
<220> FEATURE:
<223> OTHER INFORMATION: antibody sequence

<400> SEQUENCE: 461

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Glu Met Asn Trp Val Arg Gln Ala Pro Gly Lys Gly Leu Glu Trp Val
        35                  40                  45
```

-continued

```
Ser Gly Ile Ser Trp Asn Ser Gly Trp Ile Asp Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser
        115                 120
```

<210> SEQ ID NO 462
<211> LENGTH: 5
<212> TYPE: PRT
<213> ORGANISM: Artificial Sequence
<220> FEATURE:
<223> OTHER INFORMATION: antibody sequence

<400> SEQUENCE: 462

```
Ser Tyr Glu Met Asn
 1               5
```

<210> SEQ ID NO 463
<211> LENGTH: 17
<212> TYPE: PRT
<213> ORGANISM: Artificial Sequence
<220> FEATURE:
<223> OTHER INFORMATION: antibody sequence

<400> SEQUENCE: 463

```
Gly Ile Ser Trp Asn Ser Gly Trp Ile Asp Tyr Ala Asp Ser Val Lys
 1               5                  10                  15

Gly
```

<210> SEQ ID NO 464
<211> LENGTH: 14
<212> TYPE: PRT
<213> ORGANISM: Artificial Sequence
<220> FEATURE:
<223> OTHER INFORMATION: antibody sequence

<400> SEQUENCE: 464

```
Ser Gly Tyr Ser Ser Ser Trp Phe Asp Pro Asp Phe Asp Tyr
 1               5                  10
```

<210> SEQ ID NO 465
<211> LENGTH: 111
<212> TYPE: PRT
<213> ORGANISM: Artificial Sequence
<220> FEATURE:
<223> OTHER INFORMATION: antibody sequence

<400> SEQUENCE: 465

```
Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
             20                  25                  30

Tyr Asp Val His Trp Tyr Gln Gln Leu Pro Gly Thr Ala Pro Lys Leu
         35                  40                  45

Leu Ile Tyr Gly Asn Ser Asn Arg Pro Ser Gly Val Pro Asp Arg Phe
     50                  55                  60

Ser Gly Ser Lys Ser Gly Thr Ser Ala Ser Leu Ala Ile Thr Gly Leu
```

```
                  65                  70                  75                  80
Gln Ala Glu Asp Glu Ala Asp Tyr Tyr Cys Gln Ser Tyr Ala Gly Pro
                      85                  90                  95

Asn Pro Tyr Val Val Phe Gly Gly Gly Thr Lys Leu Thr Val Leu
                100                 105                 110
```

<210> SEQ ID NO 466
<211> LENGTH: 14
<212> TYPE: PRT
<213> ORGANISM: Artificial Sequence
<220> FEATURE:
<223> OTHER INFORMATION: antibody sequence

<400> SEQUENCE: 466

```
Thr Gly Ser Ser Ser Asn Ile Gly Ala Gly Tyr Asp Val His
1               5                   10
```

<210> SEQ ID NO 467
<211> LENGTH: 7
<212> TYPE: PRT
<213> ORGANISM: Artificial Sequence
<220> FEATURE:
<223> OTHER INFORMATION: antibody sequence

<400> SEQUENCE: 467

```
Gly Asn Ser Asn Arg Pro Ser
1               5
```

<210> SEQ ID NO 468
<211> LENGTH: 11
<212> TYPE: PRT
<213> ORGANISM: Artificial Sequence
<220> FEATURE:
<223> OTHER INFORMATION: antibody sequence

<400> SEQUENCE: 468

```
Gln Ser Tyr Ala Gly Pro Asn Pro Tyr Val Val
1               5                   10
```

<210> SEQ ID NO 469
<211> LENGTH: 369
<212> TYPE: DNA
<213> ORGANISM: Artificial Sequence
<220> FEATURE:
<223> OTHER INFORMATION: antibody sequence

<400> SEQUENCE: 469

| | | | | | |
|---|---|---|---|---|---|
| gaagttcagc | tgctggaatc | tggcggcgga | ctggttcaac | tggcggatc | tctgagactg | 60 |
| agctgtgccg | ccagcggctt | caccttcgat | agctacgaga | tgaactgggt | ccgacaggcc | 120 |
| cctggcaaag | gccttgaatg | ggtgtccggc | atcagctgga | atagcggctg | gatcgactac | 180 |
| gccgacagcg | tgaagggcag | attcaccatc | agccgggaca | acagcaagaa | caccctgtac | 240 |
| ctgcagatga | acagcctgag | agccgaggac | accgccgtgt | actactgtgc | cagaagcggc | 300 |
| tacagcagct | cttggtttga | ccccgacttc | gactattggg | gccagggcac | actggtcaca | 360 |
| gtctcttca | | | | | | 369 |

<210> SEQ ID NO 470
<211> LENGTH: 15
<212> TYPE: DNA
<213> ORGANISM: Artificial Sequence
<220> FEATURE:
<223> OTHER INFORMATION: antibody sequence

```
<400> SEQUENCE: 470
agctacgaga tgaac                                                        15

<210> SEQ ID NO 471
<211> LENGTH: 51
<212> TYPE: DNA
<213> ORGANISM: Artificial Sequence
<220> FEATURE:
<223> OTHER INFORMATION: antibody sequence

<400> SEQUENCE: 471
ggcatcagct ggaatagcgg ctggatcgac tacgccgaca gcgtgaaggg c                51

<210> SEQ ID NO 472
<211> LENGTH: 42
<212> TYPE: DNA
<213> ORGANISM: Artificial Sequence
<220> FEATURE:
<223> OTHER INFORMATION: antibody sequence

<400> SEQUENCE: 472
agcggctaca gcagctcttg gtttgacccc gacttcgact at                          42

<210> SEQ ID NO 473
<211> LENGTH: 333
<212> TYPE: DNA
<213> ORGANISM: Artificial Sequence
<220> FEATURE:
<223> OTHER INFORMATION: antibody sequence

<400> SEQUENCE: 473
cagtctgttc tgacacagcc tccatctgtg tctggcgccc ctggacagag agtgaccatc       60
agctgtacag gcagcagctc caatatcgga gccggctatg acgtgcactg gtatcagcag      120
ctgcctggca gcccctaa actgctgatc tacggcaaca gcaacagacc cagcggcgtg       180
cccgatagat tttccggctc taagagcggc acaagcgcca gctggctat tactggactg      240 caggccgagg acgaggccga ctactactgt cagtcttacg ctggccccaa tccttacgtg      300
gtgtttggcg gcggaacaaa gctgaccgtt cta                                  333

<210> SEQ ID NO 474
<211> LENGTH: 42
<212> TYPE: DNA
<213> ORGANISM: Artificial Sequence
<220> FEATURE:
<223> OTHER INFORMATION: antibody sequence

<400> SEQUENCE: 474
acaggcagca gctccaatat cggagccggc tatgacgtgc ac                          42

<210> SEQ ID NO 475
<211> LENGTH: 21
<212> TYPE: DNA
<213> ORGANISM: Artificial Sequence
<220> FEATURE:
<223> OTHER INFORMATION: antibody sequence

<400> SEQUENCE: 475
ggcaacagca acagacccag c                                                21

<210> SEQ ID NO 476
<211> LENGTH: 33
<212> TYPE: DNA
<213> ORGANISM: Artificial Sequence
```

```
<220> FEATURE:
<223> OTHER INFORMATION: antibody sequence

<400> SEQUENCE: 476
cagtcttacg ctggccccaa tccttacgtg gtg                                    33

<210> SEQ ID NO 477
<211> LENGTH: 453
<212> TYPE: PRT
<213> ORGANISM: Artificial Sequence
<220> FEATURE:
<223> OTHER INFORMATION: antibody sequence

<400> SEQUENCE: 477
```

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Asp | Ser | Tyr |
| | | | 20 | | | | | 25 | | | | | 30 | | |
| Glu | Met | Asn | Trp | Val | Arg | Gln | Ala | Pro | Gly | Lys | Gly | Leu | Glu | Trp | Val |
| | | | 35 | | | | | 40 | | | | | 45 | | |
| Ser | Gly | Ile | Ser | Trp | Asn | Ser | Gly | Trp | Ile | Asp | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Ser | Gly | Tyr | Ser | Ser | Ser | Trp | Phe | Asp | Pro | Asp | Phe | Asp | Tyr |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | | 115 | | | | | 120 | | | | | 125 | | |
| Pro | Ser | Val | Phe | Pro | Leu | Ala | Pro | Ser | Ser | Lys | Ser | Thr | Ser | Gly | Gly |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | | 195 | | | | | 200 | | | | | 205 | | |
| Asn | His | Lys | Pro | Ser | Asn | Thr | Lys | Val | Asp | Lys | Lys | Val | Glu | Pro | Lys |
| | 210 | | | | | 215 | | | | | 220 | | | | |
| Ser | Cys | Asp | Lys | Thr | His | Thr | Cys | Pro | Pro | Cys | Pro | Ala | Pro | Glu | Leu |
| 225 | | | | | 230 | | | | | 235 | | | | | 240 |
| Leu | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | | 275 | | | | | 280 | | | | | 285 | | |
| Glu | Val | His | Asn | Ala | Lys | Thr | Lys | Pro | Arg | Glu | Glu | Gln | Tyr | Asn | Ser |
| | 290 | | | | | 295 | | | | | 300 | | | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Pro | Ala |
| | | | | 325 | | | | | 330 | | | | | 335 | |

```
Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 478
<211> LENGTH: 217
<212> TYPE: PRT
<213> ORGANISM: Artificial Sequence
<220> FEATURE:
<223> OTHER INFORMATION: antibody sequence

<400> SEQUENCE: 478

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ala Gly Pro
                85                  90                  95

Asn Pro Tyr Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
        130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
210                 215

<210> SEQ ID NO 479
```

<211> LENGTH: 1359
<212> TYPE: DNA
<213> ORGANISM: Artificial Sequence
<220> FEATURE:
<223> OTHER INFORMATION: antibody sequence

<400> SEQUENCE: 479

| | | | | | |
|---|---|---|---|---|---|
| gaagttcagc | tgctggaatc | tggcggcgga | ctggttcaac | ctggcggatc | tctgagactg | 60 |
| agctgtgccg | ccagcggctt | caccttcgat | agctacgaga | tgaactgggt | ccgacaggcc | 120 |
| cctggcaaag | gccttgaatg | ggtgtccggc | atcagctgga | atagcggctg | gatcgactac | 180 |
| gccgacagcg | tgaagggcag | attcaccatc | agccgggaca | cagcaagaa | caccctgtac | 240 |
| ctgcagatga | acagcctgag | agccgaggac | accgccgtgt | actactgtgc | cagaagcggc | 300 |
| tacagcagct | cttggtttga | ccccgacttc | gactattggg | ccagggcac | actggtcaca | 360 |
| gtctcttcag | ccagcaccaa | gggcccagc | gtgttccctc | tggcccctag | cagcaagagc | 420 |
| acatctggcg | gaacagccgc | cctgggctgc | ctcgtgaagg | actactttcc | cgagcccgtg | 480 |
| accgtgtcct | ggaactctgg | cgctctgaca | agcggcgtgc | acacctttcc | agccgtgctg | 540 |
| cagagcagcg | gcctgtactc | tctgagcagc | gtcgtgacag | tgcccagcag | ctctctgggc | 600 |
| acccagacct | acatctgcaa | cgtgaaccac | aagcccagca | caccaaggt | ggacaagaag | 660 |
| gtggaaccca | gagctgcga | caagacccac | acctgtcccc | cttgtcctgc | cccgaactg | 720 |
| ctgggaggcc | cttccgtgtt | cctgttcccc | ccaaagccca | aggacaccct | gatgatcagc | 780 |
| cggacccccg | aagtgacctg | cgtggtggtg | gatgtgtccc | acgaggaccc | tgaagtgaag | 840 |
| ttcaattggt | acgtggacgg | cgtggaagtg | cacaacgcca | agaccaagcc | tagagaggaa | 900 |
| cagtacaaca | gcacctaccg | ggtggtgtcc | gtgctgacag | tgctgcacca | ggactggctg | 960 |
| aacggcaaag | agtacaagtg | caaggtgtcc | aacaaggccc | tgcctgcccc | catcgagaaa | 1020 |
| accatcagca | aggccaaggg | ccagccccgc | gaaccccagg | tgtacacact | gcccccaagc | 1080 |
| agggacgagc | tgaccaagaa | ccaggtgtcc | ctgacctgtc | tcgtgaaagg | cttctacccc | 1140 |
| tccgatatcg | ccgtggaatg | ggagagcaac | ggccagcccg | agaacaacta | caagaccacc | 1200 |
| cccctgtgc | tggacagcga | cggctcattc | ttcctgtaca | gcaagctgac | cgtggacaag | 1260 |
| tcccggtggc | agcagggcaa | cgtgttcagc | tgcagcgtga | tgcacgaggc | cctgcacaac | 1320 |
| cactacaccc | agaagtccct | gagcctgagc | cctggcaag | | | 1359 |

<210> SEQ ID NO 480
<211> LENGTH: 651
<212> TYPE: DNA
<213> ORGANISM: Artificial Sequence
<220> FEATURE:
<223> OTHER INFORMATION: antibody sequence

<400> SEQUENCE: 480

| | | | | | |
|---|---|---|---|---|---|
| cagtctgttc | tgacacagcc | tccatctgtg | tctggcgccc | ctggacagag | agtgaccatc | 60 |
| agctgtacag | gcagcagctc | caatatcgga | gccggctatg | acgtgcactg | gtatcagcag | 120 |
| ctgcctggca | gccccctaa | actgctgatc | tacggcaaca | gcaacagacc | cagcggcgtg | 180 |
| cccgatagat | tttccggctc | taagagcggc | acaagcgcca | gcctggctat | tactggactg | 240 |
| caggccgagg | acgaggccga | ctactactgt | cagtcttacg | ctggccccaa | tccttacgtg | 300 |
| gtgtttggcg | gcggaacaaa | gctgaccgtt | ctaggccagc | ctaaagccgc | ccctagcgtg | 360 |
| accctgttcc | ctccaagcag | cgaggaactg | caggccaaca | aggccaccct | cgtgtgcctg | 420 |
| atcagcgact | tctatcctgg | cgccgtgacc | gtggcctgga | aggccgatag | ctctcctgtg | 480 |

```
aaggccggcg tggaaaccac caccccctagc aagcagagca acaacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c             651
```

```
<210> SEQ ID NO 481
<211> LENGTH: 123
<212> TYPE: PRT
<213> ORGANISM: Artificial Sequence
<220> FEATURE:
<223> OTHER INFORMATION: antibody sequence

<400> SEQUENCE: 481

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asp Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser
        115                 120
```

```
<210> SEQ ID NO 482
<211> LENGTH: 5
<212> TYPE: PRT
<213> ORGANISM: Artificial Sequence
<220> FEATURE:
<223> OTHER INFORMATION: antibody sequence

<400> SEQUENCE: 482

Ser Tyr Glu Met Asn
1               5
```

```
<210> SEQ ID NO 483
<211> LENGTH: 17
<212> TYPE: PRT
<213> ORGANISM: Artificial Sequence
<220> FEATURE:
<223> OTHER INFORMATION: antibody sequence

<400> SEQUENCE: 483

Gly Ile Ser Trp Asn Ser Gly Trp Ile Asp Tyr Ala Asp Ser Val Lys
1               5                   10                  15

Gly
```

```
<210> SEQ ID NO 484
<211> LENGTH: 14
<212> TYPE: PRT
<213> ORGANISM: Artificial Sequence
<220> FEATURE:
<223> OTHER INFORMATION: antibody sequence

<400> SEQUENCE: 484
```

```
Ser Gly Tyr Ser Ser Ser Trp Phe Asp Pro Asp Phe Asp Tyr
1               5                   10
```

<210> SEQ ID NO 485
<211> LENGTH: 111
<212> TYPE: PRT
<213> ORGANISM: Artificial Sequence
<220> FEATURE:
<223> OTHER INFORMATION: antibody sequence

<400> SEQUENCE: 485

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ala Gly Pro
                85                  90                  95

Asn Pro Tyr Val Val Phe Gly Gly Gly Thr Lys Leu Thr Val Leu
            100                 105                 110
```

<210> SEQ ID NO 486
<211> LENGTH: 14
<212> TYPE: PRT
<213> ORGANISM: Artificial Sequence
<220> FEATURE:
<223> OTHER INFORMATION: antibody sequence

<400> SEQUENCE: 486

```
Thr Gly Ser Ser Ser Asn Ile Gly Ala Gly Tyr Asp Val His
1               5                   10
```

<210> SEQ ID NO 487
<211> LENGTH: 7
<212> TYPE: PRT
<213> ORGANISM: Artificial Sequence
<220> FEATURE:
<223> OTHER INFORMATION: antibody sequence

<400> SEQUENCE: 487

```
Gly Asn Ser Asn Arg Pro Ser
1               5
```

<210> SEQ ID NO 488
<211> LENGTH: 11
<212> TYPE: PRT
<213> ORGANISM: Artificial Sequence
<220> FEATURE:
<223> OTHER INFORMATION: antibody sequence

<400> SEQUENCE: 488

```
Gln Ser Tyr Ala Gly Pro Asn Pro Tyr Val Val
1               5                   10
```

<210> SEQ ID NO 489
<211> LENGTH: 369
<212> TYPE: DNA
<213> ORGANISM: Artificial Sequence
<220> FEATURE:

<223> OTHER INFORMATION: antibody sequence

<400> SEQUENCE: 489

```
gaagttcagc tgctggaatc tggcggcgga ctggttcaac ctggcggatc tctgagactg     60
agctgtgccg ccagcggctt cgacttcgat agctacgaga tgaactgggt ccgacaggcc    120
cctggcaaag gccttgaatg ggtgtccggc atcagctgga atagcggctg gatcgactac    180
gccgacagcg tgaagggcag attcaccatc agcggggaca acagcaagaa caccctgtac    240
ctgcagatga acagcctgag agccgaggac accgccgtgt actactgtgc cagaagcggc    300
tacagcagct cttggtttga ccccgacttc gactattggg gccagggcac actggtcaca    360
gtctcttca                                                            369
```

<210> SEQ ID NO 490
<211> LENGTH: 15
<212> TYPE: DNA
<213> ORGANISM: Artificial Sequence
<220> FEATURE:
<223> OTHER INFORMATION: antibody sequence

<400> SEQUENCE: 490

```
agctacgaga tgaac                                                      15
```

<210> SEQ ID NO 491
<211> LENGTH: 51
<212> TYPE: DNA
<213> ORGANISM: Artificial Sequence
<220> FEATURE:
<223> OTHER INFORMATION: antibody sequence

<400> SEQUENCE: 491

```
ggcatcagct ggaatagcgg ctggatcgac tacgccgaca gcgtgaaggg c              51
```

<210> SEQ ID NO 492
<211> LENGTH: 42
<212> TYPE: DNA
<213> ORGANISM: Artificial Sequence
<220> FEATURE:
<223> OTHER INFORMATION: antibody sequence

<400> SEQUENCE: 492

```
agcggctaca gcagctcttg gtttgacccc gacttcgact at                        42
```

<210> SEQ ID NO 493
<211> LENGTH: 333
<212> TYPE: DNA
<213> ORGANISM: Artificial Sequence
<220> FEATURE:
<223> OTHER INFORMATION: antibody sequence

<400> SEQUENCE: 493

```
cagtctgttc tgacacagcc tccatctgtg tctggcgccc ctggacagag agtgaccatc     60
agctgtacag gcagcagctc caatatcgga gccggctatg acgtgcactg gtatcagcag    120
ctgcctggca gcccctaa actgctgatc tacggcaaca gcaacagacc cagcggcgtg      180
cccgatagat tttccggctc taagagcggc acaagcgcca gcctggctat tactggactg    240
caggccgagg acgaggccga ctactactgt cagtcttacg ctggccccaa tccttacgtg    300
gtgtttggcg gcggaacaaa gctgaccgtt cta                                 333
```

<210> SEQ ID NO 494
<211> LENGTH: 42

```
<212> TYPE: DNA
<213> ORGANISM: Artificial Sequence
<220> FEATURE:
<223> OTHER INFORMATION: antibody sequence

<400> SEQUENCE: 494
acaggcagca gctccaatat cggagccggc tatgacgtgc ac            42

<210> SEQ ID NO 495
<211> LENGTH: 21
<212> TYPE: DNA
<213> ORGANISM: Artificial Sequence
<220> FEATURE:
<223> OTHER INFORMATION: antibody sequence

<400> SEQUENCE: 495
ggcaacagca acagacccag c                                   21

<210> SEQ ID NO 496
<211> LENGTH: 33
<212> TYPE: DNA
<213> ORGANISM: Artificial Sequence
<220> FEATURE:
<223> OTHER INFORMATION: antibody sequence

<400> SEQUENCE: 496
cagtcttacg ctggccccaa tccttacgtg gtg                      33

<210> SEQ ID NO 497
<211> LENGTH: 453
<212> TYPE: PRT
<213> ORGANISM: Artificial Sequence
<220> FEATURE:
<223> OTHER INFORMATION: antibody sequence

<400> SEQUENCE: 497
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asp Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

-continued

Thr Val Pro Ser Ser Ser Leu Gly Thr Gln Thr Tyr Ile Cys Asn Val
            195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 498
<211> LENGTH: 217
<212> TYPE: PRT
<213> ORGANISM: Artificial Sequence
<220> FEATURE:
<223> OTHER INFORMATION: antibody sequence

<400> SEQUENCE: 498

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ala Gly Pro
                85                  90                  95

```
Asn Pro Tyr Val Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
        210                 215
```

<210> SEQ ID NO 499
<211> LENGTH: 1359
<212> TYPE: DNA
<213> ORGANISM: Artificial Sequence
<220> FEATURE:
<223> OTHER INFORMATION: antibody sequence

<400> SEQUENCE: 499

```
gaagttcagc tgctggaatc tggcggcgga ctggttcaac tggcggatc tctgagactg      60
agctgtgccg ccagcggctt cgacttcgat agctacgaga tgaactgggt ccgacaggcc    120
cctggcaaag gccttgaatg ggtgtccggc atcagctgga atagcggctg gatcgactac    180
gccgacagcg tgaagggcag attcaccatc agccgggaca cagcaagaa caccctgtac    240
ctgcagatga acagcctgag agccgaggac accgccgtgt actactgtgc cagaagcggc    300
tacagcagct cttggtttga ccccgacttc gactattggg gccagggcac actggtcaca    360
gtctcttcag ccagcaccaa gggccccagc gtgttccctc tggcccctag cagcaagagc    420
acatctggcg gaacagccgc cctgggctgc ctcgtgaagg actactttcc gagcccgtg    480
accgtgtcct ggaactctgg cgctctgaca gcggcgtgc acacctttcc agccgtgctg    540
cagagcagcg gcctgtactc tctgagcagc gtcgtgacag tgcccagcag ctctctgggc    600
acccagacct acatctgcaa cgtgaaccac aagcccagca caccaaggt ggacaagaag    660
gtggaaccca gagctgcga caagacccac acctgtcccc cttgtcctgc cccgaactg    720
ctgggaggcc cttccgtgtt cctgttcccc ccaaagccca aggacaccct gatgatcagc    780
cggacccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa   1020
accatcagca aggccaaggg ccagccccgc gaacccagg tgtacacact gccccaagc    1080
agggacgagc tgaccaagaa ccaggtgtcc ctgacctgtc tcgtgaaagg cttctacccc   1140
tccgatatcg ccgtggaatg ggagagcaac ggccagcccg agaacaacta caagaccacc   1200
ccccctgtgc tggacagcga cggctcattc ttcctgtaca gcaagctgac cgtggacaag   1260
tcccggtggc agcagggcaa cgtgttcagc tgcagcgtga tgcacgaggc cctgcacaac   1320
cactacaccc agaagtccct gagcctgagc cctggcaag                          1359
```

<210> SEQ ID NO 500
<211> LENGTH: 651
<212> TYPE: DNA
<213> ORGANISM: Artificial Sequence
<220> FEATURE:
<223> OTHER INFORMATION: antibody sequence

<400> SEQUENCE: 500

```
cagtctgttc tgacacagcc tccatctgtg tctggcgccc ctggacagag agtgaccatc      60
agctgtacag gcagcagctc caatatcgga gccggctatg acgtgcactg gtatcagcag     120
ctgcctggca gccccctaaa ctgctgatc tacggcaaca gcaacagacc cagcggcgtg     180
cccgatagat tttccggctc taagagcggc acaagcgcca gcctggctat tactggactg     240
caggccgagg acgaggccga ctactactgt cagtcttacg ctggccccaa tccttacgtg     300
gtgtttggcg gcggaacaaa gctgaccgtt ctaggccagc ctaaagccgc ccctagcgtg     360
accctgttcc ctccaagcag cgaggaactg caggccaaca aggccaccct cgtgtgcctg     420
atcagcgact tctatcctgg cgccgtgacc gtggcctgga aggccgatag ctctcctgtg     480
aaggccggcg tggaaaccac cacccctagc aagcagagca caacaaata cgccgccagc     540
agctacctga gcctgacccc cgagcagtgg aagtcccaca gatcctacag ctgccaagtg     600
acccacgagg gcagcaccgt ggaaaagaca gtggccccta ccgagtgcag c              651
```

<210> SEQ ID NO 501
<211> LENGTH: 123
<212> TYPE: PRT
<213> ORGANISM: Artificial Sequence
<220> FEATURE:
<223> OTHER INFORMATION: antibody sequence

<400> SEQUENCE: 501

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser
        115                 120
```

<210> SEQ ID NO 502
<211> LENGTH: 5
<212> TYPE: PRT
<213> ORGANISM: Artificial Sequence
<220> FEATURE:
<223> OTHER INFORMATION: antibody sequence

<400> SEQUENCE: 502

```
Ser Tyr Glu Met Asn
1               5
```

```
<210> SEQ ID NO 503
<211> LENGTH: 17
<212> TYPE: PRT
<213> ORGANISM: Artificial Sequence
<220> FEATURE:
<223> OTHER INFORMATION: antibody sequence

<400> SEQUENCE: 503

Gly Ile Ser Trp Asn Ser Gly Trp Ile Asp Tyr Ala Asp Ser Val Lys
1               5                   10                  15

Gly

<210> SEQ ID NO 504
<211> LENGTH: 14
<212> TYPE: PRT
<213> ORGANISM: Artificial Sequence
<220> FEATURE:
<223> OTHER INFORMATION: antibody sequence

<400> SEQUENCE: 504

Ser Gly Tyr Ser Ser Ser Trp Phe Asp Pro Asp Phe Asp Tyr
1               5                   10

<210> SEQ ID NO 505
<211> LENGTH: 111
<212> TYPE: PRT
<213> ORGANISM: Artificial Sequence
<220> FEATURE:
<223> OTHER INFORMATION: antibody sequence

<400> SEQUENCE: 505

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asp Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ala Gly Ile
                85                  90                  95

Asn Pro Tyr Val Val Phe Gly Gly Thr Lys Leu Thr Val Leu
            100                 105                 110

<210> SEQ ID NO 506
<211> LENGTH: 14
<212> TYPE: PRT
<213> ORGANISM: Artificial Sequence
<220> FEATURE:
<223> OTHER INFORMATION: antibody sequence

<400> SEQUENCE: 506

Thr Gly Ser Ser Ser Asp Ile Gly Ala Gly Tyr Asp Val His
1               5                   10

<210> SEQ ID NO 507
<211> LENGTH: 7
<212> TYPE: PRT
<213> ORGANISM: Artificial Sequence
<220> FEATURE:
```

<223> OTHER INFORMATION: antibody sequence

<400> SEQUENCE: 507

Gly Asn Ser Asn Arg Pro Ser
1               5

<210> SEQ ID NO 508
<211> LENGTH: 11
<212> TYPE: PRT
<213> ORGANISM: Artificial Sequence
<220> FEATURE:
<223> OTHER INFORMATION: antibody sequence

<400> SEQUENCE: 508

Gln Ser Tyr Ala Gly Ile Asn Pro Tyr Val Val
1               5                   10

<210> SEQ ID NO 509
<211> LENGTH: 369
<212> TYPE: DNA
<213> ORGANISM: Artificial Sequence
<220> FEATURE:
<223> OTHER INFORMATION: antibody sequence

<400> SEQUENCE: 509

```
gaagttcagc tgctggaatc tggcggcgga ctggttcaac ctggcggatc tctgagactg      60
agctgtgccg ccagcggctt caccttcgat agctacgaga tgaactgggt ccgacaggcc     120
cctggcaaag ccttgaatg gtgtccggca tcagctgga atagcggctg gatcgactac     180
gccgacagcg tgaagggcag attcaccatc agccgggaca cagcaagaa caccctgtac     240
ctgcagatga acagcctgag agccgaggac accgccgtgt actactgtgc cagaagcggc     300
tacagcagct cttggtttga ccccgacttc gactattggg gccagggcac actggtcaca     360
gtctcttca                                                            369
```

<210> SEQ ID NO 510
<211> LENGTH: 15
<212> TYPE: DNA
<213> ORGANISM: Artificial Sequence
<220> FEATURE:
<223> OTHER INFORMATION: antibody sequence

<400> SEQUENCE: 510

```
agctacgaga tgaac                                                      15
```

<210> SEQ ID NO 511
<211> LENGTH: 51
<212> TYPE: DNA
<213> ORGANISM: Artificial Sequence
<220> FEATURE:
<223> OTHER INFORMATION: antibody sequence

<400> SEQUENCE: 511

```
ggcatcagct ggaatagcgg ctggatcgac tacgccgaca gcgtgaaggg c               51
```

<210> SEQ ID NO 512
<211> LENGTH: 42
<212> TYPE: DNA
<213> ORGANISM: Artificial Sequence
<220> FEATURE:
<223> OTHER INFORMATION: antibody sequence

<400> SEQUENCE: 512

```
agcggctaca gcagctcttg gtttgacccc gacttcgact at                        42
```

<210> SEQ ID NO 513
<211> LENGTH: 333
<212> TYPE: DNA
<213> ORGANISM: Artificial Sequence
<220> FEATURE:
<223> OTHER INFORMATION: antibody sequence

<400> SEQUENCE: 513

```
cagtctgttc tgacacagcc tccatctgtg tctggcgccc ctggacagag agtgaccatc      60
agctgtacag gcagcagctc cgatattggc gccggatacg acgtgcactg gtatcagcaa     120
ctgcctggca cagcccctaa gctgctgatc tacggcaaca gcaacagacc tagcggcgtg     180
cccgatagat tcagcggctc taagtctggc acaagcgcca gcctggccat tactggactg     240
caggccgaag atgaggccga ctactactgt cagagctacg ccggcatcaa cccctacgtg     300
gtgtttggcg gaggcaccaa gctgacagtt cta                                  333
```

<210> SEQ ID NO 514
<211> LENGTH: 42
<212> TYPE: DNA
<213> ORGANISM: Artificial Sequence
<220> FEATURE:
<223> OTHER INFORMATION: antibody sequence

<400> SEQUENCE: 514

```
acaggcagca gctccgatat tggcgccgga tacgacgtgc ac                         42
```

<210> SEQ ID NO 515
<211> LENGTH: 21
<212> TYPE: DNA
<213> ORGANISM: Artificial Sequence
<220> FEATURE:
<223> OTHER INFORMATION: antibody sequence

<400> SEQUENCE: 515

```
ggcaacagca acagacctag c                                                21
```

<210> SEQ ID NO 516
<211> LENGTH: 33
<212> TYPE: DNA
<213> ORGANISM: Artificial Sequence
<220> FEATURE:
<223> OTHER INFORMATION: antibody sequence

<400> SEQUENCE: 516

```
cagagctacg ccggcatcaa cccctacgtg gtg                                   33
```

<210> SEQ ID NO 517
<211> LENGTH: 453
<212> TYPE: PRT
<213> ORGANISM: Artificial Sequence
<220> FEATURE:
<223> OTHER INFORMATION: antibody sequence

<400> SEQUENCE: 517

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
```

```
            50                  55                  60
Lys Gly Arg Phe Thr Ile Ser Arg Asp Asn Ser Lys Asn Thr Leu Tyr
 65                      70                  75                  80

Leu Gln Met Asn Ser Leu Arg Ala Glu Asp Thr Ala Val Tyr Tyr Cys
                     85                  90                  95

Ala Arg Ser Gly Tyr Ser Ser Trp Phe Asp Pro Asp Phe Asp Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
                450

<210> SEQ ID NO 518
```

```
<211> LENGTH: 217
<212> TYPE: PRT
<213> ORGANISM: Artificial Sequence
<220> FEATURE:
<223> OTHER INFORMATION: antibody sequence

<400> SEQUENCE: 518
```

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asp Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ala Gly Ile
                85                  90                  95

Asn Pro Tyr Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

```
<210> SEQ ID NO 519
<211> LENGTH: 1359
<212> TYPE: DNA
<213> ORGANISM: Artificial Sequence
<220> FEATURE:
<223> OTHER INFORMATION: antibody sequence

<400> SEQUENCE: 519
gaagttcagc tgctggaatc tggcggcgga ctggttcaac tggcggatc  tctgagactg     60 agctgtgccg ccagcggctt caccttcgat agctacgaga tgaactgggt ccgacaggcc    120
cctggcaaag ccttgaatg gtgtccggc atcagctgga atagcggctg gatcgactac      180
gccgacagcg tgaagggcag attcaccatc agccgggaca cagcaagaa caccctgtac     240 ctgcagatga acagcctgag agccgaggac accgccgtgt actactgtgc cagaagcggc    300
tacagcagct cttggtttga ccccgacttc gactattggg gccagggcac actggtcaca    360
gtctcttcag ccagcaccaa gggcccagc gtgttccctc tggcccctag cagcaagagc     420
acatctggcg gaacagccgc cctgggctgc ctcgtgaagg actactttcc cgagcccgtg    480
accgtgtcct ggaactctgg cgctctgaca agcggcgtgc acacctttcc agccgtgctg    540
cagagcagcg gcctgtactc tctgagcagc gtcgtgacag tgcccagcag ctctctgggc    600
```

```
acccagacct acatctgcaa cgtgaaccac aagcccagca acaccaaggt ggacaagaag    660
gtggaaccca gagctgcga caagacccac acctgtcccc cttgtcctgc ccccgaactg    720 ctggaggcc cttccgtgtt cctgttcccc ccaaagccca aggacaccct gatgatcagc    780 cggaccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa   1020
accatcagca aggccaaggg ccagccccgc gaacccagg tgtacacact gcccccaagc    1080
agggacgagc tgaccaagaa ccaggtgtcc ctgacctgtc tcgtgaaagg cttctacccc    1140
tccgatatcg ccgtggaatg ggagagcaac ggccagcccg agaacaacta caagaccacc    1200
ccccctgtgc tggacagcga cggctcattc ttcctgtaca gcaagctgac cgtggacaag    1260
tcccggtggc agcagggcaa cgtgttcagc tgcagcgtga tgcacgaggc cctgcacaac    1320
cactacaccc agaagtccct gagcctgagc cctggcaag                          1359
```

<210> SEQ ID NO 520
<211> LENGTH: 651
<212> TYPE: DNA
<213> ORGANISM: Artificial Sequence
<220> FEATURE:
<223> OTHER INFORMATION: antibody sequence

<400> SEQUENCE: 520

```
cagtctgttc tgacacagcc tccatctgtg tctggcgccc tggacagag agtgaccatc     60 agctgtacag gcagcagctc cgatattggc gccggatacg acgtgcactg gtatcagcaa    120
ctgcctggca cagcccctaa gctgctgatc tacggcaaca gcaacagacc tagcggcgtg    180
cccgatagat tcagcggctc taagtctggc acaagcgcca gcctggccat tactggactg    240
caggccgaag atgaggccga ctactactgt cagagctacg ccggcataa ccctacgtg     300 gtgtttggcg gaggcaccaa gctgacagtt ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac caccccctagc aagcagagca caacaaata cgccgccagc    540 agctacctga gcctgacccc cgagcagtgg aagtcccaca gatcctacag ctgccaagtg    600
acccacgagg gcagcaccgt ggaaaagaca gtggcccta ccgagtgcag c              651
```

<210> SEQ ID NO 521
<211> LENGTH: 123
<212> TYPE: PRT
<213> ORGANISM: Artificial Sequence
<220> FEATURE:
<223> OTHER INFORMATION: antibody sequence

<400> SEQUENCE: 521

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asp Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Ser Ser Trp Phe Asp Pro Asp Phe Asp Tyr
                100                 105                 110

Trp Gly Gln Gly Thr Leu Val Thr Val Ser Ser
        115                 120
```

<210> SEQ ID NO 522
<211> LENGTH: 5
<212> TYPE: PRT
<213> ORGANISM: Artificial Sequence
<220> FEATURE:
<223> OTHER INFORMATION: antibody sequence

<400> SEQUENCE: 522

```
Ser Tyr Glu Met Asn
 1                5
```

<210> SEQ ID NO 523
<211> LENGTH: 17
<212> TYPE: PRT
<213> ORGANISM: Artificial Sequence
<220> FEATURE:
<223> OTHER INFORMATION: antibody sequence

<400> SEQUENCE: 523

```
Gly Ile Ser Trp Asn Ser Gly Trp Ile Asp Tyr Ala Asp Ser Val Lys
 1               5                  10                  15

Gly
```

<210> SEQ ID NO 524
<211> LENGTH: 14
<212> TYPE: PRT
<213> ORGANISM: Artificial Sequence
<220> FEATURE:
<223> OTHER INFORMATION: antibody sequence

<400> SEQUENCE: 524

```
Ser Gly Tyr Ser Ser Ser Trp Phe Asp Pro Asp Phe Asp Tyr
 1               5                  10
```

<210> SEQ ID NO 525
<211> LENGTH: 111
<212> TYPE: PRT
<213> ORGANISM: Artificial Sequence
<220> FEATURE:
<223> OTHER INFORMATION: antibody sequence

<400> SEQUENCE: 525

```
Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asp Ile Gly Ala Gly
                20                  25                  30

Tyr Asp Val His Trp Tyr Gln Gln Leu Pro Gly Thr Ala Pro Lys Leu
             35                  40                  45

Leu Ile Tyr Gly Asn Ser Asn Arg Pro Ser Gly Val Pro Asp Arg Phe
         50                  55                  60

Ser Gly Ser Lys Ser Gly Thr Ser Ala Ser Leu Ala Ile Thr Gly Leu
 65                  70                  75                  80
```

Gln Ala Glu Asp Glu Ala Asp Tyr Tyr Cys Ser Ser Tyr Glu Gly Ile
                85                  90                  95

Asn Pro Tyr Val Val Phe Gly Gly Gly Thr Lys Leu Thr Val Leu
            100                 105                 110

<210> SEQ ID NO 526
<211> LENGTH: 14
<212> TYPE: PRT
<213> ORGANISM: Artificial Sequence
<220> FEATURE:
<223> OTHER INFORMATION: antibody sequence

<400> SEQUENCE: 526

Thr Gly Ser Ser Ser Asp Ile Gly Ala Gly Tyr Asp Val His
1               5                   10

<210> SEQ ID NO 527
<211> LENGTH: 7
<212> TYPE: PRT
<213> ORGANISM: Artificial Sequence
<220> FEATURE:
<223> OTHER INFORMATION: antibody sequence

<400> SEQUENCE: 527

Gly Asn Ser Asn Arg Pro Ser
1               5

<210> SEQ ID NO 528
<211> LENGTH: 11
<212> TYPE: PRT
<213> ORGANISM: Artificial Sequence
<220> FEATURE:
<223> OTHER INFORMATION: antibody sequence

<400> SEQUENCE: 528

Ser Ser Tyr Glu Gly Ile Asn Pro Tyr Val Val
1               5                   10

<210> SEQ ID NO 529
<211> LENGTH: 369
<212> TYPE: DNA
<213> ORGANISM: Artificial Sequence
<220> FEATURE:
<223> OTHER INFORMATION: antibody sequence

<400> SEQUENCE: 529
gaagttcagc tgctggaatc tggcggcgga ctggttcaac tggcggatc tctgagactg        60 agctgtgccg ccagcggctt cgacttcgat agctacgaga tgaactgggt ccgacaggcc       120
cctggcaaag ccttgaatg ggtgtccggc atcagctgga atagcggctg gatcgactac       180
gccgacagcg tgaagggcag attcaccatc agccgggaca cagcaagaa caccctgtac       240 ctgcagatga acagcctgag agccgaggac accgccgtgt actactgtgc cagaagcggc       300
tacagcagct cttggttttga ccccgacttc gactattggg gccagggcac actggtcaca       360
gtctcttca                                                               369

<210> SEQ ID NO 530
<211> LENGTH: 15
<212> TYPE: DNA
<213> ORGANISM: Artificial Sequence
<220> FEATURE:
<223> OTHER INFORMATION: antibody sequence

<400> SEQUENCE: 530

```
agctacgaga tgaac                                                          15

<210> SEQ ID NO 531
<211> LENGTH: 51
<212> TYPE: DNA
<213> ORGANISM: Artificial Sequence
<220> FEATURE:
<223> OTHER INFORMATION: antibody sequence

<400> SEQUENCE: 531
ggcatcagct ggaatagcgg ctggatcgac tacgccgaca gcgtgaaggg c                  51

<210> SEQ ID NO 532
<211> LENGTH: 42
<212> TYPE: DNA
<213> ORGANISM: Artificial Sequence
<220> FEATURE:
<223> OTHER INFORMATION: antibody sequence

<400> SEQUENCE: 532
agcggctaca gcagctcttg gtttgacccc gacttcgact at                            42

<210> SEQ ID NO 533
<211> LENGTH: 333
<212> TYPE: DNA
<213> ORGANISM: Artificial Sequence
<220> FEATURE:
<223> OTHER INFORMATION: antibody sequence

<400> SEQUENCE: 533
cagtctgttc tgacacagcc tccatctgtg tctggcgccc ctggacagag agtgaccatc         60
agctgtacag gcagcagctc cgatattggc gccggatacg acgtgcactg gtatcagcaa        120
ctgcctggca gccccctaa gctgctgatc tacggcaaca gcaacagacc tagcggcgtg         180
cccgatagat tcagcggctc taagtctggc acaagcgcca gcctggccat tactggactg        240
caggccgaag atgaggccga ctactactgc agcagctacg agggcatcaa ccccctacgtg       300 gtgtttggcg gcggaacaaa gctgaccgtt cta                                     333

<210> SEQ ID NO 534
<211> LENGTH: 42
<212> TYPE: DNA
<213> ORGANISM: Artificial Sequence
<220> FEATURE:
<223> OTHER INFORMATION: antibody sequence

<400> SEQUENCE: 534
acaggcagca gctccgatat tggcgccgga tacgacgtgc ac                            42

<210> SEQ ID NO 535
<211> LENGTH: 21
<212> TYPE: DNA
<213> ORGANISM: Artificial Sequence
<220> FEATURE:
<223> OTHER INFORMATION: antibody sequence

<400> SEQUENCE: 535
ggcaacagca acagacctag c                                                   21

<210> SEQ ID NO 536
<211> LENGTH: 33
<212> TYPE: DNA
<213> ORGANISM: Artificial Sequence
<220> FEATURE:
```

-continued

<223> OTHER INFORMATION: antibody sequence

<400> SEQUENCE: 536
agcagctacg agggcatcaa cccctacgtg gtg                33

<210> SEQ ID NO 537
<211> LENGTH: 453
<212> TYPE: PRT
<213> ORGANISM: Artificial Sequence
<220> FEATURE:
<223> OTHER INFORMATION: antibody sequence

<400> SEQUENCE: 537

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asp Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Trp Phe Asp Pro Asp Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 538
<211> LENGTH: 217
<212> TYPE: PRT
<213> ORGANISM: Artificial Sequence
<220> FEATURE:
<223> OTHER INFORMATION: antibody sequence

<400> SEQUENCE: 538

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asp Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Glu Gly Ile
                85                  90                  95

Asn Pro Tyr Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 539
<211> LENGTH: 1359
```

```
<212> TYPE: DNA
<213> ORGANISM: Artificial Sequence
<220> FEATURE:
<223> OTHER INFORMATION: antibody sequence

<400> SEQUENCE: 539
gaagttcagc tgctggaatc tggcggcgga ctggttcaac ctggcggatc tctgagactg    60
agctgtgccg ccagcggctt cgacttcgat agctacgaga tgaactgggt ccgacaggcc   120
cctggcaaag gccttgaatg ggtgtccggc atcagctgga atagcggctg gatcgactac   180
gccgacagcg tgaagggcag attcaccatc agccgggaca cagcaagaa caccctgtac    240
ctgcagatga cagcctgag agccgaggac ccgccgtgt actactgtgc cagaagcggc     300
tacagcagct cttggtttga ccccgacttc gactattggg gccagggcac actggtcaca   360
gtctcttcag ccagcaccaa gggcccagc gtgttccctc tggcccctag cagcaagagc    420
acatctggcg aacagccgc cctgggctgc ctcgtgaagg actactttcc cgagcccgtg    480
accgtgtcct ggaactctgg cgctctgaca agcggcgtgc acacctttcc agccgtgctg   540
cagagcagcg gcctgtactc tctgagcagc gtcgtgacag tgcccagcag ctctctgggc   600
acccagacct acatctgcaa cgtgaaccac aagcccagca acaccaaggt ggacaagaag   660
gtggaaccca gagctgcga caagacccac acctgtcccc cttgtcctgc cccgaactg    720
ctgggaggcc cttccgtgtt cctgttcccc caaagcccaa ggacaccct gatgatcagc    780
cggaccccg aagtgacctg cgtggtggtg gatgtgtccc acgaggaccc tgaagtgaag    840
ttcaattggt acgtggacgg cgtggaagtg cacaacgcca gaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa   1020
accatcagca aggccaaggg ccagccccgc gaacccagg tgtacacact gcccccaagc   1080
agggacgagc tgaccaagaa ccaggtgtcc ctgacctgtc tcgtgaaagg cttctacccc   1140
tccgatatcg ccgtggaatg ggagagcaac ggccagcccg agaacaacta caagaccacc   1200
ccccctgtgc tggacagcga cggctcattc ttcctgtaca gcaagctgac cgtggacaag   1260
tcccggtggc agcagggcaa cgtgttcagc tgcagcgtga tgcacgaggc cctgcacaac   1320
cactacaccc agaagtccct gagcctgagc cctggcaag                          1359

<210> SEQ ID NO 540
<211> LENGTH: 651
<212> TYPE: DNA
<213> ORGANISM: Artificial Sequence
<220> FEATURE:
<223> OTHER INFORMATION: antibody sequence

<400> SEQUENCE: 540
cagtctgttc tgacacagcc tccatctgtg tctggcgccc ctggacagag agtgaccatc    60
agctgtacag gcagcagctc cgatattggc gccggatacg acgtgcactg gtatcagcaa   120
ctgcctggca cagcccctaa gctgctgatc tacggcaaca gcaacagacc tagcggcgtg   180
cccgatagat tcagcggctc taagtctggc acaagcgcca gcctggccat tactggactg   240
caggccgaag atgaggccga ctactactgc agcagctacg agggcatcaa ccctacgtg    300
gtgtttggcg gcggaacaaa gctgaccgtt ctaggccagc ctaaagccgc ccctagcgtg   360
acctgttcc ctccaagcag cgaggaactg caggccaaca aggccaccct cgtgtgcctg    420
atcagcgact tctatcctgg cgccgtgacc gtggcctgga aggccgatag ctctcctgtg   480
```

-continued

```
aaggccggcg tggaaaccac caccccctagc aagcagagca acaacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c             651
```

<210> SEQ ID NO 541
<211> LENGTH: 123
<212> TYPE: PRT
<213> ORGANISM: Artificial Sequence
<220> FEATURE:
<223> OTHER INFORMATION: antibody sequence

<400> SEQUENCE: 541

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser
        115                 120

<210> SEQ ID NO 542
<211> LENGTH: 5
<212> TYPE: PRT
<213> ORGANISM: Artificial Sequence
<220> FEATURE:
<223> OTHER INFORMATION: antibody sequence

<400> SEQUENCE: 542

Ser Tyr Glu Met Asn
1               5

<210> SEQ ID NO 543
<211> LENGTH: 17
<212> TYPE: PRT
<213> ORGANISM: Artificial Sequence
<220> FEATURE:
<223> OTHER INFORMATION: antibody sequence

<400> SEQUENCE: 543

Gly Ile Ser Trp Asn Ser Gly Trp Ile Asp Tyr Ala Asp Ser Val Lys
1               5                   10                  15

Gly

<210> SEQ ID NO 544
<211> LENGTH: 14
<212> TYPE: PRT
<213> ORGANISM: Artificial Sequence
<220> FEATURE:
<223> OTHER INFORMATION: antibody sequence

<400> SEQUENCE: 544

Ser Gly Tyr Ser Ser Ser Trp Phe Asp Pro Asp Phe Asp Tyr

```
<210> SEQ ID NO 545
<211> LENGTH: 111
<212> TYPE: PRT
<213> ORGANISM: Artificial Sequence
<220> FEATURE:
<223> OTHER INFORMATION: antibody sequence

<400> SEQUENCE: 545

Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Gly Ala Ser Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Ser Ser Tyr Glu Gly Pro
                85                  90                  95
Asn Pro Tyr Val Val Phe Gly Gly Gly Thr Lys Leu Thr Val Leu
            100                 105                 110

<210> SEQ ID NO 546
<211> LENGTH: 14
<212> TYPE: PRT
<213> ORGANISM: Artificial Sequence
<220> FEATURE:
<223> OTHER INFORMATION: antibody sequence

<400> SEQUENCE: 546

Thr Gly Ser Ser Ser Asn Ile Gly Ala Gly Tyr Asp Val His
1               5                   10

<210> SEQ ID NO 547
<211> LENGTH: 7
<212> TYPE: PRT
<213> ORGANISM: Artificial Sequence
<220> FEATURE:
<223> OTHER INFORMATION: antibody sequence

<400> SEQUENCE: 547

Gly Ala Ser Asn Arg Pro Ser
1               5

<210> SEQ ID NO 548
<211> LENGTH: 11
<212> TYPE: PRT
<213> ORGANISM: Artificial Sequence
<220> FEATURE:
<223> OTHER INFORMATION: antibody sequence

<400> SEQUENCE: 548

Ser Ser Tyr Glu Gly Pro Asn Pro Tyr Val Val
1               5                   10

<210> SEQ ID NO 549
<211> LENGTH: 369
<212> TYPE: DNA
<213> ORGANISM: Artificial Sequence
<220> FEATURE:
<223> OTHER INFORMATION: antibody sequence
```

<400> SEQUENCE: 549

```
gaagttcagc tgctggaatc tggcggcgga ctggttcaac ctggcggatc tctgagactg    60
agctgtgccg ccagcggctt cgatttcagc agctacgaga tgaactgggt ccgacaggcc   120
cctggcaaag gccttgaatg ggtgtccggc atcagctgga atagcggctg gatcgactac   180
gccgacagcg tgaagggcag attcaccatc agccgggaca acagcaagaa caccctgtac   240
ctgcagatga acagcctgag agccgaggac accgccgtgt actactgtgc cagaagcggc   300
tacagcagct cttggttga ccccgacttc gactattggg gccagggcac actggtcaca   360
gtctcttca                                                          369
```

<210> SEQ ID NO 550
<211> LENGTH: 15
<212> TYPE: DNA
<213> ORGANISM: Artificial Sequence
<220> FEATURE:
<223> OTHER INFORMATION: antibody sequence

<400> SEQUENCE: 550

```
agctacgaga tgaac                                                    15
```

<210> SEQ ID NO 551
<211> LENGTH: 51
<212> TYPE: DNA
<213> ORGANISM: Artificial Sequence
<220> FEATURE:
<223> OTHER INFORMATION: antibody sequence

<400> SEQUENCE: 551

```
ggcatcagct ggaatagcgg ctggatcgac tacgccgaca gcgtgaaggg c             51
```

<210> SEQ ID NO 552
<211> LENGTH: 42
<212> TYPE: DNA
<213> ORGANISM: Artificial Sequence
<220> FEATURE:
<223> OTHER INFORMATION: antibody sequence

<400> SEQUENCE: 552

```
agcggctaca gcagctcttg gtttgacccc gacttcgact at                       42
```

<210> SEQ ID NO 553
<211> LENGTH: 333
<212> TYPE: DNA
<213> ORGANISM: Artificial Sequence
<220> FEATURE:
<223> OTHER INFORMATION: antibody sequence

<400> SEQUENCE: 553

```
cagtctgttc tgacacagcc tccatctgtg tctggcgccc tggacagag agtgaccatc    60 agctgtacag gcagcagctc caatatcgga gccggctatg acgtgcactg gtatcagcag   120
ctgcctggca cagcccctaa actgctgatc tacgcgcca gcaatagacc tagcggcgtg   180
cccgatagat tcagcggctc taagtctggc acaagcgcca gcctggccat tactggactg   240
caggccgaag atgaggccga ctactactgc agcagctacg agggccccaa tccttacgtg   300
gtgtttggcg gcggaacaaa gctgaccgtt cta                                333
```

<210> SEQ ID NO 554
<211> LENGTH: 42
<212> TYPE: DNA

<213> ORGANISM: Artificial Sequence
<220> FEATURE:
<223> OTHER INFORMATION: antibody sequence

<400> SEQUENCE: 554
acaggcagca gctccaatat cggagccggc tatgacgtgc ac     42

<210> SEQ ID NO 555
<211> LENGTH: 21
<212> TYPE: DNA
<213> ORGANISM: Artificial Sequence
<220> FEATURE:
<223> OTHER INFORMATION: antibody sequence

<400> SEQUENCE: 555
ggcgccagca atagacctag c     21

<210> SEQ ID NO 556
<211> LENGTH: 33
<212> TYPE: DNA
<213> ORGANISM: Artificial Sequence
<220> FEATURE:
<223> OTHER INFORMATION: antibody sequence

<400> SEQUENCE: 556
agcagctacg agggccccaa tccttacgtg gtg     33

<210> SEQ ID NO 557
<211> LENGTH: 453
<212> TYPE: PRT
<213> ORGANISM: Artificial Sequence
<220> FEATURE:
<223> OTHER INFORMATION: antibody sequence

<400> SEQUENCE: 557

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ser Gly Tyr Ser Ser Ser Trp Phe Asp Pro Asp Phe Asp Tyr
        100                 105                 110

Trp Gly Gln Gly Thr Leu Val Thr Val Ser Ser Ala Ser Thr Lys Gly
    115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val

```
                195                 200                 205
Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 558
<211> LENGTH: 217
<212> TYPE: PRT
<213> ORGANISM: Artificial Sequence
<220> FEATURE:
<223> OTHER INFORMATION: antibody sequence

<400> SEQUENCE: 558

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Ala Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Glu Gly Pro
                85                  90                  95

Asn Pro Tyr Val Val Phe Gly Gly Gly Thr Lys Leu Thr Val Leu Gly
```

```
                100             105             110
Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
        130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
            210                 215
```

<210> SEQ ID NO 559
<211> LENGTH: 1359
<212> TYPE: DNA
<213> ORGANISM: Artificial Sequence
<220> FEATURE:
<223> OTHER INFORMATION: antibody sequence

<400> SEQUENCE: 559

```
gaagttcagc tgctggaatc tggcggcgga ctggttcaac tggcggatc tctgagactg      60
agctgtgccg ccagcggctt cgatttcagc agctacgaga tgaactgggt ccgacaggcc    120
cctggcaaag ccttgaatg gtgtccggc atcagctgga atagcggctg atcgactac       180
gccgacagcg tgaagggcag attcaccatc agccgggaca cagcaagaa cacccctgtac   240
ctgcagatga acagcctgag agccgaggac accgccgtgt actactgtgc cagaagcggc   300
tacagcagct cttggtttga ccccgacttc gactattggg ccagggcac actggtcaca   360
gtctcttcag ccagcaccaa gggccccagc gtgttccctc tggcccctag cagcaagagc   420
acatctggcg gaacagccgc cctgggctgc ctcgtgaagg actactttcc gagcccgtg    480
accgtgtcct ggaactctgg cgctctgaca agcggcgtgc acctttcc agccgtgctg     540
cagagcagcg gcctgtactc tctgagcagc gtcgtgacag tgcccagcag ctctctgggc   600
acccagacct acatctgcaa cgtgaaccac aagcccagca caccaaggt ggacaagaag   660
gtggaaccca gagctgcga caagacccac acctgtcccc cttgtcctgc cccgaactg     720
ctgggaggcc cttccgtgtt cctgttcccc ccaaagccca aggacaccct gatgatcagc   780
cggacccccg aagtgacctg cgtggtggtg gatgtgtccc acgaggaccc tgaagtgaag   840
ttcaattggt acgtggacgg cgtggaagtg cacaacgcca agaccaagcc tagagaggaa   900
cagtacaaca gcacctaccg ggtggtgtcc gtgctgacag tgctgcacca ggactggctg   960
aacggcaaag agtacaagtg caaggtgtcc aacaaggccc tgcctgcccc catcgagaaa  1020
accatcagca aggccaaggg ccagcccgc gaacccagg tgtacacact gccccaagc     1080
agggacgagc tgaccaagaa ccaggtgtcc ctgacctgtc tcgtgaaagg cttctaccccc  1140
tccgatatcg ccgtggaatg ggagagcaac ggccagcccg agaacaacta caagaccacc  1200
ccccctgtgc tggacagcga cggctcattc ttcctgtaca gcaagctgac cgtggacaag  1260
tcccggtggc agcagggcaa cgtgttcagc tgcagcgtga tgcacgaggc cctgcacaac  1320
cactacaccc agaagtccct gagcctgagc cctggcaag                        1359
```

<210> SEQ ID NO 560
<211> LENGTH: 651
<212> TYPE: DNA
<213> ORGANISM: Artificial Sequence
<220> FEATURE:
<223> OTHER INFORMATION: antibody sequence

<400> SEQUENCE: 560

```
cagtctgttc tgacacagcc tccatctgtg tctggcgccc ctggacagag agtgaccatc        60
agctgtacag gcagcagctc caatatcgga gccggctatg acgtgcactg gtatcagcag       120
ctgcctggca gcccctaa  actgctgatc tacggcgcca gcaatagacc tagcggcgtg       180
cccgatagat tcagcggctc taagtctggc acaagcgcca gcctggccat tactggactg       240
caggccgaag atgaggccga ctactactgc agcagctacg agggcccaa  tccttacgtg       300 gtgtttggcg gcggaacaaa gctgaccgtt ctaggccagc ctaaagccgc ccctagcgtg       360
accctgttcc ctccaagcag cgaggaactg caggccaaca aggccaccct cgtgtgcctg       420
atcagcgact tctatcctgg cgccgtgacc gtggcctgga aggccgatag ctctcctgtg       480
aaggccggcg tggaaaccac cacccctagc aagcagagca caacaaata cgccgccagc       540 agctacctga gcctgacccc cgagcagtgg aagtcccaca gatcctacag ctgccaagtg       600
acccacgagg gcagcaccgt ggaaaagaca gtggccccta ccgagtgcag c               651
```

<210> SEQ ID NO 561
<211> LENGTH: 123
<212> TYPE: PRT
<213> ORGANISM: Artificial Sequence
<220> FEATURE:
<223> OTHER INFORMATION: antibody sequence

<400> SEQUENCE: 561

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Ser Ser Trp Phe Asp Pro Asp Phe Asp Tyr
            100                 105                 110

Trp Gly Gln Gly Thr Leu Val Thr Val Ser Ser
        115                 120
```

<210> SEQ ID NO 562
<211> LENGTH: 5
<212> TYPE: PRT
<213> ORGANISM: Artificial Sequence
<220> FEATURE:
<223> OTHER INFORMATION: antibody sequence

<400> SEQUENCE: 562

```
Ser Tyr Glu Met Asn
1               5
```

<210> SEQ ID NO 563
<211> LENGTH: 17
<212> TYPE: PRT
<213> ORGANISM: Artificial Sequence
<220> FEATURE:
<223> OTHER INFORMATION: antibody sequence

<400> SEQUENCE: 563

Gly Ile Ser Trp Asn Ser Gly Trp Ile Asp Tyr Ala Asp Ser Val Lys
1               5                   10                  15

Gly

<210> SEQ ID NO 564
<211> LENGTH: 14
<212> TYPE: PRT
<213> ORGANISM: Artificial Sequence
<220> FEATURE:
<223> OTHER INFORMATION: antibody sequence

<400> SEQUENCE: 564

Ser Gly Tyr Ser Ser Ser Trp Phe Asp Pro Asp Phe Asp Tyr
1               5                   10

<210> SEQ ID NO 565
<211> LENGTH: 111
<212> TYPE: PRT
<213> ORGANISM: Artificial Sequence
<220> FEATURE:
<223> OTHER INFORMATION: antibody sequence

<400> SEQUENCE: 565

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Ala Gly Pro
                85                  90                  95

Asn Pro Tyr Val Val Phe Gly Gly Gly Thr Lys Leu Thr Val Leu
            100                 105                 110

<210> SEQ ID NO 566
<211> LENGTH: 14
<212> TYPE: PRT
<213> ORGANISM: Artificial Sequence
<220> FEATURE:
<223> OTHER INFORMATION: antibody sequence

<400> SEQUENCE: 566

Thr Gly Ser Ser Ser Asn Ile Gly Ala Gly Tyr Asp Val His
1               5                   10

<210> SEQ ID NO 567
<211> LENGTH: 7
<212> TYPE: PRT
<213> ORGANISM: Artificial Sequence
<220> FEATURE:
<223> OTHER INFORMATION: antibody sequence

```
<400> SEQUENCE: 567

Gly Asn Ser Asn Arg Pro Ser
1               5

<210> SEQ ID NO 568
<211> LENGTH: 11
<212> TYPE: PRT
<213> ORGANISM: Artificial Sequence
<220> FEATURE:
<223> OTHER INFORMATION: antibody sequence

<400> SEQUENCE: 568

Ser Ser Tyr Ala Gly Pro Asn Pro Tyr Val Val
1               5                   10

<210> SEQ ID NO 569
<211> LENGTH: 369
<212> TYPE: DNA
<213> ORGANISM: Artificial Sequence
<220> FEATURE:
<223> OTHER INFORMATION: antibody sequence

<400> SEQUENCE: 569
gaagttcagc tgctggaatc tggcggcgga ctggttcaac ctggcggatc tctgagactg      60
agctgtgccg ccagcggctt caccttcgat agctacgaga tgaactgggt ccgacaggcc     120
cctggcaaag ccttgaatg gtgtccggc atcagctgga atagcggctg gatcgactac      180
gccgacagcg tgaagggcag attcaccatc agccgggaca acagcaagaa caccctgtac     240
ctgcagatga acagcctgag agccgaggac accgccgtgt actactgtgc cagaagcggc     300
tacagcagct cttggtttga ccccgacttc gactattggg gccagggcac actggtcaca     360
gtctcttca                                                            369

<210> SEQ ID NO 570
<211> LENGTH: 15
<212> TYPE: DNA
<213> ORGANISM: Artificial Sequence
<220> FEATURE:
<223> OTHER INFORMATION: antibody sequence

<400> SEQUENCE: 570
agctacgaga tgaac                                                      15

<210> SEQ ID NO 571
<211> LENGTH: 51
<212> TYPE: DNA
<213> ORGANISM: Artificial Sequence
<220> FEATURE:
<223> OTHER INFORMATION: antibody sequence

<400> SEQUENCE: 571
ggcatcagct ggaatagcgg ctggatcgac tacgccgaca gcgtgaaggg c               51

<210> SEQ ID NO 572
<211> LENGTH: 42
<212> TYPE: DNA
<213> ORGANISM: Artificial Sequence
<220> FEATURE:
<223> OTHER INFORMATION: antibody sequence

<400> SEQUENCE: 572
agcggctaca gcagctcttg gtttgacccc gacttcgact at                        42
```

<210> SEQ ID NO 573
<211> LENGTH: 333
<212> TYPE: DNA
<213> ORGANISM: Artificial Sequence
<220> FEATURE:
<223> OTHER INFORMATION: antibody sequence

<400> SEQUENCE: 573

```
cagtctgttc tgacacagcc tccatctgtg tctggcgccc ctggacagag agtgaccatc      60
agctgtacag gcagcagctc caatatcgga gccggctatg acgtgcactg gtatcagcag     120
ctgcctggca gcccctaa actgctgatc tacggcaaca gcaacagacc cagcggcgtg      180
cccgatagat tttccggctc taagagcggc acaagcgcca gcctggctat tactggactg     240
caggccgagg acgaggccga ctactactgt agctcttacg ctggccccaa tccttacgtg     300
gtgtttggcg gcggaacaaa gctgaccgtt cta                                   333
```

<210> SEQ ID NO 574
<211> LENGTH: 42
<212> TYPE: DNA
<213> ORGANISM: Artificial Sequence
<220> FEATURE:
<223> OTHER INFORMATION: antibody sequence

<400> SEQUENCE: 574

```
acaggcagca gctccaatat cggagccggc tatgacgtgc ac                          42
```

<210> SEQ ID NO 575
<211> LENGTH: 21
<212> TYPE: DNA
<213> ORGANISM: Artificial Sequence
<220> FEATURE:
<223> OTHER INFORMATION: antibody sequence

<400> SEQUENCE: 575

```
ggcaacagca acagacccag c                                                 21
```

<210> SEQ ID NO 576
<211> LENGTH: 33
<212> TYPE: DNA
<213> ORGANISM: Artificial Sequence
<220> FEATURE:
<223> OTHER INFORMATION: antibody sequence

<400> SEQUENCE: 576

```
agctcttacg ctggccccaa tccttacgtg gtg                                    33
```

<210> SEQ ID NO 577
<211> LENGTH: 453
<212> TYPE: PRT
<213> ORGANISM: Artificial Sequence
<220> FEATURE:
<223> OTHER INFORMATION: antibody sequence

<400> SEQUENCE: 577

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Glu Met Asn Trp Val Arg Gln Ala Pro Gly Lys Gly Leu Glu Trp Val
        35                  40                  45

Ser Gly Ile Ser Trp Asn Ser Gly Trp Ile Asp Tyr Ala Asp Ser Val
    50                  55                  60
```

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Ser Ser Trp Phe Asp Pro Asp Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 578
<211> LENGTH: 217

<212> TYPE: PRT
<213> ORGANISM: Artificial Sequence
<220> FEATURE:
<223> OTHER INFORMATION: antibody sequence

<400> SEQUENCE: 578

```
Gln Ser Val Leu Thr Gln Pro Pro Ser Val Ser Gly Ala Pro Gly Gln
1               5                   10                  15
Arg Val Thr Ile Ser Cys Thr Gly Ser Ser Asn Ile Gly Ala Gly
            20                  25                  30
Tyr Asp Val His Trp Tyr Gln Gln Leu Pro Gly Thr Ala Pro Lys Leu
                35                  40                  45
Leu Ile Tyr Gly Asn Ser Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Ser Ser Tyr Ala Gly Pro
                85                  90                  95
Asn Pro Tyr Val Val Phe Gly Gly Gly Thr Lys Leu Thr Val Leu Gly
            100                 105                 110
Gln Pro Lys Ala Ala Pro Ser Val Thr Leu Phe Pro Pro Ser Ser Glu
        115                 120                 125
Glu Leu Gln Ala Asn Lys Ala Thr Leu Val Cys Leu Ile Ser Asp Phe
130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Cys Ser
    210                 215
```

<210> SEQ ID NO 579
<211> LENGTH: 1359
<212> TYPE: DNA
<213> ORGANISM: Artificial Sequence
<220> FEATURE:
<223> OTHER INFORMATION: antibody sequence

<400> SEQUENCE: 579

```
gaagttcagc tgctggaatc tggcggcgga ctggttcaac tggcggatc tctgagactg    60
agctgtgccg ccagcggctt caccttcgat agctacgaga tgaactgggt ccgacaggcc   120
cctggcaaag ccttgaatg gtgtccggc atcagctgga atagcggctg gatcgactac   180
gccgacagcg tgaagggcag attcaccatc agccgggaca cagcaagaa caccctgtac   240
ctgcagatga acagcctgag agccgaggac accgccgtgt actactgtgc cagaagcggc   300
tacagcagct cttggtttga ccccgacttc gactattggg gccagggcac actggtcaca   360
gtctcttcag ccagcaccaa gggccccagc gtgttccctc tggcccctag cagcaagagc   420
acatctggcg gaacagccgc cctgggctgc ctcgtgaagg actactttcc cgagcccgtg   480
accgtgtcct ggaactctgg cgctctgaca gcggcgtgc acacctttcc agccgtgctg   540
cagagcagcg gcctgtactc tctgagcagc gtcgtgacag tgcccagcag ctctctgggc   600
```

```
acccagacct acatctgcaa cgtgaaccac aagcccagca acaccaaggt ggacaagaag    660
gtggaaccca gagctgcga caagacccac acctgtcccc cttgtcctgc ccccgaactg    720
ctgggaggcc cttccgtgtt cctgttcccc ccaaagccca aggacaccct gatgatcagc    780
cggaccccg aagtgacctg cgtggtggtg gatgtgtccc acgaggaccc tgaagtgaag    840
ttcaattggt acgtggacgg cgtggaagtg cacaacgcca gaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa   1020
accatcagca aggccaaggg ccagccccgc gaacccagg tgtacacact gcccccaagc   1080
agggacgagc tgaccaagaa ccaggtgtcc ctgacctgtc tcgtgaaagg cttctacccc   1140
tccgatatcg ccgtggaatg ggagagcaac ggccagcccg agaacaacta caagaccacc   1200
cccctgtgc tggacagcga cggctcattc ttcctgtaca gcaagctgac cgtggacaag   1260
tcccggtggc agcagggcaa cgtgttcagc tgcagcgtga tgcacgaggc cctgcacaac   1320
cactacaccc agaagtccct gagcctgagc cctggcaag                          1359
```

<210> SEQ ID NO 580
<211> LENGTH: 651
<212> TYPE: DNA
<213> ORGANISM: Artificial Sequence
<220> FEATURE:
<223> OTHER INFORMATION: antibody sequence

<400> SEQUENCE: 580

```
cagtctgttc tgacacagcc tccatctgtg tctggcgccc ctggacagag agtgaccatc     60
agctgtacag gcagcagctc caatatcgga gccggctatg acgtgcactg gtatcagcag    120
ctgcctggca cagcccctaa actgctgatc tacggcaaca gcaacagacc cagcggcgtg    180
cccgatagat tttccggctc taagagcggc acaagcgcca gcctggctat tactggactg    240
caggccgagg acgaggccga ctactactgt agctcttacg ctggccccaa tccttacgtg    300
gtgtttggcg gcggaacaaa gctgaccgtt ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac cacccctagc aagcagagca caacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c             651
```

<210> SEQ ID NO 581
<211> LENGTH: 990
<212> TYPE: PRT
<213> ORGANISM: Homo sapiens

<400> SEQUENCE: 581

His His His His His His Lys Asn Asn Val Pro Arg Leu Lys Leu Ser
1               5                   10                  15

Tyr Lys Glu Met Leu Glu Ser Asn Asn Val Ile Thr Phe Asn Gly Leu
            20                  25                  30

Ala Asn Ser Ser Ser Tyr His Thr Phe Leu Leu Asp Glu Glu Arg Ser
        35                  40                  45

Arg Leu Tyr Val Gly Ala Lys Asp His Ile Phe Ser Phe Asp Leu Val
    50                  55                  60

Asn Ile Lys Asp Phe Gln Lys Ile Val Trp Pro Val Ser Tyr Thr Arg

```
                65                  70                  75                  80
Arg Asp Glu Cys Lys Trp Ala Gly Lys Asp Ile Leu Lys Glu Cys Ala
                        85                  90                  95
Asn Phe Ile Lys Val Leu Lys Ala Tyr Asn Gln Thr His Leu Tyr Ala
                100                 105                 110
Cys Gly Thr Gly Ala Phe His Pro Ile Cys Thr Tyr Ile Glu Ile Gly
                115                 120                 125
His His Pro Glu Asp Asn Ile Phe Lys Leu Glu Asn Ser His Phe Glu
130                 135                 140
Asn Gly Arg Gly Lys Ser Pro Tyr Asp Pro Lys Leu Leu Thr Ala Ser
145                 150                 155                 160
Leu Leu Ile Asp Gly Glu Leu Tyr Ser Gly Thr Ala Ala Asp Phe Met
                165                 170                 175
Gly Arg Asp Phe Ala Ile Phe Arg Thr Leu Gly His His Pro Ile
                180                 185                 190
Arg Thr Glu Gln His Asp Ser Arg Trp Leu Asn Asp Pro Lys Phe Ile
            195                 200                 205
Ser Ala His Leu Ile Ser Glu Ser Asp Asn Pro Glu Asp Asp Lys Val
        210                 215                 220
Tyr Phe Phe Arg Glu Asn Ala Ile Asp Gly Glu His Ser Gly Lys
225                 230                 235                 240
Ala Thr His Ala Arg Ile Gly Gln Ile Cys Lys Asn Asp Phe Gly Gly
                245                 250                 255
His Arg Ser Leu Val Asn Lys Trp Thr Thr Phe Leu Lys Ala Arg Leu
            260                 265                 270
Ile Cys Ser Val Pro Gly Pro Asn Gly Ile Asp Thr His Phe Asp Glu
        275                 280                 285
Leu Gln Asp Val Phe Leu Met Asn Phe Lys Asp Pro Lys Asn Pro Val
    290                 295                 300
Val Tyr Gly Val Phe Thr Thr Ser Ser Asn Ile Phe Lys Gly Ser Ala
305                 310                 315                 320
Val Cys Met Tyr Ser Met Ser Asp Val Arg Arg Val Phe Leu Gly Pro
                325                 330                 335
Tyr Ala His Arg Asp Gly Pro Asn Tyr Gln Trp Val Pro Tyr Gln Gly
                340                 345                 350
Arg Val Pro Tyr Pro Arg Pro Gly Thr Cys Pro Ser Lys Thr Phe Gly
            355                 360                 365
Gly Phe Asp Ser Thr Lys Asp Leu Pro Asp Asp Val Ile Thr Phe Ala
        370                 375                 380
Arg Ser His Pro Ala Met Tyr Asn Pro Val Phe Pro Met Asn Asn Arg
385                 390                 395                 400
Pro Ile Val Ile Lys Thr Asp Val Asn Tyr Gln Phe Thr Gln Ile Val
                405                 410                 415
Val Asp Arg Val Asp Ala Glu Asp Gly Gln Tyr Asp Val Met Phe Ile
            420                 425                 430
Gly Thr Asp Val Gly Thr Val Leu Lys Val Val Ser Ile Pro Lys Glu
        435                 440                 445
Thr Trp Tyr Asp Leu Glu Glu Val Leu Leu Glu Met Thr Val Phe
    450                 455                 460
Arg Glu Pro Thr Ala Ile Ser Ala Met Glu Leu Ser Thr Lys Gln Gln
465                 470                 475                 480
Gln Leu Tyr Ile Gly Ser Thr Ala Gly Val Ala Gln Leu Pro Leu His
                485                 490                 495
```

```
Arg Cys Asp Ile Tyr Gly Lys Ala Cys Ala Glu Cys Cys Leu Ala Arg
            500                 505                 510

Asp Pro Tyr Cys Ala Trp Asp Gly Ser Ala Cys Ser Arg Tyr Phe Pro
            515                 520                 525

Thr Ala Lys Arg Ala Thr Arg Ala Gln Asp Ile Arg Asn Gly Asp Pro
            530                 535                 540

Leu Thr His Cys Ser Asp Leu His His Asp Asn His His Gly His Ser
545                 550                 555                 560

Pro Glu Glu Arg Ile Ile Tyr Gly Val Glu Asn Ser Ser Thr Phe Leu
                    565                 570                 575

Glu Cys Ser Pro Lys Ser Gln Arg Ala Leu Val Tyr Trp Gln Phe Gln
            580                 585                 590

Arg Arg Asn Glu Glu Arg Lys Glu Glu Ile Arg Val Asp Asp His Ile
            595                 600                 605

Ile Arg Thr Asp Gln Gly Leu Leu Leu Arg Ser Leu Gln Gln Lys Asp
            610                 615                 620

Ser Gly Asn Tyr Leu Cys His Ala Val Glu His Gly Phe Ile Gln Thr
625                 630                 635                 640

Leu Leu Lys Val Thr Leu Glu Val Ile Asp Thr Glu His Leu Glu Glu
                    645                 650                 655

Leu Leu His Lys Asp Asp Asp Gly Asp Gly Ser Lys Thr Lys Glu Met
            660                 665                 670

Ser Asn Ser Met Thr Pro Ser Gln Lys Val Trp Tyr Arg Asp Phe Met
            675                 680                 685

Gln Leu Ile Asn His Pro Asn Leu Asn Thr Met Asp Glu Phe Cys Glu
            690                 695                 700

Gln Val Trp Lys Arg Asp Arg Lys Gln Arg Arg Gln Arg Pro Gly His
705                 710                 715                 720

Thr Pro Gly Asn Ser Asn Lys Trp Lys His Leu Gln Glu Asn Lys Lys
                    725                 730                 735

Gly Arg Asn Arg Arg Thr His Glu Phe Glu Arg Ala Pro Arg Ser Val
            740                 745                 750

Asp Ile Glu Gly Arg Met Asp Pro Lys Ser Cys Asp Lys Thr His Thr
            755                 760                 765

Cys Pro Pro Cys Pro Ala Pro Glu Leu Leu Gly Gly Pro Ser Val Phe
770                 775                 780

Leu Phe Pro Pro Lys Pro Lys Asp Thr Leu Met Ile Ser Arg Thr Pro
785                 790                 795                 800

Glu Val Thr Cys Val Val Val Asp Val Ser His Glu Asp Pro Glu Val
                    805                 810                 815

Lys Phe Asn Trp Tyr Val Asp Gly Val Glu Val His Asn Ala Lys Thr
            820                 825                 830

Lys Pro Arg Glu Glu Gln Tyr Asn Ser Thr Tyr Arg Val Val Ser Val
            835                 840                 845

Leu Thr Val Leu His Gln Asp Trp Leu Asn Gly Lys Glu Tyr Lys Cys
            850                 855                 860

Lys Val Ser Asn Lys Ala Leu Pro Ala Pro Ile Glu Lys Thr Ile Ser
865                 870                 875                 880

Lys Ala Lys Gly Gln Pro Arg Glu Pro Gln Val Tyr Thr Leu Pro Pro
                    885                 890                 895

Ser Arg Asp Glu Leu Thr Lys Asn Gln Val Ser Leu Thr Cys Leu Val
            900                 905                 910
```

```
Lys Gly Phe Tyr Pro Ser Asp Ile Ala Val Glu Trp Glu Ser Asn Gly
            915                 920                 925

Gln Pro Glu Asn Asn Tyr Lys Thr Thr Pro Pro Val Leu Asp Ser Asp
    930                 935                 940

Gly Ser Phe Phe Leu Tyr Ser Lys Leu Thr Val Asp Lys Ser Arg Trp
945                 950                 955                 960

Gln Gln Gly Asn Val Phe Ser Cys Ser Val Met His Glu Ala Leu His
                965                 970                 975

Asn His Tyr Thr Gln Lys Ser Leu Ser Leu Ser Pro Gly Lys
            980                 985                 990
```

<210> SEQ ID NO 582
<211> LENGTH: 563
<212> TYPE: PRT
<213> ORGANISM: Homo sapiens

<400> SEQUENCE: 582

```
Asn Tyr Gln Asn Gly Lys Asn Asn Val Pro Arg Leu Lys Leu Ser Tyr
1               5                   10                  15

Lys Glu Met Leu Glu Ser Asn Asn Val Ile Thr Phe Asn Gly Leu Ala
            20                  25                  30

Asn Ser Ser Ser Tyr His Thr Phe Leu Leu Asp Glu Glu Arg Ser Arg
        35                  40                  45

Leu Tyr Val Gly Ala Lys Asp His Ile Phe Ser Phe Asp Leu Val Asn
50                  55                  60

Ile Lys Asp Phe Gln Lys Ile Val Trp Pro Val Ser Tyr Thr Arg Arg
65                  70                  75                  80

Asp Glu Cys Lys Trp Ala Gly Lys Asp Ile Leu Lys Glu Cys Ala Asn
                85                  90                  95

Phe Ile Lys Val Leu Lys Ala Tyr Asn Gln Thr His Leu Tyr Ala Cys
            100                 105                 110

Gly Thr Gly Ala Phe His Pro Ile Cys Thr Tyr Ile Glu Ile Gly His
        115                 120                 125

His Pro Glu Asp Asn Ile Phe Lys Leu Glu Asn Ser His Phe Glu Asn
130                 135                 140

Gly Arg Gly Lys Ser Pro Tyr Asp Pro Lys Leu Leu Thr Ala Ser Leu
145                 150                 155                 160

Leu Ile Asp Gly Glu Leu Tyr Ser Gly Thr Ala Ala Asp Phe Met Gly
                165                 170                 175

Arg Asp Phe Ala Ile Phe Arg Thr Leu Gly His His His Pro Ile Arg
            180                 185                 190

Thr Glu Gln His Asp Ser Arg Trp Leu Asn Asp Pro Lys Phe Ile Ser
        195                 200                 205

Ala His Leu Ile Ser Glu Ser Asp Asn Pro Glu Asp Asp Lys Val Tyr
210                 215                 220

Phe Phe Phe Arg Glu Asn Ala Ile Asp Gly Glu His Ser Gly Lys Ala
225                 230                 235                 240

Thr His Ala Arg Ile Gly Gln Ile Cys Lys Asn Asp Phe Gly His Arg
                245                 250                 255

Arg Ser Leu Val Asn Lys Trp Thr Thr Phe Leu Lys Ala Arg Leu Ile
            260                 265                 270

Cys Ser Val Pro Gly Pro Asn Gly Ile Asp Thr His Phe Asp Glu Leu
        275                 280                 285

Gln Asp Val Phe Leu Met Asn Phe Lys Asp Pro Lys Asn Pro Val Val
290                 295                 300
```

```
Tyr Gly Val Phe Thr Thr Ser Ser Asn Ile Phe Lys Gly Ser Ala Val
305                 310                 315                 320

Cys Met Tyr Ser Met Ser Asp Val Arg Arg Val Phe Leu Gly Pro Tyr
            325                 330                 335

Ala His Arg Asp Gly Pro Asn Tyr Gln Trp Val Pro Tyr Gln Gly Arg
        340                 345                 350

Val Pro Tyr Pro Arg Pro Gly Thr Cys Pro Ser Lys Thr Phe Gly Gly
    355                 360                 365

Phe Asp Ser Thr Lys Asp Leu Pro Asp Val Ile Thr Phe Ala Arg
370                 375                 380

Ser His Pro Ala Met Tyr Asn Pro Val Phe Pro Met Asn Asn Arg Pro
385                 390                 395                 400

Ile Val Ile Lys Thr Asp Val Asn Tyr Gln Phe Thr Gln Ile Val Val
                405                 410                 415

Asp Arg Val Asp Ala Glu Asp Gly Gln Tyr Asp Val Met Phe Ile Gly
            420                 425                 430

Thr Asp Val Gly Thr Val Leu Lys Val Val Ser Ile Pro Lys Glu Thr
        435                 440                 445

Trp Tyr Asp Leu Glu Glu Val Leu Leu Glu Glu Met Thr Val Phe Arg
450                 455                 460

Glu Pro Thr Ala Ile Ser Ala Met Glu Leu Ser Thr Lys Gln Gln Gln
465                 470                 475                 480

Leu Tyr Ile Gly Ser Thr Ala Gly Val Ala Gln Leu Pro Leu His Arg
                485                 490                 495

Cys Asp Ile Tyr Gly Lys Ala Cys Ala Glu Cys Cys Leu Ala Arg Asp
            500                 505                 510

Pro Tyr Cys Ala Trp Asp Gly Ser Ala Cys Ser Arg Tyr Phe Pro Thr
        515                 520                 525

Ala Lys Ala Arg Thr Arg Ala Gln Asp Ile Arg Asn Gly Asp Pro Leu
    530                 535                 540

Thr His Cys Ser Asp Gly Gly Ile Glu Gly Arg Met Asp His His His
545                 550                 555                 560

His His His

<210> SEQ ID NO 583
<211> LENGTH: 563
<212> TYPE: PRT
<213> ORGANISM: Mus musculus (Mouse)

<400> SEQUENCE: 583

Asn Tyr Ala Asn Gly Lys Asn Asn Val Pro Arg Leu Lys Leu Ser Tyr
1               5                   10                  15

Lys Glu Met Leu Glu Ser Asn Asn Val Ile Thr Phe Asn Gly Leu Ala
            20                  25                  30

Asn Ser Ser Ser Tyr His Thr Phe Leu Leu Asp Glu Glu Arg Ser Arg
        35                  40                  45

Leu Tyr Val Gly Ala Lys Asp His Ile Phe Ser Phe Asn Leu Val Asn
    50                  55                  60

Ile Lys Asp Phe Gln Lys Ile Val Trp Pro Val Ser Tyr Thr Arg Arg
65                  70                  75                  80

Asp Glu Cys Lys Trp Ala Gly Lys Asp Ile Leu Lys Glu Cys Ala Asn
                85                  90                  95

Phe Ile Lys Val Leu Glu Ala Tyr Asn Gln Thr His Leu Tyr Ala Cys
            100                 105                 110
```

```
Gly Thr Gly Ala Phe His Pro Ile Cys Thr Tyr Ile Glu Val Gly His
            115                 120                 125

His Pro Glu Asp Asn Ile Phe Lys Leu Gln Asp Ser His Phe Glu Asn
        130                 135                 140

Gly Arg Gly Lys Ser Pro Tyr Asp Pro Lys Leu Leu Thr Ala Ser Leu
145                 150                 155                 160

Leu Ile Asp Gly Glu Leu Tyr Ser Gly Thr Ala Ala Asp Phe Met Gly
                165                 170                 175

Arg Asp Phe Ala Ile Phe Arg Thr Leu Gly His His Pro Ile Arg
                180                 185                 190

Thr Glu Gln His Asp Ser Arg Trp Leu Asn Asp Pro Arg Phe Ile Ser
            195                 200                 205

Ala His Leu Ile Pro Glu Ser Asp Asn Pro Glu Asp Asp Lys Val Tyr
        210                 215                 220

Phe Phe Phe Arg Glu Asn Ala Ile Asp Gly Glu His Ser Gly Lys Ala
225                 230                 235                 240

Thr His Ala Arg Ile Gly Gln Ile Cys Lys Asn Asp Phe Gly Gly His
                245                 250                 255

Arg Ser Leu Val Asn Lys Trp Thr Thr Phe Leu Lys Ala Arg Leu Ile
            260                 265                 270

Cys Ser Val Pro Gly Pro Asn Gly Ile Asp Thr His Phe Asp Glu Leu
        275                 280                 285

Gln Asp Val Phe Leu Met Asn Ser Lys Asp Pro Lys Asn Pro Ile Val
        290                 295                 300

Tyr Gly Val Phe Thr Thr Ser Ser Asn Ile Phe Lys Gly Ser Ala Val
305                 310                 315                 320

Cys Met Tyr Ser Met Ser Asp Val Arg Arg Val Phe Leu Gly Pro Tyr
                325                 330                 335

Ala His Arg Asp Gly Pro Asn Tyr Gln Trp Val Pro Tyr Gln Gly Arg
                340                 345                 350

Val Pro Tyr Pro Arg Pro Gly Thr Cys Pro Ser Lys Thr Phe Gly Gly
            355                 360                 365

Phe Asp Ser Thr Lys Asp Leu Pro Asp Val Ile Thr Phe Ala Arg
        370                 375                 380

Ser His Pro Ala Met Tyr Asn Pro Val Phe Pro Ile Asn Asn Arg Pro
385                 390                 395                 400

Ile Met Ile Lys Thr Asp Val Asn Tyr Gln Phe Thr Gln Ile Val Val
                405                 410                 415

Asp Arg Val Asp Ala Glu Asp Gly Gln Tyr Asp Val Met Phe Ile Gly
            420                 425                 430

Thr Asp Val Gly Thr Val Leu Lys Val Val Ser Val Pro Lys Glu Thr
        435                 440                 445

Trp His Asp Leu Glu Glu Ile Leu Leu Glu Glu Met Thr Val Phe Arg
        450                 455                 460

Glu Pro Thr Thr Ile Ser Ala Met Glu Leu Ser Thr Lys Gln Gln Gln
465                 470                 475                 480

Leu Tyr Ile Gly Ser Thr Ala Gly Val Ala Gln Leu Pro Leu His Arg
                485                 490                 495

Cys Asp Ile Tyr Gly Lys Ala Cys Ala Glu Cys Cys Leu Ala Arg Asp
                500                 505                 510

Pro Tyr Cys Ala Trp Asp Gly Ser Ser Cys Ser Arg Tyr Phe Pro Thr
            515                 520                 525
```

```
Ala Lys Ala Arg Thr Arg Ala Gln Asp Ile Arg Asn Gly Asp Pro Leu
    530                 535                 540

Thr His Cys Ser Asp Gly Gly Ile Glu Gly Arg Met Asp His His His
545                 550                 555                 560

His His His

<210> SEQ ID NO 584
<211> LENGTH: 563
<212> TYPE: PRT
<213> ORGANISM: Rattus norvegicus (Rat)

<400> SEQUENCE: 584

Asn Tyr Ala Asn Gly Lys Asn Asn Val Pro Arg Leu Lys Leu Ser Tyr
1               5                   10                  15

Lys Glu Met Leu Glu Ser Asn Asn Val Ile Thr Phe Asn Gly Leu Ala
            20                  25                  30

Asn Ser Ser Ser Tyr His Thr Phe Leu Leu Asp Glu Glu Arg Ser Arg
        35                  40                  45

Leu Tyr Val Gly Ala Lys Asp His Ile Phe Ser Phe Asn Leu Val Asn
50                  55                  60

Ile Lys Asp Phe Gln Lys Ile Val Trp Pro Val Ser Tyr Thr Arg Arg
65                  70                  75                  80

Asp Glu Cys Lys Trp Ala Gly Lys Asp Ile Leu Lys Glu Cys Ala Asn
                85                  90                  95

Phe Ile Lys Val Leu Lys Ala Tyr Asn Gln Thr His Leu Tyr Ala Cys
            100                 105                 110

Gly Thr Gly Ala Phe His Pro Ile Cys Thr Tyr Ile Glu Val Gly His
        115                 120                 125

His Pro Glu Asp Asn Ile Phe Lys Leu Gln Asp Ser His Phe Glu Asn
130                 135                 140

Gly Arg Gly Lys Ser Pro Tyr Asp Pro Lys Leu Leu Thr Ala Ser Leu
145                 150                 155                 160

Leu Ile Asp Gly Glu Leu Tyr Ser Gly Thr Ala Ala Asp Phe Met Gly
                165                 170                 175

Arg Asp Phe Ala Ile Phe Arg Thr Leu Gly His His His Pro Ile Arg
            180                 185                 190

Thr Glu Gln His Asp Ser Arg Trp Leu Asn Asp Pro Arg Phe Ile Ser
        195                 200                 205

Ala His Leu Ile Pro Glu Ser Asp Asn Pro Glu Asp Asp Lys Val Tyr
210                 215                 220

Phe Phe Phe Arg Glu Asn Ala Ile Asp Gly Glu His Ser Gly Lys Ala
225                 230                 235                 240

Thr His Ala Arg Ile Gly Gln Ile Cys Lys Asn Asp Phe Gly Gly His
                245                 250                 255

Arg Ser Leu Val Asn Lys Trp Thr Thr Phe Leu Lys Ala Arg Leu Ile
            260                 265                 270

Cys Ser Val Pro Gly Pro Asn Gly Ile Asp Thr His Phe Asp Glu Leu
        275                 280                 285

Gln Asp Val Phe Leu Met Asn Ser Lys Asp Pro Lys Asn Pro Ile Val
290                 295                 300

Tyr Gly Val Phe Thr Thr Ser Ser Asn Ile Phe Lys Gly Ser Ala Val
305                 310                 315                 320

Cys Met Tyr Ser Met Ser Asp Val Arg Arg Val Phe Leu Gly Pro Tyr
                325                 330                 335
```

```
Ala His Arg Asp Gly Pro Asn Tyr Gln Trp Val Pro Tyr Gln Gly Arg
            340                 345                 350

Val Pro Tyr Pro Arg Pro Gly Thr Cys Pro Ser Lys Thr Phe Gly Gly
        355                 360                 365

Phe Asp Ser Thr Lys Asp Leu Pro Asp Asp Val Ile Thr Phe Ala Arg
    370                 375                 380

Ser His Pro Ala Met Tyr Asn Pro Val Phe Pro Ile Asn Asn Arg Pro
385                 390                 395                 400

Ile Met Ile Lys Thr Asp Val Asn Tyr Gln Phe Thr Gln Ile Val Val
                405                 410                 415

Asp Arg Val Asp Ala Glu Asp Gly Gln Tyr Asp Val Met Phe Ile Gly
            420                 425                 430

Thr Asp Val Gly Thr Val Leu Lys Val Val Ser Val Pro Lys Glu Thr
        435                 440                 445

Trp His Asp Leu Glu Glu Val Leu Leu Glu Glu Met Thr Val Phe Arg
    450                 455                 460

Glu Pro Thr Thr Ile Ser Ala Met Glu Leu Ser Thr Lys Gln Gln Gln
465                 470                 475                 480

Leu Tyr Ile Gly Ser Thr Ala Gly Val Ala Gln Leu Pro Leu His Arg
                485                 490                 495

Cys Asp Ile Tyr Gly Lys Ala Cys Ala Glu Cys Cys Leu Ala Arg Asp
            500                 505                 510

Pro Tyr Cys Ala Trp Asp Gly Ser Cys Ser Arg Tyr Phe Pro Thr
        515                 520                 525

Ala Lys Ala Arg Thr Arg Ala Gln Asp Ile Arg Asn Gly Asp Pro Leu
    530                 535                 540

Thr His Cys Ser Asp Gly Gly Ile Glu Gly Arg Met Asp His His His
545                 550                 555                 560

His His His

<210> SEQ ID NO 585
<211> LENGTH: 563
<212> TYPE: PRT
<213> ORGANISM: Canis lupus familiaris (dog)

<400> SEQUENCE: 585

Asn Tyr Gln Asn Gly Lys Asn Asn Val Pro Arg Leu Lys Leu Ser Tyr
1               5                   10                  15

Lys Glu Met Leu Glu Ser Asn Ser Val Ile Thr Phe Asn Gly Leu Ala
            20                  25                  30

Asn Ser Ser Ser Tyr His Thr Phe Leu Leu Asp Glu Arg Ser Arg
        35                  40                  45

Leu Tyr Val Gly Ala Lys Asp His Ile Phe Ser Phe Asn Leu Val Asn
 50                 55                  60

Ile Lys Asp Phe Gln Lys Ile Val Trp Pro Val Ser Tyr Thr Arg Arg
65                  70                  75                  80

Asp Glu Cys Lys Trp Ala Gly Lys Asp Ile Gln Lys Glu Cys Ala Asn
            85                  90                  95

Phe Ile Lys Val Leu Lys Ala Tyr Asn Gln Thr His Leu Tyr Ala Cys
        100                 105                 110

Gly Thr Gly Ala Phe His Pro Ile Cys Thr Tyr Ile Glu Ile Gly His
    115                 120                 125

His Pro Glu Asp Asn Ile Phe Lys Leu Glu Asp Ser His Phe Glu Asn
        130                 135                 140
```

```
Gly Arg Gly Lys Ser Pro Tyr Asp Pro Lys Leu Leu Thr Ala Ser Leu
145                 150                 155                 160

Leu Ile Asp Gly Glu Leu Tyr Ser Gly Thr Ala Ala Asp Phe Met Gly
            165                 170                 175

Arg Asp Phe Ala Ile Phe Arg Thr Leu Gly His His Pro Ile Arg
            180                 185                 190

Thr Glu Gln His Asp Ser Arg Trp Leu Asn Asp Pro Arg Phe Ile Ser
            195                 200                 205

Ala His Leu Ile Pro Glu Ser Asp Asn Pro Glu Asp Lys Val Tyr
    210                 215                 220

Phe Phe Phe Arg Glu Asn Ala Ile Asp Gly Glu His Thr Gly Lys Ala
225                 230                 235                 240

Thr His Ala Arg Ile Gly Gln Ile Cys Lys Asn Asp Phe Gly Gly His
                245                 250                 255

Arg Ser Leu Val Asn Lys Trp Thr Thr Phe Leu Lys Ala Arg Leu Ile
                260                 265                 270

Cys Ser Val Pro Gly Pro Asn Gly Ile Asp Thr His Phe Asp Glu Leu
                275                 280                 285

Gln Asp Val Phe Leu Met Asn Ser Lys Asp Pro Lys Asn Pro Ile Val
    290                 295                 300

Tyr Gly Val Phe Thr Thr Ser Ser Asn Ile Phe Lys Gly Ser Ala Val
305                 310                 315                 320

Cys Met Tyr Ser Met Ser Asp Val Arg Arg Val Phe Leu Gly Pro Tyr
                325                 330                 335

Ala His Arg Asp Gly Pro Asn Tyr Gln Trp Val Pro Tyr Gln Gly Arg
            340                 345                 350

Val Pro Tyr Pro Arg Pro Gly Thr Cys Pro Ser Lys Thr Phe Gly Gly
                355                 360                 365

Phe Asp Ser Thr Lys Asp Leu Pro Asp Val Ile Thr Phe Ala Arg
370                 375                 380

Ser His Pro Ala Met Tyr Asn Pro Val Phe Pro Ile Asn Asn Arg Pro
385                 390                 395                 400

Ile Met Ile Lys Thr Asp Val Asn Tyr Gln Phe Thr Gln Ile Val Val
                405                 410                 415

Asp Arg Val Asp Ala Glu Asp Gly Gln Tyr Asp Val Met Phe Ile Gly
                420                 425                 430

Thr Asp Val Gly Thr Val Leu Lys Val Val Ser Ile Pro Lys Glu Thr
            435                 440                 445

Trp His Asp Leu Glu Glu Val Leu Leu Glu Glu Met Thr Val Phe Arg
    450                 455                 460

Glu Pro Thr Pro Ile Ser Ala Met Glu Leu Ser Thr Lys Gln His Gln
465                 470                 475                 480

Leu Tyr Ala Gly Ser Pro Ala Gly Leu Ala Gln Leu Pro Leu Gln Arg
                485                 490                 495

Cys Ala Ala Tyr Gly Arg Ala Cys Ala Glu Cys Cys Leu Ala Arg Asp
            500                 505                 510

Pro Tyr Cys Ala Trp Asp Gly Ala Ala Cys Ser Arg Tyr Phe Pro Ala
    515                 520                 525

Ala Lys Ala Arg Thr Arg Ala Gln Asp Ile Arg Asn Gly Asp Pro Leu
    530                 535                 540

Thr His Cys Ser Asp Gly Gly Ile Glu Gly Arg Met Asp His His His
545                 550                 555                 560

His His His
```

<210> SEQ ID NO 586
<211> LENGTH: 563
<212> TYPE: PRT
<213> ORGANISM: Macaca fascicularis (Cynomolgus monkey)

<400> SEQUENCE: 586

| Asn | Tyr | Gln | Asn | Gly | Lys | Asn | Val | Pro | Arg | Leu | Lys | Leu | Ser | Tyr |
| 1 | | | | 5 | | | | | 10 | | | | | 15 |

Lys Glu Met Leu Glu Ser Asn Asn Val Ile Thr Phe Asn Gly Leu Ala
                20                  25                  30

Asn Ser Ser Tyr His Thr Phe Leu Leu Asp Glu Glu Arg Ser Arg
        35                  40                  45

Leu Tyr Val Gly Ala Lys Asp His Ile Phe Ser Phe Asn Leu Val Asn
 50                  55                  60

Ile Lys Asp Phe Gln Lys Ile Val Trp Pro Val Ser Tyr Thr Arg Arg
65                  70                  75                  80

Asp Glu Cys Lys Trp Ala Gly Lys Asp Ile Leu Lys Glu Cys Ala Asn
                85                  90                  95

Phe Ile Lys Val Leu Lys Ala Tyr Asn Gln Thr His Leu Tyr Ala Cys
            100                 105                 110

Gly Thr Gly Ala Phe His Pro Ile Cys Thr Tyr Ile Glu Ile Gly His
        115                 120                 125

His Pro Glu Asp Asn Ile Phe Lys Leu Glu Asn Ser His Phe Glu Asn
    130                 135                 140

Gly Arg Gly Lys Ser Pro Tyr Asp Pro Lys Leu Leu Thr Ala Ser Leu
145                 150                 155                 160

Leu Ile Asp Gly Glu Leu Tyr Ser Gly Thr Ala Ala Asp Phe Met Gly
                165                 170                 175

Arg Asp Phe Ala Ile Phe Arg Thr Leu Gly His His His Pro Ile Arg
            180                 185                 190

Thr Glu Gln His Asp Ser Arg Trp Leu Asn Asp Pro Arg Phe Ile Ser
        195                 200                 205

Ala His Leu Ile Pro Glu Ser Asp Asn Pro Glu Asp Asp Lys Val Tyr
    210                 215                 220

Phe Phe Phe Arg Glu Asn Ala Ile Asp Gly Glu His Ser Gly Lys Ala
225                 230                 235                 240

Thr His Ala Arg Ile Gly Gln Ile Cys Lys Asn Asp Phe Gly Gly His
                245                 250                 255

Arg Ser Leu Val Asn Lys Trp Thr Thr Phe Leu Lys Ala Arg Leu Ile
            260                 265                 270

Cys Ser Val Pro Gly Pro Asn Gly Ile Asp Thr His Phe Asp Glu Leu
        275                 280                 285

Gln Asp Val Phe Leu Met Asn Phe Lys Asp Pro Lys Asn Pro Ile Val
    290                 295                 300

Tyr Gly Val Phe Thr Thr Ser Ser Asn Ile Phe Lys Gly Ser Ala Val
305                 310                 315                 320

Cys Met Tyr Ser Met Ser Asp Val Arg Arg Val Phe Leu Gly Pro Tyr
                325                 330                 335

Ala His Arg Asp Gly Pro Asn Tyr Gln Trp Val Pro Tyr Gln Gly Arg
            340                 345                 350

Val Pro Tyr Pro Arg Pro Gly Thr Cys Pro Ser Lys Thr Phe Gly Gly
        355                 360                 365

Phe Asp Ser Thr Lys Asp Leu Pro Asp Asp Val Ile Thr Phe Ala Arg

```
              370                 375                 380
Ser His Pro Ala Met Tyr Asn Pro Val Phe Pro Ile Asn Asn Arg Pro
385                 390                 395                 400

Ile Met Ile Lys Thr Asp Val Asn Tyr Gln Phe Thr Gln Ile Val Val
                405                 410                 415

Asp Arg Val Asp Ala Glu Asp Gly Gln Tyr Asp Val Met Phe Ile Gly
                420                 425                 430

Thr Asp Val Gly Thr Val Leu Lys Val Val Ser Ile Pro Lys Glu Thr
                435                 440                 445

Trp His Asp Leu Glu Glu Val Leu Leu Glu Glu Met Thr Val Phe Arg
                450                 455                 460

Glu Pro Thr Thr Ile Ser Ala Met Glu Leu Ser Thr Lys Gln Gln Gln
465                 470                 475                 480

Leu Tyr Ile Gly Ser Thr Ala Gly Ile Ala Gln Leu Pro Leu His Arg
                485                 490                 495

Cys Asp Ile Tyr Gly Lys Ala Cys Ala Glu Cys Cys Leu Ala Arg Asp
                500                 505                 510

Pro Tyr Cys Ala Trp Asp Gly Ser Ser Cys Ser Arg Tyr Phe Pro Thr
                515                 520                 525

Ala Lys Ala Arg Thr Arg Ala Gln Asp Ile Arg Asn Gly Asp Pro Leu
                530                 535                 540

Thr His Cys Ser Asp Gly Gly Ile Glu Gly Arg Met Asp His His His
545                 550                 555                 560

His His His
```

<210> SEQ ID NO 587
<211> LENGTH: 563
<212> TYPE: PRT
<213> ORGANISM: Sus scrofa (Pig)

<400> SEQUENCE: 587

```
Asn Tyr Gln Asn Gly Lys Asn Asn Val Pro Arg Leu Lys Leu Ser Tyr
1               5                   10                  15

Lys Glu Met Leu Glu Ser Asn Asn Val Ile Thr Phe Asn Gly Leu Ala
                20                  25                  30

Asn Ser Ser Ser Tyr His Thr Phe Leu Leu Asp Glu Glu Arg Ser Arg
            35                  40                  45

Leu Tyr Val Gly Ala Lys Asp His Ile Phe Ser Phe Asn Leu Val Asn
50                  55                  60

Ile Lys Asp Phe Gln Lys Ile Val Trp Pro Val Ser Tyr Thr Arg Arg
65                  70                  75                  80

Asp Glu Cys Lys Trp Ala Gly Lys Asp Ile Leu Lys Glu Cys Ala Asn
                85                  90                  95

Phe Ile Lys Val Leu Lys Ala Tyr Asn Gln Thr His Leu Tyr Ala Cys
                100                 105                 110

Gly Thr Gly Ala Phe His Pro Ile Cys Thr Tyr Ile Glu Ile Gly His
                115                 120                 125

His Pro Glu Asp Asn Ile Phe Lys Leu Glu Asp Ser His Phe Glu Asn
                130                 135                 140

Gly Arg Gly Lys Ser Pro Tyr Asp Pro Lys Leu Leu Thr Ala Ser Leu
145                 150                 155                 160

Leu Ile Asp Gly Glu Leu Tyr Ser Gly Thr Ala Ala Asp Phe Met Gly
                165                 170                 175

Arg Asp Phe Ala Ile Phe Arg Thr Leu Gly His His His Pro Ile Arg
```

```
                180             185             190
Thr Gln His Asp Ser Arg Trp Leu Asn Asp Pro Arg Phe Ile Ser
            195             200             205
Ala His Leu Ile Pro Glu Ser Asp Asn Pro Glu Asp Lys Val Tyr
        210             215             220
Phe Phe Arg Glu Asn Ala Ile Asp Gly Glu His Thr Gly Lys Ala
225             230             235             240
Thr His Ala Arg Ile Gly Gln Ile Cys Lys Asn Asp Phe Gly His
            245             250             255
Arg Ser Leu Val Asn Lys Trp Thr Thr Phe Leu Lys Ala Arg Leu Ile
        260             265             270
Cys Ser Val Pro Gly Pro Asn Gly Ile Asp Thr His Phe Asp Glu Leu
        275             280             285
Gln Asp Val Phe Leu Met Asn Ser Lys Asp Pro Lys Asn Pro Val Val
        290             295             300
Tyr Gly Val Phe Thr Thr Ser Ser Asn Ile Phe Lys Gly Ser Ala Val
305             310             315             320
Cys Met Tyr Ser Met Ser Asp Val Arg Arg Val Phe Leu Gly Pro Tyr
            325             330             335
Ala His Arg Asp Gly Pro Asn Tyr Gln Trp Val Pro Tyr Gln Gly Arg
            340             345             350
Val Pro Tyr Pro Arg Pro Gly Thr Cys Pro Ser Lys Thr Phe Gly Gly
            355             360             365
Phe Asp Ser Thr Lys Asp Leu Pro Asp Asp Val Ile Thr Phe Ala Arg
        370             375             380
Ser His Pro Ala Met Tyr Asn Pro Val Phe Pro Ile Asn Asn Arg Pro
385             390             395             400
Ile Met Ile Lys Thr Asp Val Asn Tyr Gln Phe Thr Gln Ile Val Val
            405             410             415
Asp Arg Val Asp Ala Glu Asp Gly Gln Tyr Asp Val Met Phe Ile Gly
            420             425             430
Thr Asp Val Gly Thr Val Leu Lys Val Val Ser Ile Pro Lys Glu Thr
        435             440             445
Trp His Asp Leu Glu Glu Val Leu Leu Glu Met Thr Val Phe Arg
450             455             460
Glu Pro Thr Thr Ile Ser Ala Met Glu Leu Ser Thr Lys Gln Gln Gln
465             470             475             480
Leu Tyr Val Gly Ser Ala Ala Gly Val Ala Gln Leu Pro Leu His Arg
            485             490             495
Cys Asp Ile Tyr Gly Lys Ala Cys Ala Glu Cys Cys Leu Ala Arg Asp
        500             505             510
Pro Tyr Cys Ala Trp Asp Gly Ser Ser Cys Ser Arg Tyr Phe Pro Thr
        515             520             525
Ala Lys Ala Arg Thr Arg Ala Gln Asp Ile Arg Asn Gly Asp Pro Leu
        530             535             540
Thr His Cys Ser Asp Gly Gly Ile Glu Gly Arg Met Asp His His His
545             550             555             560
His His His

<210> SEQ ID NO 588
<211> LENGTH: 5
<212> TYPE: PRT
<213> ORGANISM: artificial
<220> FEATURE:
```

```
<223> OTHER INFORMATION: antibody sequence
<220> FEATURE:
<221> NAME/KEY: site
<222> LOCATION: (3)..(3)
<223> OTHER INFORMATION: Xaa can be any naturally occurring amino acid
<220> FEATURE:
<221> NAME/KEY: site
<222> LOCATION: (5)..(5)
<223> OTHER INFORMATION: Xaa can be any naturally occurring amino acid

<400> SEQUENCE: 588

Ser Tyr Xaa Met Xaa
1               5

<210> SEQ ID NO 589
<211> LENGTH: 5
<212> TYPE: PRT
<213> ORGANISM: artificial
<220> FEATURE:
<223> OTHER INFORMATION: antibody sequence
<220> FEATURE:
<221> NAME/KEY: site
<222> LOCATION: (5)..(5)
<223> OTHER INFORMATION: Xaa can be any naturally occurring amino acid

<400> SEQUENCE: 589

Ser Tyr Ala Met Xaa
1               5

<210> SEQ ID NO 590
<211> LENGTH: 16
<212> TYPE: PRT
<213> ORGANISM: artificial
<220> FEATURE:
<223> OTHER INFORMATION: antibody sequence
<220> FEATURE:
<221> NAME/KEY: site
<222> LOCATION: (4)..(4)
<223> OTHER INFORMATION: Xaa can be any naturally occurring amino acid
<220> FEATURE:
<221> NAME/KEY: site
<222> LOCATION: (15)..(15)
<223> OTHER INFORMATION: Xaa can be any naturally occurring amino acid

<400> SEQUENCE: 590

Ala Ile Gly Xaa Gly Gly Asp Thr Tyr Tyr Ala Asp Ser Val Xaa Gly
1               5                   10                  15

<210> SEQ ID NO 591
<211> LENGTH: 16
<212> TYPE: PRT
<213> ORGANISM: artificial
<220> FEATURE:
<223> OTHER INFORMATION: antibody sequence
<220> FEATURE:
<221> NAME/KEY: site
<222> LOCATION: (4)..(4)
<223> OTHER INFORMATION: Xaa can be any naturally occurring amino acid

<400> SEQUENCE: 591

Ala Ile Gly Xaa Gly Gly Asp Thr Tyr Tyr Ala Asp Ser Val Lys Gly
1               5                   10                  15

<210> SEQ ID NO 592
<211> LENGTH: 17
<212> TYPE: PRT
<213> ORGANISM: artificial
<220> FEATURE:
<223> OTHER INFORMATION: antibody sequence
<220> FEATURE:
<221> NAME/KEY: site
```

```
<222> LOCATION: (8)..(8)
<223> OTHER INFORMATION: Xaa can be any naturally occurring amino acid
<220> FEATURE:
<221> NAME/KEY: site
<222> LOCATION: (10)..(10)
<223> OTHER INFORMATION: Xaa can be any naturally occurring amino acid

<400> SEQUENCE: 592

Gly Ile Ser Trp Asn Ser Gly Xaa Ile Xaa Tyr Ala Asp Ser Val Lys
1               5                   10                  15

Gly

<210> SEQ ID NO 593
<211> LENGTH: 17
<212> TYPE: PRT
<213> ORGANISM: artificial
<220> FEATURE:
<223> OTHER INFORMATION: antibody sequence
<220> FEATURE:
<221> NAME/KEY: site
<222> LOCATION: (10)..(10)
<223> OTHER INFORMATION: Xaa can be any naturally occurring amino acid

<400> SEQUENCE: 593

Gly Ile Ser Trp Asn Ser Gly Trp Ile Xaa Tyr Ala Asp Ser Val Lys
1               5                   10                  15

Gly

<210> SEQ ID NO 594
<211> LENGTH: 12
<212> TYPE: PRT
<213> ORGANISM: artificial
<220> FEATURE:
<223> OTHER INFORMATION: antibody sequence
<220> FEATURE:
<221> NAME/KEY: site
<222> LOCATION: (12)..(12)
<223> OTHER INFORMATION: Xaa can be any naturally occurring amino acid

<400> SEQUENCE: 594

Arg Asp Asp Tyr Thr Ser Arg Asp Ala Phe Asp Xaa
1               5                   10

<210> SEQ ID NO 595
<211> LENGTH: 14
<212> TYPE: PRT
<213> ORGANISM: artificial
<220> FEATURE:
<223> OTHER INFORMATION: antibody sequence
<220> FEATURE:
<221> NAME/KEY: site
<222> LOCATION: (6)..(6)
<223> OTHER INFORMATION: Xaa can be any naturally occurring amino acid

<400> SEQUENCE: 595

Thr Gly Ser Ser Ser Xaa Ile Gly Ala Gly Tyr Asp Val His
1               5                   10

<210> SEQ ID NO 596
<211> LENGTH: 7
<212> TYPE: PRT
<213> ORGANISM: Artificial Sequence
<220> FEATURE:
<223> OTHER INFORMATION: antibody sequence
<220> FEATURE:
<221> NAME/KEY: site
<222> LOCATION: (5)..(5)
<223> OTHER INFORMATION: Xaa can be any naturally occurring amino acid
```

```
<400> SEQUENCE: 596

Tyr Asp Asp Leu Xaa Pro Ser
1               5

<210> SEQ ID NO 597
<211> LENGTH: 7
<212> TYPE: PRT
<213> ORGANISM: artificial
<220> FEATURE:
<223> OTHER INFORMATION: antibody sequence
<220> FEATURE:
<221> NAME/KEY: site
<222> LOCATION: (2)..(2)
<223> OTHER INFORMATION: Xaa can be any naturally occurring amino acid

<400> SEQUENCE: 597

Gly Xaa Ser Asn Arg Pro Ser
1               5

<210> SEQ ID NO 598
<211> LENGTH: 12
<212> TYPE: PRT
<213> ORGANISM: artificial
<220> FEATURE:
<223> OTHER INFORMATION: antibody sequence
<220> FEATURE:
<221> NAME/KEY: site
<222> LOCATION: (1)..(1)
<223> OTHER INFORMATION: Xaa can be any naturally occurring amino acid
<220> FEATURE:
<221> NAME/KEY: site
<222> LOCATION: (9)..(11)
<223> OTHER INFORMATION: Xaa can be any naturally occurring amino acid

<400> SEQUENCE: 598

Xaa Ala Trp Asp Asp Ser Leu Asn Xaa Xaa Xaa Val
1               5                   10

<210> SEQ ID NO 599
<211> LENGTH: 11
<212> TYPE: PRT
<213> ORGANISM: artificial
<220> FEATURE:
<223> OTHER INFORMATION: antibody sequence
<220> FEATURE:
<221> NAME/KEY: site
<222> LOCATION: (1)..(1)
<223> OTHER INFORMATION: Xaa can be any naturally occurring amino acid
<220> FEATURE:
<221> NAME/KEY: site
<222> LOCATION: (4)..(4)
<223> OTHER INFORMATION: Xaa can be any naturally occurring amino acid
<220> FEATURE:
<221> NAME/KEY: site
<222> LOCATION: (6)..(6)
<223> OTHER INFORMATION: Xaa can be any naturally occurring amino acid

<400> SEQUENCE: 599

Xaa Ser Tyr Xaa Gly Xaa Asn Pro Tyr Val Val
1               5                   10

<210> SEQ ID NO 600
<211> LENGTH: 750
<212> TYPE: PRT
<213> ORGANISM: Homo sapiens

<400> SEQUENCE: 600

Tyr Gln Asn Gly Lys Asn Asn Val Pro Arg Leu Lys Leu Ser Tyr Lys
1               5                   10                  15
```

-continued

```
Glu Met Leu Glu Ser Asn Asn Val Ile Thr Phe Asn Gly Leu Ala Asn
         20                  25                  30

Ser Ser Ser Tyr His Thr Phe Leu Leu Asp Glu Glu Arg Ser Arg Leu
     35                  40                  45

Tyr Val Gly Ala Lys Asp His Ile Phe Ser Phe Asp Leu Val Asn Ile
 50                  55                  60

Lys Asp Phe Gln Lys Ile Val Trp Pro Val Ser Tyr Thr Arg Arg Asp
 65                  70                  75                  80

Glu Cys Lys Trp Ala Gly Lys Asp Ile Leu Lys Glu Cys Ala Asn Phe
                 85                  90                  95

Ile Lys Val Leu Lys Ala Tyr Asn Gln Thr His Leu Tyr Ala Cys Gly
                100                 105                 110

Thr Gly Ala Phe His Pro Ile Cys Thr Tyr Ile Glu Ile Gly His His
             115                 120                 125

Pro Glu Asp Asn Ile Phe Lys Leu Glu Asn Ser His Phe Glu Asn Gly
         130                 135                 140

Arg Gly Lys Ser Pro Tyr Asp Pro Lys Leu Leu Thr Ala Ser Leu Leu
145                 150                 155                 160

Ile Asp Gly Glu Leu Tyr Ser Gly Thr Ala Ala Asp Phe Met Gly Arg
                 165                 170                 175

Asp Phe Ala Ile Phe Arg Thr Leu Gly His His His Pro Ile Arg Thr
             180                 185                 190

Glu Gln His Asp Ser Arg Trp Leu Asn Asp Pro Lys Phe Ile Ser Ala
         195                 200                 205

His Leu Ile Ser Glu Ser Asp Asn Pro Glu Asp Asp Lys Val Tyr Phe
210                 215                 220

Phe Phe Arg Glu Asn Ala Ile Asp Gly Glu His Ser Gly Lys Ala Thr
225                 230                 235                 240

His Ala Arg Ile Gly Gln Ile Cys Lys Asn Asp Phe Gly Gly His Arg
                 245                 250                 255

Ser Leu Val Asn Lys Trp Thr Thr Phe Leu Lys Ala Arg Leu Ile Cys
             260                 265                 270

Ser Val Pro Gly Pro Asn Gly Ile Asp Thr His Phe Asp Glu Leu Gln
         275                 280                 285

Asp Val Phe Leu Met Asn Phe Lys Asp Pro Lys Asn Pro Val Val Tyr
     290                 295                 300

Gly Val Phe Thr Thr Ser Ser Asn Ile Phe Lys Gly Ser Ala Val Cys
305                 310                 315                 320

Met Tyr Ser Met Ser Asp Val Arg Arg Val Phe Leu Gly Pro Tyr Ala
                 325                 330                 335

His Arg Asp Gly Pro Asn Tyr Gln Trp Val Pro Tyr Gln Gly Arg Val
             340                 345                 350

Pro Tyr Pro Arg Pro Gly Thr Cys Pro Ser Lys Thr Phe Gly Gly Phe
         355                 360                 365

Asp Ser Thr Lys Asp Leu Pro Asp Val Ile Thr Phe Ala Arg Ser
     370                 375                 380

His Pro Ala Met Tyr Asn Pro Val Phe Pro Met Asn Asn Arg Pro Ile
385                 390                 395                 400

Val Ile Lys Thr Asp Val Asn Tyr Gln Phe Thr Gln Ile Val Val Asp
                 405                 410                 415

Arg Val Asp Ala Glu Asp Gly Gln Tyr Asp Val Met Phe Ile Gly Thr
             420                 425                 430

Asp Val Gly Thr Val Leu Lys Val Val Ser Ile Pro Lys Glu Thr Trp
```

```
                     435                 440                 445
Tyr Asp Leu Glu Glu Val Leu Leu Glu Met Thr Val Phe Arg Glu
450                 455                 460
Pro Thr Ala Ile Ser Ala Met Glu Leu Ser Thr Lys Gln Gln Leu
465                 470                 475                 480
Tyr Ile Gly Ser Thr Ala Gly Val Ala Gln Leu Pro Leu His Arg Cys
                485                 490                 495
Asp Ile Tyr Gly Lys Ala Cys Ala Glu Cys Cys Leu Ala Arg Asp Pro
                500                 505                 510
Tyr Cys Ala Trp Asp Gly Ser Ala Cys Ser Arg Tyr Phe Pro Thr Ala
                515                 520                 525
Lys Arg Arg Thr Arg Arg Gln Asp Ile Arg Asn Gly Asp Pro Leu Thr
530                 535                 540
His Cys Ser Asp Leu His His Asp Asn His His Gly His Ser Pro Glu
545                 550                 555                 560
Glu Arg Ile Ile Tyr Gly Val Glu Asn Ser Ser Thr Phe Leu Glu Cys
                565                 570                 575
Ser Pro Lys Ser Gln Arg Ala Leu Val Tyr Trp Gln Phe Gln Arg Arg
                580                 585                 590
Asn Glu Glu Arg Lys Glu Glu Ile Arg Val Asp Asp His Ile Ile Arg
                595                 600                 605
Thr Asp Gln Gly Leu Leu Leu Arg Ser Leu Gln Gln Lys Asp Ser Gly
610                 615                 620
Asn Tyr Leu Cys His Ala Val Glu His Gly Phe Ile Gln Thr Leu Leu
625                 630                 635                 640
Lys Val Thr Leu Glu Val Ile Asp Thr Glu His Leu Glu Glu Leu Leu
                645                 650                 655
His Lys Asp Asp Asp Gly Asp Gly Ser Lys Thr Lys Glu Met Ser Asn
                660                 665                 670
Ser Met Thr Pro Ser Gln Lys Val Trp Tyr Arg Asp Phe Met Gln Leu
                675                 680                 685
Ile Asn His Pro Asn Leu Asn Thr Met Asp Glu Phe Cys Glu Gln Val
690                 695                 700
Trp Lys Arg Asp Arg Lys Gln Arg Arg Gln Arg Pro Gly His Thr Pro
705                 710                 715                 720
Gly Asn Ser Asn Lys Trp Lys His Leu Gln Glu Asn Lys Lys Gly Arg
                725                 730                 735
Asn Arg Arg Thr His Glu Phe Glu Arg Ala Pro Arg Ser Val
                740                 745                 750

<210> SEQ ID NO 601
<211> LENGTH: 752
<212> TYPE: PRT
<213> ORGANISM: Mus musculus

<400> SEQUENCE: 601

Asn Tyr Ala Asn Gly Lys Asn Asn Val Pro Arg Leu Lys Leu Ser Tyr
1               5                   10                  15
Lys Glu Met Leu Glu Ser Asn Asn Val Ile Thr Phe Asn Gly Leu Ala
                20                  25                  30
Asn Ser Ser Ser Tyr His Thr Phe Leu Leu Asp Glu Glu Arg Ser Arg
            35                  40                  45
Leu Tyr Val Gly Ala Lys Asp His Ile Phe Ser Phe Asn Leu Val Asn
50                  55                  60
```

```
Ile Lys Asp Phe Gln Lys Ile Val Trp Pro Val Ser Tyr Thr Arg Arg
 65                  70                  75                  80

Asp Glu Cys Lys Trp Ala Gly Lys Asp Ile Leu Lys Glu Cys Ala Asn
                 85                  90                  95

Phe Ile Lys Val Leu Glu Ala Tyr Asn Gln Thr His Leu Tyr Ala Cys
            100                 105                 110

Gly Thr Gly Ala Phe His Pro Ile Cys Thr Tyr Ile Glu Val Gly His
        115                 120                 125

His Pro Glu Asp Asn Ile Phe Lys Leu Gln Asp Ser His Phe Glu Asn
    130                 135                 140

Gly Arg Gly Lys Ser Pro Tyr Asp Pro Lys Leu Leu Thr Ala Ser Leu
145                 150                 155                 160

Leu Ile Asp Gly Glu Leu Tyr Ser Gly Thr Ala Ala Asp Phe Met Gly
                165                 170                 175

Arg Asp Phe Ala Ile Phe Arg Thr Leu Gly His His His Pro Ile Arg
            180                 185                 190

Thr Glu Gln His Asp Ser Arg Trp Leu Asn Asp Pro Arg Phe Ile Ser
        195                 200                 205

Ala His Leu Ile Pro Glu Ser Asp Asn Pro Glu Asp Asp Lys Val Tyr
    210                 215                 220

Phe Phe Phe Arg Glu Asn Ala Ile Asp Gly Glu His Ser Gly Lys Ala
225                 230                 235                 240

Thr His Ala Arg Ile Gly Gln Ile Cys Lys Asn Asp Phe Gly Gly His
                245                 250                 255

Arg Ser Leu Val Asn Lys Trp Thr Thr Phe Leu Lys Ala Arg Leu Ile
            260                 265                 270

Cys Ser Val Pro Gly Pro Asn Gly Ile Asp Thr His Phe Asp Glu Leu
        275                 280                 285

Gln Asp Val Phe Leu Met Asn Ser Lys Asp Pro Lys Asn Pro Ile Val
    290                 295                 300

Tyr Gly Val Phe Thr Thr Ser Ser Asn Ile Phe Lys Gly Ser Ala Val
305                 310                 315                 320

Cys Met Tyr Ser Met Ser Asp Val Arg Arg Val Phe Leu Gly Pro Tyr
                325                 330                 335

Ala His Arg Asp Gly Pro Asn Tyr Gln Trp Val Pro Tyr Gln Gly Arg
            340                 345                 350

Val Pro Tyr Pro Arg Pro Gly Thr Cys Pro Ser Lys Thr Phe Gly Gly
        355                 360                 365

Phe Asp Ser Thr Lys Asp Leu Pro Asp Val Ile Thr Phe Ala Arg
    370                 375                 380

Ser His Pro Ala Met Tyr Asn Pro Val Phe Pro Ile Asn Asn Arg Pro
385                 390                 395                 400

Ile Met Ile Lys Thr Asp Val Asn Tyr Gln Phe Thr Gln Ile Val Val
                405                 410                 415

Asp Arg Val Asp Ala Glu Asp Gly Gln Tyr Asp Val Met Phe Ile Gly
            420                 425                 430

Thr Asp Val Gly Thr Val Leu Lys Val Ser Val Pro Lys Glu Thr
        435                 440                 445

Trp His Asp Leu Glu Glu Val Leu Glu Glu Met Thr Val Phe Arg
    450                 455                 460

Glu Pro Thr Thr Ile Ser Ala Met Glu Leu Ser Thr Lys Gln Gln Gln
465                 470                 475                 480

Leu Tyr Ile Gly Ser Thr Ala Gly Val Ala Gln Leu Pro Leu His Arg
```

```
                    485                 490                 495
Cys Asp Ile Tyr Gly Lys Ala Cys Glu Cys Cys Leu Ala Arg Asp
                500                 505                 510

Pro Tyr Cys Ala Trp Asp Gly Ser Cys Ser Arg Tyr Phe Pro Thr
                515                 520                 525

Ala Lys Arg Arg Thr Arg Gln Asp Ile Arg Asn Gly Asp Pro Leu
                530                 535                 540

Thr His Cys Ser Asp Leu Gln His His Asp Asn His His Gly Pro Ser
545                 550                 555                 560

Leu Glu Glu Arg Ile Ile Tyr Gly Val Glu Asn Ser Ser Thr Phe Leu
                565                 570                 575

Glu Cys Ser Pro Lys Ser Gln Arg Ala Leu Val Tyr Trp Gln Phe Gln
                580                 585                 590

Arg Arg Asn Glu Asp Arg Lys Glu Glu Ile Arg Met Gly Asp His Ile
                595                 600                 605

Ile Arg Thr Glu Gln Gly Leu Leu Leu Arg Ser Leu Gln Lys Lys Asp
                610                 615                 620

Ser Gly Asn Tyr Leu Cys His Ala Val Glu His Gly Phe Met Gln Thr
625                 630                 635                 640

Leu Leu Lys Val Thr Leu Glu Val Ile Asp Thr Glu His Leu Glu Glu
                645                 650                 655

Leu Leu His Lys Asp Asp Asp Gly Asp Gly Ser Lys Ile Lys Glu Met
                660                 665                 670

Ser Ser Ser Met Thr Pro Ser Gln Lys Val Trp Tyr Arg Asp Phe Met
                675                 680                 685

Gln Leu Ile Asn His Pro Asn Leu Asn Thr Met Asp Glu Phe Cys Glu
                690                 695                 700

Gln Val Trp Lys Arg Asp Arg Lys Gln Arg Gln Arg Pro Gly His
705                 710                 715                 720

Ser Gln Gly Ser Ser Asn Lys Trp Lys His Met Gln Glu Ser Lys Lys
                725                 730                 735

Gly Arg Asn Arg Arg Thr His Glu Phe Glu Arg Ala Pro Arg Ser Val
                740                 745                 750

<210> SEQ ID NO 602
<211> LENGTH: 772
<212> TYPE: PRT
<213> ORGANISM: Macaca fascicularis

<400> SEQUENCE: 602

Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
                20                  25                  30

Lys Leu Ser Tyr Lys Glu Met Leu Glu Ser Asn Asn Val Ile Thr Phe
                35                  40                  45

Asn Gly Leu Ala Asn Ser Ser Ser Tyr His Thr Phe Leu Leu Asp Glu
                50                  55                  60

Glu Arg Ser Arg Leu Tyr Val Gly Ala Lys Asp His Ile Phe Ser Phe
65                  70                  75                  80

Asn Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
                100                 105                 110
```

```
Glu Cys Ala Asn Phe Ile Lys Val Leu Lys Ala Tyr Asn Gln Thr His
            115                 120                 125

Leu Tyr Ala Cys Gly Thr Gly Ala Phe His Pro Ile Cys Thr Tyr Ile
        130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
210                 215                 220

Arg Phe Ile Ser Ala His Leu Ile Pro Glu Ser Asp Asn Pro Glu Asp
225                 230                 235                 240

Asp Lys Val Tyr Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
        290                 295                 300

Phe Asp Glu Leu Gln Asp Val Phe Leu Met Asn Phe Lys Asp Pro Lys
305                 310                 315                 320

Asn Pro Ile Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Ile
                405                 410                 415

Asn Asn Arg Pro Ile Met Ile Lys Thr Asp Val Asn Tyr Gln Phe Thr
            420                 425                 430

Gln Ile Val Val Asp Arg Val Asp Ala Glu Asp Gly Gln Tyr Asp Val
        435                 440                 445

Met Phe Ile Gly Thr Asp Val Gly Thr Val Leu Lys Val Val Ser Ile
450                 455                 460

Pro Lys Glu Thr Trp His Asp Leu Glu Glu Val Leu Leu Glu Glu Met
465                 470                 475                 480

Thr Val Phe Arg Glu Pro Thr Thr Ile Ser Ala Met Glu Leu Ser Thr
                485                 490                 495

Lys Gln Gln Gln Leu Tyr Ile Gly Ser Thr Ala Gly Ile Ala Gln Leu
            500                 505                 510

Pro Leu His Arg Cys Asp Ile Tyr Gly Lys Ala Cys Ala Glu Cys Cys
        515                 520                 525

Leu Ala Arg Asp Pro Tyr Cys Ala Trp Asp Gly Ser Ser Cys Ser Arg
```

```
                   530                 535                 540
Tyr Phe Pro Thr Ala Lys Arg Arg Thr Arg Arg Gln Asp Ile Arg Asn
545                 550                 555                 560

Gly Asp Pro Leu Thr His Cys Ser Asp Leu Gln His His Asp Asn His
                    565                 570                 575

His Gly His Ser Pro Glu Glu Arg Ile Ile Tyr Gly Val Glu Asn Ser
                580                 585                 590

Ser Thr Phe Leu Glu Cys Ser Pro Lys Ser Gln Arg Ala Leu Val Tyr
                595                 600                 605

Trp Gln Phe Gln Arg Arg Asn Glu Glu Arg Lys Glu Glu Ile Arg Val
                610                 615                 620

Asp Asp His Ile Ile Arg Thr Asp Gln Gly Leu Leu Leu Arg Ser Leu
625                 630                 635                 640

Gln Arg Lys Asp Ser Gly Ser Tyr Leu Cys His Ala Val Glu His Gly
                    645                 650                 655

Phe Ile Gln Thr Leu Leu Lys Val Thr Leu Glu Val Ile Asp Thr Glu
                660                 665                 670

His Leu Glu Glu Leu Leu His Lys Asp Asp Asp Gly Asp Gly Ser Lys
                675                 680                 685

Thr Lys Glu Met Ser Asn Ser Met Thr Pro Ser Gln Lys Val Trp Tyr
                690                 695                 700

Arg Asp Phe Met Gln Leu Ile Asn His Pro Asn Leu Asn Thr Met Asp
705                 710                 715                 720

Glu Phe Cys Glu Gln Val Trp Lys Arg Asp Arg Lys Gln Arg Arg Gln
                    725                 730                 735

Arg Pro Gly His Thr Gln Gly Asn Ser Asn Lys Trp Lys His Leu Gln
                740                 745                 750

Glu Asn Lys Lys Gly Arg Asn Arg Arg Thr His Glu Phe Glu Arg Ala
                755                 760                 765

Pro Arg Ser Val
    770

<210> SEQ ID NO 603
<211> LENGTH: 752
<212> TYPE: PRT
<213> ORGANISM: Rattus norvegicus

<400> SEQUENCE: 603

Asn Tyr Ala Asn Gly Lys Asn Asn Val Pro Arg Leu Lys Leu Ser Tyr
1                   5                   10                  15

Lys Glu Met Leu Glu Ser Asn Asn Val Ile Thr Phe Asn Gly Leu Ala
                20                  25                  30

Asn Ser Ser Ser Tyr His Thr Phe Leu Leu Asp Glu Glu Arg Ser Arg
                35                  40                  45

Leu Tyr Val Gly Ala Lys Asp His Ile Phe Ser Phe Asn Leu Val Asn
                50                  55                  60

Ile Lys Asp Phe Gln Lys Ile Val Trp Pro Val Ser Tyr Thr Arg Arg
65                  70                  75                  80

Asp Glu Cys Lys Trp Ala Gly Lys Asp Ile Leu Lys Glu Cys Ala Asn
                    85                  90                  95

Phe Ile Lys Val Leu Lys Ala Tyr Asn Gln Thr His Leu Tyr Ala Cys
                100                 105                 110

Gly Thr Gly Ala Phe His Pro Ile Cys Thr Tyr Ile Glu Val Gly His
                115                 120                 125
```

```
His Pro Glu Asp Asn Ile Phe Lys Leu Gln Asp Ser His Phe Glu Asn
    130                 135                 140

Gly Arg Gly Lys Ser Pro Tyr Asp Pro Lys Leu Leu Thr Ala Ser Leu
145                 150                 155                 160

Leu Ile Asp Gly Glu Leu Tyr Ser Gly Thr Ala Ala Asp Phe Met Gly
                165                 170                 175

Arg Asp Phe Ala Ile Phe Arg Thr Leu Gly His His Pro Ile Arg
        180                 185                 190

Thr Glu Gln His Asp Ser Arg Trp Leu Asn Asp Pro Arg Phe Ile Ser
            195                 200                 205

Ala His Leu Ile Pro Glu Ser Asp Asn Pro Glu Asp Asp Lys Val Tyr
    210                 215                 220

Phe Phe Phe Arg Glu Asn Ala Ile Asp Gly Glu His Ser Gly Lys Ala
225                 230                 235                 240

Thr His Ala Arg Ile Gly Gln Ile Cys Lys Asn Asp Phe Gly His
                245                 250                 255

Arg Ser Leu Val Asn Lys Trp Thr Thr Phe Leu Lys Ala Arg Leu Ile
            260                 265                 270

Cys Ser Val Pro Gly Pro Asn Gly Ile Asp Thr His Phe Asp Glu Leu
        275                 280                 285

Gln Asp Val Phe Leu Met Asn Ser Lys Asp Pro Lys Asn Pro Ile Val
    290                 295                 300

Tyr Gly Val Phe Thr Thr Ser Ser Asn Ile Phe Lys Gly Ser Ala Val
305                 310                 315                 320

Cys Met Tyr Ser Met Ser Asp Val Arg Arg Val Phe Leu Gly Pro Tyr
                325                 330                 335

Ala His Arg Asp Gly Pro Asn Tyr Gln Trp Val Pro Tyr Gln Gly Arg
            340                 345                 350

Val Pro Tyr Pro Arg Pro Gly Thr Cys Pro Ser Lys Thr Phe Gly Gly
        355                 360                 365

Phe Asp Ser Thr Lys Asp Leu Pro Asp Asp Val Ile Thr Phe Ala Arg
    370                 375                 380

Ser His Pro Ala Met Tyr Asn Pro Val Phe Pro Ile Asn Asn Arg Pro
385                 390                 395                 400

Ile Met Ile Lys Thr Asp Val Asn Tyr Gln Phe Thr Gln Ile Val Val
                405                 410                 415

Asp Arg Val Asp Ala Glu Asp Gly Gln Tyr Asp Val Met Phe Ile Gly
            420                 425                 430

Thr Asp Val Gly Thr Val Leu Lys Val Val Ser Val Pro Lys Glu Thr
        435                 440                 445

Trp His Asp Leu Glu Glu Val Leu Leu Glu Glu Met Thr Val Phe Arg
    450                 455                 460

Glu Pro Thr Thr Ile Ser Ala Met Glu Leu Ser Thr Lys Gln Gln Gln
465                 470                 475                 480

Leu Tyr Ile Gly Ser Thr Ala Gly Val Ala Gln Leu Pro Leu His Arg
                485                 490                 495

Cys Asp Ile Tyr Gly Lys Ala Cys Ala Glu Cys Cys Leu Ala Arg Asp
            500                 505                 510

Pro Tyr Cys Ala Trp Asp Gly Ser Ser Cys Ser Arg Tyr Phe Pro Thr
        515                 520                 525

Ala Lys Arg Arg Thr Arg Arg Gln Asp Ile Arg Asn Gly Asp Pro Leu
    530                 535                 540

Thr His Cys Ser Asp Leu Gln His His Asp Asn His His Gly His Ser
```

```
                    545                 550                 555                 560
Leu Glu Glu Arg Ile Ile Tyr Gly Val Glu Asn Ser Ser Thr Phe Leu
                        565                 570                 575
Glu Cys Ser Pro Lys Ser Gln Arg Ala Leu Val Tyr Trp Gln Phe Gln
                        580                 585                 590
Arg Arg Asn Glu Asp Arg Lys Glu Ile Arg Val Gly Asp His Ile
                        595                 600                 605
Ile Arg Thr Glu Gln Gly Leu Leu Arg Ser Leu Gln Lys Lys Asp
                        610                 615                 620
Ser Gly Asn Tyr Leu Cys His Ala Val Glu His Gly Phe Met Gln Thr
625                 630                 635                 640
Leu Leu Lys Val Thr Leu Glu Val Ile Asp Thr His Leu Glu Glu
                        645                 650                 655
Leu Leu His Lys Asp Asp Asp Gly Asp Gly Ser Lys Thr Lys Glu Met
                        660                 665                 670
Ser Ser Ser Met Thr Pro Ser Gln Lys Val Trp Tyr Arg Asp Phe Met
675                 680                 685
Gln Leu Ile Asn His Pro Asn Leu Asn Thr Met Asp Glu Phe Cys Glu
                        690                 695                 700
Gln Val Trp Lys Arg Asp Arg Lys Gln Arg Gln Arg Pro Gly His
705                 710                 715                 720
Ser Gln Gly Ser Ser Asn Lys Trp Lys His Met Gln Glu Ser Lys Lys
                        725                 730                 735
Gly Arg Asn Arg Arg Thr His Glu Phe Glu Arg Ala Pro Arg Ser Val
                        740                 745                 750

<210> SEQ ID NO 604
<211> LENGTH: 772
<212> TYPE: PRT
<213> ORGANISM: Sus scrofa

<400> SEQUENCE: 604

Met Gly Trp Phe Ser Arg Ile Val Cys Leu Phe Trp Gly Val Leu Leu
1               5                   10                  15
Thr Ala Arg Ala Asn Tyr Gln Asn Gly Lys Asn Val Pro Arg Leu
                20                  25                  30
Lys Leu Ser Tyr Lys Glu Met Leu Glu Ser Asn Asn Val Ile Thr Phe
                35                  40                  45
Asn Gly Leu Ala Asn Ser Ser Ser Tyr His Thr Phe Leu Leu Asp Glu
            50                  55                  60
Glu Arg Ser Arg Leu Tyr Val Gly Ala Lys Asp His Ile Phe Ser Phe
65                  70                  75                  80
Asn Leu Val Asn Ile Lys Asp Phe Gln Lys Ile Val Trp Pro Val Ser
                85                  90                  95
Tyr Thr Arg Arg Asp Glu Cys Lys Trp Ala Gly Lys Asp Ile Leu Lys
                100                 105                 110
Glu Cys Ala Asn Phe Ile Lys Val Leu Lys Ala Tyr Asn Gln Thr His
                115                 120                 125
Leu Tyr Ala Cys Gly Thr Gly Ala Phe His Pro Ile Cys Thr Tyr Ile
            130                 135                 140
Glu Ile Gly His His Pro Glu Asp Asn Ile Phe Lys Leu Glu Asp Ser
145                 150                 155                 160
His Phe Glu Asn Gly Arg Gly Lys Ser Pro Tyr Asp Pro Lys Leu Leu
                165                 170                 175
```

```
Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
            195                 200                 205

His Pro Ile Arg Thr Glu Gln His Asp Ser Arg Trp Leu Asn Asp Pro
            210                 215                 220

Arg Phe Ile Ser Ala His Leu Ile Pro Glu Ser Asp Asn Pro Glu Asp
225                 230                 235                 240

Asp Lys Val Tyr Phe Phe Arg Glu Asn Ala Ile Asp Gly Glu His
            245                 250                 255

Thr Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
            275                 280                 285

Ala Arg Leu Ile Cys Ser Val Pro Gly Pro Asn Gly Ile Asp Thr His
            290                 295                 300

Phe Asp Glu Leu Gln Asp Val Phe Leu Met Asn Ser Lys Asp Pro Lys
305                 310                 315                 320

Asn Pro Val Val Tyr Gly Val Phe Thr Thr Ser Ser Asn Ile Phe Lys
            325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
            355                 360                 365

Tyr Gln Gly Arg Val Pro Tyr Pro Arg Pro Gly Thr Cys Pro Ser Lys
            370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Ile
            405                 410                 415

Asn Asn Arg Pro Ile Met Ile Lys Thr Asp Val Asn Tyr Gln Phe Thr
            420                 425                 430

Gln Ile Val Val Asp Arg Val Asp Ala Glu Asp Gly Gln Tyr Asp Val
            435                 440                 445

Met Phe Ile Gly Thr Asp Val Gly Thr Val Leu Lys Val Val Ser Ile
            450                 455                 460

Pro Lys Glu Thr Trp His Asp Leu Glu Glu Val Leu Leu Glu Glu Met
465                 470                 475                 480

Thr Val Phe Arg Glu Pro Thr Thr Ile Ser Ala Met Glu Leu Ser Thr
            485                 490                 495

Lys Gln Gln Gln Leu Tyr Val Gly Ser Ala Ala Gly Val Ala Gln Leu
            500                 505                 510

Pro Leu His Arg Cys Asp Ile Tyr Gly Lys Ala Cys Ala Glu Cys Cys
            515                 520                 525

Leu Ala Arg Asp Pro Tyr Cys Ala Trp Asp Gly Ser Ser Cys Ser Arg
            530                 535                 540

Tyr Phe Pro Thr Ala Lys Arg Arg Thr Arg Arg Gln Asp Ile Arg Asn
545                 550                 555                 560

Gly Asp Pro Leu Thr His Cys Ser Asp Leu Gln His Asp Asn His
            565                 570                 575

Arg Gly His Asn Phe Glu Glu Arg Ile Ile Tyr Gly Val Glu Asn Ser
            580                 585                 590

Ser Thr Phe Leu Glu Cys Ser Pro Lys Ser Gln Arg Ala Leu Val Tyr
```

```
                595                 600                 605
    Trp Gln Phe Gln Arg Arg Asn Glu Glu Arg Lys Glu Glu Ile Arg Val
        610                 615                 620

Asp Asp His Ile Ile Arg Thr Glu Gln Gly Leu Leu Leu Arg Ser Leu
    625                 630                 635                 640

Gln Arg Lys Asp Ser Gly Ser Tyr Leu Cys His Ala Val Glu His Gly
                    645                 650                 655

Phe Met Gln Thr Leu Leu Lys Val Thr Leu Glu Val Ile Asp Thr Glu
                660                 665                 670

His Leu Glu Glu Leu Leu His Lys Asp Asp Asp Gly Asp Ser Ser Lys
                675                 680                 685

Thr Lys Glu Met Ser Asn Ser Met Thr Pro Ser Gln Lys Ile Trp Tyr
            690                 695                 700

Arg Asp Phe Met Gln Leu Ile Asn His Pro Asn Leu Asn Thr Met Asp
    705                 710                 715                 720

Glu Phe Cys Glu Gln Val Trp Lys Arg Asp Arg Lys Gln Arg Arg Gln
                    725                 730                 735

Arg Pro Gly His Thr Gln Gly Asn Ser Asn Lys Trp Lys His Leu Gln
                740                 745                 750

Glu Asn Lys Lys Cys Arg Asn Arg Arg Thr His Glu Phe Glu Arg Ala
            755                 760                 765

Pro Arg Ser Val
        770

<210> SEQ ID NO 605
<211> LENGTH: 772
<212> TYPE: PRT
<213> ORGANISM: Canis lupus familiaris

<400> SEQUENCE: 605

Met Gly Trp Leu Ala Arg Ile Ala Cys Leu Phe Trp Gly Val Leu Leu
    1               5                   10                  15

Thr Ala Thr Ala Asn Tyr Gln Asn Gly Lys Asn Asn Val Pro Arg Leu
                20                  25                  30

Lys Leu Ser Tyr Lys Glu Met Leu Glu Ser Asn Ser Val Ile Thr Phe
                35                  40                  45

Asn Gly Leu Ala Asn Ser Ser Ser Tyr His Thr Phe Leu Leu Asp Glu
            50                  55                  60

Glu Arg Ser Arg Leu Tyr Val Gly Ala Lys Asp His Ile Phe Ser Phe
    65                  70                  75                  80

Asn Leu Val Asn Ile Lys Asp Phe Gln Lys Ile Val Trp Pro Val Ser
                    85                  90                  95

Tyr Thr Arg Arg Asp Glu Cys Lys Trp Ala Gly Lys Asp Ile Gln Lys
                100                 105                 110

Glu Cys Ala Asn Phe Ile Lys Val Leu Lys Ala Tyr Asn Gln Thr His
                115                 120                 125

Leu Tyr Ala Cys Gly Thr Gly Ala Phe His Pro Ile Cys Thr Tyr Ile
            130                 135                 140

Glu Ile Gly His His Pro Glu Asp Asn Ile Phe Lys Leu Glu Asp Ser
    145                 150                 155                 160

His Phe Glu Asn Gly Arg Gly Lys Ser Pro Tyr Asp Pro Lys Leu Leu
                    165                 170                 175

Thr Ala Ser Leu Leu Ile Asp Gly Glu Leu Tyr Ser Gly Thr Ala Ala
                180                 185                 190
```

-continued

```
Asp Phe Met Gly Arg Asp Phe Ala Ile Phe Arg Thr Leu Gly His His
            195                 200                 205

His Pro Ile Arg Thr Glu Gln His Asp Ser Arg Trp Leu Asn Asp Pro
210                 215                 220

Arg Phe Ile Ser Ala His Leu Ile Pro Glu Ser Asp Asn Pro Glu Asp
225                 230                 235                 240

Asp Lys Val Tyr Phe Phe Arg Glu Asn Ala Ile Asp Gly Glu His
                245                 250                 255

Thr Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
            275                 280                 285

Ala Arg Leu Ile Cys Ser Val Pro Gly Pro Asn Gly Ile Asp Thr His
290                 295                 300

Phe Asp Glu Leu Gln Asp Val Phe Leu Met Asn Ser Lys Asp Pro Lys
305                 310                 315                 320

Asn Pro Ile Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
            355                 360                 365

Tyr Gln Gly Arg Val Pro Tyr Pro Arg Pro Gly Thr Cys Pro Ser Lys
            370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Ile
                405                 410                 415

Asn Asn Arg Pro Ile Met Ile Lys Thr Asp Val Asn Tyr Gln Phe Thr
                420                 425                 430

Gln Ile Val Val Asp Arg Val Asp Ala Glu Asp Gly Asn Tyr Asp Val
            435                 440                 445

Met Phe Ile Gly Thr Asp Val Gly Thr Val Leu Lys Val Val Ser Ile
450                 455                 460

Pro Lys Glu Thr Trp His Asp Leu Glu Glu Val Leu Leu Glu Glu Met
465                 470                 475                 480

Thr Val Phe Arg Glu Pro Thr Pro Ile Ser Ala Met Glu Leu Ser Thr
                485                 490                 495

Lys Gln His Gln Leu Tyr Ala Gly Ser Pro Ala Gly Leu Ala Gln Leu
            500                 505                 510

Pro Leu Gln Arg Cys Ala Ala Tyr Gly Arg Ala Cys Ala Glu Cys Cys
            515                 520                 525

Leu Ala Arg Asp Pro Tyr Cys Ala Trp Asp Gly Ala Ala Cys Ser Arg
530                 535                 540

Tyr Phe Pro Ala Ala Lys Arg Thr Arg Arg Gln Asp Ile Arg Asn
545                 550                 555                 560

Gly Asp Pro Leu Thr His Cys Ser Asp Leu Gln His His Asp Asn His
                565                 570                 575

His Ser His Ser Leu Glu Glu Arg Ile Ile Tyr Gly Val Glu Asn Ser
            580                 585                 590

Ser Thr Phe Leu Glu Cys Ser Pro Lys Ser Gln Arg Ala Leu Val Tyr
            595                 600                 605

Trp Gln Phe Gln Arg Arg Asn Glu Glu Arg Lys Glu Glu Ile Arg Val
```

```
                610             615             620
Asp Asp His Ile Ile Arg Thr Glu Gln Gly Leu Leu Arg Ser Leu
625             630             635             640

Gln Arg Lys Asp Ser Gly Asn Tyr Leu Cys His Ala Val Glu His Gly
            645             650             655

Phe Met Gln Thr Leu Leu Lys Val Thr Leu Glu Val Ile Asp Thr Glu
            660             665             670

His Leu Glu Glu Leu Leu His Lys Asp Asp Gly Asp Gly Ser Lys
            675             680             685

Thr Lys Glu Ile Ser Asn Ser Met Thr Pro Ser Gln Lys Val Trp Tyr
690             695             700

Arg Asp Phe Met Gln Leu Ile Asn His Pro Asn Leu Asn Thr Met Asp
705             710             715             720

Glu Phe Cys Glu Gln Val Trp Lys Arg Asp Arg Lys Gln Arg Gln
            725             730             735

Arg Pro Gly His Thr Gln Gly Asn Ser Asn Lys Trp Lys His Leu Gln
            740             745             750

Glu Asn Lys Lys Gly Arg Asn Arg Arg Thr His Glu Phe Glu Arg Ala
            755             760             765

Pro Arg Ser Val
    770
```

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

```
<210> SEQ ID NO 669
<400> SEQUENCE: 669
000

<210> SEQ ID NO 670
<400> SEQUENCE: 670
000

<210> SEQ ID NO 671
<400> SEQUENCE: 671
000

<210> SEQ ID NO 672
<400> SEQUENCE: 672
000

<210> SEQ ID NO 673
<400> SEQUENCE: 673
000

<210> SEQ ID NO 674
<400> SEQUENCE: 674
000

<210> SEQ ID NO 675
<400> SEQUENCE: 675
000

<210> SEQ ID NO 676
<400> SEQUENCE: 676
000

<210> SEQ ID NO 677
<400> SEQUENCE: 677
000

<210> SEQ ID NO 678
<400> SEQUENCE: 678
000

<210> SEQ ID NO 679
<400> SEQUENCE: 679
000

<210> SEQ ID NO 680
```

-continued

<400> SEQUENCE: 680

000

<210> SEQ ID NO 681
<400> SEQUENCE: 681

000

<210> SEQ ID NO 682
<400> SEQUENCE: 682

000

<210> SEQ ID NO 683
<400> SEQUENCE: 683

000

<210> SEQ ID NO 684
<400> SEQUENCE: 684

000

<210> SEQ ID NO 685
<400> SEQUENCE: 685

000

<210> SEQ ID NO 686
<400> SEQUENCE: 686

000

<210> SEQ ID NO 687
<400> SEQUENCE: 687

000

<210> SEQ ID NO 688
<400> SEQUENCE: 688

000

<210> SEQ ID NO 689
<400> SEQUENCE: 689

000

<210> SEQ ID NO 690
<400> SEQUENCE: 690

000

<210> SEQ ID NO 691
<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701

<400> SEQUENCE: 701

000

<210> SEQ ID NO 702

<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

```
<400> SEQUENCE: 714
000

<210> SEQ ID NO 715
<400> SEQUENCE: 715
000

<210> SEQ ID NO 716
<400> SEQUENCE: 716
000

<210> SEQ ID NO 717
<400> SEQUENCE: 717
000

<210> SEQ ID NO 718
<400> SEQUENCE: 718
000

<210> SEQ ID NO 719
<400> SEQUENCE: 719
000

<210> SEQ ID NO 720
<400> SEQUENCE: 720
000

<210> SEQ ID NO 721
<400> SEQUENCE: 721
000

<210> SEQ ID NO 722
<400> SEQUENCE: 722
000

<210> SEQ ID NO 723
<400> SEQUENCE: 723
000

<210> SEQ ID NO 724
<400> SEQUENCE: 724
000

<210> SEQ ID NO 725
<400> SEQUENCE: 725
```

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759

<400> SEQUENCE: 759

000

<210> SEQ ID NO 760
<400> SEQUENCE: 760

000

<210> SEQ ID NO 761
<400> SEQUENCE: 761

000

<210> SEQ ID NO 762
<400> SEQUENCE: 762

000

<210> SEQ ID NO 763
<400> SEQUENCE: 763

000

<210> SEQ ID NO 764
<400> SEQUENCE: 764

000

<210> SEQ ID NO 765
<400> SEQUENCE: 765

000

<210> SEQ ID NO 766
<400> SEQUENCE: 766

000

<210> SEQ ID NO 767
<400> SEQUENCE: 767

000

<210> SEQ ID NO 768
<400> SEQUENCE: 768

000

<210> SEQ ID NO 769
<400> SEQUENCE: 769

000

<210> SEQ ID NO 770
<400> SEQUENCE: 770

000

<210> SEQ ID NO 771
<400> SEQUENCE: 771
000

<210> SEQ ID NO 772
<400> SEQUENCE: 772
000

<210> SEQ ID NO 773
<400> SEQUENCE: 773
000

<210> SEQ ID NO 774
<400> SEQUENCE: 774
000

<210> SEQ ID NO 775
<400> SEQUENCE: 775
000

<210> SEQ ID NO 776
<400> SEQUENCE: 776
000

<210> SEQ ID NO 777
<400> SEQUENCE: 777
000

<210> SEQ ID NO 778
<400> SEQUENCE: 778
000

<210> SEQ ID NO 779
<400> SEQUENCE: 779
000

<210> SEQ ID NO 780
<400> SEQUENCE: 780
000

<210> SEQ ID NO 781
<400> SEQUENCE: 781
000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

<210> SEQ ID NO 793

<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800
<211> LENGTH: 117
<212> TYPE: PRT
<213> ORGANISM: Artificial Sequence
<220> FEATURE:
<223> OTHER INFORMATION: antibody sequence

<400> SEQUENCE: 800

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Ile Lys Ser Gly Tyr Ala Tyr Tyr Pro Asp Ser Val
    50                  55                  60

Lys Asp Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Arg Gly Gly Gln Gly Ala Met Asp Tyr Trp Gly Gln Gly Thr Thr
            100                 105                 110

Val Thr Val Ser Ser
        115

```
                        115

<210> SEQ ID NO 801
<211> LENGTH: 5
<212> TYPE: PRT
<213> ORGANISM: Artificial Sequence
<220> FEATURE:
<223> OTHER INFORMATION: antibody sequence

<400> SEQUENCE: 801

Ser Tyr Tyr Met Ser
1               5

<210> SEQ ID NO 802
<211> LENGTH: 17
<212> TYPE: PRT
<213> ORGANISM: Artificial Sequence
<220> FEATURE:
<223> OTHER INFORMATION: antibody sequence

<400> SEQUENCE: 802

Thr Ile Ile Lys Ser Gly Gly Tyr Ala Tyr Tyr Pro Asp Ser Val Lys
1               5                  10                  15

Asp

<210> SEQ ID NO 803
<211> LENGTH: 8
<212> TYPE: PRT
<213> ORGANISM: Artificial Sequence
<220> FEATURE:
<223> OTHER INFORMATION: antibody sequence

<400> SEQUENCE: 803

Gly Gly Gln Gly Ala Met Asp Tyr
1               5

<210> SEQ ID NO 804
<211> LENGTH: 107
<212> TYPE: PRT
<213> ORGANISM: Artificial Sequence
<220> FEATURE:
<223> OTHER INFORMATION: antibody sequence

<400> SEQUENCE: 804

Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Ile Gly Asp Tyr
                20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
        50                  55                  60

Ser Gly Ser Gly Thr Asp Phe Thr Leu Thr Ile Thr Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys
                100                 105

<210> SEQ ID NO 805
<211> LENGTH: 11
<212> TYPE: PRT
<213> ORGANISM: Artificial Sequence
```

```
<220> FEATURE:
<223> OTHER INFORMATION: antibody sequence

<400> SEQUENCE: 805

Arg Ala Ser Gln Ser Ile Gly Asp Tyr Leu His
1               5                   10

<210> SEQ ID NO 806
<211> LENGTH: 7
<212> TYPE: PRT
<213> ORGANISM: Artificial Sequence
<220> FEATURE:
<223> OTHER INFORMATION: antibody sequence

<400> SEQUENCE: 806

Tyr Ala Ser Gln Ser Ile Ser
1               5

<210> SEQ ID NO 807
<211> LENGTH: 9
<212> TYPE: PRT
<213> ORGANISM: Artificial Sequence
<220> FEATURE:
<223> OTHER INFORMATION: antibody sequence

<400> SEQUENCE: 807

Gln Gln Gly Tyr Ser Phe Pro Tyr Thr
1               5

<210> SEQ ID NO 808
<211> LENGTH: 351
<212> TYPE: DNA
<213> ORGANISM: Artificial Sequence
<220> FEATURE:
<223> OTHER INFORMATION: antibody sequence

<400> SEQUENCE: 808
gaagtgcagc tggtggaatc tggcggagga ctggttcaac ctggcggctc tctgagactg     60
tcttgtgccg ccagcggctt caccttcagc agctactaca tgagctgggt ccgacaggcc    120
cctggcaaag acttgaatg gtgtccacc atcatcaaga gcggcggcta cgcctactat      180
cccgacagcg tgaaggaccg gttcaccatc tccagagaca cagcaagaa caccctgtac     240 ctgcagatga gcagcctgag agccgaggat accgccgtgt actactgtgt tagaggcgga    300
cagggcgcca tggattattg gggccaggga accacagtga ccgtgtcatc a             351

<210> SEQ ID NO 809
<211> LENGTH: 321
<212> TYPE: DNA
<213> ORGANISM: Artificial Sequence
<220> FEATURE:
<223> OTHER INFORMATION: antibody sequence

<400> SEQUENCE: 809
gagattgtgc tgacacagtc tcccgccaca ctgtctctta gccctggcga aagagccaca     60
ctgagctgta gagccagcca gagcatcggc gattacctgc actggtatca gcagaagcct    120
ggacaggccc ctcggctgct gattaagtac gccagccagt ccatcagcgg catccctgcc    180 agatttctg gcagcggctc tggcaccgat ttcaccctga ccatcaccag cctggaacct     240
gaggacttcg ccgtgtacta ctgccagcag ggctacagct tcccctacac atttggcgga    300
ggcaccaagc tggaaatcaa a                                               321
```

```
<210> SEQ ID NO 810
<211> LENGTH: 447
<212> TYPE: PRT
<213> ORGANISM: Artificial Sequence
<220> FEATURE:
<223> OTHER INFORMATION: antibody sequence

<400> SEQUENCE: 810
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Tyr | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Thr | Ile | Ile | Lys | Ser | Gly | Gly | Tyr | Ala | Tyr | Tyr | Pro | Asp | Ser | Val |
| | 50 | | | | | 55 | | | | | 60 | | | | |
| Lys | Asp | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Ser | Ser | Leu | Arg | Ala | Glu | Asp | Thr | Ala | Val | Tyr | Tyr | Cys |
| | | | | 85 | | | | | 90 | | | | | 95 | |
| Val | Arg | Gly | Gly | Gln | Gly | Ala | Met | Asp | Tyr | Trp | Gly | Gln | Gly | Thr | Thr |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Ser | Ser | Lys | Ser | Thr | Ser | Gly | Gly | Thr | Ala | Ala | Leu | Gly | Cys |
| | 130 | | | | | 135 | | | | | 140 | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | 195 | | | | | 200 | | | | | 205 | | | |
| Thr | Lys | Val | Asp | Lys | Lys | Val | Glu | Pro | Lys | Ser | Cys | Asp | Lys | Thr | His |
| | 210 | | | | | 215 | | | | | 220 | | | | |
| Thr | Cys | Pro | Pro | Cys | Pro | Ala | Pro | Glu | Leu | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Tyr | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Pro | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Arg | Asp | Glu | Leu | Thr | Lys | Asn | Gln | Val | Ser | Leu | Thr | Cys | Leu |
| | | 355 | | | | | 360 | | | | | 365 | | | |
| Val | Lys | Gly | Phe | Tyr | Pro | Ser | Asp | Ile | Ala | Val | Glu | Trp | Glu | Ser | Asn |

```
                        370                 375                 380
Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 811
<211> LENGTH: 214
<212> TYPE: PRT
<213> ORGANISM: Artificial Sequence
<220> FEATURE:
<223> OTHER INFORMATION: antibody sequence

<400> SEQUENCE: 811

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
                20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
50                  55                  60

Ser Gly Ser Gly Thr Asp Phe Thr Leu Thr Ile Thr Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 812
<211> LENGTH: 1341
<212> TYPE: DNA
<213> ORGANISM: Artificial Sequence
<220> FEATURE:
<223> OTHER INFORMATION: antibody sequence

<400> SEQUENCE: 812
gaagtgcagc tggtggaatc tggcggagga ctggttcaac tggcggctc  tctgagactg      60 tcttgtgccg ccagcggctt caccttcagc agctactaca tgagctgggt ccgacaggcc    120
```

```
cctggcaaag gacttgaatg ggtgtccacc atcatcaaga gcggcggcta cgcctactat      180
cccgacagcg tgaaggaccg gttcaccatc tccagagaca acagcaagaa cacccctgtac     240 ctgcagatga gcagcctgag agccgaggat accgccgtgt actactgtgt tagaggcgga     300
cagggcgcca tggattattg gggccaggga accacagtga ccgtgtcatc agccagcacc     360
aagggcccca gcgtgttccc tctggcccct agcagcaaga gcacatctgg cggaacagcc     420
gccctgggct gcctcgtgaa ggactacttt cccgagcccg tgaccgtgtc ctggaactct     480
ggcgctctga caagcggcgt gcacaccttt ccagccgtgc tgcagagcag cggcctgtac     540
tctctgagca gcgtcgtgac agtgcccagc agctctctgg cacccagac ctacatctgc      600 aacgtgaacc acaagcccag caacaccaag gtggacaaga aggtggaacc caagagctgc     660
gacaagaccc acacctgtcc cccttgtcct gcccccgaac tgctgggagg cccttccgtg     720
ttcctgttcc ccccaaagcc caaggacacc ctgatgatca gccggacccc cgaagtgacc     780
tgcgtggtgg tggatgtgtc ccacgaggac cctgaagtga agttcaattg gtacgtggac     840
ggcgtggaag tgcacaacgc caagaccaag cctagagagg aacagtacaa cagcacctac     900
cgggtggtgt ccgtgctgac agtgctgcac caggactggc tgaacggcaa agagtacaag     960
tgcaaggtgt ccaacaaggc cctgcctgcc cccatcgaga aaaccatcag caaggccaag    1020
ggccagcccc gcgaacccca ggtgtacaca ctgcccccaa gcagggacga gctgaccaag    1080
aaccaggtgt ccctgacctg tctcgtgaaa ggcttctacc cctccgatat cgccgtggaa    1140
tgggagagca acggccagcc cgagaacaac tacaagacca ccccccctgt gctggacagc    1200
gacggctcat tcttcctgta cagcaagctg accgtggaca agtcccggtg gcagcagggc    1260
aacgtgttca gctgcagcgt gatgcacgag gccctgcaca accactacac ccagaagtcc    1320
ctgagcctga gccctggcaa g                                               1341
```

<210> SEQ ID NO 813
<211> LENGTH: 642
<212> TYPE: DNA
<213> ORGANISM: Artificial Sequence
<220> FEATURE:
<223> OTHER INFORMATION: antibody sequence

<400> SEQUENCE: 813

```
gagattgtgc tgacacagtc tcccgccaca ctgtctctta gccctggcga aagagccaca      60
ctgagctgta gagccagcca gagcatcggc gattacctgc actggtatca gcagaagcct     120
ggacaggccc ctcggctgct gattaagtac gccagccagt ccatcagcgg catccctgcc     180 agatttctg gcagcggctc tggcaccgat ttcaccctga ccatcaccag cctggaacct     240
gaggacttcg ccgtgtacta ctgccagcag ggctacagct cccctacac atttggcgga    300 ggcaccaagc tggaaatcaa acgaaccgtg gccgctccca gcgtgttcat cttcccacct     360
agcgacgagc agctgaagtc cggcacagcc tctgtcgtgt gcctgctgaa caacttctac     420
ccccgcgagg ccaaggtgca gtggaaggtg gacaatgccc tgcagagcgg caacagccag     480
gaaagcgtga ccgagcagga cagcaaggac tccacctaca gcctgagcag caccctgacc     540
ctgagcaagg ccgactacga aagcacaag gtgtacgcct gcgaagtgac ccaccagggc     600
ctgtctagcc ccgtgaccaa gagcttcaac cggggcgagt gt                       642
```

<210> SEQ ID NO 814
<211> LENGTH: 117
<212> TYPE: PRT

<213> ORGANISM: Artificial Sequence
<220> FEATURE:
<223> OTHER INFORMATION: antibody sequence

<400> SEQUENCE: 814

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Tyr Met Ser Trp Val Arg Gln Ala Pro Gly Lys Gly Leu Glu Trp Val
        35                  40                  45

Ser Thr Ile Ile Lys Ser Gly Gly Tyr Ala Tyr Tyr Pro Asp Ser Val
    50                  55                  60

Lys Asp Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Arg Gly Gly Gln Gly Ala Met Asp Tyr Trp Gly Gln Gly Thr Thr
            100                 105                 110

Val Thr Val Ser Ser
        115

<210> SEQ ID NO 815
<211> LENGTH: 5
<212> TYPE: PRT
<213> ORGANISM: Artificial Sequence
<220> FEATURE:
<223> OTHER INFORMATION: antibody sequence

<400> SEQUENCE: 815

Ser Tyr Tyr Met Ser
1               5

<210> SEQ ID NO 816
<211> LENGTH: 17
<212> TYPE: PRT
<213> ORGANISM: Artificial Sequence
<220> FEATURE:
<223> OTHER INFORMATION: antibody sequence

<400> SEQUENCE: 816

Thr Ile Ile Lys Ser Gly Gly Tyr Ala Tyr Tyr Pro Asp Ser Val Lys
1               5                   10                  15

Asp

<210> SEQ ID NO 817
<211> LENGTH: 8
<212> TYPE: PRT
<213> ORGANISM: Artificial Sequence
<220> FEATURE:
<223> OTHER INFORMATION: antibody sequence

<400> SEQUENCE: 817

Gly Gly Gln Gly Ala Met Asp Tyr
1               5

<210> SEQ ID NO 818
<211> LENGTH: 107
<212> TYPE: PRT
<213> ORGANISM: Artificial Sequence
<220> FEATURE:
<223> OTHER INFORMATION: antibody sequence -continued

<400> SEQUENCE: 818

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Thr Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys
            100                 105

<210> SEQ ID NO 819
<211> LENGTH: 11
<212> TYPE: PRT
<213> ORGANISM: Artificial Sequence
<220> FEATURE:
<223> OTHER INFORMATION: antibody sequence

<400> SEQUENCE: 819

Arg Ala Ser Gln Ser Ile Gly Asp Tyr Leu His
1               5                   10

<210> SEQ ID NO 820
<211> LENGTH: 7
<212> TYPE: PRT
<213> ORGANISM: Artificial Sequence
<220> FEATURE:
<223> OTHER INFORMATION: antibody sequence

<400> SEQUENCE: 820

Tyr Ala Ser Gln Ser Ile Ser
1               5

<210> SEQ ID NO 821
<211> LENGTH: 9
<212> TYPE: PRT
<213> ORGANISM: Artificial Sequence
<220> FEATURE:
<223> OTHER INFORMATION: antibody sequence

<400> SEQUENCE: 821

Gln Gln Gly Tyr Ser Phe Pro Tyr Thr
1               5

<210> SEQ ID NO 822
<211> LENGTH: 351
<212> TYPE: DNA
<213> ORGANISM: Artificial Sequence
<220> FEATURE:
<223> OTHER INFORMATION: antibody sequence

<400> SEQUENCE: 822
gaagtgcagc tggtggaatc tggcggagga ctggttcaac tggcggctc tctgagactg      60 tcttgtgccg cctctggctt cccattcagc agctactaca tgagctgggt ccgacaggcc    120
cctggcaaag gacttgaatg ggtgtccacc atcatcaaga gcggcggcta cgcctactat    180
cccgacagcg tgaaggaccg gttcaccatc agccgggaca acagcaagaa caccctgtac    240

```
ctgcagatga gcagcctgag agccgaggat accgccgtgt actactgtgt tagaggcgga    300
cagggcgcca tggattattg gggccaggga accacagtga ccgtgtcatc a             351
```

<210> SEQ ID NO 823
<211> LENGTH: 321
<212> TYPE: DNA
<213> ORGANISM: Artificial Sequence
<220> FEATURE:
<223> OTHER INFORMATION: antibody sequence

<400> SEQUENCE: 823

```
gagattgtgc tgacacagtc tcccgccaca ctgtctctta gccctggcga aagagccaca    60
ctgagctgta gagccagcca gagcatcggc gattacctgc actggtatca gcagaagcct    120
ggacaggccc ctcggctgct gattaagtac gccagccagt ccatcagcgg catccctgcc    180
agattttctg gcagcggctc tggcaccgat ttcaccctga ccatcaccag cctggaacct    240
gaggacttcg ccgtgtacta ctgccagcag ggctacagct tccctacac atttggcgga    300 ggcaccaagc tggaaatcaa a                                              321
```

<210> SEQ ID NO 824
<211> LENGTH: 447
<212> TYPE: PRT
<213> ORGANISM: Artificial Sequence
<220> FEATURE:
<223> OTHER INFORMATION: antibody sequence

<400> SEQUENCE: 824

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Pro Phe Ser Ser Tyr
             20                  25                  30

Tyr Met Ser Trp Val Arg Gln Ala Pro Gly Lys Gly Leu Glu Trp Val
         35                  40                  45

Ser Thr Ile Ile Lys Ser Gly Gly Tyr Ala Tyr Tyr Pro Asp Ser Val
     50                  55                  60

Lys Asp Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Val Tyr Tyr Cys
                 85                  90                  95

Val Arg Gly Gly Gln Gly Ala Met Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220
```

```
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Asp Glu Leu Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 825
<211> LENGTH: 214
<212> TYPE: PRT
<213> ORGANISM: Artificial Sequence
<220> FEATURE:
<223> OTHER INFORMATION: antibody sequence

<400> SEQUENCE: 825

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Thr Asp Phe Thr Leu Thr Ile Thr Ser Leu Glu Pro
65                  70                  75                  80

Glu Asp Phe Ala Val Tyr Tyr Cys Gln Gln Gly Tyr Ser Phe Pro Tyr
            85                  90                  95

Thr Phe Gly Gly Gly Thr Lys Leu Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 826
<211> LENGTH: 1341
<212> TYPE: DNA
<213> ORGANISM: Artificial Sequence
<220> FEATURE:
<223> OTHER INFORMATION: antibody sequence

<400> SEQUENCE: 826

```
gaagtgcagc tggtggaatc tggcggagga ctggttcaac ctggcggctc tctgagactg     60
tcttgtgccg cctctggctt cccattcagc agctactaca tgagctgggt ccgacaggcc    120
cctggcaaag acttgaatg gtgtccacc atcatcaaga gcggcggcta cgcctactat      180
cccgacagcg tgaaggaccg gttcaccatc agcagggaca cagcaagaa caccctgtac    240
ctgcagatga gcagcctgag agccgaggat accgccgtgt actactgtgt tagaggcgga    300
cagggcgcca tggattattg gggccaggga accacagtga ccgtgtcatc agccagcacc    360
aagggcccca gcgtgttccc tctggcccct agcagcaaga gcacatctgg cggaacagcc    420
gccctgggct gcctcgtgaa ggactacttt cccgagcccg tgaccgtgtc ctggaactct    480
ggcgctctga caagcggcgt gcacaccttt ccagccgtgc tgcagagcag cggcctgtac    540
tctctgagca gcgtcgtgac agtgcccagc agctctctgg caccagac ctacatctgc     600
aacgtgaacc acaagcccag caacaccaag gtggacaaga aggtggaacc caagagctgc    660
gacaagaccc acacctgtcc cccttgtcct gccccccgaac tgctgggagg cccttccgtg    720
ttcctgttcc ccccaaagcc caaggacacc ctgatgatca gccggacccc cgaagtgacc    780
tgcgtggtgg tggatgtgtc ccacgaggac cctgaagtga agttcaattg gtacgtggac    840
ggcgtggaag tgcacaacgc caagaccaag cctagagagg aacagtacaa cagcacctac    900
cgggtggtgt ccgtgctgac agtgctgcac caggactggc tgaacggcaa agagtacaag    960
tgcaaggtgt ccaacaaggc cctgcctgcc cccatcgaga aaaccatcag caaggccaag   1020
ggccagcccc gcgaaccca ggtgtacaca ctgcccccaa gcagggacga gctgaccaag   1080
aaccaggtgt ccctgacctg tctcgtgaaa ggcttctacc cctccgatat cgccgtggaa   1140
tgggagagca acggccagcc cgagaacaac tacaagacca ccccccctgt gctggacagc   1200
gacggctcat tcttcctgta cagcaagctg accgtggaca gtcccggtg cagcagggc    1260
aacgtgttca gctgcagcgt gatgcacgag gccctgcaca accactacac ccagaagtcc   1320
ctgagcctga gccctggcaa g                                             1341
```

<210> SEQ ID NO 827
<211> LENGTH: 642
<212> TYPE: DNA
<213> ORGANISM: Artificial Sequence
<220> FEATURE:
<223> OTHER INFORMATION: antibody sequence -continued

<400> SEQUENCE: 827

```
gagattgtgc tgacacagtc tcccgccaca ctgtctctta gccctggcga aagagccaca    60
ctgagctgta gagccagcca gagcatcggc gattacctgc actggtatca gcagaagcct   120
ggacaggccc ctcggctgct gattaagtac gccagccagt ccatcagcgg catccctgcc   180
agatttctg gcagcggctc tggcaccgat ttcaccctga ccatcaccag cctggaacct    240
gaggacttcg ccgtgtacta ctgccagcag ggctacagct tcccctacac atttggcgga   300
ggcaccaagc tggaaatcaa acgaaccgtg gccgctccca gcgtgttcat cttcccacct   360
agcgacgagc agctgaagtc cggcacagcc tctgtcgtgt gcctgctgaa caacttctac   420
ccccgcgagg ccaaggtgca gtggaaggtg gacaatgccc tgcagagcgg caacagccag   480
gaaagcgtga ccgagcagga cagcaaggac tccacctaca gcctgagcag caccctgacc   540
ctgagcaagg ccgactacga aagcacaag gtgtacgcct gcgaagtgac ccaccagggc   600
ctgtctagcc ccgtgaccaa gagcttcaac cggggcgagt gt                      642
```

<210> SEQ ID NO 828
<211> LENGTH: 117
<212> TYPE: PRT
<213> ORGANISM: Artificial Sequence
<220> FEATURE:
<223> OTHER INFORMATION: antibody sequence

<400> SEQUENCE: 828

```
Glu Val Gln Leu Val Glu Ser Gly Gly Gly Leu Val Gln Leu Gly Gly
1               5                   10                  15
Ser Leu Arg Leu Ser Cys Ala Ala Ser Gly Phe Thr Phe Ser Ser Tyr
            20                  25                  30
Tyr Met Ser Trp Val Arg Gln Ala Pro Gly Lys Gly Leu Glu Trp Val
        35                  40                  45
Ser Thr Ile Ile Lys Ser Gly Gly Tyr Ala Tyr Tyr Pro Asp Ser Val
    50                  55                  60
Lys Asp Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Val Lys Gly Gly Gln Gly Ala Met Asp Tyr Trp Gly Gln Gly Thr Thr
            100                 105                 110
Val Thr Val Ser Ser
        115
```

<210> SEQ ID NO 829
<211> LENGTH: 5
<212> TYPE: PRT
<213> ORGANISM: Artificial Sequence
<220> FEATURE:
<223> OTHER INFORMATION: antibody sequence

<400> SEQUENCE: 829

```
Ser Tyr Tyr Met Ser
1               5
```

<210> SEQ ID NO 830
<211> LENGTH: 17
<212> TYPE: PRT
<213> ORGANISM: Artificial Sequence
<220> FEATURE:
<223> OTHER INFORMATION: antibody sequence

```
<400> SEQUENCE: 830

Thr Ile Ile Lys Ser Gly Gly Tyr Ala Tyr Tyr Pro Asp Ser Val Lys
1               5                   10                  15

Asp

<210> SEQ ID NO 831
<211> LENGTH: 8
<212> TYPE: PRT
<213> ORGANISM: Artificial Sequence
<220> FEATURE:
<223> OTHER INFORMATION: antibody sequence

<400> SEQUENCE: 831

Gly Gly Gln Gly Ala Met Asp Tyr
1               5

<210> SEQ ID NO 832
<211> LENGTH: 107
<212> TYPE: PRT
<213> ORGANISM: Artificial Sequence
<220> FEATURE:
<223> OTHER INFORMATION: antibody sequence

<400> SEQUENCE: 832

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys
            100                 105

<210> SEQ ID NO 833
<211> LENGTH: 11
<212> TYPE: PRT
<213> ORGANISM: Artificial Sequence
<220> FEATURE:
<223> OTHER INFORMATION: antibody sequence

<400> SEQUENCE: 833

Arg Ala Ser Gln Ser Ile Gly Asp Tyr Leu His
1               5                   10

<210> SEQ ID NO 834
<211> LENGTH: 7
<212> TYPE: PRT
<213> ORGANISM: Artificial Sequence
<220> FEATURE:
<223> OTHER INFORMATION: antibody sequence

<400> SEQUENCE: 834

Tyr Ala Ser Gln Ser Ile Ser
1               5

<210> SEQ ID NO 835
```

```
<211> LENGTH: 9
<212> TYPE: PRT
<213> ORGANISM: Artificial Sequence
<220> FEATURE:
<223> OTHER INFORMATION: antibody sequence

<400> SEQUENCE: 835

Gln Gln Gly Tyr Ser Phe Pro Tyr Thr
1               5

<210> SEQ ID NO 836
<211> LENGTH: 351
<212> TYPE: DNA
<213> ORGANISM: Artificial Sequence
<220> FEATURE:
<223> OTHER INFORMATION: antibody sequence

<400> SEQUENCE: 836
gaagtgcagc tggtggaatc tggcggagga ctggttcagc tcggcggatc tctgagactg    60
tcttgtgccg ccagcggctt caccttcagc agctactaca tgagctgggt ccgacaggcc   120
cctggcaaag gacttgaatg ggtgtccacc atcatcaaga gcggcggcta cgcctactat   180
cccgacagcg tgaaggaccg gttcaccatc tccagagaca cagcaagaa cacccctgtac    240 ctgcagatga acagcctgag agccgaggac accgccgtgt actactgtgt gaaaggtgga   300
cagggcgcca tggactattg gggccaggga acaacagtga ccgtgtcctc a            351

<210> SEQ ID NO 837
<211> LENGTH: 321
<212> TYPE: DNA
<213> ORGANISM: Artificial Sequence
<220> FEATURE:
<223> OTHER INFORMATION: antibody sequence

<400> SEQUENCE: 837
gagattgtgc tgacacagtc tcccgccaca ctgtctctta gccctggcga aagagccaca    60
ctgagctgta gagccagcca gagcatcggc gattacctgc actggtatca gcagaagcct   120
ggacaggccc ctcggctgct gatctactat gccagccagt ccatcagcgg catccccgcc   180 agatttctg cagcggctc tggcaccgat ttcaccctga ccataagcag cctggaacct    240
gaggacttcg ccgtgtacta ctgccagcag ggctacagct tccccctaca ctttggcgga    300
ggcaccaagc tggaaatcaa a                                             321

<210> SEQ ID NO 838
<211> LENGTH: 447
<212> TYPE: PRT
<213> ORGANISM: Artificial Sequence
<220> FEATURE:
<223> OTHER INFORMATION: antibody sequence

<400> SEQUENCE: 838

Glu Val Gln Leu Val Glu Ser Gly Gly Gly Leu Val Gln Leu Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Ile Lys Ser Gly Gly Tyr Ala Tyr Tyr Pro Asp Ser Val
    50                  55                  60

Lys Asp Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Val Lys Gly Gly Gln Gly Ala Met Asp Tyr Trp Gly Gln Gly Thr Thr
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 839
<211> LENGTH: 214
<212> TYPE: PRT
<213> ORGANISM: Artificial Sequence
<220> FEATURE:
<223> OTHER INFORMATION: antibody sequence

<400> SEQUENCE: 839

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 840
<211> LENGTH: 1341
<212> TYPE: DNA
<213> ORGANISM: Artificial Sequence
<220> FEATURE:
<223> OTHER INFORMATION: antibody sequence

<400> SEQUENCE: 840
gaagtgcagc tggtggaatc tggcggagga ctggttcagc ctggcggatc tctgagactg      60
tcttgtgccg ccagcggctt caccttcagc agctactaca tgagctgggt ccgacaggcc     120
cctggcaaag acttgaatg ggtgtccacc atcatcaaga gcggcggcta cgcctactat     180
cccgacagcg tgaaggaccg gttcaccatc tccagagaca acagcaagaa caccctgtac     240
ctgcagatga acagcctgag agccgaggac accgccgtgt actactgtgt gaaaggtgga     300
cagggcgcca tggactattg gggccaggga caacagtga ccgtgtcctc agccagcacc     360
aagggcccca gcgtgttccc tctggcccct agcagcaaga gcacatctgg cggaacagcc     420
gccctgggct gcctcgtgaa ggactacttt cccgagcccg tgaccgtgtc ctggaactct     480
ggcgctctga caagcggcgt gcacaccttt ccagccgtgc tgcagagcag cggcctgtac     540
tctctgagca gcgtcgtgac agtgcccagc agctctctgg gcacccagac ctacatctgc     600
aacgtgaacc acaagcccag caacaccaag gtggacaaga aggtggaacc caagagctgc     660
gacaagaccc acacctgtcc ccttgtcct gccccgaac tgctggggag cccttccgtg     720
ttcctgttcc ccccaaagcc caaggacacc ctgatgatca gccggacccc cgaagtgacc     780
```

```
tgcgtggtgg tggatgtgtc ccacgaggac cctgaagtga agttcaattg gtacgtggac    840
ggcgtggaag tgcacaacgc caagaccaag cctagagagg aacagtacaa cagcacctac    900
cgggtggtgt ccgtgctgac agtgctgcac caggactggc tgaacggcaa agagtacaag    960
tgcaaggtgt ccaacaaggc cctgcctgcc cccatcgaga aaaccatcag caaggccaag   1020
ggccagcccc gcgaacccca ggtgtacaca ctgcccccaa gcagggacga gctgaccaag   1080
aaccaggtgt ccctgacctg tctcgtgaaa ggcttctacc cctccgatat cgccgtggaa   1140
tgggagagca acggccagcc cgagaacaac tacaagacca cccccctgt gctggacagc    1200 gacggctcat tcttcctgta cagcaagctg accgtggaca gtccggtg gcagcagggc    1260 aacgtgttca gctgcagcgt gatgcacgag gccctgcaca accactacac ccagaagtcc   1320
ctgagcctga gccctggcaa g                                              1341

<210> SEQ ID NO 841
<211> LENGTH: 642
<212> TYPE: DNA
<213> ORGANISM: Artificial Sequence
<220> FEATURE:
<223> OTHER INFORMATION: antibody sequence

<400> SEQUENCE: 841
gagattgtgc tgacacagtc tcccgccaca ctgtctctta gcctggcga aagagccaca     60 ctgagctgta gagccagcca gagcatcggc gattacctgc actggtatca gcagaagcct    120
ggacaggccc ctcggctgct gatctactat gccagccagt ccatcagcgg catccccgcc    180 agatttctg cagcggctc tggcaccgat ttcaccctga ccataagcag cctggaacct    240
gaggacttcg ccgtgtacta ctgccagcag ggctacagct cccctacac atttggcgga    300 ggcaccaagc tggaaatcaa acgaaccgtg gccgctccca gcgtgttcat cttcccacct    360
agcgacgagc agctgaagtc cggcacagcc tctgtcgtgt gcctgctgaa caacttctac    420 cccgcgagg ccaaggtgca gtggaaggtg gacaatgccc tgcagagcgg caacagccag    480
gaaagcgtga ccgagcagga cagcaaggac tccacctaca gcctgagcag caccctgacc    540
ctgagcaagg ccgactacga gaagcacaag gtgtacgcct gcgaagtgac ccaccagggc    600
ctgtctagcc ccgtgaccaa gagcttcaac cggggcgagt gt                      642

<210> SEQ ID NO 842
<211> LENGTH: 117
<212> TYPE: PRT
<213> ORGANISM: Artificial Sequence
<220> FEATURE:
<223> OTHER INFORMATION: antibody sequence

<400> SEQUENCE: 842

Glu Val Gln Leu Val Glu Ser Gly Gly Gly Leu Leu Gln Leu Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Ile Lys Ser Gly Gly Tyr Ala Tyr Pro Asp Ser Val
    50                  55                  60

Lys Asp Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95
```

Val Lys Gly Gly Gln Gly Ala Met Asp Tyr Trp Gly Gln Gly Thr Thr
            100                 105                 110
Val Thr Val Ser Ser
        115

<210> SEQ ID NO 843
<211> LENGTH: 5
<212> TYPE: PRT
<213> ORGANISM: Artificial Sequence
<220> FEATURE:
<223> OTHER INFORMATION: antibody sequence

<400> SEQUENCE: 843

Ser Tyr Tyr Met Ser
1               5

<210> SEQ ID NO 844
<211> LENGTH: 17
<212> TYPE: PRT
<213> ORGANISM: Artificial Sequence
<220> FEATURE:
<223> OTHER INFORMATION: antibody sequence

<400> SEQUENCE: 844

Thr Ile Ile Lys Ser Gly Gly Tyr Ala Tyr Tyr Pro Asp Ser Val Lys
1               5                   10                  15
Asp

<210> SEQ ID NO 845
<211> LENGTH: 8
<212> TYPE: PRT
<213> ORGANISM: Artificial Sequence
<220> FEATURE:
<223> OTHER INFORMATION: antibody sequence

<400> SEQUENCE: 845

Gly Gly Gln Gly Ala Met Asp Tyr
1               5

<210> SEQ ID NO 846
<211> LENGTH: 107
<212> TYPE: PRT
<213> ORGANISM: Artificial Sequence
<220> FEATURE:
<223> OTHER INFORMATION: antibody sequence

<400> SEQUENCE: 846

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys
            100                 105

<210> SEQ ID NO 847
<211> LENGTH: 11
<212> TYPE: PRT
<213> ORGANISM: Artificial Sequence
<220> FEATURE:
<223> OTHER INFORMATION: antibody sequence

<400> SEQUENCE: 847

Arg Ala Ser Gln Ser Ile Gly Asp Tyr Leu His
1               5                   10

<210> SEQ ID NO 848
<211> LENGTH: 7
<212> TYPE: PRT
<213> ORGANISM: Artificial Sequence
<220> FEATURE:
<223> OTHER INFORMATION: antibody sequence

<400> SEQUENCE: 848

Tyr Ala Ser Gln Ser Ile Ser
1               5

<210> SEQ ID NO 849
<211> LENGTH: 9
<212> TYPE: PRT
<213> ORGANISM: Artificial Sequence
<220> FEATURE:
<223> OTHER INFORMATION: antibody sequence

<400> SEQUENCE: 849

Gln Gln Gly Tyr Ser Phe Pro Tyr Thr
1               5

<210> SEQ ID NO 850
<211> LENGTH: 351
<212> TYPE: DNA
<213> ORGANISM: Artificial Sequence
<220> FEATURE:
<223> OTHER INFORMATION: antibody sequence

<400> SEQUENCE: 850
gaagtgcagc tggtggaatc tggcggagga ctgctgcagc ttggcggatc tctgagactg      60
tcttgtgccg ccagcggctt caccttcagc agctactaca tgagctgggt ccgacaggcc     120
cctggcaaag acttgaatg ggtgtccacc atcatcaaga gcggcggcta cgcctactat      180
cccgacagcg tgaaggaccg gttcaccatc tccagagaca acagcaagaa caccctgaac     240
ctgcagatga acagcctgag agccgaggac accgccgtgt actactgtgt gaaaggtgga     300
cagggcgcca tggactattg gggccaggga acaacagtga ccgtgtcctc a              351

<210> SEQ ID NO 851
<211> LENGTH: 321
<212> TYPE: DNA
<213> ORGANISM: Artificial Sequence
<220> FEATURE:
<223> OTHER INFORMATION: antibody sequence

<400> SEQUENCE: 851
gagattgtgc tgacacagtc tcccgccaca ctgtctctta gccctggcga aagagccaca      60
ctgagctgta gagccagcca gagcatcggc gattacctgc actggtatca gcagaagcct     120
ggacaggccc ctcggctgct gattaagtac gccagccagt ccatcagcgg catccctgcc     180 agatttctg gcagcggctc tggcaccgat ttcaccctga ccataagcag cctggaacct     240

-continued

```
gaggacttcg ccgtgtacta ctgccagcag ggctacagct tcccctacac atttggcgga    300
ggcaccaagc tggaaatcaa a                                              321
```

<210> SEQ ID NO 852
<211> LENGTH: 447
<212> TYPE: PRT
<213> ORGANISM: Artificial Sequence
<220> FEATURE:
<223> OTHER INFORMATION: antibody sequence

<400> SEQUENCE: 852

```
Glu Val Gln Leu Val Glu Ser Gly Gly Gly Leu Leu Gln Leu Gly Gly
1               5                  10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Ile Lys Ser Gly Gly Tyr Ala Tyr Tyr Pro Asp Ser Val
    50                  55                  60

Lys Asp Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Val Lys Gly Gly Gln Gly Ala Met Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

-continued

```
Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 853
<211> LENGTH: 214
<212> TYPE: PRT
<213> ORGANISM: Artificial Sequence
<220> FEATURE:
<223> OTHER INFORMATION: antibody sequence

<400> SEQUENCE: 853

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 854
<211> LENGTH: 1341
<212> TYPE: DNA
<213> ORGANISM: Artificial Sequence
<220> FEATURE:
<223> OTHER INFORMATION: antibody sequence
```

```
<400> SEQUENCE: 854
gaagtgcagc tggtggaatc tggcggagga ctgctgcagc ttggcggatc tctgagactg      60
tcttgtgccg ccagcggctt caccttcagc agctactaca tgagctgggt ccgacaggcc     120
cctggcaaag gacttgaatg ggtgtccacc atcatcaaga gcggcggcta cgcctactat     180
cccgacagcg tgaaggaccg gttcaccatc tccagagaca cagcaagaa cacccctgaac    240
ctgcagatga acagcctgag agccgaggac accgccgtgt actactgtgt gaaaggtgga     300
cagggcgcca tggactattg gggccaggga acaacagtga ccgtgtcctc agccagcacc     360
aagggcccca gcgtgttccc tctggcccct agcagcaaga gcacatctgg cggaacagcc     420
gccctgggct gcctcgtgaa ggactacttt cccgagcccg tgaccgtgtc ctggaactct     480
ggcgctctga caagcggcgt gcacaccttt ccagccgtgc tgcagagcag cggcctgtac     540
tctctgagca gcgtcgtgac agtgcccagc agctctctgg gcacccagac ctacatctgc     600
aacgtgaacc acaagcccag caacaccaag gtggacaaga aggtggaacc caagagctgc     660
gacaagaccc acacctgtcc cccttgtcct gcccccgaac tgctgggagg cccttccgtg     720
ttcctgttcc ccccaaagcc caaggacacc ctgatgatca gccggacccc cgaagtgacc     780
tgcgtggtgg tggatgtgtc ccacgaggac cctgaagtga agttcaattg gtacgtggac     840
ggcgtggaag tgcacaacgc caagaccaag cctagagagg aacagtacaa cagcacctac     900
cgggtggtgt ccgtgctgac agtgctgcac caggactggc tgaacggcaa agagtacaag     960
tgcaaggtgt ccaacaaggc cctgcctgcc ccatcgaga aaccatcag caaggccaag     1020
ggccagcccc gcgaaccca ggtgtacaca ctgcccccaa gcaggacga gctgaccaag     1080
aaccaggtgt ccctgacctg tctcgtgaaa ggcttctacc cctccgatat cgccgtggaa     1140
tgggagagca acggccagcc cgagaacaac tacaagacca cccccctgt gctggacagc     1200
gacggctcat tcttcctgta cagcaagctg accgtggaca agtcccggtg gcagcagggc     1260
aacgtgttca gctgcagcgt gatgcacgag gccctgcaca accactacac ccagaagtcc     1320
ctgagcctga gccctggcaa g                                               1341

<210> SEQ ID NO 855
<211> LENGTH: 642
<212> TYPE: DNA
<213> ORGANISM: Artificial Sequence
<220> FEATURE:
<223> OTHER INFORMATION: antibody sequence

<400> SEQUENCE: 855
gagattgtgc tgacacagtc tcccgccaca ctgtctctta gccctggcga aagagccaca      60
ctgagctgta gagccagcca gagcatcggc gattacctgc actggtatca gcagaagcct     120
ggacaggccc ctcggctgct gattaagtac gccagccagt ccatcagcgg catccctgcc     180
agatttctg gcagcggctc tggcaccgat ttcacccctga ccataagcag cctggaacct    240
gaggacttcg ccgtgtacta ctgccagcag ggctacagct cccctacac atttggcgga     300
ggcaccaagc tggaaatcaa acgaaccgtg gccgctccca gcgtgttcat cttcccacct     360
agcgacgagc agctgaagtc cggcacagcc tctgtcgtgt gcctgctgaa caacttctac     420
ccccgcgagg ccaaggtgca gtggaaggtg gacaatgccc tgcagagcgg caacagccag     480
gaaagcgtga ccgagcagga cagcaaggac tccacctaca gcctgagcag cacccctgacc   540
ctgagcaagg ccgactacga gaagcacaag gtgtacgcct gcgaagtgac ccaccagggc     600
ctgtctagcc ccgtgaccaa gagcttcaac cggggcgagt gt                        642
```

<210> SEQ ID NO 856
<211> LENGTH: 122
<212> TYPE: PRT
<213> ORGANISM: Artificial Sequence
<220> FEATURE:
<223> OTHER INFORMATION: antibody sequence

<400> SEQUENCE: 856

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Val His Trp Val Arg Gln Ala Pro Gly Lys Gly Leu Glu Trp Val
        35                  40                  45

Ser Ser Thr Glu Gly Ser Gly Val Gly Thr Ser Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Leu Gly Gly Gly Asn Pro Leu Asp Tyr Leu Asp Tyr Trp
            100                 105                 110

Gly Gln Gly Thr Leu Val Thr Val Ser Ser
        115                 120

<210> SEQ ID NO 857
<211> LENGTH: 5
<212> TYPE: PRT
<213> ORGANISM: Artificial Sequence
<220> FEATURE:
<223> OTHER INFORMATION: antibody sequence

<400> SEQUENCE: 857

Ser Tyr Ala Val His
1               5

<210> SEQ ID NO 858
<211> LENGTH: 17
<212> TYPE: PRT
<213> ORGANISM: Artificial Sequence
<220> FEATURE:
<223> OTHER INFORMATION: antibody sequence

<400> SEQUENCE: 858

Ser Thr Glu Gly Ser Gly Val Gly Thr Ser Tyr Thr Asp Ser Val Lys
1               5                   10                  15

Gly

<210> SEQ ID NO 859
<211> LENGTH: 13
<212> TYPE: PRT
<213> ORGANISM: Artificial Sequence
<220> FEATURE:
<223> OTHER INFORMATION: antibody sequence

<400> SEQUENCE: 859

Met Leu Gly Gly Gly Asn Pro Leu Asp Tyr Leu Asp Tyr
1               5                   10

<210> SEQ ID NO 860
<211> LENGTH: 111

```
<212> TYPE: PRT
<213> ORGANISM: Artificial Sequence
<220> FEATURE:
<223> OTHER INFORMATION: antibody sequence

<400> SEQUENCE: 860
```

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Leu Gly Glu Gly
                20                  25                  30

Tyr Asp Val His Trp Tyr Gln Gln Leu Pro Gly Lys Ala Pro Lys Leu
            35                  40                  45

Leu Ile Tyr Tyr Ser Asp Phe Arg Pro Ser Gly Val Ser Asp Arg Phe
        50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Ser Ser Gln Val Phe Gly Gly Gly Thr Gln Val Thr Val Leu
            100                 105                 110

```
<210> SEQ ID NO 861
<211> LENGTH: 14
<212> TYPE: PRT
<213> ORGANISM: Artificial Sequence
<220> FEATURE:
<223> OTHER INFORMATION: antibody sequence

<400> SEQUENCE: 861
```

Ser Gly Ser Ser Ser Asn Leu Gly Glu Gly Tyr Asp Val His
1               5                   10

```
<210> SEQ ID NO 862
<211> LENGTH: 7
<212> TYPE: PRT
<213> ORGANISM: Artificial Sequence
<220> FEATURE:
<223> OTHER INFORMATION: antibody sequence

<400> SEQUENCE: 862
```

Tyr Ser Asp Phe Arg Pro Ser
1               5

```
<210> SEQ ID NO 863
<211> LENGTH: 11
<212> TYPE: PRT
<213> ORGANISM: Artificial Sequence
<220> FEATURE:
<223> OTHER INFORMATION: antibody sequence

<400> SEQUENCE: 863
```

Ala Ala Trp Asp Asp Ser Leu Ser Ser Gln Val
1               5                   10

```
<210> SEQ ID NO 864
<211> LENGTH: 366
<212> TYPE: DNA
<213> ORGANISM: Artificial Sequence
<220> FEATURE:
<223> OTHER INFORMATION: antibody sequence

<400> SEQUENCE: 864
```
gaagttcagc tgctggaatc tggcggcgga ctggttcaac ctggcggatc tctgagactg        60

```
agctgtgccg ccagcggctt cacctttaga agctatgccg tgcactgggt ccgacaggcc      120
cctggaaaag gactggaatg ggtgtccagc accgaaggct ctggcgtggg cacaagctac      180
accgattctg tgaagggcag attcaccatc agccgggaca acagcaagaa caccctgtac      240
ctgcagatga acagcctgag agccgaggac accgccgtgt actactgtgc agaatgctc       300 ggcggaggca accctctgga ctacctggat tattggggcc agggcaccct ggtcacagtc      360
tcttca                                                                 366
```

<210> SEQ ID NO 865
<211> LENGTH: 333
<212> TYPE: DNA
<213> ORGANISM: Artificial Sequence
<220> FEATURE:
<223> OTHER INFORMATION: antibody sequence

<400> SEQUENCE: 865

```
cagtctgttc tgacacagcc tcctagcgcc tctggcacac ctggacagag agtgaccatc       60
agctgtagcg gcagcagctc caatctcggc gagggctatg acgtgcactg gtatcagcag      120
ctgcctggca aggcccctaa actgctgatc tactacagcg acttcagacc cagcggcgtg      180
tccgatagat tcagcggctc taagagcggc acatctgcca gcctggccat ctctggactg      240
cagagcgaag atgaggccga ctactattgc gccgcctggg atgatagcct gagcagccaa      300 gttttttggcg gcggaaccca agtgaccgtg cta                                  333
```

<210> SEQ ID NO 866
<211> LENGTH: 452
<212> TYPE: PRT
<213> ORGANISM: Artificial Sequence
<220> FEATURE:
<223> OTHER INFORMATION: antibody sequence

<400> SEQUENCE: 866

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Val His Trp Val Arg Gln Ala Pro Gly Lys Gly Leu Glu Trp Val
        35                  40                  45

Ser Ser Thr Glu Gly Ser Gly Val Gly Thr Ser Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Leu Gly Gly Gly Asn Pro Leu Asp Tyr Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

```
Val Pro Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
            435                 440                 445

Ser Pro Gly Lys
        450

<210> SEQ ID NO 867
<211> LENGTH: 217
<212> TYPE: PRT
<213> ORGANISM: Artificial Sequence
<220> FEATURE:
<223> OTHER INFORMATION: antibody sequence

<400> SEQUENCE: 867

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Leu Gly Glu Gly
            20                  25                  30

Tyr Asp Val His Trp Tyr Gln Gln Leu Pro Gly Lys Ala Pro Lys Leu
        35                  40                  45

Leu Ile Tyr Tyr Ser Asp Phe Arg Pro Ser Gly Val Ser Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95
```

```
Leu Ser Ser Gln Val Phe Gly Gly Thr Gln Val Thr Val Leu Gly
             100                 105                 110

Gln Pro Lys Ala Ala Pro Ser Val Thr Leu Phe Pro Pro Ser Ser Glu
         115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                 165                 170                 175

Tyr Ala Ala Ser Ser Tyr Leu Ser Leu Thr Pro Glu Gln Trp Lys Ser
                 180                 185                 190

His Arg Ser Tyr Ser Cys Gln Val Thr His Glu Gly Ser Thr Val Glu
                 195                 200                 205

Lys Thr Val Ala Pro Thr Glu Cys Ser
         210                 215
```

<210> SEQ ID NO 868
<211> LENGTH: 1356
<212> TYPE: DNA
<213> ORGANISM: Artificial Sequence
<220> FEATURE:
<223> OTHER INFORMATION: antibody sequence

<400> SEQUENCE: 868

| | | | | | |
|---|---|---|---|---|---|
| gaagttcagc | tgctggaatc | tggcggcgga | ctggttcaac | tggcggatc | tctgagactg | 60 |
| agctgtgccg | ccagcggctt | cacctttaga | agctatgccg | tgcactgggt | ccgacaggcc | 120 |
| cctggaaaag | gactgaatg | ggtgtccagc | accgaaggct | ctggcgtggg | cacaagctac | 180 |
| accgattctg | tgaagggcag | attcaccatc | agccgggaca | acagcaagaa | caccctgtac | 240 |
| ctgcagatga | acagcctgag | agccgaggac | accgccgtgt | actactgtgc | cagaatgctc | 300 |
| ggcggaggca | accctctgga | ctacctggat | tattggggcc | agggcaccct | ggtcacagtc | 360 |
| tcttcagcca | gcaccaaggg | ccccagcgtg | ttccctctgg | cccctagcag | caagagcaca | 420 |
| tctggcggaa | cagccgccct | gggctgcctc | gtgaaggact | actttcccga | gcccgtgacc | 480 |
| gtgtcctgga | actctggcgc | tctgacaagc | ggcgtgcaca | cctttccagc | cgtgctgcag | 540 |
| agcagcggcc | tgtactctct | gagcagcgtc | gtgacagtgc | ccagcagctc | tctgggcacc | 600 |
| cagacctaca | tctgcaacgt | gaaccacaag | cccagcaaca | ccaaggtgga | caagaaggtg | 660 |
| gaacccaaga | gctgcgacaa | gacccacacc | tgtcccccct | tgcctgcccc | cgaactgctg | 720 |
| ggaggccctt | ccgtgttcct | gttccccccca | aagcccaagg | acaccctgat | gatcagccgg | 780 |
| accccccgaag | tgacctgcgt | ggtggtggat | gtgtcccacg | aggaccctga | agtgaagttc | 840 |
| aattggtacg | tggacggcgt | ggaagtgcac | aacgccaaga | ccaagcctag | agaggaacag | 900 |
| tacaacagca | cctaccgggt | ggtgtccgtg | ctgacagtgc | tgcaccagga | ctggctgaac | 960 |
| ggcaaagagt | acaagtgcaa | ggtgtccaac | aaggccctgc | ctgcccccat | cgagaaaacc | 1020 |
| atcagcaagg | ccaagggcca | gccccgcgaa | ccccaggtgt | acacactgcc | cccaagcagg | 1080 |
| gacgagctga | ccaagaacca | ggtgtccctg | acctgtctcg | tgaaaggctt | ctacccctcc | 1140 |
| gatatcgccg | tggaatggga | gagcaacggc | cagcccgaga | acaactacaa | gaccaccccc | 1200 |
| cctgtgctgg | acagcgacgg | ctcattcttc | ctgtacagca | agctgaccgt | ggacaagtcc | 1260 |
| cggtggcagc | agggcaacgt | gttcagctgc | agcgtgatgc | acgaggccct | gcacaaccac | 1320 | tacacccaga agtccctgag cctgagccct ggcaag                                        1356

<210> SEQ ID NO 869
<211> LENGTH: 651
<212> TYPE: DNA
<213> ORGANISM: Artificial Sequence
<220> FEATURE:
<223> OTHER INFORMATION: antibody sequence

<400> SEQUENCE: 869
cagtctgttc tgacacagcc tcctagcgcc tctggcacac ctggacagag agtgaccatc     60
agctgtagcg gcagcagctc aatctcggc gagggctatg acgtgcactg gtatcagcag    120
ctgcctggca aggcccctaa actgctgatc tactacagcg acttcagacc cagcggcgtg    180
tccgatagat tcagcggctc taagagcggc acatctgcca gcctggccat ctctggactg    240
cagagcgaag atgaggccga ctactattgc gccgcctggg atgatagcct gagcagccaa    300
gtttttggcg gcggaaccca agtgaccgtg ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac cacccctagc aagcagagca caacaaata cgccgccagc    540
agctacctga gcctgacccc cgagcagtgg aagtcccaca gatcctacag ctgccaagtg    600
acccacgagg cagcaccgt ggaaaagaca gtggcccta ccgagtgcag c               651

<210> SEQ ID NO 870
<211> LENGTH: 122
<212> TYPE: PRT
<213> ORGANISM: Artificial Sequence
<220> FEATURE:
<223> OTHER INFORMATION: antibody sequence

<400> SEQUENCE: 870

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Val His Trp Val Arg Gln Ala Pro Gly Lys Gly Leu Glu Trp Val
        35                  40                  45

Ser Ser Thr Glu Gly Ser Gly Val Gly Thr Ser Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Leu Gly Gly Gly Asn Pro Leu Asp Tyr Leu Asp Tyr Trp
            100                 105                 110

Gly Gln Gly Thr Leu Val Thr Val Ser Ser
        115                 120

<210> SEQ ID NO 871
<211> LENGTH: 5
<212> TYPE: PRT
<213> ORGANISM: Artificial Sequence
<220> FEATURE:
<223> OTHER INFORMATION: antibody sequence

<400> SEQUENCE: 871

Ser Tyr Ala Val His

-continued

<210> SEQ ID NO 872
<211> LENGTH: 17
<212> TYPE: PRT
<213> ORGANISM: Artificial Sequence
<220> FEATURE:
<223> OTHER INFORMATION: antibody sequence

<400> SEQUENCE: 872

Ser Thr Glu Gly Ser Gly Val Gly Thr Ser Tyr Thr Asp Ser Val Lys
1               5                   10                  15

Gly

<210> SEQ ID NO 873
<211> LENGTH: 13
<212> TYPE: PRT
<213> ORGANISM: Artificial Sequence
<220> FEATURE:
<223> OTHER INFORMATION: antibody sequence

<400> SEQUENCE: 873

Met Leu Gly Gly Gly Asn Pro Leu Asp Tyr Leu Asp Tyr
1               5                   10

<210> SEQ ID NO 874
<211> LENGTH: 111
<212> TYPE: PRT
<213> ORGANISM: Artificial Sequence
<220> FEATURE:
<223> OTHER INFORMATION: antibody sequence

<400> SEQUENCE: 874

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Leu Gly Glu Gly
            20                  25                  30

Tyr Asp Val His Trp Tyr Gln Gln Leu Pro Gly Lys Ala Pro Lys Leu
        35                  40                  45

Leu Ile Tyr Tyr Ser Asp Phe Arg Pro Ser Gly Val Ser Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Ser
                85                  90                  95

Leu Ser Ser Gln Val Phe Gly Gly Gly Thr Gln Val Thr Val Leu
            100                 105                 110

<210> SEQ ID NO 875
<211> LENGTH: 14
<212> TYPE: PRT
<213> ORGANISM: Artificial Sequence
<220> FEATURE:
<223> OTHER INFORMATION: antibody sequence

<400> SEQUENCE: 875

Ser Gly Ser Ser Ser Asn Leu Gly Glu Gly Tyr Asp Val His
1               5                   10

<210> SEQ ID NO 876
<211> LENGTH: 7
<212> TYPE: PRT
<213> ORGANISM: Artificial Sequence

```
<220> FEATURE:
<223> OTHER INFORMATION: antibody sequence

<400> SEQUENCE: 876

Tyr Ser Asp Phe Arg Pro Ser
1               5

<210> SEQ ID NO 877
<211> LENGTH: 11
<212> TYPE: PRT
<213> ORGANISM: Artificial Sequence
<220> FEATURE:
<223> OTHER INFORMATION: antibody sequence

<400> SEQUENCE: 877

Ala Ala Trp Asp Asp Ser Leu Ser Ser Gln Val
1               5                   10

<210> SEQ ID NO 878
<211> LENGTH: 366
<212> TYPE: DNA
<213> ORGANISM: Artificial Sequence
<220> FEATURE:
<223> OTHER INFORMATION: antibody sequence

<400> SEQUENCE: 878
gaagttcagc tgctggaatc tggcggcgga ctggttcaac ctggcggatc tctgagactg      60
agctgtgccg ccagcggctt cacctttaga agctatgccg tgcactgggt ccgacaggcc     120
cctggaaaag gactggaatg ggtgtccagc accgaaggct ctggcgtggg cacaagctac     180
accgattctg tgaagggcag attcaccatc agccgggaca cagcaagaa caccctgtac      240 ctgcagatga acagcctgag agccgaggac accgccgtgt actactgtgc cagaatgctc     300
ggcggaggca accctctgga ctacctggat tattggggcc agggcaccct ggtcacagtc     360
tcttca                                                                366

<210> SEQ ID NO 879
<211> LENGTH: 333
<212> TYPE: DNA
<213> ORGANISM: Artificial Sequence
<220> FEATURE:
<223> OTHER INFORMATION: antibody sequence

<400> SEQUENCE: 879
cagtctgttc tgacacagcc tcctagcgcc tctggcacac ctggacagag agtgaccatc      60
agctgtagcg gcagcagctc caatctcggc gagggctatg acgtgcactg gtatcagcag     120
ctgcctggca aggcccctaa actgctgatc tactacagcg acttcagacc cagcggcgtg     180
tccgatagat tcagcggctc taagagcggc acatctgcca gcctggccat ctctggactg     240
cagagcgaag atgaggccga ctactattgc gccgcctggg atgatagcct gagcagccaa     300 gttttttggcg gcggaaccca agtgaccgtg cta                                 333

<210> SEQ ID NO 880
<211> LENGTH: 251
<212> TYPE: PRT
<213> ORGANISM: Artificial Sequence
<220> FEATURE:
<223> OTHER INFORMATION: antibody sequence

<400> SEQUENCE: 880

Glu Val Gln Leu Leu Glu Ser Gly Gly Gly Leu Val Gln Pro Gly Gly
1               5                   10                  15
```

-continued

Ser Leu Arg Leu Ser Cys Ala Ala Ser Gly Phe Thr Phe Arg Ser Tyr
            20                  25                  30

Ala Val His Trp Val Arg Gln Ala Pro Gly Lys Gly Leu Glu Trp Val
            35                  40                  45

Ser Ser Thr Glu Gly Ser Gly Val Gly Thr Ser Tyr Thr Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Leu Gly Gly Asn Pro Leu Asp Tyr Leu Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Ala Ala Gly Ser Glu Gln Lys Leu Ile Ser Glu Glu Asp Leu Ser
225                 230                 235                 240

Gly Ser Ala Ala Ala His His His His His
                245                 250

<210> SEQ ID NO 881
<211> LENGTH: 217
<212> TYPE: PRT
<213> ORGANISM: Artificial Sequence
<220> FEATURE:
<223> OTHER INFORMATION: antibody sequence

<400> SEQUENCE: 881

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Leu Gly Glu Gly
            20                  25                  30

Tyr Asp Val His Trp Tyr Gln Gln Leu Pro Gly Lys Ala Pro Lys Leu
            35                  40                  45

Leu Ile Tyr Tyr Ser Asp Phe Arg Pro Ser Gly Val Ser Asp Arg Phe
        50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Ser Ser Gln Val Phe Gly Gly Gly Thr Gln Val Thr Val Leu Gly
            100                 105                 110

Gln Pro Lys Ala Ala Pro Ser Val Thr Leu Phe Pro Pro Ser Ser Glu
            115                 120                 125

```
Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 882
<211> LENGTH: 753
<212> TYPE: DNA
<213> ORGANISM: Artificial Sequence
<220> FEATURE:
<223> OTHER INFORMATION: antibody sequence

<400> SEQUENCE: 882

```
gaagttcagc tgctggaatc tggcggcgga ctggttcaac tggcggatc tctgagactg     60
agctgtgccg ccagcggctt cacctttaga agctatgccg tgcactggt ccgacaggcc    120
cctggaaaag gactggaatg ggtgtccagc accgaaggct ctggcgtggg cacaagctac   180
accgattctg tgaagggcag attcaccatc agccgggaca cagcaagaa cacccctgtac  240
ctgcagatga acagcctgag agccgaggac accgccgtgt actactgtgc cagaatgctc  300
ggcgaggca accctctgga ctacctggat tattggggcc agggcaccct ggtcacagtc   360
tcttcagcct ccaccaaggg cccatcggtg ttccccctgg caccctcctc aagagcacc   420
tctggggca gcggccct gggctgcctg gtcaaggact acttcccga accggtgacg      480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacc   600
cagacctaca tctgcaacgt gaatcacaag cccagcaaca ccaaggtgga caagaaagtt   660
gagcccaaat cttgtgcagc gggttctgaa caaaaactca tctcagaaga ggatctgtct   720
ggatcagcgg ccgcccatca tcatcatcat cat                                753
```

<210> SEQ ID NO 883
<211> LENGTH: 651
<212> TYPE: DNA
<213> ORGANISM: Artificial Sequence
<220> FEATURE:
<223> OTHER INFORMATION: antibody sequence

<400> SEQUENCE: 883

```
cagtctgttc tgacacagcc tcctagcgcc tctggcacac tggacagag agtgaccatc     60
agctgtagcg gcagcagctc caatctcggc gagggctatg acgtgcactg gtatcagcag   120
ctgcctggca aggcccctaa actgctgatc tactacagcg acttcagacc cagcggcgtg   180
tccgatagat tcagcggctc taagagcggc acatctgcca gcctggccat ctctggactg   240
cagagcgaag atgaggccga ctactattgc gccgcctggg atgatagcct gagcagccaa   300
gttttttggcg gcggaaccca gtgaccgtg ctaggccagc ctaaagccgc ccctagcgtg   360
accctgttcc ctccaagcag cgaggaactg caggccaaca aggccaccct cgtgtgcctg   420
```

-continued

```
atcagcgact tctatcctgg cgccgtgacc gtggcctgga aggccgatag ctctcctgtg    480
aaggccggcg tggaaaccac caccccctagc aagcagagca acaacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c              651
```

<210> SEQ ID NO 884
<211> LENGTH: 563
<212> TYPE: PRT
<213> ORGANISM: Oryctolagus cuniculus (Rabbit)

<400> SEQUENCE: 884

```
Asn Tyr Gln Asn Gly Lys Asn Asn Val Pro Arg Leu Lys Leu Ser Tyr
1               5                   10                  15

Lys Glu Met Leu Glu Ser Asn Asn Val Ile Thr Phe Asn Gly Leu Ala
            20                  25                  30

Asn Ser Ser Ser Tyr His Thr Phe Leu Leu Asp Glu Glu Arg Ser Arg
        35                  40                  45

Leu Tyr Val Gly Ala Lys Asp His Ile Phe Ser Phe Asn Leu Val Asn
    50                  55                  60

Ile Lys Asp Phe Gln Lys Ile Ala Trp Pro Val Ser Tyr Thr Arg Arg
65                  70                  75                  80

Asp Glu Cys Lys Trp Ala Gly Lys Asp Ile Leu Arg Glu Cys Ala Asn
                85                  90                  95

Phe Ile Lys Val Leu Lys Val Tyr Asn Gln Thr His Leu Tyr Ala Cys
            100                 105                 110

Gly Thr Gly Ala Phe His Pro Ile Cys Thr Tyr Val Gly Ile Gly His
        115                 120                 125

His Pro Glu Asp Asn Ile Phe Lys Leu Glu Asp Ser His Phe Glu Asn
    130                 135                 140

Gly Arg Gly Lys Ser Pro Tyr Asp Pro Lys Leu Leu Thr Ala Ser Leu
145                 150                 155                 160

Leu Ile Asp Gly Glu Leu Tyr Ser Gly Thr Ala Ala Asp Phe Met Gly
                165                 170                 175

Arg Asp Phe Ala Ile Phe Arg Thr Leu Gly Gln His Pro Ile Arg
            180                 185                 190

Thr Glu Gln His Asp Ser Arg Trp Leu Asn Asp Pro Arg Phe Ile Ser
        195                 200                 205

Ala His Leu Ile Pro Glu Ser Asp Asn Pro Glu Asp Lys Val Tyr
    210                 215                 220

Phe Phe Phe Arg Glu Asn Ala Ile Asp Gly Glu His Ser Gly Lys Ala
225                 230                 235                 240

Thr His Ala Arg Ile Gly Gln Ile Cys Lys Asn Asp Phe Gly His
                245                 250                 255

Arg Ser Leu Val Asn Lys Trp Thr Thr Phe Leu Lys Ala Arg Leu Ile
            260                 265                 270

Cys Ser Val Pro Gly Pro Asn Gly Ile Asp Thr His Phe Asp Glu Leu
        275                 280                 285

Gln Asp Val Phe Leu Met Asn Ser Lys Asp Pro Lys Asn Pro Ile Val
    290                 295                 300

Tyr Gly Val Phe Thr Thr Ser Ser Asn Ile Phe Arg Gly Ser Ala Val
305                 310                 315                 320

Cys Met Tyr Ser Met Ser Asp Val Arg Arg Val Phe Leu Gly Pro Tyr
                325                 330                 335
```

```
Ala His Arg Asp Gly Pro Asn Tyr Gln Trp Val Pro Phe Gln Gly Arg
                340                 345                 350

Val Pro Tyr Pro Arg Pro Gly Thr Cys Pro Ser Lys Thr Phe Gly Gly
            355                 360                 365

Phe Glu Ser Thr Lys Asp Leu Pro Asp Asp Val Ile Thr Phe Ala Arg
        370                 375                 380

Ser His Pro Ala Met Tyr Asn Pro Val Phe Pro Ile Asn Asn Arg Pro
385                 390                 395                 400

Ile Met Val Lys Thr Asp Val Asn Tyr Gln Phe Thr Gln Ile Val Val
                405                 410                 415

Asp Arg Val Asp Ala Glu Asp Gly Gln Tyr Asp Val Met Phe Ile Gly
            420                 425                 430

Thr Asp Val Gly Thr Val Leu Lys Val Val Ser Ile Pro Lys Glu Thr
        435                 440                 445

Trp His Asp Leu Glu Glu Val Leu Leu Glu Glu Met Thr Val Phe Arg
    450                 455                 460

Glu Pro Thr Thr Ile Ser Ala Met Glu Leu Ser Thr Lys Gln Gln Gln
465                 470                 475                 480

Leu Tyr Val Gly Ser Ala Ala Gly Val Ala Gln Leu Pro Leu His Arg
                485                 490                 495

Cys Asp Ile Tyr Gly Lys Ala Cys Ala Glu Cys Cys Leu Ala Arg Asp
            500                 505                 510

Pro Tyr Cys Ala Trp Asp Gly Ser Ser Cys Ser Arg Tyr Phe Pro Thr
        515                 520                 525

Ala Lys Arg Arg Thr Arg Arg Gln Asp Ile Arg Asn Gly Asp Pro Leu
    530                 535                 540

Thr His Cys Ser Asp Gly Gly Ile Glu Gly Arg Met Asp His His His
545                 550                 555                 560

His His His

<210> SEQ ID NO 885
<211> LENGTH: 1689
<212> TYPE: DNA
<213> ORGANISM: Oryctolagus cuniculus (Rabbit)

<400> SEQUENCE: 885
aactatcaga acggcaagaa caacgtgccc cggctgaagc tgagctacaa agagatgctg      60
gaaagcaaca acgtgatcac cttcaacggc ctggccaaca gcagcagcta ccacaccttt    120
ctgctggacg aggaacggtc cagactgtac gtgggagcca aggaccacat cttcagcttc    180
aacctggtca acatcaagga cttccagaaa atcgcctggc ctgtgtccta caccagacgg    240
gatgagtgta atgggccgg caaggacatc ctgagagagt gcgccaactt catcaaggtg    300
ctgaaggtgt acaatcagac ccacctgtac gcctgtggca ccggcgcttt tcaccctatc    360
tgtacctatg tcggcatcgg ccaccatcct gaggacaata tcttcaagct cgaggacagc    420
cacttcgaga acggcagagg caagagcccc tacgatccca aactgctgac agcctctctg    480
ctgatcgacg gcgagctgta ttctggcaca gccgccgatt tcatgggcag agacttcgcc    540
atcttcagaa ccctgggcca gcatcacccc atcagaaccg agcagcacga cagcagatgg    600
ctgaacgacc ccagattcat cagcgcccat ctgatcccg agagcgacaa ccccgaggac    660
gacaaggtgt acttcttctt ccgggaaaac gccatcgacg gggagcactc tggaaaagcc    720
acacacgcca gaatcggcca gatctgcaag aacgacttcg cggcacacag atccctcgtg    780
aacaagtgga ccaccttcct gaaggcccgg ctgatctgtt ctgtgcccgg acctaatggc    840
```

```
atcgataccc acttcgacga gctgcaggac gtgttcctga tgaacagcaa ggaccccaag    900
aatcccatcg tgtacggcgt gttcaccacc agcagcaaca tctttagagg cagcgccgtg    960
tgcatgtaca gcatgtccga tgtgcggaga gtgtttctgg gcccctacgc tcacagagat   1020
ggccccaatt atcagtgggt gccattccag ggcagagtgc cctatcctag acctggcacc   1080
tgtcctagca agacctttgg cggcttcgag agcaccaagg acctgcctga cgatgtgatt   1140
accttcgcca gatctcaccc cgccatgtac aaccctgtgt tccccatcaa caacaggccc   1200
atcatggtca agaccgacgt gaactaccag ttcacccaga tcgtggtgga cagagtggat   1260
gccgaggacg gccagtacga cgtgatgttc atcggcaccg atgtgggcac cgtgctgaaa   1320
gtggtgtcta tccccaaaga gacatggcac gacctggaag aggtgctgct ggaagagatg   1380
accgtgttca gagagcccac caccatctcc gccatggaac tgagcacaaa acagcaacag   1440
ctgtatgtgg gctccgccgc tggtgttgct caactgcctc tgcacagatg cgacatctac   1500
ggcaaagcct gcgccgagtg ttgcctggcc agagatcctt actgtgcctg ggatggcagc   1560
agctgcagca gatactttcc caccgccaag cggagaacca gacggcagga tatcagaaac   1620
ggcgaccctc tgacacactg cagcgacggt ggcatcgagg gccgcatgga tcatcatcat   1680
caccatcat                                                            1689
```